US007901507B2

(12) United States Patent
Acharya et al.

(10) Patent No.: US 7,901,507 B2
(45) Date of Patent: Mar. 8, 2011

(54) CRYSTAL STRUCTURE OF AN ANGIOTENSIN-CONVERTING ENZYME (ACE) AND USES THEREOF

(75) Inventors: Ravi Acharya, Bath (GB); Edward David Sturrock, Observatory (ZA)

(73) Assignees: University of Bath, Bath (GB); University of Cape Town, Rondebosch (ZA)

( * ) Notice: Subject to any disclaimer, the term of this patent is extended or adjusted under 35 U.S.C. 154(b) by 0 days.

(21) Appl. No.: 12/172,859

(22) Filed: Jul. 14, 2008

(65) Prior Publication Data

US 2009/0142822 A1 Jun. 4, 2009

Related U.S. Application Data

(63) Continuation of application No. 10/527,707, filed as application No. PCT/GB03/03966 on Sep. 12, 2003, now Pat. No. 7,704,319.

(30) Foreign Application Priority Data

Sep. 12, 2002 (GB) .................................. 0221169.6

(51) Int. Cl.
    *C30B 29/54* (2006.01)
(52) U.S. Cl. ................ 117/68; 117/69; 117/70; 117/929
(58) Field of Classification Search .................... 117/68, 117/69, 70, 925
    See application file for complete search history.

(56) References Cited

U.S. PATENT DOCUMENTS

| 3,832,337 | A | 8/1974 | Ondetti et al. |
| 3,891,616 | A | 6/1975 | Ondetti |
| 3,947,575 | A | 3/1976 | Ondetti |
| 4,052,511 | A | 10/1977 | Cushman et al. |
| 4,053,651 | A | 10/1977 | Ondetti et al. |
| 2004/0033532 | A1* | 2/2004 | Ehlers et al. ................... 435/7.1 |
| 2004/0209344 | A1 | 10/2004 | Pantoliano et al. |

FOREIGN PATENT DOCUMENTS

| EP | 0444605 | 9/1991 |
| WO | WO-91/00354 | 1/1991 |
| WO | WO-91/11172 | 8/1991 |
| WO | WO-94/02518 | 2/1994 |
| WO | WO-98/55148 | 12/1998 |

OTHER PUBLICATIONS

Brown et al., Structure of neurolysin reveals a deep channel that limits substrate access. *Proc. Natl. Acad. Sci. USA.* 98: 3127-32 (2001).
Gordon et al., Deglycosylation, processing and cystallization of human testis angiotensin-converting enzyme. *Biochem. J.* 271: 437-42 (2003).
Gschwend et al., Molecular docking towards drug discovery, *J. Molec. Rec.* 9: 175-86 (1996).

(Continued)

*Primary Examiner* — Robert M Kunemund
(74) *Attorney, Agent, or Firm* — Marshall, Gerstein & Borun LLP

(57) ABSTRACT

The present invention relates to a crystal of ACE protein. The present invention further relates to methods, processes, ACE modulators, pharmaceutical compositions and uses of ACE crystal and the structure coordinates thereof.

12 Claims, 13 Drawing Sheets

OTHER PUBLICATIONS

Kim et al., Crystal structure of Drosophila angiotensin I-converting enzyme bound to captopril and lisinopril. *FEBS Lett.* 538: 65-70 (2003).

Liu et al., Arg-1098 is critical for the chloride dependence of human angiotensin-1 converting enzyme C-domain catalytic activity. *J. Biol. Chem.* 276: 33518-25 (2001).

Natesh et al., Crystal structure of the human angiotensin-converting enzyme-lisinopril complex. *Nature.* 421: 551-4 (2003).

Natesh et al., Database Protein Data Bank, Crystal structure of humane ACE (native), Feb. 7, 2003.

Tarentino et al., Enzymatic deglycosylation of asparagine-linked glycans: purification, properties, and specificity of oligosaccharide-cleaving enzymes from Flavobacterium meningosepticum. *Methods Enzymol.* 230: 44-57 (1994).

Whittle et al., Protein structure-based drug design annual review of biophysics and biomolecular structure. Annual Reviews Inc. Palo Alto, CA. 23: 349-75 (1994).

International Search Report, European Patent Office, PCT/GB2003/03966, dated Feb. 25, 2004.

Abrahams et al., Methods used in the structure determination of bovine mitochondrial F1 ATPase. *Acta Crystallogr. D. Biol. Crystallogr.,* 52:30-42 1996.

Aghajari et al., Structural basis of alpha-amylase activation by chloride. *Protein Sci.*, 11:1435-1441 (2002).

Altschul et al., Basic local alignment search tool. *J. Mol. Biol.*, 215:403-410 (1990).

Bartlett et al., CAVEAT: A program to facilitate the structure-derived design of biologically active moleculres. *Royal Chem. Soc.*, 78:182-196 (1989).

Beldent et al., Proteolytic release of human angiotensin-converting enzyme. Localization of the cleavage site. *J. Biol. Chem.*, 268(35):26428-26434 (1993).

Berge et al., Pharmaceutical Salts. *J. Pharm. Sci.*, 66(1):1-19 (1977).

Bohm, The computer program LUDI: a new method for the de novo design of enzyme inhibitors. *J. Comput. Aided Mol. Des.*, 6:61-78 (1992).

Brenner et al., Diverse biological actions of atrial natriuretic peptide. *Physiol. Rev.*, 70(3):665-99 (1990).

Brown et al., Black Americans have an increased rate of angiotensin converting enzyme inhibitor-associated angioedema. *Clin. Pharmacol. Ther.*, 60:8-13 (1996).

Brunger et al., Crystallography & NMR system: A new software suite for macromolecular structure determination. *Acta Crystallogr. D. Biol. Crystallogr.*, 54:905-21 (1998).

Brunger, Free R value: a novel statistical quantity for assessing the accuracy of crystal structures. *Nature*, 355:472-75 (1992).

Bunning et al., Activation of angiotensin converting enzyme by monovalent anions. *Biochemistry*, 22:110-16 (1983).

Chubb et al., Defining the boundaries of the testis angiotensin I-converting enzyme ectodomain. *Biochem. Biopshys. Res. Commun.*, 297:1225-30 (2002).

Cohen et al., Molecular modeling software and methods for medicinal chemistry. *J. Med. Chem.*, 33(3):883-94 (1990).

Collaborative Computational Project, No. 4, *Acta Crystallogr. D. Biol. Crystallogr.*, 50:760-763 (1994).

Corvol et al., Peptidyl dipeptidase A: angiotensin I-converting enzyme. *Methods Enzymol.*, 248:283-305 (1995).

Couvineau et al., Mutagenesis of N-glycosylation sites in the human vasoactive intestinal peptide 1 receptor. Evidence that asparagine 58 or 69 is crucial for correct delivery of the receptor to plasma membrane. *Biochemistry*, 35:1745-52 (1996).

Cushman et al., Design of potent competitive inhibitors of angiotensin-converting enzyme. Carboxyalkanoyl and mercaptoalkanoyl amino acids. *Biochemistry*, 16(25):5484-91 (1977).

Davis et al., Ligand binding by the immunoglobulin superfamily recognition molecule CD2 is glycosylation-indesendent. *J. Biol. Chem.*, 270: 369-75 (1995).

de La Fortelle et al., Maximum-likelihood heavy-atom parameter refinement for multiple isomorphous replacement and multiwavelegnth anomalous diffraction methods. *Methods Enzymol.*, 276:472-94 (1997).

Devereux et al., A comprehensive set of sequence analysis programs for the VAX. *Nucleic Acids Res.*, 12:387-95 (1984).

Ehlers et al., Molecular cloning of human testicular angiotensin-converting enzyme: the testis isozyme is identical to the C-terminal half of endothelial angiotensin-converting enzyme. *Proc. Natl. Acad. Sci. USA*, 86:7741-5 (1989).

Ehlers et al., Proteolytic release of membrane-bound angiotensin-converting enzyme: role of the juxtamembrane stalk sequence. *Biochemistry*, 35:9549-59 (1996).

Ehlers et al., The unique N-terminal sequence of testis angiotensin-converting enzyme is heavily O-glycosylated and unessential for activity or stability. *Biochem. Biophys. Res. Commun.*, 183:199-205 (1992).

Ehlers et al. Spontaneous solubilization of membrane-bound human testis angiotensin-converting enzyme expressed in Chinese hamster ovary cells. *Proc. Natl. Acad. Sci. USA*, 88: 1009-13 (1991).

Esther et al., The critical role of tissue angiotensin-converting enzyme as revealed by gene targeting in mice. *J. Clin. Invest.*, 99:2375-85 (1997).

Exner et al., Lesser response to angiotensin-converting-enzyme inhibitor therapy in black as compared with white patients with left ventricular dysfunction. *N. Engl. J. Med.*, 344(18):1351-7 (2001).

Goodford, A computational procedure for determining energetically favorable binding sites on biologically important macromolecules. *J. Med. Chem.*, 28:849-7 (1985).

Goodsell et al., Automated docking of substrates to proteins by simulated annealing. *Proteins*, 8:195-202 (1990).

Hagaman et al., Angiotensin-converting enzyme and male fertility. *Proc. Natl. Acad. Sci. USA*, 95:2552-7 (1998).

Holm et al., Protein folds and families: sequence and structure alignments. *Nucleic Acids Res.*, 27:244-7 (1999).

Hooper, Families of zinc metalloproteases. *FEBS Lett.*, 354:1-6 1994.

Horwell, The 'peptoid' approach to the design of non-peptide, small molecule agonists and antagonists of neuropeptides. *Trends Biotechnol.*, 13:132-4 (1995).

Howard et al., Transcription of testicular angiotensin-converting enzyme (ACE) is initiated within the 12th intron of the somatic ACE gene. *Mol. Cell Biol.*, 10: 4294-4302 (1990).

Huang et al., Genetically increased angiotensin I-converting enzyme level and renal complications in the diabetic mouse. *Proc. Natl. Acad. Sci. USA*, 98:13330-4 (2001).

Jeunemaitre et al., Absence of linkage between the angiotensin converting enzyme locus and human essential hypertension. *Nat. Genet.*, 1:72-5 (1992).

Jones et al., Improved methods for building protein models in electron density maps and the location of errors in these models. *Acta Crystallogr. A*, 47:110-19 (1991).

Junot et al., RXP 407, a selective inhibitor of the N-domain of angiotensin I-converting enzyme, blocks in vivo the degradation of hemoregulatory peptide acetyl-Ser-Asp-Lys-Pro with no effect on angiotensin I hydrolysis. *J. Pharmacol. Exp. Ther.*, 297:606-11 (2001).

Kasturi et al., Role of glycosylation in the biosynthesis and activity of rabbit testicular angiotensin-converting enzyme. *Biochemistry*, 33:6228-34 (1994).

Kasturi et al., The hydroxy amino acid in an Asn-X-Ser/Thr sequon can influence N-linked core glycosylation efficiency and the level of expression of a cell surface glycoprotein. *J. Biol. Chem.*, 270:14756-61 (1995).

Kobata, Use of endo- and exoglycosidases for structural studies of glycoconjugates. *Anal. Biochem.*, 100:1-14 (1979).

Kornfeld et al., Assembly of asparagine-linked oligosaccharides. *Annu. Rev. Biochem.*, 54:631-64 (1985).

Kraulis, Raster3D Version 2.0. A program for photorealistic molecular graphics. *J. Appl. Crystallogr.*, 24:946-50 (1991).

Krege et al., Male-female differences in fertility and blood pressure in ACE-deficient mice. *Nature*, 375:146-8 (1995).

Kroll et al., A multifunctional prokaryotic protein expression system: overproduction, affinity purification, and selective detection. *DNA Cell Biol.*, 12:441-53 (1993).

Kumar et al., Structure of testicular angiotensin-converting enzyme. A segmental mosaic isozyme. *J. Biol. Chem.*, 264:16754-8 (1989).

Kuraya et al., Release of O-linked sugar chains from glycoproteins with anhydrous hydrazine and pyridylamination of the sugar chains with improved reaction conditions. *Biochemistry.* 112:122-6 (1992).

Liu et al., Arg(1098) is critical for the chloride dependence of human angiotensin I-converting enzyme C-domain catalytic activity. *J. Biol. Chem.*, 276:33518-25 (2001).

Marshall et al., Three-dimensional structure-activity relationships. *Trends Pharmacol. Sci.*, 9:285-9 (1988).

Martin, 3D database searching in drug design. *J. Med. Chem.* 35:2145-54 (1992).

Mattei et al. Cytogenet. Cell Genet., 51:1041 (1989).

Meng et al., Automated docking with grid-based energy evaluation. *J. Comp. Chem.*, 13(4):505-24 (1992).

Merritt et al., Raster3D: photorealistic molecular graphics. *Methods Enzymol.*, 277:505-24 (1997).

Miranker et al., Functionality maps of binding sites: a multiple copy simultaneous search method. *Proteins*, 11:29-34 (1991).

Misago et al., Suppressive effects of swainsonine and N-butyldeoxynojirimycin on human bone marrow neutrophil maturation. *Biochem. Biophys. Res. Commun.*, 269:219-25 (2000).

Nachon et al., Engineering of a monomeric and low-glycosylated form of human butyrylcholinesterase: expression, purification, characterization and crystallization. *Eur. J. Biochem.*, 269:630-37 (2002).

Navia et al., Use of structural information in drug design. *Curr. Opin. Struct. Biol.*, 2:202-210 (1992).

Nishibata et al., Automatic creation of drug candidate structures based on receptor structure. Starting point for artificial lead generation. *Tetrahedron*, 47(43):8985-8990 (1991).

Otwinowski et al., Processing of x-ray diffraction data collected in oscillation mode. *Methods Enzymol.*, 276:307-326 (1997).

Porath, Immobilized metal ion affinity chromatography. *Protein Expr. Purif.*, 3:263-81 (1992).

Ramaraji et al., Selective restoration of male fertility in mice lacking angiotensin-converting enzymes by sperm-specific expression of the testicular isozyme. *J. Clin. Invest.*, 102:371-8 (1998).

Rawlings et al., Evolutionary families of metallopeptidases. *Methods Enzymol.*, 248:183-228 (1995).

Roberge et al., A strategy for a convergent synthesis of N-linked glycopeptides on a solid support. *Science*, 269:202-4 (1995).

Sadhukhan et al., Different glycosylation requirements for the synthesis of enzymatically active angiotensin-converting enzyme in mammalian cells and yeast. *J. Biol. Chem.*, 271:6429-34 (1996).

Schwager et al., Cleavage of disulfide-bridged stalk domains during shedding of angiotensin-converting enzyme occurs at multiple juxtamembrane sites. *Biochemistry*, 40:15624-30 (2001).

Schwager et al., Modulation of juxtamembrane cleavage ("shedding") of angiotensin-converting enzyme by stalk glycosylation: evidence for an alternative shedding protease. *Biochemistry*, 38:10388-97 (1999).

Schwager et al., Phorbol ester-induced juxtamembrane cleavage of angiotensin-converting enzyme is not inhibited by a stalk containing intrachain disulfides. *Biochemistry*, 37:15449-56 (1998).

Shapiro et al., Anion activation of angiotensin converting enzyme: dependence on nature of substrate. *Biochemistry*, 22:3850-7 (1983).

Simon et al., Peptoids: a modular approach to drug discovery. *Proc. Natl. Acad. Sci. USA*, 89:9367-71 (1992).

Sturrock et al., Assignment of free and disulfide-bonded cysteine residues in testis angiotensin converting enzyme: functional implications. *Biochemistry*, 35:9560-6 (1996).

Tatusova et al., Blast 2 Sequences, a new tool for comparing protein and nucleotide sequences. *FEMS Microbiol. Lett.*, 174:247-50 (1999).

Tatusova et al., Erratum to "Blast 2 Sequences, a new tool for comparing protein and nucleotide sequences." *FEMS Microbiol. Lett.*, 177:187-188 (1999).

Thornberry et al., Determination of caspase specificities using a peptide combinatorial library. *Methods Enzymol.*, 322:100-10 (2000).

Trimble et al., Identification of distinct endoglycosidase (endo) activities in Flavobacterium meningosepticum: endo F1, endo F2, and endo F3. Endo F1 and endo H hydrolyze only high mannose and hybrid glycans. *J. Biol. Chem.*, 266:1646-51 (1991).

Two bright new faces in gene therapy. *Nat Biotechnol.* 14: 556 (1996).

Ukeda et al., Peptides from peptic hydrolyzate of heated sardine meat that inhibit angiotensin I converting enzyme. *Journal of Japan Society for Bioscience, Biotechnology, and Agrochemistry*, 66: 25-29 (1992). [Translation of abstract only].

Waller et al., Three-dimensional quantitative structure-activity relationship of angiotesin-converting enzyme and thermolysin inhibitors. II. A comparison of CoMFA models incorporating molecular orbital fields and desolvation free energies based on active-analog and complementary-receptor-field alignment rules. *J. Med. Chem.* 36:2390-2403 (1993).

Wei et al., The two homologous domains of human angiotensin I-converting enzyme are both catalytically active. *J. Biol. Chem.*, 266:9002-9008 (1991).

Wheeler et al., Comparison of the N-linked glycans from soluble and GPI-anchored CD59 expressed in CHO cells. *Glycobiology*, 12:261-71 (2002).

Williams et al., Identification of two active site residues in human angiotensin I-converting enzyme. *J. Biol. Chem.*, 269: 29430-29434 (1994).

Wolff et al., The Cambrian period of nonviral gene delivery. *Nat. Biotechnol.*, 16:421-2 (1998).

Yu et al., Identification of N-linked glycosylation sites in human testis angiotensin-converting enzyme and expression of an active deglycosylated form. *J. Biol. Chem.* 272: 3511-19 (1997).

Zhou et al., Role of asparagine-linked oligosaccharides in the function of the rat PTH/PTHrP receptor. *Biochemistry*, 39:6514-20 (2000).

\* cited by examiner

Figure 7C

```
          71          81          91         101         111
    LVTDEAEASK  FVEEYDRTSQ  VVWNEYAEAN  WNYNTNITTE  TSKILLQKNM
    ∿∿∿∿∿∿∿∿∿∿∿∿∿∿∿∿∿∿∿∿∿∿∿∿∿∿∿∿∿∿∿∿∿∿∿∿∿∿—∿∿∿∿∿∿∿∿∿
                            α1
         121         131         141         151         161
    QIANHTLKYG  TQARKFDVNQ  LQNTTIKRII  KKVQDLERAA  LPAQELEEYN
    ∿∿∿∿∿∿∿∿∿∿∿∿∿∿∿∿∿∿∿∿—∿∿∿∿∿∿∿∿∿∿—∿∿∿∿∿∿∿∿∿∿∿∿∿∿∿∿
          α2         3₁₀            α3         3₁₀
         171         181         191         201         211
    KILLDMETTY  SVATVCHPNG  SCLQLEPDLT  NVMATSRKYE  DLLWAWEGWR
    ∿∿∿∿∿∿∿∿∿∿————————→————→∿∿∿∿∿∿∿∿∿∿—∿∿∿∿∿∿∿∿∿∿∿
          α4          β1     β2       α5
         221         231         241         251         261
    DKAGRAILQF  YPKYVELINQ  AARLNGYVDA  GDSWRSMSET  PSLEQDLERL
    ∿∿∿∿∿∿∿∿∿∿∿∿∿∿∿∿∿∿∿∿∿∿∿∿∿—∿∿∿∿∿∿∿∿∿∿—∿∿∿∿∿∿∿∿∿∿
             α6                         α7   3₁₀
         271         281         291         301         311
    FQELQPLYLN  LHAYVRRALH  RHYGAQHINL  EGPIPAHLLG  NMWAQTWSNI
    ∿∿∿∿∿∿∿∿∿∿∿∿∿∿∿∿∿∿∿∿∿∿∿∿∿————————→————∿∿∿
             α8                              β3         3₁₀
         321         331         341         351         361
    YDLVVPFPSA  PSMDTTEAML  KQGWTPRRMF  KEADDFFTSL  GLLPVPPEFW
    ∿∿∿———∿∿∿∿∿∿∿∿—∿∿∿∿∿∿∿∿∿∿∿∿∿∿∿∿∿∿∿∿—∿∿∿
       α9        α10            α11                    α12
         371         381         391         401         411
    NKSMLEKPTD  GREVVCHASA  WDFYNGKDFR  IKQCTTVNLE  DLVVAHHEMG
    ∿∿———————————————→——————∿∿∿∿∿∿∿∿∿∿
                      β4          β5                    α13
         421         431         441         451         461
    HIQYFMQYKD  LPVALREGAN  PGFHEAIGDV  LALSVSTPKH  LHSLNLLSSE
    ∿∿∿∿∿∿———∿∿∿∿—∿∿∿∿∿∿∿∿∿∿∿∿∿∿∿∿∿∿∿∿∿∿—
                3₁₀                  α14
         471         481         491         501         511
    GGSDEHDINF  LMKMALDKIA  FIPFSYLVDQ  WRWRVFDGSI  TKENYNQEWW
    ∿∿∿∿∿∿∿∿∿∿∿∿∿∿∿∿∿∿∿∿∿∿∿∿∿∿∿∿∿∿∿∿∿∿∿∿—∿∿∿∿
                              α15
         521         531         541         551         561
    SLRLKYQGLC  PPVPRTQGDF  DPGAFFIPS  SVPIIMFVS  FIIQFQFHEA
    ∿∿∿∿∿∿———∿∿∿∿∿∿—∿∿∿∿∿∿∿∿∿∿∿∿∿∿
      α16    β6           3₁₀                        α17
         571         581         591         601         611
    LCQAAGHTGP  LHKCDIYQSK  EAGQRLATAM  KLGFSRPWPE  AMQLITGQPN
    ∿∿∿∿—— ∿∿∿∿——∿∿∿∿∿∿∿∿∿∿———∿∿∿∿∿∿∿—
                    3₁₀          α18                α19
         621         631         641         651
    MSASAMLSYF  KPLLDWLRTE  NELHGEKLGW  PQYNWTPNS
    —∿∿∿∿∿∿∿∿∿∿∿∿∿∿∿∿∿∿∿∿∿—————
              α20
```

CRYSTAL STRUCTURE OF AN ANGIOTENSIN-CONVERTING ENZYME (ACE) AND USES THEREOF

This application is a continuation of U.S. patent application Ser. No. 10/527,707, filed Mar. 11, 2005 now U.S. Pat. No. 7,704,319, which is the U.S. National Phase under 35 U.S.C. §371 of International Application No. PCT/GB2003/003966, filed Sep. 12, 2003, which claims benefit of priority of British Patent Application No. 0221169.6 filed Sep. 12, 2002.

FIELD OF INVENTION

The present invention relates to a crystal. In particular, the present invention relates to a crystal of ACE protein.

The present invention further relates to methods, processes, ACE modulators, pharmaceutical compositions and uses of the ACE crystal and the structure co-ordinates thereof.

BACKGROUND TO THE INVENTION

Angiotensin converting enzyme (peptidyl dipeptidase A, EC 3.4.15.1, ACE) is a membrane-anchored dipeptidyl carboxypeptidase that is essential for blood pressure regulation and electrolyte homeostasis via the renin-angiotensin-aldosterone system. The enzyme is a zinc metalloprotease that converts the inactive peptide angiotensin I to angiotensin II, a potent vasoconstrictor. ACE, like many diverse membrane-bound ectoproteins, is released from the membrane by a membrane protease or secretase (1). An understanding of this cleavage-secretion mechanism is important for the development of therapeutic strategies to address the different pathologies caused by defects in the function of the secretase. Substrate determinants that specify cleavage by secretases remain incompletely characterised, but may include the physico-chemical properties of the juxtamembrane ("stalk") sequence or unidentified recognition motifs of the stalk or the extracellular domain. Cleavage of ACE occurs in the stalk sequence and the solubilizing protease is constrained topologically, in terms of the number of residues between the cleavage site and the proximal extracellular domain of ACE. However, the ACE secretase appears to be remarkably versatile in terms of its substrate specificity (2,3).

The active sites of ACE and carboxypeptidase A, a prototypic zinc metalloprotease, are understood to be very similar and this similarity is exploited in the design of the first generation of ACE inhibitors. The clinical success of these inhibitors—such as captopril and enalapril—in the treatment of hypertension and congestive heart failure is well established. However, the side effects such as persistent cough which effects up to 20% of patients and angioedema which is less common, together with limitations such as their contraindication in patients with impaired renal function and decreased efficacy in patients with low-renin hypertension, underscore the need for more specific and selective inhibitors.

There are two isoforms of ACE that are transcribed from the same gene in a tissue specific manner. In somatic tissues it exists as a glycoprotein composed of a single large polypeptide chain of 1277 amino acids whereas the germinal form is synthesised as a lower molecular mass isozyme and is thought to play a role in sperm maturation and the binding of sperm to the oviduct epithelium. The somatic form consists of two domains (N- and C-domain), each containing an active site with a conserved HEXXH zinc-binding motif and a glutamate some 24 residues downstream which forms the third zinc ligand (Williams et al., 1994). The two domains differ in their substrate specificities; inhibitor and chloride activation profiles; and physiological functions. There are two N-domain-specific substrates: the hemoregulatory peptide N-acetyl-seryl-aspartyl-lysyl-proline (AcSDKP) which controls hematopoietic stem cell differentiation and proliferation; and the bradykinin potentiating peptide angiotensin-(1-7). On the other hand, both active sites catalyse the hydrolysis of angiotensin I and the vasodilator bradykinin with similar efficiency. However, inhibition of the N-domain with a phosphinic peptide RXP407 has no effect on blood pressure regulation (Junot et al., 2001) and, furthermore, expression of the N-domain only, in transgenic mice produced a phenotype similar to the ACE knockout mice (Esther et al., 1997). Thus, the C-domain appears to be necessary and sufficient for controlling blood pressure and cardiovascular function. Testis ACE (tACE) is identical to the C-terminal half of somatic ACE, except for a unique 36-residue sequence constituting its amino terminus, thus this isoform is selected for initial efforts to obtain a three-dimensional structure.

The cDNA sequence of human testicular ACE has been described (Ehlers et al. (1989) Proc. Nat. Acad. Sci. 86: 7741-7745) and the predicted protein consists of a 732-residue preprotein including a 31-residue signal peptide. The mature polypeptide has a molecular weight of 80,073 (unglycosylated form).

Despite the pivotal role of ACE, there have been no reports disclosing that suitable crystals have been or could be obtained for this enzyme and so the X-ray crystallographic analysis of such proteins has been impossible.

SUMMARY OF THE INVENTION

The present invention is based upon the seminal finding of the first three-dimensional structure of the ACE protein.

Peptidases, for example, thermolysin and carboxypeptidase A that have been used in comparative molecular field analysis and 3D quantitative structure-activity relationship studies of ACE (Waller & Marshall, 1993) show no homology with the structure of ACE described herein. Surprisingly, ACE shows significant structural homology with that of neurolysin, a member of the M3 family of thimet oligopeptidases. The two proteins do not share any amino acid sequence identity (close to random score), yet when the two structures are optimally superimposed using DALI server (Holm & Sander, 1999), there is noticeable match with a root mean square (r.m.s.) deviation of 4.0 Å for 143 $C_\alpha$ atoms. Accordingly, the structure presented herein may be used for the development of novel, highly selective ACE modulators with the potential for greater efficacy, fewer side effects and treatment of new indications.

Thus, in a first aspect, the present invention relates to a crystal of ACE protein.

Preferably, the ACE protein is underglycosylated.

Preferably, the ACE protein is underglycosylated by removing one or more glycosylation sites and/or one or more partially glycosylated sites. More preferably, the underglycosylated ACE protein is deglycosylated at amino acids 337 and 586 or amino acids 90, 109, 155, 337 and 586 of SEQ ID No 2.

Preferably, the crystal comprises atoms arranged in a spatial relationship represented by at least a portion of the structure co-ordinates of Table A or Table B.

Preferably, the crystal belongs to the space group $P2_12_12_1$.

Preferably, the crystal has the unit cell dimensions: a=56.47 Å, b=84.90 Å and c=133.99 Å.

Preferably, the crystal is a crystal of human ACE protein.

Preferably, the crystal further comprises an entity bound to the ACE protein or a portion thereof. More preferably, the entity is bound to the ACE protein or a portion thereof by contacting one or more residues of the ACE protein selected from: His384, Ala385, Lys542, Tyr551, Tyr554, Glu415 and His544. More preferably, the entity modulates the activity of ACE. More preferably, the entity is an inhibitor of ACE—such as lisinopril or a derivative thereof.

In a second aspect, the present invention relates to a method of preparing a crystal of ACE protein comprising the steps of: (a) culturing host cells comprising an underglycosylated ACE protein; (b) purifying the underglycosylated ACE protein; and (c) crystallising the underglycosylated ACE protein.

Preferably, the ACE protein is underglycosylated by removing one or more glycosylation sites and/or one or more partially glycosylated sites. More preferably, the underglycosylated ACE protein is deglycosylated at amino acids 337 or amino acids 90, 109, 155, 337 and 586 of SEQ ID No 2.

Preferably, the ACE protein is crystallised using about 10 mM HEPES and about 0.1% PMSF with an equal volume of a reservoir solution containing about 15% PEG 4000, about 50 mM $CH_3COONa.3H_2O$ pH 4.7 and about 10 μM $ZnSO_4.7H_2O$.

Preferably, the crystal that is prepared has a structure defined by at least a portion of the structure co-ordinates of Table A or Table B.

Preferably, the crystal belongs to the space group $P2_12_12_1$.

Preferably, the crystal has the unit cell dimensions: a=56.47 Å, b=84.90 Å and c=133.99 Å.

Preferably, the ACE protein is human ACE protein.

Preferably, the crystal further comprises an entity bound to the ACE protein. More preferably, the entity modulates the activity of ACE. More preferably, the entity is an inhibitor of ACE—such as lisinopril or a derivative thereof. More preferably, the crystal that is prepared has a structure defined by at least a portion of the structure co-ordinates of Table B.

In a third aspect, the present invention relates to a method of screening for a modulator of ACE wherein the method comprises the use of a crystal according to the present invention. Preferably, the method comprises the steps of: (a) providing at least a portion of the structure co-ordinates of Table A or Table B; (b) employing at least a portion of the structure co-ordinates of Table A or Table B to design or select or synthesise a putative modulator of ACE; (c) contacting the putative modulator of ACE with ACE or a mutant, variant, homologue, derivative or fragment thereof in the presence of a substrate; and (d) screening the putative modulator of ACE in an assay for the potential to modulate ACE.

Preferably, at least a portion of the structure co-ordinates of Table A or Table B and/or the putative modulator of ACE and/or the substrate are provided on a machine-readable data storage medium comprising a data storage material encoded with machine readable data.

Preferably, the putative ACE modulator is from a library of compounds.

Preferably, the putative ACE modulator is selected from a database.

Preferably, the putative ACE modulator is designed de novo.

Preferably, the putative ACE modulator is designed from a known ACE modulator.

Preferably, the design or selection of the putative ACE modulator is performed in conjunction with computer modelling.

Preferably, the putative ACE modulator is useful in the prevention and/or treatment of an ACE related disorder. More preferably, the ACE related disorder is hypertension.

In a fourth aspect, the present invention relates to a process comprising the steps of: (a) performing the method according to the third aspect of the present invention; (b) identifying one or more modulators of ACE; and (c) preparing a quantity of those one or more ACE modulators.

In a fifth aspect, the present invention relates to a process comprising the steps of: (a) performing the method according to the third aspect of the present invention; (b) identifying one or more ACE modulators; and (c) preparing a pharmaceutical composition comprising those one or more identified ACE modulators.

In a sixth aspect, the present invention relates to a process comprising the steps of: (a) performing the method according to the third aspect of the present invention; (b) identifying one or more ACE modulators; (c) modifying those one or more ACE modulators; and (d) optionally preparing a pharmaceutical composition comprising those one or more ACE modulators.

In a seventh aspect, the present invention relates to a method of obtaining structural information about a molecule or a molecular complex of unknown structure by using at least a portion of the structure co-ordinates of ACE, comprising the steps of: (a) generating X-ray diffraction data from a crystallised molecule or molecular complex; (b) applying at least a portion of the structure coordinates of ACE to said X-ray diffraction pattern to generate a three dimensional electron density map of at least a portion of the molecule or molecular complex; and (c) using all or a portion of the structure co-ordinates of ACE to generate homology models of ACE.

In an eighth aspect, the present invention relates to an ACE modulator identified by the method according to the third aspect of the present invention. Preferably, the ACE modulator inhibits ACE.

In a ninth aspect, the present invention relates to a pharmaceutical composition comprising an ACE modulator according to the seventh aspect of the present invention and a pharmaceutically acceptable carrier, diluent, excipient or adjuvant or any combination thereof.

In a tenth aspect, the present invention relates to a method of preventing and/or treating an ACE related disorder comprising administering a modulator of ACE according to the seventh aspect of the present invention and/or a pharmaceutical according to the eighth aspect of the present invention, wherein said modulator of ACE or said pharmaceutical is capable of causing a beneficial preventative and/or therapeutic effect.

In an eleventh aspect, the present invention relates to a computer for producing a three-dimensional representation of ACE wherein said computer comprises: (a) a computer-readable data storage medium comprising a data storage material encoded with computer-readable data, wherein said data comprises the structure co-ordinates of ACE; (b) a working memory for storing instructions for processing said computer-readable data; (c) a central-processing unit coupled to said working memory and to said computer-readable data storage medium for processing said computer-machine readable data into said three-dimensional representation; and (d) a display coupled to said central-processing unit for displaying said three-dimensional representation.

In a twelfth aspect, the present invention relates to a machine-readable data storage medium comprising a data storage material encoded with machine-readable data, wherein the data is defined by at least a portion of the structure co-ordinates of ACE in Table A or Table B.

In a thirteenth aspect, the present invention relates to the use of an ACE crystal in the preparation of a medicament to prevent and/or treat an ACE related disorder. Preferably, the ACE related disorder is hypertension.

In a fourteenth aspect, the present invention relates to the use of at least a portion of the structure co-ordinates of Table A or Table B to screen for modulators of ACE.

In a fifteenth aspect, the present invention relates to the use of at least a portion of the structure co-ordinates of Table A or Table B to solve the structure of the crystalline form of any other protein with significant amino acid sequence homology to any functional domain of ACE.

In a sixteenth aspect, the present invention relates to the use of at least a portion of the structure co-ordinates of Table A or Table B in molecular design techniques to design, select and synthesise modulators of ACE.

In a seventeenth aspect, the present invention relates to the use of at least a portion of the structure co-ordinates of Table A or Table B in the development of compounds that can isomerise to reaction intermediates in the chemical reaction of a substrate or other compound that binds to ACE.

In an eighteenth aspect, the present invention relates to the use of at least a portion of the structure co-ordinates of Table A or Table B to screen small molecule databases for chemical entities or compounds that modulate ACE.

In a nineteenth aspect, the present invention relates to the use of at least a portion of the structure co-ordinates of Table A or Table B to solve the structure of the crystalline form of any other protein with significant amino acid sequence homology to any functional domain of ACE. Preferably, the structure of the crystalline form of any other protein with significant amino acid sequence homology to any functional domain of ACE is solved using molecular replacement.

In a twentieth aspect, the present invention relates to the expression vectors pLEN-tACEΔ36g(1, 2, 3, 4) and pLEN-tACEΔ36g(1,3).

DETAILED DESCRIPTION OF THE INVENTION

Ace Protein

ACE (EC 3.4.15.1) is a peptidyldipeptide hydrolase. It catalyzes the hydrolysis of the penultimate peptide bond at the C-terminal end of a variety of acylated tripeptides and larger polypeptides having an unblocked alpha-carboxy group having a free C-terminus. The reactivity of the enzyme varies markedly depending on the substrate.

As used herein, the term "ACE protein" includes all vertebrate and mammalian forms and is intended to cover mutants, variants, homologues, derivatives and fragments thereof. Preferably, the mutants, variants, homologues, derivatives and fragments thereof have the activity of the naturally occurring ACE.

There are two isoforms of ACE that are transcribed from the same gene in a tissue specific manner. In somatic tissues, it exists as a glycoprotein composed of a single large polypeptide chain of 1277 amino acids whereas the germinal form is synthesised as a lower molecular mass isozyme and is thought to play a role in sperm maturation and the binding of sperm to the oviduct epithelium. The somatic form consists of two domains (N- and C-domain), each containing an active site with a conserved HEXXH zinc-binding motif and a glutamate some 24 residues downstream which forms the third zinc ligand (Williams et al., 1994). The two domains differ in their substrate specificities; inhibitor and chloride activation profiles; and physiological functions. There are two N-domain-specific substrates: the hemoregulatory peptide N-acetyl-seryl-aspartyl-lysyl-proline (AcSDKP) which controls hematopoietic stem cell differentiation and proliferation; and the bradykinin potentiating peptide angiotensin-(1-7). On the other hand, both active sites catalyse the hydrolysis of angiotensin I and the vasodilator bradykinin with similar efficiency. However, inhibition of the N-domain with a phosphinic peptide RXP407 had no effect on blood pressure regulation (Junot et al., 2001) and, furthermore, expression of the N-domain only, in transgenic mice produced a phenotype similar to the ACE knockout mice (Esther et al., 1997). Thus, the C-domain appears to be necessary and sufficient for controlling blood pressure and cardiovascular function. Testis ACE (tACE) is identical to the C-terminal half of somatic ACE, except for a unique 36-residue sequence constituting its amino terminus.

Further background teachings on ACE have been presented by Victor A. McKusick et al. at http://www3.ncbi.nlm.nih.gov/Omin/searchomim.htm. The following information concerning ACE has been extracted from that source.

Angiotensin I-converting enzyme or kininase II, is a dipeptidyl carboxypeptidase that plays an important role in blood pressure regulation and electrolyte balance by hydrolyzing angiotensin I into angiotensin II, a potent vasopressor, and aldosterone-stimulating peptide. The enzyme is also able to inactivate bradykinin, a potent vasodilator.

Ehlers et al. (1989) *Proc. Nat. Acad. Sci.* 86: 7741-7745 determined the cDNA sequence for human testicular ACE. The predicted protein is identical, from residue 37 to its C terminus, to the second half or C-terminal domain of the endothelial ACE sequence. The inferred protein sequence consists of a 732-residue preprotein including a 31-residue signal peptide. The mature polypeptide has a molecular weight of 80,073.

Howard et al. (1990) *Mol. Cell. Biol.* 10: 429-44302, found that the testis-specific form of ACE has its own promoter within intron 12, is encoded by the 3-prime region of the gene, and is found only in postmeiotic spermatogenic cells and sperm.

Although angiotensin-converting enzyme has been studied primarily in the context of its role in blood pressure regulation, this widely distributed enzyme has many other physiologic functions. The ACE gene encodes 2 isozymes. The somatic ACE isozyme is expressed in many tissues, including vascular endothelial cells, renal epithelial cells, and testicular Leydig cells, whereas the testicular or germinal ACE isozyme is expressed only in sperm Ramaraj et al., (1998) *J. Clin. Invest.* 102: 371-378.

Brown et al. (1996) *Clin. Pharmacol. Therapeutics* 60: 8-13 found an association between the use of certain ACE inhibitors (lisinopril or enalapril vs captopril) and emergent angioedema in the African-American population of Tennessee. The adjusted relative risk of angioedema was 4.5 (95% CI, 2.9-6.8) in blacks compared to whites. The African-American patients were more severely affected: 7 of the 8 patients admitted to the intensive care unit were black as were all patients who required intubation. African-American users of ACE inhibitors tended to be younger and female when compared to their white counterparts. The rate of angioedema was highest within the first 30 days of use (5.79 per 1000 patient-years) compared to long-term use (1.04 per 1000 patient-years).

Large-scale trials of therapy for heart failure showed improvements in outcome with ACE inhibitors and beta-blockers. These results led to the recommendation that all patients who have heart failure accompanied by a low ejection fraction and who can tolerate ACE inhibitors and beta-blockers should be treated with both agents. Exner et al. (2001) *New Eng. J. Med.* 344: 1351-1357 focused on the fact that black patients with heart failure have a poorer prognosis than white patients and performed a study comparing racial groups. They found that whereas therapy with enalapril is associated with significant reduction in the risk of hospitalization for heart failure among white patients with left ventricular function, it had no such effect in similar black patients. The explanation for the lesser response to the ACE inhibitor in black patients was not clear.

Mattei et al. (1989) *Cytogenet. Cell Genet.* 51: 1041 assigned the ACE gene to 17q23 by in situ hybridization. Using a DNA marker at the growth hormone gene locus, which they characterized as 'extremely polymorphic' and which showed no recombination with ACE, Jeunemaitre et al. (1992) *Nature Genet.* 1: 72-75, mapped ACE to 17q22-q24, consistent with the in situ hybridization mapping to 17q23. A demonstration of linkage between the ACE locus and elevated blood pressure in a rat model of hypertension pointed to ACE as a candidate gene in human hypertension. In studies of hypertensive families, they found no evidence to support linkage between the ACE locus and the disease, however.

Krege et al. (1995) *Nature* 375: 146-148 investigated the role of the ACE gene in blood pressure control and reproduction using mice generated to carry an insertional mutation that was designed to inactivate both forms of Ace. All homozygous female mutants were found to be fertile, but the fertility of homozygous male mutants was greatly reduced. Heterozygous males but not females had blood pressures that were 15 to 20 mm Hg less than normal, although both male and female heterozygotes had reduced serum Ace activity.

Although significant ACE activity is found in plasma, the majority of the enzyme is bound to tissue such as vascular endothelium. Esther et al. (1997). *J. Clin. Invest.* 99: 2375-2385, used targeted homologous recombination to create mice expressing a form of ACE that lacks the C-terminal half of the molecule. This modified ACE protein was catalytically active but entirely secreted from cells. Mice that expressed only this modified ACE had significant plasma ACE activity but no tissue-bound enzyme. These animals had low blood pressure, renal vascular thickening, and a urine-concentrating defect. The phenotype was very similar to that of completely ACE-deficient mice previously reported, except that the renal pathology was less severe. These studies strongly supported the concept that the tissue-bound ACE is essential for the control of blood pressure and the structure and function of the kidney.

ACE gene knockout mice lack both isozymes and exhibit low blood pressure, kidney dysfunctions, and male infertility. Ramaraj et al. (1998) *J. Clin. Invest.* 102: 371-378, reported the use of a sperm-specific promoter and interbreeding of transgenic and gene knockout mice for generating a mouse strain that expressed ACE only in sperm. The experimental mice maintained the kidney defects of ACE −/− mice, but unlike the knockout strain, the males were fertile. Thus, Ramaraj et al. (1998) established that the role of ACE in male fertility is completely dependent on its exclusive expression in sperm. Their study demonstrated how transgenic and knockout techniques can be combined for ascribing a specific physiologic function to the expression of a multifunctional protein in a given tissue.

Hagaman et al. (1998) *Proc. Nat. Acad. Sci.* 95: 2552-2557 used transgenic mice lacking somatic and testis ACE to investigate the male fertility defect. They demonstrated that mice lacking both somatic and testis ACE isozymes have defects in sperm transport within the oviducts and in binding to zonae pellucidae. Males generated by gene targeting experiments that lack somatic ACE but retain testis ACE are fertile. Both male and female mice lacking angiotensinogen have normal fertility. The authors found that males heterozygous for the mutation inactivating both ACE enzymes had offspring of wildtype and heterozygous genotypes at the same frequency, suggesting that sperm carrying the mutation are not at a selective disadvantage.

Nephropathy of type I diabetes is associated with the D allele of the insertion/deletion (I/D) polymorphism in intron 16 of the ACE gene. The D allele determines higher enzyme levels. To address causality underlying this association, Huang et al. (2001) *Proc. Nat. Acad. Sci.* 98: 13330-13334 induced diabetes in mice having 1, 2, or 3 copies of the Ace gene, normal blood pressure, and an enzyme level range (65-162% of wildtype) comparable to that seen in humans. Twelve weeks later, the 3-copy diabetic mice had increased blood pressures and overt proteinuria. Proteinuria was correlated to plasma ACE level in the 3-copy diabetic mice. Thus, a modest genetic increase in ACE levels was sufficient to cause nephropathy in diabetic mice.

Crystal

In one aspect of the present invention, there is provided a crystal of ACE protein.

As used herein, the term "crystal" means a structure (such as a three dimensional (3D) solid aggregate) in which the plane faces intersect at definite angles and in which there is a regular structure (such as internal structure) of the constituent chemical species. Thus, the term "crystal" can include any one of: a solid physical crystal form such as an experimentally prepared crystal, a 3D model based on the crystal structure, a representation thereof—such as a schematic representation thereof, a diagrammatic representation thereof, or a data set thereof for a computer.

The crystals of the present invention may be prepared by purifying ACE protein and then crystallising the purified protein. The ACE protein may also be prepared by expressing a nucleotide sequence encoding the ACE protein in a suitable host cell.

In a preferred embodiment, the crystals of the present invention are prepared by purifying underglycosylated ACE protein and then crystallising the purified underdeglycosylated protein. The underdeglycosylated ACE protein may also be prepared by expressing a nucleotide sequence encoding the underdeglycosylated ACE protein in a suitable host cell.

ACE may be purified using various methods known to a person skilled in the art, for example, from conditioned media by affinity chromatography on a Sepharose-28-lisinopril affinity resin (Yu et al. 1997). The protein may be quantified by amino acid analysis and assayed for activity using the substrate hippuryl-L-histidyl-L-leucine, as described previously (Ehlers, M R E, Chen, Y-N, Riordan, J F (1991) *Proc. Natl. Acad. Sci. USA* 88, 1009-1013).

The purified ACE proteins may be stored at −20° C. in 10 mM HEPES and 0.1% PMSF.

Concentration may be performed with the aid of a filtration system and the protein concentrate may be immediately used for crystallisation purposes. The protein concentrate may be crystallised using, for example, the vapour diffusion hanging drop method at a temperature of from about 1° C. to about 30°

C., preferably from about 4° C. to about 20° C., more preferably at about 16° C. The crystallisation temperature may be dependent on the additives present in the protein solution.

Typically, the best crystals for ACE proteins are grown at 16° C. by the vapour diffusion hanging drop method by mixing 2 µl of the protein solution at ~11.5 mg/ml in 10 mM HEPES and 0.1% PMSF with an equal volume of a reservoir solution containing 15% PEG 4000, 50 mM $CH_3COONa.3H_2O$ pH 4.7 and 10 µM $ZnSO_4.7H_2O$. Crystals usually appear within 2 weeks and grow to their maximum size after about a month.

The design of ACE inhibitors has been based upon the assumption that the structure of ACE is related to that of peptidases—such as thermolysin (MA clan, M2 family) and carboxypeptidase A (MC clan, M14 family) as evidenced by comparative molecular field analysis and 3D quantitative structure-activity relationship studies of ACE (Waller & Marshall, 1993). Marshall & Cramer (1988) *Trends Pharamacol. Sci.* 9, 285-289 have also reported the development of predictive models for inhibitors of ACE and thermolysin. Surprisingly, the structure of ACE described herein, shows no structural homology with thermolysin but shows significant structural homology with neurolysin, a member of the M3 family of thimet oligopeptidases. Therefore, the structure presented herein, may be effectively used for the development of novel, highly selective ACE modulators with the potential for greater efficacy, fewer side effects and treatment of new indications. In addition, the unanticipated similarity with neurolysin has shown the structural conservation amongst an merging family of peptidases with a common evolutionary origin.

Without wishing to be bound by theory, it appears that the core structure of the two proteins is highly similar with different loop structures on the outer surface in the case of neurolysin. Indeed like ACE, neurolysin also belongs to the family of metallopeptidases bearing the HEXXH active site motif (Rawlings and Barrett, 1995; Brown et al., 2001). The striking similarity also extends to the active site region in neurolysin consisting of a deep narrow channel that divides the molecule into two halves. It has been speculated that using the flexible secondary structure elements in the active site cavity, the neuropeptidase can effectively cleave a variety of small peptides. Likewise in ACE, the geometry of the active site groove clearly accounts for ACE's inability to hydrolyse large, folded substrates. Furthermore, the enzyme's preference for oligopeptide substrates of about thirteen residues or less suggests that the substrate does not have the same freedom to extend outside of the channel during catalysis. Peptidases—such as thermolysin (MA clan, M4 family) and carboxypeptidase A (MC clan, M14 family)—which have been used in comparative molecular field analysis and 3D quantitative structure-activity relationship studies (Waller & Marshall, 1993) show no structural homology with ACE.

A crystal according to any one of the preceding claims comprising atoms arranged in a spatial relationship represented by at least a portion of the structure co-ordinates of Table A or Table B.

Preferably, the crystal belongs to the space group $P2_12_12_1$ and has a unit cell with dimensions of: a=56.47 Å, b=84.90 Å, c=133.99 Å.

Preferably, the crystal is a crystal of human ACE protein.

Complexes may be obtained by growing the crystals in the presence of an entity—such as a test compound. In these experiments the protein solution is mixed with the entity and an equal volume of the reservoir solution before setting up the crystallisation. Single crystals suitable for diffraction work typically appear after about 4 weeks.

Typically, the protein comprising ACE is purified to homogeneity for crystallisation. Purity of ACE may be measured by typical techniques such as SDS-PAGE, mass spectrometry and hydrophobic HPLC.

The crystal structure of the invention may contain a portion—such as at least 25%, at least 50%, at least 75%, or preferably at least 90%, at least 95%, at least 98%, or at least 99%—of the co-ordinates listed in Table A or Table B. Preferably, the crystal structure of the invention contains all of the co-ordinates listed in Table A or Table B.

Preferably, the crystal is usable in X-ray crystallography techniques.

Preferably, the crystals used can withstand exposure to X-ray beams used to produce diffraction pattern data necessary to solve the X-ray crystallographic structure.

Preferably, prior to data collection, the crystals are flash-cooled at about 100 K in a cryoprotectant. More preferably, cryoprotectant contains 15% PEG 4000, 50 mM $CH_3COONa.3H_2O$ pH 4.7, 10 µM $ZnSO_4.7H_2O$ and 25% glycerol.

The X-ray data may be collected at a Synchrotron Radiation Source. Preferably, the X-ray data are collected at a Synchrotron Radiation Source at 100° K.

Preferably, the crystal has a resolution determined by X-ray crystallography of about 3.5 Å or less, more preferably a resolution of about 2.8 Å or less, more preferably, a resolution of about 2 Å or less, more preferably, a resolution of about 1.5 Å or less, most preferably, 1 Å or less.

Deglycosylation and Underglycosylation

Many proteins in eukaryotic cells are glycoproteins that contain oligosaccharide chains covalently linked to certain amino acids. Glycosylation is known to affect protein folding, localisation and trafficking, protein solubility, antigenicity, biological activity and half-life, as well as cell-cell interactions.

Protein glycosylation can be divided into four main categories mainly depending on the linkage between the amino acid and the sugar. These are N-linked glycosylation, O-linked glycosylation, C-mannosylation and GPI anchor attachments. N-glycosylation is characterised by the addition of a sugar to the amino group of an asparagine. In O-glycosylation, a sugar is attached to the hydroxyl group of a serine or threonine residue.

For N-glycosylation, the sequence motif Asn-Xaa-Ser/Thr (wherein Xaa is any amino acid other than Pro) has been defined as a prerequisite for glycosylation. Although rare, the sequence motif Asn-Xaa-Cys can also be an acceptor site. N-glycans can be subdivided into three distinct groups called 'high mannose type', 'hybrid type', and 'complex type', with the common pentasaccharide core—Manp(alpha-1,6)-(Manp(alpha1,3))-Manp(beta1,4)-GlcpNAc(beta1,4) GlcpNAc(beta1,N)-Asn—occurring in all three groups. The relationship between all three types can be ascribed to the fact that they originate from one precursor oligosaccharide which contains the described common pentasaccharide core Man3-GlcNAc2, and some additional sugar residues and the non-reducing end, and is then processed enzymatically to yield these three types. Since the hydroxyl group of Ser/Thr is thought to be involved in hydrogen bonding during the enzymatic attachment of the oligosaccharide precursor molecule to yield a favourable conformation for the action of the oligosaccharyltransferase, it has been suggested for proline that the steric hindrance might be too large (Kornfeld (1985) Ann. Rev. Biochem. 54: 631-64), preventing glycosylation at Pro containing sites. The negative influence of aspartic acid towards glycosylation can be ascribed to the negative charge on the side chain of this residue. In addition some cases have been reported where Ser/Thr is replaced by cysteine. While Ser replacement by Cys generally leads to decreased glycosylation, it has been shown (Kasturi 1995 J. Biol. Chem. 270: 14756-61) that substitution by Thr at a given potential glycosylation site can lead to increased glycosylation. This is in accordance with the model of hydrogen bonding being an important factor during the attachment of the precursor molecule to the protein. Although there are usually many potential glycosylation sites in a protein it has been estimated that glycosylation occurs only at one third of them. Mostly at those sites where the surrounding amino acids allow the formation of a beta turn.

Various glycoforms of ACE have been described. By way of example, Sadhukhan & Sen (3a) disrupted specific glycosylation sites in rabbit tACE to elucidate the glycosylation requirements for the expression and processing of active testis ACE. There are five potential N-linked glycosylation sites in the rabbit tACE sequence, with an additional six in the somatic form (4a). A null mutant, where all five sites had been disrupted, behaved similarly to wild-type tACE expressed in the presence of the glycosylation-inhibitor, tunicamycin. It was degraded intracellularly and failed to be detected in culture medium, confirming previous findings that tACE requires N-linked glycosylation to be expressed in an active form (5a and 3a). Expression of the remaining mutants showed a preference for N-linked glycosylation at the N-terminus and that the presence of sugars at a single N-terminal site was necessary and sufficient to produce enzymatically-active tACE that was solubilised. The presence of glycosylation is not site-specific, as mutants that have either the first site or second site intact are expressed and active. However, glycosylation at the third site alone is not sufficient to produce active protein in HeLa cells, albeit this mutant was expressed in yeast (3a), indicating that the requirements for glycosylation are cell-specific.

In human testis ACE O-linked sugars are not necessary for expression, implicating the N-linked sugars in this role (6a). N-linked glycosylation of human tACE expressed in CHO cells at each site has been identified by MALDI-TOF mass spectrometry (7a). There are seven potential N-linked sites in human tACE, five of which are complementary to the sites in rabbit tACE (7a). The unique sites lie within the ectodomain (the fourth site) and in the juxtamembrane stalk region, adjacent to the cleavage site (the seventh site). As with the rabbit form, there appears to be a preference for glycosylation at the N-terminus as evidenced by MALDI-TOF mass spectrometry of glyosylation sites (7a). Inhibition of complex oligosaccharide formation using a glucosidase I inhibitor N-butyldeoxynojirimycin (NB-DNJ) led to the production of an active glycoform that was electrophoretically homogeneous (7a).

Suitably, the crystal of the ACE protein may comprise de-glycosylated ACE protein or a fragment thereof. For example, the deglycosylated ACE may comprise the sequence presented as SEQ ID No. 2.

To deglycosylate the ACE protein, various methods known to a person skilled in the art may be used. Both chemical and enzymatic methods may be used for removing oligosaccharides from glycoproteins. Hydrazinolysis of glycoproteins (Kuraya, N & Hase (1992) J Biochem (Tokyo) 112:122-126), is capable of removing both N- and O-linked sugars, although this results in the complete destruction of the protein component and is therefore not suitable if recovery of the protein is desirable. Milder chemical methods such as trifluoromethanesulphonic acid (TFMS) may be used, however this may result in incomplete sugar removal and partial protein destruction. Other methods—such as site directed mutagenesis of glycosylated amino acids may also be used.

Suitably, enzymatic methods may be used which provide for complete sugar removal with no protein degradation.

Use of the enzyme PNGase F is an effective method of removing virtually all N-linked oligosaccharides from glycoproteins (Tarentino & Plummer (1994). Methods in Enzymol 230: 44-57). The oligosaccharide is left intact and therefore suitable for further analysis (the asparagine residue from which the sugar was removed is deaminated to aspartic acid, the only modification to the protein).

Other commonly used endoglycosidases include Endoglycosidase H (Kobata (1979) Anal Biochem 100:1-14) and Endoglycosidase F (Trimble & Tarentino (1991) J. Biochem. 266:1646-1651). In a preferred method, the ACE protein is digested with Endoglycosidase H (30 mU) in a suitable buffer—such as 100 mM sodium phosphate, 0.1 mM $ZnCl_2$ and 1% BSA, pH 6.0 for 16 h at 37° C. The endo H-treated protein is passed through a lectin affinity column consisting of equal parts of concanavalin A, wheat germ, and lentil lectin, after equilibration with 20 mM Tris-HCl, 0.5 M NaCl at pH 7.4. The deglycosylated ACE is collected in the flowthrough. Free oligosaccharides and any other impurities are removed from the flowthrough fraction by a final lisinopril-Sepharose affinity chromatography step. The homogeneity of the ACE protein after deglycosylation is confirmed by SDS-PAGE on a 4-20% acrylamide gel and MALDI-TOF mass spectrometry.

Commercially available kits may also be used—such as the E-DEGLY kit (Sigma-Aldrich, UK) and the GlycoFree Deglycosylation Kit (Glyco, Novato, USA) which removes both N- and O-linked glycans from glycoproteins.

Preferably, ACE is crystallised using underglycosylated ACE protein.

As used herein, the term "underglycosylated" means that one or more of the oligosaccharide chains covalently linked to amino acids in the glycosylated protein are no longer present.

By way of example only, testis ACE is glycosylated at amino acids 72, 90 and 109 and glycosylated partially at amino acids 155, 337 and 586. Accordingly, the "underglycosylated" testis ACE may not be glycosylated a one or more of amino acids 72, 90, 109, 155, 337 and 586.

The underglycosylated ACE protein may be prepared using various methods—such as site directed mutagenesis and glycosylation inhibition methods. For example, glycosylation inhibition methods using NB-DNJ may prevent the formation of complex oligosaccharides. NB-DNJ inhibits glucosidase I and prevents maturation of the sugars.

Preferably, the underglycosylated ACE protein is prepared by culturing host cells in the presence of N-butyldeoxynojirimycin (NB-DNJ).

Preferably, underglycosylated ACE protein is prepared using site-directed mutagenesis. More preferably, the underglycosylated ACE protein comprises a mutation at amino acid 337 of SEQ ID No. 2 or amino acids 90, 109, 155, 337 and 586 of SEQ ID No. 2.

Underglycosylated mutants may yield crystals in the orthorhombic, $P2_12_12_1$ space group that diffract to 2.8 Å or less. Moreover, crystals from a truncated mutant of tACE that only have simple high mannose oligosaccharides are also grown in the orthorhombic space group $P2_12_12_1$ which may diffract to better than 2.0 Å resolution.

Preparing a Crystal of ACE Protein

In another aspect, the present invention relates to a method of preparing a crystal of ACE protein, comprising the steps of (a) culturing host cells comprising an underglycosylated ACE protein; (b) purifying the underglycosylated ACE protein; and (c) crystallising the underglycosylated ACE protein.

Preferably, the ACE protein is underglycosylated by removing one or more glycosylation sites and/or one or more partially glycosylated sites. More preferably, the underglycosylated ACE protein comprises a mutation at amino acid 337 of SEQ ID No 2 or amino acids 90, 109, 155, 337 and 586 of SEQ ID No 2.

The ACE protein may be underglycosylated and purified using the methods described herein.

Preferably, the ACE protein is crystallised using about 10 mM HEPES and about 0.1% PMSF with an equal volume of a reservoir solution containing about 15% PEG 4000, about 50 mM $CH_3COONa.3H_2O$ pH 4.7 and about 10 µM $ZnSO_4.7H_2O$.

Preferably, the ACE protein is crystallised in the presence of an entity, for example, a modulator of ACE.

Modulators of ACE

The role of ACE in the pathogenesis of hypertension has resulted in a search for modulators (e.g. inhibitors) of the enzyme that could act as antihypertensive drugs (e.g. U.S. Pat. No. 3,891,616, U.S. Pat. No. 3,947,575, U.S. Pat. No. 4,052,511 and U.S. Pat. No. 4,053,651). Therapeutic vasodepressors—such as Captopril and D-2-methyl-3-mercaptopropanoyl-L-proline—have been synthesised as ACE inhibitors. Numerous synthetic peptide derivatives have also been shown to be ACE inhibitors as disclosed in U.S. Pat. No. 3,832,337.

Natural substances that inhibit ACE include snake venom and those derived from foodstuffs—such as ACE inhibiting peptides produced by enzymatic hydrolysis of proteins, such as casein or fish meat protein (by Hiroyuki Ukeda, Nippon Nogei Kagaku Kaishi (Journal of Japan Society for Bioscience, Biotechnology, and Agrochemistry, 66(1), 25-29 (1992)).

ACE inhibiting synthetic substances include captopril (D-2-methyl-3-mercaptopropanoyl-L-proline) which has already been put to practical application as an orally administered vasodepressor.

However, many ACE inhibiting substances exhibit side effects in many cases and special attention needs be exercised in safety aspects.

The present invention permits the use of molecular design techniques to design, select and synthesise chemical entities and compounds, including ACE modulating compounds, capable of binding to ACE, in whole or in part.

Thus, in a further aspect, the present invention relates to a method of screening for a modulator of ACE wherein the method comprises the use of a crystal of ACE.

Preferably, the method comprises the steps of: (a) providing at least a portion of the structure co-ordinates of Table A or Table B; (b) employing at least a portion of the structure co-ordinates of Table A or Table B to design or select or synthesise a putative modulator of ACE; (c) contacting the putative modulator of ACE with ACE or a mutant, variant, homologue, derivative or fragment thereof in the presence of a substrate; and (d) screening the putative modulator of ACE in an assay for the potential to modulate ACE.

By way of example, the structure co-ordinates may be used to design compounds that bind to the enzyme and may alter the physical properties of the compounds (e.g. solubility) or the enzyme itself. This invention may be used to design compounds that act as modulators—such as competitive inhibitors—of ACE by binding to all or a portion of the active site of ACE. Compounds may also be designed that act as non-competitive inhibitors of ACE. These as non-competitive inhibitors may bind to all or a portion of ACE already bound to its substrate and may be more potent and specific than known ACE inhibitors that compete only for the ACE active site. Similarly, non-competitive inhibitors that bind to and inhibit ACE whether or not it is bound to another chemical entity may be designed using the structure co-ordinates of ACE as described herein.

By way of example, it may be found that the COOH-binding active site residue differs between the N and C domain active sites and/or that it may be amenable to the incorporation of a functionality that can covalently modify this residue to produce an irreversible inhibitor design. It has long been assumed that the COOH-binding residue is a positively charged arginine (M. A. Ondetti & D. W. Cushman (1981) in *Biochemical Regulation of Blood Pressure* (R. L. Soffer, ed.), Wiley, New York, 165-204), but the ACE-lisinopril X-ray crystal structure described herein, shows that it is a lysine, in the case of the C-domain active site. This may present an opportunity for covalent modification, by, for example, the introduction of an alkyl halide or halo-ketone functionality into the inhibitors that can alkylate the lysine amine, or α-ketone or aldehyde that can form a Schiff's base with the lysine amine, or the use of activated ester or thioester groups, or other modified carboxyl groups susceptible to nucleophilic attack.

In a preferred embodiment, at least a portion of the structure co-ordinates of Table A or Table B and/or the putative modulator of ACE and/or the substrate are provided on a machine-readable data storage medium comprising a data storage material encoded with machine readable data.

An ACE crystal may be probed with a variety of different chemical entities or test compounds to determine optimal sites for interaction between modulators of ACE and the enzyme. For example, X-ray diffraction data collected from crystals grown in the presence of chemical entities or test compounds may allow the elucidation of how the chemical entities or test compounds interact with ACE. Molecules that bind to those sites can then be designed and synthesised and tested for their ACE modulating activity.

The present invention may also allow the development of compounds that can isomerise to reaction intermediates in the chemical reaction of a substrate or other compound that binds to ACE. Thus, the time-dependent analysis of structural changes in ACE during its interaction with other molecules may be performed. The reaction intermediates of ACE may also be deduced from the reaction product in co-complex with ACE. Such information is especially useful to design improved analogues of known ACE modulators or to design new ACE modulators based on the reaction intermediates of the ACE enzyme and ACE-modulator complex. This may provide a new route for designing ACE modulators with high specificity and stability. Preferably, this provides a new route for designing ACE modulators with high specificity, high stability and low toxicity.

Small molecule databases or test compounds may be screened for chemical entities or compounds that can bind in whole, or in part, to ACE. Thus, in a preferred embodiment, the putative ACE modulator is from a library of compounds or a database. In this screening, the quality of fit of such entities or compounds to the binding site may be judged by various methods—such as shape complementarity or estimated interaction energy (Meng, E. C. et al., *J. Comp. Chem.*, 13, pp. 505-524 (1992)).

Because ACE protein or a mutant, variant, homologue, derivative or fragment thereof may crystallise in more than one crystal form, the structure co-ordinates of ACE, or portions thereof, may be particularly useful to solve the structure of other crystal forms of ACE. They may also be used to solve the structure of ACE mutants, ACE variants, ACE homologues, ACE derivatives, ACE fragments and ACE complexes.

Preferably, the structure co-ordinates of ACE are used to solve the structure of the crystalline form of any other protein with significant amino acid sequence homology to any functional domain of ACE. By way of example, molecular replacement may be used. In this method, the unknown crystal structure, whether it is another crystal form of ACE, an ACE mutant, an ACE variant, an ACE homologue (e.g. another protein with significant amino acid sequence homology to any functional domain of ACE), an ACE derivative, an ACE fragments or an ACE co-complex may be determined using the ACE structure co-ordinates of the present invention. This method will provide a more accurate structural form for the unknown crystal more quickly and efficiently than attempting to determine such information ab initio.

In a preferred embodiment of the present invention, the ACE crystal further comprises an entity bound to the ACE protein or a portion thereof. For example, ACE may be crystallised in complex with an entity that is an inhibitor of ACE e.g. lisinopril.

Preferably, the entity is bound to the ACE protein or a portion thereof by contacting one or more residues of the ACE protein selected from: His384, Ala385, Lys542, Tyr551, Tyr554, Glu415 and His544.

The crystal structures of a series of such complexes may then be solved by molecular replacement or in combination with MAD (Multiwavelength Anomalous Dispersion) and/or MIRAS (Multiple Isomorphous Replacement with Anomalous Scattering) procedures—and compared with that of wild-type ACE. Potential sites for modification within the binding sites of the enzyme may thus be identified. This information provides an additional tool for determining the most efficient binding interactions, for example, increased hydrophobic interactions, between ACE and a chemical entity or compound.

The structures and complexes of ACE may be refined using computer software—such as X-PLOR (Meth. Enzymol., vol. 114 & 115, H. W. Wyckoff et al., eds., Academic Press (1985)), MLPHARE (Collaborative computational project Number 4. The CCP4 Suite: Programs for Protein Crystallography (1994) Acta Crystallogr. D 50, 760-763) and SHARP [De La Fortelle, E. & Bricogne, G. Maximum-likelihood heavy-atom parameters refinement in the MIR and MAD methods (1997) Methods Enzymol. 276, 472-494). Preferably, the complexes are refined using the program CNS (Brünger et al. (1998) *Acta Crystallogr. D* 54, 905-921). During the final stages of refinement water molecules, ions and inhibitor molecules may be inserted in the structure. This information may thus be used to optimise known classes of ACE modulators, e.g. ACE inhibitors, and more importantly, to design and synthesise novel classes of ACE modulators.

The overall figure of merit may be improved by iterative solvent flattening, phase combination and phase extension with the program SOLOMON [Abrahams, J. P. & Leslie, A. G. W. Methods used in structure determination of bovine mitochondrial F1 ATPase. (1996) Acta Crystallogr. D 52, 110-119].

The structure co-ordinates of ACE mutants provided in this invention also facilitate the identification of related proteins or enzymes analogous to ACE in function, structure or both, thereby further leading to novel therapeutic modes for treating or preventing ACE related diseases.

The design of compounds that bind to or modulate ACE according to the present invention generally involves consideration of two factors. First, the compound must be capable of physically and structurally associating with ACE. Non-covalent molecular interactions important in the association of ACE with its substrate may include hydrogen bonding, van der Waals and hydrophobic interactions. Second, the compound must be able to assume a conformation that allows it to associate with ACE. Although certain portions of the compound may not directly participate in the association with ACE, those portions may still influence the overall conformation of the molecule. This may have a significant impact on potency. Such conformational requirements include the overall three-dimensional structure and orientation of the chemical entity or compound in relation to all or a portion of a binding site of ACE, or the spacing between functional groups of a compound comprising several chemical entities that directly interact with ACE.

The potential modulating or binding effect of a chemical compound on ACE may be analysed prior to its actual synthesis and testing by the use of computer modelling techniques. If the theoretical structure of the given compound suggests insufficient interaction and association with ACE, then synthesis and testing of the compound may be obviated. However, if computer modelling indicates a strong interaction, the molecule may be synthesised and tested for its ability to bind to ACE and modulate (e.g. inhibit) using the fluorescent substrate assay of Thornberry et al. (2000) *Methods Enzymol.* 322, pp 100-110. In this manner, synthesis of inactive compounds may be avoided.

A modulating or other binding compound of ACE may be computationally evaluated and designed by means of a series of steps in which chemical entities or test compounds are screened and selected for their ability to associate ACE.

A person skilled in the art may use one of several methods to screen chemical entities or test compounds for their ability to associate with ACE and more particularly with the individual binding sites of ACE. This process may begin by visual inspection of, for example, the active site on the computer screen based on the ACE co-ordinates of the present invention. Selected chemical entities or test compounds may then be positioned in a variety of orientations, or docked, with ACE. Docking may be accomplished using software such as Quanta and Sybyl, followed by energy minimisation and molecular dynamics with standard molecular mechanics force fields—such as CHARMM and AMBER.

Specialised computer programs may also assist in the process of selecting chemical entities or test compounds. These include but are not limited to MCSS (Miranker and Karplus (1991) Proteins: Structure, Function and Genetics, 11, pp. 29-34); GRID (Goodford (1985) J. Med. Chem., 28, pp. 849-857) and AUTODOCK (Goodsell and Olsen (1990), Proteins: Structure. Function, and Genetics, 8, pp. 195-202.

Once suitable chemical entities or test compounds have been selected, they may be assembled into a single compound—such as an ACE modulator. Assembly may proceed by visual inspection of the relationship of the chemical entities or test compounds in relation to the structure co-ordinates of ACE. This may be followed by manual model building using software—such as Quanta, Sybyl or O [Jones, T. A., Zou, J. Y., Cowan, S. W. & Kjeldgaard, M. Improved methods for building protein models in electron density maps and the location of errors in these models (1991) Acta Crystallogr. A 47, 110-119].

Refinement of the model may be carried out using the program CNS [Brünger, A. T. et al. Crystallography & NMR System: A new software suite for macromolecular structure determination. (1998) Acta Crystallogr. D 54, 905-921].

Various programs may be used by a skilled person to connect the individual chemical entities or test compounds— such as 3D Database systems (Martin (1992) *J. Med. Chem.,* 35, pp. 2145-2154) and CAVEAT (Bartlett et al. (1989) *Royal Chem. Soc.* 78, pp. 182-196).

Rather than build an ACE inhibitor one chemical entity at a time, modulating or other ACE binding compounds may be designed as a whole or de novo using either an empty binding site or optionally including some portion(s) of a known inhibitor(s). Such compounds may be designed using programs that may include but are not limited to LEGEND (Nishibata and Itai (1991) Tetrahedron, 47, p. 8985) and LUDI (Bohm (1992) *J. Comp. Aid. Molec. Design,* 6, pp. 61-78).

Other molecular modelling techniques may also be employed in accordance with this invention—such as those described by Cohen et al., J. Med. Chem., 33, pp. 883-894 (1990); Navia and Murcko (1992) Current Opinions in Structural Biology, 2, pp. 202-210 (1992).

Once a compound has been designed or selected by the above methods, the efficiency with which that compound may bind to ACE may be computationally evaluated. Specific computer software may be used to evaluate the efficiency of binding (e.g. to evaluate compound deformation energy and electrostatic interaction)—such as QUANTA/CHARMM (Accelrys Inc., USA) and Insight II/Discover (Biosym Technologies Inc., San Diego, Calif., USA). These programs may be implemented, for instance, using a suitable workstation. Other hardware systems and software packages will be known to those persons skilled in the art.

Once an ACE-modulating compound has been selected or designed, as described above, substitutions may be made (e.g. in atoms or side groups) to improve or modify the binding properties. The substitutions may be conservative i.e. the replacement group may have approximately the same size, shape, hydrophobicity and charge as the original group. Such substituted chemical compounds may then be analysed for efficiency of binding to ACE by the same computer methods described above.

Test compounds and modulators of ACE etc. which are identified using the crystal and the methods of the present invention may be screened in assays. Screening can be, for example in vitro, in cell culture, and/or in vivo. Biological screening assays preferably centre on activity-based response models, binding assays (which measure how well a compound binds), and bacterial, yeast and animal cell lines (which measure the biological effect of a compound in a cell). The assays can be automated for high capacity-high throughput screening (HTS) in which large numbers of compounds can be tested to identify compounds with the desired activity.

Current screening technologies are described in Handbook of Drug Screening, edited by Ramakrishna Seethala, Prabhavathi B. Fernandes. New York, N.Y., Marcel Dekker, (2001).

Ace Related Disorders

ACE related disorders include, but are not limited to, treatment of high blood pressure; treatment of heart failure; prolonging survival of patients who have had a heart attack; preventing death by heart attack and stroke in patients with vascular disease and in diabetics with other vascular risk factors; prolonging survival of patients with weak heart muscle; helping leaking heart valves; preserving kidney function in diabetics; and the treatment of new indications (e.g. polycythemia). Special groups of patients may also be treated with ACE inhibitors, including: patients with chronic pulmonary disease; patients with schleroderma; patients with atheroschlerosis; and patients with hyperuricemia.

Ace Constructs

The ACE proteins produced by a host recombinant cell may be secreted or may be contained intracellularly depending on the nucleotide sequence and/or the vector used.

As will be understood by those of skill in the art, expression vectors containing an ACE encoding nucleotide sequence or a mutant, variant, homologue, derivative or fragment thereof, may be designed with signal sequences which direct secretion of the ACE coding sequences through a particular prokaryotic or eukaryotic cell membrane.

The ACE encoding sequence may be fused (e.g. ligated) to nucleotide sequences encoding a polypeptide domain which will facilitate purification of soluble proteins (Kroll D J et al (1993) DNA Cell Biol 12:441-53). Preferably, the polypeptide domain which facilitates purification of soluble proteins is fused in frame with the ACE encoding sequence. Such purification facilitating domains include, but are not limited to, metal chelating peptides—such as histidine-tryptophan modules that allow purification on immobilised metals (Porath J (1992) Protein Expr Purif 3, 263-281), protein A domains that allow purification on immobilised immunoglobulin, and the domain utilised in the FLAGS extension/affinity purification system (Immunex Corp, Seattle, Wash.). The inclusion of a cleavable linker sequence such as Factor XA or enterokinase (Invitrogen, San Diego, Calif.) between the purification domain and ACE is useful to facilitate purification.

Preferably, the ACE construct is pEE-ACEΔNJ which encodes human tACE that lacks the heavily O-glycosylated, 36-residue N-terminal sequence and is truncated after Ser625, thereby lacking most of the juxtamembrane stalk as well as the transmembrane and cytoplasmic domains as described in (7a).

In another preferred embodiment, the ACE construct comprises an underglycosylated ACE, constructed by the removal of one or more glycosylation sites—such as one or more N-linked glycosylation sites. Glycosylation may be abolished using various methods known to a person skilled in the art as previously described. Preferably, a truncated form of tACE (tACEΔ36 lacking the first N-terminal 36 residues as well as the cytoplasmic domain is used for the construction of mutants (7a) and mutagenic oligonucleotides then used for altering the sites that are glycosylated. Preferably, the nucleotide sequence of each fragment is confirmed by DNA sequencing to ensure that only the desired mutation is created.

Preferably, the ACE construct comprising underglycosylated ACE is pLEN-tACEΔ36g(1, 2, 3, 4) or is pLEN-tACEΔ36g(1,3).

Host Cells

As used herein, the term "host cell" refers to any cell that comprises nucleotide sequences that are of use in the present invention, for example, nucleotide sequences encoding ACE.

Host cells may be transformed or transfected with a nucleotide sequence contained in a vector e.g. a cloning vector. Preferably, said nucleotide sequence is carried in a vector for the replication and/or expression of the nucleotide sequence. The cells will be chosen to be compatible with the said vector and may for example be prokaryotic (for example bacterial), fungal, yeast or plant cells.

The gram-negative bacterium *E. coli* is widely used as a host for cloning nucleotide sequences. This organism is also widely used for heterologous nucleotide sequence expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus *Bacillus* are very suitable as heterologous hosts because of their capability to secrete proteins into the culture medium. Other bacteria suitable as hosts are those from the genera *Streptomyces* and *Pseudomonas*.

Depending on the nature of the polynucleotide and/or the desirability for further processing of the expressed protein, eukaryotic hosts including yeasts or other fungi may be preferred. In general, yeast cells are preferred over fungal cells because yeast cells are easier to manipulate. However, some proteins are either poorly secreted from the yeast cell, or in some cases are not processed properly (e.g. hyperglycosylation in yeast). In these instances, a different fungal host organism should be selected.

Examples of expression hosts are fungi—such as *Aspergillus* species (such as those described in EP-A-0184438 and EP-A-0284603) and *Trichoderma* species; bacteria—such as *Bacillus* species (such as those described in EP-A-0134048 and EP-A-0253455), *Streptomyces* species and *Pseudomonas* species; yeasts—such as *Kluyveromyces* species (such as those described in EP-A-0096430 and EP-A-0301670) and *Saccharomyces* species; and mammalian cells—such as CHO-K1 cells.

The use of host cells may provide for post-translational modifications (e.g. glycosylation) as may be needed to confer optimal biological activity on recombinant expression products of the present invention.

Aspects of the present invention also relate to host cells comprising the ACE constructs of the present invention. The ACE constructs may comprise a nucleotide sequence for replication and expression of the sequence. The cells will be chosen to be compatible with the vector and may for example be prokaryotic (for example bacterial), fungal, yeast or plant cells.

In a preferred embodiment, the host cells are mammalian cells—such as CHO-K1 cells. CHO-K1 cells expressing ACE may be grown and maintained in accordance with Yu et al. (1997).

Nucleotide Sequences

As used herein, the term "nucleotide sequence" refers to nucleotide sequences, oligonucleotide sequences, polynucleotide sequences and variants, homologues, fragments and derivatives thereof (such as portions thereof) which comprise the nucleotide sequences encoding ACE, for example, testis ACE or somatic ACE.

The nucleotide sequence may be DNA or RNA of genomic or synthetic or recombinant origin, which may be double-stranded or single-stranded whether representing the sense or antisense strand or combinations thereof.

Preferably, the term nucleotide sequence is prepared by use of recombinant DNA techniques (e.g. recombinant DNA). The nucleotide sequences may include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the nucleotide sequences described herein may be modified by any method available in the art.

It will be understood by a skilled person that numerous different nucleotide sequences can encode the same protein as a result of the degeneracy of the genetic code. In addition, it is to be understood that skilled persons may, using routine techniques, make nucleotide substitutions that do not substantially affect the activity encoded by the nucleotide sequence of the present invention to reflect the codon usage of any particular host organism in which the target is to be expressed. Thus, the terms "variant", "homologue" or "derivative" in relation to nucleotide sequences include any substitution of, variation of, modification of, replacement of, deletion of or addition of one (or more) nucleic acids from or to the sequence providing the resultant nucleotide sequence encodes a functional protein according to the present invention (or even a modulator of ACE according to the present invention if said modulator comprises a nucleotide sequence or an amino acid sequence).

Amino Acid Sequences

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "protein".

Aspects of the present invention concern the use of amino acid sequences, which may be available in databases. These amino acid sequences may comprise ACE proteins.

The amino acid sequence may be isolated from a suitable source, or it may be made synthetically or it may be prepared by use of recombinant DNA techniques.

Preferably, ACE comprises SEQ ID No. 1 or SEQ ID No. 2, or a mutant, variant, homologue, derivative or fragment thereof. More preferably, ACE comprises SEQ ID No. 2, or a mutant, variant, homologue, derivative or fragment thereof.

Purity

Preferably the protein solution used for crystallisation is at least 97.5% pure. More preferably, the protein solution used for crystallisation is at least 99.0% pure. Most preferably, the protein solution used for crystallisation is at least 99.5% pure.

Model

As used herein, the term "model" refers to a structural model such as a three dimensional (3D) structural model (or representation thereof) comprising ACE.

Test compounds can be modelled that bind spatially and preferentially to ACE—such as to bind spatially and preferentially to ACE—for example, the active site of ACE.

Preferably, the crystal model comprising ACE is built from all or a portion of the structure co-ordinates presented in Table A or Table B.

Mutant

As used herein, the term "mutant" refers to ACE comprising any one or more changes in the wild-type ACE sequence shown as SEQ ID No. 1 or one or more changes in the native ACE sequence shown as SEQ ID No. 2.

The term "mutant" is not limited to any of the mutations described herein which are reflected in amino acid substitutions of the amino acid residues in ACE, but may also include, but are not limited to, other deletions or insertions of nucleotides which may result in changes in the amino acid residues in the amino acid sequence of ACE.

In a preferred embodiment, mutations are located at amino acids 337 of SEQ ID No. 2 or amino acids 90, 109, 155, 337 and 586 of SEQ ID No. 2.

The present invention also enables the solving of the crystal structure of ACE mutants. More particularly, by virtue of the present invention, the location of the active site of ACE based on its crystal structure permits the identification of desirable sites for mutation. For example, one or more mutations may be directed to a particular site—such as the active site—or combination of sites of ACE. Similarly, only a location on, at or near the enzyme surface may be replaced, resulting in an altered surface charge of one or more charge units, as compared to the wild-type enzyme. Alternatively, an amino acid residue in ACE may be chosen for replacement based on its hydrophilic or hydrophobic characteristics.

Such mutants may be characterised by any one of several different properties as compared with wild-type ACE. For example, such mutants may have altered surface charge of one or more charge units, or have an increased stability to subunit dissociation, or an altered substrate specificity in comparison with, or a higher specific activity than, wild-type ACE.

The mutants may be prepared in a number of ways that are known by a person skilled in the art. For example, mutations may be introduced by means of oligonucleotide-directed mutagenesis or other conventional methods. Alternatively, mutants of ACE may be generated by site specific replacement of a particular amino acid with an unnaturally occurring amino acid. This may be achieved by growing a host organism capable of expressing either the wild-type or mutant polypeptide on a growth medium depleted of one or more natural amino acids but enriched in one or more corresponding unnaturally occurring amino acids.

The expression, activity (e.g. kinetic constants) and/or the crystallisation properties of the mutants may be determined using the methods described herein.

Variants/Homologues/Derivatives/Fragments

The ACE described herein is intended to include any polypeptide, which has the activity of the naturally occurring ACE and includes all vertebrate and mammalian forms. Such terms also include polypeptides that differ from naturally occurring forms of ACE by having amino acid deletions, substitutions, and additions, but which retain the activity of ACE.

The term "variant" is used to mean a naturally occurring polypeptide or nucleotide sequences which differs from a wild-type or a native sequence.

The term "fragment" indicates that a polypeptide or nucleotide sequence comprises a fraction of a wild-type or a native sequence. It may comprise one or more large contiguous sections of sequence or a plurality of small sections. The sequence may also comprise other elements of sequence, for example, it may be a fusion protein with another protein. Preferably the sequence comprises at least 50%, more preferably at least 65%, more preferably at least 80%, most preferably at least 90% of the wild-type sequence.

The present invention also encompasses the use of variants, homologues and derivatives of nucleotide and amino acid sequences. Here, the term "homologue" means an entity having a certain homology with amino acid sequences or nucleotide sequences. Here, the term "homology" can be equated with "identity".

In the present context, an homologous sequence is taken to include an amino acid sequence which may be at least 75, 85 or 90% identical, preferably at least 95 or 98% identical to the subject sequence—such as ACE or a functional domain thereof.

Although homology can also be considered in terms of similarity (i.e. amino acid residues having similar chemical properties/functions), it is preferred to express homology in terms of sequence identity.

A significantly homologous amino acid sequence is taken to include an amino acid sequence which may be at least 75, 85 or 90% identical, preferably at least 95 or 98% identical to the subject sequence—such as ACE or a functional domain thereof.

An homologous sequence is taken to include a nucleotide sequence which may be at least 75, 85 or 90% identical, preferably at least 95 or 98% identical to the subject sequence—such as ACE or a functional domain thereof.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, for some applications, it is preferred to use the GCG Bestfit program. A new tool, called BLAST 2 Sequences is also available for comparing protein and nucleotide sequence (see *FEMS Microbiol Lett* 1999 174(2): 247-50; *FEMS Microbiol Lett* 1999 177(1): 187-8)

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

By way of example, homologous sequences of ACE include, but are not limited to human $ACE_S$ somatic ACE (accession number: J04144), human $ACE_T$ testis ACE (accession number: M26657), human ACEH/ACE2 (accession numbers: AAF78220; BAB40370; AAF99721), chimp $ACE_T$ (accession number: AF193487_2), rabbit $ACE_T$ mature protein (accession number: P22968), rabbit $ACE_T$ full pre-protein (accession number: P22968), mouse $ACE_T$ testis ACE (accession number: P22967), bovine Cdom $ACE_S$ C-domain, rat Cdom $ACE_S$ C-domain (derived from accession number P47820; starting D616), human Ndom $ACE_S$ N-domain (derived from accession number P12821 (J04144)), chimp Ndom $ACE_S$ N-domain (derived from accession number AF193487-1), rabbit Ndom $ACE_S$ N-domain (derived from P12822), bovine Ndom (Bovine {*Bos taurus*} $ACE_S$ N-domain), mouse Ndom $ACE_S$ N-domain (derived from accession number P09470), rat Ndom $ACE_S$ N-domain (derived from accession number P47820), chick ACE (partial ACE accession number Q10751), dros AnCE (derived from accession number Q10714), dros ACEr (derived from accession number X96913), buffalo fly ACE (derived from accession number Q10715), and silkworm ACE (derived from accession number BAA97657), tick ACE (derived from accession number U62809).

The sequences may also have deletions, insertions or substitutions of amino acid residues, which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Homologous substitution (substitution and replacement are both used herein to mean the interchange of an existing amino acid residue, with an alternative residue) may occur i.e. like-for-like substitution such as basic for basic, acidic for acidic, polar for is polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

The term "derivative" or "derivatised" as used herein includes chemical modification of an entity—such as test compound or an ACE modulator. Illustrative of such chemical modifications would be replacement of hydrogen by a halo group, an alkyl group, an acyl group or an amino group.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Test Compounds

As used herein, the term "test compound" includes, but is not limited to, a compound which may be obtainable from or produced by any suitable source, whether natural or not.

The test compound may be designed or obtained from a library of compounds, which may comprise peptides, as well as other compounds, such as small organic molecules and particularly new lead compounds. By way of example, the test compound may be a natural substance, a biological macromolecule, or an extract made from biological materials—such as bacteria, fungi, or animal (particularly mammalian) cells or tissues, an organic or an inorganic molecule, a synthetic test compound, a semi-synthetic test compound, a structural or functional mimetic, a peptide, a peptidomimetics, a derivatised test compound, a peptide cleaved from a whole protein, or a peptide synthesised synthetically (such as, by way of example, either using a peptide synthesiser or by recombinant techniques or combinations thereof, a recombinant test compound, a natural or a non-natural test compound, a fusion protein or equivalent thereof and mutants, derivatives or combinations thereof. The test compound may even be a compound that is a modulator of ACE—such as a known inhibitor of ACE—that has been modified in some way e.g. by recombinant DNA techniques or chemical synthesis techniques.

Typically, the test compound will be prepared by recombinant DNA techniques and/or chemical synthesis techniques.

Once a test compound capable of interacting ACE has been identified, further steps may be carried out to select and/or to modify the test compounds and/or to modify existing compounds, such that they are able to modulate ACE.

Modulating Ace

As herein, the term "modulating" refers to preventing, suppressing, inhibiting, alleviating, restorating, elevating, increasing or otherwise affecting ACE.

The term "ACE modulator" may refer to a single entity or a combination of entities.

The ACE modulator may be an antagonist or an agonist of ACE.

As used herein, the term "agonist" means any entity, which is capable of interacting (e.g. binding) with ACE and which is capable of increasing a proportion of the ACE that is in an active form, resulting in an increased biological response.

As used herein, the term "antagonist" means any entity, which is capable of interacting (e.g. binding) with ACE and which is capable of decreasing (e.g. inhibiting) a proportion of the ACE that is in an active form, resulting in a decreased biological response.

Preferably, the ACE modulators of the present invention are antagonists of ACE.

The modulator of ACE may be an organic compound or other chemical. The modulator of ACE may be a compound, which is obtainable from or produced by any suitable source, whether natural or artificial. The modulator of ACE may be an amino acid molecule, a polypeptide, or a chemical derivative thereof, or a combination thereof. The modulator of ACE may even be a polynucleotide molecule—which may be a sense or an anti-sense molecule. The modulator of ACE may even be an antibody.

The modulator of ACE may be designed or obtained from a library of compounds, which may comprise peptides, as well as other compounds, such as small organic molecules.

By way of example, the modulator of ACE may be a natural substance, a biological macromolecule, or an extract made from biological materials such as bacteria, fungi, or animal (particularly mammalian) cells or tissues, an organic or an inorganic molecule, a synthetic agent, a semi-synthetic agent, a structural or functional mimetic, a peptide, a peptidomimetic, a derivatised agent, a peptide cleaved from a whole protein, or a peptide synthesised synthetically (such as, by way of example, either using a peptide synthesiser or by recombinant techniques or combinations thereof, a recombinant agent, an antibody, a natural or a non-natural agent, a fusion protein or equivalent thereof and mutants, derivatives or combinations thereof).

Typically, the modulator of ACE will be an organic compound. Typically, the organic compounds will comprise two or more hydrocarbyl groups. Here, the term "hydrocarbyl group" means a group comprising at least C and H and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. For some applications, preferably the modulator of ACE comprises at least one cyclic group. The cyclic group may be a polycyclic group, such as a non-fused polycyclic group. For some applications, the modulator of ACE comprises at least the one of said cyclic groups linked to another hydrocarbyl group.

The modulator of ACE may contain halo groups, for example, fluoro, chloro, bromo or iodo groups.

The modulator of ACE may contain one or more of alkyl, alkoxy, alkenyl, alkylene and alkenylene groups—which may be unbranched- or branched-chain.

The modulator of ACE may be in the form of a pharmaceutically acceptable salt—such as an acid addition salt or a base salt—or a solvate thereof, including a hydrate thereof. For a review on suitable salts see Berge et al, (1977) *J. Pharm. Sci.* 66, 1-19.

The modulator of ACE may be structurally novel modulators of ACE.

The modulators of ACE may be analogues of known modulators of ACE—such as known inhibitors of ACE (for example, snake venom, peptides produced by enzymatic hydrolysis of casein or fish meat protein, or Benazepril, Captopril, Cilazapril, Enalapril, Fosinopril, Lisinopril, Moexipril, Perindopril, Quinapril, Ramipril, Trandolapril and Enalaprilat.

Preferably, the ACE modulators have improved properties over those previously available, for example, fewer side effects—such as cough (e.g. dry, persistent); fever and chills; hoarseness; swelling of face, mouth, hands, or feet; trouble in swallowing or breathing; itching of skin; yellow eyes or skin; dizziness, light-headedness, or fainting; skin rash, with or without itching; fever, or joint pain; abdominal pain, abdominal distention; nausea, or vomiting; chest pain, confusion; irregular heartbeat; nervousness; numbness or tingling in hands, feet, or lips; weakness or heaviness of legs; headache, diarrhea; loss of taste; nausea; unusual tiredness.

The modulator of ACE may be a mimetic.

The modulator of ACE may also be chemically modified.

The modulator of ACE may be capable of displaying other therapeutic properties.

The modulator of ACE may be used in combination with one or more other pharmaceutically active agents.

If combinations of active agents are administered, then they may be administered simultaneously, separately or sequentially.

Mimetic

As used herein, the term "mimetic" relates to any chemical which includes, but is not limited to, a peptide, polypeptide, antibody or other organic chemical which has the same qualitative activity or effect as a known compound. That is, the mimetic is a functional equivalent of a known compound.

Stereo and Geometric Isomers

Modulators of ACE may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers, and mixtures thereof.

Pharmaceutical Salt

Modulators of ACE may be administered in the form of a pharmaceutically acceptable salt.

Pharmaceutically-acceptable salts are well known to those skilled in the art, and for example include those mentioned by Berge et al, (1977) *J. Pharm. Sci.,* 66, 1-19. Suitable acid addition salts are formed from acids which form non-toxic salts and include the hydrochloride, hydrobromide, hydroiodide, nitrate, sulphate, bisulphate, phosphate, hydrogenphosphate, acetate, trifluoroacetate, gluconate, lactate, salicylate, citrate, tartrate, ascorbate, succinate, maleate, fumarate, gluconate, formate, benzoate, methanesulphonate, ethanesulphonate, benzenesulphonate and p-toluenesulphonate salts.

When one or more acidic moieties are present, suitable pharmaceutically acceptable base addition salts can be formed from bases which form non-toxic salts and include the aluminium, calcium, lithium, magnesium, potassium, sodium, zinc, and pharmaceutically-active amines such as diethanolamine, salts.

A pharmaceutically acceptable salt of a modulator of ACE may be readily prepared by mixing together solutions of the modulator of ACE and the desired acid or base, as appropriate. The salt may precipitate from solution and be collected by filtration or may be recovered by evaporation of the solvent.

The modulator of ACE may exist in polymorphic form.

The modulator of ACE may contain one or more asymmetric carbon atoms and therefore exists in two or more stereoisomeric forms. Where a modulator of ACE contains an alkenyl or alkenylene group, cis (E) and trans (Z) isomerism may also occur. The present invention includes the individual stereoisomers of the modulator of ACE and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. of a stereoisomeric mixture of the modulator of ACE or a suitable salt or derivative thereof. An individual enantiomer of the modulator of ACE may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

The modulator of ACE may also include all suitable isotopic variations of the modulator of ACE or a pharmaceutically acceptable salt thereof. An isotopic variation of an modulator of ACE or a pharmaceutically acceptable salt thereof is defined as one in which at least one atom is replaced by an atom having the same atomic number but an atomic mass different from the atomic mass usually found in nature. Examples of isotopes that can be incorporated into the modulator of ACE and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the modulator of ACE and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the modulator of ACE and pharmaceutically acceptable salts thereof of this invention can generally be prepared by conventional procedures using appropriate isotopic variations of suitable reagents.

It will be appreciated by those skilled in the art that the agent may be derived from a prodrug. Examples of prodrugs include entities that have certain protected group(s) and which may not possess pharmacological activity as such, but may, in certain instances, be administered (such as orally or parenterally) and thereafter metabolised in the body to form the modulator of ACE which is pharmacologically active.

It will be further appreciated that certain moieties known as "pro-moieties", for example as described in "Design of Prodrugs" by H. Bundgaard, Elsevier, 1985 (the disclosured of which is hereby incorporated by reference), may be placed on appropriate functionalities of the modulator of ACE. Such prodrugs are also included within the scope of the invention.

Pharmaceutically Active Salt

The modulator of ACE may be administered as a pharmaceutically acceptable salt. Typically, a pharmaceutically acceptable salt may be readily prepared by using a desired acid or base, as appropriate. The salt may precipitate from solution and be collected by filtration or may be recovered by evaporation of the solvent.

Chemical Synthesis Methods

The modulator of ACE of the present invention may be prepared by chemical synthesis techniques.

It will be apparent to those skilled in the art that sensitive functional groups may need to be protected and deprotected during synthesis of a compound of the invention. This may be achieved by conventional techniques, for example as described in "Protective Groups in Organic Synthesis" by T W Greene and P G M Wuts, John Wiley and Sons Inc. (1991), and by P. J. Kocienski, in "Protecting Groups", Georg Thieme Verlag (1994).

It is possible during some of the reactions that any stereocentres present could, under certain conditions, be racemised, for example if a base is used in a reaction with a substrate having an having an optical centre comprising a base-sensitive group. This is possible during e.g. a guanylation step. It should be possible to circumvent potential problems such as this by choice of reaction sequence, conditions, reagents, protection/deprotection regimes, etc. as is well-known in the art.

The compounds and salts may be separated and purified by conventional methods.

Separation of diastereomers may be achieved by conventional techniques, e.g. by fractional crystallisation, chromatography or H.P.L.C. of a stereoisomeric mixture of a compound of formula (I) or a suitable salt or derivative thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active acid or base.

ACE, modulators of ACE or variants, homologues, derivatives, fragments or mimetics thereof may be produced using chemical methods to synthesise the ACE or the modulator of ACE in whole or in part. For example, a ACE peptide or a modulator of ACE that is a peptide can be synthesised by solid phase techniques, cleaved from the resin, and purified by preparative high performance liquid chromatography (e.g., Creighton (1983) Proteins Structures And Molecular Principles, WH Freeman and Co, New York N.Y.). The composition of the synthetic peptides may be confirmed by amino acid analysis or sequencing (e.g., the Edman degradation procedure; Creighton, supra).

Synthesis of peptides (or variants, homologues, derivatives, fragments or mimetics thereof may be performed using various solid-phase techniques (Roberge J Y et al (1995) Science 269: 202-204) and automated synthesis may be achieved, for example, using the ABI 43 1 A Peptide Synthesizer (Perkin Elmer) in accordance with the instructions provided by the manufacturer. Additionally, the amino acid sequences comprising the modulator of ACE, may be altered during direct synthesis and/or combined using chemical methods with a sequence from other subunits, or any part thereof, to produce a variant modulator of ACE.

Chemical Modification

The modulator of ACE may be a chemically modified modulator of ACE.

The chemical modification of a modulator of ACE may either enhance or reduce interactions between the modulator of ACE and the target—such as hydrogen bonding interactions, charge interactions, hydrophobic interactions, van der Waals interactions or dipole interactions.

In one aspect, the modulator of ACE may act as a model (for example, a template) for the development of other compounds.

Pharmaceutical Compositions

The components may be administered alone but will generally be administered as a pharmaceutical composition—e.g. when the components are in a mixture with a suitable pharmaceutical excipient, diluent or carrier selected with regard to the intended route of administration and standard pharmaceutical practice.

For example, the components can be administered in the form of tablets, capsules, ovules, elixirs, solutions or suspensions, which may contain flavouring or colouring agents, for immediate-, delayed-, modified-, sustained-, pulsed- or controlled-release applications.

If the pharmaceutical is a tablet, then the tablet may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders—such as polyvinylpyrrolidone, hydroxypropylmethylcellulose (HPMC), hydroxypropylcellulose (HPC), sucrose, gelatin and acacia. Additionally, lubricating agents—such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the modulator of ACE may be combined with various sweetening or flavouring agents, colouring matter or dyes, with emulsifying and/or suspending agents and with diluents such as water, ethanol, propylene glycol and glycerin, and combinations thereof.

The routes for administration (delivery) may include, but are not limited to, one or more of oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intraventricular, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural, sublingual.

Pharmaceutical compositions of the present invention may comprise a therapeutically effective amount of ACE, one or more modulators of ACE or combinations thereof.

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be administered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be administered by a number of routes.

If the modulator of ACE is to be administered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions may be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or the pharmaceutical compositions can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The modulators of ACE may be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

If the modulator of ACE is a protein, then said protein may be prepared in situ in the subject being treated. In this respect, nucleotide sequences encoding said protein may be delivered by use of non-viral techniques (e.g. by use of liposomes) and/or viral techniques (e.g. by use of retroviral vectors) such that the said protein is expressed from said nucleotide sequence.

Dose Levels

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

Formulation

The component(s) may be formulated into a pharmaceutical composition, such as by mixing with one or more of a suitable carrier, diluent or excipient, by using techniques that are known in the art.

Vector

Aspects of the present invention relate to a vector comprising a nucleotide sequence—such as a nucleotide sequence encoding ACE or a modulator of ACE—administered to a subject.

Preferably, ACE or the modulator of ACE is prepared and/or delivered using a genetic vector.

As it is well known in the art, a vector is a tool that allows or facilitates the transfer of an entity from one environment to another. In accordance with the present invention, and by way of example, some vectors used in recombinant DNA techniques allow entities, such as a segment of DNA (such as a heterologous DNA segment, such as a heterologous cDNA segment), to be transferred into a host and/or a target cell for the purpose of replicating the vectors comprising nucleotide sequences and/or expressing the proteins encoded by the nucleotide sequences. Examples of vectors used in recombinant DNA techniques include, but are not limited to, plasmids, chromosomes, artificial chromosomes or viruses.

The term "vector" includes expression vectors and/or transformation vectors.

The term "expression vector" means a construct capable of in vivo or in vitro/ex vivo expression.

The term "transformation vector" means a construct capable of being transferred from one species to another.

Regulatory Sequences

In some applications, nucleotide sequences are operably linked to a regulatory sequence which is capable of providing for the expression of the nucleotide sequence, such as by a chosen host cell. By way of example, a vector comprising the ACE nucleotide sequence is operably linked to such a regulatory sequence i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals.

The term "promoter" is used in the normal sense of the art, e.g. an RNA polymerase binding site.

Enhanced expression of a nucleotide sequence, for example, a nucleotide sequence encoding ACE—may also be achieved by the selection of heterologous regulatory regions, e.g. promoter, secretion leader and terminator regions, which serve to increase expression and, if desired, secretion levels of the protein of interest from the chosen expression host and/or to provide for the inducible control of the expression of ACE. In eukaryotes, polyadenylation sequences may be operably connected to the ACE nucleotide sequence.

Preferably, the ACE nucleotide sequence is operably linked to at least a promoter.

Aside from the promoter native to the gene encoding the ACE nucleotide sequence, other promoters may be used to direct expression of the ACE polypeptide. The promoter may be selected for its efficiency in directing the expression of the ACE nucleotide sequence in the desired expression host.

In another embodiment, a constitutive promoter may be selected to direct the expression of the ACE nucleotide sequence of the present invention. Such an expression construct may provide additional advantages since it circumvents the need to culture the expression hosts on a medium containing an inducing substrate.

Hybrid promoters may also be used to improve inducible regulation of the expression construct.

The promoter can additionally include features to ensure or to increase expression in a suitable host. For example, the features can be conserved regions such as a Pribnow Box or a TATA box. The promoter may even contain other sequences to affect (such as to maintain, enhance, decrease) the levels of expression of the ACE nucleotide sequence. For example, suitable other sequences include the Sh1-intron or an ADH intron. Other sequences include inducible elements—such as temperature, chemical, light or stress inducible elements. Also, suitable elements to enhance transcription or translation may be present.

Expression Vector

Preferably, nucleotide sequences—such as nucleotide sequences encoding ACE or modulators of ACE—are inserted into a vector that is operably linked to a control sequence that is capable of providing for the expression of the coding sequence by the host cell.

Nucleotide sequences produced by a host recombinant cell may be secreted or may be contained intracellularly depending on the sequence and/or the vector used. As will be understood by those of skill in the art, expression vectors can be designed with signal sequences, which direct secretion of the nucleotide sequence through a particular prokaryotic or eukaryotic cell membrane.

The expression vector may be pEE-tACEΔ36NJ which encodes human tACE that lacks the heavily O-glycosylated, 36-residue N-terminal sequence and is truncated after $Ser^{625}$, thereby lacking most of the juxtamembrane stalk as well as the transmembrane and cytoplasmic domains.

In a preferred aspect, the expression vector is pLEN-tACEΔ36g(n), where n is a set of numbers defining the available N-linked glycosylation sites.

Preferably, the expression vectors are stably expressed in CHO cells as described previously (Ehlers et al. (1996) *Biochemistry* 35, 9549-9559). More preferably, the expression vectors are pLEN-tACEΔ36g(1, 2, 3, 4) and pLEN-tACEΔ36g(1,3).

Fusion Proteins

ACE or a modulator of ACE may be expressed as a fusion protein to aid extraction and purification and/or delivery of the modulator of ACE or the ACE protein to an individual and/or to facilitate the development of a screen for modulators of ACE.

Examples of fusion protein partners include glutathione-S-transferase (GST), 6×His, GAL4 (DNA binding and/or transcriptional activation domains) and β-galactosidase.

It may also be convenient to include a proteolytic cleavage site between the fusion protein partner and the protein sequence of interest to allow removal of fusion protein sequences. Preferably, the fusion protein will not hinder the activity of the protein of interest.

The fusion protein may comprise an antigen or an antigenic determinant fused to the substance of the present invention. In this embodiment, the fusion protein may be a non-naturally occurring fusion protein comprising a substance, which may act as an adjuvant in the sense of providing a generalised stimulation of the immune system. The antigen or antigenic determinant may be attached to either the amino or carboxy terminus of the substance.

Organism

The term "organism" in relation to the present invention includes any organism that could comprise ACE and/or modulators of ACE. Examples of organisms may include mammals, fungi, yeast or plants.

Preferably, the organism is a mammal. More preferably, the organism is a human.

Transformation

As indicated earlier, the host organism can be a prokaryotic or a eukaryotic organism. Examples of suitable prokaryotic hosts include *E. coli* and *Bacillus subtilis*. Teachings on the transformation of prokaryotic hosts are well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc. Examples of suitable eukaryotic hosts include mammalian cells.

If a prokaryotic host is used then the nucleotide sequence—such as the ACE nucleotide sequence—may need to be suitably modified before transformation—such as by removal of introns.

Thus, the present invention also relates to the transformation of a host cell with a nucleotide sequence—such as ACE or a modulator of ACE. Host cells transformed with the nucleotide sequence may be cultured under conditions suitable for the expression and recovery of the encoded protein from cell culture. The protein produced by a recombinant cell may be secreted or may be contained intracellularly depending on the sequence and/or the vector used. As will be understood by those of skill in the art, expression vectors containing coding sequences can be designed with signal sequences which direct secretion of the coding sequences through a particular prokaryotic or eukaryotic cell membrane. Other recombinant constructions may join the coding sequence to nucleotide sequence encoding a polypeptide domain, which will facilitate purification of soluble proteins (Kroll D J et al (1993) DNA Cell Biol 12:441-53) e.g. 6-His or Glutathione-S-transferase.

Transfection

Vectors comprising for example, the ACE nucleotide sequence, may be introduced into host cells, for example, mammalian cells, using a variety of methods.

Typical transfection methods include electroporation, DNA biolistics, lipid-mediated transfection, compacted DNA-mediated transfection, liposomes, immunoliposomes, lipofectin, cationic agent-mediated, cationic facial amphiphiles (CFAs) (*Nature Biotech*. (1996) 14, 556), multivalent cations such as spermine, cationic lipids or polylysine, 1,2,-bis(oleoyloxy)-3-(trimethylammonio) propane (DOTAP)-cholesterol complexes (Wolff and Trubetskoy 1998 Nature Biotechnology 16: 421) and combinations thereof.

Uptake of nucleic acid constructs by mammalian cells is enhanced by several known transfection techniques for example those including the use of transfection agents. Example of these agents include cationic agents (for example calcium phosphate and DEAE-dextran) and lipofectants (for example Lipofectam™ and Transfectam™). Typically, nucleic acid constructs are mixed with the transfection agent to produce a composition.

Such methods are described in many standard laboratory manuals—such as Sambrook et al., Molecular Cloning: A Laboratory Manual, 2d ed. (1989) Cold Spring Harbor Laboratory Press, Cold Spring Harbor, N.Y.

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning. A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization Principles and Practice*; Oxford University Press; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA Methods in Enzymology*, Academic Press. Each of these general texts is herein incorporated by reference.

Figure 1:
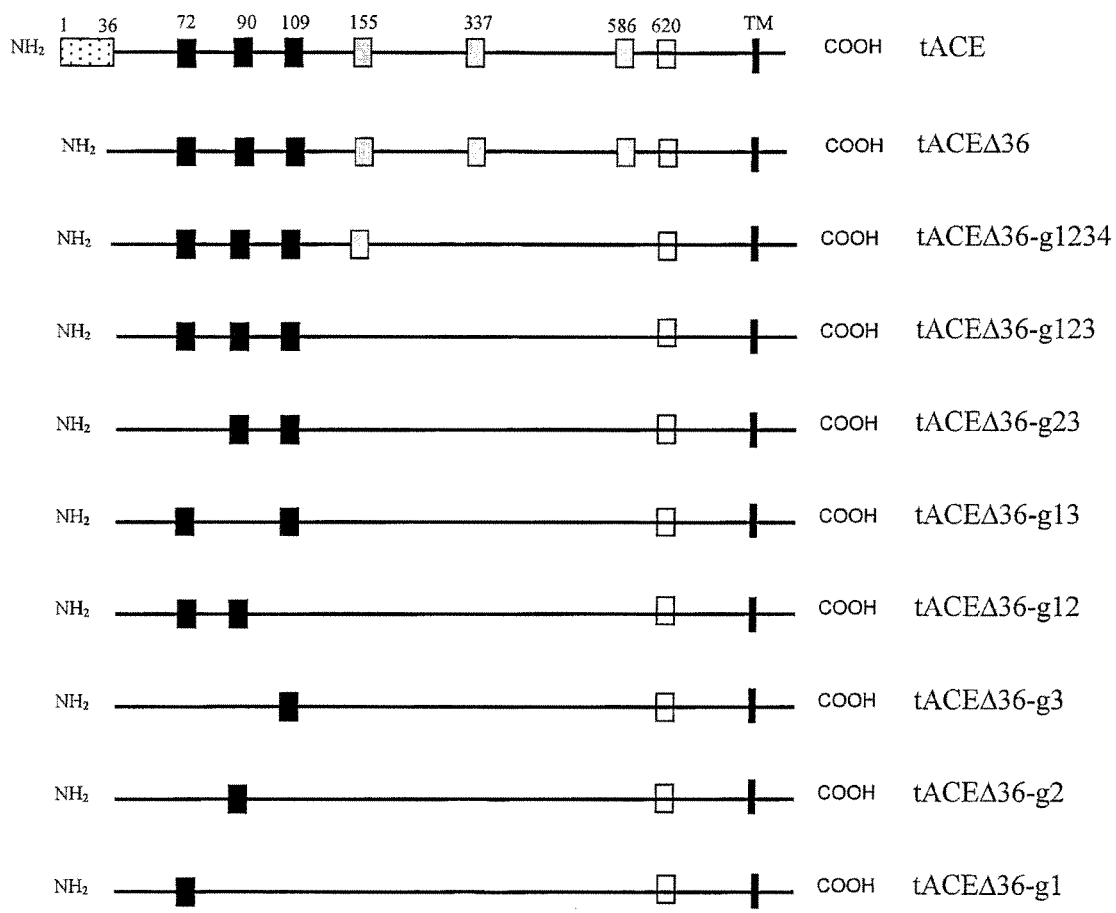
FIG. 1 is a schematic presentation of wild-type tACE (tACE) and tACEΔ36 glycosylation mutants. Glycosylation sites are shown with boxes, glycosylated always (black box), glycosylated partially (grey box) and unglycosylated (open box). The O-glycosylated region at the N-terminus of (tACE), which is absent in tACEΔ36, is shown with a stippled box. TM is the transmembrane domain.

The invention will now be further described by way of Examples, which are meant to serve to assist one of ordinary skill in the art in carrying out the invention and are not intended in any way to limit the scope of the invention.

EXAMPLES

Example 1

Materials & Methods

Materials

Endoproteinase Lys-C and Asp-N, peptide-N-glycosidase F (PNGase F), endoglycosidase H (endo H), neuraminidase, and O-glycosidase are purchased from Roche Biochemicals. Cyanogen bromide, trifluoroacetic acid, and calibration standards (angiotensin, insulin, myoglobin, oxidised insulin B-chain, and TPCK-treated trypsin) are from Sigma Chemical Co. Glycosylation inhibitor N-butyldeoxynojirimycin (NB-DNJ) was a kind gift from Dr. F. Platt, University of Oxford, UK.

Construction of Expression Vectors pEE-ACEΔ36NJ encodes human tACE that lacks the heavily O-glycosylated, 36-residue N-terminal sequence and is truncated after Ser$^{625}$, thereby lacking most of the juxtamembrane stalk as well as the transmembrane and cytoplasmic domains, and is constructed as follows. The 5' half of the ACE cDNA in the plasmid pLEN-ACE-JMΔ24 is excised by digestion with BamHI and NheI and replaced with the similarly digested fragment from plasmid pLEN-ACEΔ36N. pLEN-ACE-JMΔ24 has an engineered EcoRI site at nucleotide (nt) 1984 in the ACE cDNA. The sequence between nt 1854 (the start of the unique BclI site) and nt 1990 (the end of the codon for Ser$^{625}$) in the native ACE cDNA are amplified by the polymerase chain reaction, using a 3' primer that contains two stop codons (TAA and TAG) after the Ser$^{625}$ codon, followed by an EcoRI site. The recombinant sequence is inserted into the pLEN-ACE__36N/JMΔ24 hybrid cut with BclI and EcoRI, to generate pLEN-ACEΔ36NJ. The ACEΔ36NJ coding sequence is excised by digestion of unique XbaI (generated after first subcloning in pBluescript) and EcoRI sites and inserted into the polylinker of the expression vector pEE14, to generate pEE-ACEΔ36NJ.

Cell Culture and Transfections

CHO-K1 cells stably transfected with pLEN-ACE glycosylation mutants are grown and maintained in standard media (50% Ham's F-12/50% DME medium supplemented with 20 mM Hepes, pH 7.3) containing 2% fetal bovine serum (heated to 65° C. for 15 mins before use) and 40 μM Zn Cl$_2$. In addition, native CHO-K1 cells are cotransfected with pEE-ACEΔ36NJ (10 μg) and pSV2NEO (1 μg) by the calcium phosphate precipitate method and clones stably resistant to G418 (Geneticin, Gibco-BRL) are selected and assayed for ACE activity, by procedures detailed previously (9,11). Clones stably expressing pEE-ACEΔ36NJ are further selected for resistance to methionine sulfoximine and then amplified, as described (Davis, S J, Davies, E A, Barclay, A N, Daenke, S, Bodian, D L, Jones, E Y, Stuart, D I, Butters, T D, Dwek, R A, and van der Merwe, P A (1995) *J Biol Chem* 270, 369-375). Methionine sulfoximine-amplified cells are grown first in GMEM-10 (Gibco-BRL) containing 10% dialyzed fetal bovine serum (FBS) (Gibco-BRL) and 1.5 mM NB-DNJ for 3 days and then refed with GMEM-10, 5% dialyzed FBS, 2 mM NB-DNJ. This medium is changed twice over a period of 9 days before harvesting.

Enzyme Purification

Soluble, recombinant tACE (wild-type, ACEΔ36NJ and ACE glycosylation mutants), is purified from conditioned media by affinity chromatography on a Sepharose-28-lisinopril affinity resin. The protein is quantitated by amino acid analysis and assayed for activity using the substrate hippuryl-L-histidyl-L-leucine, as described (Ehlers, MRE, Chen, Y-N, Riordan, J F (1991) Proc Natl Acad Sci USA 88, 1009-1013).

Deglycosylation of ACE tACEΔ36NJ (12.5 mmol) purified from cultures treated with NB-DNJ is digested with endo H (30 mU) in 100 mM sodium phosphate, 0.1 mM ZnCl$_2$, 1% BSA, pH 6.0 for 16 h at 37° C. The endo H-treated ACE is passed through a lectin affinity column consisting of equal parts of concanavalin A, wheat germ, and lentil lectin, after equilibration with 20 mM Tris-HCl, 0.5 M NaCl at pH 7.4. The deglycosylated ACE is collected in the flowthrough. Free oligosaccharides and any other impurities are removed from the flowthrough fraction by a final lisinopril-Sepharose affinity chromatography step. The homogeneity of the tACEΔ36NJ after deglycosylation is confirmed by SDS-PAGE on a 4-20% acrylamide gel and MALDI-TOF mass spectrometry.

Construction of Glycosylation Mutants

Minimally glycosylated isoforms of human testis ACE are constructed by the removal of a combination of N-linked glycosylation sites. Glycosylation is abolished by site-directed mutagenesis of the site of attachment in the recognition sequon (Asn-X-Ser/Thr) through a conserved transition of the Asn to a Gln residue. A truncated form of tACE (tACEΔ36 lacking the first N-terminal 36 residues is used for the construction of all mutants. tACEΔ36 cDNA is divided into four fragments and introduced into pGEM-11Zf(+) to facilitate site-directed mutagenesis. An Eco47III site is introduced into pGEM-11Zf(+) for cloning of the first and second tACEΔ36 fragments. A 146 bp BamHI/NheI digested pBR329 fragment that contains an Eco47III site is ligated to BamHI/XbaI digested pGEM. The following mutagenic oligonucleotides are used for altering the consensus sites for N-linked glycosylation: g1-F, g2-F, g3-F, g4-F, g5-F, g6-F, g1-R, g2-R and g3-R, with the number referring to each complementary recognition sequon. The mutagenic oligonucleotides encode the Asn to Gln transition (underlined) at the glycosylation sites and a silent mutation that alters a restriction enzyme recognition site (highlighted in italics). Mutated residues are indicated by bold type:

Forward Primers:

```
g1-F (40-mer):
5'-GAGGCCAATTGGAACTACAACACCCAGATCACCACAGAG-3'
(SEQ ID NO: 3)
g2-F (36-mer):
5'-ATGCAAATAGCCCAGCACACCCTTAAGTACGGCACC-3'
(SEQ ID NO: 4)
g3-F (40-mer):
5'-GAAGTTTGATGTTAACCAGTTGCAGCAGACCACTATCAAG-3'
(SEQ ID NO: 5)
g4-F (30-mer):
5'-GTGTGCCACCCGCAAGGTAGCTGCCTGCAG-3'
(SEQ ID NO: 6)
g5-F (36-mer):
5'-CCGTGCCTCCTGAATTCTGGCAGAAGTCGATGCTGG-3'
(SEQ ID NO: 7)
g6-F (36-mer):
5'-ACGGGCCAGCCCCAGATGAGCGCTTCGGCC-3'
(SEQ ID NO: 8)
```

Reverse primers are complementary to the forward primers:

```
g1-R (40-mer):
5'-CTCTGTGGTGATCTGGGTGTTGTAGTTCCAATTGGCCTCG-3'
(SEQ ID NO: 9)
g2-R (36-mer):
5'-GGTGCCGTACTTAAGGGTGTGCTGGGCTATTTGCAT-3'
(SEQ ID NO: 10)
g3-R (40-mer):
5'-CTTGATAGTGGTCTGCTGCAACTGGTTAACATCAAACTTC-3'
(SEQ ID NO: 11)
```

In the first fragment a cDNA-containing mutation at one site served as a template for the mutagenesis of the second site thus generating five variants with either one or two sites out of the first three eliminated. The fourth, fifth and sixth sites (N155, N337 and N586) are eliminated from fragments 2, 3 and 4 respectively using primers g4-F, g5-F, g6-F. The nucleotide sequence of each fragment is confirmed by sequencing to ensure that only the desired mutation has been created. The four fragments are reassembled to produce eight tACEΔ36 glycosylation mutants (FIG. 1).

The mutants are introduced into the mammalian expression vector, pLEN, to facilitate the production of underglycosylated tACEΔ36 protein. The expression vectors pLEN-tACEΔ36g(n), where n is a set of numbers defining the available N-linked glycosylation sites, are stably expressed in CHO cells as described previously (Ehlers et al. (1996) *Biochemistry* 35, 9549-9559). Similarly, wild-type tACE (tACE-wt), retaining its 36-residue N-terminus as well as the transmembrane region and juxtamembrane stalk, is stably expressed in CHO cells. A deletion mutant, tACEΔ36NJ, truncated after Ser625, and thus lacking the cytoplasmic and TM domains as well as most of the juxtamembrane stalk, is constructed (Yu et al. (1997) *J. Biol. Chem.* 272, 3511-3519). The vector pEE14-ACEΔ36NJ is transfected into CHO cells and clones stably expressing the mutant are amplified using methionine sulfoxamine, as described (Yu et al. (1997) *J. Biol. Chem.* 272, 3511-3519).

Inhibition of tACE Glycosylation in Presence of Tunicamycin

CHO cells expressing tACE-wt are grown to confluence in 6-well plates and induced overnight in 2% medium in the absence and presence of 5 µg/ml tunicamycin. Fresh medium is added and cells are grown in the absence and presence of 5 µg/ml tunicamycin. At 6, 8, 12, 16, 20 and 24 hours detergent-solubilised cell samples are collected. After separating the proteins on 10% SDS-PAGE they are immunodetected by Western blotting.

Western Blot Analysis of Glycosylation Mutants tACE-wt, tACEΔ36, tACEΔ36-g1, -g2, -g3, -g12, -g13, -g23, -g123 and -g1234 are immunodetected by Western blotting of cell lysates and harvested medium from transfected CHO cells. Proteins are separated on 10% SDS-PAGE and transferred to nitrocellulose membrane (Hybond-C, Amersham). The membrane is probed with a polyclonal rabbit anti-human tACE antibody. The membrane is developed using the ECL chemiluminescence kit (Amersham) and visualised on autoradiographic film, as per instructions.

Analysis of Release Kinetics and Cleavage Sites

After selection for stable transfectants, kinetic analyses of rates of accumulation of soluble (released) ACE activity and changes in membrane-bound ACE activity are performed in the presence and absence of 1 µM phorbol 12,13 dibutyrate (Schwager et al. (1998) *Biochemistry* 37, 15449-15456). Identification of the stalk cleavage sites and analysis of the C-terminal glycosylation site in the released (soluble) protein is carried out using limited proteolysis and MALDI-TOF mass spectrometry by methods described previously (Schwager et al. (1998) *Biochemistry* 37, 15449-15456).

Determination of Kinetic Constants for tACE Hydrolysis of Hippuryl-L-histidyl-L-leucine (Hip-His-Leu)

The enzyme is purified from harvest medium via lisinopril affinity chromatography and rates of substrate hydrolysis are determined. Assays are performed in 100 mM potassium phosphate pH 8.3 containing 300 mM NaCl. Initial velocities are calculated over a range of Hip-His-Leu concentrations (0.2-5.0 mM) under initial rate conditions and fit to the Michaelis-Menten equation. $K_m$ and $V_{max}$ values are determined by non-linear regression analysis. Turnover numbers ($k_{cat}$) and specificity constants ($k_{cat}/K_m$) are determined using a calculated molecular mass of 100 kDa.

Mass Spectrometry

Mass spectrometry is used to verify the glycan occupancy of some of the glycosylation sites of the mutant proteins. All mass spectra are obtained on a MALDI/TOF/MS instrument (Voyager-Elite Biospectrometry Workstation, PerSeptive Biosystems, Inc.). A nitrogen laser (337 nm) is used for desorption ionization. Measurements are carried out either in the linear or reflectron mode with mass accuracies of 0.1% and 0.01%, respectively. Spectra are collected over a hundred laser shots.

Typical matrices used in these experiments are 3,5-dimethoxy-4-hydroxycinnamic acid (sinapinic acid) and α-cyano-4-hydroxycinnamic acid (Aldrich). About 1 µl of sample solution was mixed with 2 µl of the matrix solution (10 mg/ml in 50% v/v $CH_3CN$ and $H_2O$). A 0.5 µl volume (containing 1-10 pmol of peptide or peptide mixture) of the above solution is loaded on the sample plate and allowed to dry.

Crystallisation

The purified tACE-ACEΔ36NJ and ACE glycosylation mutants are stored at −20° C. in 10 mM HEPES and 0.1% PMSF. Extensive crystallisation trials using commercially available crystal screen conditions (Hampton Research) are tried. In addition ammonium sulphate, PEG and MPD matrices are also tried. The best crystals for these proteins are grown at 16° C. by the vapour diffusion hanging drop method by mixing 2 µl of the protein solution at ~11.5 mg/ml in 10 mM HEPES and 0.1% PMSF with an equal volume of a reservoir solution containing 15% PEG 4000 (Fluka), 50 mM CH$_3$COONa.3H$_2$O (Sigma Chemical Company) pH 4.7 and 10 μM ZnSO$_4$.7H$_2$O (Aldrich Chemical Company). Crystals usually appear within 2 weeks and grow to their maximum size after about a month. The crystals belong to P2$_1$2$_1$2$_1$ space group, with 1 molecule in the crystallographic asymmetric unit and some 49% of the crystal volume occupied by the solvent (cell dimensions: a=56.47 Å, b=84.90 Å, c=133.99 Å, α=90°, β=90° and γ=90°). tACE-ACEΔ36NJ crystals diffract to 2 Å while tACE-ACEΔ36NJ-g13 and tACE-ACEΔ36NJ-g1234 crystals diffract to 3.0 Å and 2.8 Å respectively on a Synchrotron Radiation Source. All crystals are isomorphous.

The tACE-lisinopril (lisinopril.dihydrate) inhibitor complex is obtained by growing the crystals in the presence of inhibitor. In these experiments the protein solution is mixed with 10 mM of the inhibitor and mixed with an equal volume of the reservoir solution before setting up the crystallisation. Single crystals belonging to the P2$_1$2$_1$2$_1$ orthorhombic space group (isomorphous with the native crystals) suitable for diffraction work appear after about 4 weeks.

X-Ray Diffraction Data Collection

Before data collection, all crystals are flash-cooled at 100 K in a cryoprotectant containing 15% PEG 4000, 50 mM CH$_3$COONa.3H$_2$O pH 4.7, 10 μM ZnSO$_4$.7H$_2$O and 25% glycerol with and without respective entities—such as ACE inhibitors. All the X-ray data are collected at 100° K. using a Synchrotron Radiation Source (ESRF-Grenoble, France). Multi-wavelength anomalous dispersion (MAD) data are collected with crystals of tACE-lisinopril complex at peak of Zn K-edge (1.2825 Å), inflection (1.28322 Å) and remote (0.95373 Å) wavelengths. An anomalous dataset at long wavelength (1.7712 Å), the closest possible wavelength to Sulphur K-edge is also collected. All other heavy atom data sets are collected at the SRS-Daresbury (UK) and processed with anomalous signal. Out of more than 32 soaks with different heavy atoms, only three are found to be useful in phasing. These three (Pt, Pd & Os) derivatives are prepared by soaking the tACE-lisinopril complex crystals for ~10 to 60 minutes in the presence of 1-5 mM heavy atom solutions. Raw data images are indexed and scaled using the DENZO and SCALEPACK modules of the HKL suite [Otwinowski M and Minor W. (1997) *Methods Enzymol* 276, 307-326].

Example 2

Expression of Glycosylation Mutants in CHO Cells and the Kinetics of Release

The role of N-linked glycosylation in the expression and processing of tACEΔ36 is investigated to establish the minimal glycosylation requirements for the expression of correctly folded enzymatically-active protein. The eight glycosylation mutants constructed are transfected into CHO cells and the effect of deglycosylation on the activity, expression and processing of tACEΔ36 is assessed by enzyme assays, immunodetection and cleavage site analysis.

Figure 2:
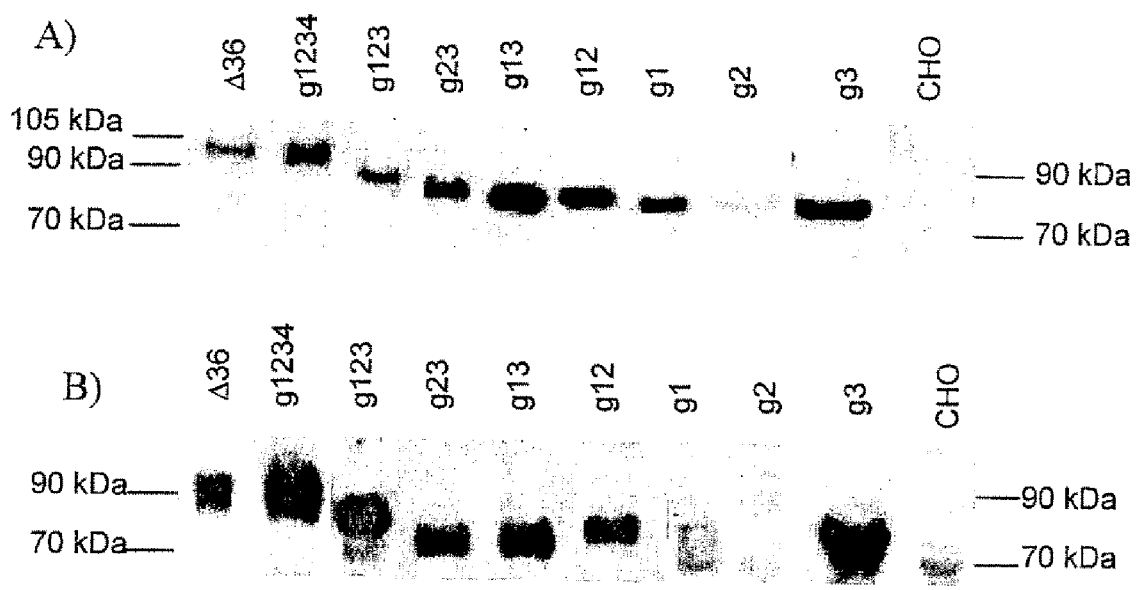
FIG. 2 illustrates the expression of tACE glycosylation mutants. Proteins are immunodetected from detergent-solubilised cells (A) and from harvested medium (B) with rabbit anti-human tACE antibody (at 1:2000). The estimated protein size is indicated. Lanes contain tACEΔ36 (Δ36), untreated CHO cells (CHO) and ACE glycosylation mutants tACEΔ36-g(n) where n equals the number of sites that are glycosylated.
Figure 3:
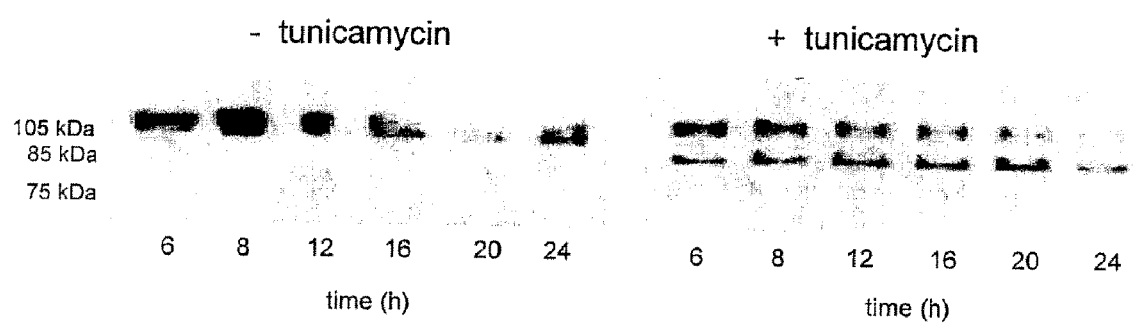
FIG. 3 illustrates the effect of tunicamycin on the expression and processing of tACE. CHO cells expressing wild-type tACE are treated with the glycosylation inhibitor tunicamycin for up to 24 h. Cell lysate from untreated (a) and treated (b) cells are analysed at the indicated times by Western blotting, protein molecular weights are given.

Western blot analysis of cellular and soluble tACEΔ36 glycoforms reveal proteins with increased mobility relative to glycosylated wild type tACE (tACE-wt) (FIG. 2) and which is dependent upon on their degree of glycosylation. Furthermore, differences are detected in the expression and processing of the various glycoforms. Comparatively low levels of tACEΔ36-g2 protein in cellular extracts (FIG. 2A), and its absence in the harvest medium (FIG. 2B), may suggest intracellular degradation and/or deficient processing of the protein. Whilst tACEΔ36-g1 demonstrates comparable levels of expression to the other proteins (FIG. 2A), processing and solubilisation appears to be less efficient than tACEΔ36-g3, -g123, and -g1234 (FIG. 2B). Tunicamycin partially inhibits the formation of mature, glycosylated tACE-wt. Western blot analysis of cellular tACE-wt in the absence of tunicamycin reveals a 105 kDa mature, glycosylated protein (FIG. 3). In the presence of tunicamycin an additional smaller, deglycosylated 85 kDa protein is detected (FIG. 3).

The K$_m$ and k$_{cat}$ values obtained for the hydrolysis of Hip-His-Leu by tACE (Table 3) are in agreement with those previously published for the C-fragment of the human endothelial isoform (K$_m$=2.0 mM) (10). Differences in the kinetic constants of glycosylated and under-glycosylated tACEΔ36 mutants are negligible and are not considered sufficiently different to reflect major alterations in the conformation and activity of the protein. Glycosylation of tACEΔ36 at one (tACEΔ36-g3) or two (tACEΔ36-g13) N-terminal glycosylation sequons is sufficient in maintaining the functional integrity of the enzyme. Furthermore, treatment of cells expressing tACEΔ36NJ with the glucosidase I inhibitor NB-DNJ, do not alter the kinetic properties of the expressed enzymes.

Example 3

Kinetics of Release and Analysis of Juxtamembrane Cleavage Sites

Figure 4:
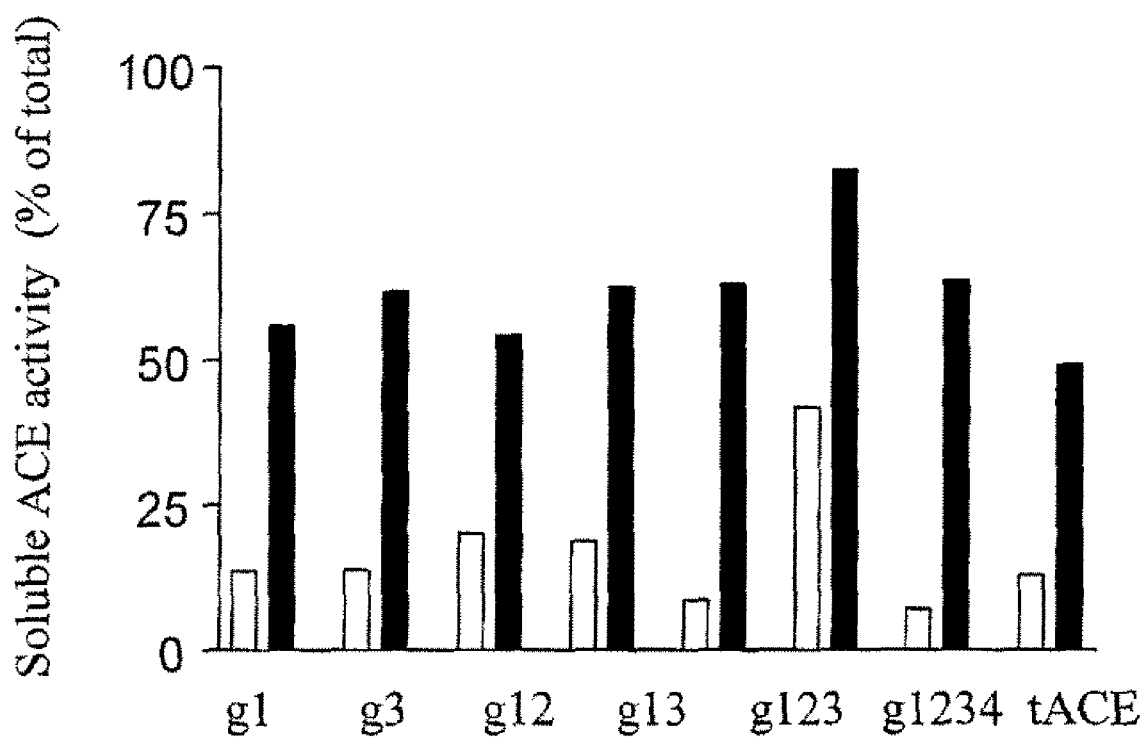
FIG. 4 illustrates the effect of phorbol ester on the levels of ACE activity. Results are expressed as percentage soluble of total (soluble plus cell associated) ACE activity. Lanes show wild-type tACE (tACE), tACEΔ36 (Δ36) and glycosylation mutants tACEΔ36 g(n), where n gives the number of sites that are glycosylated. CHO cells were grown either in the absence (open bars) or the presence (filled bars) of phorbol 12,13-dibutyrate.

Independent transfections of CHO cells with tACEΔ36-g1, -g12, -g123 and -g1234 are performed which yield consistent results for each mutant (FIG. 4). All glycosylation mutants show similar levels of phorbol ester stimulation. Thus, N-linked glycosylation does not appear to affect solubilisation of the membrane-anchored enzyme. Further protein analysis is performed to: 1) identify the C-terminal peptide to determine whether cleavage of tACEΔ36-g1, -g13 and -g1234 occurs at the same residues as tACE and 2) to investigate the glycosylation status of the seventh recognition sequon which lies seven residues proximal to the tACE cleavage site. The mass spectra of endoproteinase Lys-C digested peptides of tACEΔ36-g1, -g13 and -g1234 reveal three [M+H]$^+$ ions of m/z 1698.7, 1690.5 and 1690.9, respectively (Table 2), which are in close agreement with the theoretical mass of the C-terminal peptide (calculated m/z 1690.8).

Thus, tACEΔ36-g1, -g13 and -g1234 proteolysis occurs between Arg627 and Ser628, which is at the same site as tACE-wt. The spectra of the mutant tACEΔ36NJ reveals a [M+H]$^+$ ion at m/z 1463.1 which corresponds to the calculated mass of the peptide Leu614 to Ser625 confirming that truncation occurs at Ser625 and that there is no further limited proteolysis of the C-terminus (Table 2).

Example 4

Structure of ACE

Figure 7A:
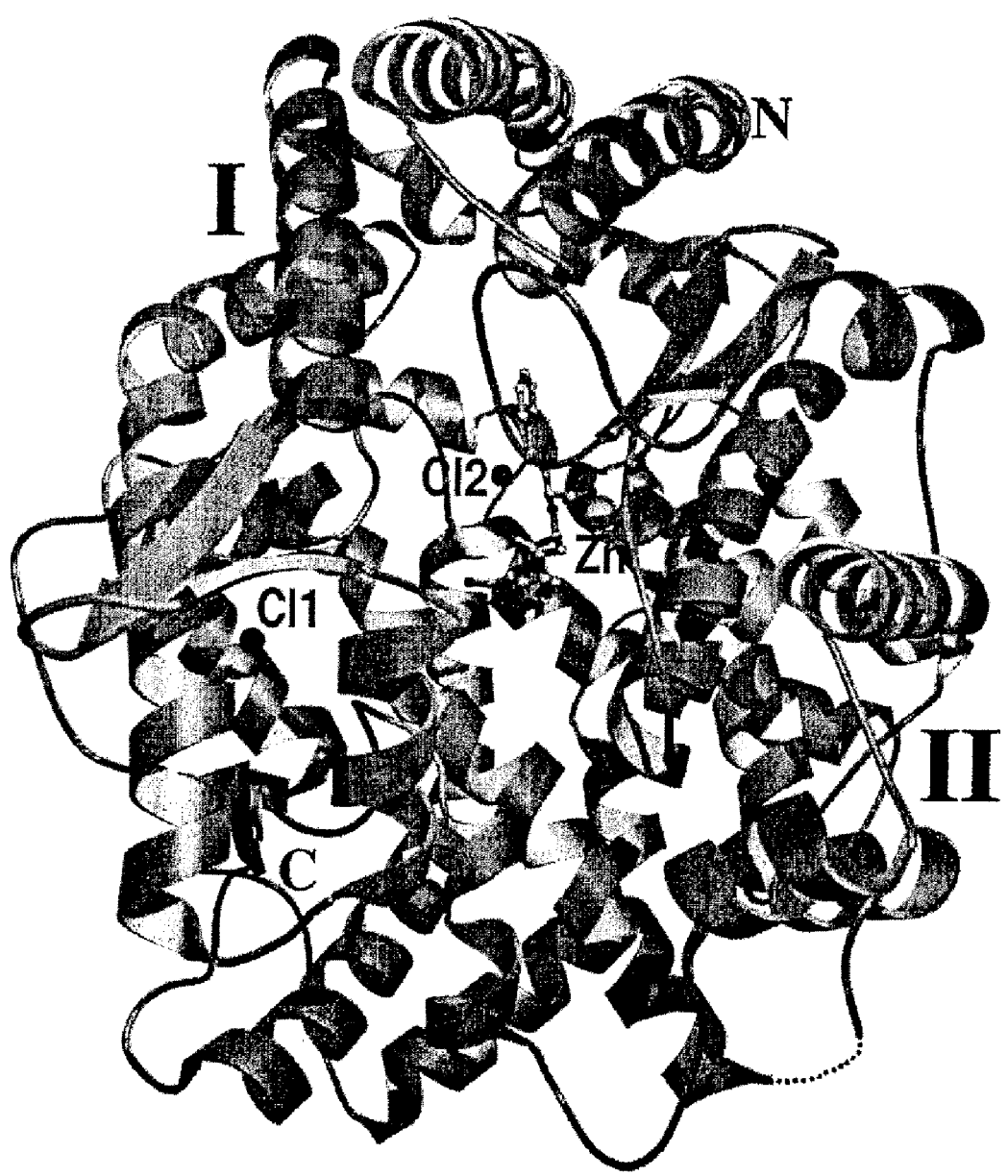
FIG. 7 illustrates the overview of the testis ACE structure. (a) Ribbon diagram of the molecule looking down on the active site. The molecule can be divided into 2 halves as domains I and II show in cyan and pink respectively. The active site zinc ion and the lisinopril molecule are shown in yellow. The two chloride ions are shown as black spheres. (b) The molecular surface representation showing the active site groove. (c) The structure-sequence relationship in ACE (SEQ ID NO: 2). The secondary structure elements (domain I—cyan; domain II—pink) follow the same colour code as in (a). The important residues which are involved in binding are marked-zinc ligands (yellow), chloride binding residues (C11—light green, C12—dark green), lisinopril binding residues (cyan) and glycosylation sites (open boxes).
Figure 7B:
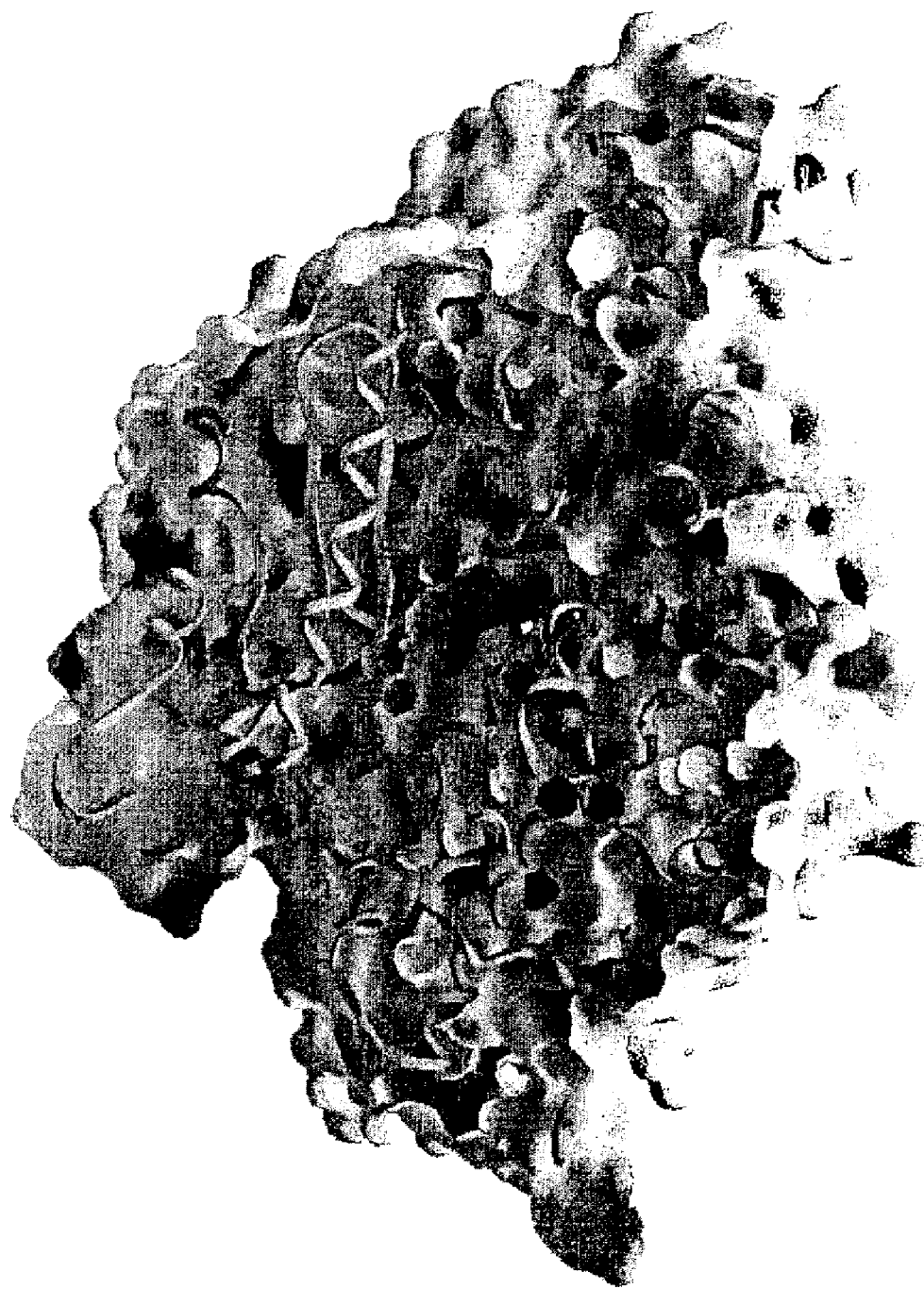

The crystal structure of the native ACE enzyme is determined to 2.0 Å resolution. The structure from residues 71-648 adopts an overall ellipsoid shape (dimensions ~72 Å×57 Å×48 Å) with a central groove that extends for about 30 Å into the molecule and effectively divides the protein into two "domains" (labelled I and II, FIG. 7a,b). On top of the molecule there is a N-terminal "flap" that allows access to the active site cleft. Like the recently determined zinc-peptidase structure-neurolysin, ACE is also bristling with helices and is comprised of twenty α-helices (with almost equal distribution of helices in both domains) and seven 3$_{10}$-helices (FIG. 7c). This makes the molecular architecture very compact and rigid as observed from the thermal parameters (crystallographic β-factors) for the structure. The only β-structure which accounts for 4% of all residues occurs as six relatively short strands, two of which are located near the active site (FIG. 7a). The boundaries of the groove are provided by domain II (α13, α14, α15, α17, β4) with part of the domain I forming the flap (α1, α2, α3). In addition the base of the scaffold is formed by helices α6 and α8 and helix α15 serves as an anchor.

Eight C-terminal residues are disordered in the crystal structure and most of this flexible region constitutes the unconstrained juxtamembrane region distal to the wild-type ACE cleavage site. The α-helix from Ala 620 to His 641 (α20) defines the C-terminal boundary of the ectodomain and this is in agreement with previous ACE mutagenesis and cleavage-secretion studies (Ehlers et al., 1996; Chubb et al., 2002). Residues Ser 466-Gly 469 are disordered in the structure. Five hundred and four ordered water molecules were identified in the native structure. All six glycosylation sites (g1-6, FIG. 7c) are exposed and g1 site is closest to the N-terminus of the molecule. Sketchy density was observed for N-linked carbohydrates in all the glycosylation sites (FIG. 7c) and modelled as N-acetylglucosamine (NAG) in the native structure. The co-ordinates of underglycosylated tACEΔ36NJ ACE are shown in Table A.

Example 5

Zinc Co-Ordination

Figure 8A:
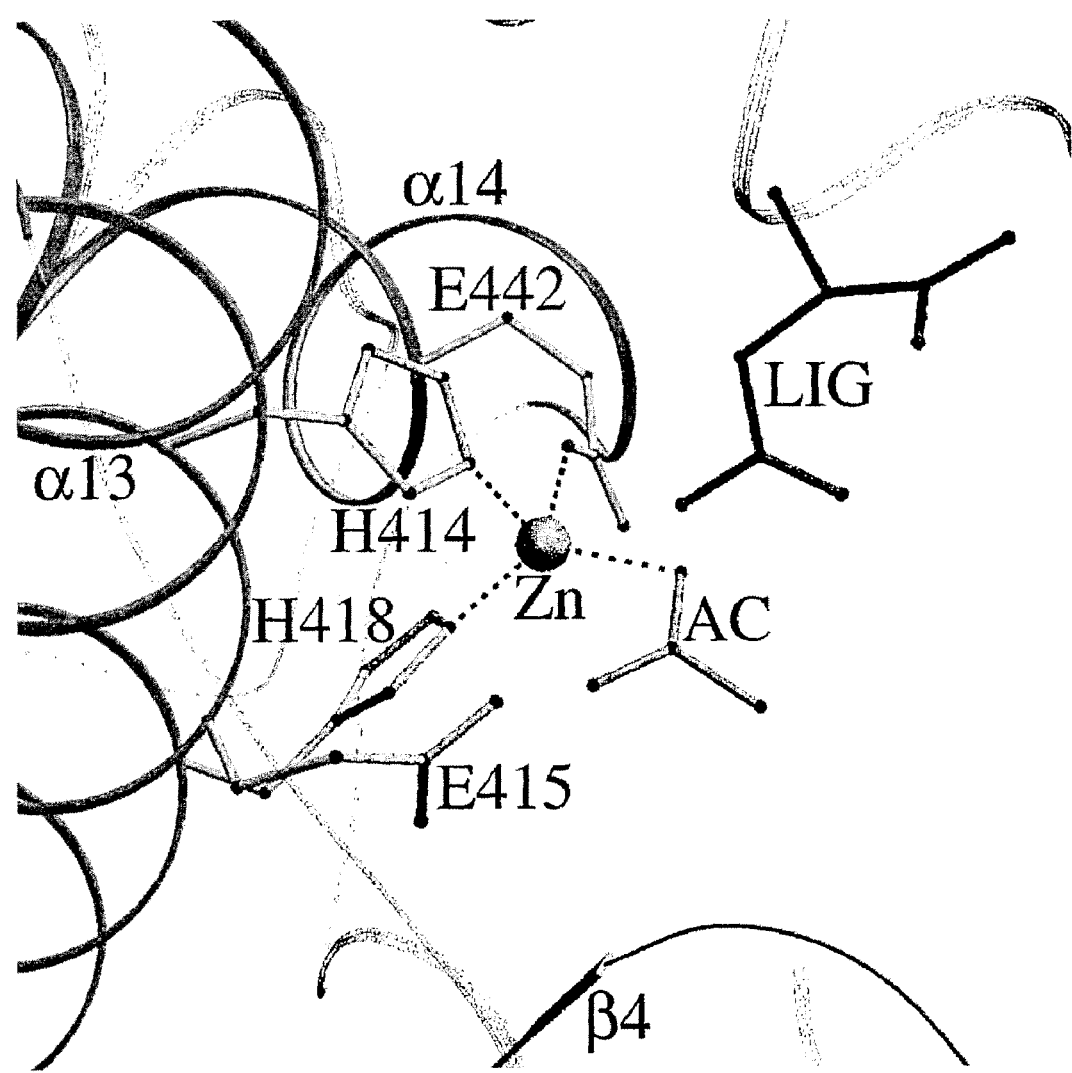
FIG. 8 illustrates details of the active site. (a) Zinc co-ordination in the native structure. Bound zinc ion, acetate ion (AC) and part of the butyl succinate moiety (LIG) are shown. (b) Details of lisinopril (LIS) interactions. Bound zinc ion is also shown.

ACE belongs to the gluzincin family of metalloproteases (Hooper, 1994). Zinc is known to be an important catalytic component of ACE. In the structure, the active site helices α13 and α14 define the substrate binding cleft of this peptidase. One highly ordered zinc ion (B-factor=16.34 $Å^2$) is bound at the active site. The helix α13 contains the HEXXH zinc binding motif (known to be important for the catalytic activity of ACE, Wei et al., 1991), with its two zinc coordinating histidines (His 414 and His 418) and Glu 442 (from α14 helix) acts as the third ligand (FIG. 7c). Additional coordination is provided by an acetate ion (from the crystallization medium) bound at the active site of the native enzyme (FIG. 8a). It has been reported previously that the recruitment of zinc ion in ACE catalysis is analogous to that in thermolysin (Williams et al., 1994; Corvol et al., 1995) and our structural data shows that the zinc binding sites in both proteins are indeed very similar (r.m.s. deviation 1.52 Å) except the acetate ion which is replaced by a water molecule in the coordination sphere in thermolysin. The active site pocket in ACE is occupied by 3 ordered water molecules. In addition, a stretch of clear electron density (at 3σ level) was observed (~5 Å away from the zinc ion) at the active site which is interpreted as part of butyl succinate (FIG. 8a).

Example 6

Activation of ACE by Chloride Ions

Substrate hydrolysis by ACE is activated by chloride anions and, whereas some substrates can be cleaved in the absence of chloride, it is an absolute requirement for angiotensin I (Bunning and Riordan, 1983; Shapiro et al., 1983). Our structure revealed the location of two chloride ions (FIG. 7a, c). The first chloride ion (Cl1, 20.7 Å away from the zinc ion) is bound to three ligands, Arg 520 (NH1), Arg 217 (NE), Trp 516 (NE1) and water and is surrounded by a hydrophobic shell of four tryptophans. The second anion (Cl2, 10.4 Å away from the zinc ion) is bound to Arg 553 (NE) in agreement with previous report showing Arg 1098 (the analogous Arg residue in the C-domain of somatic ACE) is critical for chloride dependence of ACE activity (Liu et al., 2001). Tyr 255 and a water molecule are the other two Cl2 ligands. The two chloride ions (separated by 20.3 Å) in ACE are bound almost in a triangular conformation—in accordance with the near equatorial coordination and accommodation of planar trigonal anions in α-amylase where the chloride ions are involved in the allosteric activation (Aghajari et al., 2002). In addition, the anchoring of Domain II on Domain I scaffold appears to be mediated by the chloride ions.

Mutating Arg 1098 to a lysine resulted in a 100-fold reduction in chloride binding affinity as well as a decrease in substrate affinity (Liu et al., 2001). This might be due to the contact with the NE atom of arginine as opposed to an NH1 or NH2 atom with lysine which would permit free rotation of the basic terminal nitrogens. Recent studies suggest that the affinity of chloride binding to ACE is directly related to the interactions between the chloride and enzyme as well as the substrate (Liu et al., 2001). However, based on the location of both chloride ions in the 3D structure make the latter interaction unlikely. Nevertheless, there is a van der Waals contact between Cl2 and Pro 438 (α14) that could be responsible for maintaining the active site cleft in a conformation which favours substrate accessibility and binding. Indeed α14 contain the third zinc coordinating ligand Glu 442. Thus, the chloride interactions likely cause the enzyme to adopt conformations that permit higher affinity substrate binding and that it is not important in substrate binding per se.

Example 7

Structure Determination and Refinement of an ACE-Lisinopril Complex

The crystal structure of tACE bound to the potent lisinopril inhibitor ($K_i$=27×10$^{10}$M, Wei et al., 1991) complex is determined by a combination of MAD and MIRAS (Multiple Isomorphous Replacement with Anomalous Scattering) procedures. The position of zinc atom is unambiguously identified using the anomalous difference Patterson maps calculated using diffractions data at peak wavelength. The MAD phases thus obtained are not very strong and thus additional phase information is obtained using MIRAS procedures with three—Platinum ($K_2PtCl_4$), Palladium ($K_2PdCl_4$) and Osmium ($OsCl_3$) heavy atom derivatives. The identified Zn site is used to obtain the starting phases in each derivative. Double difference Fourier maps calculated using FFT routine in CCP4 program [Collaborative computational project Number 4. The CCP4 Suite: Programs for Protein Crystallography (1994) Acta Crystallogr. D 50, 760-763] gave the first major binding site and the phases from the combined Zn and first major site are used to get additional major/minor sites for each derivative. All heavy atom binding sites and the Zn site are refined to 2.8 Å resolution using the program MLPHARE [Collaborative computational project Number 4. The CCP4 Suite: Programs for Protein Crystallography (1994) Acta Crystallogr. D 50, 760-763] and SHARP [De La Fortelle, E. & Bricogne, G. Maximum-likelihood heavy-atom parameters refinement in the MIR and MAD methods (1997) Methods Enzymol. 276, 472-494]. The overall figure of merit from SHARP is 0.38 (at 2.8 Å resolution) and is improved to 0.89 (at 2.0 Å) by iterative solvent flattening, phase combination and phase extension with the program SOLOMON [Abrahams, J. P. & Leslie, A. G. W. Methods used in structure determination of bovine mitochondrial F1 ATPase. (1996) Acta Crystallogr. D 52, 110-119]. Model building is carried out manually using the program O [Jones, T. A., Zou, J. Y., Cowan, S. W. & Kjeldgaard, M. Improved methods for building protein models in electron density maps and the location of errors in these models (1991) to Acta Crystallogr. A 47, 110-119]. Refinement of the model is carried out using the program CNS [Brünger, A. T. et al. Crystallography & NMR System: A new software suite for macromolecular structure determination. (1998) Acta Crystallogr. D 54, 905-921]. During the final stages of refinement water molecules, zinc ion and the inhibitor molecule are inserted in the respective structure. Both the native and inhibitor complex structures are refined at 2.0 Å resolution with ~94% residues in the maximum allowed region and no residue in the disallowed region of the Ramachandran map. The final structure of the tACE and ACE-lisinopril complex has an $R_{free}$ [Brünger, A. T. Free R value: a novel statistical quantity for assessing the accuracy of crystal structure. (1992) Nature 355, 472-475] of 22.08 and 21.88%, and a final $R_{cryst}$ of 18.29 and 18.14% respectively.

Figure 8B:
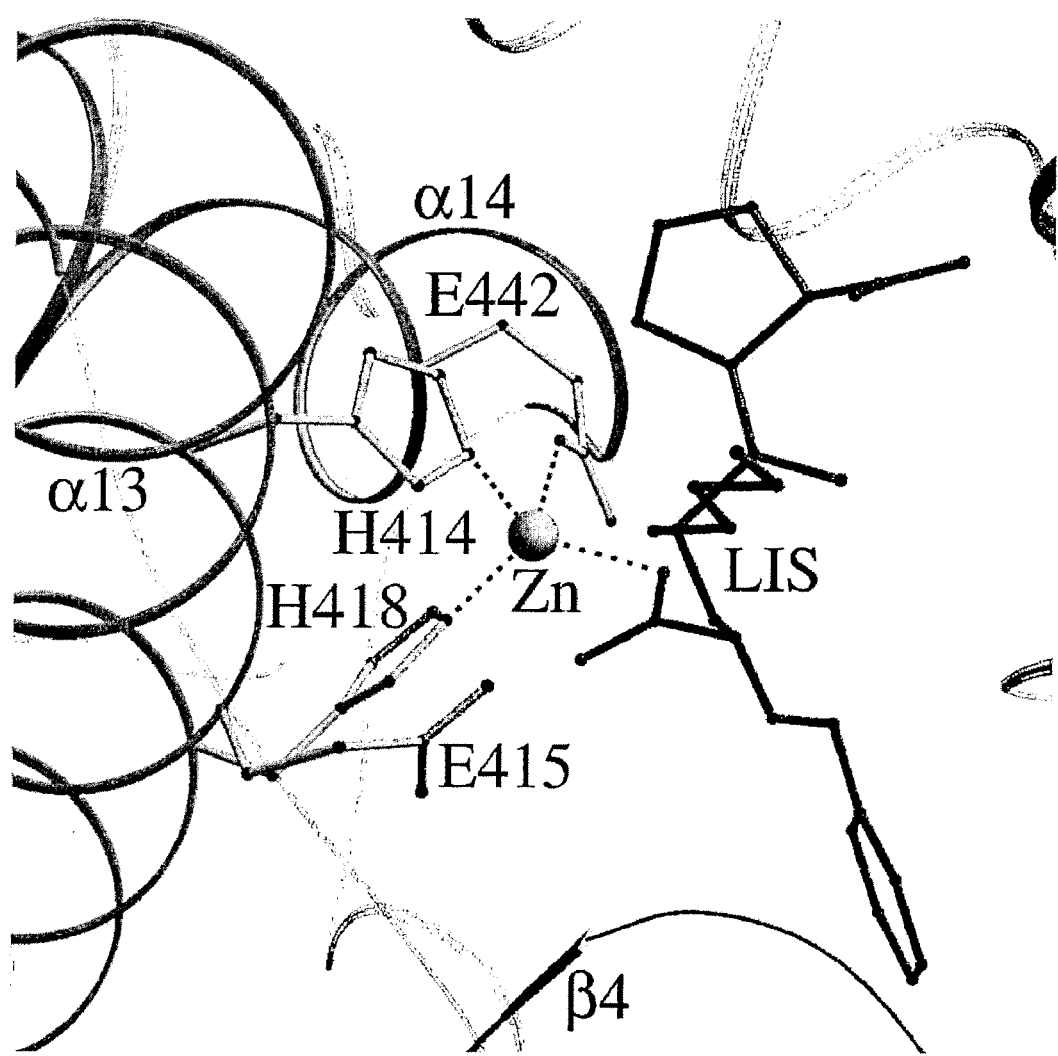
Figure 9A:
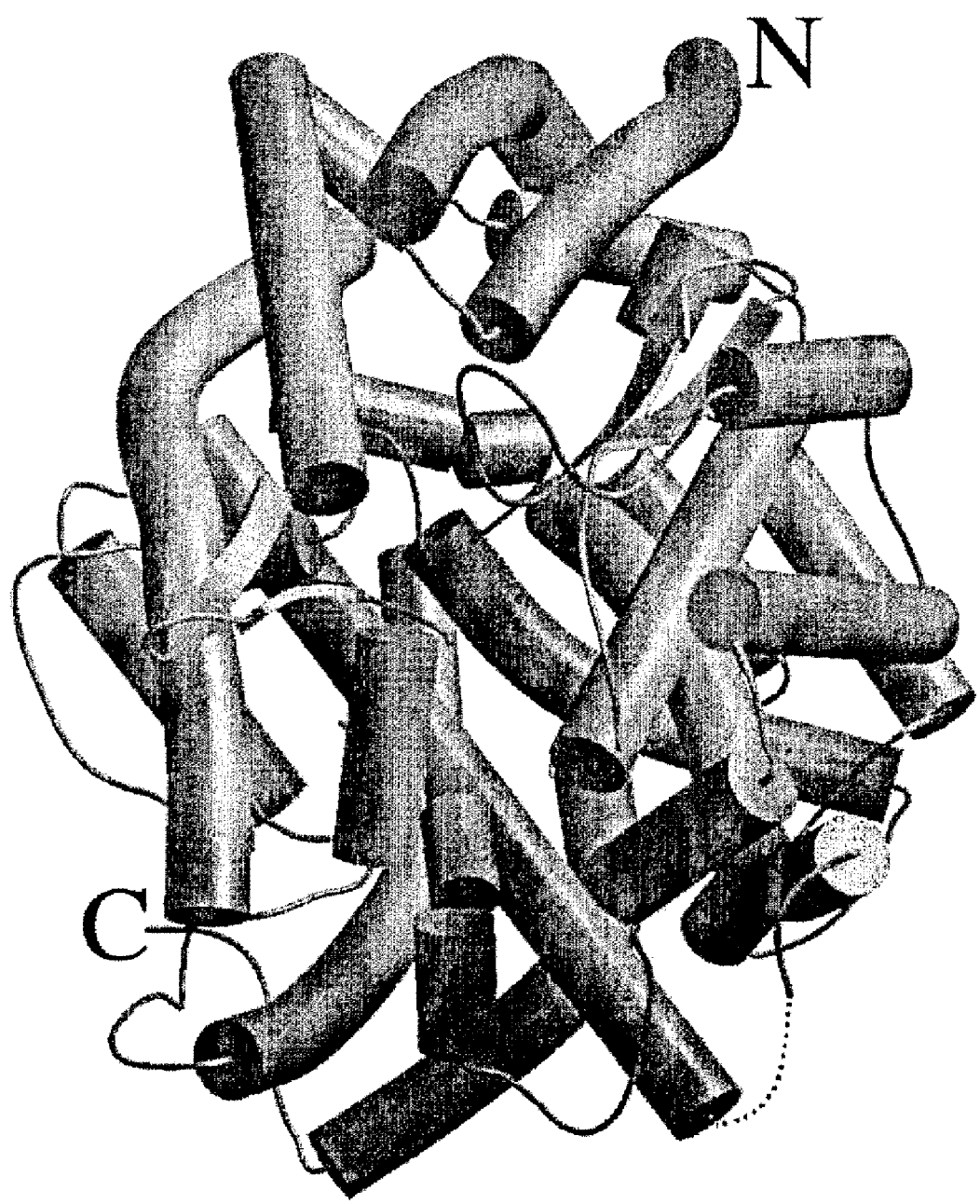
FIG. 9 illustrates the comparison of (a) ACE and (b) Neurolysin folds. The same view as in FIG. 7a has been retained.
Figure 9B:
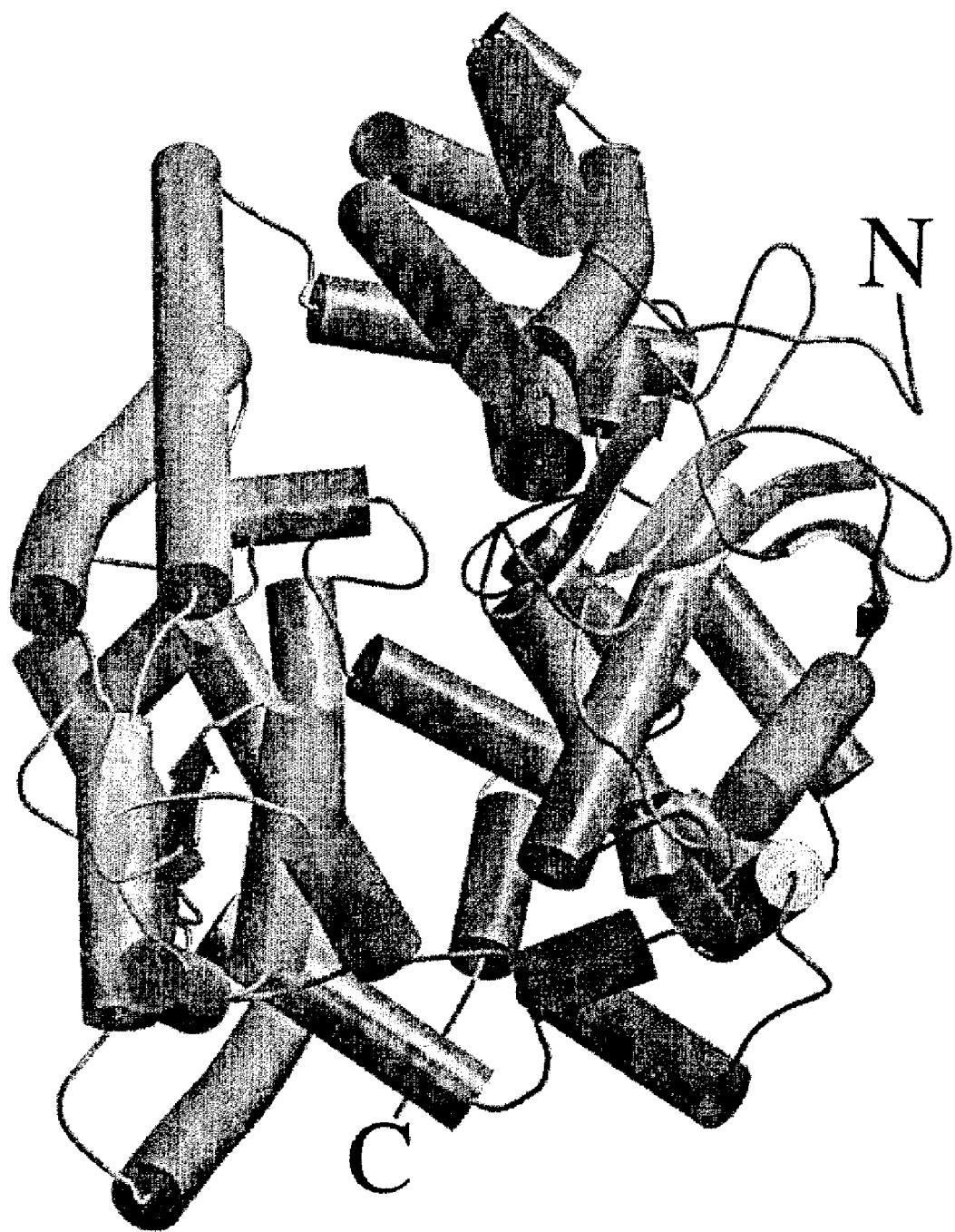

Highly ordered binding of the inhibitor (overall B-factor 15.26 Å$^2$) in an extended conformation with the aromatic phenyl group stretching towards the flap (FIG. 7a) and its lysine side chain parallel to the HEXXH motif (Table 1). Upon complex formation no significant rearrangement of active site residues was observed. The $P_1$ carboxylate of lisinopril which is substituted for the normal substrate scissile amide carbonyl is well positioned to bind to the active site zinc (located between subsites $S_1$ and $S_1$'). Thus lisinopril provides a coordinating atom (provided by an acetate ion in the native structure, FIG. 8a), while the other three (two histidines and a glutamic acid) being the same as in the native structure (FIG. 8b). The phenyl ethyl group binds to the $S_1$ subsite and the lysyl amine to Glu 193 via van der Waals interactions at the $S_1$' subsite of ACE. Surprisingly, the C-terminal carboxylate which is thought to interact with a positively charged arginine residue instead binds to a lysine (Lys 542) as well as Tyr 551. The high affinity is attributable to the presence of the S-configuration aromatic, aralkyl or aliphatic groups able to bind to the $S_1$ site (Brenner et al., 1990). The contact residues for the lisinopril complex are shown in Table 1. The co-ordinates of the underglycosylated tACEΔ36NJ ACE-lisinopril complex are shown in Table B.

Example 8

The Homology of ACE with Other Metallopeptidases

ACE belongs to the M2 family of zinc binding metallopeptidases which falls under the umbrella of the MA clan. Outside the HEXXH metal coordinating signature sequence of this family there is little sequence similarity between ACE and other members of the family. Surprisingly, peptidases such as thermolysin (MA clan, M4 family) and carboxypeptidase A (MC clan, M14 family) which have been used in comparative molecular field analysis and 3D quantitative structure-activity relationship studies (Waller & Marshall, 1993) showed no structural homology with ACE.

Surprisingly, structural comparison of ACE with other protein structures using the DALI server (Holm and Sander, 1999) showed significant structural homology with that of neurolysin (Brown et al., 2001), a protein involved in neurotensin metabolism (FIG. 3a, b). Neurolysin is a member of the M3 family of thimet oligopeptidases and like ACE, belongs to the family of metallopeptidases bearing the HEXXH active site motif (Rawlings and Barrett, 1995; Brown et al., 2001). It also comprises of an abundance of α-helices with the β-structure accounting for only 6% of all residues. The two proteins do not exhibit any amino acid sequence similarity (close to random score), yet when the two structures are optimally superimposed (using DALI server), there is noticeable match with an r.m.s. deviation of 4.0 Å for 143 $C_\alpha$ atoms. It appears that the core structure for the two proteins are highly similar with significant differences in loops on the outer surface in the case of neurolysin (FIG. 3a,b). The striking similarity also extends to the active site region in neurolysin consisting of a deep narrow channel that divides the molecule into two halves. It has been speculated that using the flexible secondary structure elements in the active site cavity, the neuropeptidase can effectively cleave a variety of small peptides. Likewise in ACE, the geometry of the active site groove clearly accounts for ACE's inability to hydrolyse large, folded substrates. Furthermore, the enzyme's preference for oligopeptide substrates of about thirteen residues or less suggests that the substrate does not have the same freedom to extend outside of the channel during catalysis.

Example 9

Substrate Specificity

The geometry of the active site channel clearly accounts for ACE's inability to hydrolyse large, folded substrates. Furthermore, the enzyme's preference for oligopeptide substrates of about thirteen residues or less suggests that the substrate does not have the same freedom to extend outside of the channel during catalysis.

Example 10

Figure 5:
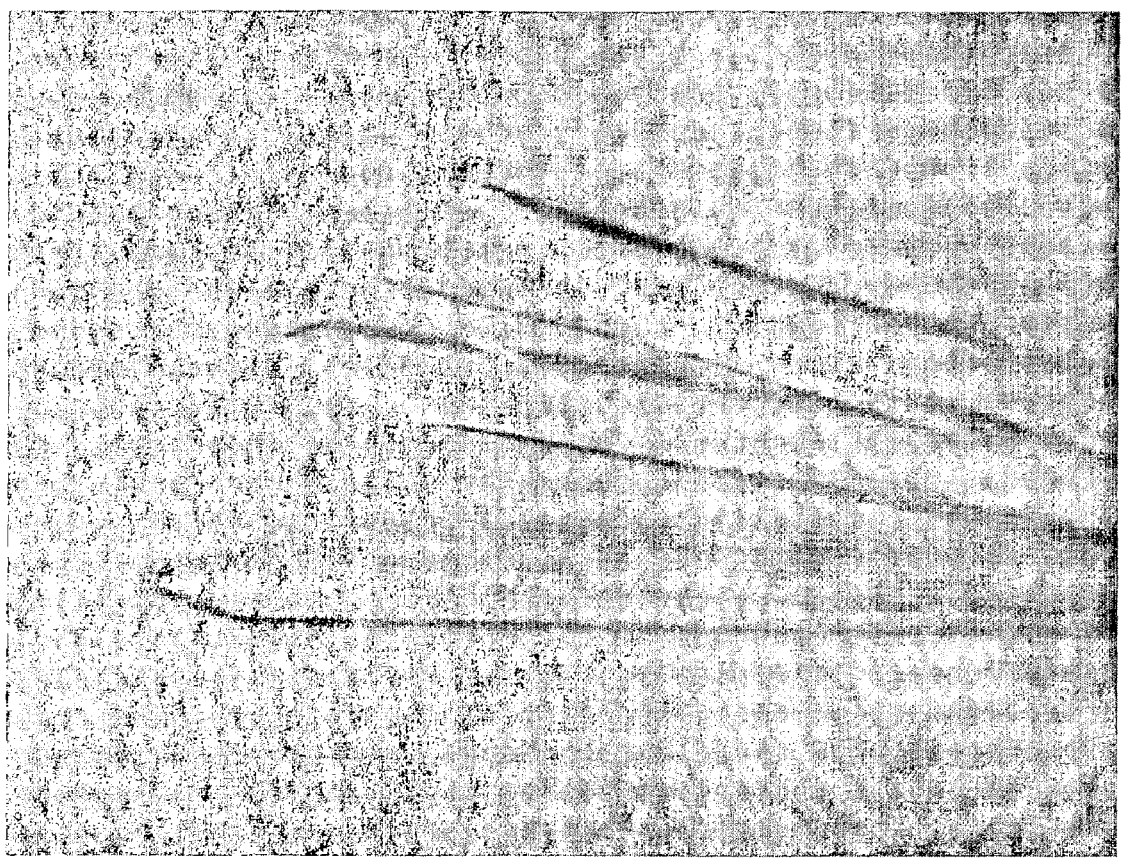
FIG. 5 represents the orthorhombic crystals of tACEΔ36.
Figure 6:
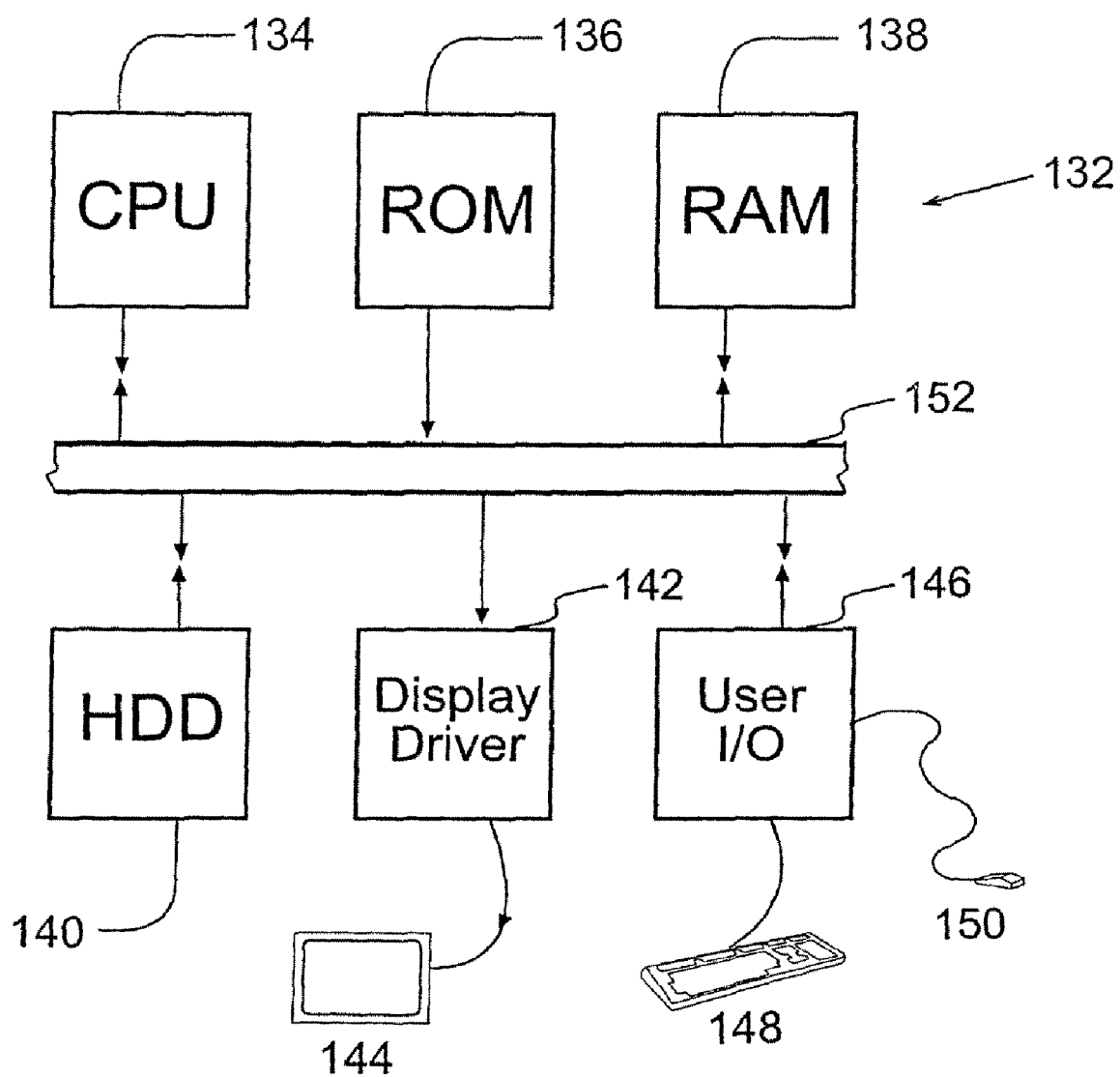
FIG. 6 schematically illustrates a general purpose computer (132) of the type that may be used in accordance with the present invention. The computer (132) includes a central processing unit (134), a read only memory (136), a random access memory (138), a hard disk drive (140), a display driver (142) and display (144) and a user input/output circuit (146) with a keyboard (148) and mouse (150) all connected via a common bus (152). The central processing unit (134) may execute program instructions stored within the ROM (136), the RAM (138) or the hard disk drive (140) to carry out processing of signal values that may be stored within the RAM (138) or the hard disk drive (140). The program may be written in a wide variety of different programming languages. The computer program itself may be stored and distributed on a recording medium, such as a compact disc, or may be downloaded over a network link (not illustrated). The general purpose computer (132) when operating under control of an appropriate computer program effectively forms an apparatus for performing aspects of the present invention.

Crystallization of ACE Mutants tACEΔ36-g1234 and tACEΔ36-g1,3 mutants are successfully crystallised under similar conditions as tACEΔ36NJ protein (FIG. 5). Preliminary diffraction experiments show that tACEΔ36-g1234 crystals diffract to at least 2.8 Å and tACEΔ36-g1,3 crystals diffract to 3.0 Å respectively and these crystals are isomorphous with tACEΔ36 crystals.

Conclusions

The minimal glycosylation requirements for the expression and processing of enzymatically-active human tACE are determined by progressive deglycosylation. To investigate which sugars are vital for tACE expression, a series of mutants are constructed that contain a limited number of sites for N-linked glycosylation. N-glycan recognition sequons within the protein sequence are disrupted by mutagenesis of the Asn to a Gln within the recognition sequon.

The removal of a large percentage of glycans does not hamper the expression of enzymatically-active tACEΔ36 and the presence of glycans at two of the three N-terminal sites is sufficient to produce protein that retain the kinetic properties of the native enzyme. Furthermore, the minimum N-linked glycosylation that allowed for enzymatically-active tACE to be expressed is the presence of glycans at the first or third site. Glycosylation at either of these sites appears to be sufficient for protein folding, whereas glycosylation of the second site only, results in rapid intracellular degradation. This is in agreement with the glycosylation requirements of active rabbit ACE expressed in mammalian cells and yeast which also has a minimal requirement of at least one of the three N-terminal sites (3a).

In the construction of the tACEΔ36 glycosylation mutants, the seventh site which is not present in rabbit tACE is not targeted as it has been shown to be unglycosylated (7a). With the removal of the glycosylated sequons, it is possible that this site may be glycosylated in order to compensate for the loss of oligosaccharide chains. However, this is not the case and that even when there is only one N-linked oligosaccharide, this does not occur.

There is a preference for oligosaccharides to be attached to sequons containing threonine residues rather than serine residues. This is observed in human tACE, where all sequons with a serine in the third position are partially glycosylated and those with threonine are fully glycosylated, except for the seventh site, which has a threonine in the third position (7a).

The fact that glycosylation at the seventh site appears to be occluded by the presence of the tryptophan, rather than the structure of the juxtamembrane region, is supported by the findings that a tACE deletion mutant, tACE-Δ6, which generates a novel Asn-Arg-Ser sequon adjacent to the wild-type cleavage site, is glycosylated (14a). The extended conformation of oligosaccharides may prevent access of the secretase at this point resulting in displacement of the wild-type cleavage site 13 residues towards the C-terminus (14a).

CHO cells expressing wild-type tACE (tACE-wt) are exposed to tunicamycin, which inhibits N-linked glycosylation, to determine the effect of complete deglycosylation on the expression and activity of tACE over time. Cellular tACE-wt activity in cells treated with tunicamycin is approximately three-fold lower than that of untreated cells (data not shown) and a smaller immature form of the protein is observed by Western blot analysis. These results are consistent with the interpretation that the smaller 85 kDa-protein is the deglycosylated form and the 105 kDa-protein, the mature glycosylated form (7a), (9a), (14a). Thus, tunicamycin inhibits the formation of mature glycosylated tACE-wt, to a certain degree, resulting in the accumulation of unglycosylated tACE-wt in the cell, without a significant decrease in the total amount of protein compared to untreated cells. Our data suggest that unglycosylated tACE-wt is not solubilised and that it requires the presence of N-glycans for proper expression, maturation and processing.

The enzymatically-active tACE-wt present in cells treated with tunicamycin is most likely the product of a pool of glycosylated tACE-wt, which is either produced prior to tunicamycin treatment or is resistant to tunicamycin. Tunicamycin may therefore not be completely effective in CHO cells, whereas in HeLa cells, Kasturi et al. found that tunicamycin-treatment resulted in the generation of deglycosylated protein that is degraded intracellularly within three-hours, with no soluble tACE being detected (5a). Thus, it appears that the effect of tunicamycin on tACE glycosylation appears to be cell-specific.

Enzymatic removal of N-linked glycans is used to produce crystals of CD2 glycoprotein that diffracted to 2.5 Å (15a). However, crystallisation trials with deglycosylated tACEΔ36NJ that has a single GlcNAc residue attached to the asparagine residue of the N-linked site only produced needle-like crystals that are not suitable for further diffraction studies. Surprisingly, tACEΔ36NJ expressed in the presence of NB-DNJ, but retaining the simple high mannose oligosaccharides (Glc$_3$Man$_7$GlcNAc$_2$) yielded the best crystals for X-ray diffraction studies and subsequent successful 3D structure determination at 2.0 Å resolution.

Interestingly, the presence of the membrane anchor increased the extent of human CD59 glycan processing (16a). Possible reasons for this difference are, that the ectodomain is held closer to the glycan-processing enzymes and/or the longer exposure to the glycosyltransferases. The oligosaccharide processing of soluble tACEΔ36NJ protein may also differ from the membrane-bound form however, expressing the protein in the presence of a glucosidase inhibitor would prevent the production of complex oligosaccharides.

Furthermore, the kinetic properties of this mutant are not influenced by NB-DNJ treatment. Similarly, Yu et al. reported identical $K_m$ values for glycosylated and deglycosylated forms of tACEΔ36NJ, in agreement with that of tACE-wt, using furanacryloyl-Phe-Gly-Gly as a substrate (7a). Glucosidase inhibitors, at concentrations required to block trimming of the terminal glucose residues and subsequent complex oligosaccharide formation, can affect cell maturation and apoptosis (Misago M, Tsukada J, Fukuda M N, Eto S (2000) Biochem Biophys Res Commun. 269, 219-225). This treatment also results in a decrease in protein expression (unpublished data). Thus, mutants lacking some of the C-terminal N-linked glycans are used with the objective of producing protein with a minimal number of oligosaccharides that would crystallise in a reproducible fashion.

Crystals of glycosylation mutants g13 and g1234 have been grown under similar condition as in the case of tACEΔ36NJ. The glycosylation mutant crystals seem to grow faster than tACEΔ36NJ crystals. However, they are smaller in size in the first instance, but have been proven to be suitable for diffraction work.

The determination of the 3D structure of ACE and ACE-lisinopril complex may be effectively used for the development of novel, highly selective ACE modulators targeted, for example, to either the N or the C domain, by structure-based rational drug design. This may produce a new generation of ACE inhibitors with the potential for greater efficacy, fewer side effects and treatment of new indications (e.g. polycythemia). In addition, the unanticipated similarity with neurolysin has shown the structural conservation amongst an emerging family of peptidases with a common evolutionary origin.

In a further aspect, the present invention relates to a composition comprising ACE in a crystalline form.

In a further aspect, the present invention relates to a scalable 3D model of ACE having at least a portion of the structure co-ordinates shown in Table A or Table B.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

REFERENCES 1

1. Beldent, V., Michaud, A., Wei, L., Chauvet, M. T., and Corvol, P. (1993) *J. Biol. Chem.* 268, 26428-26434.
2. Schwager, S. L. U., Chubb, A. J., Scholle, R. R., Brandt, W. F., Riordan, J. F., Mentele, R., Sturrock, E. D and Ehlers, M. R. W. (1999) *Biochemistry* 38, 10388-10397.
3. Schwager, S. L. U., Chubb, A. J., Woodman, Z. L., Yan, L., Mentele, R., Ehlers, M. R. W., and Sturrock, E. D. (2001) *Biochemistry* 40, 15624-15630.
4. Yu, X. C., Sturrock, E. D., Wu, Z., Biemann, K., Ehlers, M. R. W., and Riordan, J. F. (1997) *J. Biol. Chem.* 272, 3511-3519.

5. Sturrock, E. D., Yu, X. C., Wu, Z., Biemann, K., and Riordan, J. F. (1996) *Biochemistry* 35, 9560-9566.

REFERENCES 2

1a. Junot, C., Gonzales, M. F., Ezan, E., Cotton, J., Vazeux, G., Michaud, A., Azizi, M., Vassiliou, S., Yiotakis, A., Corvol, P., and Dive, V. (2001) *J. Pharmacol. Exp. Ther.* 297, 606-611.
2a. Esther, C. R., Marino, E. M., Howard, T. E., Machaud, A., Corvol, P., Capecchi, M. R., and Bernstein, K. E. (1997) *J. Clin. Invest* 99, 2375-2385.
3a. Sadhukhan, R. and Sen, I. (996) *J. Biol. Chem.* 271, 6429-6434.
4a. Kumar, R. S., Kusari, J., Roy, S. N., Soffer, R. L., and Sen, G. C. (1989) *J. Biol. Chem.* 264, 16754-16758.
5a. Kasturi, S., Jabbar, M. A., Sen, G. C., and Sen, I. (1994) *Biochemistry* 33, 6228-6234.
6a. Ehlers, M. R., Chen, Y. N., and Riordan, J. F. (1992) *Biochem. Biophys. Res. Commun.* 183, 199-205.
7a. Yu, X. C., Sturrock, E. D., Wu, Z., Biemann, K., Ehlers, M. R., and Riordan, J. F. (1997) *J. Biol. Chem.* 272, 3511-3519.
8a. Ehlers, M. R., Schwager, S. L., Scholle, R. R., Manji, G. A., Brandt, W. F., and Riordan, J. F. (1996) *Biochemistry* 35, 9549-9559.
9a. Schwager, S. L., Chubb, A. J., Scholle, R. R., Brandt, W. F., Eckerskorn, C., Sturrock, E. D., and Ehlers, M. R. (1998) *Biochemistry* 37, 15449-15456.
10a. Wei, L., Alhenc-Gelas, F., Corvol, P., and Clauser, E. (1991) *J. Biol. Chem.* 266, 9002-9008.
11a. Nachon, F., Nicolet, Y., Viguie, N., Masson, P., Fontecilla-Camps, J. C., and Lockridge, O. (2002) *Eur. J. Biochem.* 269, 630-637.
12a. Couvineau, A., Fabre, C., Gaudin, P., Maoret, J. J., and Laburthe, M. (1996) *Biochemistry* 35, 1745-1752.
13a. Zhou, A. T., Assil, I., and Abou-Samra, A. B. (2000) *Biochemistry* 39, 6514-6520.
14a. Schwager, S. L., Chubb, A. J., Scholle, R. R., Brandt, W. F., Mentele, R., Riordan, J. F., Sturrock, E. D., and Ehlers, M. R. (1999) *Biochemistry* 38, 10388-10397.
15a. Davis, S. J., Davies, E. A., Barclay, A. N., Daenke, S., Bodian, D. L., Jones, E. Y., Stuart, D. I., Butters, T. D., Dwek, R. A., and van der Merwe, P. A. (1995) *J. Biol. Chem.* 270, 369-375.
16a. Wheeler, S. F., Rudd, P. M., Davis, S. J., Dwek, R. A., and Harvey, D. J. (2002) *Glycobiology* 12, 261-271.

REFERENCES 3

Abrahams, J. P. & Leslie, A. G. W. Methods used in structure determination of bovine mitochondrial F1 ATPase. *Acta Crystallogr. D* 52, 110-119 (1996).
Aghajari, N., Feller, G., Gerday, C. & Haser, R. Structural basis of α-amylase activation by chloride. *Prot. Sci.* 11, 1435-1441 (2002).
Brenner B. N., Ballermann, B. J., Gunning, M. E. & Zeidel, M. L. Diverse biological actions of natriuretic peptide *Physiol. Rev.* 70, 665-699 (1990).
Brown, C. K., Madauss, K., Lian, W., Beck, M. R., Tolbert, W. D. & Rodgers, D. W. Structure of neurolysin reveals a deep channel that limits substrate access. *Proc. Natl. Acad. Sci. USA* 98, 3127-3132 (2001).
Brünger, A. T. Free R value: a novel statistical quantity for assessing the accuracy of crystal structure. *Nature* 355, 472-475 (1992).
Brünger, A. T. et al. Crystallography & NMR System: A new software suite for macromolecular structure determination. *Acta Crystallogr. D* 54, 905-921 (1998).
Bunning, P. & Riordan, J. F. Activation of angiotensin converting enzyme by monovalent anions. *Biochem.* 22, 110-116 (1983).
Chubb A. J. Schwager S. L. U., Woodman Z. L., Ehlers, M. R. E., and Sturrock E. D. Defining the ectodomain of angiotensin-converting enzyme. *Biochem. Biophys. Res. Comm.* (2002) in press.
Collaborative computational project Number 4. The CCP4 Suite: Programs for Protein Crystallography. *Acta Crystallogr. D* 50, 760-763 (1994).
Corval, P., Williams, T. A. & Soubrier, F. Peptidyl dipeptidase. A: angiotensin I-converting enzyme. *Methods Enzymol.* 248, 283-305 (1995).
Cushman, D. W., Cheung, H. S., Sabo, E. F. & Ondetti, M. A. Design of potent competitive inhibitors of angiotensin-converting enzyme. Carboxyalkanoyl and mercaptoalkanoyl amino acids. *Biochemistry,* 16, 5484-5491 (1977).
De La Fortelle, E. & Bricogne, G. Maximum-likelihood heavy-atom parameters refinement in the MIR and MAD methods. *Methods Enzymol.* 276, 472-494 (1997).
Holm, L. & Sander, C. Protein folds and families: sequence and structure alignments. *Nucleic Acid Res.* 27, 244-247 (1999).
Hooper, N. M. Families of zinc metalloproteases. *FEBS Lett.* 354, 1-6 (1994).
Jones, T. A., Zou, J. Y., Cowan, S. W. & Kjeldgaard, M. Improved methods for building protein models in electron density maps and the location of errors in these models. *Acta Crystallogr. A* 47, 110-119 (1991).
Kraulis, P. MOLSCRIPT: a program to produce both detailed and schematic plots of protein structures. *J. Appl. Crystallogr.* 24, 946-950 (1991).
Liu, X., Fernandez, M., Wouters, M. A., Heyberger, S. & Husain, A. Arg-1098 is critical for the chloride dependence of human angiotensin-1 converting enzyme C-domain catalytic activity. *J. Biol. Chem.* 276, 33518-33525 (2001).
Merritt, E. A. & Bacon, D. J. Raster 3D: photorealistic molecular graphics. *Methods Enzymol.* 277, 505-524 (1997).
Otwinowski, M. & Minor, W. Processing of X-ray diffraction data collected in oscillation mode. *Methods Enzymol* 276, 307-326 (1997).
Rawlings, N. D. & Barrett, A. J. Evolutionary families of metallopeptidases. *Methods Enzymol.* 248, 182-228 (1995).
Shapiro, R., Holmquist, B. & Riordan, J. F. Anion activation of angiotensin converting enzyme: dependence of nature of substrate. *Biochem.* 22, 3850-3857 (1983).
Waller, C. L. & Marshall, G. R. Three-dimensional quantitative structure-activity relationship of angiotesin-converting enzyme and thermolysin inhibitors. II. A comparison of CoMFA models incorporating molecular orbital fields and desolvation free energies based on active-analog and complementary-receptor-field alignment rules. *J. Med. Chem.* 36, 2390-2403 (1993).
Wei, L., Alhenc-Gelas, F., Corvol, P. & Clauser, E. The two homologous domains of human angiotensin-1 converting enzyme are both catalytically active. *J. Biol. Chem.* 266, 9002-9008 (1991).
Williams, T. A., Corvol, O. & Soubrier, F. Identification of two active site residues in human angiotensin I—converting enzyme. *J. Biol. Chem.* 269, 29430-29434 (1994).

TABLE 1

ACE-Lisinopril Contact Residues (hydrogen bonds at the active site)

| Ligand atoms Lisinopril atom | Interacting atoms | Distance (Å) |
|---|---|---|
| O1 | His 384 NE2 | 2.76 |
| N1 | His 384 NE2 | 3.24 |
| N1 | Ala 385 O | 2.92 |
| O4 | Lys 542 NZ | 2.93 |
| O4 | Tyr 551 OH | 2.56 |
| O3 | Tyr 554 OH | 2.77 |
| O2 | Wat | 2.82 |
| O5 | Wat | 2.68 |
| N3 | Wat | 3.01 |
| N3 | Wat | 3.26 |
| O5 | Wat | 2.77 |
| N3 | Wat | 3.11 |
| O2 | Glu 415 OE2 | 2.70 |
| O1 | His 544 NE2 | 3.11 |

Zinc Coordination-ACE-Lisinopril Complex

| Coordination | | Distance (Å) |
|---|---|---|
| Zn | His 414 NE2 | 2.04 |
| Zn | His 418 NE2 | 2.07 |
| Zn | Glu 442 OE1 | 2.00 |
| Zn | Lis O3 | 2.14 |

Lis = Lisinopril

TABLE 2

Data Collection

| Crystal | | Wavelength (Å) | Resolution range[a] (Å) | % completeness[a] | $<I>/<\sigma>$[a] | $R_{merge}$[ab] (%) |
|---|---|---|---|---|---|---|
| MAD Phasing data. | Zn Peak | 1.2825 | 50-2.00 (2.07-2.00) | 94.7 (63.2) | 11.54 (1.93) | 5.4 (22.3) |
| | Zn infl. | 1.2832 | 50-2.01 (2.08-2.01) | 95.9 (72.1) | 11.55 (1.98) | 5.8 (23.8) |
| | Zn rem. | 0.9537 | 50-1.98 (2.05-1.98) | 94.1 (65.8) | 15.48 (2.63) | 4.8 (14.9) |
| | Long Wavelength | 1.7712 | 50-2.66 (2.76-2.66) | 99.6 (97.0) | 22.92 (4.94) | 8.3 (21.8) |
| MIRAS Phasing data | | | | | | |
| Pt | | 0.87 | 20-2.80 (2.9-2.8) | 90.2 (83.6) | 9.94 (4.52) | 11.2 (27.1) |
| Pt25 | | 0.87 | 20-2.60 (2.69-2.6) | 89.9 (75.9) | 13.6 (4.17) | 8.8 (27.8) |
| Pd | | 0.978 | 50-2.18 (2.26-2.18) | 89.4 (81.2) | 26.14 (6.73) | 5.8 (25.8) |
| Pd2 | | 0.978 | 30-2.60 (2.69-2.6) | 95.2 (86.7) | 16.95 (5.46) | 9.5 (35.7) |
| Oscl | | 1.488 | 50-2.80 (2.9-2.8) | 96.6 (91.4) | 18.51 (6.16) | 13.1 (40.4) |
| Native Data | | 1.488 | 50-2.00 (2.07-2.0) | 98.8 (95.7) | 22.46 (4.44) | 8.1 (43.2) |

Refinement

| Model | Resolution (Å) | Reflections working/test | $R_{cryst}$[c] (%) | $R_{free}$[d] (%) | Rms deviations Bond length (Å) | Rms deviations Bond angle (°) | B factor Rmsd (Å²) Bonded Main Chain Atoms | B factor Rmsd (Å²) Bonded Side Chain Atoms |
|---|---|---|---|---|---|---|---|---|
| Native (ACE) | 47.14-2.0 | 39727/1675 | 18.29 | 22.08 | 0.005 | 1.22 | 1.281 | 2.126 |
| Lisinopril complex (ACE-LIS) | 47.14-2.0 | 76164/3094 | 18.14 | 21.88 | 0.0055 | 1.24 | 1.174 | 2.048 |

[a]Values in parentheses are for the outer resolution shell.
[b]$R_{merge} = \Sigma|I - <I>|/\Sigma I$, where I is the observed intensity and $<I>$ is the average intensity obtained from multiple observations of symmetry related reflections.
[c]$R_{cryst} = \Sigma|Fo| - |Fc|/\Sigma|Fo|$ where Fo and Fc are observed and calculated structure factors respectively.
[d]$R_{free}$ is obtained for a test set of reflections, consisting of a randomly selected ~4% of reflections.

TABLE 3

Kinetic parameters for the hydrolysis of Hip-His-Leu by various tACE glycoforms

|  | $K_m$ (mM) | $k_{cat}$ (sec$^{-1}$) | $k_{cat}/K_m$ (sec$^{-1}$mM$^{-1}$) |
|---|---|---|---|
| tACE-wt | 2.7 | 193 | 72 |
| tACEΔ36-g1 | 1.6 | 128 | 79 |
| tACEΔ36-g3 | 2.5 | 111 | 44 |
| tACEΔ36-g13 | 2.7 | 170 | 63 |
| tACEΔ36-g2 | inactive | inactive | inactive |
| tACEΔ36-g12 | 2.1 | 195 | 94 |
| tACEΔ36-g123 | 2.7 | 189 | 71 |
| tACEΔ36-g1234 | 1.5 | 85 | 56 |
| tACEΔ36-NJ[1] | 2.6 | 253 | 99 |
| tACEΔ36-NJ[2] | 4.1 | 289 | 70 |

[1] Expressed in CHO cells treated with NB-DNJ.
[2] Expressed in NB-DNJ-untreated CHO cells.

TABLE 4

Mass Spectral Analysis of C-Terminal Endoproteinase Lys-C Peptides[a]

| Peptide (residue no.[b]) | tACEΔ36-g1 | tACEΔ36g-1 | tACEΔ36-g1234 | tACEΔ36NJ |
|---|---|---|---|---|
| 598-613[c] | 1951.6 (1951.2) | 1950.6 (1951.2) | 1950.2 (1951.2) | 1951.5 (1951.2) |
| 614-627[d] | 1689.7 (1690.8) | 1690.5 (1690.8) | 1690.9 (1690.5) |  |
| 614-625[d] |  |  |  | 1463.1 (1463.5) |

[a]Soluble (shed) ACE proteins were purified from conditioned medium of transfected cells, digested with endoproteinase Lys-C and analyzed by MALDI-TOF mass spectrometry.
[b]Amino acid residue numbering refers to wild type tACE (Ehlers et al 1989). Shown are the masses of the penultimate
[c]and ultimate
[d]C-terminal peptides. All values are calculated for protonated isotopically averaged molecular masses m/z. In parentheses are expected masses.

TABLE A

Co-ordinates of underglycosylated tACEΔ36NJ ACE

```
REMARK   coordinates from minimization refinement
REMARK   refinement resolution: 47.14-2.0 A
REMARK   starting    r = 0.1829 free_r = 0.2206
REMARK   final       r = 0.1829 free_r = 0.2208
REMARK   rmsd bonds = 0.005706 rmsd angles = 1.22440
REMARK   wa = 0.837519
REMARK   target = mlf cycles = 1 steps = 20
REMARK   sg = P2(1)2(1)2(1) a = 56.621 b = 85.062 c = 133.791 alpha = 90 beta = 90 gamma = 90
REMARK   ncs = none
REMARK   B-correction resolution: 6.0-2.0
REMARK   initial B-factor correction applied to fobs:
REMARK       B11 =   2.826 B22 =  -1.896 B33 =  -0.930
REMARK       B12 =   0.000 B13 =   0.000 B23 =   0.000
REMARK   B-factor correction applied to coordinate array B:     0.207
REMARK   bulk solvent: density level = 0.355826 e/A^3, B-factor = 50.0907 A^2
REMARK   reflections with |Fobs|/sigma_F < 0.0 rejected
REMARK   reflections with |Fobs| > 10000 * rms(Fobs) rejected
REMARK   theoretical total number of refl. in resol. range: 44472 ( 100.0% )
REMARK   number of unobserved reflections (no entry or |F| = 0): 3070 ( 6.9% )
REMARK   number of reflections rejected:              0 (  0.0% )
REMARK   total number of reflections used:        41402 ( 93.1% )
REMARK   number of reflections in working set:    39727 ( 89.3% )
REMARK   number of reflections in test set:        1675 (  3.8% )
CRYST1   56.621  85.062  133.791   90.00   90.00   90.00 P 21 21 21
REMARK   VERSION: 1.1
ATOM     1   CB   ALA   71   34.205   71.662   65.620   1.00   47.11
ATOM     2   C    ALA   71   36.244   70.263   65.985   1.00   47.34
ATOM     3   O    ALA   71   36.117   69.044   65.862   1.00   47.51
ATOM     4   N    ALA   71   35.784   72.211   67.437   1.00   47.96
ATOM     5   CA   ALA   71   35.164   71.098   66.663   1.00   47.50
ATOM     6   N    GLU   72   37.307   70.929   65.547   1.00   46.68
ATOM     7   CA   GLU   72   38.419   70.260   64.882   1.00   46.09
ATOM     8   CB   GLU   72   39.315   71.298   64.200   1.00   46.87
ATOM     9   CG   GLU   72   40.370   70.727   63.262   1.00   47.65
ATOM    10   CD   GLU   72   39.776   70.111   62.005   1.00   48.95
ATOM    11   OE1  GLU   72   38.997   70.801   61.309   1.00   48.20
ATOM    12   OE2  GLU   72   40.096   68.939   61.708   1.00   49.03
ATOM    13   C    GLU   72   39.223   69.474   65.916   1.00   45.81
```

TABLE A-continued

| | | | | | | | | | |
|---|---|---|---|---|---|---|---|---|---|
| ATOM | 14 | O | GLU | 72 | 39.862 | 68.466 | 65.594 | 1.00 | 45.67 |
| ATOM | 15 | N | ALA | 73 | 39.184 | 69.941 | 67.161 | 1.00 | 43.82 |
| ATOM | 16 | CA | ALA | 73 | 39.905 | 69.292 | 68.249 | 1.00 | 42.35 |
| ATOM | 17 | CB | ALA | 73 | 39.995 | 70.229 | 69.446 | 1.00 | 42.98 |
| ATOM | 18 | C | ALA | 73 | 39.210 | 67.996 | 68.646 | 1.00 | 40.96 |
| ATOM | 19 | O | ALA | 73 | 39.863 | 66.990 | 68.926 | 1.00 | 39.62 |
| ATOM | 20 | N | GLU | 74 | 37.881 | 68.028 | 68.680 | 1.00 | 40.60 |
| ATOM | 21 | CA | GLU | 74 | 37.104 | 66.844 | 69.025 | 1.00 | 40.79 |
| ATOM | 22 | CB | GLU | 74 | 35.620 | 67.190 | 69.157 | 1.00 | 42.97 |
| ATOM | 23 | CG | GLU | 74 | 35.138 | 67.389 | 70.581 | 1.00 | 48.05 |
| ATOM | 24 | CD | GLU | 74 | 33.642 | 67.644 | 70.649 | 1.00 | 51.91 |
| ATOM | 25 | OE1 | GLU | 74 | 32.869 | 66.798 | 70.142 | 1.00 | 53.53 |
| ATOM | 26 | OE2 | GLU | 74 | 33.239 | 68.687 | 71.210 | 1.00 | 53.71 |
| ATOM | 27 | C | GLU | 74 | 37.272 | 65.799 | 67.931 | 1.00 | 38.90 |
| ATOM | 28 | O | GLU | 74 | 37.217 | 64.597 | 68.192 | 1.00 | 38.20 |
| ATOM | 29 | N | ALA | 75 | 37.482 | 66.273 | 66.706 | 1.00 | 37.33 |
| ATOM | 30 | CA | ALA | 75 | 37.643 | 65.395 | 65.552 | 1.00 | 35.44 |
| ATOM | 31 | CB | ALA | 75 | 37.619 | 66.217 | 64.268 | 1.00 | 34.80 |
| ATOM | 32 | C | ALA | 75 | 38.917 | 64.558 | 65.613 | 1.00 | 33.72 |
| ATOM | 33 | O | ALA | 75 | 38.871 | 63.343 | 65.434 | 1.00 | 34.25 |
| ATOM | 34 | N | SER | 76 | 40.053 | 65.204 | 65.856 | 1.00 | 32.28 |
| ATOM | 35 | CA | SER | 76 | 41.319 | 64.486 | 65.932 | 1.00 | 32.11 |
| ATOM | 36 | CB | SER | 76 | 42.486 | 65.468 | 66.012 | 1.00 | 33.65 |
| ATOM | 37 | OG | SER | 76 | 42.391 | 66.266 | 67.175 | 1.00 | 40.00 |
| ATOM | 38 | C | SER | 76 | 41.326 | 63.562 | 67.148 | 1.00 | 30.77 |
| ATOM | 39 | O | SER | 76 | 41.948 | 62.501 | 67.126 | 1.00 | 30.49 |
| ATOM | 40 | N | LYS | 77 | 40.631 | 63.974 | 68.204 | 1.00 | 29.20 |
| ATOM | 41 | CA | LYS | 77 | 40.534 | 63.179 | 69.424 | 1.00 | 29.11 |
| ATOM | 42 | CB | LYS | 77 | 39.924 | 64.021 | 70.547 | 1.00 | 32.76 |
| ATOM | 43 | CG | LYS | 77 | 39.438 | 63.219 | 71.745 | 1.00 | 35.84 |
| ATOM | 44 | CD | LYS | 77 | 38.889 | 64.135 | 72.830 | 1.00 | 42.05 |
| ATOM | 45 | CE | LYS | 77 | 38.072 | 63.355 | 73.847 | 1.00 | 44.16 |
| ATOM | 46 | NZ | LYS | 77 | 36.868 | 62.741 | 73.208 | 1.00 | 47.21 |
| ATOM | 47 | C | LYS | 77 | 39.662 | 61.952 | 69.160 | 1.00 | 28.16 |
| ATOM | 48 | O | LYS | 77 | 39.966 | 60.844 | 69.613 | 1.00 | 25.92 |
| ATOM | 49 | N | PHE | 78 | 38.573 | 62.163 | 68.427 | 1.00 | 26.59 |
| ATOM | 50 | CA | PHE | 78 | 37.661 | 61.079 | 68.083 | 1.00 | 26.14 |
| ATOM | 51 | CB | PHE | 78 | 36.495 | 61.610 | 67.250 | 1.00 | 26.37 |
| ATOM | 52 | CG | PHE | 78 | 35.634 | 60.527 | 66.657 | 1.00 | 28.09 |
| ATOM | 53 | CD1 | PHE | 78 | 34.772 | 59.788 | 67.459 | 1.00 | 27.07 |
| ATOM | 54 | CD2 | PHE | 78 | 35.700 | 60.238 | 65.297 | 1.00 | 27.78 |
| ATOM | 55 | CE1 | PHE | 78 | 33.983 | 58.776 | 66.916 | 1.00 | 28.93 |
| ATOM | 56 | CE2 | PHE | 78 | 34.914 | 59.224 | 64.745 | 1.00 | 29.96 |
| ATOM | 57 | CZ | PHE | 78 | 34.055 | 58.493 | 65.558 | 1.00 | 27.46 |
| ATOM | 58 | C | PHE | 78 | 38.407 | 60.018 | 67.281 | 1.00 | 24.51 |
| ATOM | 59 | O | PHE | 78 | 38.293 | 58.825 | 67.555 | 1.00 | 25.03 |
| ATOM | 60 | N | VAL | 79 | 39.174 | 60.460 | 66.290 | 1.00 | 24.17 |
| ATOM | 61 | CA | VAL | 79 | 39.928 | 59.539 | 65.448 | 1.00 | 25.75 |
| ATOM | 62 | CB | VAL | 79 | 40.647 | 60.296 | 64.315 | 1.00 | 27.26 |
| ATOM | 63 | CG1 | VAL | 79 | 41.588 | 59.362 | 63.574 | 1.00 | 29.96 |
| ATOM | 64 | CG2 | VAL | 79 | 39.618 | 60.868 | 63.352 | 1.00 | 26.11 |
| ATOM | 65 | C | VAL | 79 | 40.944 | 58.732 | 66.255 | 1.00 | 26.10 |
| ATOM | 66 | O | VAL | 79 | 41.109 | 57.527 | 66.030 | 1.00 | 26.21 |
| ATOM | 67 | N | GLU | 80 | 41.624 | 59.390 | 67.191 | 1.00 | 25.41 |
| ATOM | 68 | CA | GLU | 80 | 42.605 | 58.707 | 68.031 | 1.00 | 26.15 |
| ATOM | 69 | CB | GLU | 80 | 43.302 | 59.699 | 68.974 | 1.00 | 30.36 |
| ATOM | 70 | CG | GLU | 80 | 44.036 | 60.832 | 68.267 | 1.00 | 34.75 |
| ATOM | 71 | CD | GLU | 80 | 44.759 | 61.760 | 69.233 | 1.00 | 39.99 |
| ATOM | 72 | OE1 | GLU | 80 | 44.149 | 62.161 | 70.251 | 1.00 | 41.71 |
| ATOM | 73 | OE2 | GLU | 80 | 45.934 | 62.096 | 68.971 | 1.00 | 40.92 |
| ATOM | 74 | C | GLU | 80 | 41.910 | 57.627 | 68.858 | 1.00 | 23.94 |
| ATOM | 75 | O | GLU | 80 | 42.408 | 56.504 | 68.979 | 1.00 | 22.22 |
| ATOM | 76 | N | GLU | 81 | 40.759 | 57.969 | 69.431 | 1.00 | 22.01 |
| ATOM | 77 | CA | GLU | 81 | 40.011 | 57.013 | 70.237 | 1.00 | 22.46 |
| ATOM | 78 | CB | GLU | 81 | 38.831 | 57.706 | 70.927 | 1.00 | 25.23 |
| ATOM | 79 | CG | GLU | 81 | 39.227 | 58.391 | 72.231 | 1.00 | 29.28 |
| ATOM | 80 | CD | GLU | 81 | 38.161 | 59.326 | 72.773 | 1.00 | 32.89 |
| ATOM | 81 | OE1 | GLU | 81 | 36.960 | 58.986 | 72.693 | 1.00 | 34.63 |
| ATOM | 82 | OE2 | GLU | 81 | 38.531 | 60.399 | 73.298 | 1.00 | 35.89 |
| ATOM | 83 | C | GLU | 81 | 39.524 | 55.860 | 69.369 | 1.00 | 21.38 |
| ATOM | 84 | O | GLU | 81 | 39.678 | 54.686 | 69.725 | 1.00 | 19.63 |
| ATOM | 85 | N | TYR | 82 | 38.948 | 56.197 | 68.220 | 1.00 | 19.43 |
| ATOM | 86 | CA | TYR | 82 | 38.461 | 55.179 | 67.303 | 1.00 | 19.72 |
| ATOM | 87 | CB | TYR | 82 | 37.927 | 55.832 | 66.024 | 1.00 | 19.77 |
| ATOM | 88 | CG | TYR | 82 | 37.545 | 54.837 | 64.951 | 1.00 | 20.35 |
| ATOM | 89 | CD1 | TYR | 82 | 36.376 | 54.078 | 65.054 | 1.00 | 19.98 |
| ATOM | 90 | CE1 | TYR | 82 | 36.033 | 53.145 | 64.074 | 1.00 | 20.16 |
| ATOM | 91 | CD2 | TYR | 82 | 38.363 | 54.638 | 63.842 | 1.00 | 20.13 |
| ATOM | 92 | CE2 | TYR | 82 | 38.033 | 53.708 | 62.858 | 1.00 | 21.53 |
| ATOM | 93 | CZ | TYR | 82 | 36.866 | 52.967 | 62.980 | 1.00 | 20.57 |

TABLE A-continued

| | | | | | | | | |
|---|---|---|---|---|---|---|---|---|
| ATOM | 94 | OH | TYR | 82 | 36.538 | 52.053 | 62.011 | 1.00 | 19.33 |
| ATOM | 95 | C | TYR | 82 | 39.581 | 54.201 | 66.940 | 1.00 | 18.48 |
| ATOM | 96 | O | TYR | 82 | 39.382 | 52.987 | 66.944 | 1.00 | 19.79 |
| ATOM | 97 | N | ASP | 83 | 40.760 | 54.734 | 66.637 | 1.00 | 20.94 |
| ATOM | 98 | CA | ASP | 83 | 41.889 | 53.897 | 66.236 | 1.00 | 23.21 |
| ATOM | 99 | CB | ASP | 83 | 43.052 | 54.766 | 65.748 | 1.00 | 25.46 |
| ATOM | 100 | CG | ASP | 83 | 44.149 | 53.945 | 65.092 | 1.00 | 31.10 |
| ATOM | 101 | OD1 | ASP | 83 | 43.862 | 53.293 | 64.065 | 1.00 | 33.90 |
| ATOM | 102 | OD2 | ASP | 83 | 45.293 | 53.941 | 65.597 | 1.00 | 31.88 |
| ATOM | 103 | C | ASP | 83 | 42.398 | 52.937 | 67.307 | 1.00 | 23.85 |
| ATOM | 104 | O | ASP | 83 | 42.600 | 51.751 | 67.037 | 1.00 | 23.74 |
| ATOM | 105 | N | ARG | 84 | 42.617 | 53.431 | 68.521 | 1.00 | 23.48 |
| ATOM | 106 | CA | ARG | 84 | 43.117 | 52.548 | 69.565 | 1.00 | 24.21 |
| ATOM | 107 | CB | ARG | 84 | 43.576 | 53.351 | 70.792 | 1.00 | 25.95 |
| ATOM | 108 | CG | ARG | 84 | 42.574 | 54.331 | 71.350 | 1.00 | 28.39 |
| ATOM | 109 | CD | ARG | 84 | 43.155 | 55.060 | 72.557 | 1.00 | 29.91 |
| ATOM | 110 | NE | ARG | 84 | 44.269 | 55.945 | 72.220 | 1.00 | 28.71 |
| ATOM | 111 | CZ | ARG | 84 | 44.211 | 57.273 | 72.280 | 1.00 | 29.24 |
| ATOM | 112 | NH1 | ARG | 84 | 43.093 | 57.877 | 72.660 | 1.00 | 28.18 |
| ATOM | 113 | NH2 | ARG | 84 | 45.278 | 58.001 | 71.982 | 1.00 | 30.94 |
| ATOM | 114 | C | ARG | 84 | 42.107 | 51.474 | 69.959 | 1.00 | 22.21 |
| ATOM | 115 | O | ARG | 84 | 42.489 | 50.332 | 70.192 | 1.00 | 20.72 |
| ATOM | 116 | N | THR | 85 | 40.824 | 51.823 | 70.010 | 1.00 | 20.97 |
| ATOM | 117 | CA | THR | 85 | 39.796 | 50.845 | 70.365 | 1.00 | 21.86 |
| ATOM | 118 | CB | THR | 85 | 38.457 | 51.528 | 70.752 | 1.00 | 22.90 |
| ATOM | 119 | OG1 | THR | 85 | 37.996 | 52.349 | 69.673 | 1.00 | 24.14 |
| ATOM | 120 | CG2 | THR | 85 | 38.637 | 52.389 | 72.006 | 1.00 | 22.66 |
| ATOM | 121 | C | THR | 85 | 39.531 | 49.853 | 69.227 | 1.00 | 22.63 |
| ATOM | 122 | O | THR | 85 | 39.271 | 48.671 | 69.468 | 1.00 | 23.06 |
| ATOM | 123 | N | SER | 86 | 39.597 | 50.331 | 67.988 | 1.00 | 22.84 |
| ATOM | 124 | CA | SER | 86 | 39.364 | 49.467 | 66.833 | 1.00 | 23.43 |
| ATOM | 125 | CB | SER | 86 | 39.358 | 50.290 | 65.542 | 1.00 | 20.63 |
| ATOM | 126 | OG | SER | 86 | 38.201 | 51.101 | 65.469 | 1.00 | 22.91 |
| ATOM | 127 | C | SER | 86 | 40.420 | 48.375 | 66.737 | 1.00 | 23.93 |
| ATOM | 128 | O | SER | 86 | 40.107 | 47.224 | 66.431 | 1.00 | 26.22 |
| ATOM | 129 | N | GLN | 87 | 41.671 | 48.739 | 66.996 | 1.00 | 25.11 |
| ATOM | 130 | CA | GLN | 87 | 42.764 | 47.777 | 66.934 | 1.00 | 27.65 |
| ATOM | 131 | CB | GLN | 87 | 44.076 | 48.441 | 67.349 | 1.00 | 29.31 |
| ATOM | 132 | CG | GLN | 87 | 44.611 | 49.434 | 66.340 | 1.00 | 34.89 |
| ATOM | 133 | CD | GLN | 87 | 45.901 | 50.079 | 66.797 | 1.00 | 38.51 |
| ATOM | 134 | OE1 | GLN | 87 | 46.854 | 49.392 | 67.170 | 1.00 | 39.63 |
| ATOM | 135 | NE2 | GLN | 87 | 45.942 | 51.407 | 66.766 | 1.00 | 40.39 |
| ATOM | 136 | C | GLN | 87 | 42.494 | 46.575 | 67.832 | 1.00 | 27.47 |
| ATOM | 137 | O | GLN | 87 | 42.700 | 45.430 | 67.430 | 1.00 | 27.09 |
| ATOM | 138 | N | VAL | 88 | 42.027 | 46.843 | 69.049 | 1.00 | 27.70 |
| ATOM | 139 | CA | VAL | 88 | 41.732 | 45.784 | 70.009 | 1.00 | 27.09 |
| ATOM | 140 | CB | VAL | 88 | 41.457 | 46.363 | 71.418 | 1.00 | 28.38 |
| ATOM | 141 | CG1 | VAL | 88 | 41.137 | 45.231 | 72.392 | 1.00 | 28.68 |
| ATOM | 142 | CG2 | VAL | 88 | 42.666 | 47.156 | 71.902 | 1.00 | 28.04 |
| ATOM | 143 | C | VAL | 88 | 40.531 | 44.933 | 69.597 | 1.00 | 26.88 |
| ATOM | 144 | O | VAL | 88 | 40.628 | 43.711 | 69.537 | 1.00 | 26.76 |
| ATOM | 145 | N | VAL | 89 | 39.403 | 45.577 | 69.318 | 1.00 | 25.88 |
| ATOM | 146 | CA | VAL | 89 | 38.199 | 44.852 | 68.928 | 1.00 | 26.99 |
| ATOM | 147 | CB | VAL | 89 | 36.985 | 45.813 | 68.803 | 1.00 | 27.18 |
| ATOM | 148 | CG1 | VAL | 89 | 37.315 | 46.950 | 67.862 | 1.00 | 32.87 |
| ATOM | 149 | CG2 | VAL | 89 | 35.765 | 45.060 | 68.306 | 1.00 | 31.36 |
| ATOM | 150 | C | VAL | 89 | 38.375 | 44.071 | 67.616 | 1.00 | 27.29 |
| ATOM | 151 | O | VAL | 89 | 37.906 | 42.937 | 67.497 | 1.00 | 25.50 |
| ATOM | 152 | N | TRP | 90 | 39.048 | 44.674 | 66.637 | 1.00 | 26.45 |
| ATOM | 153 | CA | TRP | 90 | 39.273 | 44.010 | 65.354 | 1.00 | 27.47 |
| ATOM | 154 | CB | TRP | 90 | 39.817 | 45.003 | 64.325 | 1.00 | 29.71 |
| ATOM | 155 | CG | TRP | 90 | 38.809 | 46.020 | 63.873 | 1.00 | 33.63 |
| ATOM | 156 | CD2 | TRP | 90 | 38.891 | 46.847 | 62.707 | 1.00 | 35.80 |
| ATOM | 157 | CE2 | TRP | 90 | 37.752 | 47.684 | 62.707 | 1.00 | 37.41 |
| ATOM | 158 | CE3 | TRP | 90 | 39.817 | 46.965 | 61.663 | 1.00 | 37.42 |
| ATOM | 159 | CD1 | TRP | 90 | 37.656 | 46.375 | 64.513 | 1.00 | 34.94 |
| ATOM | 160 | NE1 | TRP | 90 | 37.015 | 47.373 | 63.819 | 1.00 | 36.40 |
| ATOM | 161 | CZ2 | TRP | 90 | 37.514 | 48.629 | 61.700 | 1.00 | 38.33 |
| ATOM | 162 | CZ3 | TRP | 90 | 39.582 | 47.906 | 60.661 | 1.00 | 39.67 |
| ATOM | 163 | CH2 | TRP | 90 | 38.437 | 48.726 | 60.690 | 1.00 | 40.02 |
| ATOM | 164 | C | TRP | 90 | 40.243 | 42.846 | 65.510 | 1.00 | 27.07 |
| ATOM | 165 | O | TRP | 90 | 40.121 | 41.831 | 64.824 | 1.00 | 27.40 |
| ATOM | 166 | N | ASN | 91 | 41.210 | 42.991 | 66.409 | 1.00 | 25.74 |
| ATOM | 167 | CA | ASN | 91 | 42.167 | 41.920 | 66.634 | 1.00 | 26.47 |
| ATOM | 168 | CB | ASN | 91 | 43.271 | 42.364 | 67.597 | 1.00 | 26.15 |
| ATOM | 169 | CG | ASN | 91 | 44.156 | 41.212 | 68.033 | 1.00 | 29.44 |
| ATOM | 170 | OD1 | ASN | 91 | 43.840 | 40.502 | 68.987 | 1.00 | 30.76 |
| ATOM | 171 | ND2 | ASN | 91 | 45.261 | 41.005 | 67.319 | 1.00 | 28.75 |
| ATOM | 172 | C | ASN | 91 | 41.442 | 40.705 | 67.196 | 1.00 | 27.08 |
| ATOM | 173 | O | ASN | 91 | 41.697 | 39.574 | 66.780 | 1.00 | 26.40 |

TABLE A-continued

| | | | | | | | | |
|---|---|---|---|---|---|---|---|---|
| ATOM | 174 | N | GLU | 92 | 40.533 | 40.942 | 68.138 | 1.00 26.14 |
| ATOM | 175 | CA | GLU | 92 | 39.768 | 39.858 | 68.734 | 1.00 27.35 |
| ATOM | 176 | CB | GLU | 92 | 38.906 | 40.378 | 69.888 | 1.00 30.98 |
| ATOM | 177 | CG | GLU | 92 | 39.643 | 40.460 | 71.214 | 1.00 37.75 |
| ATOM | 178 | CD | GLU | 92 | 38.847 | 41.182 | 72.288 | 1.00 40.97 |
| ATOM | 179 | OE1 | GLU | 92 | 37.654 | 40.855 | 72.466 | 1.00 43.05 |
| ATOM | 180 | OE2 | GLU | 92 | 39.421 | 42.070 | 72.955 | 1.00 41.95 |
| ATOM | 181 | C | GLU | 92 | 38.881 | 39.174 | 67.705 | 1.00 25.71 |
| ATOM | 182 | O | GLU | 92 | 38.777 | 37.952 | 67.689 | 1.00 25.50 |
| ATOM | 183 | N | TYR | 93 | 38.238 | 39.961 | 66.849 | 1.00 25.38 |
| ATOM | 184 | CA | TYR | 93 | 37.367 | 39.396 | 65.825 | 1.00 25.52 |
| ATOM | 185 | CB | TYR | 93 | 36.693 | 40.503 | 65.012 | 1.00 25.32 |
| ATOM | 186 | CG | TYR | 93 | 35.790 | 39.961 | 63.929 | 1.00 28.08 |
| ATOM | 187 | CD1 | TYR | 93 | 34.578 | 39.348 | 64.248 | 1.00 28.32 |
| ATOM | 188 | CE1 | TYR | 93 | 33.761 | 38.804 | 63.260 | 1.00 31.75 |
| ATOM | 189 | CD2 | TYR | 93 | 36.165 | 40.021 | 62.588 | 1.00 29.39 |
| ATOM | 190 | CE2 | TYR | 93 | 35.355 | 39.477 | 61.589 | 1.00 33.01 |
| ATOM | 191 | CZ | TYR | 93 | 34.155 | 38.872 | 61.933 | 1.00 33.10 |
| ATOM | 192 | OH | TYR | 93 | 33.354 | 38.334 | 60.952 | 1.00 36.34 |
| ATOM | 193 | C | TYR | 93 | 38.161 | 38.501 | 64.878 | 1.00 23.80 |
| ATOM | 194 | O | TYR | 93 | 37.725 | 37.404 | 64.528 | 1.00 24.56 |
| ATOM | 195 | N | ALA | 94 | 39.325 | 38.984 | 64.461 | 1.00 23.33 |
| ATOM | 196 | CA | ALA | 94 | 40.184 | 38.241 | 63.552 | 1.00 24.84 |
| ATOM | 197 | CB | ALA | 94 | 41.461 | 39.034 | 63.274 | 1.00 22.84 |
| ATOM | 198 | C | ALA | 94 | 40.526 | 36.876 | 64.143 | 1.00 24.40 |
| ATOM | 199 | O | ALA | 94 | 40.589 | 35.876 | 63.427 | 1.00 23.49 |
| ATOM | 200 | N | ALA | 95 | 40.739 | 36.840 | 65.454 | 1.00 25.55 |
| ATOM | 201 | CA | ALA | 95 | 41.069 | 35.593 | 66.136 | 1.00 25.36 |
| ATOM | 202 | CB | ALA | 95 | 41.361 | 35.864 | 67.609 | 1.00 30.67 |
| ATOM | 203 | C | ALA | 95 | 39.928 | 34.593 | 66.007 | 1.00 24.83 |
| ATOM | 204 | O | ALA | 95 | 40.138 | 33.440 | 65.630 | 1.00 26.02 |
| ATOM | 205 | N | ALA | 96 | 38.718 | 35.038 | 66.326 | 1.00 23.74 |
| ATOM | 206 | CA | ALA | 96 | 37.547 | 34.177 | 66.244 | 1.00 23.43 |
| ATOM | 207 | CB | ALA | 96 | 36.329 | 34.904 | 66.794 | 1.00 22.21 |
| ATOM | 208 | C | ALA | 96 | 37.284 | 33.742 | 64.803 | 1.00 23.35 |
| ATOM | 209 | O | ALA | 96 | 36.934 | 32.589 | 64.545 | 1.00 22.60 |
| ATOM | 210 | N | ASN | 97 | 37.451 | 34.673 | 63.870 | 1.00 21.81 |
| ATOM | 211 | CA | ASN | 97 | 37.224 | 34.389 | 62.456 | 1.00 22.42 |
| ATOM | 212 | CB | ASN | 97 | 37.308 | 35.695 | 61.651 | 1.00 21.62 |
| ATOM | 213 | CG | ASN | 97 | 36.768 | 35.553 | 60.241 | 1.00 22.75 |
| ATOM | 214 | OD1 | ASN | 97 | 35.968 | 34.660 | 59.955 | 1.00 22.10 |
| ATOM | 215 | ND2 | ASN | 97 | 37.186 | 36.450 | 59.356 | 1.00 21.12 |
| ATOM | 216 | C | ASN | 97 | 38.257 | 33.373 | 61.965 | 1.00 21.42 |
| ATOM | 217 | O | ASN | 97 | 37.941 | 32.480 | 61.183 | 1.00 22.56 |
| ATOM | 218 | N | TRP | 98 | 39.490 | 33.502 | 62.447 | 1.00 22.34 |
| ATOM | 219 | CA | TRP | 98 | 40.552 | 32.585 | 62.059 | 1.00 22.66 |
| ATOM | 220 | CB | TRP | 98 | 41.901 | 33.085 | 62.583 | 1.00 22.16 |
| ATOM | 221 | CG | TRP | 98 | 43.016 | 32.098 | 62.384 | 1.00 23.43 |
| ATOM | 222 | CD2 | TRP | 98 | 43.883 | 32.003 | 61.246 | 1.00 22.99 |
| ATOM | 223 | CE2 | TRP | 98 | 44.749 | 30.907 | 61.470 | 1.00 24.37 |
| ATOM | 224 | CE3 | TRP | 98 | 44.010 | 32.735 | 60.055 | 1.00 21.19 |
| ATOM | 225 | CD1 | TRP | 98 | 43.381 | 31.086 | 63.229 | 1.00 25.02 |
| ATOM | 226 | NE1 | TRP | 98 | 44.421 | 30.365 | 62.686 | 1.00 25.09 |
| ATOM | 227 | CZ2 | TRP | 98 | 45.733 | 30.526 | 60.547 | 1.00 23.12 |
| ATOM | 228 | CZ3 | TRP | 98 | 44.989 | 32.354 | 59.134 | 1.00 21.49 |
| ATOM | 229 | CH2 | TRP | 98 | 45.837 | 31.258 | 59.389 | 1.00 20.86 |
| ATOM | 230 | C | TRP | 98 | 40.286 | 31.170 | 62.578 | 1.00 23.96 |
| ATOM | 231 | O | TRP | 98 | 40.444 | 30.190 | 61.840 | 1.00 22.16 |
| ATOM | 232 | N | ASN | 99 | 39.876 | 31.071 | 63.841 | 1.00 24.47 |
| ATOM | 233 | CA | ASN | 99 | 39.596 | 29.770 | 64.455 | 1.00 26.36 |
| ATOM | 234 | CB | ASN | 99 | 39.230 | 29.936 | 65.937 | 1.00 27.31 |
| ATOM | 235 | CG | ASN | 99 | 40.368 | 30.524 | 66.760 | 1.00 29.77 |
| ATOM | 236 | OD1 | ASN | 99 | 41.537 | 30.432 | 66.382 | 1.00 28.77 |
| ATOM | 237 | ND2 | ASN | 99 | 40.028 | 31.119 | 67.899 | 1.00 30.82 |
| ATOM | 238 | C | ASN | 99 | 38.480 | 29.026 | 63.724 | 1.00 25.35 |
| ATOM | 239 | O | ASN | 99 | 38.523 | 27.802 | 63.588 | 1.00 23.96 |
| ATOM | 240 | N | TYR | 100 | 37.477 | 29.762 | 63.258 | 1.00 24.11 |
| ATOM | 241 | CA | TYR | 100 | 36.380 | 29.145 | 62.518 | 1.00 24.41 |
| ATOM | 242 | CB | TYR | 100 | 35.242 | 30.153 | 62.308 | 1.00 27.59 |
| ATOM | 243 | CG | TYR | 100 | 34.348 | 29.829 | 61.127 | 1.00 28.29 |
| ATOM | 244 | CD1 | TYR | 100 | 33.375 | 28.834 | 61.209 | 1.00 30.33 |
| ATOM | 245 | CE1 | TYR | 100 | 32.581 | 28.505 | 60.101 | 1.00 29.75 |
| ATOM | 246 | CD2 | TYR | 100 | 34.508 | 30.494 | 59.912 | 1.00 31.13 |
| ATOM | 247 | CE2 | TYR | 100 | 33.725 | 30.174 | 58.800 | 1.00 31.87 |
| ATOM | 248 | CZ | TYR | 100 | 32.765 | 29.180 | 58.902 | 1.00 32.09 |
| ATOM | 249 | OH | TYR | 100 | 31.995 | 28.868 | 57.799 | 1.00 31.48 |
| ATOM | 250 | C | TYR | 100 | 36.892 | 28.674 | 61.157 | 1.00 24.55 |
| ATOM | 251 | O | TYR | 100 | 36.698 | 27.521 | 60.770 | 1.00 23.28 |
| ATOM | 252 | N | ASN | 101 | 37.538 | 29.588 | 60.436 | 1.00 22.98 |
| ATOM | 253 | CA | ASN | 101 | 38.083 | 29.312 | 59.111 | 1.00 21.52 |

TABLE A-continued

| | | | | | | | | |
|---|---|---|---|---|---|---|---|---|
| ATOM | 254 | CB | ASN | 101 | 38.799 | 30.555 | 58.573 | 1.00 22.42 |
| ATOM | 255 | CG | ASN | 101 | 37.883 | 31.452 | 57.766 | 1.00 20.70 |
| ATOM | 256 | OD1 | ASN | 101 | 37.843 | 31.369 | 56.541 | 1.00 20.36 |
| ATOM | 257 | ND2 | ASN | 101 | 37.131 | 32.307 | 58.452 | 1.00 20.18 |
| ATOM | 258 | C | ASN | 101 | 39.048 | 28.130 | 59.074 | 1.00 22.49 |
| ATOM | 259 | O | ASN | 101 | 39.092 | 27.398 | 58.085 | 1.00 22.22 |
| ATOM | 260 | N | THR | 102 | 39.821 | 27.953 | 60.144 | 1.00 21.87 |
| ATOM | 261 | CA | THR | 102 | 40.799 | 26.866 | 60.209 | 1.00 23.29 |
| ATOM | 262 | CB | THR | 102 | 42.153 | 27.364 | 60.773 | 1.00 22.46 |
| ATOM | 263 | OG1 | THR | 102 | 41.985 | 27.779 | 62.132 | 1.00 21.26 |
| ATOM | 264 | CG2 | THR | 102 | 42.675 | 28.544 | 59.956 | 1.00 22.88 |
| ATOM | 265 | C | THR | 102 | 40.332 | 25.682 | 61.055 | 1.00 25.33 |
| ATOM | 266 | O | THR | 102 | 41.100 | 24.755 | 61.312 | 1.00 26.63 |
| ATOM | 267 | N | ASN | 103 | 39.073 | 25.709 | 61.478 | 1.00 26.22 |
| ATOM | 268 | CA | ASN | 103 | 38.513 | 24.633 | 62.293 | 1.00 27.70 |
| ATOM | 269 | CB | ASN | 103 | 39.154 | 24.648 | 63.691 | 1.00 28.15 |
| ATOM | 270 | CG | ASN | 103 | 38.674 | 23.499 | 64.576 | 1.00 31.04 |
| ATOM | 271 | OD1 | ASN | 103 | 38.244 | 22.457 | 64.074 | 1.00 29.17 |
| ATOM | 272 | ND2 | ASN | 103 | 38.761 | 23.701 | 65.892 | 1.00 32.86 |
| ATOM | 273 | C | ASN | 103 | 37.005 | 24.834 | 62.382 | 1.00 26.39 |
| ATOM | 274 | O | ASN | 103 | 36.486 | 25.297 | 63.395 | 1.00 28.11 |
| ATOM | 275 | N | ILE | 104 | 36.312 | 24.487 | 61.304 | 1.00 27.62 |
| ATOM | 276 | CA | ILE | 104 | 34.864 | 24.640 | 61.225 | 1.00 28.58 |
| ATOM | 277 | CB | ILE | 104 | 34.370 | 24.456 | 59.770 | 1.00 28.41 |
| ATOM | 278 | CG2 | ILE | 104 | 32.849 | 24.581 | 59.710 | 1.00 29.27 |
| ATOM | 279 | CG1 | ILE | 104 | 35.032 | 25.498 | 58.861 | 1.00 28.67 |
| ATOM | 280 | CD1 | ILE | 104 | 34.674 | 25.359 | 57.387 | 1.00 27.85 |
| ATOM | 281 | C | ILE | 104 | 34.128 | 23.655 | 62.127 | 1.00 30.90 |
| ATOM | 282 | O | ILE | 104 | 34.063 | 22.460 | 61.839 | 1.00 31.19 |
| ATOM | 283 | N | THR | 105 | 33.579 | 24.171 | 63.222 | 1.00 32.51 |
| ATOM | 284 | CA | THR | 105 | 32.831 | 23.360 | 64.177 | 1.00 33.92 |
| ATOM | 285 | CB | THR | 105 | 33.688 | 22.982 | 65.399 | 1.00 34.56 |
| ATOM | 286 | OG1 | THR | 105 | 34.015 | 24.169 | 66.133 | 1.00 35.94 |
| ATOM | 287 | CG2 | THR | 105 | 34.972 | 22.284 | 64.965 | 1.00 33.74 |
| ATOM | 288 | C | THR | 105 | 31.649 | 24.176 | 64.677 | 1.00 34.62 |
| ATOM | 289 | O | THR | 105 | 31.575 | 25.384 | 64.450 | 1.00 34.35 |
| ATOM | 290 | N | THR | 106 | 30.722 | 23.518 | 65.360 | 1.00 34.69 |
| ATOM | 291 | CA | THR | 106 | 29.564 | 24.220 | 65.889 | 1.00 35.91 |
| ATOM | 292 | CB | THR | 106 | 28.546 | 23.229 | 66.510 | 1.00 36.94 |
| ATOM | 293 | OG1 | THR | 106 | 27.453 | 23.956 | 67.085 | 1.00 40.00 |
| ATOM | 294 | CG2 | THR | 106 | 29.205 | 22.386 | 67.582 | 1.00 36.78 |
| ATOM | 295 | C | THR | 106 | 30.041 | 25.219 | 66.945 | 1.00 35.21 |
| ATOM | 296 | O | THR | 106 | 29.499 | 26.318 | 67.069 | 1.00 34.43 |
| ATOM | 297 | N | GLU | 107 | 31.084 | 24.840 | 67.679 | 1.00 35.12 |
| ATOM | 298 | CA | GLU | 107 | 31.638 | 25.692 | 68.725 | 1.00 35.53 |
| ATOM | 299 | CB | GLU | 107 | 32.640 | 24.905 | 69.576 | 1.00 38.54 |
| ATOM | 300 | CG | GLU | 107 | 32.084 | 23.613 | 70.185 | 1.00 44.28 |
| ATOM | 301 | CD | GLU | 107 | 32.317 | 22.385 | 69.310 | 1.00 47.02 |
| ATOM | 302 | OE1 | GLU | 107 | 31.828 | 22.356 | 68.161 | 1.00 48.87 |
| ATOM | 303 | OE2 | GLU | 107 | 32.998 | 21.444 | 69.775 | 1.00 50.21 |
| ATOM | 304 | C | GLU | 107 | 32.309 | 26.957 | 68.180 | 1.00 34.45 |
| ATOM | 305 | O | GLU | 107 | 32.003 | 28.066 | 68.623 | 1.00 32.19 |
| ATOM | 306 | N | THR | 108 | 33.227 | 26.796 | 67.229 | 1.00 33.18 |
| ATOM | 307 | CA | THR | 108 | 33.913 | 27.949 | 66.651 | 1.00 32.17 |
| ATOM | 308 | CB | THR | 108 | 35.048 | 27.527 | 65.687 | 1.00 31.68 |
| ATOM | 309 | OG1 | THR | 108 | 34.528 | 26.660 | 64.673 | 1.00 31.48 |
| ATOM | 310 | CG2 | THR | 108 | 36.157 | 26.818 | 66.452 | 1.00 31.84 |
| ATOM | 311 | C | THR | 108 | 32.925 | 28.834 | 65.897 | 1.00 31.26 |
| ATOM | 312 | O | THR | 108 | 33.107 | 30.045 | 65.815 | 1.00 30.78 |
| ATOM | 313 | N | SER | 109 | 31.878 | 28.228 | 65.347 | 1.00 31.59 |
| ATOM | 314 | CA | SER | 109 | 30.865 | 28.989 | 64.623 | 1.00 32.27 |
| ATOM | 315 | CB | SER | 109 | 29.888 | 28.054 | 63.905 | 1.00 32.03 |
| ATOM | 316 | OG | SER | 109 | 30.511 | 27.388 | 62.819 | 1.00 33.62 |
| ATOM | 317 | C | SER | 109 | 30.094 | 29.863 | 65.602 | 1.00 33.27 |
| ATOM | 318 | O | SER | 109 | 29.871 | 31.046 | 65.352 | 1.00 31.52 |
| ATOM | 319 | N | LYS | 110 | 29.695 | 29.268 | 66.722 | 1.00 34.58 |
| ATOM | 320 | CA | LYS | 110 | 28.943 | 29.985 | 67.741 | 1.00 36.62 |
| ATOM | 321 | CB | LYS | 110 | 28.570 | 29.031 | 68.880 | 1.00 39.13 |
| ATOM | 322 | CG | LYS | 110 | 27.494 | 29.561 | 69.819 | 1.00 43.25 |
| ATOM | 323 | CD | LYS | 110 | 27.052 | 28.487 | 70.807 | 1.00 46.60 |
| ATOM | 324 | CE | LYS | 110 | 25.859 | 28.943 | 71.639 | 1.00 48.32 |
| ATOM | 325 | NZ | LYS | 110 | 25.369 | 27.861 | 72.547 | 1.00 49.35 |
| ATOM | 326 | C | LYS | 110 | 29.755 | 31.162 | 68.279 | 1.00 35.77 |
| ATOM | 327 | O | LYS | 110 | 29.234 | 32.264 | 68.449 | 1.00 36.40 |
| ATOM | 328 | N | ILE | 111 | 31.037 | 30.927 | 68.535 | 1.00 34.36 |
| ATOM | 329 | CA | ILE | 111 | 31.909 | 31.974 | 69.054 | 1.00 33.18 |
| ATOM | 330 | CB | ILE | 111 | 33.296 | 31.410 | 69.408 | 1.00 33.61 |
| ATOM | 331 | CG2 | ILE | 111 | 34.226 | 32.537 | 69.837 | 1.00 33.24 |
| ATOM | 332 | CG1 | ILE | 111 | 33.154 | 30.364 | 70.517 | 1.00 34.16 |
| ATOM | 333 | CD1 | ILE | 111 | 34.458 | 29.696 | 70.907 | 1.00 33.43 |

TABLE A-continued

| | | | | | | | | | |
|---|---|---|---|---|---|---|---|---|---|
| ATOM | 334 | C | ILE | 111 | 32.073 | 33.107 | 68.044 | 1.00 | 32.41 |
| ATOM | 335 | O | ILE | 111 | 32.075 | 34.284 | 68.410 | 1.00 | 32.05 |
| ATOM | 336 | N | LEU | 112 | 32.212 | 32.749 | 66.772 | 1.00 | 30.05 |
| ATOM | 337 | CA | LEU | 112 | 32.364 | 33.752 | 65.731 | 1.00 | 28.87 |
| ATOM | 338 | CB | LEU | 112 | 32.591 | 33.084 | 64.371 | 1.00 | 28.19 |
| ATOM | 339 | CG | LEU | 112 | 32.709 | 34.015 | 63.157 | 1.00 | 28.67 |
| ATOM | 340 | CD1 | LEU | 112 | 33.778 | 35.063 | 63.405 | 1.00 | 28.05 |
| ATOM | 341 | CD2 | LEU | 112 | 33.035 | 33.198 | 61.918 | 1.00 | 27.39 |
| ATOM | 342 | C | LEU | 112 | 31.127 | 34.645 | 65.672 | 1.00 | 28.87 |
| ATOM | 343 | O | LEU | 112 | 31.243 | 35.867 | 65.612 | 1.00 | 27.96 |
| ATOM | 344 | N | LEU | 113 | 29.942 | 34.040 | 65.700 | 1.00 | 28.83 |
| ATOM | 345 | CA | LEU | 113 | 28.710 | 34.821 | 65.641 | 1.00 | 29.55 |
| ATOM | 346 | CB | LEU | 113 | 27.488 | 33.897 | 65.581 | 1.00 | 28.66 |
| ATOM | 347 | CG | LEU | 113 | 27.358 | 33.047 | 64.313 | 1.00 | 27.25 |
| ATOM | 348 | CD1 | LEU | 113 | 26.146 | 32.144 | 64.423 | 1.00 | 28.60 |
| ATOM | 349 | CD2 | LEU | 113 | 27.238 | 33.955 | 63.090 | 1.00 | 29.42 |
| ATOM | 350 | C | LEU | 113 | 28.595 | 35.772 | 66.827 | 1.00 | 30.99 |
| ATOM | 351 | O | LEU | 113 | 28.035 | 36.861 | 66.703 | 1.00 | 30.68 |
| ATOM | 352 | N | GLN | 114 | 29.134 | 35.364 | 67.973 | 1.00 | 32.59 |
| ATOM | 353 | CA | GLN | 114 | 29.096 | 36.205 | 69.164 | 1.00 | 34.05 |
| ATOM | 354 | CB | GLN | 114 | 29.461 | 35.393 | 70.414 | 1.00 | 35.86 |
| ATOM | 355 | CG | GLN | 114 | 28.397 | 34.363 | 70.797 | 1.00 | 41.83 |
| ATOM | 356 | CD | GLN | 114 | 28.802 | 33.483 | 71.970 | 1.00 | 44.71 |
| ATOM | 357 | OE1 | GLN | 114 | 29.028 | 33.966 | 73.080 | 1.00 | 47.69 |
| ATOM | 358 | NE2 | GLN | 114 | 28.892 | 32.180 | 71.726 | 1.00 | 47.51 |
| ATOM | 359 | C | GLN | 114 | 30.056 | 37.375 | 68.992 | 1.00 | 33.41 |
| ATOM | 360 | O | GLN | 114 | 29.746 | 38.500 | 69.380 | 1.00 | 33.15 |
| ATOM | 361 | N | LYS | 115 | 31.222 | 37.114 | 68.409 | 1.00 | 33.19 |
| ATOM | 362 | CA | LYS | 115 | 32.194 | 38.177 | 68.185 | 1.00 | 33.34 |
| ATOM | 363 | CB | LYS | 115 | 33.527 | 37.604 | 67.695 | 1.00 | 35.03 |
| ATOM | 364 | CG | LYS | 115 | 34.397 | 37.022 | 68.802 | 1.00 | 39.16 |
| ATOM | 365 | CD | LYS | 115 | 34.872 | 38.111 | 69.757 | 1.00 | 41.08 |
| ATOM | 366 | CE | LYS | 115 | 35.682 | 37.534 | 70.912 | 1.00 | 43.92 |
| ATOM | 367 | NZ | LYS | 115 | 36.142 | 38.597 | 71.855 | 1.00 | 43.32 |
| ATOM | 368 | C | LYS | 115 | 31.655 | 39.180 | 67.172 | 1.00 | 32.53 |
| ATOM | 369 | O | LYS | 115 | 32.033 | 40.351 | 67.192 | 1.00 | 30.99 |
| ATOM | 370 | N | ASN | 116 | 30.779 | 38.717 | 66.283 | 1.00 | 33.42 |
| ATOM | 371 | CA | ASN | 116 | 30.180 | 39.597 | 65.279 | 1.00 | 34.57 |
| ATOM | 372 | CB | ASN | 116 | 29.219 | 38.820 | 64.368 | 1.00 | 36.23 |
| ATOM | 373 | CG | ASN | 116 | 29.938 | 37.996 | 63.314 | 1.00 | 37.73 |
| ATOM | 374 | OD1 | ASN | 116 | 30.671 | 38.530 | 62.479 | 1.00 | 37.42 |
| ATOM | 375 | ND2 | ASN | 116 | 29.719 | 36.685 | 63.340 | 1.00 | 41.84 |
| ATOM | 376 | C | ASN | 116 | 29.404 | 40.694 | 66.001 | 1.00 | 34.49 |
| ATOM | 377 | O | ASN | 116 | 29.531 | 41.874 | 65.683 | 1.00 | 33.34 |
| ATOM | 378 | N | MET | 117 | 28.597 | 40.286 | 66.975 | 1.00 | 34.71 |
| ATOM | 379 | CA | MET | 117 | 27.794 | 41.217 | 67.757 | 1.00 | 36.39 |
| ATOM | 380 | CB | MET | 117 | 26.943 | 40.448 | 68.772 | 1.00 | 39.17 |
| ATOM | 381 | CG | MET | 117 | 25.518 | 40.138 | 68.319 | 1.00 | 43.08 |
| ATOM | 382 | SD | MET | 117 | 25.294 | 40.020 | 66.531 | 1.00 | 49.27 |
| ATOM | 383 | CE | MET | 117 | 23.829 | 41.035 | 66.302 | 1.00 | 47.42 |
| ATOM | 384 | C | MET | 117 | 28.670 | 42.228 | 68.488 | 1.00 | 35.39 |
| ATOM | 385 | O | MET | 117 | 28.320 | 43.402 | 68.590 | 1.00 | 34.85 |
| ATOM | 386 | N | GLN | 118 | 29.814 | 41.772 | 68.989 | 1.00 | 34.91 |
| ATOM | 387 | CA | GLN | 118 | 30.722 | 42.648 | 69.719 | 1.00 | 35.11 |
| ATOM | 388 | CB | GLN | 118 | 31.818 | 41.826 | 70.405 | 1.00 | 38.55 |
| ATOM | 389 | CG | GLN | 118 | 31.278 | 40.731 | 71.319 | 1.00 | 44.24 |
| ATOM | 390 | CD | GLN | 118 | 32.340 | 40.138 | 72.229 | 1.00 | 47.30 |
| ATOM | 391 | OE1 | GLN | 118 | 33.397 | 39.702 | 71.771 | 1.00 | 49.53 |
| ATOM | 392 | NE2 | GLN | 118 | 32.060 | 40.115 | 73.528 | 1.00 | 47.80 |
| ATOM | 393 | C | GLN | 118 | 31.352 | 43.714 | 68.831 | 1.00 | 32.85 |
| ATOM | 394 | O | GLN | 118 | 31.371 | 44.895 | 69.188 | 1.00 | 31.35 |
| ATOM | 395 | N | ILE | 119 | 31.869 | 43.308 | 67.676 | 1.00 | 29.57 |
| ATOM | 396 | CA | ILE | 119 | 32.492 | 44.269 | 66.776 | 1.00 | 28.83 |
| ATOM | 397 | CB | ILE | 119 | 33.274 | 43.563 | 65.644 | 1.00 | 29.00 |
| ATOM | 398 | CG2 | ILE | 119 | 32.319 | 42.794 | 64.742 | 1.00 | 29.58 |
| ATOM | 399 | CG1 | ILE | 119 | 34.063 | 44.599 | 64.844 | 1.00 | 31.09 |
| ATOM | 400 | CD1 | ILE | 119 | 35.045 | 43.992 | 63.864 | 1.00 | 33.97 |
| ATOM | 401 | C | ILE | 119 | 31.435 | 45.195 | 66.179 | 1.00 | 26.91 |
| ATOM | 402 | O | ILE | 119 | 31.709 | 46.358 | 65.872 | 1.00 | 25.48 |
| ATOM | 403 | N | ALA | 120 | 30.220 | 44.683 | 66.024 | 1.00 | 25.38 |
| ATOM | 404 | CA | ALA | 120 | 29.135 | 45.492 | 65.481 | 1.00 | 26.14 |
| ATOM | 405 | CB | ALA | 120 | 27.918 | 44.623 | 65.202 | 1.00 | 24.25 |
| ATOM | 406 | C | ALA | 120 | 28.790 | 46.568 | 66.509 | 1.00 | 25.83 |
| ATOM | 407 | O | ALA | 120 | 28.566 | 47.727 | 66.165 | 1.00 | 25.53 |
| ATOM | 408 | N | ASN | 121 | 28.755 | 46.178 | 67.778 | 1.00 | 25.13 |
| ATOM | 409 | CA | ASN | 121 | 28.443 | 47.131 | 68.834 | 1.00 | 25.64 |
| ATOM | 410 | CB | ASN | 121 | 28.407 | 46.426 | 70.191 | 1.00 | 28.05 |
| ATOM | 411 | CG | ASN | 121 | 27.945 | 47.341 | 71.304 | 1.00 | 33.48 |
| ATOM | 412 | OD1 | ASN | 121 | 28.666 | 48.256 | 71.704 | 1.00 | 37.03 |
| ATOM | 413 | ND2 | ASN | 121 | 26.732 | 47.107 | 71.797 | 1.00 | 35.02 |

TABLE A-continued

| | | | | | | | | | |
|---|---|---|---|---|---|---|---|---|---|
| ATOM | 414 | C | ASN | 121 | 29.474 | 48.256 | 68.843 | 1.00 | 23.48 |
| ATOM | 415 | O | ASN | 121 | 29.131 | 49.421 | 69.052 | 1.00 | 24.86 |
| ATOM | 416 | N | HIS | 122 | 30.735 | 47.910 | 68.603 | 1.00 | 21.49 |
| ATOM | 417 | CA | HIS | 122 | 31.799 | 48.908 | 68.565 | 1.00 | 21.72 |
| ATOM | 418 | CB | HIS | 122 | 33.171 | 48.227 | 68.499 | 1.00 | 21.96 |
| ATOM | 419 | CG | HIS | 122 | 34.297 | 49.165 | 68.190 | 1.00 | 23.78 |
| ATOM | 420 | CD2 | HIS | 122 | 35.094 | 49.902 | 69.002 | 1.00 | 22.69 |
| ATOM | 421 | ND1 | HIS | 122 | 34.694 | 49.456 | 66.901 | 1.00 | 25.06 |
| ATOM | 422 | CE1 | HIS | 122 | 35.684 | 50.330 | 66.934 | 1.00 | 24.61 |
| ATOM | 423 | NE2 | HIS | 122 | 35.946 | 50.618 | 68.197 | 1.00 | 22.29 |
| ATOM | 424 | C | HIS | 122 | 31.624 | 49.822 | 67.354 | 1.00 | 22.77 |
| ATOM | 425 | O | HIS | 122 | 31.801 | 51.041 | 67.445 | 1.00 | 21.87 |
| ATOM | 426 | N | THR | 123 | 31.278 | 49.224 | 66.218 | 1.00 | 20.58 |
| ATOM | 427 | CA | THR | 123 | 31.083 | 49.979 | 64.987 | 1.00 | 21.80 |
| ATOM | 428 | CB | THR | 123 | 30.823 | 49.034 | 63.795 | 1.00 | 22.75 |
| ATOM | 429 | OG1 | THR | 123 | 31.945 | 48.155 | 63.632 | 1.00 | 22.95 |
| ATOM | 430 | CG2 | THR | 123 | 30.618 | 49.832 | 62.509 | 1.00 | 23.24 |
| ATOM | 431 | C | THR | 123 | 29.905 | 50.940 | 65.128 | 1.00 | 21.91 |
| ATOM | 432 | O | THR | 123 | 29.972 | 52.085 | 64.692 | 1.00 | 21.95 |
| ATOM | 433 | N | LEU | 124 | 28.829 | 50.468 | 65.747 | 1.00 | 23.43 |
| ATOM | 434 | CA | LEU | 124 | 27.643 | 51.291 | 65.945 | 1.00 | 24.99 |
| ATOM | 435 | CB | LEU | 124 | 26.538 | 50.458 | 66.590 | 1.00 | 27.24 |
| ATOM | 436 | CG | LEU | 124 | 25.215 | 51.170 | 66.870 | 1.00 | 29.20 |
| ATOM | 437 | CD1 | LEU | 124 | 24.575 | 51.621 | 65.556 | 1.00 | 31.28 |
| ATOM | 438 | CD2 | LEU | 124 | 24.294 | 50.228 | 67.622 | 1.00 | 30.06 |
| ATOM | 439 | C | LEU | 124 | 27.953 | 52.501 | 66.830 | 1.00 | 25.57 |
| ATOM | 440 | O | LEU | 124 | 27.559 | 53.628 | 66.526 | 1.00 | 23.70 |
| ATOM | 441 | N | LYS | 125 | 28.664 | 52.256 | 67.924 | 1.00 | 24.93 |
| ATOM | 442 | CA | LYS | 125 | 29.018 | 53.316 | 68.855 | 1.00 | 26.17 |
| ATOM | 443 | CB | LYS | 125 | 29.818 | 52.747 | 70.026 | 1.00 | 27.56 |
| ATOM | 444 | CG | LYS | 125 | 30.174 | 53.788 | 71.072 | 1.00 | 32.44 |
| ATOM | 445 | CD | LYS | 125 | 31.157 | 53.249 | 72.093 | 1.00 | 34.92 |
| ATOM | 446 | CE | LYS | 125 | 31.464 | 54.302 | 73.144 | 1.00 | 38.23 |
| ATOM | 447 | NZ | LYS | 125 | 31.907 | 55.587 | 72.522 | 1.00 | 40.02 |
| ATOM | 448 | C | LYS | 125 | 29.830 | 54.422 | 68.192 | 1.00 | 25.74 |
| ATOM | 449 | O | LYS | 125 | 29.455 | 55.593 | 68.244 | 1.00 | 25.50 |
| ATOM | 450 | N | TYR | 126 | 30.948 | 54.053 | 67.575 | 1.00 | 23.64 |
| ATOM | 451 | CA | TYR | 126 | 31.793 | 55.044 | 66.930 | 1.00 | 23.63 |
| ATOM | 452 | CB | TYR | 126 | 33.193 | 54.477 | 66.688 | 1.00 | 23.98 |
| ATOM | 453 | CG | TYR | 126 | 34.005 | 54.436 | 67.961 | 1.00 | 24.33 |
| ATOM | 454 | CD1 | TYR | 126 | 33.877 | 53.380 | 68.865 | 1.00 | 24.10 |
| ATOM | 455 | CE1 | TYR | 126 | 34.539 | 53.401 | 70.094 | 1.00 | 24.70 |
| ATOM | 456 | CD2 | TYR | 126 | 34.822 | 55.509 | 68.314 | 1.00 | 25.19 |
| ATOM | 457 | CE2 | TYR | 126 | 35.484 | 55.540 | 69.534 | 1.00 | 25.45 |
| ATOM | 458 | CZ | TYR | 126 | 35.337 | 54.489 | 70.420 | 1.00 | 24.76 |
| ATOM | 459 | OH | TYR | 126 | 35.971 | 54.545 | 71.640 | 1.00 | 26.84 |
| ATOM | 460 | C | TYR | 126 | 31.199 | 55.594 | 65.644 | 1.00 | 23.81 |
| ATOM | 461 | O | TYR | 126 | 31.426 | 56.756 | 65.303 | 1.00 | 24.01 |
| ATOM | 462 | N | GLY | 127 | 30.426 | 54.764 | 64.945 | 1.00 | 23.08 |
| ATOM | 463 | CA | GLY | 127 | 29.791 | 55.198 | 63.713 | 1.00 | 22.50 |
| ATOM | 464 | C | GLY | 127 | 28.741 | 56.255 | 63.994 | 1.00 | 23.32 |
| ATOM | 465 | O | GLY | 127 | 28.616 | 57.237 | 63.259 | 1.00 | 21.48 |
| ATOM | 466 | N | THR | 128 | 27.981 | 56.050 | 65.066 | 1.00 | 24.15 |
| ATOM | 467 | CA | THR | 128 | 26.945 | 56.996 | 65.468 | 1.00 | 25.03 |
| ATOM | 468 | CB | THR | 128 | 26.166 | 56.474 | 66.687 | 1.00 | 24.73 |
| ATOM | 469 | OG1 | THR | 128 | 25.558 | 55.221 | 66.357 | 1.00 | 25.50 |
| ATOM | 470 | CG2 | THR | 128 | 25.088 | 57.468 | 67.103 | 1.00 | 23.72 |
| ATOM | 471 | C | THR | 128 | 27.601 | 58.332 | 65.821 | 1.00 | 25.94 |
| ATOM | 472 | O | THR | 128 | 27.138 | 59.390 | 65.397 | 1.00 | 26.44 |
| ATOM | 473 | N | GLN | 129 | 28.680 | 58.275 | 66.597 | 1.00 | 27.23 |
| ATOM | 474 | CA | GLN | 129 | 29.408 | 59.481 | 66.980 | 1.00 | 28.25 |
| ATOM | 475 | CB | GLN | 129 | 30.587 | 59.138 | 67.901 | 1.00 | 32.26 |
| ATOM | 476 | CG | GLN | 129 | 30.285 | 59.178 | 69.396 | 1.00 | 38.49 |
| ATOM | 477 | CD | GLN | 129 | 31.487 | 58.779 | 70.249 | 1.00 | 42.52 |
| ATOM | 478 | OE1 | GLN | 129 | 31.786 | 57.594 | 70.412 | 1.00 | 44.86 |
| ATOM | 479 | NE2 | GLN | 129 | 32.187 | 59.772 | 70.787 | 1.00 | 45.22 |
| ATOM | 480 | C | GLN | 129 | 29.943 | 60.182 | 65.737 | 1.00 | 27.53 |
| ATOM | 481 | O | GLN | 129 | 29.824 | 61.399 | 65.601 | 1.00 | 26.41 |
| ATOM | 482 | N | ALA | 130 | 30.531 | 59.405 | 64.831 | 1.00 | 25.80 |
| ATOM | 483 | CA | ALA | 130 | 31.104 | 59.944 | 63.600 | 1.00 | 24.69 |
| ATOM | 484 | CB | ALA | 130 | 31.699 | 58.810 | 62.766 | 1.00 | 25.45 |
| ATOM | 485 | C | ALA | 130 | 30.100 | 60.729 | 62.757 | 1.00 | 25.28 |
| ATOM | 486 | O | ALA | 130 | 30.448 | 61.739 | 62.141 | 1.00 | 24.63 |
| ATOM | 487 | N | ARG | 131 | 28.860 | 60.256 | 62.723 | 1.00 | 24.09 |
| ATOM | 488 | CA | ARG | 131 | 27.819 | 60.908 | 61.945 | 1.00 | 26.32 |
| ATOM | 489 | CB | ARG | 131 | 26.600 | 59.994 | 61.836 | 1.00 | 25.28 |
| ATOM | 490 | CG | ARG | 131 | 26.859 | 58.750 | 61.015 | 1.00 | 26.20 |
| ATOM | 491 | CD | ARG | 131 | 25.613 | 57.904 | 60.897 | 1.00 | 26.32 |
| ATOM | 492 | NE | ARG | 131 | 25.805 | 56.792 | 59.972 | 1.00 | 25.16 |
| ATOM | 493 | CZ | ARG | 131 | 24.853 | 55.925 | 59.648 | 1.00 | 26.49 |

TABLE A-continued

| | | | | | | | | | |
|---|---|---|---|---|---|---|---|---|---|
| ATOM | 494 | NH1 | ARG | 131 | 23.640 | 56.041 | 60.180 | 1.00 | 25.08 |
| ATOM | 495 | NH2 | ARG | 131 | 25.108 | 54.953 | 58.780 | 1.00 | 27.31 |
| ATOM | 496 | C | ARG | 131 | 27.398 | 62.254 | 62.519 | 1.00 | 27.69 |
| ATOM | 497 | O | ARG | 131 | 26.722 | 63.033 | 61.848 | 1.00 | 27.22 |
| ATOM | 498 | N | LYS | 132 | 27.792 | 62.524 | 63.758 | 1.00 | 28.78 |
| ATOM | 499 | CA | LYS | 132 | 27.444 | 63.785 | 64.397 | 1.00 | 31.07 |
| ATOM | 500 | CB | LYS | 132 | 27.480 | 63.629 | 65.920 | 1.00 | 32.98 |
| ATOM | 501 | CG | LYS | 132 | 26.404 | 62.682 | 66.437 | 1.00 | 37.31 |
| ATOM | 502 | CD | LYS | 132 | 26.517 | 62.422 | 67.931 | 1.00 | 40.01 |
| ATOM | 503 | CE | LYS | 132 | 25.419 | 61.469 | 68.386 | 1.00 | 42.18 |
| ATOM | 504 | NZ | LYS | 132 | 25.551 | 61.088 | 69.821 | 1.00 | 44.23 |
| ATOM | 505 | C | LYS | 132 | 28.371 | 64.906 | 63.946 | 1.00 | 30.99 |
| ATOM | 506 | O | LYS | 132 | 28.104 | 66.082 | 64.194 | 1.00 | 30.45 |
| ATOM | 507 | N | PHE | 133 | 29.461 | 64.543 | 63.278 | 1.00 | 31.38 |
| ATOM | 508 | CA | PHE | 133 | 30.401 | 65.542 | 62.776 | 1.00 | 32.92 |
| ATOM | 509 | CB | PHE | 133 | 31.825 | 64.980 | 62.665 | 1.00 | 32.55 |
| ATOM | 510 | CG | PHE | 133 | 32.531 | 64.825 | 63.977 | 1.00 | 32.74 |
| ATOM | 511 | CD1 | PHE | 133 | 32.357 | 63.682 | 64.746 | 1.00 | 33.65 |
| ATOM | 512 | CD2 | PHE | 133 | 33.376 | 65.828 | 64.444 | 1.00 | 34.44 |
| ATOM | 513 | CE1 | PHE | 133 | 33.017 | 63.535 | 65.965 | 1.00 | 35.01 |
| ATOM | 514 | CE2 | PHE | 133 | 34.041 | 65.695 | 65.664 | 1.00 | 34.23 |
| ATOM | 515 | CZ | PHE | 133 | 33.861 | 64.546 | 66.425 | 1.00 | 35.80 |
| ATOM | 516 | C | PHE | 133 | 29.970 | 65.978 | 61.390 | 1.00 | 33.66 |
| ATOM | 517 | O | PHE | 133 | 29.487 | 65.165 | 60.601 | 1.00 | 33.46 |
| ATOM | 518 | N | ASP | 134 | 30.136 | 67.262 | 61.095 | 1.00 | 34.13 |
| ATOM | 519 | CA | ASP | 134 | 29.804 | 67.769 | 59.772 | 1.00 | 34.82 |
| ATOM | 520 | CB | ASP | 134 | 29.286 | 69.209 | 59.836 | 1.00 | 35.44 |
| ATOM | 521 | CG | ASP | 134 | 28.831 | 69.724 | 58.477 | 1.00 | 35.56 |
| ATOM | 522 | OD1 | ASP | 134 | 29.439 | 69.336 | 57.459 | 1.00 | 36.13 |
| ATOM | 523 | OD2 | ASP | 134 | 27.873 | 70.522 | 58.425 | 1.00 | 36.65 |
| ATOM | 524 | C | ASP | 134 | 31.121 | 67.737 | 59.014 | 1.00 | 34.27 |
| ATOM | 525 | O | ASP | 134 | 31.909 | 68.677 | 59.089 | 1.00 | 34.87 |
| ATOM | 526 | N | VAL | 135 | 31.361 | 66.644 | 58.298 | 1.00 | 35.15 |
| ATOM | 527 | CA | VAL | 135 | 32.595 | 66.478 | 57.540 | 1.00 | 35.95 |
| ATOM | 528 | CB | VAL | 135 | 32.530 | 65.218 | 56.657 | 1.00 | 36.58 |
| ATOM | 529 | CG1 | VAL | 135 | 33.794 | 65.095 | 55.833 | 1.00 | 37.87 |
| ATOM | 530 | CG2 | VAL | 135 | 32.355 | 63.988 | 57.530 | 1.00 | 36.85 |
| ATOM | 531 | C | VAL | 135 | 32.915 | 67.682 | 56.660 | 1.00 | 36.83 |
| ATOM | 532 | O | VAL | 135 | 34.084 | 67.983 | 56.415 | 1.00 | 36.31 |
| ATOM | 533 | N | ASN | 136 | 31.880 | 68.371 | 56.189 | 1.00 | 37.34 |
| ATOM | 534 | CA | ASN | 136 | 32.077 | 69.540 | 55.340 | 1.00 | 39.98 |
| ATOM | 535 | CB | ASN | 136 | 30.729 | 70.105 | 54.873 | 1.00 | 39.64 |
| ATOM | 536 | CG | ASN | 136 | 29.961 | 69.138 | 53.996 | 1.00 | 40.40 |
| ATOM | 537 | OD1 | ASN | 136 | 30.488 | 68.633 | 53.004 | 1.00 | 39.43 |
| ATOM | 538 | ND2 | ASN | 136 | 28.703 | 68.879 | 54.354 | 1.00 | 39.64 |
| ATOM | 539 | C | ASN | 136 | 32.851 | 70.639 | 56.061 | 1.00 | 41.21 |
| ATOM | 540 | O | ASN | 136 | 33.593 | 71.396 | 55.437 | 1.00 | 42.44 |
| ATOM | 541 | N | GLN | 137 | 32.684 | 70.716 | 57.377 | 1.00 | 42.26 |
| ATOM | 542 | CA | GLN | 137 | 33.354 | 71.741 | 58.173 | 1.00 | 43.46 |
| ATOM | 543 | CB | GLN | 137 | 32.486 | 72.104 | 59.381 | 1.00 | 44.53 |
| ATOM | 544 | CG | GLN | 137 | 31.077 | 72.557 | 59.023 | 1.00 | 47.29 |
| ATOM | 545 | CD | GLN | 137 | 31.064 | 73.786 | 58.130 | 1.00 | 49.81 |
| ATOM | 546 | OE1 | GLN | 137 | 31.620 | 74.830 | 58.480 | 1.00 | 51.43 |
| ATOM | 547 | NE2 | GLN | 137 | 30.424 | 73.668 | 56.971 | 1.00 | 50.55 |
| ATOM | 548 | C | GLN | 137 | 34.755 | 71.355 | 58.648 | 1.00 | 43.13 |
| ATOM | 549 | O | GLN | 137 | 35.518 | 72.209 | 59.101 | 1.00 | 42.91 |
| ATOM | 550 | N | LEU | 138 | 35.096 | 70.074 | 58.549 | 1.00 | 43.61 |
| ATOM | 551 | CA | LEU | 138 | 36.411 | 69.608 | 58.983 | 1.00 | 43.43 |
| ATOM | 552 | CB | LEU | 138 | 36.432 | 68.078 | 59.043 | 1.00 | 43.64 |
| ATOM | 553 | CG | LEU | 138 | 36.358 | 67.475 | 60.451 | 1.00 | 44.21 |
| ATOM | 554 | CD1 | LEU | 138 | 35.308 | 68.189 | 61.286 | 1.00 | 44.64 |
| ATOM | 555 | CD2 | LEU | 138 | 36.049 | 65.994 | 60.349 | 1.00 | 44.83 |
| ATOM | 556 | C | LEU | 138 | 37.530 | 70.124 | 58.087 | 1.00 | 43.49 |
| ATOM | 557 | O | LEU | 138 | 37.443 | 70.055 | 56.862 | 1.00 | 43.96 |
| ATOM | 558 | N | GLN | 139 | 38.585 | 70.635 | 58.716 | 1.00 | 43.92 |
| ATOM | 559 | CA | GLN | 139 | 39.729 | 71.199 | 58.005 | 1.00 | 44.02 |
| ATOM | 560 | CB | GLN | 139 | 40.392 | 72.275 | 58.867 | 1.00 | 46.53 |
| ATOM | 561 | CG | GLN | 139 | 40.683 | 73.572 | 58.137 | 1.00 | 49.82 |
| ATOM | 562 | CD | GLN | 139 | 39.418 | 74.318 | 57.762 | 1.00 | 52.02 |
| ATOM | 563 | OE1 | GLN | 139 | 38.581 | 73.813 | 57.012 | 1.00 | 53.40 |
| ATOM | 564 | NE2 | GLN | 139 | 39.269 | 75.530 | 58.288 | 1.00 | 53.64 |
| ATOM | 565 | C | GLN | 139 | 40.778 | 70.167 | 57.603 | 1.00 | 43.28 |
| ATOM | 566 | O | GLN | 139 | 41.149 | 70.075 | 56.434 | 1.00 | 44.53 |
| ATOM | 567 | N | ASN | 140 | 41.268 | 69.403 | 58.575 | 1.00 | 41.60 |
| ATOM | 568 | CA | ASN | 140 | 42.280 | 68.385 | 58.307 | 1.00 | 39.70 |
| ATOM | 569 | CB | ASN | 140 | 42.721 | 67.719 | 59.614 | 1.00 | 38.65 |
| ATOM | 570 | CG | ASN | 140 | 43.904 | 66.782 | 59.425 | 1.00 | 38.74 |
| ATOM | 571 | OD1 | ASN | 140 | 43.860 | 65.877 | 58.587 | 1.00 | 39.03 |
| ATOM | 572 | ND2 | ASN | 140 | 44.959 | 67.007 | 60.208 | 1.00 | 38.01 |
| ATOM | 573 | C | ASN | 140 | 41.715 | 67.336 | 57.353 | 1.00 | 39.03 |

TABLE A-continued

| | | | | | | | | | |
|---|---|---|---|---|---|---|---|---|---|
| ATOM | 574 | O | ASN | 140 | 40.752 | 66.640 | 57.682 | 1.00 | 37.85 |
| ATOM | 575 | N | THR | 141 | 42.319 | 67.222 | 56.175 | 1.00 | 38.84 |
| ATOM | 576 | CA | THR | 141 | 41.862 | 66.265 | 55.175 | 1.00 | 39.36 |
| ATOM | 577 | CB | THR | 141 | 42.689 | 66.377 | 53.878 | 1.00 | 40.12 |
| ATOM | 578 | OG1 | THR | 141 | 44.072 | 66.148 | 54.168 | 1.00 | 42.67 |
| ATOM | 579 | CG2 | THR | 141 | 42.527 | 67.761 | 53.263 | 1.00 | 40.55 |
| ATOM | 580 | C | THR | 141 | 41.910 | 64.820 | 55.673 | 1.00 | 38.70 |
| ATOM | 581 | O | THR | 141 | 40.965 | 64.060 | 55.469 | 1.00 | 39.63 |
| ATOM | 582 | N | THR | 142 | 43.003 | 64.442 | 56.327 | 1.00 | 37.88 |
| ATOM | 583 | CA | THR | 142 | 43.141 | 63.082 | 56.843 | 1.00 | 36.04 |
| ATOM | 584 | CB | THR | 142 | 44.516 | 62.870 | 57.509 | 1.00 | 36.83 |
| ATOM | 585 | OG1 | THR | 142 | 45.547 | 63.012 | 56.524 | 1.00 | 36.96 |
| ATOM | 586 | CG2 | THR | 142 | 44.605 | 61.481 | 58.126 | 1.00 | 37.59 |
| ATOM | 587 | C | THR | 142 | 42.045 | 62.770 | 57.857 | 1.00 | 35.01 |
| ATOM | 588 | O | THR | 142 | 41.465 | 61.686 | 57.836 | 1.00 | 34.20 |
| ATOM | 589 | N | ILE | 143 | 41.770 | 63.719 | 58.747 | 1.00 | 33.02 |
| ATOM | 590 | CA | ILE | 143 | 40.728 | 63.538 | 59.754 | 1.00 | 32.35 |
| ATOM | 591 | CB | ILE | 143 | 40.706 | 64.721 | 60.754 | 1.00 | 33.52 |
| ATOM | 592 | CG2 | ILE | 143 | 39.488 | 64.620 | 61.664 | 1.00 | 31.47 |
| ATOM | 593 | CG1 | ILE | 143 | 42.000 | 64.736 | 61.573 | 1.00 | 33.85 |
| ATOM | 594 | CD1 | ILE | 143 | 42.192 | 63.512 | 62.442 | 1.00 | 36.23 |
| ATOM | 595 | C | ILE | 143 | 39.379 | 63.467 | 59.048 | 1.00 | 31.17 |
| ATOM | 596 | O | ILE | 143 | 38.503 | 62.679 | 59.413 | 1.00 | 29.34 |
| ATOM | 597 | N | LYS | 144 | 39.231 | 64.306 | 58.028 | 1.00 | 30.98 |
| ATOM | 598 | CA | LYS | 144 | 38.016 | 64.386 | 57.228 | 1.00 | 30.73 |
| ATOM | 599 | CB | LYS | 144 | 38.208 | 65.462 | 56.153 | 1.00 | 33.49 |
| ATOM | 600 | CG | LYS | 144 | 36.993 | 65.776 | 55.306 | 1.00 | 37.03 |
| ATOM | 601 | CD | LYS | 144 | 37.360 | 66.779 | 54.219 | 1.00 | 40.12 |
| ATOM | 602 | CE | LYS | 144 | 36.174 | 67.118 | 53.325 | 1.00 | 42.45 |
| ATOM | 603 | NZ | LYS | 144 | 35.112 | 67.865 | 54.051 | 1.00 | 43.36 |
| ATOM | 604 | C | LYS | 144 | 37.712 | 63.034 | 56.574 | 1.00 | 28.35 |
| ATOM | 605 | O | LYS | 144 | 36.590 | 62.526 | 56.645 | 1.00 | 27.74 |
| ATOM | 606 | N | ARG | 145 | 38.734 | 62.459 | 55.951 | 1.00 | 26.86 |
| ATOM | 607 | CA | ARG | 145 | 38.631 | 61.179 | 55.254 | 1.00 | 24.41 |
| ATOM | 608 | CB | ARG | 145 | 39.943 | 60.913 | 54.512 | 1.00 | 24.91 |
| ATOM | 609 | CG | ARG | 145 | 39.934 | 59.733 | 53.549 | 1.00 | 23.83 |
| ATOM | 610 | CD | ARG | 145 | 41.194 | 59.763 | 52.692 | 1.00 | 24.48 |
| ATOM | 611 | NE | ARG | 145 | 41.334 | 58.608 | 51.806 | 1.00 | 23.26 |
| ATOM | 612 | CZ | ARG | 145 | 40.576 | 58.376 | 50.738 | 1.00 | 25.83 |
| ATOM | 613 | NH1 | ARG | 145 | 39.606 | 59.221 | 50.410 | 1.00 | 23.61 |
| ATOM | 614 | NH2 | ARG | 145 | 40.796 | 57.300 | 49.988 | 1.00 | 23.06 |
| ATOM | 615 | C | ARG | 145 | 38.302 | 60.009 | 56.187 | 1.00 | 24.55 |
| ATOM | 616 | O | ARG | 145 | 37.457 | 59.168 | 55.871 | 1.00 | 22.27 |
| ATOM | 617 | N | ILE | 146 | 38.971 | 59.949 | 57.333 | 1.00 | 23.82 |
| ATOM | 618 | CA | ILE | 146 | 38.720 | 58.876 | 58.288 | 1.00 | 24.41 |
| ATOM | 619 | CB | ILE | 146 | 39.720 | 58.935 | 59.468 | 1.00 | 25.21 |
| ATOM | 620 | CG2 | ILE | 146 | 39.251 | 58.033 | 60.600 | 1.00 | 22.70 |
| ATOM | 621 | CG1 | ILE | 146 | 41.113 | 58.519 | 58.979 | 1.00 | 25.19 |
| ATOM | 622 | CD1 | ILE | 146 | 42.202 | 58.625 | 60.028 | 1.00 | 26.27 |
| ATOM | 623 | C | ILE | 146 | 37.296 | 58.932 | 58.838 | 1.00 | 24.39 |
| ATOM | 624 | O | ILE | 146 | 36.591 | 57.922 | 58.858 | 1.00 | 24.78 |
| ATOM | 625 | N | ILE | 147 | 36.874 | 60.116 | 59.274 | 1.00 | 23.99 |
| ATOM | 626 | CA | ILE | 147 | 35.539 | 60.283 | 59.832 | 1.00 | 24.23 |
| ATOM | 627 | CB | ILE | 147 | 35.337 | 61.724 | 60.381 | 1.00 | 24.80 |
| ATOM | 628 | CG2 | ILE | 147 | 33.871 | 61.960 | 60.733 | 1.00 | 25.96 |
| ATOM | 629 | CG1 | ILE | 147 | 36.219 | 61.924 | 61.622 | 1.00 | 25.41 |
| ATOM | 630 | CD1 | ILE | 147 | 36.029 | 63.261 | 62.324 | 1.00 | 25.15 |
| ATOM | 631 | C | ILE | 147 | 34.441 | 59.947 | 58.822 | 1.00 | 23.88 |
| ATOM | 632 | O | ILE | 147 | 33.459 | 59.293 | 59.168 | 1.00 | 22.19 |
| ATOM | 633 | N | ALA | 148 | 34.603 | 60.392 | 57.579 | 1.00 | 25.35 |
| ATOM | 634 | CA | ALA | 148 | 33.610 | 60.099 | 56.549 | 1.00 | 26.35 |
| ATOM | 635 | CB | ALA | 148 | 34.041 | 60.704 | 55.206 | 1.00 | 26.72 |
| ATOM | 636 | C | ALA | 148 | 33.470 | 58.584 | 56.424 | 1.00 | 26.20 |
| ATOM | 637 | O | ALA | 148 | 32.366 | 58.055 | 56.296 | 1.00 | 26.64 |
| ATOM | 638 | N | LYS | 149 | 34.604 | 57.892 | 56.476 | 1.00 | 26.33 |
| ATOM | 639 | CA | LYS | 149 | 34.632 | 56.439 | 56.372 | 1.00 | 25.57 |
| ATOM | 640 | CB | LYS | 149 | 36.080 | 55.970 | 56.205 | 1.00 | 28.20 |
| ATOM | 641 | CG | LYS | 149 | 36.244 | 54.497 | 55.885 | 1.00 | 32.16 |
| ATOM | 642 | CD | LYS | 149 | 37.640 | 54.228 | 55.333 | 1.00 | 36.26 |
| ATOM | 643 | CE | LYS | 149 | 37.815 | 52.773 | 54.930 | 1.00 | 37.26 |
| ATOM | 644 | NZ | LYS | 149 | 37.763 | 51.868 | 56.105 | 1.00 | 39.38 |
| ATOM | 645 | C | LYS | 149 | 33.989 | 55.754 | 57.581 | 1.00 | 24.69 |
| ATOM | 646 | O | LYS | 149 | 33.302 | 54.739 | 57.435 | 1.00 | 24.36 |
| ATOM | 647 | N | VAL | 150 | 34.205 | 56.307 | 58.772 | 1.00 | 22.37 |
| ATOM | 648 | CA | VAL | 150 | 33.632 | 55.727 | 59.981 | 1.00 | 22.59 |
| ATOM | 649 | CB | VAL | 150 | 34.270 | 56.341 | 61.254 | 1.00 | 23.63 |
| ATOM | 650 | CG1 | VAL | 150 | 33.651 | 55.723 | 62.502 | 1.00 | 20.79 |
| ATOM | 651 | CG2 | VAL | 150 | 35.776 | 56.099 | 61.243 | 1.00 | 22.23 |
| ATOM | 652 | C | VAL | 150 | 32.111 | 55.899 | 60.035 | 1.00 | 21.68 |
| ATOM | 653 | O | VAL | 150 | 31.426 | 55.151 | 60.730 | 1.00 | 21.12 |

TABLE A-continued

| | | | | | | | | | |
|---|---|---|---|---|---|---|---|---|---|
| ATOM | 654 | N | GLN | 151 | 31.581 | 56.871 | 59.294 | 1.00 | 20.83 |
| ATOM | 655 | CA | GLN | 151 | 30.133 | 57.097 | 59.267 | 1.00 | 21.36 |
| ATOM | 656 | CB | GLN | 151 | 29.804 | 58.423 | 58.566 | 1.00 | 21.83 |
| ATOM | 657 | CG | GLN | 151 | 30.424 | 59.658 | 59.216 | 1.00 | 22.21 |
| ATOM | 658 | CD | GLN | 151 | 30.025 | 60.949 | 58.514 | 1.00 | 26.18 |
| ATOM | 659 | OE1 | GLN | 151 | 29.786 | 60.960 | 57.306 | 1.00 | 26.64 |
| ATOM | 660 | NE2 | GLN | 151 | 29.969 | 62.046 | 59.266 | 1.00 | 23.87 |
| ATOM | 661 | C | GLN | 151 | 29.405 | 55.948 | 58.555 | 1.00 | 21.63 |
| ATOM | 662 | O | GLN | 151 | 28.178 | 55.831 | 58.637 | 1.00 | 21.51 |
| ATOM | 663 | N | ASP | 152 | 30.162 | 55.111 | 57.848 | 1.00 | 19.66 |
| ATOM | 664 | CA | ASP | 152 | 29.596 | 53.958 | 57.141 | 1.00 | 21.29 |
| ATOM | 665 | CB | ASP | 152 | 30.413 | 53.657 | 55.875 | 1.00 | 19.46 |
| ATOM | 666 | CG | ASP | 152 | 29.783 | 52.574 | 55.004 | 1.00 | 21.81 |
| ATOM | 667 | OD1 | ASP | 152 | 29.034 | 51.724 | 55.528 | 1.00 | 21.84 |
| ATOM | 668 | OD2 | ASP | 152 | 30.056 | 52.563 | 53.784 | 1.00 | 22.86 |
| ATOM | 669 | C | ASP | 152 | 29.690 | 52.781 | 58.109 | 1.00 | 20.99 |
| ATOM | 670 | O | ASP | 152 | 30.772 | 52.240 | 58.323 | 1.00 | 20.95 |
| ATOM | 671 | N | LEU | 153 | 28.558 | 52.386 | 58.688 | 1.00 | 22.58 |
| ATOM | 672 | CA | LEU | 153 | 28.535 | 51.292 | 59.661 | 1.00 | 22.39 |
| ATOM | 673 | CB | LEU | 153 | 27.330 | 51.433 | 60.593 | 1.00 | 22.04 |
| ATOM | 674 | CG | LEU | 153 | 26.824 | 52.837 | 60.927 | 1.00 | 25.61 |
| ATOM | 675 | CD1 | LEU | 153 | 25.697 | 52.735 | 61.951 | 1.00 | 25.99 |
| ATOM | 676 | CD2 | LEU | 153 | 27.956 | 53.680 | 61.460 | 1.00 | 22.76 |
| ATOM | 677 | C | LEU | 153 | 28.460 | 49.919 | 59.013 | 1.00 | 22.78 |
| ATOM | 678 | O | LEU | 153 | 28.512 | 48.902 | 59.704 | 1.00 | 21.91 |
| ATOM | 679 | N | GLU | 154 | 28.341 | 49.894 | 57.691 | 1.00 | 22.03 |
| ATOM | 680 | CA | GLU | 154 | 28.202 | 48.644 | 56.965 | 1.00 | 23.75 |
| ATOM | 681 | CB | GLU | 154 | 29.540 | 47.902 | 56.894 | 1.00 | 26.94 |
| ATOM | 682 | CG | GLU | 154 | 30.179 | 48.049 | 55.508 | 1.00 | 34.66 |
| ATOM | 683 | CD | GLU | 154 | 31.604 | 48.553 | 55.547 | 1.00 | 38.29 |
| ATOM | 684 | OE1 | GLU | 154 | 32.505 | 47.776 | 55.938 | 1.00 | 41.36 |
| ATOM | 685 | OE2 | GLU | 154 | 31.825 | 49.729 | 55.185 | 1.00 | 42.09 |
| ATOM | 686 | C | GLU | 154 | 27.103 | 47.792 | 57.603 | 1.00 | 21.61 |
| ATOM | 687 | O | GLU | 154 | 26.055 | 48.324 | 57.952 | 1.00 | 22.87 |
| ATOM | 688 | N | ARG | 155 | 27.323 | 46.493 | 57.773 | 1.00 | 20.09 |
| ATOM | 689 | CA | ARG | 155 | 26.275 | 45.646 | 58.340 | 1.00 | 21.46 |
| ATOM | 690 | CB | ARG | 155 | 26.742 | 44.192 | 58.430 | 1.00 | 20.77 |
| ATOM | 691 | CG | ARG | 155 | 27.718 | 43.918 | 59.551 | 1.00 | 19.96 |
| ATOM | 692 | CD | ARG | 155 | 28.186 | 42.480 | 59.509 | 1.00 | 23.32 |
| ATOM | 693 | NE | ARG | 155 | 28.950 | 42.205 | 58.299 | 1.00 | 25.43 |
| ATOM | 694 | CZ | ARG | 155 | 29.456 | 41.017 | 57.994 | 1.00 | 29.86 |
| ATOM | 695 | NH1 | ARG | 155 | 29.274 | 39.987 | 58.814 | 1.00 | 28.71 |
| ATOM | 696 | NH2 | ARG | 155 | 30.152 | 40.858 | 56.873 | 1.00 | 31.49 |
| ATOM | 697 | C | ARG | 155 | 25.784 | 46.105 | 59.712 | 1.00 | 21.73 |
| ATOM | 698 | O | ARG | 155 | 24.638 | 45.846 | 60.084 | 1.00 | 21.61 |
| ATOM | 699 | N | ALA | 156 | 26.645 | 46.787 | 60.461 | 1.00 | 21.87 |
| ATOM | 700 | CA | ALA | 156 | 26.270 | 47.264 | 61.789 | 1.00 | 24.11 |
| ATOM | 701 | CB | ALA | 156 | 27.478 | 47.878 | 62.490 | 1.00 | 24.00 |
| ATOM | 702 | C | ALA | 156 | 25.117 | 48.270 | 61.749 | 1.00 | 24.29 |
| ATOM | 703 | O | ALA | 156 | 24.566 | 48.620 | 62.788 | 1.00 | 24.68 |
| ATOM | 704 | N | ALA | 157 | 24.748 | 48.735 | 60.557 | 1.00 | 22.56 |
| ATOM | 705 | CA | ALA | 157 | 23.642 | 49.684 | 60.447 | 1.00 | 22.76 |
| ATOM | 706 | CB | ALA | 157 | 23.721 | 50.438 | 59.125 | 1.00 | 21.66 |
| ATOM | 707 | C | ALA | 157 | 22.297 | 48.966 | 60.554 | 1.00 | 22.55 |
| ATOM | 708 | O | ALA | 157 | 21.258 | 49.598 | 60.749 | 1.00 | 23.01 |
| ATOM | 709 | N | LEU | 158 | 22.322 | 47.642 | 60.429 | 1.00 | 22.24 |
| ATOM | 710 | CA | LEU | 158 | 21.103 | 46.834 | 60.490 | 1.00 | 21.40 |
| ATOM | 711 | CB | LEU | 158 | 21.365 | 45.441 | 59.912 | 1.00 | 19.45 |
| ATOM | 712 | CG | LEU | 158 | 21.629 | 45.249 | 58.418 | 1.00 | 16.15 |
| ATOM | 713 | CD1 | LEU | 158 | 22.085 | 43.821 | 58.168 | 1.00 | 18.41 |
| ATOM | 714 | CD2 | LEU | 158 | 20.357 | 45.554 | 57.632 | 1.00 | 14.90 |
| ATOM | 715 | C | LEU | 158 | 20.542 | 46.655 | 61.900 | 1.00 | 22.60 |
| ATOM | 716 | O | LEU | 158 | 21.296 | 46.550 | 62.861 | 1.00 | 21.61 |
| ATOM | 717 | N | PRO | 159 | 19.202 | 46.616 | 62.033 | 1.00 | 23.33 |
| ATOM | 718 | CD | PRO | 159 | 18.180 | 46.863 | 60.999 | 1.00 | 22.87 |
| ATOM | 719 | CA | PRO | 159 | 18.582 | 46.430 | 63.348 | 1.00 | 24.44 |
| ATOM | 720 | CB | PRO | 159 | 17.096 | 46.342 | 63.017 | 1.00 | 23.93 |
| ATOM | 721 | CG | PRO | 159 | 16.970 | 47.241 | 61.824 | 1.00 | 24.99 |
| ATOM | 722 | C | PRO | 159 | 19.122 | 45.111 | 63.897 | 1.00 | 25.67 |
| ATOM | 723 | O | PRO | 159 | 19.384 | 44.182 | 63.128 | 1.00 | 24.90 |
| ATOM | 724 | N | ALA | 160 | 19.289 | 45.035 | 65.213 | 1.00 | 25.35 |
| ATOM | 725 | CA | ALA | 160 | 19.818 | 43.841 | 65.866 | 1.00 | 26.14 |
| ATOM | 726 | CB | ALA | 160 | 19.536 | 43.909 | 67.366 | 1.00 | 26.95 |
| ATOM | 727 | C | ALA | 160 | 19.296 | 42.516 | 65.303 | 1.00 | 26.55 |
| ATOM | 728 | O | ALA | 160 | 20.071 | 41.584 | 65.078 | 1.00 | 23.79 |
| ATOM | 729 | N | GLN | 161 | 17.989 | 42.431 | 65.077 | 1.00 | 26.32 |
| ATOM | 730 | CA | GLN | 161 | 17.397 | 41.201 | 64.563 | 1.00 | 29.37 |
| ATOM | 731 | CB | GLN | 161 | 15.871 | 41.313 | 64.542 | 1.00 | 31.38 |
| ATOM | 732 | CG | GLN | 161 | 15.167 | 40.022 | 64.158 | 1.00 | 37.44 |
| ATOM | 733 | CD | GLN | 161 | 13.656 | 40.124 | 64.267 | 1.00 | 41.02 |

TABLE A-continued

| | | | | | | | | | |
|---|---|---|---|---|---|---|---|---|---|
| ATOM | 734 | OE1 | GLN | 161 | 13.114 | 40.363 | 65.349 | 1.00 | 43.87 |
| ATOM | 735 | NE2 | GLN | 161 | 12.967 | 39.947 | 63.144 | 1.00 | 43.01 |
| ATOM | 736 | C | GLN | 161 | 17.909 | 40.844 | 63.169 | 1.00 | 28.25 |
| ATOM | 737 | O | GLN | 161 | 18.313 | 39.705 | 62.922 | 1.00 | 27.07 |
| ATOM | 738 | N | GLU | 162 | 17.884 | 41.815 | 62.262 | 1.00 | 27.58 |
| ATOM | 739 | CA | GLU | 162 | 18.353 | 41.595 | 60.898 | 1.00 | 28.12 |
| ATOM | 740 | CB | GLU | 162 | 18.056 | 42.812 | 60.014 | 1.00 | 30.05 |
| ATOM | 741 | CG | GLU | 162 | 16.648 | 42.872 | 59.439 | 1.00 | 36.16 |
| ATOM | 742 | CD | GLU | 162 | 15.596 | 43.218 | 60.474 | 1.00 | 40.46 |
| ATOM | 743 | OE1 | GLU | 162 | 15.349 | 42.396 | 61.383 | 1.00 | 43.71 |
| ATOM | 744 | OE2 | GLU | 162 | 15.015 | 44.320 | 60.376 | 1.00 | 42.20 |
| ATOM | 745 | C | GLU | 162 | 19.852 | 41.319 | 60.875 | 1.00 | 25.64 |
| ATOM | 746 | O | GLU | 162 | 20.338 | 40.564 | 60.036 | 1.00 | 24.67 |
| ATOM | 747 | N | LEU | 163 | 20.583 | 41.933 | 61.798 | 1.00 | 23.77 |
| ATOM | 748 | CA | LEU | 163 | 22.027 | 41.741 | 61.856 | 1.00 | 23.77 |
| ATOM | 749 | CB | LEU | 163 | 22.658 | 42.686 | 62.886 | 1.00 | 23.27 |
| ATOM | 750 | CG | LEU | 163 | 24.167 | 42.535 | 63.139 | 1.00 | 22.82 |
| ATOM | 751 | CD1 | LEU | 163 | 24.947 | 42.725 | 61.843 | 1.00 | 24.01 |
| ATOM | 752 | CD2 | LEU | 163 | 24.614 | 43.548 | 64.179 | 1.00 | 23.32 |
| ATOM | 753 | C | LEU | 163 | 22.382 | 40.299 | 62.192 | 1.00 | 24.03 |
| ATOM | 754 | O | LEU | 163 | 23.248 | 39.700 | 61.546 | 1.00 | 23.44 |
| ATOM | 755 | N | GLU | 164 | 21.717 | 39.728 | 63.192 | 1.00 | 23.75 |
| ATOM | 756 | CA | GLU | 164 | 22.031 | 38.356 | 63.562 | 1.00 | 25.00 |
| ATOM | 757 | CB | GLU | 164 | 21.362 | 37.974 | 64.893 | 1.00 | 28.77 |
| ATOM | 758 | CG | GLU | 164 | 19.950 | 37.445 | 64.807 | 1.00 | 35.39 |
| ATOM | 759 | CD | GLU | 164 | 19.405 | 37.035 | 66.171 | 1.00 | 40.22 |
| ATOM | 760 | OE1 | GLU | 164 | 18.302 | 36.450 | 66.224 | 1.00 | 41.83 |
| ATOM | 761 | OE2 | GLU | 164 | 20.080 | 37.303 | 67.193 | 1.00 | 41.78 |
| ATOM | 762 | C | GLU | 164 | 21.628 | 37.401 | 62.445 | 1.00 | 23.01 |
| ATOM | 763 | O | GLU | 164 | 22.319 | 36.414 | 62.185 | 1.00 | 22.51 |
| ATOM | 764 | N | GLU | 165 | 20.524 | 37.703 | 61.768 | 1.00 | 22.62 |
| ATOM | 765 | CA | GLU | 165 | 20.073 | 36.857 | 60.670 | 1.00 | 24.34 |
| ATOM | 766 | CB | GLU | 165 | 18.669 | 37.265 | 60.209 | 1.00 | 24.26 |
| ATOM | 767 | CG | GLU | 165 | 18.195 | 36.512 | 58.973 | 1.00 | 26.97 |
| ATOM | 768 | CD | GLU | 165 | 16.781 | 36.876 | 58.560 | 1.00 | 28.34 |
| ATOM | 769 | OE1 | GLU | 165 | 16.329 | 37.996 | 58.886 | 1.00 | 28.72 |
| ATOM | 770 | OE2 | GLU | 165 | 16.127 | 36.045 | 57.893 | 1.00 | 28.15 |
| ATOM | 771 | C | GLU | 165 | 21.065 | 36.968 | 59.509 | 1.00 | 24.93 |
| ATOM | 772 | O | GLU | 165 | 21.395 | 35.967 | 58.865 | 1.00 | 24.77 |
| ATOM | 773 | N | TYR | 166 | 21.552 | 38.181 | 59.260 | 1.00 | 23.07 |
| ATOM | 774 | CA | TYR | 166 | 22.514 | 38.402 | 58.188 | 1.00 | 23.12 |
| ATOM | 775 | CB | TYR | 166 | 22.764 | 39.903 | 57.993 | 1.00 | 21.91 |
| ATOM | 776 | CG | TYR | 166 | 23.736 | 40.235 | 56.875 | 1.00 | 21.83 |
| ATOM | 777 | CD1 | TYR | 166 | 23.502 | 39.807 | 55.568 | 1.00 | 22.95 |
| ATOM | 778 | CE1 | TYR | 166 | 24.390 | 40.119 | 54.532 | 1.00 | 22.34 |
| ATOM | 779 | CD2 | TYR | 166 | 24.886 | 40.985 | 57.125 | 1.00 | 21.46 |
| ATOM | 780 | CE2 | TYR | 166 | 25.780 | 41.301 | 56.102 | 1.00 | 22.52 |
| ATOM | 781 | CZ | TYR | 166 | 25.526 | 40.865 | 54.808 | 1.00 | 23.28 |
| ATOM | 782 | OH | TYR | 166 | 26.403 | 41.176 | 53.795 | 1.00 | 23.78 |
| ATOM | 783 | C | TYR | 166 | 23.831 | 37.687 | 58.503 | 1.00 | 23.03 |
| ATOM | 784 | O | TYR | 166 | 24.412 | 37.040 | 57.633 | 1.00 | 23.00 |
| ATOM | 785 | N | ASN | 167 | 24.302 | 37.794 | 59.743 | 1.00 | 22.34 |
| ATOM | 786 | CA | ASN | 167 | 25.551 | 37.129 | 60.112 | 1.00 | 22.66 |
| ATOM | 787 | CB | ASN | 167 | 25.979 | 37.493 | 61.539 | 1.00 | 23.67 |
| ATOM | 788 | CG | ASN | 167 | 26.499 | 38.915 | 61.649 | 1.00 | 24.93 |
| ATOM | 789 | OD1 | ASN | 167 | 27.226 | 39.393 | 60.777 | 1.00 | 26.06 |
| ATOM | 790 | ND2 | ASN | 167 | 26.140 | 39.594 | 62.731 | 1.00 | 25.88 |
| ATOM | 791 | C | ASN | 167 | 25.430 | 35.616 | 59.994 | 1.00 | 22.26 |
| ATOM | 792 | O | ASN | 167 | 26.363 | 34.950 | 59.552 | 1.00 | 21.60 |
| ATOM | 793 | N | LYS | 168 | 24.280 | 35.073 | 60.382 | 1.00 | 20.98 |
| ATOM | 794 | CA | LYS | 168 | 24.079 | 33.632 | 60.307 | 1.00 | 21.98 |
| ATOM | 795 | CB | LYS | 168 | 22.809 | 33.214 | 61.055 | 1.00 | 23.33 |
| ATOM | 796 | CG | LYS | 168 | 22.528 | 31.729 | 60.936 | 1.00 | 27.37 |
| ATOM | 797 | CD | LYS | 168 | 21.405 | 31.270 | 61.844 | 1.00 | 32.52 |
| ATOM | 798 | CE | LYS | 168 | 21.082 | 29.808 | 61.567 | 1.00 | 35.29 |
| ATOM | 799 | NZ | LYS | 168 | 22.320 | 28.969 | 61.554 | 1.00 | 35.98 |
| ATOM | 800 | C | LYS | 168 | 24.006 | 33.159 | 58.860 | 1.00 | 20.98 |
| ATOM | 801 | O | LYS | 168 | 24.509 | 32.085 | 58.525 | 1.00 | 20.06 |
| ATOM | 802 | N | ILE | 169 | 23.374 | 33.959 | 58.007 | 1.00 | 19.85 |
| ATOM | 803 | CA | ILE | 169 | 23.260 | 33.615 | 56.595 | 1.00 | 21.24 |
| ATOM | 804 | CB | ILE | 169 | 22.368 | 34.631 | 55.846 | 1.00 | 21.43 |
| ATOM | 805 | CG2 | ILE | 169 | 22.611 | 34.554 | 54.338 | 1.00 | 23.74 |
| ATOM | 806 | CG1 | ILE | 169 | 20.900 | 34.340 | 56.159 | 1.00 | 24.06 |
| ATOM | 807 | CD1 | ILE | 169 | 19.930 | 35.302 | 55.515 | 1.00 | 24.63 |
| ATOM | 808 | C | ILE | 169 | 24.643 | 33.554 | 55.944 | 1.00 | 19.54 |
| ATOM | 809 | O | ILE | 169 | 24.936 | 32.632 | 55.188 | 1.00 | 21.81 |
| ATOM | 810 | N | LEU | 170 | 25.491 | 34.530 | 56.244 | 1.00 | 19.05 |
| ATOM | 811 | CA | LEU | 170 | 26.837 | 34.562 | 55.687 | 1.00 | 19.74 |
| ATOM | 812 | CB | LEU | 170 | 27.565 | 35.834 | 56.131 | 1.00 | 19.37 |
| ATOM | 813 | CG | LEU | 170 | 27.041 | 37.157 | 55.559 | 1.00 | 21.50 |

TABLE A-continued

| | | | | | | | | | |
|---|---|---|---|---|---|---|---|---|---|
| ATOM | 814 | CD1 | LEU | 170 | 27.810 | 38.328 | 56.170 | 1.00 | 20.18 |
| ATOM | 815 | CD2 | LEU | 170 | 27.188 | 37.151 | 54.044 | 1.00 | 19.99 |
| ATOM | 816 | C | LEU | 170 | 27.620 | 33.332 | 56.140 | 1.00 | 21.61 |
| ATOM | 817 | O | LEU | 170 | 28.300 | 32.682 | 55.344 | 1.00 | 21.28 |
| ATOM | 818 | N | LEU | 171 | 27.511 | 33.009 | 57.423 | 1.00 | 21.65 |
| ATOM | 819 | CA | LEU | 171 | 28.217 | 31.862 | 57.969 | 1.00 | 23.32 |
| ATOM | 820 | CB | LEU | 171 | 28.042 | 31.811 | 59.490 | 1.00 | 25.33 |
| ATOM | 821 | CG | LEU | 171 | 28.968 | 30.869 | 60.262 | 1.00 | 28.92 |
| ATOM | 822 | CD1 | LEU | 171 | 30.414 | 31.241 | 59.990 | 1.00 | 30.99 |
| ATOM | 823 | CD2 | LEU | 171 | 28.681 | 30.977 | 61.756 | 1.00 | 32.45 |
| ATOM | 824 | C | LEU | 171 | 27.714 | 30.569 | 57.337 | 1.00 | 22.19 |
| ATOM | 825 | O | LEU | 171 | 28.511 | 29.705 | 56.975 | 1.00 | 22.62 |
| ATOM | 826 | N | ASP | 172 | 26.396 | 30.439 | 57.202 | 1.00 | 20.90 |
| ATOM | 827 | CA | ASP | 172 | 25.817 | 29.237 | 56.615 | 1.00 | 21.82 |
| ATOM | 828 | CB | ASP | 172 | 24.283 | 29.261 | 56.698 | 1.00 | 22.55 |
| ATOM | 829 | CG | ASP | 172 | 23.766 | 29.076 | 58.121 | 1.00 | 24.93 |
| ATOM | 830 | OD1 | ASP | 172 | 24.489 | 28.493 | 58.952 | 1.00 | 24.24 |
| ATOM | 831 | OD2 | ASP | 172 | 22.625 | 29.502 | 58.404 | 1.00 | 26.64 |
| ATOM | 832 | C | ASP | 172 | 26.244 | 29.060 | 55.161 | 1.00 | 22.04 |
| ATOM | 833 | O | ASP | 172 | 26.501 | 27.940 | 54.720 | 1.00 | 21.02 |
| ATOM | 834 | N | MET | 173 | 26.315 | 30.156 | 54.411 | 1.00 | 20.30 |
| ATOM | 835 | CA | MET | 173 | 26.731 | 30.057 | 53.014 | 1.00 | 20.02 |
| ATOM | 836 | CB | MET | 173 | 26.524 | 31.389 | 52.277 | 1.00 | 16.36 |
| ATOM | 837 | CG | MET | 173 | 25.055 | 31.743 | 52.047 | 1.00 | 14.73 |
| ATOM | 838 | SD | MET | 173 | 24.812 | 32.982 | 50.748 | 1.00 | 18.57 |
| ATOM | 839 | CE | MET | 173 | 25.587 | 34.426 | 51.501 | 1.00 | 15.06 |
| ATOM | 840 | C | MET | 173 | 28.195 | 29.639 | 52.925 | 1.00 | 19.90 |
| ATOM | 841 | O | MET | 173 | 28.560 | 28.773 | 52.129 | 1.00 | 18.15 |
| ATOM | 842 | N | GLU | 174 | 29.033 | 30.251 | 53.751 | 1.00 | 21.27 |
| ATOM | 843 | CA | GLU | 174 | 30.452 | 29.931 | 53.745 | 1.00 | 24.34 |
| ATOM | 844 | CB | GLU | 174 | 31.209 | 30.830 | 54.719 | 1.00 | 26.33 |
| ATOM | 845 | CG | GLU | 174 | 32.700 | 30.567 | 54.706 | 1.00 | 31.24 |
| ATOM | 846 | CD | GLU | 174 | 33.296 | 30.741 | 53.321 | 1.00 | 34.04 |
| ATOM | 847 | OE1 | GLU | 174 | 33.424 | 31.900 | 52.874 | 1.00 | 33.83 |
| ATOM | 848 | OE2 | GLU | 174 | 33.624 | 29.716 | 52.678 | 1.00 | 34.64 |
| ATOM | 849 | C | GLU | 174 | 30.686 | 28.477 | 54.122 | 1.00 | 23.73 |
| ATOM | 850 | O | GLU | 174 | 31.454 | 27.768 | 53.464 | 1.00 | 23.77 |
| ATOM | 851 | N | THR | 175 | 30.024 | 28.037 | 55.187 | 1.00 | 22.79 |
| ATOM | 852 | CA | THR | 175 | 30.166 | 26.664 | 55.650 | 1.00 | 23.63 |
| ATOM | 853 | CB | THR | 175 | 29.363 | 26.425 | 56.941 | 1.00 | 23.79 |
| ATOM | 854 | OG1 | THR | 175 | 29.850 | 27.294 | 57.971 | 1.00 | 23.95 |
| ATOM | 855 | CG2 | THR | 175 | 29.502 | 24.973 | 57.391 | 1.00 | 23.49 |
| ATOM | 856 | C | THR | 175 | 29.693 | 25.671 | 54.593 | 1.00 | 22.90 |
| ATOM | 857 | O | THR | 175 | 30.391 | 24.701 | 54.279 | 1.00 | 24.74 |
| ATOM | 858 | N | THR | 176 | 28.507 | 25.917 | 54.050 | 1.00 | 19.50 |
| ATOM | 859 | CA | THR | 176 | 27.937 | 25.052 | 53.025 | 1.00 | 21.93 |
| ATOM | 860 | CB | THR | 176 | 26.605 | 25.616 | 52.494 | 1.00 | 21.32 |
| ATOM | 861 | OG1 | THR | 176 | 25.646 | 25.661 | 53.559 | 1.00 | 22.38 |
| ATOM | 862 | CG2 | THR | 176 | 26.068 | 24.740 | 51.358 | 1.00 | 20.84 |
| ATOM | 863 | C | THR | 176 | 28.884 | 24.870 | 51.842 | 1.00 | 21.08 |
| ATOM | 864 | O | THR | 176 | 29.060 | 23.761 | 51.342 | 1.00 | 22.40 |
| ATOM | 865 | N | TYR | 177 | 29.492 | 25.963 | 51.395 | 1.00 | 20.72 |
| ATOM | 866 | CA | TYR | 177 | 30.406 | 25.906 | 50.260 | 1.00 | 19.26 |
| ATOM | 867 | CB | TYR | 177 | 30.784 | 27.327 | 49.816 | 1.00 | 18.41 |
| ATOM | 868 | CG | TYR | 177 | 31.707 | 27.374 | 48.610 | 1.00 | 18.79 |
| ATOM | 869 | CD1 | TYR | 177 | 31.196 | 27.356 | 47.311 | 1.00 | 16.82 |
| ATOM | 870 | CE1 | TYR | 177 | 32.044 | 27.376 | 46.197 | 1.00 | 16.82 |
| ATOM | 871 | CD2 | TYR | 177 | 33.094 | 27.410 | 48.770 | 1.00 | 17.18 |
| ATOM | 872 | CE2 | TYR | 177 | 33.954 | 27.424 | 47.662 | 1.00 | 17.14 |
| ATOM | 873 | CZ | TYR | 177 | 33.418 | 27.406 | 46.382 | 1.00 | 18.38 |
| ATOM | 874 | OH | TYR | 177 | 34.256 | 27.403 | 45.289 | 1.00 | 18.18 |
| ATOM | 875 | C | TYR | 177 | 31.682 | 25.126 | 50.581 | 1.00 | 19.83 |
| ATOM | 876 | O | TYR | 177 | 32.089 | 24.244 | 49.826 | 1.00 | 19.73 |
| ATOM | 877 | N | SER | 178 | 32.298 | 25.448 | 51.712 | 1.00 | 19.67 |
| ATOM | 878 | CA | SER | 178 | 33.555 | 24.828 | 52.117 | 1.00 | 22.76 |
| ATOM | 879 | CB | SER | 178 | 34.208 | 25.678 | 53.211 | 1.00 | 23.75 |
| ATOM | 880 | OG | SER | 178 | 34.560 | 26.953 | 52.702 | 1.00 | 28.52 |
| ATOM | 881 | C | SER | 178 | 33.543 | 23.363 | 52.556 | 1.00 | 22.80 |
| ATOM | 882 | O | SER | 178 | 34.606 | 22.752 | 52.672 | 1.00 | 22.47 |
| ATOM | 883 | N | VAL | 179 | 32.368 | 22.796 | 52.803 | 1.00 | 22.17 |
| ATOM | 884 | CA | VAL | 179 | 32.309 | 21.401 | 53.219 | 1.00 | 23.76 |
| ATOM | 885 | CB | VAL | 179 | 31.676 | 21.255 | 54.631 | 1.00 | 24.20 |
| ATOM | 886 | CG1 | VAL | 179 | 32.400 | 22.160 | 55.617 | 1.00 | 23.61 |
| ATOM | 887 | CG2 | VAL | 179 | 30.189 | 21.584 | 54.588 | 1.00 | 23.11 |
| ATOM | 888 | C | VAL | 179 | 31.527 | 20.541 | 52.231 | 1.00 | 23.17 |
| ATOM | 889 | O | VAL | 179 | 31.277 | 19.366 | 52.482 | 1.00 | 24.77 |
| ATOM | 890 | N | ALA | 180 | 31.153 | 21.122 | 51.098 | 1.00 | 22.77 |
| ATOM | 891 | CA | ALA | 180 | 30.395 | 20.384 | 50.093 | 1.00 | 21.75 |
| ATOM | 892 | CB | ALA | 180 | 29.810 | 21.352 | 49.064 | 1.00 | 19.82 |
| ATOM | 893 | C | ALA | 180 | 31.247 | 19.329 | 49.391 | 1.00 | 21.47 |

TABLE A-continued

| | | | | | | | | | |
|---|---|---|---|---|---|---|---|---|---|
| ATOM | 894 | O | ALA | 180 | 32.429 | 19.549 | 49.121 | 1.00 | 20.99 |
| ATOM | 895 | N | THR | 181 | 30.644 | 18.179 | 49.106 | 1.00 | 21.38 |
| ATOM | 896 | CA | THR | 181 | 31.354 | 17.111 | 48.411 | 1.00 | 22.06 |
| ATOM | 897 | CB | THR | 181 | 31.768 | 15.957 | 49.371 | 1.00 | 23.05 |
| ATOM | 898 | OG1 | THR | 181 | 30.598 | 15.325 | 49.901 | 1.00 | 25.28 |
| ATOM | 899 | CG2 | THR | 181 | 32.615 | 16.487 | 50.520 | 1.00 | 22.65 |
| ATOM | 900 | C | THR | 181 | 30.491 | 16.527 | 47.298 | 1.00 | 22.17 |
| ATOM | 901 | O | THR | 181 | 29.266 | 16.673 | 47.294 | 1.00 | 22.75 |
| ATOM | 902 | N | VAL | 182 | 31.145 | 15.881 | 46.343 | 1.00 | 22.72 |
| ATOM | 903 | CA | VAL | 182 | 30.459 | 15.244 | 45.228 | 1.00 | 24.25 |
| ATOM | 904 | CB | VAL | 182 | 30.941 | 15.813 | 43.884 | 1.00 | 23.11 |
| ATOM | 905 | CG1 | VAL | 182 | 30.204 | 15.133 | 42.738 | 1.00 | 23.43 |
| ATOM | 906 | CG2 | VAL | 182 | 30.707 | 17.324 | 43.852 | 1.00 | 22.55 |
| ATOM | 907 | C | VAL | 182 | 30.819 | 13.767 | 45.329 | 1.00 | 26.05 |
| ATOM | 908 | O | VAL | 182 | 31.990 | 13.404 | 45.239 | 1.00 | 26.03 |
| ATOM | 909 | N | CYS | 183 | 29.813 | 12.920 | 45.522 | 1.00 | 30.03 |
| ATOM | 910 | CA | CYS | 183 | 30.051 | 11.489 | 45.689 | 1.00 | 34.00 |
| ATOM | 911 | C | CYS | 183 | 29.670 | 10.596 | 44.514 | 1.00 | 36.77 |
| ATOM | 912 | O | CYS | 183 | 28.800 | 10.927 | 43.711 | 1.00 | 37.04 |
| ATOM | 913 | CB | CYS | 183 | 29.301 | 10.976 | 46.916 | 1.00 | 33.01 |
| ATOM | 914 | SG | CYS | 183 | 29.491 | 11.922 | 48.460 | 1.00 | 34.26 |
| ATOM | 915 | N | HIS | 184 | 30.333 | 9.443 | 44.450 | 1.00 | 40.51 |
| ATOM | 916 | CA | HIS | 184 | 30.085 | 8.433 | 43.427 | 1.00 | 43.09 |
| ATOM | 917 | CB | HIS | 184 | 31.392 | 7.748 | 43.028 | 1.00 | 43.26 |
| ATOM | 918 | CG | HIS | 184 | 32.240 | 8.552 | 42.097 | 1.00 | 44.35 |
| ATOM | 919 | CD2 | HIS | 184 | 33.423 | 9.183 | 42.287 | 1.00 | 44.78 |
| ATOM | 920 | ND1 | HIS | 184 | 31.902 | 8.761 | 40.777 | 1.00 | 45.33 |
| ATOM | 921 | CE1 | HIS | 184 | 32.842 | 9.483 | 40.194 | 1.00 | 45.93 |
| ATOM | 922 | NE2 | HIS | 184 | 33.777 | 9.752 | 41.088 | 1.00 | 46.19 |
| ATOM | 923 | C | HIS | 184 | 29.141 | 7.394 | 44.027 | 1.00 | 45.42 |
| ATOM | 924 | O | HIS | 184 | 28.935 | 7.360 | 45.243 | 1.00 | 45.31 |
| ATOM | 925 | N | PRO | 185 | 28.554 | 6.531 | 43.181 | 1.00 | 47.60 |
| ATOM | 926 | CD | PRO | 185 | 28.637 | 6.523 | 41.709 | 1.00 | 48.72 |
| ATOM | 927 | CA | PRO | 185 | 27.632 | 5.493 | 43.654 | 1.00 | 48.59 |
| ATOM | 928 | CB | PRO | 185 | 27.370 | 4.674 | 42.394 | 1.00 | 48.70 |
| ATOM | 929 | CG | PRO | 185 | 27.411 | 5.721 | 41.320 | 1.00 | 48.86 |
| ATOM | 930 | C | PRO | 185 | 28.231 | 4.651 | 44.780 | 1.00 | 49.38 |
| ATOM | 931 | O | PRO | 185 | 27.577 | 4.403 | 45.795 | 1.00 | 49.51 |
| ATOM | 932 | N | ASN | 186 | 29.478 | 4.220 | 44.597 | 1.00 | 49.61 |
| ATOM | 933 | CA | ASN | 186 | 30.154 | 3.407 | 45.602 | 1.00 | 50.29 |
| ATOM | 934 | CB | ASN | 186 | 31.594 | 3.082 | 45.168 | 1.00 | 49.31 |
| ATOM | 935 | CG | ASN | 186 | 32.299 | 4.260 | 44.507 | 1.00 | 47.77 |
| ATOM | 936 | OD1 | ASN | 186 | 32.262 | 5.384 | 45.012 | 1.00 | 47.20 |
| ATOM | 937 | ND2 | ASN | 186 | 32.955 | 3.993 | 43.377 | 1.00 | 45.72 |
| ATOM | 938 | C | ASN | 186 | 30.164 | 4.072 | 46.974 | 1.00 | 50.98 |
| ATOM | 939 | O | ASN | 186 | 29.525 | 3.592 | 47.913 | 1.00 | 53.09 |
| ATOM | 940 | N | GLY | 187 | 30.885 | 5.180 | 47.086 | 1.00 | 50.22 |
| ATOM | 941 | CA | GLY | 187 | 30.964 | 5.881 | 48.353 | 1.00 | 47.28 |
| ATOM | 942 | C | GLY | 187 | 32.148 | 6.822 | 48.369 | 1.00 | 45.22 |
| ATOM | 943 | O | GLY | 187 | 32.458 | 7.432 | 49.392 | 1.00 | 46.04 |
| ATOM | 944 | N | SER | 188 | 32.824 | 6.927 | 47.232 | 1.00 | 42.88 |
| ATOM | 945 | CA | SER | 188 | 33.965 | 7.821 | 47.122 | 1.00 | 41.34 |
| ATOM | 946 | CB | SER | 188 | 34.855 | 7.415 | 45.948 | 1.00 | 41.68 |
| ATOM | 947 | OG | SER | 188 | 35.413 | 6.130 | 46.160 | 1.00 | 45.75 |
| ATOM | 948 | C | SER | 188 | 33.431 | 9.230 | 46.904 | 1.00 | 38.80 |
| ATOM | 949 | O | SER | 188 | 32.807 | 9.517 | 45.884 | 1.00 | 37.31 |
| ATOM | 950 | N | CYS | 189 | 33.655 | 10.096 | 47.883 | 1.00 | 36.07 |
| ATOM | 951 | CA | CYS | 189 | 33.202 | 11.471 | 47.793 | 1.00 | 33.90 |
| ATOM | 952 | C | CYS | 189 | 34.416 | 12.358 | 47.579 | 1.00 | 32.06 |
| ATOM | 953 | O | CYS | 189 | 35.459 | 12.159 | 48.202 | 1.00 | 33.88 |
| ATOM | 954 | CB | CYS | 189 | 32.479 | 11.883 | 49.070 | 1.00 | 34.32 |
| ATOM | 955 | SG | CYS | 189 | 30.963 | 10.949 | 49.464 | 1.00 | 35.61 |
| ATOM | 956 | N | LEU | 190 | 34.280 | 13.331 | 46.689 | 1.00 | 28.75 |
| ATOM | 957 | CA | LEU | 190 | 35.377 | 14.237 | 46.387 | 1.00 | 26.04 |
| ATOM | 958 | CB | LEU | 190 | 35.644 | 14.252 | 44.875 | 1.00 | 26.05 |
| ATOM | 959 | CG | LEU | 190 | 36.265 | 13.013 | 44.216 | 1.00 | 27.11 |
| ATOM | 960 | CD1 | LEU | 190 | 35.318 | 11.828 | 44.314 | 1.00 | 28.50 |
| ATOM | 961 | CD2 | LEU | 190 | 36.569 | 13.323 | 42.753 | 1.00 | 27.77 |
| ATOM | 962 | C | LEU | 190 | 35.107 | 15.659 | 46.866 | 1.00 | 24.84 |
| ATOM | 963 | O | LEU | 190 | 33.988 | 16.159 | 46.765 | 1.00 | 23.97 |
| ATOM | 964 | N | GLN | 191 | 36.138 | 16.297 | 47.405 | 1.00 | 24.09 |
| ATOM | 965 | CA | GLN | 191 | 36.028 | 17.677 | 47.857 | 1.00 | 25.37 |
| ATOM | 966 | CB | GLN | 191 | 36.881 | 17.902 | 49.109 | 1.00 | 27.00 |
| ATOM | 967 | CG | GLN | 191 | 36.405 | 17.122 | 50.329 | 1.00 | 31.92 |
| ATOM | 968 | CD | GLN | 191 | 37.279 | 17.348 | 51.546 | 1.00 | 34.94 |
| ATOM | 969 | OE1 | GLN | 191 | 38.476 | 17.061 | 51.527 | 1.00 | 38.38 |
| ATOM | 970 | NE2 | GLN | 191 | 36.684 | 17.862 | 52.614 | 1.00 | 37.18 |
| ATOM | 971 | C | GLN | 191 | 36.550 | 18.534 | 46.704 | 1.00 | 23.81 |
| ATOM | 972 | O | GLN | 191 | 37.239 | 18.024 | 45.818 | 1.00 | 21.41 |
| ATOM | 973 | N | LEU | 192 | 36.222 | 19.824 | 46.705 | 1.00 | 23.17 |

TABLE A-continued

| | | | | | | | | |
|---|---|---|---|---|---|---|---|---|
| ATOM | 974 | CA | LEU | 192 | 36.680 | 20.709 | 45.639 | 1.00 | 22.33 |
| ATOM | 975 | CB | LEU | 192 | 36.151 | 22.131 | 45.856 | 1.00 | 21.16 |
| ATOM | 976 | CG | LEU | 192 | 36.586 | 23.161 | 44.808 | 1.00 | 19.56 |
| ATOM | 977 | CD1 | LEU | 192 | 36.115 | 22.726 | 43.425 | 1.00 | 19.50 |
| ATOM | 978 | CD2 | LEU | 192 | 36.015 | 24.527 | 45.166 | 1.00 | 21.09 |
| ATOM | 979 | C | LEU | 192 | 38.206 | 20.719 | 45.582 | 1.00 | 23.46 |
| ATOM | 980 | O | LEU | 192 | 38.801 | 20.494 | 44.533 | 1.00 | 23.60 |
| ATOM | 981 | N | GLU | 193 | 38.844 | 20.973 | 46.716 | 1.00 | 25.17 |
| ATOM | 982 | CA | GLU | 193 | 40.297 | 20.989 | 46.751 | 1.00 | 27.25 |
| ATOM | 983 | CB | GLU | 193 | 40.796 | 22.297 | 47.367 | 1.00 | 31.24 |
| ATOM | 984 | CG | GLU | 193 | 40.244 | 23.527 | 46.662 | 1.00 | 37.45 |
| ATOM | 985 | CD | GLU | 193 | 41.081 | 24.769 | 46.892 | 1.00 | 43.41 |
| ATOM | 986 | OE1 | GLU | 193 | 41.256 | 25.170 | 48.060 | 1.00 | 46.60 |
| ATOM | 987 | OE2 | GLU | 193 | 41.564 | 25.348 | 45.896 | 1.00 | 48.13 |
| ATOM | 988 | C | GLU | 193 | 40.789 | 19.794 | 47.558 | 1.00 | 27.24 |
| ATOM | 989 | O | GLU | 193 | 40.398 | 19.614 | 48.710 | 1.00 | 28.55 |
| ATOM | 990 | N | PRO | 194 | 41.663 | 18.964 | 46.965 | 1.00 | 26.18 |
| ATOM | 991 | CD | PRO | 194 | 42.458 | 17.987 | 47.737 | 1.00 | 26.80 |
| ATOM | 992 | CA | PRO | 194 | 42.200 | 19.094 | 45.607 | 1.00 | 24.97 |
| ATOM | 993 | CB | PRO | 194 | 43.662 | 18.750 | 45.806 | 1.00 | 26.63 |
| ATOM | 994 | CG | PRO | 194 | 43.547 | 17.564 | 46.737 | 1.00 | 25.86 |
| ATOM | 995 | C | PRO | 194 | 41.558 | 18.143 | 44.595 | 1.00 | 23.91 |
| ATOM | 996 | O | PRO | 194 | 41.868 | 18.203 | 43.404 | 1.00 | 22.16 |
| ATOM | 997 | N | ASP | 195 | 40.672 | 17.273 | 45.072 | 1.00 | 22.30 |
| ATOM | 998 | CA | ASP | 195 | 40.037 | 16.269 | 44.225 | 1.00 | 21.76 |
| ATOM | 999 | CB | ASP | 195 | 39.029 | 15.452 | 45.036 | 1.00 | 22.60 |
| ATOM | 1000 | CG | ASP | 195 | 39.608 | 14.946 | 46.341 | 1.00 | 26.35 |
| ATOM | 1001 | OD1 | ASP | 195 | 40.763 | 14.474 | 46.339 | 1.00 | 26.43 |
| ATOM | 1002 | OD2 | ASP | 195 | 38.902 | 15.018 | 47.369 | 1.00 | 29.80 |
| ATOM | 1003 | C | ASP | 195 | 39.365 | 16.754 | 42.945 | 1.00 | 21.71 |
| ATOM | 1004 | O | ASP | 195 | 39.793 | 16.392 | 41.850 | 1.00 | 23.10 |
| ATOM | 1005 | N | LEU | 196 | 38.308 | 17.551 | 43.068 | 1.00 | 19.29 |
| ATOM | 1006 | CA | LEU | 196 | 37.604 | 18.027 | 41.875 | 1.00 | 19.93 |
| ATOM | 1007 | CB | LEU | 196 | 36.316 | 18.753 | 42.273 | 1.00 | 19.22 |
| ATOM | 1008 | CG | LEU | 196 | 35.288 | 17.859 | 42.971 | 1.00 | 21.05 |
| ATOM | 1009 | CD1 | LEU | 196 | 34.177 | 18.719 | 43.553 | 1.00 | 21.19 |
| ATOM | 1010 | CD2 | LEU | 196 | 34.726 | 16.834 | 41.978 | 1.00 | 18.71 |
| ATOM | 1011 | C | LEU | 196 | 38.473 | 18.933 | 41.020 | 1.00 | 18.92 |
| ATOM | 1012 | O | LEU | 196 | 38.405 | 18.887 | 39.794 | 1.00 | 19.13 |
| ATOM | 1013 | N | THR | 197 | 39.287 | 19.757 | 41.673 | 1.00 | 19.32 |
| ATOM | 1014 | CA | THR | 197 | 40.179 | 20.667 | 40.968 | 1.00 | 20.23 |
| ATOM | 1015 | CB | THR | 197 | 40.994 | 21.530 | 41.962 | 1.00 | 21.09 |
| ATOM | 1016 | OG1 | THR | 197 | 40.098 | 22.333 | 42.739 | 1.00 | 23.68 |
| ATOM | 1017 | CG2 | THR | 197 | 41.962 | 22.444 | 41.212 | 1.00 | 23.82 |
| ATOM | 1018 | C | THR | 197 | 41.138 | 19.855 | 40.103 | 1.00 | 20.96 |
| ATOM | 1019 | O | THR | 197 | 41.408 | 20.203 | 38.950 | 1.00 | 18.55 |
| ATOM | 1020 | N | ASN | 198 | 41.649 | 18.762 | 40.660 | 1.00 | 20.33 |
| ATOM | 1021 | CA | ASN | 198 | 42.566 | 17.916 | 39.910 | 1.00 | 21.82 |
| ATOM | 1022 | CB | ASN | 198 | 43.144 | 16.820 | 40.800 | 1.00 | 24.76 |
| ATOM | 1023 | CG | ASN | 198 | 44.158 | 15.971 | 40.068 | 1.00 | 29.65 |
| ATOM | 1024 | OD1 | ASN | 198 | 45.283 | 16.409 | 39.812 | 1.00 | 31.73 |
| ATOM | 1025 | ND2 | ASN | 198 | 43.759 | 14.757 | 39.701 | 1.00 | 31.98 |
| ATOM | 1026 | C | ASN | 198 | 41.876 | 17.272 | 38.706 | 1.00 | 19.19 |
| ATOM | 1027 | O | ASN | 198 | 42.457 | 17.200 | 37.624 | 1.00 | 21.70 |
| ATOM | 1028 | N | VAL | 199 | 40.645 | 16.800 | 38.893 | 1.00 | 18.96 |
| ATOM | 1029 | CA | VAL | 199 | 39.907 | 16.180 | 37.795 | 1.00 | 18.37 |
| ATOM | 1030 | CB | VAL | 199 | 38.516 | 15.666 | 38.257 | 1.00 | 19.57 |
| ATOM | 1031 | CG1 | VAL | 199 | 37.680 | 15.275 | 37.048 | 1.00 | 18.46 |
| ATOM | 1032 | CG2 | VAL | 199 | 38.682 | 14.451 | 39.187 | 1.00 | 20.39 |
| ATOM | 1033 | C | VAL | 199 | 39.715 | 17.182 | 36.650 | 1.00 | 18.73 |
| ATOM | 1034 | O | VAL | 199 | 39.965 | 16.869 | 35.485 | 1.00 | 15.90 |
| ATOM | 1035 | N | MET | 200 | 39.279 | 18.392 | 36.988 | 1.00 | 18.95 |
| ATOM | 1036 | CA | MET | 200 | 39.063 | 19.423 | 35.980 | 1.00 | 17.76 |
| ATOM | 1037 | CB | MET | 200 | 38.475 | 20.680 | 36.630 | 1.00 | 18.24 |
| ATOM | 1038 | CG | MET | 200 | 37.084 | 20.494 | 37.227 | 1.00 | 16.87 |
| ATOM | 1039 | SD | MET | 200 | 35.914 | 19.807 | 36.056 | 1.00 | 20.02 |
| ATOM | 1040 | CE | MET | 200 | 35.798 | 21.162 | 34.832 | 1.00 | 21.44 |
| ATOM | 1041 | C | MET | 200 | 40.353 | 19.794 | 35.244 | 1.00 | 16.67 |
| ATOM | 1042 | O | MET | 200 | 40.328 | 20.125 | 34.060 | 1.00 | 17.29 |
| ATOM | 1043 | N | ALA | 201 | 41.478 | 19.724 | 35.944 | 1.00 | 15.31 |
| ATOM | 1044 | CA | ALA | 201 | 42.764 | 20.088 | 35.356 | 1.00 | 16.45 |
| ATOM | 1045 | CB | ALA | 201 | 43.708 | 20.570 | 36.458 | 1.00 | 14.53 |
| ATOM | 1046 | C | ALA | 201 | 43.473 | 19.014 | 34.530 | 1.00 | 17.34 |
| ATOM | 1047 | O | ALA | 201 | 44.191 | 19.336 | 33.580 | 1.00 | 18.65 |
| ATOM | 1048 | N | THR | 202 | 43.263 | 17.750 | 34.875 | 1.00 | 14.75 |
| ATOM | 1049 | CA | THR | 202 | 43.963 | 16.665 | 34.199 | 1.00 | 15.77 |
| ATOM | 1050 | CB | THR | 202 | 44.717 | 15.818 | 35.230 | 1.00 | 16.12 |
| ATOM | 1051 | OG1 | THR | 202 | 43.773 | 15.222 | 36.124 | 1.00 | 17.60 |
| ATOM | 1052 | CG2 | THR | 202 | 45.669 | 16.694 | 36.042 | 1.00 | 16.30 |
| ATOM | 1053 | C | THR | 202 | 43.151 | 15.721 | 33.322 | 1.00 | 17.01 |

TABLE A-continued

| | | | | | | | | |
|---|---|---|---|---|---|---|---|---|
| ATOM | 1054 | O | THR | 202 | 43.680 | 15.157 | 32.364 | 1.00 17.58 |
| ATOM | 1055 | N | SER | 203 | 41.876 | 15.531 | 33.634 | 1.00 16.36 |
| ATOM | 1056 | CA | SER | 203 | 41.070 | 14.635 | 32.816 | 1.00 16.62 |
| ATOM | 1057 | CB | SER | 203 | 39.717 | 14.379 | 33.471 | 1.00 17.45 |
| ATOM | 1058 | OG | SER | 203 | 38.883 | 13.637 | 32.592 | 1.00 17.94 |
| ATOM | 1059 | C | SER | 203 | 40.841 | 15.190 | 31.411 | 1.00 17.76 |
| ATOM | 1060 | O | SER | 203 | 40.627 | 16.390 | 31.231 | 1.00 16.09 |
| ATOM | 1061 | N | ARG | 204 | 40.894 | 14.305 | 30.420 | 1.00 17.37 |
| ATOM | 1062 | CA | ARG | 204 | 40.656 | 14.675 | 29.029 | 1.00 18.83 |
| ATOM | 1063 | CB | ARG | 204 | 41.899 | 14.394 | 28.175 | 1.00 21.32 |
| ATOM | 1064 | CG | ARG | 204 | 42.806 | 15.601 | 27.910 | 1.00 25.72 |
| ATOM | 1065 | CD | ARG | 204 | 42.784 | 16.603 | 29.041 | 1.00 24.96 |
| ATOM | 1066 | NE | ARG | 204 | 44.009 | 17.391 | 29.117 | 1.00 25.28 |
| ATOM | 1067 | CZ | ARG | 204 | 44.224 | 18.329 | 30.035 | 1.00 25.48 |
| ATOM | 1068 | NH1 | ARG | 204 | 45.366 | 18.998 | 30.055 | 1.00 27.49 |
| ATOM | 1069 | NH2 | ARG | 204 | 43.287 | 18.610 | 30.928 | 1.00 26.72 |
| ATOM | 1070 | C | ARG | 204 | 39.473 | 13.859 | 28.510 | 1.00 18.41 |
| ATOM | 1071 | O | ARG | 204 | 39.333 | 13.648 | 27.306 | 1.00 18.06 |
| ATOM | 1072 | N | LYS | 205 | 38.629 | 13.394 | 29.427 | 1.00 19.07 |
| ATOM | 1073 | CA | LYS | 205 | 37.449 | 12.614 | 29.058 | 1.00 19.70 |
| ATOM | 1074 | CB | LYS | 205 | 37.396 | 11.320 | 29.876 | 1.00 20.49 |
| ATOM | 1075 | CG | LYS | 205 | 38.655 | 10.464 | 29.712 | 1.00 25.63 |
| ATOM | 1076 | CD | LYS | 205 | 38.499 | 9.071 | 30.304 | 1.00 27.27 |
| ATOM | 1077 | CE | LYS | 205 | 37.450 | 8.267 | 29.552 | 1.00 32.01 |
| ATOM | 1078 | NZ | LYS | 205 | 37.428 | 6.847 | 30.001 | 1.00 36.31 |
| ATOM | 1079 | C | LYS | 205 | 36.181 | 13.441 | 29.276 | 1.00 18.76 |
| ATOM | 1080 | O | LYS | 205 | 35.836 | 13.786 | 30.412 | 1.00 16.76 |
| ATOM | 1081 | N | TYR | 206 | 35.499 | 13.750 | 28.175 | 1.00 17.94 |
| ATOM | 1082 | CA | TYR | 206 | 34.280 | 14.564 | 28.187 | 1.00 18.82 |
| ATOM | 1083 | CB | TYR | 206 | 33.561 | 14.456 | 26.834 | 1.00 17.41 |
| ATOM | 1084 | CG | TYR | 206 | 32.581 | 15.582 | 26.551 | 1.00 17.19 |
| ATOM | 1085 | CD1 | TYR | 206 | 32.960 | 16.682 | 25.782 | 1.00 17.56 |
| ATOM | 1086 | CE1 | TYR | 206 | 32.068 | 17.718 | 25.509 | 1.00 17.54 |
| ATOM | 1087 | CD2 | TYR | 206 | 31.276 | 15.546 | 27.049 | 1.00 18.96 |
| ATOM | 1088 | CE2 | TYR | 206 | 30.373 | 16.581 | 26.787 | 1.00 19.27 |
| ATOM | 1089 | CZ | TYR | 206 | 30.778 | 17.666 | 26.015 | 1.00 20.83 |
| ATOM | 1090 | OH | TYR | 206 | 29.908 | 18.711 | 25.768 | 1.00 21.81 |
| ATOM | 1091 | C | TYR | 206 | 33.298 | 14.209 | 29.303 | 1.00 18.43 |
| ATOM | 1092 | O | TYR | 206 | 32.820 | 15.092 | 30.016 | 1.00 18.33 |
| ATOM | 1093 | N | GLU | 207 | 32.996 | 12.922 | 29.454 | 1.00 17.90 |
| ATOM | 1094 | CA | GLU | 207 | 32.049 | 12.492 | 30.479 | 1.00 18.16 |
| ATOM | 1095 | CB | GLU | 207 | 31.598 | 11.046 | 30.224 | 1.00 20.18 |
| ATOM | 1096 | CG | GLU | 207 | 30.791 | 10.830 | 28.943 | 1.00 20.70 |
| ATOM | 1097 | CD | GLU | 207 | 29.494 | 11.633 | 28.895 | 1.00 23.77 |
| ATOM | 1098 | OE1 | GLU | 207 | 28.760 | 11.661 | 29.907 | 1.00 22.24 |
| ATOM | 1099 | OE2 | GLU | 207 | 29.202 | 12.226 | 27.833 | 1.00 24.84 |
| ATOM | 1100 | C | GLU | 207 | 32.548 | 12.619 | 31.917 | 1.00 17.41 |
| ATOM | 1101 | O | GLU | 207 | 31.752 | 12.866 | 32.821 | 1.00 16.71 |
| ATOM | 1102 | N | ASP | 208 | 33.848 | 12.443 | 32.145 | 1.00 16.59 |
| ATOM | 1103 | CA | ASP | 208 | 34.373 | 12.560 | 33.506 | 1.00 17.48 |
| ATOM | 1104 | CB | ASP | 208 | 35.774 | 11.944 | 33.617 | 1.00 19.01 |
| ATOM | 1105 | CG | ASP | 208 | 35.779 | 10.440 | 33.362 | 1.00 24.16 |
| ATOM | 1106 | OD1 | ASP | 208 | 34.689 | 9.830 | 33.331 | 1.00 26.06 |
| ATOM | 1107 | OD2 | ASP | 208 | 36.875 | 9.865 | 33.201 | 1.00 23.40 |
| ATOM | 1108 | C | ASP | 208 | 34.416 | 14.033 | 33.906 | 1.00 16.55 |
| ATOM | 1109 | O | ASP | 208 | 34.133 | 14.389 | 35.052 | 1.00 13.04 |
| ATOM | 1110 | N | LEU | 209 | 34.769 | 14.885 | 32.951 | 1.00 15.38 |
| ATOM | 1111 | CA | LEU | 209 | 34.822 | 16.319 | 33.200 | 1.00 16.48 |
| ATOM | 1112 | CB | LEU | 209 | 35.386 | 17.048 | 31.974 | 1.00 14.57 |
| ATOM | 1113 | CG | LEU | 209 | 36.893 | 16.869 | 31.731 | 1.00 14.85 |
| ATOM | 1114 | CD1 | LEU | 209 | 37.298 | 17.512 | 30.412 | 1.00 14.52 |
| ATOM | 1115 | CD2 | LEU | 209 | 37.668 | 17.501 | 32.880 | 1.00 14.67 |
| ATOM | 1116 | C | LEU | 209 | 33.404 | 16.803 | 33.499 | 1.00 16.80 |
| ATOM | 1117 | O | LEU | 209 | 33.192 | 17.636 | 34.385 | 1.00 17.09 |
| ATOM | 1118 | N | LEU | 210 | 32.434 | 16.258 | 32.768 | 1.00 15.84 |
| ATOM | 1119 | CA | LEU | 210 | 31.037 | 16.631 | 32.955 | 1.00 15.80 |
| ATOM | 1120 | CB | LEU | 210 | 30.160 | 15.971 | 31.881 | 1.00 18.19 |
| ATOM | 1121 | CG | LEU | 210 | 28.670 | 16.336 | 31.924 | 1.00 18.57 |
| ATOM | 1122 | CD1 | LEU | 210 | 28.524 | 17.850 | 31.917 | 1.00 23.32 |
| ATOM | 1123 | CD2 | LEU | 210 | 27.942 | 15.731 | 30.735 | 1.00 22.22 |
| ATOM | 1124 | C | LEU | 210 | 30.530 | 16.250 | 34.342 | 1.00 16.05 |
| ATOM | 1125 | O | LEU | 210 | 29.840 | 17.037 | 34.998 | 1.00 16.25 |
| ATOM | 1126 | N | TRP | 211 | 30.869 | 15.042 | 34.784 | 1.00 15.85 |
| ATOM | 1127 | CA | TRP | 211 | 30.452 | 14.556 | 36.099 | 1.00 16.79 |
| ATOM | 1128 | CB | TRP | 211 | 31.033 | 13.159 | 36.362 | 1.00 19.10 |
| ATOM | 1129 | CG | TRP | 211 | 30.687 | 12.625 | 37.721 | 1.00 22.86 |
| ATOM | 1130 | CD2 | TRP | 211 | 31.472 | 12.746 | 38.916 | 1.00 24.67 |
| ATOM | 1131 | CE2 | TRP | 211 | 30.727 | 12.167 | 39.967 | 1.00 26.17 |
| ATOM | 1132 | CE3 | TRP | 211 | 32.731 | 13.290 | 39.199 | 1.00 25.03 |
| ATOM | 1133 | CD1 | TRP | 211 | 29.531 | 11.991 | 38.086 | 1.00 25.13 |

TABLE A-continued

| | | | | | | | | |
|---|---|---|---|---|---|---|---|---|
| ATOM | 1134 | NE1 | TRP | 211 | 29.549 | 11.714 | 39.436 | 1.00 25.08 |
| ATOM | 1135 | CZ2 | TRP | 211 | 31.202 | 12.119 | 41.284 | 1.00 27.62 |
| ATOM | 1136 | CZ3 | TRP | 211 | 33.203 | 13.241 | 40.509 | 1.00 26.84 |
| ATOM | 1137 | CH2 | TRP | 211 | 32.439 | 12.659 | 41.533 | 1.00 27.01 |
| ATOM | 1138 | C | TRP | 211 | 30.914 | 15.505 | 37.208 | 1.00 15.76 |
| ATOM | 1139 | O | TRP | 211 | 30.139 | 15.871 | 38.091 | 1.00 15.00 |
| ATOM | 1140 | N | ALA | 212 | 32.181 | 15.899 | 37.158 | 1.00 16.39 |
| ATOM | 1141 | CA | ALA | 212 | 32.739 | 16.796 | 38.162 | 1.00 15.16 |
| ATOM | 1142 | CB | ALA | 212 | 34.256 | 16.863 | 38.010 | 1.00 14.42 |
| ATOM | 1143 | C | ALA | 212 | 32.142 | 18.200 | 38.063 | 1.00 15.48 |
| ATOM | 1144 | O | ALA | 212 | 31.839 | 18.826 | 39.080 | 1.00 16.14 |
| ATOM | 1145 | N | TRP | 213 | 31.982 | 18.684 | 36.835 | 1.00 15.80 |
| ATOM | 1146 | CA | TRP | 213 | 31.436 | 20.019 | 36.581 | 1.00 16.29 |
| ATOM | 1147 | CB | TRP | 213 | 31.506 | 20.331 | 35.082 | 1.00 15.34 |
| ATOM | 1148 | CG | TRP | 213 | 31.110 | 21.741 | 34.725 | 1.00 15.79 |
| ATOM | 1149 | CD2 | TRP | 213 | 29.792 | 22.209 | 34.413 | 1.00 15.16 |
| ATOM | 1150 | CE2 | TRP | 213 | 29.885 | 23.601 | 34.179 | 1.00 16.51 |
| ATOM | 1151 | CE3 | TRP | 213 | 28.538 | 21.588 | 34.312 | 1.00 16.54 |
| ATOM | 1152 | CD1 | TRP | 213 | 31.929 | 22.837 | 34.666 | 1.00 16.30 |
| ATOM | 1153 | NE1 | TRP | 213 | 31.199 | 23.958 | 34.338 | 1.00 15.53 |
| ATOM | 1154 | CZ2 | TRP | 213 | 28.771 | 24.382 | 33.849 | 1.00 14.24 |
| ATOM | 1155 | CZ3 | TRP | 213 | 27.432 | 22.366 | 33.985 | 1.00 16.40 |
| ATOM | 1156 | CH2 | TRP | 213 | 27.558 | 23.748 | 33.756 | 1.00 15.28 |
| ATOM | 1157 | C | TRP | 213 | 29.985 | 20.138 | 37.057 | 1.00 15.56 |
| ATOM | 1158 | O | TRP | 213 | 29.634 | 21.070 | 37.779 | 1.00 13.86 |
| ATOM | 1159 | N | GLU | 214 | 29.149 | 19.192 | 36.639 | 1.00 15.67 |
| ATOM | 1160 | CA | GLU | 214 | 27.741 | 19.178 | 37.019 | 1.00 15.17 |
| ATOM | 1161 | CB | GLU | 214 | 26.982 | 18.139 | 36.187 | 1.00 17.45 |
| ATOM | 1162 | CG | GLU | 214 | 25.473 | 18.101 | 36.444 | 1.00 19.85 |
| ATOM | 1163 | CD | GLU | 214 | 24.785 | 19.410 | 36.087 | 1.00 23.48 |
| ATOM | 1164 | OE1 | GLU | 214 | 25.012 | 19.911 | 34.968 | 1.00 25.84 |
| ATOM | 1165 | OE2 | GLU | 214 | 24.012 | 19.938 | 36.918 | 1.00 26.74 |
| ATOM | 1166 | C | GLU | 214 | 27.576 | 18.857 | 38.499 | 1.00 16.13 |
| ATOM | 1167 | O | GLU | 214 | 26.791 | 19.497 | 39.206 | 1.00 15.22 |
| ATOM | 1168 | N | GLY | 215 | 28.321 | 17.858 | 38.962 | 1.00 17.03 |
| ATOM | 1169 | CA | GLY | 215 | 28.244 | 17.452 | 40.352 | 1.00 17.32 |
| ATOM | 1170 | C | GLY | 215 | 28.530 | 18.576 | 41.328 | 1.00 18.14 |
| ATOM | 1171 | O | GLY | 215 | 27.812 | 18.750 | 42.312 | 1.00 18.29 |
| ATOM | 1172 | N | TRP | 216 | 29.584 | 19.340 | 41.067 | 1.00 17.32 |
| ATOM | 1173 | CA | TRP | 216 | 29.940 | 20.440 | 41.952 | 1.00 16.83 |
| ATOM | 1174 | CB | TRP | 216 | 31.209 | 21.145 | 41.459 | 1.00 15.21 |
| ATOM | 1175 | CG | TRP | 216 | 31.605 | 22.288 | 42.345 | 1.00 16.54 |
| ATOM | 1176 | CD2 | TRP | 216 | 31.879 | 22.226 | 43.751 | 1.00 17.16 |
| ATOM | 1177 | CE2 | TRP | 216 | 32.141 | 23.544 | 44.185 | 1.00 16.95 |
| ATOM | 1178 | CE3 | TRP | 216 | 31.924 | 21.182 | 44.689 | 1.00 17.45 |
| ATOM | 1179 | CD1 | TRP | 216 | 31.716 | 23.603 | 41.991 | 1.00 14.98 |
| ATOM | 1180 | NE1 | TRP | 216 | 32.036 | 24.364 | 43.092 | 1.00 17.71 |
| ATOM | 1181 | CZ2 | TRP | 216 | 32.444 | 23.849 | 45.518 | 1.00 16.83 |
| ATOM | 1182 | CZ3 | TRP | 216 | 32.225 | 21.487 | 46.016 | 1.00 17.47 |
| ATOM | 1183 | CH2 | TRP | 216 | 32.480 | 22.811 | 46.415 | 1.00 18.90 |
| ATOM | 1184 | C | TRP | 216 | 28.796 | 21.441 | 42.028 | 1.00 15.17 |
| ATOM | 1185 | O | TRP | 216 | 28.422 | 21.900 | 43.105 | 1.00 17.84 |
| ATOM | 1186 | N | ARG | 217 | 28.234 | 21.779 | 40.878 | 1.00 15.34 |
| ATOM | 1187 | CA | ARG | 217 | 27.136 | 22.724 | 40.854 | 1.00 16.45 |
| ATOM | 1188 | CB | ARG | 217 | 26.868 | 23.142 | 39.407 | 1.00 13.86 |
| ATOM | 1189 | CG | ARG | 217 | 27.981 | 24.074 | 38.923 | 1.00 16.46 |
| ATOM | 1190 | CD | ARG | 217 | 28.079 | 24.265 | 37.416 | 1.00 15.80 |
| ATOM | 1191 | NE | ARG | 217 | 29.144 | 25.230 | 37.139 | 1.00 15.22 |
| ATOM | 1192 | CZ | ARG | 217 | 30.444 | 24.974 | 37.269 | 1.00 15.55 |
| ATOM | 1193 | NH1 | ARG | 217 | 31.333 | 25.920 | 37.009 | 1.00 16.82 |
| ATOM | 1194 | NH2 | ARG | 217 | 30.860 | 23.766 | 37.632 | 1.00 15.71 |
| ATOM | 1195 | C | ARG | 217 | 25.903 | 22.145 | 41.547 | 1.00 17.65 |
| ATOM | 1196 | O | ARG | 217 | 25.202 | 22.858 | 42.263 | 1.00 17.39 |
| ATOM | 1197 | N | ASP | 218 | 25.661 | 20.848 | 41.374 | 1.00 18.73 |
| ATOM | 1198 | CA | ASP | 218 | 24.513 | 20.215 | 42.021 | 1.00 20.64 |
| ATOM | 1199 | CB | ASP | 218 | 24.388 | 18.745 | 41.612 | 1.00 22.06 |
| ATOM | 1200 | CG | ASP | 218 | 24.011 | 18.570 | 40.161 | 1.00 24.98 |
| ATOM | 1201 | OD1 | ASP | 218 | 23.555 | 19.550 | 39.537 | 1.00 24.48 |
| ATOM | 1202 | OD2 | ASP | 218 | 24.158 | 17.437 | 39.648 | 1.00 26.98 |
| ATOM | 1203 | C | ASP | 218 | 24.610 | 20.272 | 43.545 | 1.00 19.56 |
| ATOM | 1204 | O | ASP | 218 | 23.619 | 20.520 | 44.227 | 1.00 19.81 |
| ATOM | 1205 | N | LYS | 219 | 25.807 | 20.043 | 44.077 | 1.00 20.45 |
| ATOM | 1206 | CA | LYS | 219 | 26.003 | 20.031 | 45.525 | 1.00 21.29 |
| ATOM | 1207 | CB | LYS | 219 | 27.121 | 19.051 | 45.890 | 1.00 21.65 |
| ATOM | 1208 | CG | LYS | 219 | 26.895 | 17.629 | 45.373 | 1.00 25.13 |
| ATOM | 1209 | CD | LYS | 219 | 25.543 | 17.058 | 45.813 | 1.00 28.05 |
| ATOM | 1210 | CE | LYS | 219 | 25.447 | 16.918 | 47.328 | 1.00 29.00 |
| ATOM | 1211 | NZ | LYS | 219 | 26.538 | 16.060 | 47.868 | 1.00 30.61 |
| ATOM | 1212 | C | LYS | 219 | 26.279 | 21.378 | 46.183 | 1.00 21.42 |
| ATOM | 1213 | O | LYS | 219 | 25.719 | 21.678 | 47.236 | 1.00 24.45 |

TABLE A-continued

| | | | | | | | | | |
|---|---|---|---|---|---|---|---|---|---|
| ATOM | 1214 | N | ALA | 220 | 27.143 | 22.188 | 45.579 | 1.00 | 21.30 |
| ATOM | 1215 | CA | ALA | 220 | 27.468 | 23.492 | 46.153 | 1.00 | 20.70 |
| ATOM | 1216 | CB | ALA | 220 | 28.902 | 23.878 | 45.799 | 1.00 | 20.00 |
| ATOM | 1217 | C | ALA | 220 | 26.504 | 24.578 | 45.685 | 1.00 | 19.99 |
| ATOM | 1218 | O | ALA | 220 | 25.902 | 25.276 | 46.501 | 1.00 | 21.16 |
| ATOM | 1219 | N | GLY | 221 | 26.358 | 24.711 | 44.370 | 1.00 | 18.26 |
| ATOM | 1220 | CA | GLY | 221 | 25.476 | 25.722 | 43.819 | 1.00 | 18.25 |
| ATOM | 1221 | C | GLY | 221 | 24.028 | 25.653 | 44.275 | 1.00 | 19.99 |
| ATOM | 1222 | O | GLY | 221 | 23.496 | 26.628 | 44.808 | 1.00 | 19.79 |
| ATOM | 1223 | N | ARG | 222 | 23.378 | 24.512 | 44.067 | 1.00 | 17.04 |
| ATOM | 1224 | CA | ARG | 222 | 21.982 | 24.377 | 44.467 | 1.00 | 19.12 |
| ATOM | 1225 | CB | ARG | 222 | 21.443 | 22.989 | 44.091 | 1.00 | 17.89 |
| ATOM | 1226 | CG | ARG | 222 | 21.397 | 22.730 | 42.592 | 1.00 | 19.59 |
| ATOM | 1227 | CD | ARG | 222 | 20.767 | 21.367 | 42.283 | 1.00 | 24.35 |
| ATOM | 1228 | NE | ARG | 222 | 20.643 | 21.152 | 40.845 | 1.00 | 30.28 |
| ATOM | 1229 | CZ | ARG | 222 | 20.353 | 19.984 | 40.276 | 1.00 | 33.18 |
| ATOM | 1230 | NH1 | ARG | 222 | 20.150 | 18.901 | 41.021 | 1.00 | 31.51 |
| ATOM | 1231 | NH2 | ARG | 222 | 20.281 | 19.896 | 38.954 | 1.00 | 33.98 |
| ATOM | 1232 | C | ARG | 222 | 21.800 | 24.611 | 45.965 | 1.00 | 18.43 |
| ATOM | 1233 | O | ARG | 222 | 20.803 | 25.193 | 46.385 | 1.00 | 19.58 |
| ATOM | 1234 | N | ALA | 223 | 22.771 | 24.171 | 46.757 | 1.00 | 16.28 |
| ATOM | 1235 | CA | ALA | 223 | 22.715 | 24.317 | 48.210 | 1.00 | 19.92 |
| ATOM | 1236 | CB | ALA | 223 | 23.824 | 23.483 | 48.859 | 1.00 | 19.14 |
| ATOM | 1237 | C | ALA | 223 | 22.815 | 25.767 | 48.681 | 1.00 | 19.46 |
| ATOM | 1238 | O | ALA | 223 | 22.435 | 26.089 | 49.806 | 1.00 | 22.30 |
| ATOM | 1239 | N | ILE | 224 | 23.329 | 26.646 | 47.833 | 1.00 | 18.66 |
| ATOM | 1240 | CA | ILE | 224 | 23.457 | 28.045 | 48.222 | 1.00 | 17.34 |
| ATOM | 1241 | CB | ILE | 224 | 24.679 | 28.705 | 47.522 | 1.00 | 16.89 |
| ATOM | 1242 | CG2 | ILE | 224 | 24.729 | 30.202 | 47.819 | 1.00 | 15.15 |
| ATOM | 1243 | CG1 | ILE | 224 | 25.966 | 28.023 | 47.993 | 1.00 | 14.94 |
| ATOM | 1244 | CD1 | ILE | 224 | 26.218 | 28.141 | 49.488 | 1.00 | 15.97 |
| ATOM | 1245 | C | ILE | 224 | 22.187 | 28.830 | 47.897 | 1.00 | 17.43 |
| ATOM | 1246 | O | ILE | 224 | 21.883 | 29.825 | 48.550 | 1.00 | 18.29 |
| ATOM | 1247 | N | LEU | 225 | 21.435 | 28.360 | 46.907 | 1.00 | 16.61 |
| ATOM | 1248 | CA | LEU | 225 | 20.217 | 29.044 | 46.480 | 1.00 | 18.87 |
| ATOM | 1249 | CB | LEU | 225 | 19.511 | 28.233 | 45.386 | 1.00 | 17.28 |
| ATOM | 1250 | CG | LEU | 225 | 18.251 | 28.880 | 44.803 | 1.00 | 17.62 |
| ATOM | 1251 | CD1 | LEU | 225 | 18.591 | 30.250 | 44.247 | 1.00 | 15.98 |
| ATOM | 1252 | CD2 | LEU | 225 | 17.664 | 27.993 | 43.712 | 1.00 | 17.36 |
| ATOM | 1253 | C | LEU | 225 | 19.208 | 29.387 | 47.582 | 1.00 | 20.30 |
| ATOM | 1254 | O | LEU | 225 | 18.573 | 30.440 | 47.529 | 1.00 | 21.05 |
| ATOM | 1255 | N | GLN | 226 | 19.054 | 28.522 | 48.582 | 1.00 | 20.59 |
| ATOM | 1256 | CA | GLN | 226 | 18.086 | 28.812 | 49.635 | 1.00 | 20.98 |
| ATOM | 1257 | CB | GLN | 226 | 17.887 | 27.602 | 50.554 | 1.00 | 22.39 |
| ATOM | 1258 | CG | GLN | 226 | 19.098 | 27.206 | 51.373 | 1.00 | 22.59 |
| ATOM | 1259 | CD | GLN | 226 | 18.743 | 26.255 | 52.506 | 1.00 | 28.86 |
| ATOM | 1260 | OE1 | GLN | 226 | 19.401 | 25.236 | 52.708 | 1.00 | 29.99 |
| ATOM | 1261 | NE2 | GLN | 226 | 17.702 | 26.594 | 53.259 | 1.00 | 30.07 |
| ATOM | 1262 | C | GLN | 226 | 18.460 | 30.027 | 50.476 | 1.00 | 20.99 |
| ATOM | 1263 | O | GLN | 226 | 17.594 | 30.624 | 51.113 | 1.00 | 20.68 |
| ATOM | 1264 | N | PHE | 227 | 19.738 | 30.402 | 50.472 | 1.00 | 17.78 |
| ATOM | 1265 | CA | PHE | 227 | 20.188 | 31.548 | 51.261 | 1.00 | 18.81 |
| ATOM | 1266 | CB | PHE | 227 | 21.555 | 31.278 | 51.901 | 1.00 | 18.57 |
| ATOM | 1267 | CG | PHE | 227 | 21.626 | 30.016 | 52.709 | 1.00 | 20.93 |
| ATOM | 1268 | CD1 | PHE | 227 | 22.241 | 28.881 | 52.191 | 1.00 | 19.23 |
| ATOM | 1269 | CD2 | PHE | 227 | 21.106 | 29.970 | 53.998 | 1.00 | 19.89 |
| ATOM | 1270 | CE1 | PHE | 227 | 22.340 | 27.720 | 52.945 | 1.00 | 20.37 |
| ATOM | 1271 | CE2 | PHE | 227 | 21.198 | 28.812 | 54.763 | 1.00 | 20.86 |
| ATOM | 1272 | CZ | PHE | 227 | 21.818 | 27.683 | 54.236 | 1.00 | 21.52 |
| ATOM | 1273 | C | PHE | 227 | 20.320 | 32.875 | 50.515 | 1.00 | 18.52 |
| ATOM | 1274 | O | PHE | 227 | 20.150 | 33.936 | 51.116 | 1.00 | 18.03 |
| ATOM | 1275 | N | TYR | 228 | 20.631 | 32.824 | 49.220 | 1.00 | 17.84 |
| ATOM | 1276 | CA | TYR | 228 | 20.870 | 34.046 | 48.458 | 1.00 | 15.89 |
| ATOM | 1277 | CB | TYR | 228 | 21.267 | 33.716 | 47.013 | 1.00 | 14.37 |
| ATOM | 1278 | CG | TYR | 228 | 22.396 | 34.599 | 46.526 | 1.00 | 13.39 |
| ATOM | 1279 | CD1 | TYR | 228 | 23.678 | 34.485 | 47.068 | 1.00 | 11.77 |
| ATOM | 1280 | CE1 | TYR | 228 | 24.720 | 35.322 | 46.653 | 1.00 | 12.65 |
| ATOM | 1281 | CD2 | TYR | 228 | 22.178 | 35.573 | 45.555 | 1.00 | 14.08 |
| ATOM | 1282 | CE2 | TYR | 228 | 23.207 | 36.420 | 45.134 | 1.00 | 13.53 |
| ATOM | 1283 | CZ | TYR | 228 | 24.472 | 36.289 | 45.685 | 1.00 | 14.24 |
| ATOM | 1284 | OH | TYR | 228 | 25.484 | 37.127 | 45.274 | 1.00 | 15.11 |
| ATOM | 1285 | C | TYR | 228 | 19.817 | 35.146 | 48.437 | 1.00 | 16.77 |
| ATOM | 1286 | O | TYR | 228 | 20.143 | 36.313 | 48.645 | 1.00 | 16.17 |
| ATOM | 1287 | N | PRO | 229 | 18.546 | 34.805 | 48.173 | 1.00 | 16.14 |
| ATOM | 1288 | CD | PRO | 229 | 17.939 | 33.525 | 47.766 | 1.00 | 16.20 |
| ATOM | 1289 | CA | PRO | 229 | 17.556 | 35.887 | 48.156 | 1.00 | 16.22 |
| ATOM | 1290 | CB | PRO | 229 | 16.240 | 35.150 | 47.888 | 1.00 | 16.46 |
| ATOM | 1291 | CG | PRO | 229 | 16.688 | 33.982 | 47.027 | 1.00 | 16.36 |
| ATOM | 1292 | C | PRO | 229 | 17.525 | 36.702 | 49.451 | 1.00 | 16.67 |
| ATOM | 1293 | O | PRO | 229 | 17.395 | 37.924 | 49.414 | 1.00 | 18.90 |

TABLE A-continued

| | | | | | | | | | |
|---|---|---|---|---|---|---|---|---|---|
| ATOM | 1294 | N | LYS | 230 | 17.655 | 36.030 | 50.590 | 1.00 | 17.12 |
| ATOM | 1295 | CA | LYS | 230 | 17.629 | 36.717 | 51.881 | 1.00 | 18.28 |
| ATOM | 1296 | CB | LYS | 230 | 17.459 | 35.711 | 53.019 | 1.00 | 20.03 |
| ATOM | 1297 | CG | LYS | 230 | 16.968 | 36.337 | 54.314 | 1.00 | 24.93 |
| ATOM | 1298 | CD | LYS | 230 | 15.626 | 37.010 | 54.076 | 1.00 | 29.71 |
| ATOM | 1299 | CE | LYS | 230 | 14.991 | 37.481 | 55.356 | 1.00 | 33.08 |
| ATOM | 1300 | NZ | LYS | 230 | 13.687 | 38.138 | 55.078 | 1.00 | 33.19 |
| ATOM | 1301 | C | LYS | 230 | 18.909 | 37.525 | 52.090 | 1.00 | 17.96 |
| ATOM | 1302 | O | LYS | 230 | 18.886 | 38.617 | 52.662 | 1.00 | 15.33 |
| ATOM | 1303 | N | TYR | 231 | 20.022 | 36.971 | 51.627 | 1.00 | 16.71 |
| ATOM | 1304 | CA | TYR | 231 | 21.314 | 37.638 | 51.715 | 1.00 | 16.94 |
| ATOM | 1305 | CB | TYR | 231 | 22.383 | 36.730 | 51.107 | 1.00 | 14.95 |
| ATOM | 1306 | CG | TYR | 231 | 23.567 | 37.445 | 50.490 | 1.00 | 13.63 |
| ATOM | 1307 | CD1 | TYR | 231 | 24.576 | 37.988 | 51.286 | 1.00 | 13.32 |
| ATOM | 1308 | CE1 | TYR | 231 | 25.693 | 38.608 | 50.715 | 1.00 | 14.67 |
| ATOM | 1309 | CD2 | TYR | 231 | 23.694 | 37.543 | 49.101 | 1.00 | 14.54 |
| ATOM | 1310 | CE2 | TYR | 231 | 24.802 | 38.162 | 48.518 | 1.00 | 13.31 |
| ATOM | 1311 | CZ | TYR | 231 | 25.797 | 38.688 | 49.329 | 1.00 | 12.39 |
| ATOM | 1312 | OH | TYR | 231 | 26.899 | 39.279 | 48.764 | 1.00 | 13.70 |
| ATOM | 1313 | C | TYR | 231 | 21.251 | 38.961 | 50.949 | 1.00 | 14.98 |
| ATOM | 1314 | O | TYR | 231 | 21.702 | 39.997 | 51.434 | 1.00 | 14.92 |
| ATOM | 1315 | N | VAL | 232 | 20.695 | 38.910 | 49.742 | 1.00 | 16.25 |
| ATOM | 1316 | CA | VAL | 232 | 20.568 | 40.091 | 48.888 | 1.00 | 15.73 |
| ATOM | 1317 | CB | VAL | 232 | 19.978 | 39.693 | 47.511 | 1.00 | 16.32 |
| ATOM | 1318 | CG1 | VAL | 232 | 19.518 | 40.922 | 46.744 | 1.00 | 14.95 |
| ATOM | 1319 | CG2 | VAL | 232 | 21.041 | 38.931 | 46.706 | 1.00 | 14.49 |
| ATOM | 1320 | C | VAL | 232 | 19.705 | 41.168 | 49.546 | 1.00 | 17.00 |
| ATOM | 1321 | O | VAL | 232 | 20.044 | 42.359 | 49.532 | 1.00 | 14.95 |
| ATOM | 1322 | N | GLU | 233 | 18.596 | 40.742 | 50.136 | 1.00 | 16.77 |
| ATOM | 1323 | CA | GLU | 233 | 17.695 | 41.670 | 50.802 | 1.00 | 18.55 |
| ATOM | 1324 | CB | GLU | 233 | 16.459 | 40.919 | 51.315 | 1.00 | 20.59 |
| ATOM | 1325 | CG | GLU | 233 | 15.554 | 41.728 | 52.234 | 1.00 | 27.30 |
| ATOM | 1326 | CD | GLU | 233 | 14.310 | 40.956 | 52.658 | 1.00 | 32.53 |
| ATOM | 1327 | OE1 | GLU | 233 | 14.424 | 39.751 | 52.977 | 1.00 | 32.64 |
| ATOM | 1328 | OE2 | GLU | 233 | 13.217 | 41.561 | 52.679 | 1.00 | 38.43 |
| ATOM | 1329 | C | GLU | 233 | 18.413 | 42.355 | 51.959 | 1.00 | 17.80 |
| ATOM | 1330 | O | GLU | 233 | 18.380 | 43.576 | 52.081 | 1.00 | 17.11 |
| ATOM | 1331 | N | LEU | 234 | 19.084 | 41.566 | 52.791 | 1.00 | 17.72 |
| ATOM | 1332 | CA | LEU | 234 | 19.782 | 42.107 | 53.951 | 1.00 | 17.47 |
| ATOM | 1333 | CB | LEU | 234 | 20.161 | 40.971 | 54.906 | 1.00 | 17.40 |
| ATOM | 1334 | CG | LEU | 234 | 18.941 | 40.262 | 55.503 | 1.00 | 22.59 |
| ATOM | 1335 | CD1 | LEU | 234 | 19.386 | 39.093 | 56.366 | 1.00 | 22.34 |
| ATOM | 1336 | CD2 | LEU | 234 | 18.119 | 41.256 | 56.319 | 1.00 | 22.15 |
| ATOM | 1337 | C | LEU | 234 | 21.006 | 42.963 | 53.638 | 1.00 | 17.17 |
| ATOM | 1338 | O | LEU | 234 | 21.205 | 43.995 | 54.273 | 1.00 | 16.30 |
| ATOM | 1339 | N | ILE | 235 | 21.823 | 42.560 | 52.666 | 1.00 | 14.58 |
| ATOM | 1340 | CA | ILE | 235 | 23.000 | 43.363 | 52.355 | 1.00 | 14.01 |
| ATOM | 1341 | CB | ILE | 235 | 24.023 | 42.592 | 51.472 | 1.00 | 13.57 |
| ATOM | 1342 | CG2 | ILE | 235 | 23.462 | 42.349 | 50.074 | 1.00 | 12.52 |
| ATOM | 1343 | CG1 | ILE | 235 | 25.331 | 43.389 | 51.395 | 1.00 | 11.74 |
| ATOM | 1344 | CD1 | ILE | 235 | 26.469 | 42.632 | 50.735 | 1.00 | 11.93 |
| ATOM | 1345 | C | ILE | 235 | 22.563 | 44.661 | 51.679 | 1.00 | 14.36 |
| ATOM | 1346 | O | ILE | 235 | 23.193 | 45.705 | 51.857 | 1.00 | 13.51 |
| ATOM | 1347 | N | ASN | 236 | 21.474 | 44.600 | 50.916 | 1.00 | 14.39 |
| ATOM | 1348 | CA | ASN | 236 | 20.951 | 45.798 | 50.261 | 1.00 | 15.23 |
| ATOM | 1349 | CB | ASN | 236 | 19.837 | 45.448 | 49.264 | 1.00 | 15.19 |
| ATOM | 1350 | CG | ASN | 236 | 20.365 | 45.201 | 47.862 | 1.00 | 15.72 |
| ATOM | 1351 | OD1 | ASN | 236 | 21.519 | 45.501 | 47.560 | 1.00 | 15.27 |
| ATOM | 1352 | ND2 | ASN | 236 | 19.512 | 44.667 | 46.992 | 1.00 | 18.17 |
| ATOM | 1353 | C | ASN | 236 | 20.394 | 46.751 | 51.322 | 1.00 | 15.66 |
| ATOM | 1354 | O | ASN | 236 | 20.570 | 47.964 | 51.231 | 1.00 | 16.15 |
| ATOM | 1355 | N | GLN | 237 | 19.721 | 46.190 | 52.322 | 1.00 | 17.57 |
| ATOM | 1356 | CA | GLN | 237 | 19.146 | 46.989 | 53.404 | 1.00 | 18.43 |
| ATOM | 1357 | CB | GLN | 237 | 18.391 | 46.090 | 54.391 | 1.00 | 19.68 |
| ATOM | 1358 | CG | GLN | 237 | 17.537 | 46.858 | 55.391 | 1.00 | 22.74 |
| ATOM | 1359 | CD | GLN | 237 | 16.845 | 45.947 | 56.397 | 1.00 | 25.62 |
| ATOM | 1360 | OE1 | GLN | 237 | 16.460 | 44.821 | 56.073 | 1.00 | 25.13 |
| ATOM | 1361 | NE2 | GLN | 237 | 16.667 | 46.441 | 57.620 | 1.00 | 25.08 |
| ATOM | 1362 | C | GLN | 237 | 20.261 | 47.727 | 54.139 | 1.00 | 17.44 |
| ATOM | 1363 | O | GLN | 237 | 20.158 | 48.924 | 54.402 | 1.00 | 17.22 |
| ATOM | 1364 | N | ALA | 238 | 21.323 | 47.003 | 54.478 | 1.00 | 15.64 |
| ATOM | 1365 | CA | ALA | 238 | 22.460 | 47.604 | 55.162 | 1.00 | 16.63 |
| ATOM | 1366 | CB | ALA | 238 | 23.530 | 46.549 | 55.436 | 1.00 | 14.09 |
| ATOM | 1367 | C | ALA | 238 | 23.038 | 48.727 | 54.303 | 1.00 | 16.39 |
| ATOM | 1368 | O | ALA | 238 | 23.385 | 49.790 | 54.813 | 1.00 | 18.77 |
| ATOM | 1369 | N | ALA | 239 | 23.142 | 48.484 | 52.998 | 1.00 | 15.79 |
| ATOM | 1370 | CA | ALA | 239 | 23.672 | 49.482 | 52.076 | 1.00 | 16.70 |
| ATOM | 1371 | CB | ALA | 239 | 23.725 | 48.921 | 50.650 | 1.00 | 14.56 |
| ATOM | 1372 | C | ALA | 239 | 22.827 | 50.758 | 52.102 | 1.00 | 17.22 |
| ATOM | 1373 | O | ALA | 239 | 23.369 | 51.866 | 52.172 | 1.00 | 14.26 |

TABLE A-continued

| | | | | | | | | | |
|---|---|---|---|---|---|---|---|---|---|
| ATOM | 1374 | N | ARG | 240 | 21.505 | 50.606 | 52.043 | 1.00 | 15.36 |
| ATOM | 1375 | CA | ARG | 240 | 20.622 | 51.774 | 52.064 | 1.00 | 17.46 |
| ATOM | 1376 | CB | ARG | 240 | 19.162 | 51.376 | 51.793 | 1.00 | 15.33 |
| ATOM | 1377 | CG | ARG | 240 | 18.893 | 50.824 | 50.388 | 1.00 | 17.28 |
| ATOM | 1378 | CD | ARG | 240 | 17.393 | 50.778 | 50.080 | 1.00 | 16.93 |
| ATOM | 1379 | NE | ARG | 240 | 16.638 | 50.067 | 51.108 | 1.00 | 19.77 |
| ATOM | 1380 | CZ | ARG | 240 | 16.521 | 48.744 | 51.180 | 1.00 | 22.01 |
| ATOM | 1381 | NH1 | ARG | 240 | 17.107 | 47.966 | 50.271 | 1.00 | 19.52 |
| ATOM | 1382 | NH2 | ARG | 240 | 15.823 | 48.197 | 52.169 | 1.00 | 18.66 |
| ATOM | 1383 | C | ARG | 240 | 20.701 | 52.506 | 53.404 | 1.00 | 17.66 |
| ATOM | 1384 | O | ARG | 240 | 20.569 | 53.729 | 53.460 | 1.00 | 16.54 |
| ATOM | 1385 | N | LEU | 241 | 20.916 | 51.759 | 54.482 | 1.00 | 17.65 |
| ATOM | 1386 | CA | LEU | 241 | 21.005 | 52.374 | 55.800 | 1.00 | 19.55 |
| ATOM | 1387 | CB | LEU | 241 | 20.827 | 51.315 | 56.898 | 1.00 | 19.64 |
| ATOM | 1388 | CG | LEU | 241 | 19.413 | 50.726 | 57.017 | 1.00 | 19.83 |
| ATOM | 1389 | CD1 | LEU | 241 | 19.416 | 49.573 | 57.999 | 1.00 | 20.06 |
| ATOM | 1390 | CD2 | LEU | 241 | 18.434 | 51.804 | 57.470 | 1.00 | 22.50 |
| ATOM | 1391 | C | LEU | 241 | 22.326 | 53.117 | 55.973 | 1.00 | 19.27 |
| ATOM | 1392 | O | LEU | 241 | 22.548 | 53.783 | 56.986 | 1.00 | 20.50 |
| ATOM | 1393 | N | ASN | 242 | 23.202 | 53.001 | 54.980 | 1.00 | 16.73 |
| ATOM | 1394 | CA | ASN | 242 | 24.481 | 53.693 | 55.021 | 1.00 | 16.25 |
| ATOM | 1395 | CB | ASN | 242 | 25.636 | 52.697 | 54.897 | 1.00 | 15.12 |
| ATOM | 1396 | CG | ASN | 242 | 25.891 | 51.952 | 56.195 | 1.00 | 19.42 |
| ATOM | 1397 | OD1 | ASN | 242 | 26.139 | 52.571 | 57.234 | 1.00 | 19.98 |
| ATOM | 1398 | ND2 | ASN | 242 | 25.825 | 50.622 | 56.148 | 1.00 | 18.09 |
| ATOM | 1399 | C | ASN | 242 | 24.572 | 54.763 | 53.934 | 1.00 | 17.24 |
| ATOM | 1400 | O | ASN | 242 | 25.652 | 55.290 | 53.655 | 1.00 | 17.37 |
| ATOM | 1401 | N | GLY | 243 | 23.429 | 55.066 | 53.321 | 1.00 | 15.75 |
| ATOM | 1402 | CA | GLY | 243 | 23.373 | 56.099 | 52.299 | 1.00 | 16.87 |
| ATOM | 1403 | C | GLY | 243 | 23.543 | 55.696 | 50.844 | 1.00 | 15.89 |
| ATOM | 1404 | O | GLY | 243 | 23.626 | 56.565 | 49.978 | 1.00 | 15.97 |
| ATOM | 1405 | N | TYR | 244 | 23.608 | 54.398 | 50.565 | 1.00 | 16.21 |
| ATOM | 1406 | CA | TYR | 244 | 23.764 | 53.922 | 49.189 | 1.00 | 14.57 |
| ATOM | 1407 | CB | TYR | 244 | 24.761 | 52.757 | 49.135 | 1.00 | 14.48 |
| ATOM | 1408 | CG | TYR | 244 | 26.167 | 53.146 | 49.521 | 1.00 | 15.74 |
| ATOM | 1409 | CD1 | TYR | 244 | 26.665 | 52.860 | 50.787 | 1.00 | 14.52 |
| ATOM | 1410 | CE1 | TYR | 244 | 27.951 | 53.250 | 51.158 | 1.00 | 16.68 |
| ATOM | 1411 | CD2 | TYR | 244 | 26.989 | 53.833 | 48.627 | 1.00 | 16.81 |
| ATOM | 1412 | CE2 | TYR | 244 | 28.274 | 54.231 | 48.988 | 1.00 | 16.81 |
| ATOM | 1413 | CZ | TYR | 244 | 28.747 | 53.935 | 50.255 | 1.00 | 16.66 |
| ATOM | 1414 | OH | TYR | 244 | 30.013 | 54.329 | 50.619 | 1.00 | 20.02 |
| ATOM | 1415 | C | TYR | 244 | 22.423 | 53.462 | 48.628 | 1.00 | 15.50 |
| ATOM | 1416 | O | TYR | 244 | 21.483 | 53.254 | 49.385 | 1.00 | 17.45 |
| ATOM | 1417 | N | VAL | 245 | 22.325 | 53.308 | 47.307 | 1.00 | 15.80 |
| ATOM | 1418 | CA | VAL | 245 | 21.069 | 52.854 | 46.713 | 1.00 | 15.94 |
| ATOM | 1419 | CB | VAL | 245 | 20.945 | 53.283 | 45.227 | 1.00 | 19.25 |
| ATOM | 1420 | CG1 | VAL | 245 | 20.843 | 54.804 | 45.137 | 1.00 | 21.35 |
| ATOM | 1421 | CG2 | VAL | 245 | 22.133 | 52.795 | 44.436 | 1.00 | 19.37 |
| ATOM | 1422 | C | VAL | 245 | 20.926 | 51.335 | 46.830 | 1.00 | 15.52 |
| ATOM | 1423 | O | VAL | 245 | 19.810 | 50.817 | 46.890 | 1.00 | 16.08 |
| ATOM | 1424 | N | ASP | 246 | 22.057 | 50.630 | 46.871 | 1.00 | 12.67 |
| ATOM | 1425 | CA | ASP | 246 | 22.077 | 49.169 | 47.017 | 1.00 | 12.71 |
| ATOM | 1426 | CB | ASP | 246 | 21.487 | 48.477 | 45.776 | 1.00 | 10.13 |
| ATOM | 1427 | CG | ASP | 246 | 22.273 | 48.765 | 44.509 | 1.00 | 12.08 |
| ATOM | 1428 | OD1 | ASP | 246 | 23.483 | 48.446 | 44.453 | 1.00 | 15.10 |
| ATOM | 1429 | OD2 | ASP | 246 | 21.676 | 49.312 | 43.561 | 1.00 | 15.37 |
| ATOM | 1430 | C | ASP | 246 | 23.507 | 48.677 | 47.273 | 1.00 | 11.44 |
| ATOM | 1431 | O | ASP | 246 | 24.450 | 49.463 | 47.236 | 1.00 | 12.92 |
| ATOM | 1432 | N | ALA | 247 | 23.666 | 47.381 | 47.537 | 1.00 | 12.55 |
| ATOM | 1433 | CA | ALA | 247 | 24.986 | 46.813 | 47.819 | 1.00 | 12.99 |
| ATOM | 1434 | CB | ALA | 247 | 24.855 | 45.318 | 48.148 | 1.00 | 12.30 |
| ATOM | 1435 | C | ALA | 247 | 26.016 | 47.011 | 46.704 | 1.00 | 11.82 |
| ATOM | 1436 | O | ALA | 247 | 27.204 | 47.218 | 46.975 | 1.00 | 12.97 |
| ATOM | 1437 | N | GLY | 248 | 25.570 | 46.935 | 45.453 | 1.00 | 10.87 |
| ATOM | 1438 | CA | GLY | 248 | 26.484 | 47.116 | 44.335 | 1.00 | 10.26 |
| ATOM | 1439 | C | GLY | 248 | 27.077 | 48.512 | 44.352 | 1.00 | 13.13 |
| ATOM | 1440 | O | GLY | 248 | 28.277 | 48.708 | 44.134 | 1.00 | 13.09 |
| ATOM | 1441 | N | ASP | 249 | 26.214 | 49.490 | 44.606 | 1.00 | 14.71 |
| ATOM | 1442 | CA | ASP | 249 | 26.615 | 50.894 | 44.685 | 1.00 | 15.46 |
| ATOM | 1443 | CB | ASP | 249 | 25.369 | 51.744 | 44.977 | 1.00 | 15.97 |
| ATOM | 1444 | CG | ASP | 249 | 25.671 | 53.226 | 45.132 | 1.00 | 17.81 |
| ATOM | 1445 | OD1 | ASP | 249 | 26.503 | 53.765 | 44.373 | 1.00 | 16.36 |
| ATOM | 1446 | OD2 | ASP | 249 | 25.040 | 53.856 | 46.005 | 1.00 | 18.13 |
| ATOM | 1447 | C | ASP | 249 | 27.652 | 51.008 | 45.804 | 1.00 | 15.19 |
| ATOM | 1448 | O | ASP | 249 | 28.718 | 51.598 | 45.626 | 1.00 | 14.88 |
| ATOM | 1449 | N | SER | 250 | 27.346 | 50.418 | 46.954 | 1.00 | 15.48 |
| ATOM | 1450 | CA | SER | 250 | 28.267 | 50.448 | 48.083 | 1.00 | 15.85 |
| ATOM | 1451 | CB | SER | 250 | 27.669 | 49.667 | 49.257 | 1.00 | 18.56 |
| ATOM | 1452 | OG | SER | 250 | 28.534 | 49.703 | 50.376 | 1.00 | 19.16 |
| ATOM | 1453 | C | SER | 250 | 29.650 | 49.877 | 47.723 | 1.00 | 15.52 |

TABLE A-continued

| | | | | | | | | | |
|---|---|---|---|---|---|---|---|---|---|
| ATOM | 1454 | O | SER | 250 | 30.680 | 50.479 | 48.036 | 1.00 | 13.65 |
| ATOM | 1455 | N | TRP | 251 | 29.676 | 48.718 | 47.065 | 1.00 | 14.06 |
| ATOM | 1456 | CA | TRP | 251 | 30.945 | 48.093 | 46.672 | 1.00 | 14.44 |
| ATOM | 1457 | CB | TRP | 251 | 30.700 | 46.698 | 46.082 | 1.00 | 13.11 |
| ATOM | 1458 | CG | TRP | 251 | 30.248 | 45.674 | 47.075 | 1.00 | 14.95 |
| ATOM | 1459 | CD2 | TRP | 251 | 30.022 | 44.282 | 46.820 | 1.00 | 15.48 |
| ATOM | 1460 | CE2 | TRP | 251 | 29.626 | 43.691 | 48.041 | 1.00 | 17.39 |
| ATOM | 1461 | CE3 | TRP | 251 | 30.117 | 43.477 | 45.676 | 1.00 | 12.92 |
| ATOM | 1462 | CD1 | TRP | 251 | 29.985 | 45.868 | 48.405 | 1.00 | 16.16 |
| ATOM | 1463 | NE1 | TRP | 251 | 29.612 | 44.680 | 48.992 | 1.00 | 16.30 |
| ATOM | 1464 | CZ2 | TRP | 251 | 29.323 | 42.323 | 48.151 | 1.00 | 16.20 |
| ATOM | 1465 | CZ3 | TRP | 251 | 29.817 | 42.120 | 45.784 | 1.00 | 15.52 |
| ATOM | 1466 | CH2 | TRP | 251 | 29.425 | 41.558 | 47.014 | 1.00 | 15.29 |
| ATOM | 1467 | C | TRP | 251 | 31.735 | 48.923 | 45.662 | 1.00 | 14.40 |
| ATOM | 1468 | O | TRP | 251 | 32.956 | 49.057 | 45.776 | 1.00 | 11.76 |
| ATOM | 1469 | N | ARG | 252 | 31.043 | 49.471 | 44.665 | 1.00 | 14.90 |
| ATOM | 1470 | CA | ARG | 252 | 31.714 | 50.272 | 43.655 | 1.00 | 13.31 |
| ATOM | 1471 | CB | ARG | 252 | 30.740 | 50.668 | 42.528 | 1.00 | 14.60 |
| ATOM | 1472 | CG | ARG | 252 | 30.243 | 49.494 | 41.672 | 1.00 | 14.42 |
| ATOM | 1473 | CD | ARG | 252 | 29.472 | 49.970 | 40.447 | 1.00 | 12.08 |
| ATOM | 1474 | NE | ARG | 252 | 28.233 | 50.687 | 40.771 | 1.00 | 13.50 |
| ATOM | 1475 | CZ | ARG | 252 | 27.063 | 50.107 | 41.037 | 1.00 | 14.82 |
| ATOM | 1476 | NH1 | ARG | 252 | 26.002 | 50.854 | 41.319 | 1.00 | 13.27 |
| ATOM | 1477 | NH2 | ARG | 252 | 26.942 | 48.783 | 41.011 | 1.00 | 13.16 |
| ATOM | 1478 | C | ARG | 252 | 32.337 | 51.527 | 44.267 | 1.00 | 16.12 |
| ATOM | 1479 | O | ARG | 252 | 33.361 | 52.004 | 43.787 | 1.00 | 14.85 |
| ATOM | 1480 | N | SER | 253 | 31.730 | 52.050 | 45.332 | 1.00 | 15.54 |
| ATOM | 1481 | CA | SER | 253 | 32.239 | 53.260 | 45.977 | 1.00 | 16.04 |
| ATOM | 1482 | CB | SER | 253 | 31.309 | 53.703 | 47.112 | 1.00 | 16.20 |
| ATOM | 1483 | OG | SER | 253 | 31.590 | 52.997 | 48.309 | 1.00 | 20.61 |
| ATOM | 1484 | C | SER | 253 | 33.652 | 53.086 | 46.527 | 1.00 | 14.43 |
| ATOM | 1485 | O | SER | 253 | 34.339 | 54.069 | 46.789 | 1.00 | 14.48 |
| ATOM | 1486 | N | MET | 254 | 34.085 | 51.840 | 46.697 | 1.00 | 14.27 |
| ATOM | 1487 | CA | MET | 254 | 35.429 | 51.562 | 47.209 | 1.00 | 16.48 |
| ATOM | 1488 | CB | MET | 254 | 35.657 | 50.051 | 47.360 | 1.00 | 17.80 |
| ATOM | 1489 | CG | MET | 254 | 34.740 | 49.358 | 48.359 | 1.00 | 21.06 |
| ATOM | 1490 | SD | MET | 254 | 35.187 | 47.614 | 48.574 | 1.00 | 31.02 |
| ATOM | 1491 | CE | MET | 254 | 34.226 | 46.857 | 47.338 | 1.00 | 27.13 |
| ATOM | 1492 | C | MET | 254 | 36.517 | 52.121 | 46.298 | 1.00 | 15.51 |
| ATOM | 1493 | O | MET | 254 | 37.666 | 52.265 | 46.714 | 1.00 | 16.06 |
| ATOM | 1494 | N | TYR | 255 | 36.163 | 52.423 | 45.053 | 1.00 | 14.88 |
| ATOM | 1495 | CA | TYR | 255 | 37.135 | 52.956 | 44.105 | 1.00 | 15.20 |
| ATOM | 1496 | CB | TYR | 255 | 36.904 | 52.360 | 42.704 | 1.00 | 15.30 |
| ATOM | 1497 | CG | TYR | 255 | 37.206 | 50.880 | 42.631 | 1.00 | 13.36 |
| ATOM | 1498 | CD1 | TYR | 255 | 36.245 | 49.935 | 42.986 | 1.00 | 12.66 |
| ATOM | 1499 | CE1 | TYR | 255 | 36.544 | 48.568 | 43.000 | 1.00 | 13.69 |
| ATOM | 1500 | CD2 | TYR | 255 | 38.479 | 50.427 | 42.281 | 1.00 | 12.94 |
| ATOM | 1501 | CE2 | TYR | 255 | 38.792 | 49.064 | 42.293 | 1.00 | 14.05 |
| ATOM | 1502 | CZ | TYR | 255 | 37.818 | 48.143 | 42.659 | 1.00 | 13.41 |
| ATOM | 1503 | OH | TYR | 255 | 38.129 | 46.806 | 42.721 | 1.00 | 13.11 |
| ATOM | 1504 | C | TYR | 255 | 37.126 | 54.479 | 44.023 | 1.00 | 14.46 |
| ATOM | 1505 | O | TYR | 255 | 38.000 | 55.068 | 43.393 | 1.00 | 14.81 |
| ATOM | 1506 | N | GLU | 256 | 36.139 | 55.111 | 44.654 | 1.00 | 15.24 |
| ATOM | 1507 | CA | GLU | 256 | 36.028 | 56.574 | 44.642 | 1.00 | 16.61 |
| ATOM | 1508 | CB | GLU | 256 | 37.103 | 57.195 | 45.539 | 1.00 | 17.37 |
| ATOM | 1509 | CG | GLU | 256 | 37.109 | 56.665 | 46.966 | 1.00 | 22.10 |
| ATOM | 1510 | CD | GLU | 256 | 38.044 | 57.453 | 47.878 | 1.00 | 23.83 |
| ATOM | 1511 | OE1 | GLU | 256 | 39.253 | 57.535 | 47.579 | 1.00 | 26.54 |
| ATOM | 1512 | OE2 | GLU | 256 | 37.565 | 57.988 | 48.894 | 1.00 | 26.05 |
| ATOM | 1513 | C | GLU | 256 | 36.191 | 57.103 | 43.222 | 1.00 | 15.97 |
| ATOM | 1514 | O | GLU | 256 | 36.852 | 58.114 | 42.991 | 1.00 | 16.36 |
| ATOM | 1515 | N | THR | 257 | 35.575 | 56.413 | 42.273 | 1.00 | 16.18 |
| ATOM | 1516 | CA | THR | 257 | 35.678 | 56.786 | 40.872 | 1.00 | 17.13 |
| ATOM | 1517 | CB | THR | 257 | 36.628 | 55.824 | 40.144 | 1.00 | 18.70 |
| ATOM | 1518 | OG1 | THR | 257 | 37.905 | 55.848 | 40.796 | 1.00 | 17.37 |
| ATOM | 1519 | CG2 | THR | 257 | 36.789 | 56.226 | 38.679 | 1.00 | 17.93 |
| ATOM | 1520 | C | THR | 257 | 34.309 | 56.761 | 40.201 | 1.00 | 16.00 |
| ATOM | 1521 | O | THR | 257 | 33.818 | 55.707 | 39.797 | 1.00 | 15.27 |
| ATOM | 1522 | N | PRO | 258 | 33.673 | 57.936 | 40.077 | 1.00 | 15.23 |
| ATOM | 1523 | CD | PRO | 258 | 34.141 | 59.242 | 40.584 | 1.00 | 15.95 |
| ATOM | 1524 | CA | PRO | 258 | 32.349 | 58.057 | 39.456 | 1.00 | 15.97 |
| ATOM | 1525 | CB | PRO | 258 | 32.120 | 59.569 | 39.426 | 1.00 | 16.42 |
| ATOM | 1526 | CG | PRO | 258 | 32.851 | 60.041 | 40.663 | 1.00 | 16.92 |
| ATOM | 1527 | C | PRO | 258 | 32.254 | 57.434 | 38.064 | 1.00 | 15.58 |
| ATOM | 1528 | O | PRO | 258 | 31.208 | 56.909 | 37.683 | 1.00 | 16.29 |
| ATOM | 1529 | N | SER | 259 | 33.348 | 57.487 | 37.310 | 1.00 | 15.31 |
| ATOM | 1530 | CA | SER | 259 | 33.355 | 56.939 | 35.953 | 1.00 | 15.70 |
| ATOM | 1531 | CB | SER | 259 | 34.330 | 57.740 | 35.085 | 1.00 | 17.61 |
| ATOM | 1532 | OG | SER | 259 | 35.657 | 57.612 | 35.573 | 1.00 | 18.28 |
| ATOM | 1533 | C | SER | 259 | 33.728 | 55.452 | 35.884 | 1.00 | 14.57 |

TABLE A-continued

| | | | | | | | | | |
|---|---|---|---|---|---|---|---|---|---|
| ATOM | 1534 | O | SER | 259 | 33.917 | 54.913 | 34.798 | 1.00 | 13.39 |
| ATOM | 1535 | N | LEU | 260 | 33.810 | 54.790 | 37.036 | 1.00 | 13.86 |
| ATOM | 1536 | CA | LEU | 260 | 34.200 | 53.376 | 37.094 | 1.00 | 14.52 |
| ATOM | 1537 | CB | LEU | 260 | 33.936 | 52.806 | 38.497 | 1.00 | 14.33 |
| ATOM | 1538 | CG | LEU | 260 | 34.446 | 51.379 | 38.763 | 1.00 | 17.84 |
| ATOM | 1539 | CD1 | LEU | 260 | 35.965 | 51.348 | 38.632 | 1.00 | 17.38 |
| ATOM | 1540 | CD2 | LEU | 260 | 34.033 | 50.922 | 40.161 | 1.00 | 17.16 |
| ATOM | 1541 | C | LEU | 260 | 33.577 | 52.437 | 36.056 | 1.00 | 13.87 |
| ATOM | 1542 | O | LEU | 260 | 34.299 | 51.777 | 35.311 | 1.00 | 9.84 |
| ATOM | 1543 | N | GLU | 261 | 32.248 | 52.363 | 36.003 | 1.00 | 13.07 |
| ATOM | 1544 | CA | GLU | 261 | 31.607 | 51.448 | 35.061 | 1.00 | 14.77 |
| ATOM | 1545 | CB | GLU | 261 | 30.079 | 51.514 | 35.191 | 1.00 | 12.37 |
| ATOM | 1546 | CG | GLU | 261 | 29.591 | 51.176 | 36.596 | 1.00 | 15.59 |
| ATOM | 1547 | CD | GLU | 261 | 28.174 | 50.633 | 36.623 | 1.00 | 17.28 |
| ATOM | 1548 | OE1 | GLU | 261 | 27.524 | 50.604 | 35.560 | 1.00 | 21.19 |
| ATOM | 1549 | OE2 | GLU | 261 | 27.714 | 50.234 | 37.712 | 1.00 | 18.05 |
| ATOM | 1550 | C | GLU | 261 | 32.030 | 51.664 | 33.618 | 1.00 | 14.11 |
| ATOM | 1551 | O | GLU | 261 | 32.295 | 50.704 | 32.895 | 1.00 | 14.05 |
| ATOM | 1552 | N | GLN | 262 | 32.108 | 52.919 | 33.200 | 1.00 | 15.79 |
| ATOM | 1553 | CA | GLN | 262 | 32.522 | 53.232 | 31.839 | 1.00 | 16.53 |
| ATOM | 1554 | CB | GLN | 262 | 32.280 | 54.712 | 31.547 | 1.00 | 21.41 |
| ATOM | 1555 | CG | GLN | 262 | 30.809 | 55.095 | 31.459 | 1.00 | 27.97 |
| ATOM | 1556 | CD | GLN | 262 | 30.587 | 56.587 | 31.641 | 1.00 | 32.44 |
| ATOM | 1557 | OE1 | GLN | 262 | 29.655 | 57.162 | 31.077 | 1.00 | 34.42 |
| ATOM | 1558 | NE2 | GLN | 262 | 31.439 | 57.220 | 32.447 | 1.00 | 33.41 |
| ATOM | 1559 | C | GLN | 262 | 34.001 | 52.901 | 31.642 | 1.00 | 17.20 |
| ATOM | 1560 | O | GLN | 262 | 34.382 | 52.314 | 30.625 | 1.00 | 15.46 |
| ATOM | 1561 | N | ASP | 263 | 34.830 | 53.280 | 32.612 | 1.00 | 16.67 |
| ATOM | 1562 | CA | ASP | 263 | 36.263 | 53.011 | 32.524 | 1.00 | 15.94 |
| ATOM | 1563 | CB | ASP | 263 | 36.998 | 53.485 | 33.781 | 1.00 | 19.14 |
| ATOM | 1564 | CG | ASP | 263 | 37.032 | 54.998 | 33.914 | 1.00 | 22.47 |
| ATOM | 1565 | OD1 | ASP | 263 | 37.016 | 55.698 | 32.878 | 1.00 | 21.52 |
| ATOM | 1566 | OD2 | ASP | 263 | 37.097 | 55.486 | 35.060 | 1.00 | 22.10 |
| ATOM | 1567 | C | ASP | 263 | 36.535 | 51.519 | 32.346 | 1.00 | 16.31 |
| ATOM | 1568 | O | ASP | 263 | 37.341 | 51.121 | 31.507 | 1.00 | 17.06 |
| ATOM | 1569 | N | LEU | 264 | 35.866 | 50.696 | 33.146 | 1.00 | 15.79 |
| ATOM | 1570 | CA | LEU | 264 | 36.056 | 49.251 | 33.082 | 1.00 | 16.11 |
| ATOM | 1571 | CB | LEU | 264 | 35.334 | 48.585 | 34.258 | 1.00 | 17.87 |
| ATOM | 1572 | CG | LEU | 264 | 35.807 | 49.044 | 35.641 | 1.00 | 18.11 |
| ATOM | 1573 | CD1 | LEU | 264 | 35.050 | 48.285 | 36.717 | 1.00 | 19.50 |
| ATOM | 1574 | CD2 | LEU | 264 | 37.303 | 48.819 | 35.781 | 1.00 | 19.36 |
| ATOM | 1575 | C | LEU | 264 | 35.567 | 48.667 | 31.757 | 1.00 | 16.10 |
| ATOM | 1576 | O | LEU | 264 | 36.175 | 47.746 | 31.215 | 1.00 | 14.50 |
| ATOM | 1577 | N | GLU | 265 | 34.468 | 49.206 | 31.240 | 1.00 | 17.12 |
| ATOM | 1578 | CA | GLU | 265 | 33.911 | 48.745 | 29.970 | 1.00 | 18.85 |
| ATOM | 1579 | CB | GLU | 265 | 32.571 | 49.440 | 29.708 | 1.00 | 21.26 |
| ATOM | 1580 | CG | GLU | 265 | 31.924 | 49.123 | 28.364 | 1.00 | 27.69 |
| ATOM | 1581 | CD | GLU | 265 | 31.617 | 47.648 | 28.189 | 1.00 | 34.09 |
| ATOM | 1582 | OE1 | GLU | 265 | 31.001 | 47.050 | 29.100 | 1.00 | 36.70 |
| ATOM | 1583 | OE2 | GLU | 265 | 31.984 | 47.087 | 27.134 | 1.00 | 37.08 |
| ATOM | 1584 | C | GLU | 265 | 34.890 | 49.034 | 28.830 | 1.00 | 19.85 |
| ATOM | 1585 | O | GLU | 265 | 35.077 | 48.207 | 27.935 | 1.00 | 19.78 |
| ATOM | 1586 | N | ARG | 266 | 35.515 | 50.210 | 28.859 | 1.00 | 17.74 |
| ATOM | 1587 | CA | ARG | 266 | 36.475 | 50.567 | 27.822 | 1.00 | 17.75 |
| ATOM | 1588 | CB | ARG | 266 | 36.920 | 52.026 | 27.970 | 1.00 | 20.40 |
| ATOM | 1589 | CG | ARG | 266 | 35.885 | 53.041 | 27.507 | 1.00 | 25.02 |
| ATOM | 1590 | CD | ARG | 266 | 36.506 | 54.424 | 27.397 | 1.00 | 28.27 |
| ATOM | 1591 | NE | ARG | 266 | 36.724 | 55.042 | 28.701 | 1.00 | 34.44 |
| ATOM | 1592 | CZ | ARG | 266 | 35.776 | 55.660 | 29.401 | 1.00 | 36.31 |
| ATOM | 1593 | NH1 | ARG | 266 | 34.541 | 55.747 | 28.920 | 1.00 | 36.59 |
| ATOM | 1594 | NH2 | ARG | 266 | 36.061 | 56.191 | 30.582 | 1.00 | 36.92 |
| ATOM | 1595 | C | ARG | 266 | 37.686 | 49.645 | 27.894 | 1.00 | 16.78 |
| ATOM | 1596 | O | ARG | 266 | 38.203 | 49.206 | 26.867 | 1.00 | 15.67 |
| ATOM | 1597 | N | LEU | 267 | 38.140 | 49.352 | 29.108 | 1.00 | 15.01 |
| ATOM | 1598 | CA | LEU | 267 | 39.280 | 48.459 | 29.289 | 1.00 | 14.82 |
| ATOM | 1599 | CB | LEU | 267 | 39.646 | 48.362 | 30.773 | 1.00 | 16.36 |
| ATOM | 1600 | CG | LEU | 267 | 40.160 | 49.672 | 31.381 | 1.00 | 16.60 |
| ATOM | 1601 | CD1 | LEU | 267 | 40.344 | 49.515 | 32.884 | 1.00 | 16.07 |
| ATOM | 1602 | CD2 | LEU | 267 | 41.486 | 50.064 | 30.709 | 1.00 | 15.87 |
| ATOM | 1603 | C | LEU | 267 | 38.932 | 47.076 | 28.743 | 1.00 | 17.23 |
| ATOM | 1604 | O | LEU | 267 | 39.737 | 46.439 | 28.054 | 1.00 | 15.82 |
| ATOM | 1605 | N | PHE | 268 | 37.723 | 46.616 | 29.046 | 1.00 | 15.48 |
| ATOM | 1606 | CA | PHE | 268 | 37.286 | 45.314 | 28.569 | 1.00 | 16.55 |
| ATOM | 1607 | CB | PHE | 268 | 35.879 | 44.994 | 29.062 | 1.00 | 18.24 |
| ATOM | 1608 | CG | PHE | 268 | 35.345 | 43.707 | 28.512 | 1.00 | 21.70 |
| ATOM | 1609 | CD1 | PHE | 268 | 35.826 | 42.488 | 28.981 | 1.00 | 22.36 |
| ATOM | 1610 | CD2 | PHE | 268 | 34.425 | 43.711 | 27.468 | 1.00 | 21.62 |
| ATOM | 1611 | CE1 | PHE | 268 | 35.403 | 41.292 | 28.415 | 1.00 | 24.19 |
| ATOM | 1612 | CE2 | PHE | 268 | 33.996 | 42.517 | 26.894 | 1.00 | 23.63 |
| ATOM | 1613 | CZ | PHE | 268 | 34.489 | 41.306 | 27.371 | 1.00 | 22.93 |

TABLE A-continued

| | | | | | | | | |
|---|---|---|---|---|---|---|---|---|
| ATOM | 1614 | C | PHE | 268 | 37.291 | 45.258 | 27.043 | 1.00 | 17.17 |
| ATOM | 1615 | O | PHE | 268 | 37.776 | 44.295 | 26.445 | 1.00 | 15.21 |
| ATOM | 1616 | N | GLN | 269 | 36.739 | 46.292 | 26.416 | 1.00 | 16.96 |
| ATOM | 1617 | CA | GLN | 269 | 36.677 | 46.361 | 24.962 | 1.00 | 17.31 |
| ATOM | 1618 | CB | GLN | 269 | 35.905 | 47.606 | 24.517 | 1.00 | 19.68 |
| ATOM | 1619 | CG | GLN | 269 | 34.408 | 47.569 | 24.831 | 1.00 | 24.90 |
| ATOM | 1620 | CD | GLN | 269 | 33.706 | 46.381 | 24.198 | 1.00 | 28.78 |
| ATOM | 1621 | OE1 | GLN | 269 | 33.938 | 46.057 | 23.032 | 1.00 | 31.92 |
| ATOM | 1622 | NE2 | GLN | 269 | 32.832 | 45.732 | 24.960 | 1.00 | 30.59 |
| ATOM | 1623 | C | GLN | 269 | 38.048 | 46.354 | 24.292 | 1.00 | 16.49 |
| ATOM | 1624 | O | GLN | 269 | 38.197 | 45.811 | 23.207 | 1.00 | 15.38 |
| ATOM | 1625 | N | GLU | 270 | 39.046 | 46.960 | 24.926 | 1.00 | 16.98 |
| ATOM | 1626 | CA | GLU | 270 | 40.386 | 46.992 | 24.345 | 1.00 | 20.14 |
| ATOM | 1627 | CB | GLU | 270 | 41.288 | 47.941 | 25.129 | 1.00 | 23.65 |
| ATOM | 1628 | CG | GLU | 270 | 40.839 | 49.382 | 25.073 | 1.00 | 30.06 |
| ATOM | 1629 | CD | GLU | 270 | 41.821 | 50.306 | 25.743 | 1.00 | 35.93 |
| ATOM | 1630 | OE1 | GLU | 270 | 42.956 | 50.432 | 25.234 | 1.00 | 40.83 |
| ATOM | 1631 | OE2 | GLU | 270 | 41.465 | 50.903 | 26.779 | 1.00 | 39.30 |
| ATOM | 1632 | C | GLU | 270 | 41.032 | 45.614 | 24.291 | 1.00 | 19.09 |
| ATOM | 1633 | O | GLU | 270 | 41.861 | 45.344 | 23.420 | 1.00 | 17.60 |
| ATOM | 1634 | N | LEU | 271 | 40.652 | 44.745 | 25.222 | 1.00 | 17.35 |
| ATOM | 1635 | CA | LEU | 271 | 41.197 | 43.393 | 25.269 | 1.00 | 18.44 |
| ATOM | 1636 | CB | LEU | 271 | 41.356 | 42.961 | 26.726 | 1.00 | 20.14 |
| ATOM | 1637 | CG | LEU | 271 | 42.655 | 43.506 | 27.322 | 1.00 | 24.11 |
| ATOM | 1638 | CD1 | LEU | 271 | 42.449 | 43.927 | 28.754 | 1.00 | 26.75 |
| ATOM | 1639 | CD2 | LEU | 271 | 43.731 | 42.429 | 27.210 | 1.00 | 25.08 |
| ATOM | 1640 | C | LEU | 271 | 40.366 | 42.366 | 24.495 | 1.00 | 18.59 |
| ATOM | 1641 | O | LEU | 271 | 40.722 | 41.188 | 24.434 | 1.00 | 17.40 |
| ATOM | 1642 | N | GLN | 272 | 39.270 | 42.818 | 23.894 | 1.00 | 18.72 |
| ATOM | 1643 | CA | GLN | 272 | 38.395 | 41.941 | 23.117 | 1.00 | 21.08 |
| ATOM | 1644 | CB | GLN | 272 | 37.207 | 42.734 | 22.565 | 1.00 | 22.80 |
| ATOM | 1645 | CG | GLN | 272 | 35.993 | 42.745 | 23.461 | 1.00 | 24.90 |
| ATOM | 1646 | CD | GLN | 272 | 35.383 | 41.367 | 23.607 | 1.00 | 27.57 |
| ATOM | 1647 | OE1 | GLN | 272 | 35.940 | 40.495 | 24.274 | 1.00 | 28.36 |
| ATOM | 1648 | NE2 | GLN | 272 | 34.235 | 41.161 | 22.973 | 1.00 | 28.83 |
| ATOM | 1649 | C | GLN | 272 | 39.098 | 41.233 | 21.960 | 1.00 | 21.24 |
| ATOM | 1650 | O | GLN | 272 | 39.024 | 40.010 | 21.835 | 1.00 | 23.38 |
| ATOM | 1651 | N | PRO | 273 | 39.783 | 41.992 | 21.091 | 1.00 | 21.84 |
| ATOM | 1652 | CD | PRO | 273 | 39.893 | 43.462 | 21.019 | 1.00 | 22.66 |
| ATOM | 1653 | CA | PRO | 273 | 40.476 | 41.364 | 19.961 | 1.00 | 22.92 |
| ATOM | 1654 | CB | PRO | 273 | 41.237 | 42.531 | 19.336 | 1.00 | 23.77 |
| ATOM | 1655 | CG | PRO | 273 | 40.304 | 43.685 | 19.570 | 1.00 | 21.85 |
| ATOM | 1656 | C | PRO | 273 | 41.398 | 40.223 | 20.381 | 1.00 | 22.91 |
| ATOM | 1657 | O | PRO | 273 | 41.432 | 39.162 | 19.745 | 1.00 | 23.26 |
| ATOM | 1658 | N | LEU | 274 | 42.142 | 40.442 | 21.457 | 1.00 | 22.09 |
| ATOM | 1659 | CA | LEU | 274 | 43.062 | 39.433 | 21.951 | 1.00 | 19.44 |
| ATOM | 1660 | CB | LEU | 274 | 43.971 | 40.044 | 23.017 | 1.00 | 21.98 |
| ATOM | 1661 | CG | LEU | 274 | 45.175 | 39.249 | 23.520 | 1.00 | 26.32 |
| ATOM | 1662 | CD1 | LEU | 274 | 45.869 | 38.537 | 22.366 | 1.00 | 25.68 |
| ATOM | 1663 | CD2 | LEU | 274 | 46.138 | 40.216 | 24.215 | 1.00 | 26.73 |
| ATOM | 1664 | C | LEU | 274 | 42.294 | 38.234 | 22.511 | 1.00 | 18.52 |
| ATOM | 1665 | O | LEU | 274 | 42.607 | 37.087 | 22.186 | 1.00 | 16.12 |
| ATOM | 1666 | N | TYR | 275 | 41.286 | 38.487 | 23.345 | 1.00 | 15.05 |
| ATOM | 1667 | CA | TYR | 275 | 40.520 | 37.376 | 23.897 | 1.00 | 16.26 |
| ATOM | 1668 | CB | TYR | 275 | 39.462 | 37.844 | 24.898 | 1.00 | 14.51 |
| ATOM | 1669 | CG | TYR | 275 | 38.655 | 36.674 | 25.425 | 1.00 | 15.81 |
| ATOM | 1670 | CD1 | TYR | 275 | 39.259 | 35.687 | 26.205 | 1.00 | 14.55 |
| ATOM | 1671 | CE1 | TYR | 275 | 38.550 | 34.567 | 26.627 | 1.00 | 15.08 |
| ATOM | 1672 | CD2 | TYR | 275 | 37.313 | 36.512 | 25.082 | 1.00 | 15.17 |
| ATOM | 1673 | CE2 | TYR | 275 | 36.592 | 35.394 | 25.499 | 1.00 | 14.87 |
| ATOM | 1674 | CZ | TYR | 275 | 37.217 | 34.427 | 26.271 | 1.00 | 13.90 |
| ATOM | 1675 | OH | TYR | 275 | 36.513 | 33.326 | 26.697 | 1.00 | 13.75 |
| ATOM | 1676 | C | TYR | 275 | 39.816 | 36.576 | 22.801 | 1.00 | 14.63 |
| ATOM | 1677 | O | TYR | 275 | 39.852 | 35.346 | 22.803 | 1.00 | 13.73 |
| ATOM | 1678 | N | LEU | 276 | 39.174 | 37.268 | 21.865 | 1.00 | 14.03 |
| ATOM | 1679 | CA | LEU | 276 | 38.458 | 36.567 | 20.799 | 1.00 | 15.37 |
| ATOM | 1680 | CB | LEU | 276 | 37.718 | 37.563 | 19.906 | 1.00 | 15.87 |
| ATOM | 1681 | CG | LEU | 276 | 36.570 | 38.318 | 20.588 | 1.00 | 18.77 |
| ATOM | 1682 | CD1 | LEU | 276 | 35.991 | 39.340 | 19.620 | 1.00 | 17.96 |
| ATOM | 1683 | CD2 | LEU | 276 | 35.494 | 37.336 | 21.039 | 1.00 | 19.76 |
| ATOM | 1684 | C | LEU | 276 | 39.381 | 35.691 | 19.960 | 1.00 | 15.77 |
| ATOM | 1685 | O | LEU | 276 | 38.986 | 34.612 | 19.513 | 1.00 | 15.97 |
| ATOM | 1686 | N | ASN | 277 | 40.609 | 36.151 | 19.740 | 1.00 | 13.92 |
| ATOM | 1687 | CA | ASN | 277 | 41.558 | 35.367 | 18.965 | 1.00 | 14.44 |
| ATOM | 1688 | CB | ASN | 277 | 42.734 | 36.239 | 18.528 | 1.00 | 14.75 |
| ATOM | 1689 | CG | ASN | 277 | 42.463 | 36.954 | 17.219 | 1.00 | 17.20 |
| ATOM | 1690 | OD1 | ASN | 277 | 42.442 | 36.330 | 16.157 | 1.00 | 16.39 |
| ATOM | 1691 | ND2 | ASN | 277 | 42.239 | 38.266 | 17.288 | 1.00 | 16.71 |
| ATOM | 1692 | C | ASN | 277 | 42.044 | 34.158 | 19.760 | 1.00 | 14.54 |
| ATOM | 1693 | O | ASN | 277 | 42.272 | 33.090 | 19.199 | 1.00 | 12.53 |

TABLE A-continued

| | | | | | | | | |
|---|---|---|---|---|---|---|---|---|
| ATOM | 1694 | N | LEU | 278 | 42.192 | 34.319 | 21.071 | 1.00 | 12.24 |
| ATOM | 1695 | CA | LEU | 278 | 42.635 | 33.204 | 21.900 | 1.00 | 13.24 |
| ATOM | 1696 | CB | LEU | 278 | 42.986 | 33.691 | 23.311 | 1.00 | 12.96 |
| ATOM | 1697 | CG | LEU | 278 | 43.378 | 32.597 | 24.310 | 1.00 | 12.38 |
| ATOM | 1698 | CD1 | LEU | 278 | 44.717 | 31.969 | 23.898 | 1.00 | 12.63 |
| ATOM | 1699 | CD2 | LEU | 278 | 43.484 | 33.201 | 25.713 | 1.00 | 14.10 |
| ATOM | 1700 | C | LEU | 278 | 41.507 | 32.173 | 21.972 | 1.00 | 12.49 |
| ATOM | 1701 | O | LEU | 278 | 41.747 | 30.969 | 21.906 | 1.00 | 10.75 |
| ATOM | 1702 | N | HIS | 279 | 40.280 | 32.669 | 22.111 | 1.00 | 12.22 |
| ATOM | 1703 | CA | HIS | 279 | 39.080 | 31.837 | 22.190 | 1.00 | 13.07 |
| ATOM | 1704 | CB | HIS | 279 | 37.847 | 32.740 | 22.333 | 1.00 | 11.98 |
| ATOM | 1705 | CG | HIS | 279 | 36.539 | 32.007 | 22.308 | 1.00 | 12.16 |
| ATOM | 1706 | CD2 | HIS | 279 | 35.775 | 31.586 | 21.273 | 1.00 | 9.43 |
| ATOM | 1707 | ND1 | HIS | 279 | 35.844 | 31.678 | 23.454 | 1.00 | 14.66 |
| ATOM | 1708 | CE1 | HIS | 279 | 34.707 | 31.091 | 23.126 | 1.00 | 10.50 |
| ATOM | 1709 | NE2 | HIS | 279 | 34.641 | 31.022 | 21.808 | 1.00 | 16.46 |
| ATOM | 1710 | C | HIS | 279 | 38.946 | 30.972 | 20.936 | 1.00 | 13.49 |
| ATOM | 1711 | O | HIS | 279 | 38.766 | 29.759 | 21.026 | 1.00 | 14.71 |
| ATOM | 1712 | N | ALA | 280 | 39.037 | 31.603 | 19.769 | 1.00 | 11.17 |
| ATOM | 1713 | CA | ALA | 280 | 38.918 | 30.891 | 18.501 | 1.00 | 12.70 |
| ATOM | 1714 | CB | ALA | 280 | 38.966 | 31.887 | 17.342 | 1.00 | 11.01 |
| ATOM | 1715 | C | ALA | 280 | 40.010 | 29.828 | 18.328 | 1.00 | 13.11 |
| ATOM | 1716 | O | ALA | 280 | 39.752 | 28.728 | 17.828 | 1.00 | 14.49 |
| ATOM | 1717 | N | TYR | 281 | 41.231 | 30.161 | 18.734 | 1.00 | 14.23 |
| ATOM | 1718 | CA | TYR | 281 | 42.349 | 29.230 | 18.624 | 1.00 | 14.13 |
| ATOM | 1719 | CB | TYR | 281 | 43.658 | 29.942 | 18.979 | 1.00 | 13.18 |
| ATOM | 1720 | CG | TYR | 281 | 44.863 | 29.030 | 19.022 | 1.00 | 15.59 |
| ATOM | 1721 | CD1 | TYR | 281 | 45.465 | 28.571 | 17.849 | 1.00 | 16.24 |
| ATOM | 1722 | CE1 | TYR | 281 | 46.565 | 27.709 | 17.889 | 1.00 | 16.63 |
| ATOM | 1723 | CD2 | TYR | 281 | 45.390 | 28.609 | 20.239 | 1.00 | 14.46 |
| ATOM | 1724 | CE2 | TYR | 281 | 46.482 | 27.753 | 20.291 | 1.00 | 19.39 |
| ATOM | 1725 | CZ | TYR | 281 | 47.065 | 27.305 | 19.114 | 1.00 | 18.64 |
| ATOM | 1726 | OH | TYR | 281 | 48.143 | 26.448 | 19.182 | 1.00 | 19.16 |
| ATOM | 1727 | C | TYR | 281 | 42.142 | 28.025 | 19.544 | 1.00 | 14.20 |
| ATOM | 1728 | O | TYR | 281 | 42.339 | 26.876 | 19.140 | 1.00 | 12.95 |
| ATOM | 1729 | N | VAL | 282 | 41.747 | 28.291 | 20.785 | 1.00 | 13.42 |
| ATOM | 1730 | CA | VAL | 282 | 41.514 | 27.217 | 21.744 | 1.00 | 13.04 |
| ATOM | 1731 | CB | VAL | 282 | 41.263 | 27.790 | 23.156 | 1.00 | 12.69 |
| ATOM | 1732 | CG1 | VAL | 282 | 40.806 | 26.681 | 24.113 | 1.00 | 10.82 |
| ATOM | 1733 | CG2 | VAL | 282 | 42.544 | 28.439 | 23.674 | 1.00 | 11.44 |
| ATOM | 1734 | C | VAL | 282 | 40.328 | 26.351 | 21.309 | 1.00 | 13.40 |
| ATOM | 1735 | O | VAL | 282 | 40.356 | 25.129 | 21.451 | 1.00 | 12.76 |
| ATOM | 1736 | N | ARG | 283 | 39.294 | 26.989 | 20.770 | 1.00 | 12.27 |
| ATOM | 1737 | CA | ARG | 283 | 38.112 | 26.276 | 20.301 | 1.00 | 12.41 |
| ATOM | 1738 | CB | ARG | 283 | 37.073 | 27.280 | 19.788 | 1.00 | 10.58 |
| ATOM | 1739 | CG | ARG | 283 | 35.801 | 26.655 | 19.227 | 1.00 | 10.97 |
| ATOM | 1740 | CD | ARG | 283 | 34.793 | 27.732 | 18.829 | 1.00 | 11.14 |
| ATOM | 1741 | NE | ARG | 283 | 35.374 | 28.708 | 17.911 | 1.00 | 12.22 |
| ATOM | 1742 | CZ | ARG | 283 | 34.815 | 29.873 | 17.593 | 1.00 | 14.58 |
| ATOM | 1743 | NH1 | ARG | 283 | 33.647 | 30.225 | 18.119 | 1.00 | 12.82 |
| ATOM | 1744 | NH2 | ARG | 283 | 35.431 | 30.691 | 16.744 | 1.00 | 13.94 |
| ATOM | 1745 | C | ARG | 283 | 38.497 | 25.290 | 19.189 | 1.00 | 15.02 |
| ATOM | 1746 | O | ARG | 283 | 37.973 | 24.174 | 19.121 | 1.00 | 14.50 |
| ATOM | 1747 | N | ARG | 284 | 39.415 | 25.705 | 18.320 | 1.00 | 15.37 |
| ATOM | 1748 | CA | ARG | 284 | 39.865 | 24.842 | 17.231 | 1.00 | 16.53 |
| ATOM | 1749 | CB | ARG | 284 | 40.791 | 25.619 | 16.289 | 1.00 | 15.14 |
| ATOM | 1750 | CG | ARG | 284 | 41.532 | 24.771 | 15.262 | 1.00 | 17.18 |
| ATOM | 1751 | CD | ARG | 284 | 40.608 | 24.186 | 14.201 | 1.00 | 17.98 |
| ATOM | 1752 | NE | ARG | 284 | 39.899 | 25.226 | 13.458 | 1.00 | 17.50 |
| ATOM | 1753 | CZ | ARG | 284 | 39.121 | 24.987 | 12.406 | 1.00 | 20.20 |
| ATOM | 1754 | NH1 | ARG | 284 | 38.505 | 25.989 | 11.789 | 1.00 | 17.52 |
| ATOM | 1755 | NH2 | ARG | 284 | 38.967 | 23.742 | 11.963 | 1.00 | 18.66 |
| ATOM | 1756 | C | ARG | 284 | 40.592 | 23.615 | 17.793 | 1.00 | 17.62 |
| ATOM | 1757 | O | ARG | 284 | 40.369 | 22.490 | 17.340 | 1.00 | 16.82 |
| ATOM | 1758 | N | ALA | 285 | 41.456 | 23.838 | 18.782 | 1.00 | 16.05 |
| ATOM | 1759 | CA | ALA | 285 | 42.213 | 22.751 | 19.400 | 1.00 | 16.40 |
| ATOM | 1760 | CB | ALA | 285 | 43.247 | 23.312 | 20.369 | 1.00 | 15.81 |
| ATOM | 1761 | C | ALA | 285 | 41.288 | 21.770 | 20.122 | 1.00 | 17.14 |
| ATOM | 1762 | O | ALA | 285 | 41.527 | 20.560 | 20.111 | 1.00 | 15.20 |
| ATOM | 1763 | N | LEU | 286 | 40.237 | 22.289 | 20.748 | 1.00 | 14.27 |
| ATOM | 1764 | CA | LEU | 286 | 39.285 | 21.428 | 21.492 | 1.00 | 16.86 |
| ATOM | 1765 | CB | LEU | 286 | 38.331 | 22.266 | 22.301 | 1.00 | 15.32 |
| ATOM | 1766 | CG | LEU | 286 | 38.945 | 22.925 | 23.542 | 1.00 | 17.90 |
| ATOM | 1767 | CD1 | LEU | 286 | 37.887 | 23.785 | 24.230 | 1.00 | 15.75 |
| ATOM | 1768 | CD2 | LEU | 286 | 39.470 | 21.850 | 24.505 | 1.00 | 13.91 |
| ATOM | 1769 | C | LEU | 286 | 38.502 | 20.615 | 20.422 | 1.00 | 17.67 |
| ATOM | 1770 | O | LEU | 286 | 38.172 | 19.452 | 20.651 | 1.00 | 17.19 |
| ATOM | 1771 | N | HIS | 287 | 38.212 | 21.245 | 19.286 | 1.00 | 16.68 |
| ATOM | 1772 | CA | HIS | 287 | 37.494 | 20.601 | 18.196 | 1.00 | 18.26 |
| ATOM | 1773 | CB | HIS | 287 | 37.292 | 21.621 | 17.062 | 1.00 | 18.41 |

TABLE A-continued

| | | | | | | | | |
|---|---|---|---|---|---|---|---|---|
| ATOM | 1774 | CG | HIS | 287 | 36.648 | 21.061 | 15.831 | 1.00 | 18.72 |
| ATOM | 1775 | CD2 | HIS | 287 | 35.373 | 21.137 | 15.380 | 1.00 | 17.00 |
| ATOM | 1776 | ND1 | HIS | 287 | 37.351 | 20.359 | 14.875 | 1.00 | 18.34 |
| ATOM | 1777 | CE1 | HIS | 287 | 36.537 | 20.031 | 13.887 | 1.00 | 14.90 |
| ATOM | 1778 | NE2 | HIS | 287 | 35.332 | 20.492 | 14.169 | 1.00 | 16.90 |
| ATOM | 1779 | C | HIS | 287 | 38.361 | 19.421 | 17.740 | 1.00 | 19.03 |
| ATOM | 1780 | O | HIS | 287 | 37.866 | 18.327 | 17.471 | 1.00 | 17.36 |
| ATOM | 1781 | N | ARG | 288 | 39.666 | 19.659 | 17.700 | 1.00 | 18.55 |
| ATOM | 1782 | CA | ARG | 288 | 40.649 | 18.662 | 17.295 | 1.00 | 20.61 |
| ATOM | 1783 | CB | ARG | 288 | 42.028 | 19.320 | 17.254 | 1.00 | 23.74 |
| ATOM | 1784 | CG | ARG | 288 | 42.870 | 19.014 | 16.032 | 1.00 | 30.47 |
| ATOM | 1785 | CD | ARG | 288 | 43.922 | 20.102 | 15.857 | 1.00 | 33.76 |
| ATOM | 1786 | NE | ARG | 288 | 44.686 | 20.306 | 17.083 | 1.00 | 33.81 |
| ATOM | 1787 | CZ | ARG | 288 | 45.113 | 21.487 | 17.514 | 1.00 | 35.70 |
| ATOM | 1788 | NH1 | ARG | 288 | 44.852 | 22.587 | 16.817 | 1.00 | 35.23 |
| ATOM | 1789 | NH2 | ARG | 288 | 45.800 | 21.569 | 18.646 | 1.00 | 36.87 |
| ATOM | 1790 | C | ARG | 288 | 40.679 | 17.468 | 18.253 | 1.00 | 20.35 |
| ATOM | 1791 | O | ARG | 288 | 40.773 | 16.314 | 17.825 | 1.00 | 19.01 |
| ATOM | 1792 | N | HIS | 289 | 40.586 | 17.747 | 19.550 | 1.00 | 19.12 |
| ATOM | 1793 | CA | HIS | 289 | 40.641 | 16.692 | 20.559 | 1.00 | 20.16 |
| ATOM | 1794 | CB | HIS | 289 | 41.247 | 17.230 | 21.858 | 1.00 | 21.21 |
| ATOM | 1795 | CG | HIS | 289 | 41.407 | 16.184 | 22.916 | 1.00 | 23.81 |
| ATOM | 1796 | CD2 | HIS | 289 | 40.632 | 15.866 | 23.980 | 1.00 | 24.22 |
| ATOM | 1797 | ND1 | HIS | 289 | 42.440 | 15.270 | 22.909 | 1.00 | 26.00 |
| ATOM | 1798 | CE1 | HIS | 289 | 42.292 | 14.433 | 23.921 | 1.00 | 24.08 |
| ATOM | 1799 | NE2 | HIS | 289 | 41.202 | 14.772 | 24.585 | 1.00 | 27.58 |
| ATOM | 1800 | C | HIS | 289 | 39.327 | 15.997 | 20.903 | 1.00 | 20.43 |
| ATOM | 1801 | O | HIS | 289 | 39.276 | 14.768 | 20.978 | 1.00 | 20.43 |
| ATOM | 1802 | N | TYR | 290 | 38.270 | 16.772 | 21.123 | 1.00 | 19.15 |
| ATOM | 1803 | CA | TYR | 290 | 36.990 | 16.194 | 21.503 | 1.00 | 18.20 |
| ATOM | 1804 | CB | TYR | 290 | 36.298 | 17.098 | 22.527 | 1.00 | 17.79 |
| ATOM | 1805 | CG | TYR | 290 | 37.025 | 17.158 | 23.859 | 1.00 | 17.11 |
| ATOM | 1806 | CD1 | TYR | 290 | 37.840 | 18.242 | 24.188 | 1.00 | 14.34 |
| ATOM | 1807 | CE1 | TYR | 290 | 38.538 | 18.284 | 25.403 | 1.00 | 15.63 |
| ATOM | 1808 | CD2 | TYR | 290 | 36.922 | 16.111 | 24.778 | 1.00 | 17.43 |
| ATOM | 1809 | CE2 | TYR | 290 | 37.616 | 16.140 | 25.990 | 1.00 | 16.23 |
| ATOM | 1810 | CZ | TYR | 290 | 38.421 | 17.227 | 26.296 | 1.00 | 17.84 |
| ATOM | 1811 | OH | TYR | 290 | 39.117 | 17.242 | 27.485 | 1.00 | 16.73 |
| ATOM | 1812 | C | TYR | 290 | 36.026 | 15.842 | 20.375 | 1.00 | 19.53 |
| ATOM | 1813 | O | TYR | 290 | 34.985 | 15.235 | 20.624 | 1.00 | 19.64 |
| ATOM | 1814 | N | GLY | 291 | 36.359 | 16.224 | 19.145 | 1.00 | 19.76 |
| ATOM | 1815 | CA | GLY | 291 | 35.503 | 15.890 | 18.017 | 1.00 | 19.38 |
| ATOM | 1816 | C | GLY | 291 | 34.552 | 16.967 | 17.537 | 1.00 | 17.77 |
| ATOM | 1817 | O | GLY | 291 | 34.058 | 17.772 | 18.317 | 1.00 | 16.36 |
| ATOM | 1818 | N | ALA | 292 | 34.279 | 16.958 | 16.237 | 1.00 | 18.00 |
| ATOM | 1819 | CA | ALA | 292 | 33.392 | 17.939 | 15.620 | 1.00 | 17.85 |
| ATOM | 1820 | CB | ALA | 292 | 33.401 | 17.757 | 14.094 | 1.00 | 18.60 |
| ATOM | 1821 | C | ALA | 292 | 31.961 | 17.871 | 16.142 | 1.00 | 17.75 |
| ATOM | 1822 | O | ALA | 292 | 31.235 | 18.859 | 16.095 | 1.00 | 17.45 |
| ATOM | 1823 | N | GLN | 293 | 31.548 | 16.705 | 16.631 | 1.00 | 17.76 |
| ATOM | 1824 | CA | GLN | 293 | 30.194 | 16.544 | 17.149 | 1.00 | 17.65 |
| ATOM | 1825 | CB | GLN | 293 | 29.845 | 15.053 | 17.276 | 1.00 | 19.36 |
| ATOM | 1826 | CG | GLN | 293 | 29.784 | 14.287 | 15.947 | 1.00 | 18.52 |
| ATOM | 1827 | CD | GLN | 293 | 28.512 | 14.554 | 15.153 | 1.00 | 19.88 |
| ATOM | 1828 | OE1 | GLN | 293 | 27.616 | 15.264 | 15.606 | 1.00 | 19.17 |
| ATOM | 1829 | NE2 | GLN | 293 | 28.428 | 13.973 | 13.959 | 1.00 | 18.08 |
| ATOM | 1830 | C | GLN | 293 | 30.005 | 17.229 | 18.503 | 1.00 | 18.04 |
| ATOM | 1831 | O | GLN | 293 | 28.873 | 17.405 | 18.960 | 1.00 | 17.48 |
| ATOM | 1832 | N | HIS | 294 | 31.105 | 17.630 | 19.137 | 1.00 | 16.33 |
| ATOM | 1833 | CA | HIS | 294 | 31.021 | 18.277 | 20.446 | 1.00 | 17.25 |
| ATOM | 1834 | CB | HIS | 294 | 31.784 | 17.445 | 21.478 | 1.00 | 18.66 |
| ATOM | 1835 | CG | HIS | 294 | 31.345 | 16.014 | 21.532 | 1.00 | 21.25 |
| ATOM | 1836 | CD2 | HIS | 294 | 31.954 | 14.879 | 21.111 | 1.00 | 21.69 |
| ATOM | 1837 | ND1 | HIS | 294 | 30.114 | 15.631 | 22.021 | 1.00 | 22.71 |
| ATOM | 1838 | CE1 | HIS | 294 | 29.982 | 14.322 | 21.894 | 1.00 | 23.73 |
| ATOM | 1839 | NE2 | HIS | 294 | 31.084 | 13.842 | 21.344 | 1.00 | 24.62 |
| ATOM | 1840 | C | HIS | 294 | 31.519 | 19.720 | 20.480 | 1.00 | 18.08 |
| ATOM | 1841 | O | HIS | 294 | 31.356 | 20.409 | 21.488 | 1.00 | 19.39 |
| ATOM | 1842 | N | ILE | 295 | 32.122 | 20.180 | 19.387 | 1.00 | 17.59 |
| ATOM | 1843 | CA | ILE | 295 | 32.625 | 21.552 | 19.323 | 1.00 | 17.39 |
| ATOM | 1844 | CB | ILE | 295 | 34.177 | 21.600 | 19.335 | 1.00 | 18.25 |
| ATOM | 1845 | CG2 | ILE | 295 | 34.650 | 23.050 | 19.161 | 1.00 | 19.44 |
| ATOM | 1846 | CG1 | ILE | 295 | 34.724 | 20.998 | 20.634 | 1.00 | 19.74 |
| ATOM | 1847 | CD1 | ILE | 295 | 34.452 | 21.827 | 21.889 | 1.00 | 19.50 |
| ATOM | 1848 | C | ILE | 295 | 32.150 | 22.259 | 18.060 | 1.00 | 15.69 |
| ATOM | 1849 | O | ILE | 295 | 32.467 | 21.836 | 16.948 | 1.00 | 16.28 |
| ATOM | 1850 | N | ASN | 296 | 31.381 | 23.328 | 18.234 | 1.00 | 14.98 |
| ATOM | 1851 | CA | ASN | 296 | 30.896 | 24.112 | 17.105 | 1.00 | 17.48 |
| ATOM | 1852 | CB | ASN | 296 | 29.559 | 24.766 | 17.450 | 1.00 | 18.21 |
| ATOM | 1853 | CG | ASN | 296 | 28.995 | 25.586 | 16.304 | 1.00 | 20.95 |

TABLE A-continued

| | | | | | | | | |
|---|---|---|---|---|---|---|---|---|
| ATOM | 1854 | OD1 | ASN | 296 | 29.639 | 25.764 | 15.271 | 1.00 | 18.66 |
| ATOM | 1855 | ND2 | ASN | 296 | 27.786 | 26.096 | 16.487 | 1.00 | 24.30 |
| ATOM | 1856 | C | ASN | 296 | 31.946 | 25.194 | 16.840 | 1.00 | 17.45 |
| ATOM | 1857 | O | ASN | 296 | 32.135 | 26.091 | 17.662 | 1.00 | 17.17 |
| ATOM | 1858 | N | LEU | 297 | 32.621 | 25.105 | 15.697 | 1.00 | 15.65 |
| ATOM | 1859 | CA | LEU | 297 | 33.670 | 26.060 | 15.333 | 1.00 | 17.18 |
| ATOM | 1860 | CB | LEU | 297 | 34.357 | 25.613 | 14.042 | 1.00 | 15.85 |
| ATOM | 1861 | CG | LEU | 297 | 35.202 | 24.338 | 14.136 | 1.00 | 15.74 |
| ATOM | 1862 | CD1 | LEU | 297 | 35.632 | 23.934 | 12.741 | 1.00 | 17.98 |
| ATOM | 1863 | CD2 | LEU | 297 | 36.415 | 24.565 | 15.032 | 1.00 | 15.34 |
| ATOM | 1864 | C | LEU | 297 | 33.192 | 27.502 | 15.182 | 1.00 | 17.65 |
| ATOM | 1865 | O | LEU | 297 | 34.006 | 28.418 | 15.037 | 1.00 | 15.95 |
| ATOM | 1866 | N | GLU | 298 | 31.877 | 27.702 | 15.214 | 1.00 | 17.41 |
| ATOM | 1867 | CA | GLU | 298 | 31.311 | 29.041 | 15.101 | 1.00 | 19.65 |
| ATOM | 1868 | CB | GLU | 298 | 30.460 | 29.158 | 13.830 | 1.00 | 22.80 |
| ATOM | 1869 | CG | GLU | 298 | 31.163 | 28.684 | 12.570 | 1.00 | 27.54 |
| ATOM | 1870 | CD | GLU | 298 | 30.365 | 28.977 | 11.309 | 1.00 | 31.19 |
| ATOM | 1871 | OE1 | GLU | 298 | 29.148 | 28.692 | 11.282 | 1.00 | 32.45 |
| ATOM | 1872 | OE2 | GLU | 298 | 30.961 | 29.488 | 10.342 | 1.00 | 32.93 |
| ATOM | 1873 | C | GLU | 298 | 30.445 | 29.366 | 16.317 | 1.00 | 18.22 |
| ATOM | 1874 | O | GLU | 298 | 29.660 | 30.318 | 16.294 | 1.00 | 20.41 |
| ATOM | 1875 | N | GLY | 299 | 30.588 | 28.581 | 17.381 | 1.00 | 14.98 |
| ATOM | 1876 | CA | GLY | 299 | 29.785 | 28.818 | 18.567 | 1.00 | 12.99 |
| ATOM | 1877 | C | GLY | 299 | 30.562 | 28.885 | 19.867 | 1.00 | 13.29 |
| ATOM | 1878 | O | GLY | 299 | 31.793 | 28.909 | 19.858 | 1.00 | 13.77 |
| ATOM | 1879 | N | PRO | 300 | 29.864 | 28.918 | 21.014 | 1.00 | 14.38 |
| ATOM | 1880 | CD | PRO | 300 | 28.397 | 28.934 | 21.180 | 1.00 | 14.36 |
| ATOM | 1881 | CA | PRO | 300 | 30.539 | 28.982 | 22.311 | 1.00 | 15.04 |
| ATOM | 1882 | CB | PRO | 300 | 29.411 | 29.353 | 23.263 | 1.00 | 15.56 |
| ATOM | 1883 | CG | PRO | 300 | 28.232 | 28.651 | 22.661 | 1.00 | 16.94 |
| ATOM | 1884 | C | PRO | 300 | 31.217 | 27.660 | 22.676 | 1.00 | 15.92 |
| ATOM | 1885 | O | PRO | 300 | 30.914 | 26.614 | 22.100 | 1.00 | 14.68 |
| ATOM | 1886 | N | ILE | 301 | 32.131 | 27.724 | 23.639 | 1.00 | 14.52 |
| ATOM | 1887 | CA | ILE | 301 | 32.885 | 26.560 | 24.090 | 1.00 | 13.49 |
| ATOM | 1888 | CB | ILE | 301 | 34.345 | 26.958 | 24.416 | 1.00 | 14.98 |
| ATOM | 1889 | CG2 | ILE | 301 | 35.104 | 25.763 | 25.013 | 1.00 | 13.64 |
| ATOM | 1890 | CG1 | ILE | 301 | 35.033 | 27.492 | 23.158 | 1.00 | 15.50 |
| ATOM | 1891 | CD1 | ILE | 301 | 36.413 | 28.053 | 23.409 | 1.00 | 14.09 |
| ATOM | 1892 | C | ILE | 301 | 32.275 | 25.957 | 25.351 | 1.00 | 13.55 |
| ATOM | 1893 | O | ILE | 301 | 31.946 | 26.681 | 26.288 | 1.00 | 9.28 |
| ATOM | 1894 | N | PRO | 302 | 32.097 | 24.623 | 25.380 | 1.00 | 12.22 |
| ATOM | 1895 | CD | PRO | 302 | 32.236 | 23.667 | 24.271 | 1.00 | 12.83 |
| ATOM | 1896 | CA | PRO | 302 | 31.528 | 23.966 | 26.562 | 1.00 | 13.66 |
| ATOM | 1897 | CB | PRO | 302 | 31.608 | 22.487 | 26.200 | 1.00 | 12.81 |
| ATOM | 1898 | CG | PRO | 302 | 31.360 | 22.510 | 24.733 | 1.00 | 13.21 |
| ATOM | 1899 | C | PRO | 302 | 32.387 | 24.325 | 27.777 | 1.00 | 12.95 |
| ATOM | 1900 | O | PRO | 302 | 33.606 | 24.133 | 27.772 | 1.00 | 10.63 |
| ATOM | 1901 | N | ALA | 303 | 31.731 | 24.835 | 28.814 | 1.00 | 13.88 |
| ATOM | 1902 | CA | ALA | 303 | 32.386 | 25.304 | 30.033 | 1.00 | 13.20 |
| ATOM | 1903 | CB | ALA | 303 | 31.348 | 25.984 | 30.917 | 1.00 | 12.25 |
| ATOM | 1904 | C | ALA | 303 | 33.197 | 24.326 | 30.876 | 1.00 | 14.39 |
| ATOM | 1905 | O | ALA | 303 | 33.897 | 24.752 | 31.798 | 1.00 | 14.70 |
| ATOM | 1906 | N | HIS | 304 | 33.125 | 23.032 | 30.583 | 1.00 | 13.10 |
| ATOM | 1907 | CA | HIS | 304 | 33.861 | 22.065 | 31.391 | 1.00 | 15.86 |
| ATOM | 1908 | CB | HIS | 304 | 32.972 | 20.847 | 31.673 | 1.00 | 14.23 |
| ATOM | 1909 | CG | HIS | 304 | 32.622 | 20.057 | 30.448 | 1.00 | 16.26 |
| ATOM | 1910 | CD2 | HIS | 304 | 32.663 | 18.725 | 30.202 | 1.00 | 14.69 |
| ATOM | 1911 | ND1 | HIS | 304 | 32.138 | 20.644 | 29.297 | 1.00 | 16.27 |
| ATOM | 1912 | CE1 | HIS | 304 | 31.896 | 19.708 | 28.396 | 1.00 | 16.80 |
| ATOM | 1913 | NE2 | HIS | 304 | 32.205 | 18.534 | 28.920 | 1.00 | 16.57 |
| ATOM | 1914 | C | HIS | 304 | 35.175 | 21.596 | 30.772 | 1.00 | 15.34 |
| ATOM | 1915 | O | HIS | 304 | 35.876 | 20.776 | 31.362 | 1.00 | 13.95 |
| ATOM | 1916 | N | LEU | 305 | 35.519 | 22.136 | 29.605 | 1.00 | 14.97 |
| ATOM | 1917 | CA | LEU | 305 | 36.725 | 21.716 | 28.891 | 1.00 | 14.04 |
| ATOM | 1918 | CB | LEU | 305 | 36.383 | 21.531 | 27.405 | 1.00 | 12.83 |
| ATOM | 1919 | CG | LEU | 305 | 35.144 | 20.690 | 27.076 | 1.00 | 12.75 |
| ATOM | 1920 | CD1 | LEU | 305 | 34.877 | 20.727 | 25.564 | 1.00 | 9.86 |
| ATOM | 1921 | CD2 | LEU | 305 | 35.367 | 19.260 | 27.559 | 1.00 | 10.56 |
| ATOM | 1922 | C | LEU | 305 | 37.947 | 22.624 | 28.991 | 1.00 | 15.10 |
| ATOM | 1923 | O | LEU | 305 | 38.921 | 22.424 | 28.262 | 1.00 | 16.46 |
| ATOM | 1924 | N | LEU | 306 | 37.925 | 23.602 | 29.896 | 1.00 | 14.31 |
| ATOM | 1925 | CA | LEU | 306 | 39.047 | 24.527 | 29.972 | 1.00 | 15.42 |
| ATOM | 1926 | CB | LEU | 306 | 38.524 | 25.972 | 30.053 | 1.00 | 13.51 |
| ATOM | 1927 | CG | LEU | 306 | 37.764 | 26.550 | 28.848 | 1.00 | 14.73 |
| ATOM | 1928 | CD1 | LEU | 306 | 38.592 | 26.362 | 27.577 | 1.00 | 14.30 |
| ATOM | 1929 | CD2 | LEU | 306 | 36.410 | 25.870 | 28.694 | 1.00 | 15.38 |
| ATOM | 1930 | C | LEU | 306 | 40.080 | 24.275 | 31.070 | 1.00 | 15.84 |
| ATOM | 1931 | O | LEU | 306 | 40.937 | 25.124 | 31.313 | 1.00 | 15.82 |
| ATOM | 1932 | N | GLY | 307 | 39.997 | 23.120 | 31.728 | 1.00 | 16.01 |
| ATOM | 1933 | CA | GLY | 307 | 40.967 | 22.766 | 32.758 | 1.00 | 15.85 |

TABLE A-continued

| | | | | | | | | |
|---|---|---|---|---|---|---|---|---|
| ATOM | 1934 | C | GLY | 307 | 40.780 | 23.392 | 34.126 | 1.00 | 16.19 |
| ATOM | 1935 | O | GLY | 307 | 41.595 | 23.195 | 35.035 | 1.00 | 14.81 |
| ATOM | 1936 | N | ASN | 308 | 39.692 | 24.137 | 34.275 | 1.00 | 15.62 |
| ATOM | 1937 | CA | ASN | 308 | 39.381 | 24.815 | 35.522 | 1.00 | 15.37 |
| ATOM | 1938 | CB | ASN | 308 | 39.878 | 26.265 | 35.430 | 1.00 | 14.32 |
| ATOM | 1939 | CG | ASN | 308 | 39.391 | 27.132 | 36.570 | 1.00 | 15.28 |
| ATOM | 1940 | OD1 | ASN | 308 | 38.277 | 27.654 | 36.530 | 1.00 | 15.45 |
| ATOM | 1941 | ND2 | ASN | 308 | 40.226 | 27.292 | 37.598 | 1.00 | 13.64 |
| ATOM | 1942 | C | ASN | 308 | 37.869 | 24.734 | 35.769 | 1.00 | 14.00 |
| ATOM | 1943 | O | ASN | 308 | 37.072 | 24.858 | 34.842 | 1.00 | 12.08 |
| ATOM | 1944 | N | MET | 309 | 37.486 | 24.519 | 37.023 | 1.00 | 13.86 |
| ATOM | 1945 | CA | MET | 309 | 36.077 | 24.368 | 37.390 | 1.00 | 14.00 |
| ATOM | 1946 | CB | MET | 309 | 35.951 | 24.234 | 38.916 | 1.00 | 14.12 |
| ATOM | 1947 | CG | MET | 309 | 34.527 | 24.008 | 39.414 | 1.00 | 15.15 |
| ATOM | 1948 | SD | MET | 309 | 33.787 | 22.492 | 38.767 | 1.00 | 16.63 |
| ATOM | 1949 | CE | MET | 309 | 34.428 | 21.288 | 39.947 | 1.00 | 16.22 |
| ATOM | 1950 | C | MET | 309 | 35.155 | 25.478 | 36.884 | 1.00 | 14.78 |
| ATOM | 1951 | O | MET | 309 | 33.996 | 25.220 | 36.548 | 1.00 | 13.18 |
| ATOM | 1952 | N | TRP | 310 | 35.671 | 26.703 | 36.812 | 1.00 | 11.51 |
| ATOM | 1953 | CA | TRP | 310 | 34.872 | 27.843 | 36.366 | 1.00 | 14.25 |
| ATOM | 1954 | CB | TRP | 310 | 34.970 | 28.968 | 37.403 | 1.00 | 12.20 |
| ATOM | 1955 | CG | TRP | 310 | 34.625 | 28.480 | 38.772 | 1.00 | 12.52 |
| ATOM | 1956 | CD2 | TRP | 310 | 35.538 | 27.959 | 39.745 | 1.00 | 12.82 |
| ATOM | 1957 | CE2 | TRP | 310 | 34.764 | 27.461 | 40.817 | 1.00 | 13.24 |
| ATOM | 1958 | CE3 | TRP | 310 | 36.937 | 27.855 | 39.810 | 1.00 | 13.78 |
| ATOM | 1959 | CD1 | TRP | 310 | 33.373 | 28.295 | 39.283 | 1.00 | 11.84 |
| ATOM | 1960 | NE1 | TRP | 310 | 33.447 | 27.681 | 40.509 | 1.00 | 12.66 |
| ATOM | 1961 | CZ2 | TRP | 310 | 35.340 | 26.866 | 41.948 | 1.00 | 12.55 |
| ATOM | 1962 | CZ3 | TRP | 310 | 37.513 | 27.260 | 40.934 | 1.00 | 13.31 |
| ATOM | 1963 | CH2 | TRP | 310 | 36.708 | 26.773 | 41.990 | 1.00 | 12.52 |
| ATOM | 1964 | C | TRP | 310 | 35.309 | 28.360 | 35.001 | 1.00 | 13.97 |
| ATOM | 1965 | O | TRP | 310 | 34.772 | 29.348 | 34.508 | 1.00 | 12.98 |
| ATOM | 1966 | N | ALA | 311 | 36.269 | 27.670 | 34.388 | 1.00 | 14.15 |
| ATOM | 1967 | CA | ALA | 311 | 36.799 | 28.086 | 33.096 | 1.00 | 13.77 |
| ATOM | 1968 | CB | ALA | 311 | 35.719 | 27.964 | 32.021 | 1.00 | 14.05 |
| ATOM | 1969 | C | ALA | 311 | 37.297 | 29.534 | 33.179 | 1.00 | 13.58 |
| ATOM | 1970 | O | ALA | 311 | 37.249 | 30.263 | 32.189 | 1.00 | 13.90 |
| ATOM | 1971 | N | GLN | 312 | 37.761 | 29.952 | 34.358 | 1.00 | 13.19 |
| ATOM | 1972 | CA | GLN | 312 | 38.247 | 31.325 | 34.541 | 1.00 | 13.69 |
| ATOM | 1973 | CB | GLN | 312 | 38.088 | 31.770 | 36.000 | 1.00 | 12.28 |
| ATOM | 1974 | CG | GLN | 312 | 38.917 | 30.995 | 36.999 | 1.00 | 14.52 |
| ATOM | 1975 | CD | GLN | 312 | 38.542 | 31.318 | 38.433 | 1.00 | 17.57 |
| ATOM | 1976 | OE1 | GLN | 312 | 37.382 | 31.187 | 38.828 | 1.00 | 15.61 |
| ATOM | 1977 | NE2 | GLN | 312 | 39.522 | 31.739 | 39.220 | 1.00 | 19.96 |
| ATOM | 1978 | C | GLN | 312 | 39.700 | 31.485 | 34.102 | 1.00 | 13.47 |
| ATOM | 1979 | O | GLN | 312 | 40.137 | 32.587 | 33.771 | 1.00 | 11.19 |
| ATOM | 1980 | N | THR | 313 | 40.442 | 30.382 | 34.124 | 1.00 | 12.33 |
| ATOM | 1981 | CA | THR | 313 | 41.835 | 30.354 | 33.687 | 1.00 | 13.83 |
| ATOM | 1982 | CB | THR | 313 | 42.826 | 30.403 | 34.875 | 1.00 | 16.20 |
| ATOM | 1983 | OG1 | THR | 313 | 42.468 | 29.425 | 35.858 | 1.00 | 16.40 |
| ATOM | 1984 | CG2 | THR | 313 | 42.819 | 31.789 | 35.511 | 1.00 | 17.20 |
| ATOM | 1985 | C | THR | 313 | 41.964 | 29.040 | 32.918 | 1.00 | 16.52 |
| ATOM | 1986 | O | THR | 313 | 41.415 | 28.021 | 33.335 | 1.00 | 14.73 |
| ATOM | 1987 | N | TRP | 314 | 42.675 | 29.065 | 31.795 | 1.00 | 14.06 |
| ATOM | 1988 | CA | TRP | 314 | 42.788 | 27.881 | 30.948 | 1.00 | 15.86 |
| ATOM | 1989 | CB | TRP | 314 | 42.318 | 28.216 | 29.529 | 1.00 | 15.32 |
| ATOM | 1990 | CG | TRP | 314 | 40.991 | 28.934 | 29.408 | 1.00 | 13.99 |
| ATOM | 1991 | CD2 | TRP | 314 | 40.457 | 29.529 | 28.219 | 1.00 | 13.70 |
| ATOM | 1992 | CE2 | TRP | 314 | 39.164 | 30.012 | 28.534 | 1.00 | 14.95 |
| ATOM | 1993 | CE3 | TRP | 314 | 40.943 | 29.698 | 26.915 | 1.00 | 12.93 |
| ATOM | 1994 | CD1 | TRP | 314 | 40.032 | 29.079 | 30.372 | 1.00 | 14.30 |
| ATOM | 1995 | NE1 | TRP | 314 | 38.929 | 29.725 | 29.854 | 1.00 | 13.72 |
| ATOM | 1996 | CZ2 | TRP | 314 | 38.355 | 30.650 | 27.592 | 1.00 | 13.70 |
| ATOM | 1997 | CZ3 | TRP | 314 | 40.137 | 30.332 | 25.979 | 1.00 | 16.03 |
| ATOM | 1998 | CH2 | TRP | 314 | 38.853 | 30.800 | 26.325 | 1.00 | 16.16 |
| ATOM | 1999 | C | TRP | 314 | 44.171 | 27.255 | 30.816 | 1.00 | 17.18 |
| ATOM | 2000 | O | TRP | 314 | 44.363 | 26.402 | 29.950 | 1.00 | 16.26 |
| ATOM | 2001 | N | SER | 315 | 45.125 | 27.655 | 31.648 | 1.00 | 16.81 |
| ATOM | 2002 | CA | SER | 315 | 46.482 | 27.131 | 31.514 | 1.00 | 18.73 |
| ATOM | 2003 | CB | SER | 315 | 47.429 | 27.840 | 32.493 | 1.00 | 19.48 |
| ATOM | 2004 | OG | SER | 315 | 47.078 | 27.573 | 33.834 | 1.00 | 23.23 |
| ATOM | 2005 | C | SER | 315 | 46.628 | 25.618 | 31.658 | 1.00 | 17.43 |
| ATOM | 2006 | O | SER | 315 | 47.599 | 25.043 | 31.165 | 1.00 | 16.20 |
| ATOM | 2007 | N | ASN | 316 | 45.669 | 24.967 | 32.309 | 1.00 | 16.52 |
| ATOM | 2008 | CA | ASN | 316 | 45.758 | 23.526 | 32.487 | 1.00 | 16.72 |
| ATOM | 2009 | CB | ASN | 316 | 44.827 | 23.068 | 33.617 | 1.00 | 16.47 |
| ATOM | 2010 | CG | ASN | 316 | 45.342 | 23.494 | 34.991 | 1.00 | 18.32 |
| ATOM | 2011 | OD1 | ASN | 316 | 46.504 | 23.262 | 35.323 | 1.00 | 19.09 |
| ATOM | 2012 | ND2 | ASN | 316 | 44.484 | 24.116 | 35.788 | 1.00 | 15.86 |
| ATOM | 2013 | C | ASN | 316 | 45.540 | 22.700 | 31.219 | 1.00 | 17.50 |

TABLE A-continued

| | | | | | | | | | |
|---|---|---|---|---|---|---|---|---|---|
| ATOM | 2014 | O | ASN | 316 | 45.834 | 21.508 | 31.210 | 1.00 | 17.87 |
| ATOM | 2015 | N | ILE | 317 | 45.028 | 23.311 | 30.150 | 1.00 | 17.39 |
| ATOM | 2016 | CA | ILE | 317 | 44.869 | 22.568 | 28.901 | 1.00 | 17.13 |
| ATOM | 2017 | CB | ILE | 317 | 43.479 | 22.759 | 28.246 | 1.00 | 16.82 |
| ATOM | 2018 | CG2 | ILE | 317 | 42.394 | 22.220 | 29.170 | 1.00 | 16.53 |
| ATOM | 2019 | CG1 | ILE | 317 | 43.242 | 24.230 | 27.902 | 1.00 | 17.65 |
| ATOM | 2020 | CD1 | ILE | 317 | 42.036 | 24.444 | 27.019 | 1.00 | 18.86 |
| ATOM | 2021 | C | ILE | 317 | 45.947 | 23.014 | 27.915 | 1.00 | 18.07 |
| ATOM | 2022 | O | ILE | 317 | 45.793 | 22.892 | 26.697 | 1.00 | 16.69 |
| ATOM | 2023 | N | TYR | 318 | 47.047 | 23.536 | 28.454 | 1.00 | 18.93 |
| ATOM | 2024 | CA | TYR | 318 | 48.155 | 23.983 | 27.618 | 1.00 | 20.39 |
| ATOM | 2025 | CB | TYR | 318 | 49.337 | 24.421 | 28.479 | 1.00 | 21.07 |
| ATOM | 2026 | CG | TYR | 318 | 50.567 | 24.757 | 27.667 | 1.00 | 23.88 |
| ATOM | 2027 | CD1 | TYR | 318 | 50.635 | 25.931 | 26.917 | 1.00 | 22.79 |
| ATOM | 2028 | CE1 | TYR | 318 | 51.749 | 26.225 | 26.138 | 1.00 | 25.90 |
| ATOM | 2029 | CD2 | TYR | 318 | 51.652 | 23.879 | 27.618 | 1.00 | 25.81 |
| ATOM | 2030 | CE2 | TYR | 318 | 52.774 | 24.163 | 26.841 | 1.00 | 26.76 |
| ATOM | 2031 | CZ | TYR | 318 | 52.815 | 25.335 | 26.105 | 1.00 | 27.14 |
| ATOM | 2032 | OH | TYR | 318 | 53.919 | 25.616 | 25.338 | 1.00 | 27.90 |
| ATOM | 2033 | C | TYR | 318 | 48.609 | 22.861 | 26.682 | 1.00 | 20.54 |
| ATOM | 2034 | O | TYR | 318 | 48.933 | 23.108 | 25.525 | 1.00 | 19.56 |
| ATOM | 2035 | N | ASP | 319 | 48.624 | 21.634 | 27.194 | 1.00 | 21.68 |
| ATOM | 2036 | CA | ASP | 319 | 49.041 | 20.468 | 26.415 | 1.00 | 24.93 |
| ATOM | 2037 | CB | ASP | 319 | 48.942 | 19.205 | 27.273 | 1.00 | 27.75 |
| ATOM | 2038 | CG | ASP | 319 | 47.532 | 18.947 | 27.770 | 1.00 | 33.89 |
| ATOM | 2039 | OD1 | ASP | 319 | 46.943 | 19.866 | 28.377 | 1.00 | 37.33 |
| ATOM | 2040 | OD2 | ASP | 319 | 47.009 | 17.829 | 27.560 | 1.00 | 36.71 |
| ATOM | 2041 | C | ASP | 319 | 48.214 | 20.275 | 25.144 | 1.00 | 24.42 |
| ATOM | 2042 | O | ASP | 319 | 48.721 | 19.790 | 24.133 | 1.00 | 24.30 |
| ATOM | 2043 | N | LEU | 320 | 46.940 | 20.648 | 25.200 | 1.00 | 22.05 |
| ATOM | 2044 | CA | LEU | 320 | 46.057 | 20.502 | 24.048 | 1.00 | 21.65 |
| ATOM | 2045 | CB | LEU | 320 | 44.594 | 20.431 | 24.503 | 1.00 | 21.37 |
| ATOM | 2046 | CG | LEU | 320 | 44.138 | 19.298 | 25.429 | 1.00 | 20.50 |
| ATOM | 2047 | CD1 | LEU | 320 | 42.647 | 19.458 | 25.712 | 1.00 | 20.57 |
| ATOM | 2048 | CD2 | LEU | 320 | 44.414 | 17.946 | 24.780 | 1.00 | 20.05 |
| ATOM | 2049 | C | LEU | 320 | 46.190 | 21.626 | 23.023 | 1.00 | 20.30 |
| ATOM | 2050 | O | LEU | 320 | 45.750 | 21.476 | 21.884 | 1.00 | 20.89 |
| ATOM | 2051 | N | VAL | 321 | 46.803 | 22.743 | 23.411 | 1.00 | 18.20 |
| ATOM | 2052 | CA | VAL | 321 | 46.911 | 23.878 | 22.497 | 1.00 | 17.14 |
| ATOM | 2053 | CB | VAL | 321 | 46.014 | 25.051 | 22.986 | 1.00 | 15.95 |
| ATOM | 2054 | CG1 | VAL | 321 | 44.637 | 24.529 | 23.358 | 1.00 | 16.89 |
| ATOM | 2055 | CG2 | VAL | 321 | 46.648 | 25.737 | 24.182 | 1.00 | 13.25 |
| ATOM | 2056 | C | VAL | 321 | 48.319 | 24.420 | 22.267 | 1.00 | 18.07 |
| ATOM | 2057 | O | VAL | 321 | 48.477 | 25.496 | 21.697 | 1.00 | 19.68 |
| ATOM | 2058 | N | VAL | 322 | 49.342 | 23.689 | 22.699 | 1.00 | 20.47 |
| ATOM | 2059 | CA | VAL | 322 | 50.715 | 24.154 | 22.516 | 1.00 | 23.25 |
| ATOM | 2060 | CB | VAL | 322 | 51.735 | 23.050 | 22.893 | 1.00 | 25.43 |
| ATOM | 2061 | CG1 | VAL | 322 | 51.487 | 21.801 | 22.069 | 1.00 | 27.69 |
| ATOM | 2062 | CG2 | VAL | 322 | 53.156 | 23.561 | 22.680 | 1.00 | 27.11 |
| ATOM | 2063 | C | VAL | 322 | 50.975 | 24.620 | 21.077 | 1.00 | 22.80 |
| ATOM | 2064 | O | VAL | 322 | 50.758 | 23.875 | 20.123 | 1.00 | 23.34 |
| ATOM | 2065 | N | PRO | 323 | 51.432 | 25.874 | 20.904 | 1.00 | 23.14 |
| ATOM | 2066 | CD | PRO | 323 | 51.589 | 26.917 | 21.934 | 1.00 | 21.86 |
| ATOM | 2067 | CA | PRO | 323 | 51.712 | 26.414 | 19.566 | 1.00 | 24.47 |
| ATOM | 2068 | CB | PRO | 323 | 52.152 | 27.848 | 19.855 | 1.00 | 23.04 |
| ATOM | 2069 | CG | PRO | 323 | 51.422 | 28.181 | 21.134 | 1.00 | 22.71 |
| ATOM | 2070 | C | PRO | 323 | 52.790 | 25.620 | 18.821 | 1.00 | 26.42 |
| ATOM | 2071 | O | PRO | 323 | 52.615 | 25.255 | 17.658 | 1.00 | 26.23 |
| ATOM | 2072 | N | PHE | 324 | 53.905 | 25.359 | 19.494 | 1.00 | 27.57 |
| ATOM | 2073 | CA | PHE | 324 | 54.996 | 24.606 | 18.885 | 1.00 | 28.92 |
| ATOM | 2074 | CB | PHE | 324 | 56.232 | 25.494 | 18.707 | 1.00 | 29.24 |
| ATOM | 2075 | CG | PHE | 324 | 56.003 | 26.667 | 17.801 | 1.00 | 28.40 |
| ATOM | 2076 | CD1 | PHE | 324 | 55.591 | 27.890 | 18.314 | 1.00 | 28.05 |
| ATOM | 2077 | CD2 | PHE | 324 | 56.159 | 26.538 | 16.426 | 1.00 | 30.34 |
| ATOM | 2078 | CE1 | PHE | 324 | 55.333 | 28.964 | 17.473 | 1.00 | 28.58 |
| ATOM | 2079 | CE2 | PHE | 324 | 55.903 | 27.605 | 15.575 | 1.00 | 28.99 |
| ATOM | 2080 | CZ | PHE | 324 | 55.490 | 28.823 | 16.099 | 1.00 | 29.77 |
| ATOM | 2081 | C | PHE | 324 | 55.339 | 23.400 | 19.738 | 1.00 | 29.62 |
| ATOM | 2082 | O | PHE | 324 | 56.221 | 23.460 | 20.596 | 1.00 | 27.80 |
| ATOM | 2083 | N | PRO | 325 | 54.633 | 22.280 | 19.514 | 1.00 | 31.43 |
| ATOM | 2084 | CD | PRO | 325 | 53.589 | 22.095 | 18.491 | 1.00 | 32.36 |
| ATOM | 2085 | CA | PRO | 325 | 54.855 | 21.042 | 20.263 | 1.00 | 34.46 |
| ATOM | 2086 | CB | PRO | 325 | 53.756 | 20.118 | 19.737 | 1.00 | 33.87 |
| ATOM | 2087 | CG | PRO | 325 | 53.560 | 20.595 | 18.336 | 1.00 | 33.40 |
| ATOM | 2088 | C | PRO | 325 | 56.257 | 20.463 | 20.083 | 1.00 | 36.18 |
| ATOM | 2089 | O | PRO | 325 | 56.677 | 19.593 | 20.849 | 1.00 | 37.18 |
| ATOM | 2090 | N | SER | 326 | 56.980 | 20.947 | 19.077 | 1.00 | 37.49 |
| ATOM | 2091 | CA | SER | 326 | 58.337 | 20.473 | 18.832 | 1.00 | 41.11 |
| ATOM | 2092 | CB | SER | 326 | 58.858 | 20.989 | 17.490 | 1.00 | 42.68 |
| ATOM | 2093 | OG | SER | 326 | 58.218 | 20.326 | 16.416 | 1.00 | 46.06 |

TABLE A-continued

| | | | | | | | | | |
|---|---|---|---|---|---|---|---|---|---|
| ATOM | 2094 | C | SER | 326 | 59.259 | 20.936 | 19.949 | 1.00 | 41.74 |
| ATOM | 2095 | O | SER | 326 | 60.210 | 20.246 | 20.300 | 1.00 | 42.06 |
| ATOM | 2096 | N | ALA | 327 | 58.974 | 22.113 | 20.498 | 1.00 | 42.81 |
| ATOM | 2097 | CA | ALA | 327 | 59.767 | 22.663 | 21.591 | 1.00 | 44.30 |
| ATOM | 2098 | CB | ALA | 327 | 59.778 | 24.183 | 21.516 | 1.00 | 44.00 |
| ATOM | 2099 | C | ALA | 327 | 59.138 | 22.200 | 22.903 | 1.00 | 45.75 |
| ATOM | 2100 | O | ALA | 327 | 58.246 | 22.857 | 23.440 | 1.00 | 45.98 |
| ATOM | 2101 | N | PRO | 328 | 59.601 | 21.059 | 23.439 | 1.00 | 46.83 |
| ATOM | 2102 | CD | PRO | 328 | 60.768 | 20.265 | 23.013 | 1.00 | 47.01 |
| ATOM | 2103 | CA | PRO | 328 | 59.051 | 20.539 | 24.692 | 1.00 | 48.00 |
| ATOM | 2104 | CB | PRO | 328 | 59.746 | 19.189 | 24.834 | 1.00 | 48.21 |
| ATOM | 2105 | CG | PRO | 328 | 61.100 | 19.469 | 24.262 | 1.00 | 48.04 |
| ATOM | 2106 | C | PRO | 328 | 59.297 | 21.448 | 25.890 | 1.00 | 48.18 |
| ATOM | 2107 | O | PRO | 328 | 60.282 | 22.187 | 25.940 | 1.00 | 46.83 |
| ATOM | 2108 | N | ALA | 329 | 58.381 | 21.388 | 26.849 | 1.00 | 49.04 |
| ATOM | 2109 | CA | ALA | 329 | 58.484 | 22.185 | 28.063 | 1.00 | 50.15 |
| ATOM | 2110 | CB | ALA | 329 | 57.284 | 23.123 | 28.183 | 1.00 | 50.22 |
| ATOM | 2111 | C | ALA | 329 | 58.521 | 21.222 | 29.240 | 1.00 | 49.64 |
| ATOM | 2112 | O | ALA | 329 | 57.741 | 20.270 | 29.293 | 1.00 | 49.91 |
| ATOM | 2113 | N | MET | 330 | 59.432 | 21.462 | 30.177 | 1.00 | 49.53 |
| ATOM | 2114 | CA | MET | 330 | 59.547 | 20.599 | 31.340 | 1.00 | 49.53 |
| ATOM | 2115 | CB | MET | 330 | 60.673 | 21.070 | 32.257 | 1.00 | 51.15 |
| ATOM | 2116 | CG | MET | 330 | 62.029 | 20.527 | 31.884 | 1.00 | 53.03 |
| ATOM | 2117 | SD | MET | 330 | 63.171 | 20.647 | 33.253 | 1.00 | 57.37 |
| ATOM | 2118 | CE | MET | 330 | 62.679 | 19.231 | 34.226 | 1.00 | 55.84 |
| ATOM | 2119 | C | MET | 330 | 58.262 | 20.525 | 32.144 | 1.00 | 48.79 |
| ATOM | 2120 | O | MET | 330 | 57.481 | 21.475 | 32.183 | 1.00 | 49.29 |
| ATOM | 2121 | N | ASP | 331 | 58.048 | 19.381 | 32.781 | 1.00 | 47.29 |
| ATOM | 2122 | CA | ASP | 331 | 56.874 | 19.182 | 33.615 | 1.00 | 45.73 |
| ATOM | 2123 | CB | ASP | 331 | 56.656 | 17.689 | 33.862 | 1.00 | 47.61 |
| ATOM | 2124 | CG | ASP | 331 | 55.342 | 17.400 | 34.557 | 1.00 | 48.84 |
| ATOM | 2125 | OD1 | ASP | 331 | 54.962 | 18.178 | 35.459 | 1.00 | 49.28 |
| ATOM | 2126 | OD2 | ASP | 331 | 54.698 | 16.388 | 34.211 | 1.00 | 49.53 |
| ATOM | 2127 | C | ASP | 331 | 57.190 | 19.889 | 34.932 | 1.00 | 43.86 |
| ATOM | 2128 | O | ASP | 331 | 57.723 | 19.279 | 35.860 | 1.00 | 42.31 |
| ATOM | 2129 | N | THR | 332 | 56.872 | 21.178 | 34.999 | 1.00 | 41.74 |
| ATOM | 2130 | CA | THR | 332 | 57.140 | 21.978 | 36.191 | 1.00 | 40.58 |
| ATOM | 2131 | CB | THR | 332 | 56.484 | 23.371 | 36.090 | 1.00 | 41.27 |
| ATOM | 2132 | OG1 | THR | 332 | 56.908 | 24.016 | 34.881 | 1.00 | 42.14 |
| ATOM | 2133 | CG2 | THR | 332 | 56.896 | 24.236 | 37.275 | 1.00 | 42.66 |
| ATOM | 2134 | C | THR | 332 | 56.669 | 21.307 | 37.476 | 1.00 | 39.17 |
| ATOM | 2135 | O | THR | 332 | 57.411 | 21.245 | 38.457 | 1.00 | 37.70 |
| ATOM | 2136 | N | THR | 333 | 55.437 | 20.807 | 37.472 | 1.00 | 37.74 |
| ATOM | 2137 | CA | THR | 333 | 54.890 | 20.144 | 38.648 | 1.00 | 36.86 |
| ATOM | 2138 | CB | THR | 333 | 53.427 | 19.719 | 38.418 | 1.00 | 37.40 |
| ATOM | 2139 | OG1 | THR | 333 | 52.628 | 20.882 | 38.169 | 1.00 | 36.62 |
| ATOM | 2140 | CG2 | THR | 333 | 52.886 | 18.984 | 39.635 | 1.00 | 37.24 |
| ATOM | 2141 | C | THR | 333 | 55.722 | 18.914 | 38.981 | 1.00 | 36.88 |
| ATOM | 2142 | O | THR | 333 | 56.088 | 18.692 | 40.137 | 1.00 | 36.19 |
| ATOM | 2143 | N | ALA | 334 | 56.023 | 18.116 | 37.960 | 1.00 | 36.39 |
| ATOM | 2144 | CA | ALA | 334 | 56.826 | 16.917 | 38.153 | 1.00 | 35.82 |
| ATOM | 2145 | CB | ALA | 334 | 57.017 | 16.187 | 36.828 | 1.00 | 36.09 |
| ATOM | 2146 | C | ALA | 334 | 58.176 | 17.327 | 38.725 | 1.00 | 35.55 |
| ATOM | 2147 | O | ALA | 334 | 58.707 | 16.666 | 39.618 | 1.00 | 36.24 |
| ATOM | 2148 | N | ALA | 335 | 58.723 | 18.424 | 38.209 | 1.00 | 34.21 |
| ATOM | 2149 | CA | ALA | 335 | 60.009 | 18.923 | 38.675 | 1.00 | 33.61 |
| ATOM | 2150 | CB | ALA | 335 | 60.436 | 20.128 | 37.846 | 1.00 | 33.15 |
| ATOM | 2151 | C | ALA | 335 | 59.901 | 19.304 | 40.146 | 1.00 | 33.27 |
| ATOM | 2152 | O | ALA | 335 | 60.704 | 18.866 | 40.965 | 1.00 | 31.41 |
| ATOM | 2153 | N | MET | 336 | 58.894 | 20.107 | 40.482 | 1.00 | 34.57 |
| ATOM | 2154 | CA | MET | 336 | 58.688 | 20.531 | 41.866 | 1.00 | 34.78 |
| ATOM | 2155 | CB | MET | 336 | 57.427 | 21.394 | 41.975 | 1.00 | 32.50 |
| ATOM | 2156 | CG | MET | 336 | 57.541 | 22.735 | 41.264 | 1.00 | 29.70 |
| ATOM | 2157 | SD | MET | 336 | 56.074 | 23.759 | 41.452 | 1.00 | 28.38 |
| ATOM | 2158 | CE | MET | 336 | 56.194 | 24.182 | 43.188 | 1.00 | 22.94 |
| ATOM | 2159 | C | MET | 336 | 58.578 | 19.323 | 42.795 | 1.00 | 35.93 |
| ATOM | 2160 | O | MET | 336 | 59.274 | 19.241 | 43.810 | 1.00 | 35.89 |
| ATOM | 2161 | N | LEU | 337 | 57.706 | 18.384 | 42.440 | 1.00 | 37.76 |
| ATOM | 2162 | CA | LEU | 337 | 57.524 | 17.178 | 43.239 | 1.00 | 40.14 |
| ATOM | 2163 | CB | LEU | 337 | 56.380 | 16.334 | 42.666 | 1.00 | 40.76 |
| ATOM | 2164 | CG | LEU | 337 | 54.971 | 16.932 | 42.725 | 1.00 | 41.59 |
| ATOM | 2165 | CD1 | LEU | 337 | 54.024 | 16.102 | 41.871 | 1.00 | 41.83 |
| ATOM | 2166 | CD2 | LEU | 337 | 54.491 | 16.982 | 44.171 | 1.00 | 41.58 |
| ATOM | 2167 | C | LEU | 337 | 58.817 | 16.365 | 43.241 | 1.00 | 41.26 |
| ATOM | 2168 | O | LEU | 337 | 59.253 | 15.871 | 44.283 | 1.00 | 41.87 |
| ATOM | 2169 | N | ALA | 338 | 59.430 | 16.242 | 42.067 | 1.00 | 41.93 |
| ATOM | 2170 | CA | ALA | 338 | 60.671 | 15.490 | 41.913 | 1.00 | 42.20 |
| ATOM | 2171 | CB | ALA | 338 | 61.200 | 15.641 | 40.495 | 1.00 | 43.26 |
| ATOM | 2172 | C | ALA | 338 | 61.736 | 15.922 | 42.909 | 1.00 | 42.52 |
| ATOM | 2173 | O | ALA | 338 | 62.386 | 15.081 | 43.530 | 1.00 | 42.44 |

TABLE A-continued

| | | | | | | | | | |
|---|---|---|---|---|---|---|---|---|---|
| ATOM | 2174 | N | GLN | 339 | 61.926 | 17.230 | 43.062 | 1.00 | 42.25 |
| ATOM | 2175 | CA | GLN | 339 | 62.928 | 17.713 | 44.001 | 1.00 | 41.65 |
| ATOM | 2176 | CB | GLN | 339 | 63.734 | 18.859 | 43.394 | 1.00 | 42.74 |
| ATOM | 2177 | CG | GLN | 339 | 63.026 | 19.643 | 42.327 | 1.00 | 44.14 |
| ATOM | 2178 | CD | GLN | 339 | 63.993 | 20.157 | 41.285 | 1.00 | 45.56 |
| ATOM | 2179 | OE1 | GLN | 339 | 64.984 | 20.807 | 41.613 | 1.00 | 47.00 |
| ATOM | 2180 | NE2 | GLN | 339 | 63.715 | 19.862 | 40.019 | 1.00 | 45.62 |
| ATOM | 2181 | C | GLN | 339 | 62.357 | 18.113 | 45.350 | 1.00 | 40.44 |
| ATOM | 2182 | O | GLN | 339 | 62.847 | 19.031 | 46.004 | 1.00 | 41.27 |
| ATOM | 2183 | N | GLY | 340 | 61.312 | 17.399 | 45.752 | 1.00 | 39.31 |
| ATOM | 2184 | CA | GLY | 340 | 60.678 | 17.619 | 47.038 | 1.00 | 38.16 |
| ATOM | 2185 | C | GLY | 340 | 60.257 | 19.015 | 47.451 | 1.00 | 35.80 |
| ATOM | 2186 | O | GLY | 340 | 60.453 | 19.396 | 48.603 | 1.00 | 35.38 |
| ATOM | 2187 | N | TRP | 341 | 59.690 | 19.788 | 46.533 | 1.00 | 34.88 |
| ATOM | 2188 | CA | TRP | 341 | 59.229 | 21.119 | 46.900 | 1.00 | 33.70 |
| ATOM | 2189 | CB | TRP | 341 | 58.805 | 21.916 | 45.663 | 1.00 | 32.35 |
| ATOM | 2190 | CG | TRP | 341 | 59.926 | 22.667 | 45.025 | 1.00 | 32.45 |
| ATOM | 2191 | CD2 | TRP | 341 | 59.992 | 24.080 | 44.792 | 1.00 | 33.12 |
| ATOM | 2192 | CE2 | TRP | 341 | 61.228 | 24.341 | 44.163 | 1.00 | 33.53 |
| ATOM | 2193 | CE3 | TRP | 341 | 59.125 | 25.151 | 45.053 | 1.00 | 33.17 |
| ATOM | 2194 | CD1 | TRP | 341 | 61.089 | 22.146 | 44.544 | 1.00 | 33.26 |
| ATOM | 2195 | NE1 | TRP | 341 | 61.877 | 23.143 | 44.024 | 1.00 | 33.74 |
| ATOM | 2196 | CZ2 | TRP | 341 | 61.624 | 25.632 | 43.788 | 1.00 | 33.86 |
| ATOM | 2197 | CZ3 | TRP | 341 | 59.517 | 26.435 | 44.681 | 1.00 | 33.83 |
| ATOM | 2198 | CH2 | TRP | 341 | 60.758 | 26.663 | 44.054 | 1.00 | 33.79 |
| ATOM | 2199 | C | TRP | 341 | 58.035 | 20.916 | 47.822 | 1.00 | 32.71 |
| ATOM | 2200 | O | TRP | 341 | 57.268 | 19.968 | 47.650 | 1.00 | 32.15 |
| ATOM | 2201 | N | THR | 342 | 57.892 | 21.790 | 48.812 | 1.00 | 31.61 |
| ATOM | 2202 | CA | THR | 342 | 56.782 | 21.697 | 49.754 | 1.00 | 30.86 |
| ATOM | 2203 | CB | THR | 342 | 57.271 | 21.368 | 51.176 | 1.00 | 31.36 |
| ATOM | 2204 | OG1 | THR | 342 | 58.015 | 22.481 | 51.687 | 1.00 | 30.07 |
| ATOM | 2205 | CG2 | THR | 342 | 58.158 | 20.128 | 51.170 | 1.00 | 32.63 |
| ATOM | 2206 | C | THR | 342 | 56.072 | 23.042 | 49.825 | 1.00 | 29.61 |
| ATOM | 2207 | O | THR | 342 | 56.577 | 24.044 | 49.324 | 1.00 | 28.37 |
| ATOM | 2208 | N | PRO | 343 | 54.882 | 23.078 | 50.442 | 1.00 | 29.45 |
| ATOM | 2209 | CD | PRO | 343 | 54.024 | 21.946 | 50.843 | 1.00 | 27.29 |
| ATOM | 2210 | CA | PRO | 343 | 54.160 | 24.347 | 50.552 | 1.00 | 28.24 |
| ATOM | 2211 | CB | PRO | 343 | 52.937 | 23.969 | 51.378 | 1.00 | 27.42 |
| ATOM | 2212 | CG | PRO | 343 | 52.646 | 22.579 | 50.887 | 1.00 | 27.57 |
| ATOM | 2213 | C | PRO | 343 | 55.036 | 25.393 | 51.247 | 1.00 | 28.41 |
| ATOM | 2214 | O | PRO | 343 | 55.105 | 26.543 | 50.816 | 1.00 | 28.24 |
| ATOM | 2215 | N | ARG | 344 | 55.721 | 24.982 | 52.311 | 1.00 | 29.01 |
| ATOM | 2216 | CA | ARG | 344 | 56.588 | 25.896 | 53.052 | 1.00 | 30.23 |
| ATOM | 2217 | CB | ARG | 344 | 57.207 | 25.183 | 54.260 | 1.00 | 32.72 |
| ATOM | 2218 | CG | ARG | 344 | 57.690 | 26.117 | 55.376 | 1.00 | 38.15 |
| ATOM | 2219 | CD | ARG | 344 | 58.192 | 25.317 | 56.580 | 1.00 | 41.91 |
| ATOM | 2220 | NE | ARG | 344 | 58.217 | 26.096 | 57.821 | 1.00 | 46.21 |
| ATOM | 2221 | CZ | ARG | 344 | 59.095 | 27.056 | 58.100 | 1.00 | 46.40 |
| ATOM | 2222 | NH1 | ARG | 344 | 59.026 | 27.700 | 59.258 | 1.00 | 46.37 |
| ATOM | 2223 | NH2 | ARG | 344 | 60.046 | 27.368 | 57.232 | 1.00 | 48.36 |
| ATOM | 2224 | C | ARG | 344 | 57.689 | 26.436 | 52.140 | 1.00 | 29.35 |
| ATOM | 2225 | O | ARG | 344 | 58.016 | 27.620 | 52.183 | 1.00 | 28.16 |
| ATOM | 2226 | N | ARG | 345 | 58.248 | 25.565 | 51.304 | 1.00 | 28.94 |
| ATOM | 2227 | CA | ARG | 345 | 59.302 | 25.968 | 50.378 | 1.00 | 28.91 |
| ATOM | 2228 | CB | ARG | 345 | 59.793 | 24.764 | 49.567 | 1.00 | 32.39 |
| ATOM | 2229 | CG | ARG | 345 | 61.304 | 24.601 | 49.543 | 1.00 | 38.26 |
| ATOM | 2230 | CD | ARG | 345 | 62.016 | 25.852 | 49.048 | 1.00 | 41.91 |
| ATOM | 2231 | NE | ARG | 345 | 62.441 | 25.769 | 47.650 | 1.00 | 47.14 |
| ATOM | 2232 | CZ | ARG | 345 | 63.250 | 24.830 | 47.163 | 1.00 | 48.30 |
| ATOM | 2233 | NH1 | ARG | 345 | 63.724 | 23.877 | 47.955 | 1.00 | 50.47 |
| ATOM | 2234 | NH2 | ARG | 345 | 63.609 | 24.858 | 45.888 | 1.00 | 48.82 |
| ATOM | 2235 | C | ARG | 345 | 58.771 | 27.020 | 49.414 | 1.00 | 26.66 |
| ATOM | 2236 | O | ARG | 345 | 59.443 | 28.008 | 49.117 | 1.00 | 25.29 |
| ATOM | 2237 | N | MET | 346 | 57.558 | 26.783 | 48.925 | 1.00 | 24.67 |
| ATOM | 2238 | CA | MET | 346 | 56.909 | 27.680 | 47.981 | 1.00 | 23.82 |
| ATOM | 2239 | CB | MET | 346 | 55.538 | 27.115 | 47.593 | 1.00 | 22.88 |
| ATOM | 2240 | CG | MET | 346 | 55.631 | 25.817 | 46.789 | 1.00 | 22.60 |
| ATOM | 2241 | SD | MET | 346 | 54.099 | 24.884 | 46.702 | 1.00 | 23.12 |
| ATOM | 2242 | CE | MET | 346 | 53.193 | 25.800 | 45.456 | 1.00 | 22.77 |
| ATOM | 2243 | C | MET | 346 | 56.776 | 29.087 | 48.548 | 1.00 | 22.51 |
| ATOM | 2244 | O | MET | 346 | 57.111 | 30.061 | 47.877 | 1.00 | 22.36 |
| ATOM | 2245 | N | PHE | 347 | 56.299 | 29.198 | 49.783 | 1.00 | 22.71 |
| ATOM | 2246 | CA | PHE | 347 | 56.154 | 30.512 | 50.397 | 1.00 | 23.33 |
| ATOM | 2247 | CB | PHE | 347 | 55.272 | 30.431 | 51.650 | 1.00 | 21.23 |
| ATOM | 2248 | CG | PHE | 347 | 53.810 | 30.232 | 51.344 | 1.00 | 20.37 |
| ATOM | 2249 | CD1 | PHE | 347 | 53.280 | 28.957 | 51.191 | 1.00 | 20.90 |
| ATOM | 2250 | CD2 | PHE | 347 | 52.974 | 31.328 | 51.156 | 1.00 | 20.68 |
| ATOM | 2251 | CE1 | PHE | 347 | 51.937 | 28.775 | 50.855 | 1.00 | 22.83 |
| ATOM | 2252 | CE2 | PHE | 347 | 51.633 | 31.158 | 50.820 | 1.00 | 19.46 |
| ATOM | 2253 | CZ | PHE | 347 | 51.113 | 29.879 | 50.668 | 1.00 | 20.69 |

TABLE A-continued

| | | | | | | | | | |
|---|---|---|---|---|---|---|---|---|---|
| ATOM | 2254 | C | PHE | 347 | 57.521 | 31.109 | 50.731 | 1.00 | 24.58 |
| ATOM | 2255 | O | PHE | 347 | 57.698 | 32.329 | 50.701 | 1.00 | 23.58 |
| ATOM | 2256 | N | LYS | 348 | 58.489 | 30.248 | 51.039 | 1.00 | 25.53 |
| ATOM | 2257 | CA | LYS | 348 | 59.838 | 30.708 | 51.349 | 1.00 | 25.95 |
| ATOM | 2258 | CB | LYS | 348 | 60.726 | 29.531 | 51.772 | 1.00 | 29.39 |
| ATOM | 2259 | CG | LYS | 348 | 60.529 | 29.067 | 53.209 | 1.00 | 32.76 |
| ATOM | 2260 | CD | LYS | 348 | 61.020 | 30.117 | 54.201 | 1.00 | 37.96 |
| ATOM | 2261 | CE | LYS | 348 | 60.995 | 29.590 | 55.633 | 1.00 | 38.41 |
| ATOM | 2262 | NZ | LYS | 348 | 61.587 | 30.556 | 56.606 | 1.00 | 38.93 |
| ATOM | 2263 | C | LYS | 348 | 60.428 | 31.383 | 50.115 | 1.00 | 25.86 |
| ATOM | 2264 | O | LYS | 348 | 61.081 | 32.418 | 50.223 | 1.00 | 26.39 |
| ATOM | 2265 | N | GLU | 349 | 60.197 | 30.796 | 48.941 | 1.00 | 25.73 |
| ATOM | 2266 | CA | GLU | 349 | 60.701 | 31.375 | 47.696 | 1.00 | 25.00 |
| ATOM | 2267 | CB | GLU | 349 | 60.425 | 30.445 | 46.510 | 1.00 | 27.57 |
| ATOM | 2268 | CG | GLU | 349 | 61.252 | 29.163 | 46.476 | 1.00 | 32.10 |
| ATOM | 2269 | CD | GLU | 349 | 62.754 | 29.418 | 46.536 | 1.00 | 34.82 |
| ATOM | 2270 | OE1 | GLU | 349 | 63.207 | 30.487 | 46.066 | 1.00 | 35.04 |
| ATOM | 2271 | OE2 | GLU | 349 | 63.484 | 28.538 | 47.041 | 1.00 | 36.16 |
| ATOM | 2272 | C | GLU | 349 | 60.031 | 32.727 | 47.446 | 1.00 | 24.44 |
| ATOM | 2273 | O | GLU | 349 | 60.679 | 33.684 | 47.018 | 1.00 | 23.97 |
| ATOM | 2274 | N | ALA | 350 | 58.727 | 32.797 | 47.702 | 1.00 | 23.38 |
| ATOM | 2275 | CA | ALA | 350 | 57.985 | 34.043 | 47.522 | 1.00 | 22.42 |
| ATOM | 2276 | CB | ALA | 350 | 56.511 | 33.829 | 47.857 | 1.00 | 22.54 |
| ATOM | 2277 | C | ALA | 350 | 58.579 | 35.104 | 48.444 | 1.00 | 21.24 |
| ATOM | 2278 | O | ALA | 350 | 58.844 | 36.233 | 48.027 | 1.00 | 21.74 |
| ATOM | 2279 | N | ASP | 351 | 58.787 | 34.732 | 49.702 | 1.00 | 20.72 |
| ATOM | 2280 | CA | ASP | 351 | 59.353 | 35.652 | 50.682 | 1.00 | 21.66 |
| ATOM | 2281 | CB | ASP | 351 | 59.499 | 34.949 | 52.037 | 1.00 | 23.19 |
| ATOM | 2282 | CG | ASP | 351 | 59.901 | 35.900 | 53.150 | 1.00 | 26.89 |
| ATOM | 2283 | OD1 | ASP | 351 | 59.198 | 36.914 | 53.364 | 1.00 | 26.58 |
| ATOM | 2284 | OD2 | ASP | 351 | 60.921 | 35.633 | 53.818 | 1.00 | 26.96 |
| ATOM | 2285 | C | ASP | 351 | 60.708 | 36.163 | 50.198 | 1.00 | 22.19 |
| ATOM | 2286 | O | ASP | 351 | 61.051 | 37.330 | 50.392 | 1.00 | 22.86 |
| ATOM | 2287 | N | ASP | 352 | 61.472 | 35.289 | 49.548 | 1.00 | 23.64 |
| ATOM | 2288 | CA | ASP | 352 | 62.787 | 35.667 | 49.041 | 1.00 | 23.82 |
| ATOM | 2289 | CB | ASP | 352 | 63.553 | 34.430 | 48.548 | 1.00 | 23.91 |
| ATOM | 2290 | CG | ASP | 352 | 64.921 | 34.780 | 47.988 | 1.00 | 26.32 |
| ATOM | 2291 | OD1 | ASP | 352 | 65.096 | 34.724 | 46.753 | 1.00 | 25.02 |
| ATOM | 2292 | OD2 | ASP | 352 | 65.821 | 35.124 | 48.786 | 1.00 | 28.34 |
| ATOM | 2293 | C | ASP | 352 | 62.680 | 36.688 | 47.916 | 1.00 | 23.50 |
| ATOM | 2294 | O | ASP | 352 | 63.486 | 37.612 | 47.836 | 1.00 | 22.72 |
| ATOM | 2295 | N | PHE | 353 | 61.681 | 36.534 | 47.051 | 1.00 | 23.52 |
| ATOM | 2296 | CA | PHE | 353 | 61.522 | 37.475 | 45.953 | 1.00 | 22.24 |
| ATOM | 2297 | CB | PHE | 353 | 60.397 | 37.045 | 45.001 | 1.00 | 21.06 |
| ATOM | 2298 | CG | PHE | 353 | 60.542 | 37.609 | 43.607 | 1.00 | 19.58 |
| ATOM | 2299 | CD1 | PHE | 353 | 60.744 | 36.767 | 42.516 | 1.00 | 21.35 |
| ATOM | 2300 | CD2 | PHE | 353 | 60.528 | 38.984 | 43.392 | 1.00 | 19.63 |
| ATOM | 2301 | CE1 | PHE | 353 | 60.935 | 37.288 | 41.230 | 1.00 | 19.63 |
| ATOM | 2302 | CE2 | PHE | 353 | 60.718 | 39.513 | 42.115 | 1.00 | 19.63 |
| ATOM | 2303 | CZ | PHE | 353 | 60.923 | 38.660 | 41.029 | 1.00 | 19.46 |
| ATOM | 2304 | C | PHE | 353 | 61.237 | 38.870 | 46.504 | 1.00 | 20.90 |
| ATOM | 2305 | O | PHE | 353 | 61.837 | 39.849 | 46.059 | 1.00 | 22.16 |
| ATOM | 2306 | N | PHE | 354 | 60.329 | 38.968 | 47.471 | 1.00 | 20.76 |
| ATOM | 2307 | CA | PHE | 354 | 60.019 | 40.269 | 48.057 | 1.00 | 20.13 |
| ATOM | 2308 | CB | PHE | 354 | 58.915 | 40.143 | 49.115 | 1.00 | 20.30 |
| ATOM | 2309 | CG | PHE | 354 | 57.526 | 40.045 | 48.535 | 1.00 | 18.25 |
| ATOM | 2310 | CD1 | PHE | 354 | 56.932 | 38.805 | 48.306 | 1.00 | 17.88 |
| ATOM | 2311 | CD2 | PHE | 354 | 56.826 | 41.200 | 48.187 | 1.00 | 19.40 |
| ATOM | 2312 | CE1 | PHE | 354 | 55.662 | 38.713 | 47.738 | 1.00 | 17.04 |
| ATOM | 2313 | CE2 | PHE | 354 | 55.548 | 41.123 | 47.612 | 1.00 | 18.88 |
| ATOM | 2314 | CZ | PHE | 354 | 54.968 | 39.875 | 47.388 | 1.00 | 19.24 |
| ATOM | 2315 | C | PHE | 354 | 61.258 | 40.935 | 48.671 | 1.00 | 21.10 |
| ATOM | 2316 | O | PHE | 354 | 61.517 | 42.120 | 48.427 | 1.00 | 19.45 |
| ATOM | 2317 | N | THR | 355 | 62.028 | 40.184 | 49.456 | 1.00 | 22.06 |
| ATOM | 2318 | CA | THR | 355 | 63.224 | 40.748 | 50.081 | 1.00 | 24.14 |
| ATOM | 2319 | CB | THR | 355 | 63.849 | 39.787 | 51.126 | 1.00 | 24.56 |
| ATOM | 2320 | OG1 | THR | 355 | 64.083 | 38.505 | 50.533 | 1.00 | 26.60 |
| ATOM | 2321 | CG2 | THR | 355 | 62.926 | 39.633 | 52.326 | 1.00 | 25.22 |
| ATOM | 2322 | C | THR | 355 | 64.289 | 41.118 | 49.055 | 1.00 | 23.51 |
| ATOM | 2323 | O | THR | 355 | 65.042 | 42.070 | 49.257 | 1.00 | 25.42 |
| ATOM | 2324 | N | SER | 356 | 64.342 | 40.386 | 47.948 | 1.00 | 23.09 |
| ATOM | 2325 | CA | SER | 356 | 65.332 | 40.676 | 46.913 | 1.00 | 22.30 |
| ATOM | 2326 | CB | SER | 356 | 65.256 | 39.642 | 45.784 | 1.00 | 23.31 |
| ATOM | 2327 | OG | SER | 356 | 64.163 | 39.901 | 44.915 | 1.00 | 25.00 |
| ATOM | 2328 | C | SER | 356 | 65.088 | 42.068 | 46.345 | 1.00 | 22.33 |
| ATOM | 2329 | O | SER | 356 | 66.005 | 42.707 | 45.824 | 1.00 | 22.15 |
| ATOM | 2330 | N | LEU | 357 | 63.846 | 42.535 | 46.452 | 1.00 | 20.54 |
| ATOM | 2331 | CA | LEU | 357 | 63.477 | 43.855 | 45.951 | 1.00 | 21.18 |
| ATOM | 2332 | CB | LEU | 357 | 62.007 | 43.874 | 45.515 | 1.00 | 20.21 |
| ATOM | 2333 | CG | LEU | 357 | 61.567 | 42.939 | 44.386 | 1.00 | 22.18 |

TABLE A-continued

| | | | | | | | | |
|---|---|---|---|---|---|---|---|---|
| ATOM | 2334 | CD1 | LEU | 357 | 60.089 | 43.169 | 44.092 | 1.00 | 20.93 |
| ATOM | 2335 | CD2 | LEU | 357 | 62.391 | 43.197 | 43.140 | 1.00 | 19.15 |
| ATOM | 2336 | C | LEU | 357 | 63.687 | 44.929 | 47.015 | 1.00 | 21.10 |
| ATOM | 2337 | O | LEU | 357 | 63.448 | 46.113 | 46.769 | 1.00 | 21.69 |
| ATOM | 2338 | N | GLY | 358 | 64.133 | 44.513 | 48.193 | 1.00 | 20.78 |
| ATOM | 2339 | CA | GLY | 358 | 64.340 | 45.465 | 49.269 | 1.00 | 22.52 |
| ATOM | 2340 | C | GLY | 358 | 63.086 | 45.581 | 50.120 | 1.00 | 23.30 |
| ATOM | 2341 | O | GLY | 358 | 63.053 | 46.339 | 51.091 | 1.00 | 23.76 |
| ATOM | 2342 | N | LEU | 359 | 62.051 | 44.826 | 49.754 | 1.00 | 20.72 |
| ATOM | 2343 | CA | LEU | 359 | 60.792 | 44.844 | 50.487 | 1.00 | 21.07 |
| ATOM | 2344 | CB | LEU | 359 | 59.667 | 44.293 | 49.604 | 1.00 | 17.66 |
| ATOM | 2345 | CG | LEU | 359 | 59.417 | 45.174 | 48.371 | 1.00 | 19.03 |
| ATOM | 2346 | CD1 | LEU | 359 | 58.362 | 44.551 | 47.459 | 1.00 | 16.52 |
| ATOM | 2347 | CD2 | LEU | 359 | 58.977 | 46.563 | 48.829 | 1.00 | 16.74 |
| ATOM | 2348 | C | LEU | 359 | 60.909 | 44.062 | 51.797 | 1.00 | 21.60 |
| ATOM | 2349 | O | LEU | 359 | 61.932 | 43.424 | 52.058 | 1.00 | 21.13 |
| ATOM | 2350 | N | LEU | 360 | 59.863 | 44.112 | 52.616 | 1.00 | 21.11 |
| ATOM | 2351 | CA | LEU | 360 | 59.869 | 43.451 | 53.921 | 1.00 | 22.96 |
| ATOM | 2352 | CB | LEU | 360 | 58.815 | 44.093 | 54.830 | 1.00 | 23.88 |
| ATOM | 2353 | CG | LEU | 360 | 58.982 | 45.575 | 55.174 | 1.00 | 27.26 |
| ATOM | 2354 | CD1 | LEU | 360 | 57.692 | 46.100 | 55.788 | 1.00 | 27.98 |
| ATOM | 2355 | CD2 | LEU | 360 | 60.162 | 45.756 | 56.131 | 1.00 | 25.65 |
| ATOM | 2356 | C | LEU | 360 | 59.654 | 41.942 | 53.937 | 1.00 | 23.76 |
| ATOM | 2357 | O | LEU | 360 | 58.870 | 41.401 | 53.163 | 1.00 | 24.22 |
| ATOM | 2358 | N | PRO | 361 | 60.355 | 41.241 | 54.840 | 1.00 | 25.33 |
| ATOM | 2359 | CD | PRO | 361 | 61.465 | 41.730 | 55.683 | 1.00 | 26.75 |
| ATOM | 2360 | CA | PRO | 361 | 60.217 | 39.791 | 54.953 | 1.00 | 25.45 |
| ATOM | 2361 | CB | PRO | 361 | 61.562 | 39.373 | 55.529 | 1.00 | 27.39 |
| ATOM | 2362 | CG | PRO | 361 | 61.851 | 40.492 | 56.480 | 1.00 | 27.59 |
| ATOM | 2363 | C | PRO | 361 | 59.071 | 39.538 | 55.926 | 1.00 | 25.74 |
| ATOM | 2364 | O | PRO | 361 | 58.773 | 40.394 | 56.759 | 1.00 | 26.40 |
| ATOM | 2365 | N | VAL | 362 | 58.412 | 38.390 | 55.827 | 1.00 | 25.30 |
| ATOM | 2366 | CA | VAL | 362 | 57.323 | 38.115 | 56.757 | 1.00 | 25.65 |
| ATOM | 2367 | CB | VAL | 362 | 56.462 | 36.916 | 56.303 | 1.00 | 24.53 |
| ATOM | 2368 | CG1 | VAL | 362 | 55.770 | 37.249 | 54.980 | 1.00 | 23.68 |
| ATOM | 2369 | CG2 | VAL | 362 | 57.327 | 35.674 | 56.167 | 1.00 | 23.66 |
| ATOM | 2370 | C | VAL | 362 | 57.926 | 37.820 | 58.127 | 1.00 | 27.19 |
| ATOM | 2371 | O | VAL | 362 | 59.013 | 37.247 | 58.221 | 1.00 | 27.05 |
| ATOM | 2372 | N | PRO | 363 | 57.235 | 38.226 | 59.207 | 1.00 | 26.80 |
| ATOM | 2373 | CD | PRO | 363 | 56.022 | 39.063 | 59.229 | 1.00 | 26.99 |
| ATOM | 2374 | CA | PRO | 363 | 57.726 | 37.995 | 60.570 | 1.00 | 27.57 |
| ATOM | 2375 | CB | PRO | 363 | 56.685 | 38.706 | 61.441 | 1.00 | 26.11 |
| ATOM | 2376 | CG | PRO | 363 | 56.169 | 39.793 | 60.545 | 1.00 | 27.52 |
| ATOM | 2377 | C | PRO | 363 | 57.826 | 36.513 | 60.911 | 1.00 | 27.67 |
| ATOM | 2378 | O | PRO | 363 | 57.114 | 35.684 | 60.340 | 1.00 | 27.28 |
| ATOM | 2379 | N | PRO | 364 | 58.722 | 36.160 | 61.847 | 1.00 | 28.91 |
| ATOM | 2380 | CD | PRO | 364 | 59.688 | 37.033 | 62.542 | 1.00 | 30.07 |
| ATOM | 2381 | CA | PRO | 364 | 58.888 | 34.761 | 62.252 | 1.00 | 27.66 |
| ATOM | 2382 | CB | PRO | 364 | 59.844 | 34.864 | 63.437 | 1.00 | 30.48 |
| ATOM | 2383 | CG | PRO | 364 | 60.707 | 36.037 | 63.061 | 1.00 | 31.62 |
| ATOM | 2384 | C | PRO | 364 | 57.537 | 34.165 | 62.650 | 1.00 | 27.12 |
| ATOM | 2385 | O | PRO | 364 | 57.245 | 33.003 | 62.369 | 1.00 | 25.49 |
| ATOM | 2386 | N | GLU | 365 | 56.715 | 34.985 | 63.297 | 1.00 | 28.48 |
| ATOM | 2387 | CA | GLU | 365 | 55.387 | 34.578 | 63.755 | 1.00 | 29.40 |
| ATOM | 2388 | CB | GLU | 365 | 54.705 | 35.769 | 64.439 | 1.00 | 31.16 |
| ATOM | 2389 | CG | GLU | 365 | 53.287 | 35.524 | 64.907 | 1.00 | 34.46 |
| ATOM | 2390 | CD | GLU | 365 | 52.757 | 36.659 | 65.770 | 1.00 | 37.66 |
| ATOM | 2391 | OE1 | GLU | 365 | 53.118 | 37.831 | 65.518 | 1.00 | 38.25 |
| ATOM | 2392 | OE2 | GLU | 365 | 51.967 | 36.381 | 66.696 | 1.00 | 38.79 |
| ATOM | 2393 | C | GLU | 365 | 54.511 | 34.039 | 62.617 | 1.00 | 29.17 |
| ATOM | 2394 | O | GLU | 365 | 53.653 | 33.178 | 62.832 | 1.00 | 29.47 |
| ATOM | 2395 | N | PHE | 366 | 54.736 | 34.549 | 61.409 | 1.00 | 28.47 |
| ATOM | 2396 | CA | PHE | 366 | 53.990 | 34.128 | 60.222 | 1.00 | 26.31 |
| ATOM | 2397 | CB | PHE | 366 | 54.487 | 34.904 | 58.997 | 1.00 | 25.09 |
| ATOM | 2398 | CG | PHE | 366 | 53.986 | 34.361 | 57.680 | 1.00 | 23.73 |
| ATOM | 2399 | CD1 | PHE | 366 | 52.829 | 34.865 | 57.096 | 1.00 | 22.77 |
| ATOM | 2400 | CD2 | PHE | 366 | 54.681 | 33.348 | 57.023 | 1.00 | 24.15 |
| ATOM | 2401 | CE1 | PHE | 366 | 52.368 | 34.371 | 55.873 | 1.00 | 21.92 |
| ATOM | 2402 | CE2 | PHE | 366 | 54.228 | 32.845 | 55.799 | 1.00 | 22.88 |
| ATOM | 2403 | CZ | PHE | 366 | 53.071 | 33.358 | 55.225 | 1.00 | 22.34 |
| ATOM | 2404 | C | PHE | 366 | 54.162 | 32.632 | 59.965 | 1.00 | 25.92 |
| ATOM | 2405 | O | PHE | 366 | 53.190 | 31.899 | 59.774 | 1.00 | 24.62 |
| ATOM | 2406 | N | TRP | 367 | 55.414 | 32.189 | 59.948 | 1.00 | 26.49 |
| ATOM | 2407 | CA | TRP | 367 | 55.724 | 30.788 | 59.699 | 1.00 | 28.05 |
| ATOM | 2408 | CB | TRP | 367 | 57.242 | 30.605 | 59.640 | 1.00 | 27.25 |
| ATOM | 2409 | CG | TRP | 367 | 57.869 | 31.421 | 58.559 | 1.00 | 26.72 |
| ATOM | 2410 | CD2 | TRP | 367 | 57.708 | 31.235 | 57.148 | 1.00 | 24.28 |
| ATOM | 2411 | CE2 | TRP | 367 | 58.450 | 32.249 | 56.508 | 1.00 | 24.53 |
| ATOM | 2412 | CE3 | TRP | 367 | 57.007 | 30.308 | 56.363 | 1.00 | 25.77 |
| ATOM | 2413 | CD1 | TRP | 367 | 58.678 | 32.507 | 58.713 | 1.00 | 26.27 |

TABLE A-continued

| | | | | | | | | |
|---|---|---|---|---|---|---|---|---|
| ATOM | 2414 | NE1 | TRP | 367 | 59.032 | 33.011 | 57.486 | 1.00 24.78 |
| ATOM | 2415 | CZ2 | TRP | 367 | 58.515 | 32.367 | 55.115 | 1.00 25.59 |
| ATOM | 2416 | CZ3 | TRP | 367 | 57.070 | 30.423 | 54.975 | 1.00 25.39 |
| ATOM | 2417 | CH2 | TRP | 367 | 57.820 | 31.446 | 54.368 | 1.00 26.81 |
| ATOM | 2418 | C | TRP | 367 | 55.128 | 29.845 | 60.737 | 1.00 28.77 |
| ATOM | 2419 | O | TRP | 367 | 54.818 | 28.693 | 60.436 | 1.00 29.68 |
| ATOM | 2420 | N | ASN | 368 | 54.948 | 30.341 | 61.955 | 1.00 29.29 |
| ATOM | 2421 | CA | ASN | 368 | 54.407 | 29.517 | 63.023 | 1.00 30.04 |
| ATOM | 2422 | CB | ASN | 368 | 54.955 | 29.999 | 64.369 | 1.00 33.90 |
| ATOM | 2423 | CG | ASN | 368 | 54.405 | 29.197 | 65.545 | 1.00 37.17 |
| ATOM | 2424 | OD1 | ASN | 368 | 53.214 | 29.307 | 65.846 | 1.00 41.44 |
| ATOM | 2425 | ND2 | ASN | 368 | 55.233 | 28.397 | 66.223 | 1.00 37.16 |
| ATOM | 2426 | C | ASN | 368 | 52.882 | 29.448 | 63.097 | 1.00 30.01 |
| ATOM | 2427 | O | ASN | 368 | 52.323 | 28.404 | 63.431 | 1.00 27.10 |
| ATOM | 2428 | N | LYS | 369 | 52.206 | 30.547 | 62.780 | 1.00 28.47 |
| ATOM | 2429 | CA | LYS | 369 | 50.753 | 30.567 | 62.870 | 1.00 29.06 |
| ATOM | 2430 | CB | LYS | 369 | 50.308 | 31.882 | 63.513 | 1.00 30.23 |
| ATOM | 2431 | CG | LYS | 369 | 50.848 | 32.067 | 64.931 | 1.00 32.99 |
| ATOM | 2432 | CD | LYS | 369 | 50.314 | 33.335 | 65.573 | 1.00 38.01 |
| ATOM | 2433 | CE | LYS | 369 | 50.831 | 33.502 | 66.996 | 1.00 40.47 |
| ATOM | 2434 | NZ | LYS | 369 | 50.244 | 34.711 | 67.648 | 1.00 43.23 |
| ATOM | 2435 | C | LYS | 369 | 49.964 | 30.320 | 61.584 | 1.00 28.08 |
| ATOM | 2436 | O | LYS | 369 | 48.788 | 29.961 | 61.645 | 1.00 29.11 |
| ATOM | 2437 | N | SER | 370 | 50.594 | 30.498 | 60.426 | 1.00 27.36 |
| ATOM | 2438 | CA | SER | 370 | 49.904 | 30.288 | 59.151 | 1.00 26.35 |
| ATOM | 2439 | CB | SER | 370 | 50.774 | 30.764 | 57.977 | 1.00 24.78 |
| ATOM | 2440 | OG | SER | 370 | 50.954 | 32.171 | 57.991 | 1.00 22.65 |
| ATOM | 2441 | C | SER | 370 | 49.524 | 28.830 | 58.908 | 1.00 27.44 |
| ATOM | 2442 | O | SER | 370 | 50.158 | 27.911 | 59.430 | 1.00 27.46 |
| ATOM | 2443 | N | MET | 371 | 48.475 | 28.628 | 58.117 | 1.00 27.03 |
| ATOM | 2444 | CA | MET | 371 | 48.029 | 27.288 | 57.749 | 1.00 27.37 |
| ATOM | 2445 | CB | MET | 371 | 46.524 | 27.117 | 57.973 | 1.00 25.87 |
| ATOM | 2446 | CG | MET | 371 | 46.028 | 25.700 | 57.695 | 1.00 23.55 |
| ATOM | 2447 | SD | MET | 371 | 44.257 | 25.591 | 57.365 | 1.00 24.62 |
| ATOM | 2448 | CE | MET | 371 | 44.241 | 25.865 | 55.602 | 1.00 23.28 |
| ATOM | 2449 | C | MET | 371 | 48.336 | 27.186 | 56.259 | 1.00 28.01 |
| ATOM | 2450 | O | MET | 371 | 47.493 | 27.511 | 55.419 | 1.00 27.83 |
| ATOM | 2451 | N | LEU | 372 | 49.547 | 26.742 | 55.935 | 1.00 28.67 |
| ATOM | 2452 | CA | LEU | 372 | 49.976 | 26.636 | 54.544 | 1.00 27.98 |
| ATOM | 2453 | CB | LEU | 372 | 51.488 | 26.849 | 54.463 | 1.00 26.09 |
| ATOM | 2454 | CG | LEU | 372 | 52.000 | 28.142 | 55.109 | 1.00 26.99 |
| ATOM | 2455 | CD1 | LEU | 372 | 53.516 | 28.186 | 55.014 | 1.00 25.50 |
| ATOM | 2456 | CD2 | LEU | 372 | 51.382 | 29.362 | 54.421 | 1.00 25.38 |
| ATOM | 2457 | C | LEU | 372 | 49.597 | 25.325 | 53.861 | 1.00 29.45 |
| ATOM | 2458 | O | LEU | 372 | 49.835 | 25.154 | 52.664 | 1.00 29.43 |
| ATOM | 2459 | N | GLU | 373 | 49.002 | 24.407 | 54.618 | 1.00 30.71 |
| ATOM | 2460 | CA | GLU | 373 | 48.589 | 23.115 | 54.074 | 1.00 33.88 |
| ATOM | 2461 | CB | GLU | 373 | 49.576 | 22.012 | 54.460 | 1.00 36.25 |
| ATOM | 2462 | CG | GLU | 373 | 51.022 | 22.277 | 54.127 | 1.00 43.43 |
| ATOM | 2463 | CD | GLU | 373 | 51.929 | 21.197 | 54.686 | 1.00 46.04 |
| ATOM | 2464 | OE1 | GLU | 373 | 51.953 | 21.025 | 55.924 | 1.00 49.71 |
| ATOM | 2465 | OE2 | GLU | 373 | 52.609 | 20.515 | 53.892 | 1.00 48.87 |
| ATOM | 2466 | C | GLU | 373 | 47.230 | 22.718 | 54.622 | 1.00 33.50 |
| ATOM | 2467 | O | GLU | 373 | 46.854 | 23.115 | 55.726 | 1.00 32.75 |
| ATOM | 2468 | N | LYS | 374 | 46.506 | 21.917 | 53.851 | 1.00 33.65 |
| ATOM | 2469 | CA | LYS | 374 | 45.200 | 21.429 | 54.271 | 1.00 35.26 |
| ATOM | 2470 | CB | LYS | 374 | 44.523 | 20.687 | 53.121 | 1.00 35.25 |
| ATOM | 2471 | CG | LYS | 374 | 43.155 | 20.120 | 53.456 | 1.00 35.45 |
| ATOM | 2472 | CD | LYS | 374 | 42.518 | 19.531 | 52.208 | 1.00 35.40 |
| ATOM | 2473 | CE | LYS | 374 | 41.132 | 18.994 | 52.483 | 1.00 36.09 |
| ATOM | 2474 | NZ | LYS | 374 | 40.514 | 18.496 | 51.224 | 1.00 36.76 |
| ATOM | 2475 | C | LYS | 374 | 45.432 | 20.474 | 55.435 | 1.00 36.99 |
| ATOM | 2476 | O | LYS | 374 | 46.171 | 19.496 | 55.307 | 1.00 37.40 |
| ATOM | 2477 | N | PRO | 375 | 44.813 | 20.747 | 56.591 | 1.00 38.18 |
| ATOM | 2478 | CD | PRO | 375 | 44.031 | 21.941 | 56.951 | 1.00 38.24 |
| ATOM | 2479 | CA | PRO | 375 | 44.992 | 19.873 | 57.753 | 1.00 40.05 |
| ATOM | 2480 | CB | PRO | 375 | 44.133 | 20.545 | 58.822 | 1.00 39.71 |
| ATOM | 2481 | CG | PRO | 375 | 44.209 | 21.993 | 58.451 | 1.00 39.38 |
| ATOM | 2482 | C | PRO | 375 | 44.570 | 18.427 | 57.509 | 1.00 41.45 |
| ATOM | 2483 | O | PRO | 375 | 43.595 | 18.159 | 56.808 | 1.00 40.45 |
| ATOM | 2484 | N | THR | 376 | 45.330 | 17.502 | 58.084 | 1.00 43.87 |
| ATOM | 2485 | CA | THR | 376 | 45.042 | 16.077 | 57.989 | 1.00 46.82 |
| ATOM | 2486 | CB | THR | 376 | 46.331 | 15.268 | 57.766 | 1.00 47.11 |
| ATOM | 2487 | OG1 | THR | 376 | 47.272 | 15.569 | 58.804 | 1.00 48.76 |
| ATOM | 2488 | CG2 | THR | 376 | 46.946 | 15.622 | 56.425 | 1.00 46.74 |
| ATOM | 2489 | C | THR | 376 | 44.450 | 15.750 | 59.355 | 1.00 48.06 |
| ATOM | 2490 | O | THR | 376 | 44.102 | 14.612 | 59.664 | 1.00 49.50 |
| ATOM | 2491 | N | ASP | 377 | 44.345 | 16.808 | 60.151 | 1.00 49.79 |
| ATOM | 2492 | CA | ASP | 377 | 43.821 | 16.801 | 61.510 | 1.00 50.68 |
| ATOM | 2493 | CB | ASP | 377 | 43.722 | 18.252 | 61.991 | 1.00 51.52 |

TABLE A-continued

| | | | | | | | | |
|---|---|---|---|---|---|---|---|---|
| ATOM | 2494 | CG | ASP | 377 | 44.084 | 18.416 | 63.445 | 1.00 | 53.90 |
| ATOM | 2495 | OD1 | ASP | 377 | 43.505 | 17.705 | 64.293 | 1.00 | 56.14 |
| ATOM | 2496 | OD2 | ASP | 377 | 44.950 | 19.267 | 63.737 | 1.00 | 54.87 |
| ATOM | 2497 | C | ASP | 377 | 42.439 | 16.162 | 61.607 | 1.00 | 50.48 |
| ATOM | 2498 | O | ASP | 377 | 41.919 | 15.965 | 62.705 | 1.00 | 50.57 |
| ATOM | 2499 | N | GLY | 378 | 41.845 | 15.831 | 60.465 | 1.00 | 50.81 |
| ATOM | 2500 | CA | GLY | 378 | 40.504 | 15.280 | 60.486 | 1.00 | 50.66 |
| ATOM | 2501 | C | GLY | 378 | 39.635 | 16.487 | 60.795 | 1.00 | 50.28 |
| ATOM | 2502 | O | GLY | 378 | 38.488 | 16.379 | 61.230 | 1.00 | 51.71 |
| ATOM | 2503 | N | ARG | 379 | 40.231 | 17.653 | 60.560 | 1.00 | 48.17 |
| ATOM | 2504 | CA | ARG | 379 | 39.613 | 18.954 | 60.788 | 1.00 | 45.10 |
| ATOM | 2505 | CB | ARG | 379 | 40.688 | 19.934 | 61.261 | 1.00 | 45.50 |
| ATOM | 2506 | CG | ARG | 379 | 40.269 | 20.913 | 62.332 | 1.00 | 44.65 |
| ATOM | 2507 | CD | ARG | 379 | 41.270 | 22.052 | 62.408 | 1.00 | 44.87 |
| ATOM | 2508 | NE | ARG | 379 | 42.651 | 21.577 | 62.397 | 1.00 | 44.55 |
| ATOM | 2509 | CZ | ARG | 379 | 43.705 | 22.356 | 62.170 | 1.00 | 44.28 |
| ATOM | 2510 | NH1 | ARG | 379 | 43.540 | 23.651 | 61.933 | 1.00 | 42.73 |
| ATOM | 2511 | NH2 | ARG | 379 | 44.927 | 21.841 | 62.174 | 1.00 | 44.56 |
| ATOM | 2512 | C | ARG | 379 | 39.013 | 19.464 | 59.477 | 1.00 | 41.98 |
| ATOM | 2513 | O | ARG | 379 | 39.522 | 19.167 | 58.398 | 1.00 | 42.26 |
| ATOM | 2514 | N | GLU | 380 | 37.932 | 20.227 | 59.573 | 1.00 | 38.86 |
| ATOM | 2515 | CA | GLU | 380 | 37.286 | 20.788 | 58.390 | 1.00 | 35.74 |
| ATOM | 2516 | CB | GLU | 380 | 35.767 | 20.654 | 58.508 | 1.00 | 37.72 |
| ATOM | 2517 | CG | GLU | 380 | 35.008 | 20.940 | 57.225 | 1.00 | 41.39 |
| ATOM | 2518 | CD | GLU | 380 | 34.671 | 19.679 | 56.439 | 1.00 | 44.40 |
| ATOM | 2519 | OE1 | GLU | 380 | 33.991 | 18.792 | 57.003 | 1.00 | 45.17 |
| ATOM | 2520 | OE2 | GLU | 380 | 35.075 | 19.577 | 55.260 | 1.00 | 43.36 |
| ATOM | 2521 | C | GLU | 380 | 37.681 | 22.266 | 58.330 | 1.00 | 31.68 |
| ATOM | 2522 | O | GLU | 380 | 37.643 | 22.958 | 59.346 | 1.00 | 28.60 |
| ATOM | 2523 | N | VAL | 381 | 38.066 | 22.749 | 57.150 | 1.00 | 29.12 |
| ATOM | 2524 | CA | VAL | 381 | 38.480 | 24.145 | 57.013 | 1.00 | 25.82 |
| ATOM | 2525 | CB | VAL | 381 | 40.022 | 24.281 | 57.096 | 1.00 | 26.30 |
| ATOM | 2526 | CG1 | VAL | 381 | 40.546 | 23.600 | 58.347 | 1.00 | 26.29 |
| ATOM | 2527 | CG2 | VAL | 381 | 40.669 | 23.673 | 55.855 | 1.00 | 26.07 |
| ATOM | 2528 | C | VAL | 381 | 38.041 | 24.806 | 55.708 | 1.00 | 25.16 |
| ATOM | 2529 | O | VAL | 381 | 37.528 | 24.150 | 54.799 | 1.00 | 24.70 |
| ATOM | 2530 | N | VAL | 382 | 38.238 | 26.120 | 55.637 | 1.00 | 22.13 |
| ATOM | 2531 | CA | VAL | 382 | 37.929 | 26.879 | 54.433 | 1.00 | 22.57 |
| ATOM | 2532 | CB | VAL | 382 | 37.533 | 28.341 | 54.764 | 1.00 | 23.19 |
| ATOM | 2533 | CG1 | VAL | 382 | 37.289 | 29.122 | 53.479 | 1.00 | 22.36 |
| ATOM | 2534 | CG2 | VAL | 382 | 36.279 | 28.355 | 55.636 | 1.00 | 21.95 |
| ATOM | 2535 | C | VAL | 382 | 39.254 | 26.864 | 53.679 | 1.00 | 22.05 |
| ATOM | 2536 | O | VAL | 382 | 40.199 | 27.551 | 54.056 | 1.00 | 22.15 |
| ATOM | 2537 | N | CYS | 383 | 39.331 | 26.059 | 52.626 | 1.00 | 22.87 |
| ATOM | 2538 | CA | CYS | 383 | 40.561 | 25.937 | 51.857 | 1.00 | 22.31 |
| ATOM | 2539 | C | CYS | 383 | 40.946 | 27.106 | 50.957 | 1.00 | 22.33 |
| ATOM | 2540 | O | CYS | 383 | 42.134 | 27.335 | 50.723 | 1.00 | 22.41 |
| ATOM | 2541 | CB | CYS | 383 | 40.521 | 24.664 | 51.018 | 1.00 | 23.58 |
| ATOM | 2542 | SG | CYS | 383 | 41.168 | 23.197 | 51.879 | 1.00 | 25.88 |
| ATOM | 2543 | N | HIS | 384 | 39.958 | 27.841 | 50.456 | 1.00 | 21.14 |
| ATOM | 2544 | CA | HIS | 384 | 40.231 | 28.961 | 49.558 | 1.00 | 19.98 |
| ATOM | 2545 | CB | HIS | 384 | 38.954 | 29.761 | 49.286 | 1.00 | 17.69 |
| ATOM | 2546 | CG | HIS | 384 | 39.075 | 30.695 | 48.123 | 1.00 | 16.80 |
| ATOM | 2547 | CD2 | HIS | 384 | 39.392 | 32.009 | 48.067 | 1.00 | 16.85 |
| ATOM | 2548 | ND1 | HIS | 384 | 38.954 | 30.273 | 46.816 | 1.00 | 17.45 |
| ATOM | 2549 | CE1 | HIS | 384 | 39.196 | 31.287 | 46.004 | 1.00 | 17.61 |
| ATOM | 2550 | NE2 | HIS | 384 | 39.466 | 32.352 | 46.737 | 1.00 | 20.78 |
| ATOM | 2551 | C | HIS | 384 | 41.309 | 29.884 | 50.124 | 1.00 | 19.92 |
| ATOM | 2552 | O | HIS | 384 | 41.173 | 30.412 | 51.226 | 1.00 | 19.94 |
| ATOM | 2553 | N | ALA | 385 | 42.376 | 30.080 | 49.355 | 1.00 | 19.69 |
| ATOM | 2554 | CA | ALA | 385 | 43.497 | 30.917 | 49.779 | 1.00 | 18.75 |
| ATOM | 2555 | CB | ALA | 385 | 44.529 | 31.007 | 48.657 | 1.00 | 16.28 |
| ATOM | 2556 | C | ALA | 385 | 43.110 | 32.322 | 50.228 | 1.00 | 17.94 |
| ATOM | 2557 | O | ALA | 385 | 42.298 | 32.990 | 49.589 | 1.00 | 16.36 |
| ATOM | 2558 | N | SER | 386 | 43.708 | 32.769 | 51.328 | 1.00 | 19.03 |
| ATOM | 2559 | CA | SER | 386 | 43.450 | 34.110 | 51.847 | 1.00 | 19.74 |
| ATOM | 2560 | CB | SER | 386 | 42.098 | 34.163 | 52.581 | 1.00 | 20.01 |
| ATOM | 2561 | OG | SER | 386 | 42.041 | 33.244 | 53.656 | 1.00 | 24.98 |
| ATOM | 2562 | C | SER | 386 | 44.576 | 34.584 | 52.767 | 1.00 | 19.49 |
| ATOM | 2563 | O | SER | 386 | 45.305 | 33.775 | 53.355 | 1.00 | 20.16 |
| ATOM | 2564 | N | ALA | 387 | 44.721 | 35.903 | 52.860 | 1.00 | 19.32 |
| ATOM | 2565 | CA | ALA | 387 | 45.744 | 36.541 | 53.682 | 1.00 | 18.05 |
| ATOM | 2566 | CB | ALA | 387 | 46.571 | 37.502 | 52.840 | 1.00 | 18.53 |
| ATOM | 2567 | C | ALA | 387 | 45.048 | 37.292 | 54.804 | 1.00 | 19.41 |
| ATOM | 2568 | O | ALA | 387 | 44.006 | 37.922 | 54.594 | 1.00 | 18.50 |
| ATOM | 2569 | N | TRP | 388 | 45.641 | 37.243 | 55.988 | 1.00 | 18.57 |
| ATOM | 2570 | CA | TRP | 388 | 45.043 | 37.862 | 57.157 | 1.00 | 20.63 |
| ATOM | 2571 | CB | TRP | 388 | 44.672 | 36.764 | 58.158 | 1.00 | 20.94 |
| ATOM | 2572 | CG | TRP | 388 | 43.693 | 35.759 | 57.626 | 1.00 | 20.63 |
| ATOM | 2573 | CD2 | TRP | 388 | 42.423 | 35.424 | 58.195 | 1.00 | 20.38 |

TABLE A-continued

| | | | | | | | | |
|---|---|---|---|---|---|---|---|---|
| ATOM | 2574 | CE2 | TRP | 388 | 41.847 | 34.427 | 57.374 | 1.00 20.45 |
| ATOM | 2575 | CE3 | TRP | 388 | 41.715 | 35.872 | 59.321 | 1.00 20.78 |
| ATOM | 2576 | CD1 | TRP | 388 | 43.834 | 34.974 | 56.513 | 1.00 21.13 |
| ATOM | 2577 | NE1 | TRP | 388 | 42.728 | 34.171 | 56.356 | 1.00 19.97 |
| ATOM | 2578 | CZ2 | TRP | 388 | 40.591 | 33.867 | 57.645 | 1.00 21.53 |
| ATOM | 2579 | CZ3 | TRP | 388 | 40.464 | 35.315 | 59.590 | 1.00 22.62 |
| ATOM | 2580 | CH2 | TRP | 388 | 39.917 | 34.323 | 58.754 | 1.00 22.52 |
| ATOM | 2581 | C | TRP | 388 | 45.873 | 38.923 | 57.877 | 1.00 21.09 |
| ATOM | 2582 | O | TRP | 388 | 47.062 | 38.734 | 58.148 | 1.00 20.91 |
| ATOM | 2583 | N | ASP | 389 | 45.222 | 40.040 | 58.183 | 1.00 20.21 |
| ATOM | 2584 | CA | ASP | 389 | 45.845 | 41.127 | 58.922 | 1.00 20.18 |
| ATOM | 2585 | CB | ASP | 389 | 45.577 | 42.472 | 58.241 | 1.00 18.75 |
| ATOM | 2586 | CG | ASP | 389 | 46.327 | 43.615 | 58.900 | 1.00 19.53 |
| ATOM | 2587 | OD1 | ASP | 389 | 46.749 | 43.451 | 60.065 | 1.00 19.53 |
| ATOM | 2588 | OD2 | ASP | 389 | 46.492 | 44.676 | 58.261 | 1.00 18.57 |
| ATOM | 2589 | C | ASP | 389 | 45.140 | 41.091 | 60.283 | 1.00 21.39 |
| ATOM | 2590 | O | ASP | 389 | 43.913 | 41.234 | 60.350 | 1.00 19.21 |
| ATOM | 2591 | N | PHE | 390 | 45.894 | 40.875 | 61.358 | 1.00 21.15 |
| ATOM | 2592 | CA | PHE | 390 | 45.286 | 40.819 | 62.687 | 1.00 23.78 |
| ATOM | 2593 | CB | PHE | 390 | 45.959 | 39.741 | 63.546 | 1.00 22.15 |
| ATOM | 2594 | CG | PHE | 390 | 45.567 | 38.341 | 63.165 | 1.00 23.26 |
| ATOM | 2595 | CD1 | PHE | 390 | 46.029 | 37.771 | 61.983 | 1.00 21.17 |
| ATOM | 2596 | CD2 | PHE | 390 | 44.707 | 37.604 | 63.974 | 1.00 23.14 |
| ATOM | 2597 | CE1 | PHE | 390 | 45.640 | 36.490 | 61.608 | 1.00 22.67 |
| ATOM | 2598 | CE2 | PHE | 390 | 44.310 | 36.321 | 63.610 | 1.00 25.19 |
| ATOM | 2599 | CZ | PHE | 390 | 44.780 | 35.761 | 62.420 | 1.00 24.11 |
| ATOM | 2600 | C | PHE | 390 | 45.289 | 42.159 | 63.414 | 1.00 24.86 |
| ATOM | 2601 | O | PHE | 390 | 45.079 | 42.226 | 64.627 | 1.00 26.08 |
| ATOM | 2602 | N | TYR | 391 | 45.529 | 43.218 | 62.649 | 1.00 26.25 |
| ATOM | 2603 | CA | TYR | 391 | 45.535 | 44.597 | 63.133 | 1.00 29.34 |
| ATOM | 2604 | CB | TYR | 391 | 44.097 | 45.083 | 63.329 | 1.00 32.35 |
| ATOM | 2605 | CG | TYR | 391 | 43.174 | 44.734 | 62.188 | 1.00 36.14 |
| ATOM | 2606 | CD1 | TYR | 391 | 42.490 | 43.521 | 62.172 | 1.00 38.33 |
| ATOM | 2607 | CE1 | TYR | 391 | 41.645 | 43.185 | 61.126 | 1.00 41.84 |
| ATOM | 2608 | CD2 | TYR | 391 | 42.992 | 45.609 | 61.118 | 1.00 39.05 |
| ATOM | 2609 | CE2 | TYR | 391 | 42.148 | 45.281 | 60.059 | 1.00 42.44 |
| ATOM | 2610 | CZ | TYR | 391 | 41.477 | 44.068 | 60.074 | 1.00 42.85 |
| ATOM | 2611 | OH | TYR | 391 | 40.630 | 43.737 | 59.042 | 1.00 48.25 |
| ATOM | 2612 | C | TYR | 391 | 46.334 | 44.960 | 64.382 | 1.00 29.54 |
| ATOM | 2613 | O | TYR | 391 | 45.897 | 45.802 | 65.166 | 1.00 30.88 |
| ATOM | 2614 | N | ASN | 392 | 47.492 | 44.342 | 64.583 | 1.00 28.09 |
| ATOM | 2615 | CA | ASN | 392 | 48.317 | 44.697 | 65.732 | 1.00 26.46 |
| ATOM | 2616 | CB | ASN | 392 | 48.375 | 43.554 | 66.762 | 1.00 25.72 |
| ATOM | 2617 | CG | ASN | 392 | 49.069 | 42.311 | 66.238 | 1.00 24.13 |
| ATOM | 2618 | OD1 | ASN | 392 | 49.450 | 42.234 | 65.074 | 1.00 19.92 |
| ATOM | 2619 | ND2 | ASN | 392 | 49.232 | 41.324 | 67.110 | 1.00 24.99 |
| ATOM | 2620 | C | ASN | 392 | 49.703 | 45.042 | 65.208 | 1.00 26.86 |
| ATOM | 2621 | O | ASN | 392 | 50.630 | 45.301 | 65.974 | 1.00 26.07 |
| ATOM | 2622 | N | GLY | 393 | 49.820 | 45.051 | 63.880 | 1.00 26.09 |
| ATOM | 2623 | CA | GLY | 393 | 51.075 | 45.371 | 63.225 | 1.00 24.15 |
| ATOM | 2624 | C | GLY | 393 | 52.155 | 44.325 | 63.404 | 1.00 24.36 |
| ATOM | 2625 | O | GLY | 393 | 53.313 | 44.560 | 63.061 | 1.00 25.32 |
| ATOM | 2626 | N | LYS | 394 | 51.784 | 43.159 | 63.916 | 1.00 23.94 |
| ATOM | 2627 | CA | LYS | 394 | 52.763 | 42.107 | 64.147 | 1.00 26.37 |
| ATOM | 2628 | CB | LYS | 394 | 53.069 | 42.017 | 65.645 | 1.00 29.65 |
| ATOM | 2629 | CG | LYS | 394 | 54.522 | 42.251 | 65.990 | 1.00 35.63 |
| ATOM | 2630 | CD | LYS | 394 | 54.954 | 43.660 | 65.631 | 1.00 38.94 |
| ATOM | 2631 | CE | LYS | 394 | 54.438 | 44.665 | 66.640 | 1.00 42.85 |
| ATOM | 2632 | NZ | LYS | 394 | 55.031 | 44.415 | 67.988 | 1.00 44.66 |
| ATOM | 2633 | C | LYS | 394 | 52.336 | 40.732 | 63.647 | 1.00 25.74 |
| ATOM | 2634 | O | LYS | 394 | 53.145 | 39.984 | 63.097 | 1.00 26.30 |
| ATOM | 2635 | N | ASP | 395 | 51.062 | 40.413 | 63.839 | 1.00 24.66 |
| ATOM | 2636 | CA | ASP | 395 | 50.514 | 39.117 | 63.461 | 1.00 24.69 |
| ATOM | 2637 | CB | ASP | 395 | 49.529 | 38.674 | 64.549 | 1.00 22.82 |
| ATOM | 2638 | CG | ASP | 395 | 49.088 | 37.237 | 64.402 | 1.00 24.52 |
| ATOM | 2639 | OD1 | ASP | 395 | 49.389 | 36.602 | 63.368 | 1.00 24.94 |
| ATOM | 2640 | OD2 | ASP | 395 | 48.424 | 36.738 | 65.333 | 1.00 27.00 |
| ATOM | 2641 | C | ASP | 395 | 49.830 | 39.102 | 62.086 | 1.00 25.11 |
| ATOM | 2642 | O | ASP | 395 | 48.725 | 39.631 | 61.919 | 1.00 23.47 |
| ATOM | 2643 | N | PHE | 396 | 50.498 | 38.498 | 61.106 | 1.00 24.32 |
| ATOM | 2644 | CA | PHE | 396 | 49.955 | 38.383 | 59.750 | 1.00 23.41 |
| ATOM | 2645 | CB | PHE | 396 | 50.783 | 39.188 | 58.743 | 1.00 23.60 |
| ATOM | 2646 | CG | PHE | 396 | 51.136 | 40.571 | 59.203 | 1.00 24.38 |
| ATOM | 2647 | CD1 | PHE | 396 | 52.341 | 40.813 | 59.858 | 1.00 25.69 |
| ATOM | 2648 | CD2 | PHE | 396 | 50.274 | 41.641 | 58.965 | 1.00 25.33 |
| ATOM | 2649 | CE1 | PHE | 396 | 52.687 | 42.104 | 60.267 | 1.00 23.83 |
| ATOM | 2650 | CE2 | PHE | 396 | 50.611 | 42.934 | 59.371 | 1.00 23.41 |
| ATOM | 2651 | CZ | PHE | 396 | 51.821 | 43.164 | 60.023 | 1.00 23.93 |
| ATOM | 2652 | C | PHE | 396 | 50.027 | 36.910 | 59.379 | 1.00 23.79 |
| ATOM | 2653 | O | PHE | 396 | 51.023 | 36.246 | 59.670 | 1.00 24.61 |

TABLE A-continued

| | | | | | | | | |
|---|---|---|---|---|---|---|---|---|
| ATOM | 2654 | N | ARG | 397 | 48.984 | 36.394 | 58.736 | 1.00 | 23.34 |
| ATOM | 2655 | CA | ARG | 397 | 48.973 | 34.984 | 58.371 | 1.00 | 21.97 |
| ATOM | 2656 | CB | ARG | 397 | 48.245 | 34.166 | 59.443 | 1.00 | 22.90 |
| ATOM | 2657 | CG | ARG | 397 | 48.555 | 34.552 | 60.881 | 1.00 | 23.65 |
| ATOM | 2658 | CD | ARG | 397 | 47.710 | 33.717 | 61.832 | 1.00 | 24.02 |
| ATOM | 2659 | NE | ARG | 397 | 47.685 | 34.268 | 63.183 | 1.00 | 24.58 |
| ATOM | 2660 | CZ | ARG | 397 | 46.977 | 33.755 | 64.184 | 1.00 | 25.68 |
| ATOM | 2661 | NH1 | ARG | 397 | 46.235 | 32.672 | 63.988 | 1.00 | 24.67 |
| ATOM | 2662 | NH2 | ARG | 397 | 46.998 | 34.333 | 65.377 | 1.00 | 25.68 |
| ATOM | 2663 | C | ARG | 397 | 48.312 | 34.679 | 57.035 | 1.00 | 22.32 |
| ATOM | 2664 | O | ARG | 397 | 47.522 | 35.468 | 56.507 | 1.00 | 20.61 |
| ATOM | 2665 | N | ILE | 398 | 48.636 | 33.504 | 56.505 | 1.00 | 22.29 |
| ATOM | 2666 | CA | ILE | 398 | 48.057 | 33.029 | 55.260 | 1.00 | 20.95 |
| ATOM | 2667 | CB | ILE | 398 | 49.137 | 32.891 | 54.154 | 1.00 | 20.55 |
| ATOM | 2668 | CG2 | ILE | 398 | 48.629 | 32.009 | 53.016 | 1.00 | 21.09 |
| ATOM | 2669 | CG1 | ILE | 398 | 49.502 | 34.282 | 53.625 | 1.00 | 18.02 |
| ATOM | 2670 | CD1 | ILE | 398 | 50.575 | 34.283 | 52.548 | 1.00 | 17.26 |
| ATOM | 2671 | C | ILE | 398 | 47.400 | 31.679 | 55.544 | 1.00 | 21.59 |
| ATOM | 2672 | O | ILE | 398 | 47.938 | 30.862 | 56.300 | 1.00 | 21.62 |
| ATOM | 2673 | N | LYS | 399 | 46.214 | 31.478 | 54.971 | 1.00 | 20.68 |
| ATOM | 2674 | CA | LYS | 399 | 45.453 | 30.239 | 55.115 | 1.00 | 19.59 |
| ATOM | 2675 | CB | LYS | 399 | 44.115 | 30.495 | 55.818 | 1.00 | 19.25 |
| ATOM | 2676 | CG | LYS | 399 | 43.236 | 29.248 | 55.912 | 1.00 | 20.50 |
| ATOM | 2677 | CD | LYS | 399 | 41.796 | 29.585 | 56.296 | 1.00 | 20.84 |
| ATOM | 2678 | CE | LYS | 399 | 41.143 | 30.517 | 55.274 | 1.00 | 19.03 |
| ATOM | 2679 | NZ | LYS | 399 | 41.207 | 29.974 | 53.882 | 1.00 | 17.95 |
| ATOM | 2680 | C | LYS | 399 | 45.188 | 29.723 | 53.704 | 1.00 | 20.32 |
| ATOM | 2681 | O | LYS | 399 | 44.379 | 30.291 | 52.966 | 1.00 | 17.80 |
| ATOM | 2682 | N | GLN | 400 | 45.857 | 28.638 | 53.335 | 1.00 | 19.73 |
| ATOM | 2683 | CA | GLN | 400 | 45.716 | 28.092 | 51.993 | 1.00 | 19.81 |
| ATOM | 2684 | CB | GLN | 400 | 46.701 | 28.819 | 51.074 | 1.00 | 20.96 |
| ATOM | 2685 | CG | GLN | 400 | 46.652 | 28.439 | 49.606 | 1.00 | 22.65 |
| ATOM | 2686 | CD | GLN | 400 | 47.679 | 29.200 | 48.788 | 1.00 | 23.34 |
| ATOM | 2687 | OE1 | GLN | 400 | 47.979 | 30.360 | 49.073 | 1.00 | 23.98 |
| ATOM | 2688 | NE2 | GLN | 400 | 48.213 | 28.556 | 47.757 | 1.00 | 25.85 |
| ATOM | 2689 | C | GLN | 400 | 46.013 | 26.601 | 51.986 | 1.00 | 20.97 |
| ATOM | 2690 | O | GLN | 400 | 47.011 | 26.173 | 52.559 | 1.00 | 19.21 |
| ATOM | 2691 | N | CYS | 401 | 45.148 | 25.810 | 51.356 | 1.00 | 22.51 |
| ATOM | 2692 | CA | CYS | 401 | 45.389 | 24.372 | 51.268 | 1.00 | 24.18 |
| ATOM | 2693 | C | CYS | 401 | 46.241 | 24.204 | 50.017 | 1.00 | 24.54 |
| ATOM | 2694 | O | CYS | 401 | 45.795 | 23.703 | 48.982 | 1.00 | 24.83 |
| ATOM | 2695 | CB | CYS | 401 | 44.077 | 23.602 | 51.144 | 1.00 | 24.18 |
| ATOM | 2696 | SG | CYS | 401 | 42.962 | 23.853 | 52.560 | 1.00 | 26.68 |
| ATOM | 2697 | N | THR | 402 | 47.481 | 24.653 | 50.145 | 1.00 | 23.39 |
| ATOM | 2698 | CA | THR | 402 | 48.455 | 24.649 | 49.072 | 1.00 | 23.83 |
| ATOM | 2699 | CB | THR | 402 | 49.761 | 25.296 | 49.553 | 1.00 | 24.60 |
| ATOM | 2700 | OG1 | THR | 402 | 49.458 | 26.532 | 50.214 | 1.00 | 24.98 |
| ATOM | 2701 | CG2 | THR | 402 | 50.694 | 25.564 | 48.377 | 1.00 | 24.72 |
| ATOM | 2702 | C | THR | 402 | 48.789 | 23.295 | 48.468 | 1.00 | 23.55 |
| ATOM | 2703 | O | THR | 402 | 49.037 | 22.323 | 49.178 | 1.00 | 22.36 |
| ATOM | 2704 | N | THR | 403 | 48.790 | 23.250 | 47.142 | 1.00 | 24.22 |
| ATOM | 2705 | CA | THR | 403 | 49.142 | 22.044 | 46.407 | 1.00 | 25.66 |
| ATOM | 2706 | CB | THR | 403 | 48.096 | 21.716 | 45.323 | 1.00 | 26.94 |
| ATOM | 2707 | OG1 | THR | 403 | 46.879 | 21.298 | 45.953 | 1.00 | 31.08 |
| ATOM | 2708 | CG2 | THR | 403 | 48.589 | 20.597 | 44.421 | 1.00 | 30.68 |
| ATOM | 2709 | C | THR | 403 | 50.482 | 22.350 | 45.752 | 1.00 | 24.67 |
| ATOM | 2710 | O | THR | 403 | 50.747 | 23.494 | 45.377 | 1.00 | 24.35 |
| ATOM | 2711 | N | VAL | 404 | 51.329 | 21.337 | 45.618 | 1.00 | 25.92 |
| ATOM | 2712 | CA | VAL | 404 | 52.644 | 21.533 | 45.021 | 1.00 | 25.04 |
| ATOM | 2713 | CB | VAL | 404 | 53.648 | 20.485 | 45.549 | 1.00 | 25.96 |
| ATOM | 2714 | CG1 | VAL | 404 | 55.024 | 20.725 | 44.949 | 1.00 | 24.79 |
| ATOM | 2715 | CG2 | VAL | 404 | 53.716 | 20.557 | 47.068 | 1.00 | 24.67 |
| ATOM | 2716 | C | VAL | 404 | 52.632 | 21.494 | 43.493 | 1.00 | 25.52 |
| ATOM | 2717 | O | VAL | 404 | 52.737 | 20.429 | 42.881 | 1.00 | 26.04 |
| ATOM | 2718 | N | ASN | 405 | 52.491 | 22.671 | 42.893 | 1.00 | 24.32 |
| ATOM | 2719 | CA | ASN | 405 | 52.490 | 22.835 | 41.440 | 1.00 | 24.14 |
| ATOM | 2720 | CB | ASN | 405 | 51.176 | 22.345 | 40.818 | 1.00 | 24.83 |
| ATOM | 2721 | CG | ASN | 405 | 49.954 | 22.969 | 41.456 | 1.00 | 27.35 |
| ATOM | 2722 | OD1 | ASN | 405 | 49.858 | 24.187 | 41.591 | 1.00 | 29.21 |
| ATOM | 2723 | ND2 | ASN | 405 | 49.004 | 22.132 | 41.842 | 1.00 | 28.69 |
| ATOM | 2724 | C | ASN | 405 | 52.702 | 24.311 | 41.133 | 1.00 | 24.79 |
| ATOM | 2725 | O | ASN | 405 | 52.667 | 25.150 | 42.041 | 1.00 | 22.13 |
| ATOM | 2726 | N | LEU | 406 | 52.922 | 24.629 | 39.862 | 1.00 | 22.38 |
| ATOM | 2727 | CA | LEU | 406 | 53.167 | 26.005 | 39.459 | 1.00 | 24.32 |
| ATOM | 2728 | CB | LEU | 406 | 53.582 | 26.056 | 37.986 | 1.00 | 24.24 |
| ATOM | 2729 | CG | LEU | 406 | 53.912 | 27.439 | 37.417 | 1.00 | 26.51 |
| ATOM | 2730 | CD1 | LEU | 406 | 54.969 | 28.127 | 38.280 | 1.00 | 25.09 |
| ATOM | 2731 | CD2 | LEU | 406 | 54.403 | 27.288 | 35.980 | 1.00 | 27.04 |
| ATOM | 2732 | C | LEU | 406 | 51.978 | 26.931 | 39.691 | 1.00 | 24.77 |
| ATOM | 2733 | O | LEU | 406 | 52.152 | 28.082 | 40.082 | 1.00 | 24.88 |

TABLE A-continued

| | | | | | | | | | |
|---|---|---|---|---|---|---|---|---|---|
| ATOM | 2734 | N | GLU | 407 | 50.773 | 26.428 | 39.452 | 1.00 | 24.97 |
| ATOM | 2735 | CA | GLU | 407 | 49.571 | 27.231 | 39.635 | 1.00 | 27.47 |
| ATOM | 2736 | CB | GLU | 407 | 48.334 | 26.392 | 39.285 | 1.00 | 29.90 |
| ATOM | 2737 | CG | GLU | 407 | 47.011 | 27.143 | 39.341 | 1.00 | 33.59 |
| ATOM | 2738 | CD | GLU | 407 | 45.921 | 26.457 | 38.527 | 1.00 | 36.42 |
| ATOM | 2739 | OE1 | GLU | 407 | 45.788 | 25.218 | 38.627 | 1.00 | 36.53 |
| ATOM | 2740 | OE2 | GLU | 407 | 45.193 | 27.159 | 37.791 | 1.00 | 37.68 |
| ATOM | 2741 | C | GLU | 407 | 49.482 | 27.767 | 41.066 | 1.00 | 26.40 |
| ATOM | 2742 | O | GLU | 407 | 49.209 | 28.948 | 41.278 | 1.00 | 27.12 |
| ATOM | 2743 | N | ASP | 408 | 49.729 | 26.901 | 42.043 | 1.00 | 25.56 |
| ATOM | 2744 | CA | ASP | 408 | 49.683 | 27.303 | 43.448 | 1.00 | 26.24 |
| ATOM | 2745 | CB | ASP | 408 | 49.567 | 26.070 | 44.345 | 1.00 | 28.50 |
| ATOM | 2746 | CG | ASP | 408 | 48.160 | 25.857 | 44.850 | 1.00 | 32.70 |
| ATOM | 2747 | OD1 | ASP | 408 | 47.216 | 26.002 | 44.047 | 1.00 | 38.19 |
| ATOM | 2748 | OD2 | ASP | 408 | 47.992 | 25.541 | 46.046 | 1.00 | 36.12 |
| ATOM | 2749 | C | ASP | 408 | 50.895 | 28.132 | 43.866 | 1.00 | 25.11 |
| ATOM | 2750 | O | ASP | 408 | 50.853 | 28.837 | 44.873 | 1.00 | 23.90 |
| ATOM | 2751 | N | LEU | 409 | 51.980 | 28.039 | 43.103 | 1.00 | 22.82 |
| ATOM | 2752 | CA | LEU | 409 | 53.170 | 28.819 | 43.416 | 1.00 | 22.42 |
| ATOM | 2753 | CB | LEU | 409 | 54.349 | 28.401 | 42.532 | 1.00 | 23.11 |
| ATOM | 2754 | CG | LEU | 409 | 55.660 | 29.142 | 42.815 | 1.00 | 23.64 |
| ATOM | 2755 | CD1 | LEU | 409 | 56.084 | 28.889 | 44.253 | 1.00 | 23.67 |
| ATOM | 2756 | CD2 | LEU | 409 | 56.739 | 28.674 | 41.855 | 1.00 | 23.00 |
| ATOM | 2757 | C | LEU | 409 | 52.811 | 30.274 | 43.140 | 1.00 | 21.63 |
| ATOM | 2758 | O | LEU | 409 | 53.165 | 31.175 | 43.906 | 1.00 | 19.27 |
| ATOM | 2759 | N | VAL | 410 | 52.100 | 30.491 | 42.037 | 1.00 | 19.69 |
| ATOM | 2760 | CA | VAL | 410 | 51.664 | 31.829 | 41.666 | 1.00 | 20.55 |
| ATOM | 2761 | CB | VAL | 410 | 50.977 | 31.834 | 40.282 | 1.00 | 21.61 |
| ATOM | 2762 | CG1 | VAL | 410 | 50.409 | 33.215 | 39.983 | 1.00 | 20.73 |
| ATOM | 2763 | CG2 | VAL | 410 | 51.981 | 31.433 | 39.209 | 1.00 | 24.65 |
| ATOM | 2764 | C | VAL | 410 | 50.678 | 32.332 | 42.717 | 1.00 | 19.32 |
| ATOM | 2765 | O | VAL | 410 | 50.747 | 33.485 | 43.138 | 1.00 | 20.39 |
| ATOM | 2766 | N | VAL | 411 | 49.766 | 31.465 | 43.150 | 1.00 | 19.65 |
| ATOM | 2767 | CA | VAL | 411 | 48.790 | 31.858 | 44.163 | 1.00 | 20.22 |
| ATOM | 2768 | CB | VAL | 411 | 47.767 | 30.730 | 44.439 | 1.00 | 20.61 |
| ATOM | 2769 | CG1 | VAL | 411 | 46.824 | 31.137 | 45.578 | 1.00 | 19.72 |
| ATOM | 2770 | CG2 | VAL | 411 | 46.957 | 30.447 | 43.174 | 1.00 | 18.85 |
| ATOM | 2771 | C | VAL | 411 | 49.497 | 32.226 | 45.466 | 1.00 | 21.47 |
| ATOM | 2772 | O | VAL | 411 | 49.085 | 33.150 | 46.171 | 1.00 | 20.05 |
| ATOM | 2773 | N | ALA | 412 | 50.572 | 31.510 | 45.776 | 1.00 | 20.65 |
| ATOM | 2774 | CA | ALA | 412 | 51.332 | 31.781 | 46.989 | 1.00 | 20.54 |
| ATOM | 2775 | CB | ALA | 412 | 52.448 | 30.755 | 47.145 | 1.00 | 20.33 |
| ATOM | 2776 | C | ALA | 412 | 51.912 | 33.196 | 46.935 | 1.00 | 20.50 |
| ATOM | 2777 | O | ALA | 412 | 51.902 | 33.915 | 47.934 | 1.00 | 20.25 |
| ATOM | 2778 | N | HIS | 413 | 52.422 | 33.591 | 45.769 | 1.00 | 19.01 |
| ATOM | 2779 | CA | HIS | 413 | 52.979 | 34.931 | 45.605 | 1.00 | 18.24 |
| ATOM | 2780 | CB | HIS | 413 | 53.653 | 35.084 | 44.236 | 1.00 | 18.06 |
| ATOM | 2781 | CG | HIS | 413 | 55.006 | 34.452 | 44.161 | 1.00 | 17.97 |
| ATOM | 2782 | CD2 | HIS | 413 | 56.243 | 35.001 | 44.109 | 1.00 | 17.44 |
| ATOM | 2783 | ND1 | HIS | 413 | 55.193 | 33.087 | 44.199 | 1.00 | 18.68 |
| ATOM | 2784 | CE1 | HIS | 413 | 56.488 | 32.822 | 44.176 | 1.00 | 17.45 |
| ATOM | 2785 | NE2 | HIS | 413 | 57.146 | 33.965 | 44.123 | 1.00 | 17.19 |
| ATOM | 2786 | C | HIS | 413 | 51.861 | 35.950 | 45.736 | 1.00 | 16.58 |
| ATOM | 2787 | O | HIS | 413 | 52.041 | 37.005 | 46.339 | 1.00 | 15.66 |
| ATOM | 2788 | N | HIS | 414 | 50.708 | 35.623 | 45.158 | 1.00 | 16.88 |
| ATOM | 2789 | CA | HIS | 414 | 49.534 | 36.492 | 45.212 | 1.00 | 16.63 |
| ATOM | 2790 | CB | HIS | 414 | 48.320 | 35.785 | 44.596 | 1.00 | 17.03 |
| ATOM | 2791 | CG | HIS | 414 | 47.034 | 36.539 | 44.760 | 1.00 | 17.66 |
| ATOM | 2792 | CD2 | HIS | 414 | 46.091 | 36.491 | 45.732 | 1.00 | 16.85 |
| ATOM | 2793 | ND1 | HIS | 414 | 46.612 | 37.497 | 43.863 | 1.00 | 17.56 |
| ATOM | 2794 | CE1 | HIS | 414 | 45.463 | 38.005 | 44.275 | 1.00 | 17.61 |
| ATOM | 2795 | NE2 | HIS | 414 | 45.125 | 37.411 | 45.406 | 1.00 | 17.08 |
| ATOM | 2796 | C | HIS | 414 | 49.218 | 36.835 | 46.662 | 1.00 | 16.06 |
| ATOM | 2797 | O | HIS | 414 | 49.070 | 38.006 | 47.017 | 1.00 | 17.09 |
| ATOM | 2798 | N | GLU | 415 | 49.118 | 35.799 | 47.493 | 1.00 | 15.07 |
| ATOM | 2799 | CA | GLU | 415 | 48.807 | 35.964 | 48.910 | 1.00 | 16.06 |
| ATOM | 2800 | CB | GLU | 415 | 48.527 | 34.600 | 49.553 | 1.00 | 16.75 |
| ATOM | 2801 | CG | GLU | 415 | 47.327 | 33.845 | 48.972 | 1.00 | 16.11 |
| ATOM | 2802 | CD | GLU | 415 | 46.013 | 34.599 | 49.145 | 1.00 | 16.59 |
| ATOM | 2803 | OE1 | GLU | 415 | 45.878 | 35.334 | 50.142 | 1.00 | 17.28 |
| ATOM | 2804 | OE2 | GLU | 415 | 45.109 | 34.444 | 48.292 | 1.00 | 15.42 |
| ATOM | 2805 | C | GLU | 415 | 49.920 | 36.679 | 49.676 | 1.00 | 17.92 |
| ATOM | 2806 | O | GLU | 415 | 49.642 | 37.486 | 50.570 | 1.00 | 18.35 |
| ATOM | 2807 | N | MET | 416 | 51.174 | 36.383 | 49.338 | 1.00 | 16.54 |
| ATOM | 2808 | CA | MET | 416 | 52.295 | 37.034 | 50.008 | 1.00 | 17.95 |
| ATOM | 2809 | CB | MET | 416 | 53.619 | 36.392 | 49.583 | 1.00 | 17.54 |
| ATOM | 2810 | CG | MET | 416 | 53.855 | 35.041 | 50.243 | 1.00 | 19.19 |
| ATOM | 2811 | SD | MET | 416 | 54.175 | 35.197 | 52.034 | 1.00 | 21.75 |
| ATOM | 2812 | CE | MET | 416 | 55.966 | 35.333 | 52.015 | 1.00 | 20.55 |
| ATOM | 2813 | C | MET | 416 | 52.280 | 38.522 | 49.670 | 1.00 | 18.12 |

TABLE A-continued

| | | | | | | | | | |
|---|---|---|---|---|---|---|---|---|---|
| ATOM | 2814 | O   | MET | 416 | 52.789 | 39.356 | 50.427 | 1.00 | 15.13 |
| ATOM | 2815 | N   | GLY | 417 | 51.680 | 38.840 | 48.526 | 1.00 | 17.95 |
| ATOM | 2816 | CA  | GLY | 417 | 51.561 | 40.222 | 48.109 | 1.00 | 15.72 |
| ATOM | 2817 | C   | GLY | 417 | 50.621 | 40.942 | 49.066 | 1.00 | 15.92 |
| ATOM | 2818 | O   | GLY | 417 | 50.856 | 42.094 | 49.413 | 1.00 | 14.01 |
| ATOM | 2819 | N   | HIS | 418 | 49.551 | 40.268 | 49.487 | 1.00 | 16.50 |
| ATOM | 2820 | CA  | HIS | 418 | 48.603 | 40.861 | 50.434 | 1.00 | 17.17 |
| ATOM | 2821 | CB  | HIS | 418 | 47.415 | 39.931 | 50.697 | 1.00 | 15.51 |
| ATOM | 2822 | CG  | HIS | 418 | 46.421 | 39.866 | 49.578 | 1.00 | 17.03 |
| ATOM | 2823 | CD2 | HIS | 418 | 45.843 | 38.807 | 48.963 | 1.00 | 15.43 |
| ATOM | 2824 | ND1 | HIS | 418 | 45.848 | 40.991 | 49.022 | 1.00 | 19.32 |
| ATOM | 2825 | CE1 | HIS | 418 | 44.958 | 40.626 | 48.115 | 1.00 | 17.79 |
| ATOM | 2826 | NE2 | HIS | 418 | 44.935 | 39.306 | 48.060 | 1.00 | 17.55 |
| ATOM | 2827 | C   | HIS | 418 | 49.320 | 41.110 | 51.758 | 1.00 | 17.69 |
| ATOM | 2828 | O   | HIS | 418 | 49.163 | 42.167 | 52.370 | 1.00 | 16.65 |
| ATOM | 2829 | N   | ILE | 419 | 50.100 | 40.126 | 52.199 | 1.00 | 16.39 |
| ATOM | 2830 | CA  | ILE | 419 | 50.848 | 40.239 | 53.450 | 1.00 | 18.31 |
| ATOM | 2831 | CB  | ILE | 419 | 51.640 | 38.941 | 53.745 | 1.00 | 17.86 |
| ATOM | 2832 | CG2 | ILE | 419 | 52.498 | 39.115 | 54.995 | 1.00 | 17.98 |
| ATOM | 2833 | CG1 | ILE | 419 | 50.668 | 37.767 | 53.910 | 1.00 | 17.08 |
| ATOM | 2834 | CD1 | ILE | 419 | 49.723 | 37.907 | 55.078 | 1.00 | 16.70 |
| ATOM | 2835 | C   | ILE | 419 | 51.821 | 41.417 | 53.410 | 1.00 | 17.09 |
| ATOM | 2836 | O   | ILE | 419 | 51.988 | 42.127 | 54.403 | 1.00 | 18.17 |
| ATOM | 2837 | N   | GLN | 420 | 52.457 | 41.628 | 52.260 | 1.00 | 17.68 |
| ATOM | 2838 | CA  | GLN | 420 | 53.404 | 42.728 | 52.115 | 1.00 | 16.85 |
| ATOM | 2839 | CB  | GLN | 420 | 54.093 | 42.677 | 50.746 | 1.00 | 17.05 |
| ATOM | 2840 | CG  | GLN | 420 | 55.148 | 43.766 | 50.562 | 1.00 | 17.55 |
| ATOM | 2841 | CD  | GLN | 420 | 56.380 | 43.547 | 51.428 | 1.00 | 18.80 |
| ATOM | 2842 | OE1 | GLN | 420 | 57.049 | 44.501 | 51.824 | 1.00 | 17.97 |
| ATOM | 2843 | NE2 | GLN | 420 | 56.694 | 42.286 | 51.710 | 1.00 | 18.82 |
| ATOM | 2844 | C   | GLN | 420 | 52.671 | 44.054 | 52.274 | 1.00 | 17.71 |
| ATOM | 2845 | O   | GLN | 420 | 53.171 | 44.985 | 52.909 | 1.00 | 17.12 |
| ATOM | 2846 | N   | TYR | 421 | 51.479 | 44.138 | 51.695 | 1.00 | 18.42 |
| ATOM | 2847 | CA  | TYR | 421 | 50.688 | 45.356 | 51.792 | 1.00 | 18.42 |
| ATOM | 2848 | CB  | TYR | 421 | 49.418 | 45.217 | 50.943 | 1.00 | 16.41 |
| ATOM | 2849 | CG  | TYR | 421 | 49.113 | 46.419 | 50.075 | 1.00 | 15.65 |
| ATOM | 2850 | CD1 | TYR | 421 | 48.661 | 46.257 | 48.764 | 1.00 | 14.49 |
| ATOM | 2851 | CE1 | TYR | 421 | 48.335 | 47.352 | 47.973 | 1.00 | 14.23 |
| ATOM | 2852 | CD2 | TYR | 421 | 49.237 | 47.717 | 50.570 | 1.00 | 16.14 |
| ATOM | 2853 | CE2 | TYR | 421 | 48.913 | 48.825 | 49.783 | 1.00 | 15.24 |
| ATOM | 2854 | CZ  | TYR | 421 | 48.459 | 48.633 | 48.486 | 1.00 | 16.86 |
| ATOM | 2855 | OH  | TYR | 421 | 48.108 | 49.718 | 47.703 | 1.00 | 14.61 |
| ATOM | 2856 | C   | TYR | 421 | 50.344 | 45.619 | 53.266 | 1.00 | 19.47 |
| ATOM | 2857 | O   | TYR | 421 | 50.473 | 46.746 | 53.744 | 1.00 | 19.23 |
| ATOM | 2858 | N   | PHE | 422 | 49.928 | 44.577 | 53.986 | 1.00 | 19.13 |
| ATOM | 2859 | CA  | PHE | 422 | 49.591 | 44.716 | 55.407 | 1.00 | 20.97 |
| ATOM | 2860 | CB  | PHE | 422 | 49.260 | 43.353 | 56.029 | 1.00 | 19.61 |
| ATOM | 2861 | CG  | PHE | 422 | 48.029 | 42.690 | 55.463 | 1.00 | 19.85 |
| ATOM | 2862 | CD1 | PHE | 422 | 47.863 | 41.309 | 55.574 | 1.00 | 20.06 |
| ATOM | 2863 | CD2 | PHE | 422 | 47.038 | 43.434 | 54.829 | 1.00 | 18.91 |
| ATOM | 2864 | CE1 | PHE | 422 | 46.731 | 40.675 | 55.058 | 1.00 | 19.40 |
| ATOM | 2865 | CE2 | PHE | 422 | 45.898 | 42.807 | 54.312 | 1.00 | 18.30 |
| ATOM | 2866 | CZ  | PHE | 422 | 45.748 | 41.425 | 54.427 | 1.00 | 18.76 |
| ATOM | 2867 | C   | PHE | 422 | 50.771 | 45.314 | 56.170 | 1.00 | 21.67 |
| ATOM | 2868 | O   | PHE | 422 | 50.619 | 46.274 | 56.923 | 1.00 | 21.52 |
| ATOM | 2869 | N   | MET | 423 | 51.950 | 44.737 | 55.964 | 1.00 | 21.08 |
| ATOM | 2870 | CA  | MET | 423 | 53.153 | 45.196 | 56.644 | 1.00 | 21.47 |
| ATOM | 2871 | CB  | MET | 423 | 54.316 | 44.237 | 56.373 | 1.00 | 21.55 |
| ATOM | 2872 | CG  | MET | 423 | 54.057 | 42.811 | 56.820 | 1.00 | 23.09 |
| ATOM | 2873 | SD  | MET | 423 | 55.572 | 41.828 | 56.883 | 1.00 | 26.45 |
| ATOM | 2874 | CE  | MET | 423 | 55.812 | 41.441 | 55.121 | 1.00 | 20.52 |
| ATOM | 2875 | C   | MET | 423 | 53.560 | 46.610 | 56.257 | 1.00 | 22.13 |
| ATOM | 2876 | O   | MET | 423 | 54.024 | 47.375 | 57.104 | 1.00 | 21.14 |
| ATOM | 2877 | N   | GLN | 424 | 53.381 | 46.957 | 54.985 | 1.00 | 21.08 |
| ATOM | 2878 | CA  | GLN | 424 | 53.747 | 48.281 | 54.499 | 1.00 | 21.09 |
| ATOM | 2879 | CB  | GLN | 424 | 53.668 | 48.326 | 52.967 | 1.00 | 21.81 |
| ATOM | 2880 | CG  | GLN | 424 | 54.783 | 47.570 | 52.238 | 1.00 | 20.30 |
| ATOM | 2881 | CD  | GLN | 424 | 56.145 | 48.214 | 52.419 | 1.00 | 21.34 |
| ATOM | 2882 | OE1 | GLN | 424 | 56.248 | 49.415 | 52.677 | 1.00 | 21.87 |
| ATOM | 2883 | NE2 | GLN | 424 | 57.200 | 47.422 | 52.262 | 1.00 | 20.74 |
| ATOM | 2884 | C   | GLN | 424 | 52.921 | 49.431 | 55.082 | 1.00 | 22.17 |
| ATOM | 2885 | O   | GLN | 424 | 53.460 | 50.514 | 55.319 | 1.00 | 21.22 |
| ATOM | 2886 | N   | TYR | 425 | 51.624 | 49.219 | 55.308 | 1.00 | 21.31 |
| ATOM | 2887 | CA  | TYR | 425 | 50.791 | 50.293 | 55.861 | 1.00 | 20.51 |
| ATOM | 2888 | CB  | TYR | 425 | 49.551 | 50.538 | 54.975 | 1.00 | 18.49 |
| ATOM | 2889 | CG  | TYR | 425 | 48.603 | 49.360 | 54.753 | 1.00 | 18.46 |
| ATOM | 2890 | CD1 | TYR | 425 | 48.144 | 48.581 | 55.820 | 1.00 | 16.90 |
| ATOM | 2891 | CE1 | TYR | 425 | 47.193 | 47.564 | 55.624 | 1.00 | 16.58 |
| ATOM | 2892 | CD2 | TYR | 425 | 48.091 | 49.089 | 53.478 | 1.00 | 16.81 |
| ATOM | 2893 | CE2 | TYR | 425 | 47.139 | 48.083 | 53.272 | 1.00 | 16.87 |

TABLE A-continued

| | | | | | | | | |
|---|---|---|---|---|---|---|---|---|
| ATOM | 2894 | CZ | TYR | 425 | 46.694 | 47.324 | 54.349 | 1.00 | 18.42 |
| ATOM | 2895 | OH | TYR | 425 | 45.744 | 46.342 | 54.150 | 1.00 | 17.95 |
| ATOM | 2896 | C | TYR | 425 | 50.354 | 50.082 | 57.310 | 1.00 | 21.09 |
| ATOM | 2897 | O | TYR | 425 | 49.447 | 50.758 | 57.795 | 1.00 | 21.46 |
| ATOM | 2898 | N | LYS | 426 | 51.018 | 49.162 | 58.003 | 1.00 | 21.85 |
| ATOM | 2899 | CA | LYS | 426 | 50.678 | 48.840 | 59.391 | 1.00 | 24.15 |
| ATOM | 2900 | CB | LYS | 426 | 51.593 | 47.727 | 59.912 | 1.00 | 23.65 |
| ATOM | 2901 | CG | LYS | 426 | 53.048 | 48.138 | 60.077 | 1.00 | 27.12 |
| ATOM | 2902 | CD | LYS | 426 | 53.883 | 46.986 | 60.636 | 1.00 | 29.68 |
| ATOM | 2903 | CE | LYS | 426 | 55.337 | 47.396 | 60.853 | 1.00 | 32.06 |
| ATOM | 2904 | NZ | LYS | 426 | 55.457 | 48.484 | 61.862 | 1.00 | 35.07 |
| ATOM | 2905 | C | LYS | 426 | 50.708 | 50.007 | 60.383 | 1.00 | 24.45 |
| ATOM | 2906 | O | LYS | 426 | 50.117 | 49.914 | 61.460 | 1.00 | 24.16 |
| ATOM | 2907 | N | ASP | 427 | 51.385 | 51.098 | 60.033 | 1.00 | 25.44 |
| ATOM | 2908 | CA | ASP | 427 | 51.473 | 52.238 | 60.941 | 1.00 | 27.31 |
| ATOM | 2909 | CB | ASP | 427 | 52.888 | 52.816 | 60.921 | 1.00 | 29.17 |
| ATOM | 2910 | CG | ASP | 427 | 53.919 | 51.824 | 61.410 | 1.00 | 32.66 |
| ATOM | 2911 | OD1 | ASP | 427 | 53.697 | 51.226 | 62.484 | 1.00 | 34.11 |
| ATOM | 2912 | OD2 | ASP | 427 | 54.948 | 51.644 | 60.727 | 1.00 | 35.93 |
| ATOM | 2913 | C | ASP | 427 | 50.466 | 53.354 | 60.686 | 1.00 | 27.40 |
| ATOM | 2914 | O | ASP | 427 | 50.487 | 54.382 | 61.362 | 1.00 | 27.53 |
| ATOM | 2915 | N | LEU | 428 | 49.586 | 53.163 | 59.711 | 1.00 | 26.71 |
| ATOM | 2916 | CA | LEU | 428 | 48.581 | 54.175 | 59.417 | 1.00 | 25.14 |
| ATOM | 2917 | CB | LEU | 428 | 48.159 | 54.110 | 57.946 | 1.00 | 25.72 |
| ATOM | 2918 | CG | LEU | 428 | 49.169 | 54.334 | 56.819 | 1.00 | 24.48 |
| ATOM | 2919 | CD1 | LEU | 428 | 48.466 | 54.097 | 55.487 | 1.00 | 23.73 |
| ATOM | 2920 | CD2 | LEU | 428 | 49.731 | 55.743 | 56.878 | 1.00 | 24.31 |
| ATOM | 2921 | C | LEU | 428 | 47.356 | 53.897 | 60.271 | 1.00 | 23.90 |
| ATOM | 2922 | O | LEU | 428 | 47.199 | 52.798 | 60.801 | 1.00 | 23.96 |
| ATOM | 2923 | N | PRO | 429 | 46.477 | 54.897 | 60.433 | 1.00 | 23.83 |
| ATOM | 2924 | CD | PRO | 429 | 46.585 | 56.303 | 60.003 | 1.00 | 22.86 |
| ATOM | 2925 | CA | PRO | 429 | 45.267 | 54.676 | 61.232 | 1.00 | 24.74 |
| ATOM | 2926 | CB | PRO | 429 | 44.497 | 55.977 | 61.046 | 1.00 | 22.89 |
| ATOM | 2927 | CG | PRO | 429 | 45.593 | 56.993 | 60.911 | 1.00 | 23.44 |
| ATOM | 2928 | C | PRO | 429 | 44.555 | 53.484 | 60.584 | 1.00 | 25.64 |
| ATOM | 2929 | O | PRO | 429 | 44.529 | 53.380 | 59.356 | 1.00 | 25.40 |
| ATOM | 2930 | N | VAL | 430 | 43.986 | 52.590 | 61.390 | 1.00 | 26.24 |
| ATOM | 2931 | CA | VAL | 430 | 43.320 | 51.404 | 60.854 | 1.00 | 26.47 |
| ATOM | 2932 | CB | VAL | 430 | 42.621 | 50.590 | 61.972 | 1.00 | 29.13 |
| ATOM | 2933 | CG1 | VAL | 430 | 43.660 | 50.035 | 62.933 | 1.00 | 28.70 |
| ATOM | 2934 | CG2 | VAL | 430 | 41.620 | 51.467 | 62.708 | 1.00 | 30.53 |
| ATOM | 2935 | C | VAL | 430 | 42.307 | 51.672 | 59.743 | 1.00 | 25.82 |
| ATOM | 2936 | O | VAL | 430 | 42.148 | 50.856 | 58.837 | 1.00 | 24.60 |
| ATOM | 2937 | N | ALA | 431 | 41.629 | 52.812 | 59.802 | 1.00 | 24.76 |
| ATOM | 2938 | CA | ALA | 431 | 40.639 | 53.143 | 58.786 | 1.00 | 24.41 |
| ATOM | 2939 | CB | ALA | 431 | 39.898 | 54.419 | 59.171 | 1.00 | 26.53 |
| ATOM | 2940 | C | ALA | 431 | 41.286 | 53.313 | 57.419 | 1.00 | 23.48 |
| ATOM | 2941 | O | ALA | 431 | 40.623 | 53.198 | 56.391 | 1.00 | 23.10 |
| ATOM | 2942 | N | LEU | 432 | 42.587 | 53.583 | 57.407 | 1.00 | 23.44 |
| ATOM | 2943 | CA | LEU | 432 | 43.297 | 53.785 | 56.153 | 1.00 | 22.88 |
| ATOM | 2944 | CB | LEU | 432 | 44.143 | 55.059 | 56.236 | 1.00 | 23.01 |
| ATOM | 2945 | CG | LEU | 432 | 43.365 | 56.321 | 56.628 | 1.00 | 22.58 |
| ATOM | 2946 | CD1 | LEU | 432 | 44.321 | 57.500 | 56.716 | 1.00 | 21.61 |
| ATOM | 2947 | CD2 | LEU | 432 | 42.267 | 56.597 | 55.606 | 1.00 | 24.25 |
| ATOM | 2948 | C | LEU | 432 | 44.178 | 52.595 | 55.787 | 1.00 | 23.45 |
| ATOM | 2949 | O | LEU | 432 | 44.974 | 52.666 | 54.844 | 1.00 | 23.80 |
| ATOM | 2950 | N | ARG | 433 | 44.030 | 51.501 | 56.529 | 1.00 | 22.08 |
| ATOM | 2951 | CA | ARG | 433 | 44.815 | 50.303 | 56.260 | 1.00 | 22.75 |
| ATOM | 2952 | CB | ARG | 433 | 45.026 | 49.497 | 57.546 | 1.00 | 23.50 |
| ATOM | 2953 | CG | ARG | 433 | 45.849 | 50.225 | 58.607 | 1.00 | 26.73 |
| ATOM | 2954 | CD | ARG | 433 | 46.193 | 49.307 | 59.779 | 1.00 | 29.04 |
| ATOM | 2955 | NE | ARG | 433 | 46.793 | 50.044 | 60.888 | 1.00 | 32.42 |
| ATOM | 2956 | CZ | ARG | 433 | 47.191 | 49.492 | 62.031 | 1.00 | 33.50 |
| ATOM | 2957 | NH1 | ARG | 433 | 47.061 | 48.187 | 62.229 | 1.00 | 33.63 |
| ATOM | 2958 | NH2 | ARG | 433 | 47.710 | 50.252 | 62.986 | 1.00 | 35.11 |
| ATOM | 2959 | C | ARG | 433 | 44.162 | 49.424 | 55.188 | 1.00 | 21.02 |
| ATOM | 2960 | O | ARG | 433 | 43.635 | 48.347 | 55.474 | 1.00 | 19.37 |
| ATOM | 2961 | N | GLU | 434 | 44.188 | 49.914 | 53.954 | 1.00 | 20.40 |
| ATOM | 2962 | CA | GLU | 434 | 43.644 | 49.196 | 52.803 | 1.00 | 21.33 |
| ATOM | 2963 | CB | GLU | 434 | 42.172 | 49.560 | 52.567 | 1.00 | 24.12 |
| ATOM | 2964 | CG | GLU | 434 | 41.226 | 49.009 | 53.624 | 1.00 | 34.46 |
| ATOM | 2965 | CD | GLU | 434 | 40.542 | 50.099 | 54.420 | 1.00 | 38.95 |
| ATOM | 2966 | OE1 | GLU | 434 | 41.253 | 50.975 | 54.958 | 1.00 | 42.61 |
| ATOM | 2967 | OE2 | GLU | 434 | 39.295 | 50.078 | 54.515 | 1.00 | 42.67 |
| ATOM | 2968 | C | GLU | 434 | 44.476 | 49.606 | 51.604 | 1.00 | 18.30 |
| ATOM | 2969 | O | GLU | 434 | 45.303 | 50.507 | 51.713 | 1.00 | 16.88 |
| ATOM | 2970 | N | GLY | 435 | 44.271 | 48.945 | 50.466 | 1.00 | 19.36 |
| ATOM | 2971 | CA | GLY | 435 | 45.031 | 49.296 | 49.276 | 1.00 | 18.55 |
| ATOM | 2972 | C | GLY | 435 | 44.491 | 50.578 | 48.679 | 1.00 | 18.67 |
| ATOM | 2973 | O | GLY | 435 | 43.400 | 51.005 | 49.055 | 1.00 | 17.09 |

TABLE A-continued

| | | | | | | | | |
|---|---|---|---|---|---|---|---|---|
| ATOM | 2974 | N | ALA | 436 | 45.246 | 51.204 | 47.775 | 1.00 | 19.08 |
| ATOM | 2975 | CA | ALA | 436 | 44.799 | 52.442 | 47.123 | 1.00 | 17.26 |
| ATOM | 2976 | CB | ALA | 436 | 45.667 | 52.731 | 45.906 | 1.00 | 17.85 |
| ATOM | 2977 | C | ALA | 436 | 43.336 | 52.215 | 46.722 | 1.00 | 16.59 |
| ATOM | 2978 | O | ALA | 436 | 42.493 | 53.097 | 46.842 | 1.00 | 16.06 |
| ATOM | 2979 | N | ASN | 437 | 43.066 | 51.020 | 46.212 | 1.00 | 16.87 |
| ATOM | 2980 | CA | ASN | 437 | 41.712 | 50.570 | 45.889 | 1.00 | 16.03 |
| ATOM | 2981 | CB | ASN | 437 | 41.185 | 51.088 | 44.526 | 1.00 | 14.52 |
| ATOM | 2982 | CG | ASN | 437 | 41.872 | 50.474 | 43.324 | 1.00 | 14.43 |
| ATOM | 2983 | OD1 | ASN | 437 | 42.105 | 49.269 | 43.261 | 1.00 | 15.44 |
| ATOM | 2984 | ND2 | ASN | 437 | 42.162 | 51.311 | 42.335 | 1.00 | 13.55 |
| ATOM | 2985 | C | ASN | 437 | 41.865 | 49.054 | 45.948 | 1.00 | 16.39 |
| ATOM | 2986 | O | ASN | 437 | 42.988 | 48.551 | 45.956 | 1.00 | 15.77 |
| ATOM | 2987 | N | PRO | 438 | 40.756 | 48.306 | 46.030 | 1.00 | 15.87 |
| ATOM | 2988 | CD | PRO | 438 | 39.350 | 48.730 | 46.157 | 1.00 | 14.94 |
| ATOM | 2989 | CA | PRO | 438 | 40.869 | 46.846 | 46.105 | 1.00 | 13.68 |
| ATOM | 2990 | CB | PRO | 438 | 39.413 | 46.391 | 46.059 | 1.00 | 14.60 |
| ATOM | 2991 | CG | PRO | 438 | 38.712 | 47.508 | 46.793 | 1.00 | 16.23 |
| ATOM | 2992 | C | PRO | 438 | 41.737 | 46.185 | 45.039 | 1.00 | 14.27 |
| ATOM | 2993 | O | PRO | 438 | 42.379 | 45.170 | 45.306 | 1.00 | 14.30 |
| ATOM | 2994 | N | GLY | 439 | 41.760 | 46.760 | 43.840 | 1.00 | 13.68 |
| ATOM | 2995 | CA | GLY | 439 | 42.563 | 46.201 | 42.766 | 1.00 | 13.77 |
| ATOM | 2996 | C | GLY | 439 | 44.051 | 46.182 | 43.070 | 1.00 | 14.65 |
| ATOM | 2997 | O | GLY | 439 | 44.741 | 45.203 | 42.776 | 1.00 | 12.71 |
| ATOM | 2998 | N | PHE | 440 | 44.553 | 47.269 | 43.649 | 1.00 | 14.29 |
| ATOM | 2999 | CA | PHE | 440 | 45.968 | 47.364 | 44.006 | 1.00 | 14.09 |
| ATOM | 3000 | CB | PHE | 440 | 46.262 | 48.708 | 44.691 | 1.00 | 14.69 |
| ATOM | 3001 | CG | PHE | 440 | 46.467 | 49.856 | 43.736 | 1.00 | 17.06 |
| ATOM | 3002 | CD1 | PHE | 440 | 45.474 | 50.226 | 42.836 | 1.00 | 16.87 |
| ATOM | 3003 | CD2 | PHE | 440 | 47.658 | 50.580 | 43.753 | 1.00 | 16.76 |
| ATOM | 3004 | CE1 | PHE | 440 | 45.663 | 51.307 | 41.962 | 1.00 | 16.34 |
| ATOM | 3005 | CE2 | PHE | 440 | 47.856 | 51.655 | 42.890 | 1.00 | 16.34 |
| ATOM | 3006 | CZ | PHE | 440 | 46.857 | 52.019 | 41.993 | 1.00 | 16.50 |
| ATOM | 3007 | C | PHE | 440 | 46.369 | 46.235 | 44.954 | 1.00 | 13.76 |
| ATOM | 3008 | O | PHE | 440 | 47.432 | 45.629 | 44.807 | 1.00 | 12.46 |
| ATOM | 3009 | N | HIS | 441 | 45.521 | 45.962 | 45.940 | 1.00 | 14.94 |
| ATOM | 3010 | CA | HIS | 441 | 45.813 | 44.911 | 46.910 | 1.00 | 15.78 |
| ATOM | 3011 | CB | HIS | 441 | 44.703 | 44.833 | 47.964 | 1.00 | 17.07 |
| ATOM | 3012 | CG | HIS | 441 | 45.209 | 44.750 | 49.374 | 1.00 | 15.66 |
| ATOM | 3013 | CD2 | HIS | 441 | 44.960 | 45.526 | 50.456 | 1.00 | 15.15 |
| ATOM | 3014 | ND1 | HIS | 441 | 46.073 | 43.763 | 49.802 | 1.00 | 16.88 |
| ATOM | 3015 | CE1 | HIS | 441 | 46.332 | 43.935 | 51.087 | 1.00 | 14.94 |
| ATOM | 3016 | NE2 | HIS | 441 | 45.669 | 44.998 | 51.508 | 1.00 | 15.07 |
| ATOM | 3017 | C | HIS | 441 | 45.958 | 43.555 | 46.220 | 1.00 | 16.92 |
| ATOM | 3018 | O | HIS | 441 | 46.813 | 42.747 | 46.592 | 1.00 | 15.31 |
| ATOM | 3019 | N | GLU | 442 | 45.122 | 43.311 | 45.214 | 1.00 | 16.74 |
| ATOM | 3020 | CA | GLU | 442 | 45.162 | 42.049 | 44.482 | 1.00 | 15.92 |
| ATOM | 3021 | CB | GLU | 442 | 43.861 | 41.851 | 43.701 | 1.00 | 15.02 |
| ATOM | 3022 | CG | GLU | 442 | 42.590 | 41.822 | 44.542 | 1.00 | 11.10 |
| ATOM | 3023 | CD | GLU | 442 | 42.635 | 40.757 | 45.617 | 1.00 | 11.15 |
| ATOM | 3024 | OE1 | GLU | 442 | 43.250 | 39.697 | 45.371 | 1.00 | 14.00 |
| ATOM | 3025 | OE2 | GLU | 442 | 42.055 | 40.975 | 46.699 | 1.00 | 11.81 |
| ATOM | 3026 | C | GLU | 442 | 46.329 | 41.955 | 43.497 | 1.00 | 17.24 |
| ATOM | 3027 | O | GLU | 442 | 46.778 | 40.859 | 43.162 | 1.00 | 16.84 |
| ATOM | 3028 | N | ALA | 443 | 46.826 | 43.100 | 43.039 | 1.00 | 15.95 |
| ATOM | 3029 | CA | ALA | 443 | 47.894 | 43.114 | 42.041 | 1.00 | 17.36 |
| ATOM | 3030 | CB | ALA | 443 | 47.799 | 44.404 | 41.221 | 1.00 | 15.87 |
| ATOM | 3031 | C | ALA | 443 | 49.343 | 42.907 | 42.491 | 1.00 | 16.95 |
| ATOM | 3032 | O | ALA | 443 | 50.135 | 42.328 | 41.750 | 1.00 | 17.94 |
| ATOM | 3033 | N | ILE | 444 | 49.692 | 43.374 | 43.686 | 1.00 | 16.73 |
| ATOM | 3034 | CA | ILE | 444 | 51.070 | 43.264 | 44.176 | 1.00 | 15.92 |
| ATOM | 3035 | CB | ILE | 444 | 51.166 | 43.630 | 45.671 | 1.00 | 15.04 |
| ATOM | 3036 | CG2 | ILE | 444 | 52.631 | 43.664 | 46.095 | 1.00 | 16.89 |
| ATOM | 3037 | CG1 | ILE | 444 | 50.502 | 44.990 | 45.927 | 1.00 | 14.90 |
| ATOM | 3038 | CD1 | ILE | 444 | 51.112 | 46.139 | 45.153 | 1.00 | 15.89 |
| ATOM | 3039 | C | ILE | 444 | 51.744 | 41.902 | 43.980 | 1.00 | 16.43 |
| ATOM | 3040 | O | ILE | 444 | 52.792 | 41.807 | 43.332 | 1.00 | 15.13 |
| ATOM | 3041 | N | GLY | 445 | 51.155 | 40.858 | 44.554 | 1.00 | 15.53 |
| ATOM | 3042 | CA | GLY | 445 | 51.724 | 39.528 | 44.427 | 1.00 | 16.88 |
| ATOM | 3043 | C | GLY | 445 | 51.844 | 39.072 | 42.985 | 1.00 | 18.50 |
| ATOM | 3044 | O | GLY | 445 | 52.866 | 38.512 | 42.581 | 1.00 | 17.19 |
| ATOM | 3045 | N | ASP | 446 | 50.796 | 39.317 | 42.205 | 1.00 | 16.96 |
| ATOM | 3046 | CA | ASP | 446 | 50.775 | 38.935 | 40.795 | 1.00 | 17.24 |
| ATOM | 3047 | CB | ASP | 446 | 49.438 | 39.334 | 40.157 | 1.00 | 15.35 |
| ATOM | 3048 | CG | ASP | 446 | 48.291 | 38.426 | 40.579 | 1.00 | 17.38 |
| ATOM | 3049 | OD1 | ASP | 446 | 48.298 | 37.936 | 41.728 | 1.00 | 14.96 |
| ATOM | 3050 | OD2 | ASP | 446 | 47.370 | 38.212 | 39.761 | 1.00 | 16.72 |
| ATOM | 3051 | C | ASP | 446 | 51.919 | 39.572 | 40.016 | 1.00 | 18.31 |
| ATOM | 3052 | O | ASP | 446 | 52.503 | 38.939 | 39.132 | 1.00 | 16.77 |
| ATOM | 3053 | N | VAL | 447 | 52.234 | 40.829 | 40.328 | 1.00 | 18.18 |

TABLE A-continued

| | | | | | | | | |
|---|---|---|---|---|---|---|---|---|
| ATOM | 3054 | CA | VAL | 447 | 53.314 | 41.508 | 39.629 | 1.00 | 18.02 |
| ATOM | 3055 | CB | VAL | 447 | 53.542 | 42.935 | 40.158 | 1.00 | 17.59 |
| ATOM | 3056 | CG1 | VAL | 447 | 54.795 | 43.520 | 39.514 | 1.00 | 20.25 |
| ATOM | 3057 | CG2 | VAL | 447 | 52.330 | 43.816 | 39.831 | 1.00 | 15.79 |
| ATOM | 3058 | C | VAL | 447 | 54.611 | 40.716 | 39.765 | 1.00 | 18.36 |
| ATOM | 3059 | O | VAL | 447 | 55.293 | 40.471 | 38.773 | 1.00 | 17.66 |
| ATOM | 3060 | N | LEU | 448 | 54.948 | 40.312 | 40.986 | 1.00 | 18.09 |
| ATOM | 3061 | CA | LEU | 448 | 56.167 | 39.543 | 41.194 | 1.00 | 18.49 |
| ATOM | 3062 | CB | LEU | 448 | 56.464 | 39.378 | 42.691 | 1.00 | 17.75 |
| ATOM | 3063 | CG | LEU | 448 | 57.233 | 40.500 | 43.405 | 1.00 | 18.33 |
| ATOM | 3064 | CD1 | LEU | 448 | 56.458 | 41.811 | 43.359 | 1.00 | 17.13 |
| ATOM | 3065 | CD2 | LEU | 448 | 57.487 | 40.082 | 44.848 | 1.00 | 18.72 |
| ATOM | 3066 | C | LEU | 448 | 56.053 | 38.170 | 40.529 | 1.00 | 19.50 |
| ATOM | 3067 | O | LEU | 448 | 57.011 | 37.682 | 39.930 | 1.00 | 20.72 |
| ATOM | 3068 | N | ALA | 449 | 54.879 | 37.551 | 40.627 | 1.00 | 18.48 |
| ATOM | 3069 | CA | ALA | 449 | 54.671 | 36.240 | 40.028 | 1.00 | 18.81 |
| ATOM | 3070 | CB | ALA | 449 | 53.260 | 35.731 | 40.337 | 1.00 | 18.00 |
| ATOM | 3071 | C | ALA | 449 | 54.905 | 36.272 | 38.518 | 1.00 | 17.58 |
| ATOM | 3072 | O | ALA | 449 | 55.285 | 35.261 | 37.925 | 1.00 | 17.76 |
| ATOM | 3073 | N | LEU | 450 | 54.677 | 37.424 | 37.890 | 1.00 | 16.49 |
| ATOM | 3074 | CA | LEU | 450 | 54.898 | 37.536 | 36.449 | 1.00 | 16.51 |
| ATOM | 3075 | CB | LEU | 450 | 54.516 | 38.933 | 35.935 | 1.00 | 15.69 |
| ATOM | 3076 | CG | LEU | 450 | 53.027 | 39.294 | 35.797 | 1.00 | 14.12 |
| ATOM | 3077 | CD1 | LEU | 450 | 52.887 | 40.749 | 35.374 | 1.00 | 12.95 |
| ATOM | 3078 | CD2 | LEU | 450 | 52.356 | 38.385 | 34.770 | 1.00 | 15.02 |
| ATOM | 3079 | C | LEU | 450 | 56.376 | 37.262 | 36.150 | 1.00 | 18.30 |
| ATOM | 3080 | O | LEU | 450 | 56.702 | 36.552 | 35.196 | 1.00 | 17.45 |
| ATOM | 3081 | N | SER | 451 | 57.266 | 37.824 | 36.966 | 1.00 | 18.19 |
| ATOM | 3082 | CA | SER | 451 | 58.701 | 37.617 | 36.777 | 1.00 | 18.99 |
| ATOM | 3083 | CB | SER | 451 | 59.507 | 38.572 | 37.663 | 1.00 | 16.95 |
| ATOM | 3084 | OG | SER | 451 | 59.480 | 39.890 | 37.141 | 1.00 | 17.53 |
| ATOM | 3085 | C | SER | 451 | 59.092 | 36.178 | 37.092 | 1.00 | 19.71 |
| ATOM | 3086 | O | SER | 451 | 59.896 | 35.575 | 36.383 | 1.00 | 20.72 |
| ATOM | 3087 | N | VAL | 452 | 58.520 | 35.635 | 38.160 | 1.00 | 21.54 |
| ATOM | 3088 | CA | VAL | 452 | 58.798 | 34.263 | 38.574 | 1.00 | 22.76 |
| ATOM | 3089 | CB | VAL | 452 | 57.997 | 33.893 | 39.843 | 1.00 | 22.77 |
| ATOM | 3090 | CG1 | VAL | 452 | 58.217 | 32.428 | 40.195 | 1.00 | 25.58 |
| ATOM | 3091 | CG2 | VAL | 452 | 58.419 | 34.781 | 40.997 | 1.00 | 25.93 |
| ATOM | 3092 | C | VAL | 452 | 58.435 | 33.259 | 37.482 | 1.00 | 24.01 |
| ATOM | 3093 | O | VAL | 452 | 59.112 | 32.243 | 37.307 | 1.00 | 23.13 |
| ATOM | 3094 | N | SER | 453 | 57.358 | 33.552 | 36.757 | 1.00 | 22.60 |
| ATOM | 3095 | CA | SER | 453 | 56.870 | 32.678 | 35.693 | 1.00 | 23.40 |
| ATOM | 3096 | CB | SER | 453 | 55.434 | 33.067 | 35.317 | 1.00 | 21.89 |
| ATOM | 3097 | OG | SER | 453 | 54.546 | 32.810 | 36.393 | 1.00 | 20.22 |
| ATOM | 3098 | C | SER | 453 | 57.715 | 32.622 | 34.424 | 1.00 | 22.87 |
| ATOM | 3099 | O | SER | 453 | 57.563 | 31.697 | 33.631 | 1.00 | 22.16 |
| ATOM | 3100 | N | THR | 454 | 58.592 | 33.602 | 34.219 | 1.00 | 23.18 |
| ATOM | 3101 | CA | THR | 454 | 59.420 | 33.601 | 33.016 | 1.00 | 24.33 |
| ATOM | 3102 | CB | THR | 454 | 60.373 | 34.817 | 32.972 | 1.00 | 23.24 |
| ATOM | 3103 | OG1 | THR | 454 | 61.199 | 34.827 | 34.143 | 1.00 | 24.32 |
| ATOM | 3104 | CG2 | THR | 454 | 59.576 | 36.115 | 32.894 | 1.00 | 24.49 |
| ATOM | 3105 | C | THR | 454 | 60.240 | 32.313 | 32.940 | 1.00 | 25.55 |
| ATOM | 3106 | O | THR | 454 | 60.749 | 31.827 | 33.949 | 1.00 | 25.28 |
| ATOM | 3107 | N | PRO | 455 | 60.368 | 31.738 | 31.734 | 1.00 | 25.92 |
| ATOM | 3108 | CD | PRO | 455 | 59.860 | 32.211 | 30.433 | 1.00 | 26.48 |
| ATOM | 3109 | CA | PRO | 455 | 61.134 | 30.499 | 31.574 | 1.00 | 27.37 |
| ATOM | 3110 | CB | PRO | 455 | 61.238 | 30.351 | 30.058 | 1.00 | 27.14 |
| ATOM | 3111 | CG | PRO | 455 | 59.949 | 30.959 | 29.578 | 1.00 | 25.75 |
| ATOM | 3112 | C | PRO | 455 | 62.499 | 30.573 | 32.245 | 1.00 | 27.20 |
| ATOM | 3113 | O | PRO | 455 | 62.909 | 29.646 | 32.946 | 1.00 | 26.66 |
| ATOM | 3114 | N | LYS | 456 | 63.193 | 31.688 | 32.045 | 1.00 | 28.50 |
| ATOM | 3115 | CA | LYS | 456 | 64.513 | 31.851 | 32.626 | 1.00 | 29.18 |
| ATOM | 3116 | CB | LYS | 456 | 65.150 | 33.161 | 32.164 | 1.00 | 31.89 |
| ATOM | 3117 | CG | LYS | 456 | 66.669 | 33.142 | 32.280 | 1.00 | 36.40 |
| ATOM | 3118 | CD | LYS | 456 | 67.296 | 34.487 | 31.959 | 1.00 | 39.36 |
| ATOM | 3119 | CE | LYS | 456 | 68.815 | 34.374 | 31.932 | 1.00 | 40.98 |
| ATOM | 3120 | NZ | LYS | 456 | 69.335 | 33.657 | 33.129 | 1.00 | 43.02 |
| ATOM | 3121 | C | LYS | 456 | 64.501 | 31.795 | 34.151 | 1.00 | 29.42 |
| ATOM | 3122 | O | LYS | 456 | 65.366 | 31.151 | 34.753 | 1.00 | 28.75 |
| ATOM | 3123 | N | HIS | 457 | 63.534 | 32.458 | 34.785 | 1.00 | 24.85 |
| ATOM | 3124 | CA | HIS | 457 | 63.486 | 32.427 | 36.242 | 1.00 | 23.20 |
| ATOM | 3125 | CB | HIS | 457 | 62.439 | 33.397 | 36.791 | 1.00 | 23.95 |
| ATOM | 3126 | CG | HIS | 457 | 62.503 | 33.558 | 38.278 | 1.00 | 23.17 |
| ATOM | 3127 | CD2 | HIS | 457 | 61.930 | 32.846 | 39.277 | 1.00 | 23.50 |
| ATOM | 3128 | ND1 | HIS | 457 | 63.300 | 34.501 | 38.892 | 1.00 | 24.07 |
| ATOM | 3129 | CE1 | HIS | 457 | 63.218 | 34.360 | 40.203 | 1.00 | 25.29 |
| ATOM | 3130 | NE2 | HIS | 457 | 62.393 | 33.361 | 40.463 | 1.00 | 25.90 |
| ATOM | 3131 | C | HIS | 457 | 63.167 | 31.019 | 36.738 | 1.00 | 23.20 |
| ATOM | 3132 | O | HIS | 457 | 63.768 | 30.541 | 37.701 | 1.00 | 21.36 |
| ATOM | 3133 | N | LEU | 458 | 62.208 | 30.362 | 36.089 | 1.00 | 24.06 |

TABLE A-continued

| | | | | | | | | |
|---|---|---|---|---|---|---|---|---|
| ATOM | 3134 | CA | LEU | 458 | 61.835 | 29.010 | 36.481 | 1.00 | 25.22 |
| ATOM | 3135 | CB | LEU | 458 | 60.694 | 28.486 | 35.600 | 1.00 | 25.32 |
| ATOM | 3136 | CG | LEU | 458 | 59.302 | 29.096 | 35.812 | 1.00 | 24.79 |
| ATOM | 3137 | CD1 | LEU | 458 | 58.314 | 28.482 | 34.827 | 1.00 | 24.94 |
| ATOM | 3138 | CD2 | LEU | 458 | 58.848 | 28.852 | 37.249 | 1.00 | 24.07 |
| ATOM | 3139 | C | LEU | 458 | 63.058 | 28.105 | 36.350 | 1.00 | 26.11 |
| ATOM | 3140 | O | LEU | 458 | 63.265 | 27.204 | 37.157 | 1.00 | 24.93 |
| ATOM | 3141 | N | HIS | 459 | 63.875 | 28.356 | 35.334 | 1.00 | 28.43 |
| ATOM | 3142 | CA | HIS | 459 | 65.070 | 27.548 | 35.140 | 1.00 | 31.28 |
| ATOM | 3143 | CB | HIS | 459 | 65.731 | 27.872 | 33.799 | 1.00 | 33.71 |
| ATOM | 3144 | CG | HIS | 459 | 66.959 | 27.060 | 33.521 | 1.00 | 39.54 |
| ATOM | 3145 | CD2 | HIS | 459 | 67.152 | 25.977 | 32.730 | 1.00 | 40.92 |
| ATOM | 3146 | ND1 | HIS | 459 | 68.174 | 27.316 | 34.120 | 1.00 | 42.70 |
| ATOM | 3147 | CE1 | HIS | 459 | 69.062 | 26.427 | 33.711 | 1.00 | 42.68 |
| ATOM | 3148 | NE2 | HIS | 459 | 68.467 | 25.603 | 32.867 | 1.00 | 43.45 |
| ATOM | 3149 | C | HIS | 459 | 66.053 | 27.782 | 36.283 | 1.00 | 30.04 |
| ATOM | 3150 | O | HIS | 459 | 66.755 | 26.861 | 36.699 | 1.00 | 29.57 |
| ATOM | 3151 | N | SER | 460 | 66.087 | 29.008 | 36.803 | 1.00 | 28.70 |
| ATOM | 3152 | CA | SER | 460 | 66.997 | 29.335 | 37.897 | 1.00 | 27.62 |
| ATOM | 3153 | CB | SER | 460 | 67.034 | 30.850 | 38.142 | 1.00 | 27.69 |
| ATOM | 3154 | OG | SER | 460 | 65.945 | 31.283 | 38.942 | 1.00 | 27.73 |
| ATOM | 3155 | C | SER | 460 | 66.579 | 28.613 | 39.174 | 1.00 | 27.55 |
| ATOM | 3156 | O | SER | 460 | 67.380 | 28.446 | 40.091 | 1.00 | 26.24 |
| ATOM | 3157 | N | LEU | 461 | 65.321 | 28.186 | 39.228 | 1.00 | 26.91 |
| ATOM | 3158 | CA | LEU | 461 | 64.808 | 27.463 | 40.388 | 1.00 | 29.43 |
| ATOM | 3159 | CB | LEU | 461 | 63.337 | 27.813 | 40.641 | 1.00 | 27.64 |
| ATOM | 3160 | CG | LEU | 461 | 63.027 | 29.239 | 41.101 | 1.00 | 28.24 |
| ATOM | 3161 | CD1 | LEU | 461 | 61.523 | 29.462 | 41.111 | 1.00 | 28.05 |
| ATOM | 3162 | CD2 | LEU | 461 | 63.611 | 29.461 | 42.488 | 1.00 | 27.97 |
| ATOM | 3163 | C | LEU | 461 | 64.931 | 25.971 | 40.119 | 1.00 | 30.51 |
| ATOM | 3164 | O | LEU | 461 | 64.528 | 25.142 | 40.938 | 1.00 | 31.19 |
| ATOM | 3165 | N | ASN | 462 | 65.491 | 25.649 | 38.957 | 1.00 | 32.47 |
| ATOM | 3166 | CA | ASN | 462 | 65.684 | 24.272 | 38.523 | 1.00 | 34.80 |
| ATOM | 3167 | CB | ASN | 462 | 66.447 | 23.484 | 39.594 | 1.00 | 35.75 |
| ATOM | 3168 | CG | ASN | 462 | 67.114 | 22.241 | 39.036 | 1.00 | 38.55 |
| ATOM | 3169 | OD1 | ASN | 462 | 67.732 | 22.283 | 37.973 | 1.00 | 38.16 |
| ATOM | 3170 | ND2 | ASN | 462 | 67.006 | 21.132 | 39.758 | 1.00 | 39.43 |
| ATOM | 3171 | C | ASN | 462 | 64.337 | 23.607 | 38.222 | 1.00 | 36.15 |
| ATOM | 3172 | O | ASN | 462 | 64.154 | 22.414 | 38.466 | 1.00 | 35.72 |
| ATOM | 3173 | N | LEU | 463 | 63.402 | 24.391 | 37.689 | 1.00 | 36.82 |
| ATOM | 3174 | CA | LEU | 463 | 62.074 | 23.886 | 37.345 | 1.00 | 39.43 |
| ATOM | 3175 | CB | LEU | 463 | 60.987 | 24.713 | 38.038 | 1.00 | 37.66 |
| ATOM | 3176 | CG | LEU | 463 | 60.997 | 24.667 | 39.569 | 1.00 | 37.31 |
| ATOM | 3177 | CD1 | LEU | 463 | 59.836 | 25.492 | 40.111 | 1.00 | 36.51 |
| ATOM | 3178 | CD2 | LEU | 463 | 60.898 | 23.227 | 40.046 | 1.00 | 36.47 |
| ATOM | 3179 | C | LEU | 463 | 61.851 | 23.900 | 35.839 | 1.00 | 41.12 |
| ATOM | 3180 | O | LEU | 463 | 60.771 | 23.568 | 35.355 | 1.00 | 42.26 |
| ATOM | 3181 | N | LEU | 464 | 62.880 | 24.307 | 35.105 | 1.00 | 43.53 |
| ATOM | 3182 | CA | LEU | 464 | 62.832 | 24.341 | 33.647 | 1.00 | 46.78 |
| ATOM | 3183 | CB | LEU | 464 | 62.358 | 25.707 | 33.131 | 1.00 | 47.15 |
| ATOM | 3184 | CG | LEU | 464 | 60.846 | 25.963 | 33.126 | 1.00 | 47.86 |
| ATOM | 3185 | CD1 | LEU | 464 | 60.553 | 27.253 | 32.374 | 1.00 | 48.43 |
| ATOM | 3186 | CD2 | LEU | 464 | 60.122 | 24.801 | 32.457 | 1.00 | 48.04 |
| ATOM | 3187 | C | LEU | 464 | 64.217 | 24.032 | 33.097 | 1.00 | 47.91 |
| ATOM | 3188 | O | LEU | 464 | 65.208 | 24.081 | 33.830 | 1.00 | 48.74 |
| ATOM | 3189 | N | SER | 465 | 64.282 | 23.702 | 31.812 | 1.00 | 49.72 |
| ATOM | 3190 | CA | SER | 465 | 65.552 | 23.375 | 31.173 | 1.00 | 51.10 |
| ATOM | 3191 | CB | SER | 465 | 65.619 | 21.873 | 30.887 | 1.00 | 51.49 |
| ATOM | 3192 | OG | SER | 465 | 64.505 | 21.452 | 30.117 | 1.00 | 52.92 |
| ATOM | 3193 | C | SER | 465 | 65.745 | 24.157 | 29.879 | 1.00 | 51.56 |
| ATOM | 3194 | O | SER | 465 | 66.428 | 25.182 | 29.860 | 1.00 | 52.18 |
| ATOM | 3195 | N | GLY | 470 | 64.653 | 32.326 | 21.785 | 1.00 | 48.10 |
| ATOM | 3196 | CA | GLY | 470 | 63.950 | 31.478 | 20.839 | 1.00 | 48.51 |
| ATOM | 3197 | C | GLY | 470 | 62.522 | 31.928 | 20.591 | 1.00 | 47.84 |
| ATOM | 3198 | O | GLY | 470 | 61.718 | 31.998 | 21.520 | 1.00 | 48.31 |
| ATOM | 3199 | N | ALA | 471 | 62.202 | 32.229 | 19.336 | 1.00 | 46.54 |
| ATOM | 3200 | CA | ALA | 471 | 60.864 | 32.681 | 18.976 | 1.00 | 45.12 |
| ATOM | 3201 | CB | ALA | 471 | 60.799 | 32.979 | 17.485 | 1.00 | 46.24 |
| ATOM | 3202 | C | ALA | 471 | 59.799 | 31.654 | 19.351 | 1.00 | 44.20 |
| ATOM | 3203 | O | ALA | 471 | 58.843 | 31.976 | 20.056 | 1.00 | 44.05 |
| ATOM | 3204 | N | GLU | 472 | 59.965 | 30.420 | 18.883 | 1.00 | 41.85 |
| ATOM | 3205 | CA | GLU | 472 | 59.002 | 29.367 | 19.178 | 1.00 | 40.72 |
| ATOM | 3206 | CB | GLU | 472 | 59.411 | 28.062 | 18.492 | 1.00 | 40.77 |
| ATOM | 3207 | CG | GLU | 472 | 59.039 | 28.041 | 17.019 | 1.00 | 43.32 |
| ATOM | 3208 | CD | GLU | 472 | 59.363 | 26.728 | 16.336 | 1.00 | 44.64 |
| ATOM | 3209 | OE1 | GLU | 472 | 59.319 | 25.675 | 17.008 | 1.00 | 44.66 |
| ATOM | 3210 | OE2 | GLU | 472 | 59.641 | 26.753 | 15.117 | 1.00 | 46.17 |
| ATOM | 3211 | C | GLU | 472 | 58.810 | 29.146 | 20.672 | 1.00 | 39.99 |
| ATOM | 3212 | O | GLU | 472 | 57.724 | 28.762 | 21.111 | 1.00 | 37.39 |
| ATOM | 3213 | N | HIS | 473 | 59.859 | 29.380 | 21.454 | 1.00 | 39.00 |

TABLE A-continued

| | | | | | | | | | |
|---|---|---|---|---|---|---|---|---|---|
| ATOM | 3214 | CA | HIS | 473 | 59.746 | 29.226 | 22.896 | 1.00 | 38.09 |
| ATOM | 3215 | CB | HIS | 473 | 61.121 | 29.080 | 23.551 | 1.00 | 40.74 |
| ATOM | 3216 | CG | HIS | 473 | 61.664 | 27.684 | 23.510 | 1.00 | 43.40 |
| ATOM | 3217 | CD2 | HIS | 473 | 61.475 | 26.632 | 24.341 | 1.00 | 44.06 |
| ATOM | 3218 | ND1 | HIS | 473 | 62.501 | 27.236 | 22.510 | 1.00 | 45.60 |
| ATOM | 3219 | CE1 | HIS | 473 | 62.805 | 25.969 | 22.729 | 1.00 | 45.16 |
| ATOM | 3220 | NE2 | HIS | 473 | 62.195 | 25.578 | 23.833 | 1.00 | 45.60 |
| ATOM | 3221 | C | HIS | 473 | 59.032 | 30.449 | 23.453 | 1.00 | 36.31 |
| ATOM | 3222 | O | HIS | 473 | 58.367 | 30.368 | 24.482 | 1.00 | 36.98 |
| ATOM | 3223 | N | ASP | 474 | 59.172 | 31.581 | 22.766 | 1.00 | 34.37 |
| ATOM | 3224 | CA | ASP | 474 | 58.516 | 32.810 | 23.187 | 1.00 | 34.17 |
| ATOM | 3225 | CB | ASP | 474 | 59.000 | 34.009 | 22.365 | 1.00 | 38.03 |
| ATOM | 3226 | CG | ASP | 474 | 60.243 | 34.647 | 22.937 | 1.00 | 41.09 |
| ATOM | 3227 | OD1 | ASP | 474 | 60.257 | 34.930 | 24.154 | 1.00 | 42.53 |
| ATOM | 3228 | OD2 | ASP | 474 | 61.202 | 34.878 | 22.169 | 1.00 | 43.99 |
| ATOM | 3229 | C | ASP | 474 | 57.007 | 32.692 | 23.021 | 1.00 | 32.16 |
| ATOM | 3230 | O | ASP | 474 | 56.248 | 33.095 | 23.903 | 1.00 | 30.43 |
| ATOM | 3231 | N | ILE | 475 | 56.580 | 32.153 | 21.880 | 1.00 | 28.89 |
| ATOM | 3232 | CA | ILE | 475 | 55.159 | 31.996 | 21.595 | 1.00 | 25.76 |
| ATOM | 3233 | CB | ILE | 475 | 54.922 | 31.577 | 20.122 | 1.00 | 26.10 |
| ATOM | 3234 | CG2 | ILE | 475 | 53.425 | 31.456 | 19.838 | 1.00 | 22.06 |
| ATOM | 3235 | CG1 | ILE | 475 | 55.544 | 32.613 | 19.183 | 1.00 | 23.79 |
| ATOM | 3236 | CD1 | ILE | 475 | 54.998 | 34.015 | 19.363 | 1.00 | 25.45 |
| ATOM | 3237 | C | ILE | 475 | 54.539 | 30.962 | 22.526 | 1.00 | 24.56 |
| ATOM | 3238 | O | ILE | 475 | 53.422 | 31.150 | 23.009 | 1.00 | 23.51 |
| ATOM | 3239 | N | ASN | 476 | 55.258 | 29.869 | 22.775 | 1.00 | 22.07 |
| ATOM | 3240 | CA | ASN | 476 | 54.749 | 28.843 | 23.673 | 1.00 | 22.59 |
| ATOM | 3241 | CB | ASN | 476 | 55.718 | 27.658 | 23.777 | 1.00 | 22.82 |
| ATOM | 3242 | CG | ASN | 476 | 55.557 | 26.656 | 22.640 | 1.00 | 23.84 |
| ATOM | 3243 | OD1 | ASN | 476 | 54.640 | 26.756 | 21.822 | 1.00 | 23.67 |
| ATOM | 3244 | ND2 | ASN | 476 | 56.451 | 25.674 | 22.595 | 1.00 | 22.00 |
| ATOM | 3245 | C | ASN | 476 | 54.564 | 29.465 | 25.057 | 1.00 | 22.14 |
| ATOM | 3246 | O | ASN | 476 | 53.554 | 29.231 | 25.721 | 1.00 | 20.32 |
| ATOM | 3247 | N | PHE | 477 | 55.544 | 30.258 | 25.487 | 1.00 | 19.74 |
| ATOM | 3248 | CA | PHE | 477 | 55.473 | 30.907 | 26.795 | 1.00 | 20.07 |
| ATOM | 3249 | CB | PHE | 477 | 56.779 | 31.630 | 27.118 | 1.00 | 19.28 |
| ATOM | 3250 | CG | PHE | 477 | 56.697 | 32.491 | 28.348 | 1.00 | 19.26 |
| ATOM | 3251 | CD1 | PHE | 477 | 56.387 | 31.930 | 29.582 | 1.00 | 19.77 |
| ATOM | 3252 | CD2 | PHE | 477 | 56.908 | 33.861 | 28.270 | 1.00 | 18.99 |
| ATOM | 3253 | CE1 | PHE | 477 | 56.288 | 32.721 | 30.723 | 1.00 | 20.49 |
| ATOM | 3254 | CE2 | PHE | 477 | 56.811 | 34.664 | 29.404 | 1.00 | 21.68 |
| ATOM | 3255 | CZ | PHE | 477 | 56.501 | 34.091 | 30.634 | 1.00 | 20.79 |
| ATOM | 3256 | C | PHE | 477 | 54.327 | 31.910 | 26.879 | 1.00 | 18.41 |
| ATOM | 3257 | O | PHE | 477 | 53.558 | 31.907 | 27.840 | 1.00 | 17.57 |
| ATOM | 3258 | N | LEU | 478 | 54.230 | 32.782 | 25.882 | 1.00 | 16.70 |
| ATOM | 3259 | CA | LEU | 478 | 53.171 | 33.778 | 25.858 | 1.00 | 17.73 |
| ATOM | 3260 | CB | LEU | 478 | 53.315 | 34.692 | 24.634 | 1.00 | 18.54 |
| ATOM | 3261 | CG | LEU | 478 | 54.441 | 35.733 | 24.725 | 1.00 | 18.88 |
| ATOM | 3262 | CD1 | LEU | 478 | 54.594 | 36.453 | 23.399 | 1.00 | 20.51 |
| ATOM | 3263 | CD2 | LEU | 478 | 54.133 | 36.732 | 25.835 | 1.00 | 21.13 |
| ATOM | 3264 | C | LEU | 478 | 51.808 | 33.094 | 25.857 | 1.00 | 17.77 |
| ATOM | 3265 | O | LEU | 478 | 50.859 | 33.602 | 26.454 | 1.00 | 16.81 |
| ATOM | 3266 | N | MET | 479 | 51.710 | 31.943 | 25.192 | 1.00 | 16.85 |
| ATOM | 3267 | CA | MET | 479 | 50.447 | 31.207 | 25.155 | 1.00 | 16.42 |
| ATOM | 3268 | CB | MET | 479 | 50.523 | 30.020 | 24.187 | 1.00 | 16.54 |
| ATOM | 3269 | CG | MET | 479 | 49.265 | 29.145 | 24.170 | 1.00 | 15.90 |
| ATOM | 3270 | SD | MET | 479 | 47.741 | 30.068 | 23.800 | 1.00 | 20.51 |
| ATOM | 3271 | CE | MET | 479 | 47.978 | 30.453 | 22.101 | 1.00 | 14.74 |
| ATOM | 3272 | C | MET | 479 | 50.112 | 30.697 | 26.552 | 1.00 | 18.16 |
| ATOM | 3273 | O | MET | 479 | 48.965 | 30.772 | 26.987 | 1.00 | 16.49 |
| ATOM | 3274 | N | LYS | 480 | 51.108 | 30.169 | 27.257 | 1.00 | 17.20 |
| ATOM | 3275 | CA | LYS | 480 | 50.852 | 29.673 | 28.600 | 1.00 | 19.57 |
| ATOM | 3276 | CB | LYS | 480 | 52.117 | 29.038 | 29.191 | 1.00 | 22.36 |
| ATOM | 3277 | CG | LYS | 480 | 51.837 | 28.140 | 30.387 | 1.00 | 27.80 |
| ATOM | 3278 | CD | LYS | 480 | 53.012 | 27.221 | 30.741 | 1.00 | 33.74 |
| ATOM | 3279 | CE | LYS | 480 | 54.250 | 28.002 | 31.184 | 1.00 | 37.33 |
| ATOM | 3280 | NZ | LYS | 480 | 55.332 | 27.126 | 31.746 | 1.00 | 39.64 |
| ATOM | 3281 | C | LYS | 480 | 50.368 | 30.835 | 29.478 | 1.00 | 17.85 |
| ATOM | 3282 | O | LYS | 480 | 49.420 | 30.689 | 30.247 | 1.00 | 18.61 |
| ATOM | 3283 | N | MET | 481 | 51.006 | 31.992 | 29.343 | 1.00 | 15.91 |
| ATOM | 3284 | CA | MET | 481 | 50.619 | 33.165 | 30.123 | 1.00 | 16.21 |
| ATOM | 3285 | CB | MET | 481 | 51.627 | 34.302 | 29.925 | 1.00 | 15.78 |
| ATOM | 3286 | CG | MET | 481 | 53.019 | 34.045 | 30.504 | 1.00 | 17.36 |
| ATOM | 3287 | SD | MET | 481 | 53.024 | 33.719 | 32.288 | 1.00 | 23.53 |
| ATOM | 3288 | CE | MET | 481 | 52.210 | 35.205 | 32.913 | 1.00 | 14.65 |
| ATOM | 3289 | C | MET | 481 | 49.224 | 33.662 | 29.740 | 1.00 | 14.73 |
| ATOM | 3290 | O | MET | 481 | 48.430 | 34.029 | 30.605 | 1.00 | 15.28 |
| ATOM | 3291 | N | ALA | 482 | 48.930 | 33.672 | 28.444 | 1.00 | 12.83 |
| ATOM | 3292 | CA | ALA | 482 | 47.635 | 34.144 | 27.966 | 1.00 | 14.42 |
| ATOM | 3293 | CB | ALA | 482 | 47.640 | 34.229 | 26.440 | 1.00 | 12.60 |

TABLE A-continued

| | | | | | | | | |
|---|---|---|---|---|---|---|---|---|
| ATOM | 3294 | C | ALA | 482 | 46.485 | 33.254 | 28.432 | 1.00 | 13.98 |
| ATOM | 3295 | O | ALA | 482 | 45.404 | 33.737 | 28.742 | 1.00 | 12.54 |
| ATOM | 3296 | N | LEU | 483 | 46.721 | 31.950 | 28.469 | 1.00 | 12.96 |
| ATOM | 3297 | CA | LEU | 483 | 45.687 | 31.019 | 28.889 | 1.00 | 15.49 |
| ATOM | 3298 | CB | LEU | 483 | 46.221 | 29.581 | 28.845 | 1.00 | 13.86 |
| ATOM | 3299 | CG | LEU | 483 | 46.433 | 29.004 | 27.438 | 1.00 | 12.19 |
| ATOM | 3300 | CD1 | LEU | 483 | 47.119 | 27.645 | 27.522 | 1.00 | 12.00 |
| ATOM | 3301 | CD2 | LEU | 483 | 45.099 | 28.868 | 26.744 | 1.00 | 11.05 |
| ATOM | 3302 | C | LEU | 483 | 45.172 | 31.377 | 30.286 | 1.00 | 15.60 |
| ATOM | 3303 | O | LEU | 483 | 44.029 | 31.076 | 30.633 | 1.00 | 13.79 |
| ATOM | 3304 | N | ASP | 484 | 46.011 | 32.026 | 31.088 | 1.00 | 17.99 |
| ATOM | 3305 | CA | ASP | 484 | 45.579 | 32.432 | 32.421 | 1.00 | 19.85 |
| ATOM | 3306 | CB | ASP | 484 | 46.675 | 32.186 | 33.457 | 1.00 | 23.35 |
| ATOM | 3307 | CG | ASP | 484 | 46.697 | 30.752 | 33.950 | 1.00 | 31.47 |
| ATOM | 3308 | OD1 | ASP | 484 | 45.708 | 30.017 | 33.703 | 1.00 | 32.89 |
| ATOM | 3309 | OD2 | ASP | 484 | 47.692 | 30.358 | 34.590 | 1.00 | 35.68 |
| ATOM | 3310 | C | ASP | 484 | 45.159 | 33.900 | 32.469 | 1.00 | 19.15 |
| ATOM | 3311 | O | ASP | 484 | 44.016 | 34.205 | 32.801 | 1.00 | 19.40 |
| ATOM | 3312 | N | LYS | 485 | 46.074 | 34.797 | 32.106 | 1.00 | 15.90 |
| ATOM | 3313 | CA | LYS | 485 | 45.809 | 36.233 | 32.153 | 1.00 | 15.26 |
| ATOM | 3314 | CB | LYS | 485 | 47.115 | 37.013 | 31.937 | 1.00 | 16.44 |
| ATOM | 3315 | CG | LYS | 485 | 48.221 | 36.683 | 32.935 | 1.00 | 17.03 |
| ATOM | 3316 | CD | LYS | 485 | 47.780 | 36.925 | 34.376 | 1.00 | 16.07 |
| ATOM | 3317 | CE | LYS | 485 | 48.914 | 36.634 | 35.355 | 1.00 | 16.43 |
| ATOM | 3318 | NZ | LYS | 485 | 48.526 | 36.873 | 36.774 | 1.00 | 15.12 |
| ATOM | 3319 | C | LYS | 485 | 44.743 | 36.792 | 31.207 | 1.00 | 15.09 |
| ATOM | 3320 | O | LYS | 485 | 43.963 | 37.655 | 31.608 | 1.00 | 14.86 |
| ATOM | 3321 | N | ILE | 486 | 44.720 | 36.338 | 29.954 | 1.00 | 12.89 |
| ATOM | 3322 | CA | ILE | 486 | 43.738 | 36.845 | 28.997 | 1.00 | 12.96 |
| ATOM | 3323 | CB | ILE | 486 | 44.206 | 36.634 | 27.534 | 1.00 | 12.31 |
| ATOM | 3324 | CG2 | ILE | 486 | 43.111 | 37.083 | 26.564 | 1.00 | 11.47 |
| ATOM | 3325 | CG1 | ILE | 486 | 45.492 | 37.431 | 27.269 | 1.00 | 14.69 |
| ATOM | 3326 | CD1 | ILE | 486 | 45.378 | 38.921 | 27.561 | 1.00 | 14.14 |
| ATOM | 3327 | C | ILE | 486 | 42.370 | 36.185 | 29.177 | 1.00 | 13.40 |
| ATOM | 3328 | O | ILE | 486 | 41.339 | 36.856 | 29.155 | 1.00 | 13.09 |
| ATOM | 3329 | N | ALA | 487 | 42.363 | 34.868 | 29.343 | 1.00 | 13.68 |
| ATOM | 3330 | CA | ALA | 487 | 41.108 | 34.143 | 29.523 | 1.00 | 13.77 |
| ATOM | 3331 | CB | ALA | 487 | 41.381 | 32.640 | 29.672 | 1.00 | 13.45 |
| ATOM | 3332 | C | ALA | 487 | 40.356 | 34.655 | 30.746 | 1.00 | 12.99 |
| ATOM | 3333 | O | ALA | 487 | 39.130 | 34.653 | 30.773 | 1.00 | 14.04 |
| ATOM | 3334 | N | PHE | 488 | 41.095 | 35.111 | 31.750 | 1.00 | 11.52 |
| ATOM | 3335 | CA | PHE | 488 | 40.488 | 35.595 | 32.984 | 1.00 | 12.47 |
| ATOM | 3336 | CB | PHE | 488 | 41.548 | 35.663 | 34.079 | 1.00 | 10.72 |
| ATOM | 3337 | CG | PHE | 488 | 41.002 | 35.979 | 35.445 | 1.00 | 13.51 |
| ATOM | 3338 | CD1 | PHE | 488 | 40.295 | 35.019 | 36.172 | 1.00 | 11.90 |
| ATOM | 3339 | CD2 | PHE | 488 | 41.245 | 37.216 | 36.031 | 1.00 | 12.70 |
| ATOM | 3340 | CE1 | PHE | 488 | 39.850 | 35.286 | 37.467 | 1.00 | 12.84 |
| ATOM | 3341 | CE2 | PHE | 488 | 40.803 | 37.492 | 37.324 | 1.00 | 12.47 |
| ATOM | 3342 | CZ | PHE | 488 | 40.106 | 36.524 | 38.043 | 1.00 | 11.48 |
| ATOM | 3343 | C | PHE | 488 | 39.806 | 36.957 | 32.858 | 1.00 | 12.87 |
| ATOM | 3344 | O | PHE | 488 | 38.944 | 37.290 | 33.669 | 1.00 | 14.49 |
| ATOM | 3345 | N | ILE | 489 | 40.190 | 37.738 | 31.851 | 1.00 | 13.59 |
| ATOM | 3346 | CA | ILE | 489 | 39.616 | 39.064 | 31.661 | 1.00 | 12.89 |
| ATOM | 3347 | CB | ILE | 489 | 40.200 | 39.758 | 30.404 | 1.00 | 14.05 |
| ATOM | 3348 | CG2 | ILE | 489 | 39.399 | 41.024 | 30.076 | 1.00 | 11.51 |
| ATOM | 3349 | CG1 | ILE | 489 | 41.677 | 40.100 | 30.636 | 1.00 | 15.42 |
| ATOM | 3350 | CD1 | ILE | 489 | 41.931 | 41.022 | 31.840 | 1.00 | 16.62 |
| ATOM | 3351 | C | ILE | 489 | 38.083 | 39.080 | 31.581 | 1.00 | 14.01 |
| ATOM | 3352 | O | ILE | 489 | 37.433 | 39.771 | 32.361 | 1.00 | 13.07 |
| ATOM | 3353 | N | PRO | 490 | 37.486 | 38.340 | 30.630 | 1.00 | 11.60 |
| ATOM | 3354 | CD | PRO | 490 | 38.036 | 37.616 | 29.470 | 1.00 | 12.38 |
| ATOM | 3355 | CA | PRO | 490 | 36.022 | 38.377 | 30.580 | 1.00 | 12.27 |
| ATOM | 3356 | CB | PRO | 490 | 35.694 | 37.643 | 29.276 | 1.00 | 12.12 |
| ATOM | 3357 | CG | PRO | 490 | 36.876 | 36.749 | 29.062 | 1.00 | 14.13 |
| ATOM | 3358 | C | PRO | 490 | 35.339 | 37.767 | 31.802 | 1.00 | 11.71 |
| ATOM | 3359 | O | PRO | 490 | 34.267 | 38.218 | 32.202 | 1.00 | 11.51 |
| ATOM | 3360 | N | PHE | 491 | 35.950 | 36.747 | 32.401 | 1.00 | 10.88 |
| ATOM | 3361 | CA | PHE | 491 | 35.346 | 36.126 | 33.581 | 1.00 | 10.74 |
| ATOM | 3362 | CB | PHE | 491 | 36.113 | 34.871 | 34.017 | 1.00 | 9.32 |
| ATOM | 3363 | CG | PHE | 491 | 35.556 | 34.230 | 35.269 | 1.00 | 9.41 |
| ATOM | 3364 | CD1 | PHE | 491 | 34.443 | 33.396 | 35.206 | 1.00 | 10.06 |
| ATOM | 3365 | CD2 | PHE | 491 | 36.121 | 34.492 | 36.511 | 1.00 | 9.76 |
| ATOM | 3366 | CE1 | PHE | 491 | 33.901 | 32.834 | 36.365 | 1.00 | 12.14 |
| ATOM | 3367 | CE2 | PHE | 491 | 35.589 | 33.937 | 37.679 | 1.00 | 11.37 |
| ATOM | 3368 | CZ | PHE | 491 | 34.476 | 33.104 | 37.606 | 1.00 | 11.49 |
| ATOM | 3369 | C | PHE | 491 | 35.337 | 37.110 | 34.745 | 1.00 | 10.49 |
| ATOM | 3370 | O | PHE | 491 | 34.308 | 37.310 | 35.390 | 1.00 | 11.46 |
| ATOM | 3371 | N | SER | 492 | 36.482 | 37.732 | 35.005 | 1.00 | 10.88 |
| ATOM | 3372 | CA | SER | 492 | 36.584 | 38.673 | 36.117 | 1.00 | 12.32 |
| ATOM | 3373 | CB | SER | 492 | 38.031 | 39.125 | 36.308 | 1.00 | 11.29 |

TABLE A-continued

| | | | | | | | | |
|---|---|---|---|---|---|---|---|---|
| ATOM | 3374 | OG | SER | 492 | 38.510 | 39.836 | 35.181 | 1.00 | 11.99 |
| ATOM | 3375 | C | SER | 492 | 35.679 | 39.888 | 35.940 | 1.00 | 13.79 |
| ATOM | 3376 | O | SER | 492 | 35.297 | 40.533 | 36.919 | 1.00 | 15.69 |
| ATOM | 3377 | N | TYR | 493 | 35.340 | 40.190 | 34.693 | 1.00 | 12.01 |
| ATOM | 3378 | CA | TYR | 493 | 34.468 | 41.320 | 34.374 | 1.00 | 12.81 |
| ATOM | 3379 | CB | TYR | 493 | 34.633 | 41.700 | 32.897 | 1.00 | 14.65 |
| ATOM | 3380 | CG | TYR | 493 | 33.937 | 42.983 | 32.493 | 1.00 | 16.68 |
| ATOM | 3381 | CD1 | TYR | 493 | 34.362 | 44.214 | 32.989 | 1.00 | 18.71 |
| ATOM | 3382 | CE1 | TYR | 493 | 33.724 | 45.398 | 32.624 | 1.00 | 20.68 |
| ATOM | 3383 | CD2 | TYR | 493 | 32.852 | 42.966 | 31.617 | 1.00 | 17.79 |
| ATOM | 3384 | CE2 | TYR | 493 | 32.207 | 44.147 | 31.245 | 1.00 | 20.59 |
| ATOM | 3385 | CZ | TYR | 493 | 32.649 | 45.357 | 31.753 | 1.00 | 19.58 |
| ATOM | 3386 | OH | TYR | 493 | 32.014 | 46.526 | 31.400 | 1.00 | 18.46 |
| ATOM | 3387 | C | TYR | 493 | 33.010 | 40.948 | 34.621 | 1.00 | 13.40 |
| ATOM | 3388 | O | TYR | 493 | 32.227 | 41.727 | 35.162 | 1.00 | 13.85 |
| ATOM | 3389 | N | LEU | 494 | 32.666 | 39.733 | 34.217 | 1.00 | 12.33 |
| ATOM | 3390 | CA | LEU | 494 | 31.313 | 39.197 | 34.311 | 1.00 | 13.77 |
| ATOM | 3391 | CB | LEU | 494 | 31.293 | 37.864 | 33.551 | 1.00 | 16.44 |
| ATOM | 3392 | CG | LEU | 494 | 30.246 | 36.756 | 33.614 | 1.00 | 23.07 |
| ATOM | 3393 | CD1 | LEU | 494 | 30.665 | 35.692 | 32.600 | 1.00 | 23.72 |
| ATOM | 3394 | CD2 | LEU | 494 | 30.142 | 36.150 | 34.994 | 1.00 | 18.70 |
| ATOM | 3395 | C | LEU | 494 | 30.713 | 39.016 | 35.704 | 1.00 | 11.84 |
| ATOM | 3396 | O | LEU | 494 | 29.542 | 39.330 | 35.925 | 1.00 | 13.02 |
| ATOM | 3397 | N | VAL | 495 | 31.505 | 38.516 | 36.643 | 1.00 | 10.62 |
| ATOM | 3398 | CA | VAL | 495 | 30.990 | 38.236 | 37.979 | 1.00 | 11.98 |
| ATOM | 3399 | CB | VAL | 495 | 32.112 | 37.768 | 38.922 | 1.00 | 11.36 |
| ATOM | 3400 | CG1 | VAL | 495 | 31.552 | 37.498 | 40.309 | 1.00 | 9.21 |
| ATOM | 3401 | CG2 | VAL | 495 | 32.751 | 36.504 | 38.362 | 1.00 | 13.56 |
| ATOM | 3402 | C | VAL | 495 | 30.207 | 39.360 | 38.642 | 1.00 | 12.05 |
| ATOM | 3403 | O | VAL | 495 | 29.064 | 39.150 | 39.050 | 1.00 | 8.92 |
| ATOM | 3404 | N | ASP | 496 | 30.802 | 40.543 | 38.760 | 1.00 | 11.08 |
| ATOM | 3405 | CA | ASP | 496 | 30.086 | 41.641 | 39.391 | 1.00 | 11.99 |
| ATOM | 3406 | CB | ASP | 496 | 31.056 | 42.624 | 40.061 | 1.00 | 11.20 |
| ATOM | 3407 | CG | ASP | 496 | 31.579 | 42.096 | 41.400 | 1.00 | 12.07 |
| ATOM | 3408 | OD1 | ASP | 496 | 31.048 | 41.069 | 41.881 | 1.00 | 13.72 |
| ATOM | 3409 | OD2 | ASP | 496 | 32.507 | 42.695 | 41.980 | 1.00 | 10.70 |
| ATOM | 3410 | C | ASP | 496 | 29.120 | 42.358 | 38.453 | 1.00 | 13.14 |
| ATOM | 3411 | O | ASP | 496 | 28.297 | 43.151 | 38.906 | 1.00 | 12.97 |
| ATOM | 3412 | N | GLN | 497 | 29.207 | 42.096 | 37.151 | 1.00 | 12.75 |
| ATOM | 3413 | CA | GLN | 497 | 28.234 | 42.711 | 36.255 | 1.00 | 12.19 |
| ATOM | 3414 | CB | GLN | 497 | 28.561 | 42.447 | 34.781 | 1.00 | 14.86 |
| ATOM | 3415 | CG | GLN | 497 | 29.789 | 43.181 | 34.232 | 1.00 | 15.25 |
| ATOM | 3416 | CD | GLN | 497 | 29.717 | 44.698 | 34.383 | 1.00 | 19.00 |
| ATOM | 3417 | OE1 | GLN | 497 | 28.641 | 45.290 | 34.356 | 1.00 | 17.62 |
| ATOM | 3418 | NE2 | GLN | 497 | 30.875 | 45.330 | 34.526 | 1.00 | 19.82 |
| ATOM | 3419 | C | GLN | 497 | 26.926 | 42.008 | 36.633 | 1.00 | 14.20 |
| ATOM | 3420 | O | GLN | 497 | 25.857 | 42.615 | 36.640 | 1.00 | 12.70 |
| ATOM | 3421 | N | TRP | 498 | 27.033 | 40.720 | 36.964 | 1.00 | 12.15 |
| ATOM | 3422 | CA | TRP | 498 | 25.876 | 39.927 | 37.371 | 1.00 | 13.21 |
| ATOM | 3423 | CB | TRP | 498 | 26.230 | 38.435 | 37.414 | 1.00 | 12.05 |
| ATOM | 3424 | CG | TRP | 498 | 25.081 | 37.551 | 37.820 | 1.00 | 12.38 |
| ATOM | 3425 | CD2 | TRP | 498 | 24.828 | 37.025 | 39.124 | 1.00 | 11.96 |
| ATOM | 3426 | CE2 | TRP | 498 | 23.647 | 36.251 | 39.043 | 1.00 | 14.37 |
| ATOM | 3427 | CE3 | TRP | 498 | 25.487 | 37.129 | 40.357 | 1.00 | 12.53 |
| ATOM | 3428 | CD1 | TRP | 498 | 24.068 | 37.091 | 37.018 | 1.00 | 13.82 |
| ATOM | 3429 | NE1 | TRP | 498 | 23.204 | 36.309 | 37.747 | 1.00 | 13.23 |
| ATOM | 3430 | CZ2 | TRP | 498 | 23.111 | 35.584 | 40.150 | 1.00 | 12.76 |
| ATOM | 3431 | CZ3 | TRP | 498 | 24.953 | 36.463 | 41.458 | 1.00 | 14.42 |
| ATOM | 3432 | CH2 | TRP | 498 | 23.777 | 35.702 | 41.345 | 1.00 | 12.98 |
| ATOM | 3433 | C | TRP | 498 | 25.388 | 40.363 | 38.757 | 1.00 | 12.74 |
| ATOM | 3434 | O | TRP | 498 | 24.202 | 40.609 | 38.945 | 1.00 | 12.76 |
| ATOM | 3435 | N | ARG | 499 | 26.297 | 40.458 | 39.726 | 1.00 | 14.02 |
| ATOM | 3436 | CA | ARG | 499 | 25.907 | 40.862 | 41.080 | 1.00 | 14.05 |
| ATOM | 3437 | CB | ARG | 499 | 27.069 | 40.693 | 42.066 | 1.00 | 13.99 |
| ATOM | 3438 | CG | ARG | 499 | 27.111 | 39.317 | 42.732 | 1.00 | 15.24 |
| ATOM | 3439 | CD | ARG | 499 | 28.018 | 39.283 | 43.967 | 1.00 | 14.11 |
| ATOM | 3440 | NE | ARG | 499 | 29.427 | 39.442 | 43.618 | 1.00 | 12.25 |
| ATOM | 3441 | CZ | ARG | 499 | 30.435 | 38.959 | 44.333 | 1.00 | 14.41 |
| ATOM | 3442 | NH1 | ARG | 499 | 30.195 | 38.280 | 45.453 | 1.00 | 13.25 |
| ATOM | 3443 | NH2 | ARG | 499 | 31.686 | 39.137 | 43.917 | 1.00 | 12.95 |
| ATOM | 3444 | C | ARG | 499 | 25.362 | 42.289 | 41.177 | 1.00 | 15.06 |
| ATOM | 3445 | O | ARG | 499 | 24.423 | 42.539 | 41.936 | 1.00 | 13.96 |
| ATOM | 3446 | N | TRP | 500 | 25.942 | 43.223 | 40.427 | 1.00 | 12.32 |
| ATOM | 3447 | CA | TRP | 500 | 25.454 | 44.600 | 40.469 | 1.00 | 14.74 |
| ATOM | 3448 | CB | TRP | 500 | 26.277 | 45.529 | 39.561 | 1.00 | 11.23 |
| ATOM | 3449 | CG | TRP | 500 | 27.692 | 45.753 | 39.989 | 1.00 | 12.02 |
| ATOM | 3450 | CD2 | TRP | 500 | 28.757 | 46.277 | 39.181 | 1.00 | 11.01 |
| ATOM | 3451 | CE2 | TRP | 500 | 29.916 | 46.302 | 39.984 | 1.00 | 10.87 |
| ATOM | 3452 | CE3 | TRP | 500 | 28.841 | 46.728 | 37.855 | 1.00 | 13.39 |
| ATOM | 3453 | CD1 | TRP | 500 | 28.233 | 45.495 | 41.214 | 1.00 | 10.03 |

TABLE A-continued

| | | | | | | | | |
|---|---|---|---|---|---|---|---|---|
| ATOM | 3454 | NE1 | TRP | 500 | 29.567 | 45.819 | 41.218 | 1.00 | 10.74 |
| ATOM | 3455 | CZ2 | TRP | 500 | 31.153 | 46.759 | 39.508 | 1.00 | 8.74 |
| ATOM | 3456 | CZ3 | TRP | 500 | 30.073 | 47.186 | 37.378 | 1.00 | 11.68 |
| ATOM | 3457 | CH2 | TRP | 500 | 31.210 | 47.195 | 38.205 | 1.00 | 11.27 |
| ATOM | 3458 | C | TRP | 500 | 23.997 | 44.651 | 40.015 | 1.00 | 15.43 |
| ATOM | 3459 | O | TRP | 500 | 23.213 | 45.457 | 40.513 | 1.00 | 14.95 |
| ATOM | 3460 | N | ARG | 501 | 23.643 | 43.799 | 39.056 | 1.00 | 15.05 |
| ATOM | 3461 | CA | ARG | 501 | 22.275 | 43.769 | 38.551 | 1.00 | 15.13 |
| ATOM | 3462 | CB | ARG | 501 | 22.249 | 43.170 | 37.142 | 1.00 | 17.81 |
| ATOM | 3463 | CG | ARG | 501 | 22.833 | 44.107 | 36.088 | 1.00 | 22.48 |
| ATOM | 3464 | CD | ARG | 501 | 22.988 | 43.403 | 34.751 | 1.00 | 29.90 |
| ATOM | 3465 | NE | ARG | 501 | 21.713 | 42.901 | 34.245 | 1.00 | 35.03 |
| ATOM | 3466 | CZ | ARG | 501 | 21.596 | 41.864 | 33.422 | 1.00 | 37.06 |
| ATOM | 3467 | NH1 | ARG | 501 | 22.678 | 41.213 | 33.012 | 1.00 | 37.13 |
| ATOM | 3468 | NH2 | ARG | 501 | 20.397 | 41.481 | 33.004 | 1.00 | 36.72 |
| ATOM | 3469 | C | ARG | 501 | 21.346 | 43.006 | 39.493 | 1.00 | 15.12 |
| ATOM | 3470 | O | ARG | 501 | 20.129 | 43.222 | 39.497 | 1.00 | 13.20 |
| ATOM | 3471 | N | VAL | 502 | 21.917 | 42.102 | 40.284 | 1.00 | 13.23 |
| ATOM | 3472 | CA | VAL | 502 | 21.126 | 41.367 | 41.262 | 1.00 | 14.21 |
| ATOM | 3473 | CB | VAL | 502 | 21.910 | 40.175 | 41.854 | 1.00 | 10.98 |
| ATOM | 3474 | CG1 | VAL | 502 | 21.207 | 39.660 | 43.102 | 1.00 | 11.32 |
| ATOM | 3475 | CG2 | VAL | 502 | 22.003 | 39.052 | 40.816 | 1.00 | 14.99 |
| ATOM | 3476 | C | VAL | 502 | 20.820 | 42.369 | 42.373 | 1.00 | 14.19 |
| ATOM | 3477 | O | VAL | 502 | 19.678 | 42.513 | 42.813 | 1.00 | 14.12 |
| ATOM | 3478 | N | PHE | 503 | 21.862 | 43.072 | 42.802 | 1.00 | 14.50 |
| ATOM | 3479 | CA | PHE | 503 | 21.749 | 44.070 | 43.856 | 1.00 | 15.39 |
| ATOM | 3480 | CB | PHE | 503 | 23.139 | 44.614 | 44.197 | 1.00 | 14.83 |
| ATOM | 3481 | CG | PHE | 503 | 23.999 | 43.647 | 44.971 | 1.00 | 14.46 |
| ATOM | 3482 | CD1 | PHE | 503 | 25.383 | 43.722 | 44.901 | 1.00 | 14.93 |
| ATOM | 3483 | CD2 | PHE | 503 | 23.422 | 42.677 | 45.793 | 1.00 | 16.22 |
| ATOM | 3484 | CE1 | PHE | 503 | 26.186 | 42.848 | 45.640 | 1.00 | 14.36 |
| ATOM | 3485 | CE2 | PHE | 503 | 24.218 | 41.797 | 46.537 | 1.00 | 12.05 |
| ATOM | 3486 | CZ | PHE | 503 | 25.598 | 41.886 | 46.459 | 1.00 | 15.10 |
| ATOM | 3487 | C | PHE | 503 | 20.802 | 45.221 | 43.509 | 1.00 | 15.02 |
| ATOM | 3488 | O | PHE | 503 | 20.022 | 45.650 | 44.359 | 1.00 | 14.79 |
| ATOM | 3489 | N | ASP | 504 | 20.853 | 45.722 | 42.274 | 1.00 | 14.97 |
| ATOM | 3490 | CA | ASP | 504 | 19.963 | 46.820 | 41.916 | 1.00 | 15.11 |
| ATOM | 3491 | CB | ASP | 504 | 20.575 | 47.716 | 40.819 | 1.00 | 15.57 |
| ATOM | 3492 | CG | ASP | 504 | 20.520 | 47.100 | 39.426 | 1.00 | 16.33 |
| ATOM | 3493 | OD1 | ASP | 504 | 19.860 | 46.057 | 39.220 | 1.00 | 17.34 |
| ATOM | 3494 | OD2 | ASP | 504 | 21.144 | 47.689 | 38.522 | 1.00 | 17.52 |
| ATOM | 3495 | C | ASP | 504 | 18.565 | 46.356 | 41.516 | 1.00 | 16.58 |
| ATOM | 3496 | O | ASP | 504 | 17.756 | 47.153 | 41.044 | 1.00 | 17.20 |
| ATOM | 3497 | N | GLY | 505 | 18.287 | 45.067 | 41.708 | 1.00 | 16.74 |
| ATOM | 3498 | CA | GLY | 505 | 16.971 | 44.527 | 41.400 | 1.00 | 17.30 |
| ATOM | 3499 | C | GLY | 505 | 16.636 | 44.167 | 39.961 | 1.00 | 17.93 |
| ATOM | 3500 | O | GLY | 505 | 15.520 | 43.732 | 39.693 | 1.00 | 18.99 |
| ATOM | 3501 | N | SER | 506 | 17.578 | 44.341 | 39.039 | 1.00 | 17.16 |
| ATOM | 3502 | CA | SER | 506 | 17.350 | 44.013 | 37.630 | 1.00 | 18.82 |
| ATOM | 3503 | CB | SER | 506 | 18.514 | 44.514 | 36.771 | 1.00 | 19.99 |
| ATOM | 3504 | OG | SER | 506 | 18.605 | 45.920 | 36.805 | 1.00 | 25.35 |
| ATOM | 3505 | C | SER | 506 | 17.185 | 42.509 | 37.401 | 1.00 | 18.71 |
| ATOM | 3506 | O | SER | 506 | 16.500 | 42.089 | 36.470 | 1.00 | 19.68 |
| ATOM | 3507 | N | ILE | 507 | 17.837 | 41.709 | 38.241 | 1.00 | 17.20 |
| ATOM | 3508 | CA | ILE | 507 | 17.767 | 40.253 | 38.147 | 1.00 | 17.19 |
| ATOM | 3509 | CB | ILE | 507 | 19.184 | 39.630 | 38.004 | 1.00 | 16.86 |
| ATOM | 3510 | CG2 | ILE | 507 | 19.076 | 38.112 | 37.912 | 1.00 | 15.71 |
| ATOM | 3511 | CG1 | ILE | 507 | 19.890 | 40.193 | 36.767 | 1.00 | 17.34 |
| ATOM | 3512 | CD1 | ILE | 507 | 21.357 | 39.746 | 36.640 | 1.00 | 15.06 |
| ATOM | 3513 | C | ILE | 507 | 17.123 | 39.695 | 39.420 | 1.00 | 17.07 |
| ATOM | 3514 | O | ILE | 507 | 17.689 | 39.807 | 40.509 | 1.00 | 16.98 |
| ATOM | 3515 | N | THR | 508 | 15.940 | 39.105 | 39.281 | 1.00 | 17.01 |
| ATOM | 3516 | CA | THR | 508 | 15.227 | 38.531 | 40.421 | 1.00 | 18.33 |
| ATOM | 3517 | CB | THR | 508 | 13.710 | 38.551 | 40.196 | 1.00 | 18.44 |
| ATOM | 3518 | OG1 | THR | 508 | 13.365 | 37.586 | 39.191 | 1.00 | 20.70 |
| ATOM | 3519 | CG2 | THR | 508 | 13.263 | 39.931 | 39.734 | 1.00 | 20.95 |
| ATOM | 3520 | C | THR | 508 | 15.671 | 37.088 | 40.581 | 1.00 | 18.12 |
| ATOM | 3521 | O | THR | 508 | 16.318 | 36.540 | 39.689 | 1.00 | 17.12 |
| ATOM | 3522 | N | LYS | 509 | 15.312 | 36.469 | 41.703 | 1.00 | 20.57 |
| ATOM | 3523 | CA | LYS | 509 | 15.702 | 35.087 | 41.961 | 1.00 | 23.09 |
| ATOM | 3524 | CB | LYS | 509 | 15.240 | 34.637 | 43.352 | 1.00 | 24.96 |
| ATOM | 3525 | CG | LYS | 509 | 13.763 | 34.281 | 43.465 | 1.00 | 29.41 |
| ATOM | 3526 | CD | LYS | 509 | 13.455 | 33.746 | 44.859 | 1.00 | 32.03 |
| ATOM | 3527 | CE | LYS | 509 | 12.017 | 33.278 | 44.988 | 1.00 | 33.33 |
| ATOM | 3528 | NZ | LYS | 509 | 11.724 | 32.824 | 46.378 | 1.00 | 34.91 |
| ATOM | 3529 | C | LYS | 509 | 15.142 | 34.148 | 40.909 | 1.00 | 24.36 |
| ATOM | 3530 | O | LYS | 509 | 15.601 | 33.018 | 40.769 | 1.00 | 25.76 |
| ATOM | 3531 | N | GLU | 510 | 14.146 | 34.619 | 40.169 | 1.00 | 25.33 |
| ATOM | 3532 | CA | GLU | 510 | 13.534 | 33.819 | 39.116 | 1.00 | 26.94 |
| ATOM | 3533 | CB | GLU | 510 | 12.240 | 34.481 | 38.649 | 1.00 | 31.14 |

TABLE A-continued

| | | | | | | | | |
|---|---|---|---|---|---|---|---|---|
| ATOM | 3534 | CG | GLU | 510 | 11.420 | 35.078 | 39.776 | 1.00 | 39.75 |
| ATOM | 3535 | CD | GLU | 510 | 10.187 | 34.265 | 40.094 | 1.00 | 42.36 |
| ATOM | 3536 | OE1 | GLU | 510 | 9.312 | 34.169 | 39.212 | 1.00 | 46.25 |
| ATOM | 3537 | OE2 | GLU | 510 | 10.094 | 33.725 | 41.217 | 1.00 | 45.33 |
| ATOM | 3538 | C | GLU | 510 | 14.489 | 33.726 | 37.927 | 1.00 | 26.01 |
| ATOM | 3539 | O | GLU | 510 | 14.458 | 32.758 | 37.163 | 1.00 | 25.45 |
| ATOM | 3540 | N | ASN | 511 | 15.343 | 34.736 | 37.780 | 1.00 | 22.90 |
| ATOM | 3541 | CA | ASN | 511 | 16.271 | 34.785 | 36.657 | 1.00 | 21.40 |
| ATOM | 3542 | CB | ASN | 511 | 15.973 | 36.028 | 35.811 | 1.00 | 23.82 |
| ATOM | 3543 | CG | ASN | 511 | 14.538 | 36.057 | 35.315 | 1.00 | 29.85 |
| ATOM | 3544 | OD1 | ASN | 511 | 14.086 | 35.126 | 34.646 | 1.00 | 30.15 |
| ATOM | 3545 | ND2 | ASN | 511 | 13.811 | 37.122 | 35.647 | 1.00 | 28.53 |
| ATOM | 3546 | C | ASN | 511 | 17.759 | 34.747 | 37.000 | 1.00 | 18.64 |
| ATOM | 3547 | O | ASN | 511 | 18.593 | 34.993 | 36.131 | 1.00 | 16.50 |
| ATOM | 3548 | N | TYR | 512 | 18.089 | 34.441 | 38.251 | 1.00 | 15.85 |
| ATOM | 3549 | CA | TYR | 512 | 19.487 | 34.360 | 38.681 | 1.00 | 15.32 |
| ATOM | 3550 | CB | TYR | 512 | 19.604 | 33.604 | 40.007 | 1.00 | 14.72 |
| ATOM | 3551 | CG | TYR | 512 | 19.244 | 34.359 | 41.266 | 1.00 | 14.45 |
| ATOM | 3552 | CD1 | TYR | 512 | 19.008 | 33.667 | 42.450 | 1.00 | 14.67 |
| ATOM | 3553 | CE1 | TYR | 512 | 18.736 | 34.335 | 43.637 | 1.00 | 16.30 |
| ATOM | 3554 | CD2 | TYR | 512 | 19.194 | 35.753 | 41.295 | 1.00 | 14.34 |
| ATOM | 3555 | CE2 | TYR | 512 | 18.920 | 36.435 | 42.484 | 1.00 | 17.16 |
| ATOM | 3556 | CZ | TYR | 512 | 18.695 | 35.714 | 43.648 | 1.00 | 18.10 |
| ATOM | 3557 | OH | TYR | 512 | 18.451 | 36.361 | 44.837 | 1.00 | 21.96 |
| ATOM | 3558 | C | TYR | 512 | 20.378 | 33.613 | 37.688 | 1.00 | 16.40 |
| ATOM | 3559 | O | TYR | 512 | 21.318 | 34.171 | 37.108 | 1.00 | 13.43 |
| ATOM | 3560 | N | ASN | 513 | 20.077 | 32.328 | 37.521 | 1.00 | 15.11 |
| ATOM | 3561 | CA | ASN | 513 | 20.877 | 31.461 | 36.673 | 1.00 | 14.44 |
| ATOM | 3562 | CB | ASN | 513 | 20.478 | 29.999 | 36.894 | 1.00 | 14.83 |
| ATOM | 3563 | CG | ASN | 513 | 21.677 | 29.073 | 36.872 | 1.00 | 13.79 |
| ATOM | 3564 | OD1 | ASN | 513 | 22.620 | 29.261 | 37.634 | 1.00 | 15.96 |
| ATOM | 3565 | ND2 | ASN | 513 | 21.652 | 28.078 | 35.993 | 1.00 | 13.24 |
| ATOM | 3566 | C | ASN | 513 | 20.840 | 31.778 | 35.198 | 1.00 | 14.91 |
| ATOM | 3567 | O | ASN | 513 | 21.865 | 31.701 | 34.517 | 1.00 | 12.27 |
| ATOM | 3568 | N | GLN | 514 | 19.664 | 32.133 | 34.697 | 1.00 | 13.28 |
| ATOM | 3569 | CA | GLN | 514 | 19.539 | 32.441 | 33.285 | 1.00 | 16.41 |
| ATOM | 3570 | CB | GLN | 514 | 18.062 | 32.642 | 32.924 | 1.00 | 18.43 |
| ATOM | 3571 | CG | GLN | 514 | 17.219 | 31.363 | 33.087 | 1.00 | 25.86 |
| ATOM | 3572 | CD | GLN | 514 | 16.628 | 31.163 | 34.492 | 1.00 | 27.97 |
| ATOM | 3573 | OE1 | GLN | 514 | 17.184 | 31.606 | 35.501 | 1.00 | 22.77 |
| ATOM | 3574 | NE2 | GLN | 514 | 15.493 | 30.468 | 34.551 | 1.00 | 32.36 |
| ATOM | 3575 | C | GLN | 514 | 20.378 | 33.660 | 32.900 | 1.00 | 16.35 |
| ATOM | 3576 | O | GLN | 514 | 21.004 | 33.682 | 31.830 | 1.00 | 14.47 |
| ATOM | 3577 | N | GLU | 515 | 20.406 | 34.668 | 33.769 | 1.00 | 14.45 |
| ATOM | 3578 | CA | GLU | 515 | 21.188 | 35.872 | 33.486 | 1.00 | 15.60 |
| ATOM | 3579 | CB | GLU | 515 | 20.762 | 37.023 | 34.398 | 1.00 | 17.63 |
| ATOM | 3580 | CG | GLU | 515 | 19.361 | 37.553 | 34.107 | 1.00 | 23.50 |
| ATOM | 3581 | CD | GLU | 515 | 19.200 | 37.998 | 32.663 | 1.00 | 29.39 |
| ATOM | 3582 | OE1 | GLU | 515 | 20.051 | 38.776 | 32.177 | 1.00 | 29.30 |
| ATOM | 3583 | OE2 | GLU | 515 | 18.220 | 37.570 | 32.016 | 1.00 | 31.22 |
| ATOM | 3584 | C | GLU | 515 | 22.680 | 35.591 | 33.656 | 1.00 | 13.08 |
| ATOM | 3585 | O | GLU | 515 | 23.512 | 36.209 | 32.992 | 1.00 | 14.72 |
| ATOM | 3586 | N | TRP | 516 | 23.018 | 34.671 | 34.555 | 1.00 | 11.64 |
| ATOM | 3587 | CA | TRP | 516 | 24.423 | 34.303 | 34.752 | 1.00 | 12.26 |
| ATOM | 3588 | CB | TRP | 516 | 24.559 | 33.298 | 35.901 | 1.00 | 10.60 |
| ATOM | 3589 | CG | TRP | 516 | 25.924 | 32.648 | 36.038 | 1.00 | 13.26 |
| ATOM | 3590 | CD2 | TRP | 516 | 27.086 | 33.201 | 36.671 | 1.00 | 13.09 |
| ATOM | 3591 | CE2 | TRP | 516 | 28.110 | 32.228 | 36.593 | 1.00 | 14.57 |
| ATOM | 3592 | CE3 | TRP | 516 | 27.362 | 34.423 | 37.300 | 1.00 | 14.40 |
| ATOM | 3593 | CD1 | TRP | 516 | 26.281 | 31.402 | 35.612 | 1.00 | 15.30 |
| ATOM | 3594 | NE1 | TRP | 516 | 27.593 | 31.140 | 35.943 | 1.00 | 14.97 |
| ATOM | 3595 | CZ2 | TRP | 516 | 29.392 | 32.438 | 37.119 | 1.00 | 14.78 |
| ATOM | 3596 | CZ3 | TRP | 516 | 28.640 | 34.632 | 37.827 | 1.00 | 15.38 |
| ATOM | 3597 | CH2 | TRP | 516 | 29.636 | 33.642 | 37.731 | 1.00 | 16.29 |
| ATOM | 3598 | C | TRP | 516 | 24.945 | 33.701 | 33.450 | 1.00 | 12.53 |
| ATOM | 3599 | O | TRP | 516 | 26.014 | 34.081 | 32.967 | 1.00 | 15.24 |
| ATOM | 3600 | N | TRP | 517 | 24.186 | 32.778 | 32.864 | 1.00 | 11.64 |
| ATOM | 3601 | CA | TRP | 517 | 24.631 | 32.169 | 31.618 | 1.00 | 12.88 |
| ATOM | 3602 | CB | TRP | 517 | 23.892 | 30.850 | 31.371 | 1.00 | 11.74 |
| ATOM | 3603 | CG | TRP | 517 | 24.494 | 29.780 | 32.238 | 1.00 | 11.07 |
| ATOM | 3604 | CD2 | TRP | 517 | 25.768 | 29.150 | 32.047 | 1.00 | 10.34 |
| ATOM | 3605 | CE2 | TRP | 517 | 26.014 | 28.349 | 33.182 | 1.00 | 11.07 |
| ATOM | 3606 | CE3 | TRP | 517 | 26.730 | 29.193 | 31.028 | 1.00 | 13.21 |
| ATOM | 3607 | CD1 | TRP | 517 | 24.028 | 29.338 | 33.442 | 1.00 | 10.52 |
| ATOM | 3608 | NE1 | TRP | 517 | 24.937 | 28.480 | 34.019 | 1.00 | 12.71 |
| ATOM | 3609 | CZ2 | TRP | 517 | 27.185 | 27.596 | 33.328 | 1.00 | 11.38 |
| ATOM | 3610 | CZ3 | TRP | 517 | 27.899 | 28.441 | 31.174 | 1.00 | 13.92 |
| ATOM | 3611 | CH2 | TRP | 517 | 28.112 | 27.657 | 32.315 | 1.00 | 11.19 |
| ATOM | 3612 | C | TRP | 517 | 24.571 | 33.092 | 30.402 | 1.00 | 13.68 |
| ATOM | 3613 | O | TRP | 517 | 25.360 | 32.937 | 29.473 | 1.00 | 13.23 |

TABLE A-continued

| | | | | | | | | |
|---|---|---|---|---|---|---|---|---|
| ATOM | 3614 | N | SER | 518 | 23.662 | 34.063 | 30.403 | 1.00 | 13.61 |
| ATOM | 3615 | CA | SER | 518 | 23.606 | 35.001 | 29.289 | 1.00 | 13.77 |
| ATOM | 3616 | CB | SER | 518 | 22.406 | 35.938 | 29.429 | 1.00 | 16.27 |
| ATOM | 3617 | OG | SER | 518 | 21.198 | 35.215 | 29.273 | 1.00 | 25.55 |
| ATOM | 3618 | C | SER | 518 | 24.908 | 35.812 | 29.306 | 1.00 | 13.80 |
| ATOM | 3619 | O | SER | 518 | 25.438 | 36.174 | 28.261 | 1.00 | 11.73 |
| ATOM | 3620 | N | LEU | 519 | 25.420 | 36.085 | 30.503 | 1.00 | 12.48 |
| ATOM | 3621 | CA | LEU | 519 | 26.664 | 36.835 | 30.642 | 1.00 | 13.86 |
| ATOM | 3622 | CB | LEU | 519 | 26.792 | 37.386 | 32.065 | 1.00 | 13.18 |
| ATOM | 3623 | CG | LEU | 519 | 25.820 | 38.521 | 32.408 | 1.00 | 17.32 |
| ATOM | 3624 | CD1 | LEU | 519 | 25.996 | 38.936 | 33.869 | 1.00 | 15.81 |
| ATOM | 3625 | CD2 | LEU | 519 | 26.082 | 39.706 | 31.497 | 1.00 | 18.32 |
| ATOM | 3626 | C | LEU | 519 | 27.854 | 35.936 | 30.315 | 1.00 | 14.53 |
| ATOM | 3627 | O | LEU | 519 | 28.833 | 36.374 | 29.701 | 1.00 | 13.21 |
| ATOM | 3628 | N | ARG | 520 | 27.763 | 34.680 | 30.740 | 1.00 | 12.53 |
| ATOM | 3629 | CA | ARG | 520 | 28.811 | 33.698 | 30.483 | 1.00 | 14.43 |
| ATOM | 3630 | CB | ARG | 520 | 28.415 | 32.342 | 31.080 | 1.00 | 12.24 |
| ATOM | 3631 | CG | ARG | 520 | 28.505 | 32.295 | 32.602 | 1.00 | 10.71 |
| ATOM | 3632 | CD | ARG | 520 | 29.933 | 32.016 | 33.047 | 1.00 | 11.25 |
| ATOM | 3633 | NE | ARG | 520 | 30.126 | 30.601 | 33.360 | 1.00 | 11.37 |
| ATOM | 3634 | CZ | ARG | 520 | 31.309 | 30.021 | 33.547 | 1.00 | 14.25 |
| ATOM | 3635 | NH1 | ARG | 520 | 31.364 | 28.728 | 33.843 | 1.00 | 11.46 |
| ATOM | 3636 | NH2 | ARG | 520 | 32.435 | 30.722 | 33.418 | 1.00 | 8.82 |
| ATOM | 3637 | C | ARG | 520 | 29.018 | 33.581 | 28.975 | 1.00 | 15.32 |
| ATOM | 3638 | O | ARG | 520 | 30.154 | 33.479 | 28.499 | 1.00 | 14.29 |
| ATOM | 3639 | N | LEU | 521 | 27.914 | 33.602 | 28.232 | 1.00 | 14.48 |
| ATOM | 3640 | CA | LEU | 521 | 27.964 | 33.534 | 26.775 | 1.00 | 15.03 |
| ATOM | 3641 | CB | LEU | 521 | 26.570 | 33.237 | 26.197 | 1.00 | 14.34 |
| ATOM | 3642 | CG | LEU | 521 | 26.464 | 33.320 | 24.663 | 1.00 | 17.99 |
| ATOM | 3643 | CD1 | LEU | 521 | 27.277 | 32.193 | 24.036 | 1.00 | 14.70 |
| ATOM | 3644 | CD2 | LEU | 521 | 25.003 | 33.225 | 24.221 | 1.00 | 19.69 |
| ATOM | 3645 | C | LEU | 521 | 28.463 | 34.862 | 26.195 | 1.00 | 15.14 |
| ATOM | 3646 | O | LEU | 521 | 29.426 | 34.901 | 25.433 | 1.00 | 16.02 |
| ATOM | 3647 | N | LYS | 522 | 27.800 | 35.952 | 26.564 | 1.00 | 15.84 |
| ATOM | 3648 | CA | LYS | 522 | 28.156 | 37.273 | 26.053 | 1.00 | 16.80 |
| ATOM | 3649 | CB | LYS | 522 | 27.257 | 38.340 | 26.691 | 1.00 | 20.30 |
| ATOM | 3650 | CG | LYS | 522 | 27.614 | 39.767 | 26.290 | 1.00 | 25.17 |
| ATOM | 3651 | CD | LYS | 522 | 26.641 | 40.777 | 26.885 | 1.00 | 25.79 |
| ATOM | 3652 | CE | LYS | 522 | 27.035 | 42.197 | 26.505 | 1.00 | 27.00 |
| ATOM | 3653 | NZ | LYS | 522 | 26.061 | 43.202 | 27.014 | 1.00 | 29.07 |
| ATOM | 3654 | C | LYS | 522 | 29.618 | 37.664 | 26.245 | 1.00 | 15.29 |
| ATOM | 3655 | O | LYS | 522 | 30.254 | 38.159 | 25.322 | 1.00 | 15.94 |
| ATOM | 3656 | N | TYR | 523 | 30.159 | 37.446 | 27.437 | 1.00 | 14.11 |
| ATOM | 3657 | CA | TYR | 523 | 31.545 | 37.823 | 27.689 | 1.00 | 14.39 |
| ATOM | 3658 | CB | TYR | 523 | 31.672 | 38.370 | 29.115 | 1.00 | 16.01 |
| ATOM | 3659 | CG | TYR | 523 | 30.969 | 39.699 | 29.274 | 1.00 | 19.66 |
| ATOM | 3660 | CD1 | TYR | 523 | 29.842 | 39.833 | 30.085 | 1.00 | 22.54 |
| ATOM | 3661 | CE1 | TYR | 523 | 29.159 | 41.054 | 30.173 | 1.00 | 24.34 |
| ATOM | 3662 | CD2 | TYR | 523 | 31.400 | 40.816 | 28.560 | 1.00 | 21.80 |
| ATOM | 3663 | CE2 | TYR | 523 | 30.730 | 42.029 | 28.641 | 1.00 | 24.56 |
| ATOM | 3664 | CZ | TYR | 523 | 29.611 | 42.142 | 29.444 | 1.00 | 24.26 |
| ATOM | 3665 | OH | TYR | 523 | 28.946 | 43.346 | 29.493 | 1.00 | 30.82 |
| ATOM | 3666 | C | TYR | 523 | 32.605 | 36.752 | 27.437 | 1.00 | 14.99 |
| ATOM | 3667 | O | TYR | 523 | 33.610 | 37.023 | 26.781 | 1.00 | 12.52 |
| ATOM | 3668 | N | GLN | 524 | 32.389 | 35.537 | 27.935 | 1.00 | 13.32 |
| ATOM | 3669 | CA | GLN | 524 | 33.382 | 34.470 | 27.751 | 1.00 | 12.95 |
| ATOM | 3670 | CB | GLN | 524 | 33.425 | 33.566 | 28.980 | 1.00 | 11.02 |
| ATOM | 3671 | CG | GLN | 524 | 33.970 | 34.205 | 30.230 | 1.00 | 12.37 |
| ATOM | 3672 | CD | GLN | 524 | 34.033 | 33.207 | 31.356 | 1.00 | 10.81 |
| ATOM | 3673 | OE1 | GLN | 524 | 33.043 | 32.974 | 32.049 | 1.00 | 12.38 |
| ATOM | 3674 | NE2 | GLN | 524 | 35.191 | 32.577 | 31.520 | 1.00 | 10.48 |
| ATOM | 3675 | C | GLN | 524 | 33.162 | 33.584 | 26.534 | 1.00 | 11.74 |
| ATOM | 3676 | O | GLN | 524 | 34.059 | 32.845 | 26.137 | 1.00 | 12.11 |
| ATOM | 3677 | N | GLY | 525 | 31.973 | 33.637 | 25.949 | 1.00 | 12.72 |
| ATOM | 3678 | CA | GLY | 525 | 31.709 | 32.785 | 24.804 | 1.00 | 13.19 |
| ATOM | 3679 | C | GLY | 525 | 31.674 | 31.328 | 25.237 | 1.00 | 13.82 |
| ATOM | 3680 | O | GLY | 525 | 32.180 | 30.444 | 24.540 | 1.00 | 12.99 |
| ATOM | 3681 | N | LEU | 526 | 31.087 | 31.074 | 26.403 | 1.00 | 12.01 |
| ATOM | 3682 | CA | LEU | 526 | 30.975 | 29.710 | 26.913 | 1.00 | 11.37 |
| ATOM | 3683 | CB | LEU | 526 | 31.581 | 29.598 | 28.317 | 1.00 | 11.79 |
| ATOM | 3684 | CG | LEU | 526 | 33.052 | 29.983 | 28.498 | 1.00 | 11.39 |
| ATOM | 3685 | CD1 | LEU | 526 | 33.439 | 29.852 | 29.978 | 1.00 | 12.76 |
| ATOM | 3686 | CD2 | LEU | 526 | 33.926 | 29.084 | 27.625 | 1.00 | 9.67 |
| ATOM | 3687 | C | LEU | 526 | 29.515 | 29.289 | 26.989 | 1.00 | 14.13 |
| ATOM | 3688 | O | LEU | 526 | 28.617 | 30.134 | 27.059 | 1.00 | 14.75 |
| ATOM | 3689 | N | CYS | 527 | 29.284 | 27.978 | 26.963 | 1.00 | 13.45 |
| ATOM | 3690 | CA | CYS | 527 | 27.939 | 27.429 | 27.078 | 1.00 | 15.05 |
| ATOM | 3691 | CB | CYS | 527 | 27.424 | 26.919 | 25.722 | 1.00 | 15.05 |
| ATOM | 3692 | SG | CYS | 527 | 28.474 | 25.702 | 24.876 | 1.00 | 19.74 |
| ATOM | 3693 | C | CYS | 527 | 27.978 | 26.287 | 28.091 | 1.00 | 15.94 |

TABLE A-continued

| | | | | | | | | | |
|---|---|---|---|---|---|---|---|---|---|
| ATOM | 3694 | O | CYS | 527 | 29.019 | 25.653 | 28.289 | 1.00 | 15.05 |
| ATOM | 3695 | N | PRO | 528 | 26.854 | 26.034 | 28.773 | 1.00 | 15.16 |
| ATOM | 3696 | CD | PRO | 528 | 25.587 | 26.794 | 28.757 | 1.00 | 16.64 |
| ATOM | 3697 | CA | PRO | 528 | 26.816 | 24.952 | 29.761 | 1.00 | 15.93 |
| ATOM | 3698 | CB | PRO | 528 | 25.579 | 25.291 | 30.588 | 1.00 | 15.52 |
| ATOM | 3699 | CG | PRO | 528 | 24.653 | 25.904 | 29.560 | 1.00 | 17.39 |
| ATOM | 3700 | C | PRO | 528 | 26.706 | 23.606 | 29.040 | 1.00 | 16.28 |
| ATOM | 3701 | O | PRO | 528 | 25.832 | 23.426 | 28.195 | 1.00 | 16.69 |
| ATOM | 3702 | N | PRO | 529 | 27.602 | 22.650 | 29.359 | 1.00 | 15.89 |
| ATOM | 3703 | CD | PRO | 529 | 28.620 | 22.713 | 30.423 | 1.00 | 17.16 |
| ATOM | 3704 | CA | PRO | 529 | 27.595 | 21.325 | 28.728 | 1.00 | 16.53 |
| ATOM | 3705 | CB | PRO | 529 | 28.813 | 20.646 | 29.347 | 1.00 | 16.86 |
| ATOM | 3706 | CG | PRO | 529 | 28.864 | 21.250 | 30.719 | 1.00 | 17.60 |
| ATOM | 3707 | C | PRO | 529 | 26.299 | 20.564 | 28.979 | 1.00 | 16.93 |
| ATOM | 3708 | O | PRO | 529 | 25.929 | 19.675 | 28.214 | 1.00 | 19.21 |
| ATOM | 3709 | N | VAL | 530 | 25.620 | 20.919 | 30.064 | 1.00 | 15.31 |
| ATOM | 3710 | CA | VAL | 530 | 24.345 | 20.309 | 30.421 | 1.00 | 18.95 |
| ATOM | 3711 | CB | VAL | 530 | 24.447 | 19.514 | 31.747 | 1.00 | 18.21 |
| ATOM | 3712 | CG1 | VAL | 530 | 23.057 | 19.197 | 32.277 | 1.00 | 20.68 |
| ATOM | 3713 | CG2 | VAL | 530 | 25.221 | 18.216 | 31.516 | 1.00 | 20.27 |
| ATOM | 3714 | C | VAL | 530 | 23.331 | 21.439 | 30.591 | 1.00 | 18.93 |
| ATOM | 3715 | O | VAL | 530 | 23.586 | 22.402 | 31.320 | 1.00 | 17.96 |
| ATOM | 3716 | N | PRO | 531 | 22.179 | 21.351 | 29.908 | 1.00 | 19.85 |
| ATOM | 3717 | CD | PRO | 531 | 21.701 | 20.311 | 28.982 | 1.00 | 21.08 |
| ATOM | 3718 | CA | PRO | 531 | 21.186 | 22.422 | 30.055 | 1.00 | 20.04 |
| ATOM | 3719 | CB | PRO | 531 | 20.019 | 21.940 | 29.186 | 1.00 | 23.88 |
| ATOM | 3720 | CG | PRO | 531 | 20.207 | 20.436 | 29.134 | 1.00 | 24.49 |
| ATOM | 3721 | C | PRO | 531 | 20.806 | 22.624 | 31.519 | 1.00 | 20.47 |
| ATOM | 3722 | O | PRO | 531 | 20.590 | 21.660 | 32.258 | 1.00 | 19.22 |
| ATOM | 3723 | N | ARG | 532 | 20.748 | 23.880 | 31.946 | 1.00 | 17.94 |
| ATOM | 3724 | CA | ARG | 532 | 20.408 | 24.173 | 33.331 | 1.00 | 19.58 |
| ATOM | 3725 | CB | ARG | 532 | 20.850 | 25.597 | 33.698 | 1.00 | 17.12 |
| ATOM | 3726 | CG | ARG | 532 | 22.203 | 26.006 | 33.109 | 1.00 | 17.15 |
| ATOM | 3727 | CD | ARG | 532 | 23.261 | 24.916 | 33.259 | 1.00 | 14.33 |
| ATOM | 3728 | NE | ARG | 532 | 23.625 | 24.670 | 34.650 | 1.00 | 16.72 |
| ATOM | 3729 | CZ | ARG | 532 | 23.756 | 23.457 | 35.175 | 1.00 | 18.54 |
| ATOM | 3730 | NH1 | ARG | 532 | 23.548 | 22.382 | 34.418 | 1.00 | 18.00 |
| ATOM | 3731 | NH2 | ARG | 532 | 24.100 | 23.316 | 36.447 | 1.00 | 16.39 |
| ATOM | 3732 | C | ARG | 532 | 18.903 | 24.018 | 33.538 | 1.00 | 20.97 |
| ATOM | 3733 | O | ARG | 532 | 18.125 | 24.148 | 32.593 | 1.00 | 21.91 |
| ATOM | 3734 | N | THR | 533 | 18.502 | 23.735 | 34.773 | 1.00 | 21.56 |
| ATOM | 3735 | CA | THR | 533 | 17.089 | 23.560 | 35.099 | 1.00 | 23.91 |
| ATOM | 3736 | CB | THR | 533 | 16.743 | 22.075 | 35.337 | 1.00 | 24.39 |
| ATOM | 3737 | OG1 | THR | 533 | 17.593 | 21.542 | 36.363 | 1.00 | 26.32 |
| ATOM | 3738 | CG2 | THR | 533 | 16.930 | 21.273 | 34.054 | 1.00 | 26.00 |
| ATOM | 3739 | C | THR | 533 | 16.734 | 24.342 | 36.354 | 1.00 | 24.49 |
| ATOM | 3740 | O | THR | 533 | 17.622 | 24.792 | 37.088 | 1.00 | 22.75 |
| ATOM | 3741 | N | GLN | 534 | 15.436 | 24.494 | 36.601 | 1.00 | 25.56 |
| ATOM | 3742 | CA | GLN | 534 | 14.963 | 25.227 | 37.769 | 1.00 | 27.46 |
| ATOM | 3743 | CB | GLN | 534 | 13.429 | 25.173 | 37.845 | 1.00 | 29.98 |
| ATOM | 3744 | CG | GLN | 534 | 12.834 | 26.077 | 38.917 | 1.00 | 34.85 |
| ATOM | 3745 | CD | GLN | 534 | 12.498 | 25.332 | 40.196 | 1.00 | 38.40 |
| ATOM | 3746 | OE1 | GLN | 534 | 13.144 | 24.341 | 40.542 | 1.00 | 39.55 |
| ATOM | 3747 | NE2 | GLN | 534 | 11.487 | 25.815 | 40.914 | 1.00 | 40.66 |
| ATOM | 3748 | C | GLN | 534 | 15.589 | 24.628 | 39.023 | 1.00 | 26.85 |
| ATOM | 3749 | O | GLN | 534 | 15.630 | 23.410 | 39.195 | 1.00 | 28.91 |
| ATOM | 3750 | N | GLY | 535 | 16.088 | 25.486 | 39.900 | 1.00 | 26.04 |
| ATOM | 3751 | CA | GLY | 535 | 16.722 | 24.988 | 41.103 | 1.00 | 22.99 |
| ATOM | 3752 | C | GLY | 535 | 18.230 | 25.145 | 41.032 | 1.00 | 20.56 |
| ATOM | 3753 | O | GLY | 535 | 18.893 | 25.172 | 42.062 | 1.00 | 21.12 |
| ATOM | 3754 | N | ASP | 536 | 18.783 | 25.236 | 39.824 | 1.00 | 19.34 |
| ATOM | 3755 | CA | ASP | 536 | 20.229 | 25.412 | 39.690 | 1.00 | 18.42 |
| ATOM | 3756 | CB | ASP | 536 | 20.710 | 25.126 | 38.262 | 1.00 | 18.23 |
| ATOM | 3757 | CG | ASP | 536 | 20.693 | 23.647 | 37.917 | 1.00 | 17.73 |
| ATOM | 3758 | OD1 | ASP | 536 | 20.885 | 22.814 | 38.829 | 1.00 | 16.38 |
| ATOM | 3759 | OD2 | ASP | 536 | 20.509 | 23.326 | 36.726 | 1.00 | 18.51 |
| ATOM | 3760 | C | ASP | 536 | 20.617 | 26.845 | 40.039 | 1.00 | 17.25 |
| ATOM | 3761 | O | ASP | 536 | 19.893 | 27.786 | 39.722 | 1.00 | 17.90 |
| ATOM | 3762 | N | PHE | 537 | 21.761 | 26.996 | 40.694 | 1.00 | 15.41 |
| ATOM | 3763 | CA | PHE | 537 | 22.285 | 28.309 | 41.069 | 1.00 | 15.10 |
| ATOM | 3764 | CB | PHE | 537 | 21.914 | 28.654 | 42.511 | 1.00 | 13.69 |
| ATOM | 3765 | CG | PHE | 537 | 22.344 | 30.031 | 42.934 | 1.00 | 14.67 |
| ATOM | 3766 | CD1 | PHE | 537 | 21.970 | 31.150 | 42.190 | 1.00 | 14.51 |
| ATOM | 3767 | CD2 | PHE | 537 | 23.127 | 30.211 | 44.073 | 1.00 | 14.42 |
| ATOM | 3768 | CE1 | PHE | 537 | 22.372 | 32.434 | 42.576 | 1.00 | 16.76 |
| ATOM | 3769 | CE2 | PHE | 537 | 23.535 | 31.490 | 44.469 | 1.00 | 16.13 |
| ATOM | 3770 | CZ | PHE | 537 | 23.155 | 32.602 | 43.717 | 1.00 | 16.55 |
| ATOM | 3771 | C | PHE | 537 | 23.798 | 28.188 | 40.929 | 1.00 | 14.34 |
| ATOM | 3772 | O | PHE | 537 | 24.534 | 28.107 | 41.910 | 1.00 | 11.59 |
| ATOM | 3773 | N | ASP | 538 | 24.246 | 28.160 | 39.683 | 1.00 | 13.08 |

TABLE A-continued

| ATOM | 3774 | CA | ASP | 538 | 25.656 | 28.013 | 39.380 | 1.00 | 12.91 |
|---|---|---|---|---|---|---|---|---|---|
| ATOM | 3775 | CB | ASP | 538 | 25.812 | 27.915 | 37.858 | 1.00 | 14.42 |
| ATOM | 3776 | CG | ASP | 538 | 24.984 | 26.761 | 37.275 | 1.00 | 13.98 |
| ATOM | 3777 | OD1 | ASP | 538 | 24.869 | 25.725 | 37.959 | 1.00 | 15.77 |
| ATOM | 3778 | OD2 | ASP | 538 | 24.456 | 26.875 | 36.148 | 1.00 | 16.17 |
| ATOM | 3779 | C | ASP | 538 | 26.546 | 29.093 | 40.005 | 1.00 | 13.57 |
| ATOM | 3780 | O | ASP | 538 | 27.680 | 28.814 | 40.391 | 1.00 | 14.25 |
| ATOM | 3781 | N | PRO | 539 | 26.049 | 30.336 | 40.125 | 1.00 | 12.45 |
| ATOM | 3782 | CD | PRO | 539 | 24.833 | 30.944 | 39.554 | 1.00 | 12.63 |
| ATOM | 3783 | CA | PRO | 539 | 26.903 | 31.362 | 40.738 | 1.00 | 14.07 |
| ATOM | 3784 | CB | PRO | 539 | 25.998 | 32.596 | 40.760 | 1.00 | 13.43 |
| ATOM | 3785 | CG | PRO | 539 | 25.203 | 32.428 | 39.495 | 1.00 | 14.83 |
| ATOM | 3786 | C | PRO | 539 | 27.318 | 30.945 | 42.149 | 1.00 | 14.32 |
| ATOM | 3787 | O | PRO | 539 | 28.405 | 31.290 | 42.620 | 1.00 | 15.96 |
| ATOM | 3788 | N | GLY | 540 | 26.443 | 30.201 | 42.818 | 1.00 | 13.56 |
| ATOM | 3789 | CA | GLY | 540 | 26.726 | 29.759 | 44.173 | 1.00 | 13.06 |
| ATOM | 3790 | C | GLY | 540 | 27.880 | 28.779 | 44.262 | 1.00 | 14.35 |
| ATOM | 3791 | O | GLY | 540 | 28.410 | 28.530 | 45.350 | 1.00 | 14.78 |
| ATOM | 3792 | N | ALA | 541 | 28.278 | 28.233 | 43.116 | 1.00 | 13.27 |
| ATOM | 3793 | CA | ALA | 541 | 29.374 | 27.268 | 43.057 | 1.00 | 13.82 |
| ATOM | 3794 | CB | ALA | 541 | 29.142 | 26.282 | 41.908 | 1.00 | 13.95 |
| ATOM | 3795 | C | ALA | 541 | 30.736 | 27.948 | 42.899 | 1.00 | 14.23 |
| ATOM | 3796 | O | ALA | 541 | 31.755 | 27.277 | 42.723 | 1.00 | 14.48 |
| ATOM | 3797 | N | LYS | 542 | 30.744 | 29.278 | 42.950 | 1.00 | 13.31 |
| ATOM | 3798 | CA | LYS | 542 | 31.981 | 30.051 | 42.845 | 1.00 | 13.43 |
| ATOM | 3799 | CB | LYS | 542 | 31.854 | 31.131 | 41.758 | 1.00 | 11.46 |
| ATOM | 3800 | CG | LYS | 542 | 33.080 | 32.052 | 41.629 | 1.00 | 11.83 |
| ATOM | 3801 | CD | LYS | 542 | 34.363 | 31.258 | 41.356 | 1.00 | 11.07 |
| ATOM | 3802 | CE | LYS | 542 | 35.594 | 32.152 | 41.434 | 1.00 | 13.88 |
| ATOM | 3803 | NZ | LYS | 542 | 36.866 | 31.380 | 41.387 | 1.00 | 13.39 |
| ATOM | 3804 | C | LYS | 542 | 32.195 | 30.690 | 44.215 | 1.00 | 14.23 |
| ATOM | 3805 | O | LYS | 542 | 31.363 | 31.472 | 44.678 | 1.00 | 13.83 |
| ATOM | 3806 | N | PHE | 543 | 33.309 | 30.346 | 44.857 | 1.00 | 14.52 |
| ATOM | 3807 | CA | PHE | 543 | 33.640 | 30.842 | 46.197 | 1.00 | 15.65 |
| ATOM | 3808 | CB | PHE | 543 | 35.156 | 30.803 | 46.422 | 1.00 | 16.34 |
| ATOM | 3809 | CG | PHE | 543 | 35.581 | 31.353 | 47.760 | 1.00 | 16.35 |
| ATOM | 3810 | CD1 | PHE | 543 | 35.489 | 30.574 | 48.909 | 1.00 | 18.40 |
| ATOM | 3811 | CD2 | PHE | 543 | 36.047 | 32.661 | 47.875 | 1.00 | 19.53 |
| ATOM | 3812 | CE1 | PHE | 543 | 35.858 | 31.090 | 50.161 | 1.00 | 18.32 |
| ATOM | 3813 | CE2 | PHE | 543 | 36.418 | 33.188 | 49.120 | 1.00 | 18.19 |
| ATOM | 3814 | CZ | PHE | 543 | 36.323 | 32.399 | 50.263 | 1.00 | 18.52 |
| ATOM | 3815 | C | PHE | 543 | 33.159 | 32.242 | 46.577 | 1.00 | 16.50 |
| ATOM | 3816 | O | PHE | 543 | 32.411 | 32.411 | 47.540 | 1.00 | 17.35 |
| ATOM | 3817 | N | HIS | 544 | 33.603 | 33.242 | 45.822 | 1.00 | 13.72 |
| ATOM | 3818 | CA | HIS | 544 | 33.284 | 34.635 | 46.119 | 1.00 | 14.78 |
| ATOM | 3819 | CB | HIS | 544 | 34.006 | 35.543 | 45.116 | 1.00 | 13.88 |
| ATOM | 3820 | CG | HIS | 544 | 35.484 | 35.298 | 45.050 | 1.00 | 13.02 |
| ATOM | 3821 | CD2 | HIS | 544 | 36.536 | 36.070 | 45.408 | 1.00 | 10.61 |
| ATOM | 3822 | ND1 | HIS | 544 | 36.017 | 34.106 | 44.606 | 1.00 | 14.71 |
| ATOM | 3823 | CE1 | HIS | 544 | 37.335 | 34.155 | 44.693 | 1.00 | 13.70 |
| ATOM | 3824 | NE2 | HIS | 544 | 37.678 | 35.335 | 45.176 | 1.00 | 13.80 |
| ATOM | 3825 | C | HIS | 544 | 31.808 | 35.016 | 46.213 | 1.00 | 14.84 |
| ATOM | 3826 | O | HIS | 544 | 31.470 | 36.034 | 46.826 | 1.00 | 14.80 |
| ATOM | 3827 | N | ILE | 545 | 30.930 | 34.212 | 45.622 | 1.00 | 14.32 |
| ATOM | 3828 | CA | ILE | 545 | 29.504 | 34.511 | 45.670 | 1.00 | 13.72 |
| ATOM | 3829 | CB | ILE | 545 | 28.733 | 33.701 | 44.598 | 1.00 | 14.44 |
| ATOM | 3830 | CG2 | ILE | 545 | 27.234 | 33.908 | 44.749 | 1.00 | 12.67 |
| ATOM | 3831 | CG1 | ILE | 545 | 29.190 | 34.138 | 43.199 | 1.00 | 16.16 |
| ATOM | 3832 | CD1 | ILE | 545 | 29.032 | 35.621 | 42.922 | 1.00 | 16.96 |
| ATOM | 3833 | C | ILE | 545 | 28.954 | 34.249 | 47.079 | 1.00 | 14.60 |
| ATOM | 3834 | O | ILE | 545 | 28.518 | 35.182 | 47.757 | 1.00 | 13.03 |
| ATOM | 3835 | N | PRO | 546 | 28.976 | 32.986 | 47.549 | 1.00 | 15.66 |
| ATOM | 3836 | CD | PRO | 546 | 29.355 | 31.713 | 46.909 | 1.00 | 13.25 |
| ATOM | 3837 | CA | PRO | 546 | 28.457 | 32.750 | 48.903 | 1.00 | 15.17 |
| ATOM | 3838 | CB | PRO | 546 | 28.453 | 31.222 | 49.014 | 1.00 | 16.53 |
| ATOM | 3839 | CG | PRO | 546 | 29.579 | 30.812 | 48.111 | 1.00 | 17.51 |
| ATOM | 3840 | C | PRO | 546 | 29.305 | 33.419 | 49.990 | 1.00 | 16.68 |
| ATOM | 3841 | O | PRO | 546 | 28.799 | 33.732 | 51.074 | 1.00 | 15.08 |
| ATOM | 3842 | N | SER | 547 | 30.589 | 33.641 | 49.701 | 1.00 | 13.81 |
| ATOM | 3843 | CA | SER | 547 | 31.488 | 34.284 | 50.659 | 1.00 | 15.60 |
| ATOM | 3844 | CB | SER | 547 | 32.947 | 33.918 | 50.362 | 1.00 | 18.79 |
| ATOM | 3845 | OG | SER | 547 | 33.183 | 32.536 | 50.565 | 1.00 | 22.02 |
| ATOM | 3846 | C | SER | 547 | 31.342 | 35.803 | 50.646 | 1.00 | 13.58 |
| ATOM | 3847 | O | SER | 547 | 31.965 | 36.499 | 51.443 | 1.00 | 13.34 |
| ATOM | 3848 | N | SER | 548 | 30.529 | 36.312 | 49.727 | 1.00 | 13.46 |
| ATOM | 3849 | CA | SER | 548 | 30.288 | 37.751 | 49.617 | 1.00 | 13.96 |
| ATOM | 3850 | CB | SER | 548 | 29.427 | 38.231 | 50.791 | 1.00 | 14.80 |
| ATOM | 3851 | OG | SER | 548 | 28.929 | 39.544 | 50.566 | 1.00 | 14.76 |
| ATOM | 3852 | C | SER | 548 | 31.571 | 38.587 | 49.542 | 1.00 | 15.62 |
| ATOM | 3853 | O | SER | 548 | 31.743 | 39.553 | 50.288 | 1.00 | 15.61 |

TABLE A-continued

| | | | | | | | | |
|---|---|---|---|---|---|---|---|---|
| ATOM | 3854 | N | VAL | 549 | 32.464 | 38.201 | 48.637 | 1.00 14.22 |
| ATOM | 3855 | CA | VAL | 549 | 33.718 | 38.914 | 48.413 | 1.00 14.31 |
| ATOM | 3856 | CB | VAL | 549 | 34.936 | 37.957 | 48.426 | 1.00 14.24 |
| ATOM | 3857 | CG1 | VAL | 549 | 36.200 | 38.716 | 48.029 | 1.00 15.66 |
| ATOM | 3858 | CG2 | VAL | 549 | 35.105 | 37.337 | 49.813 | 1.00 15.47 |
| ATOM | 3859 | C | VAL | 549 | 33.611 | 39.538 | 47.023 | 1.00 13.23 |
| ATOM | 3860 | O | VAL | 549 | 33.448 | 38.826 | 46.034 | 1.00 14.20 |
| ATOM | 3861 | N | PRO | 550 | 33.680 | 40.877 | 46.931 | 1.00 13.00 |
| ATOM | 3862 | CD | PRO | 550 | 33.789 | 41.840 | 48.040 | 1.00 12.51 |
| ATOM | 3863 | CA | PRO | 550 | 33.588 | 41.572 | 45.637 | 1.00 13.72 |
| ATOM | 3864 | CB | PRO | 550 | 33.870 | 43.026 | 46.007 | 1.00 12.92 |
| ATOM | 3865 | CG | PRO | 550 | 33.282 | 43.120 | 47.399 | 1.00 13.93 |
| ATOM | 3866 | C | PRO | 550 | 34.597 | 41.006 | 44.640 | 1.00 13.40 |
| ATOM | 3867 | O | PRO | 550 | 35.694 | 40.602 | 45.027 | 1.00 12.68 |
| ATOM | 3868 | N | TYR | 551 | 34.238 | 40.996 | 43.357 | 1.00 12.51 |
| ATOM | 3869 | CA | TYR | 551 | 35.111 | 40.419 | 42.337 | 1.00 11.74 |
| ATOM | 3870 | CB | TYR | 551 | 34.343 | 39.339 | 41.565 | 1.00 12.26 |
| ATOM | 3871 | CG | TYR | 551 | 35.216 | 38.181 | 41.146 | 1.00 11.10 |
| ATOM | 3872 | CD1 | TYR | 551 | 35.589 | 37.201 | 42.069 | 1.00 12.21 |
| ATOM | 3873 | CE1 | TYR | 551 | 36.445 | 36.163 | 41.716 | 1.00 11.38 |
| ATOM | 3874 | CD2 | TYR | 551 | 35.717 | 38.092 | 39.849 | 1.00 10.70 |
| ATOM | 3875 | CE2 | TYR | 551 | 36.578 | 37.052 | 39.479 | 1.00 11.88 |
| ATOM | 3876 | CZ | TYR | 551 | 36.936 | 36.095 | 40.422 | 1.00 12.73 |
| ATOM | 3877 | OH | TYR | 551 | 37.789 | 35.078 | 40.077 | 1.00 12.21 |
| ATOM | 3878 | C | TYR | 551 | 35.758 | 41.362 | 41.316 | 1.00 12.92 |
| ATOM | 3879 | O | TYR | 551 | 36.772 | 41.009 | 40.713 | 1.00 12.28 |
| ATOM | 3880 | N | ILE | 552 | 35.182 | 42.543 | 41.106 | 1.00 10.57 |
| ATOM | 3881 | CA | ILE | 552 | 35.729 | 43.474 | 40.123 | 1.00 10.70 |
| ATOM | 3882 | CB | ILE | 552 | 34.866 | 44.760 | 40.042 | 1.00 10.46 |
| ATOM | 3883 | CG2 | ILE | 552 | 35.175 | 45.681 | 41.219 | 1.00 10.81 |
| ATOM | 3884 | CG1 | ILE | 552 | 35.111 | 45.464 | 38.706 | 1.00 11.02 |
| ATOM | 3885 | CD1 | ILE | 552 | 34.654 | 44.656 | 37.494 | 1.00 11.29 |
| ATOM | 3886 | C | ILE | 552 | 37.195 | 43.826 | 40.404 | 1.00 11.68 |
| ATOM | 3887 | O | ILE | 552 | 37.940 | 44.198 | 39.499 | 1.00 12.19 |
| ATOM | 3888 | N | ARG | 553 | 37.607 | 43.692 | 41.660 | 1.00 11.17 |
| ATOM | 3889 | CA | ARG | 553 | 38.989 | 43.952 | 42.055 | 1.00 10.89 |
| ATOM | 3890 | CB | ARG | 553 | 39.156 | 43.668 | 43.549 | 1.00 11.30 |
| ATOM | 3891 | CG | ARG | 553 | 38.686 | 42.265 | 43.958 | 1.00 13.00 |
| ATOM | 3892 | CD | ARG | 553 | 38.704 | 42.074 | 45.474 | 1.00 13.72 |
| ATOM | 3893 | NE | ARG | 553 | 37.886 | 43.088 | 46.134 | 1.00 10.87 |
| ATOM | 3894 | CZ | ARG | 553 | 37.634 | 43.123 | 47.439 | 1.00 13.84 |
| ATOM | 3895 | NH1 | ARG | 553 | 38.132 | 42.196 | 48.247 | 1.00 11.15 |
| ATOM | 3896 | NH2 | ARG | 553 | 36.889 | 44.100 | 47.941 | 1.00 13.85 |
| ATOM | 3897 | C | ARG | 553 | 39.971 | 43.071 | 41.260 | 1.00 12.16 |
| ATOM | 3898 | O | ARG | 553 | 41.105 | 43.478 | 40.990 | 1.00 11.49 |
| ATOM | 3899 | N | TYR | 554 | 39.539 | 41.871 | 40.881 | 1.00 10.69 |
| ATOM | 3900 | CA | TYR | 554 | 40.408 | 40.965 | 40.130 | 1.00 12.89 |
| ATOM | 3901 | CB | TYR | 554 | 39.882 | 39.525 | 40.215 | 1.00 10.20 |
| ATOM | 3902 | CG | TYR | 554 | 39.814 | 39.009 | 41.640 | 1.00 12.03 |
| ATOM | 3903 | CD1 | TYR | 554 | 38.586 | 38.818 | 42.274 | 1.00 14.17 |
| ATOM | 3904 | CE1 | TYR | 554 | 38.515 | 38.381 | 43.599 | 1.00 13.54 |
| ATOM | 3905 | CD2 | TYR | 554 | 40.978 | 38.750 | 42.367 | 1.00 12.66 |
| ATOM | 3906 | CE2 | TYR | 554 | 40.920 | 38.317 | 43.695 | 1.00 13.05 |
| ATOM | 3907 | CZ | TYR | 554 | 39.683 | 38.133 | 44.302 | 1.00 13.70 |
| ATOM | 3908 | OH | TYR | 554 | 39.603 | 37.697 | 45.610 | 1.00 13.05 |
| ATOM | 3909 | C | TYR | 554 | 40.558 | 41.394 | 38.672 | 1.00 12.72 |
| ATOM | 3910 | O | TYR | 554 | 41.599 | 41.152 | 38.051 | 1.00 12.24 |
| ATOM | 3911 | N | PHE | 555 | 39.515 | 42.016 | 38.128 | 1.00 10.68 |
| ATOM | 3912 | CA | PHE | 555 | 39.550 | 42.509 | 36.750 | 1.00 11.93 |
| ATOM | 3913 | CB | PHE | 555 | 38.154 | 42.980 | 36.317 | 1.00 11.21 |
| ATOM | 3914 | CG | PHE | 555 | 38.125 | 43.646 | 34.968 | 1.00 14.00 |
| ATOM | 3915 | CD1 | PHE | 555 | 38.050 | 42.892 | 33.801 | 1.00 14.57 |
| ATOM | 3916 | CD2 | PHE | 555 | 38.193 | 45.031 | 34.867 | 1.00 15.09 |
| ATOM | 3917 | CE1 | PHE | 555 | 38.043 | 43.510 | 32.549 | 1.00 16.67 |
| ATOM | 3918 | CE2 | PHE | 555 | 38.189 | 45.660 | 33.619 | 1.00 17.16 |
| ATOM | 3919 | CZ | PHE | 555 | 38.113 | 44.899 | 32.458 | 1.00 17.19 |
| ATOM | 3920 | C | PHE | 555 | 40.527 | 43.689 | 36.735 | 1.00 13.11 |
| ATOM | 3921 | O | PHE | 555 | 41.400 | 43.779 | 35.872 | 1.00 13.19 |
| ATOM | 3922 | N | VAL | 556 | 40.366 | 44.592 | 37.698 | 1.00 10.88 |
| ATOM | 3923 | CA | VAL | 556 | 41.239 | 45.753 | 37.809 | 1.00 11.92 |
| ATOM | 3924 | CB | VAL | 556 | 40.830 | 46.642 | 39.004 | 1.00 11.44 |
| ATOM | 3925 | CG1 | VAL | 556 | 41.847 | 47.767 | 39.202 | 1.00 13.68 |
| ATOM | 3926 | CG2 | VAL | 556 | 39.433 | 47.226 | 38.757 | 1.00 12.64 |
| ATOM | 3927 | C | VAL | 556 | 42.683 | 45.276 | 37.989 | 1.00 12.43 |
| ATOM | 3928 | O | VAL | 556 | 43.590 | 45.746 | 37.308 | 1.00 12.45 |
| ATOM | 3929 | N | SER | 557 | 42.882 | 44.325 | 38.895 | 1.00 12.83 |
| ATOM | 3930 | CA | SER | 557 | 44.211 | 43.781 | 39.156 | 1.00 13.38 |
| ATOM | 3931 | CB | SER | 557 | 44.124 | 42.658 | 40.195 | 1.00 14.45 |
| ATOM | 3932 | OG | SER | 557 | 45.366 | 41.981 | 40.321 | 1.00 15.47 |
| ATOM | 3933 | C | SER | 557 | 44.915 | 43.252 | 37.908 | 1.00 14.80 |

TABLE A-continued

| | | | | | | | | |
|---|---|---|---|---|---|---|---|---|
| ATOM | 3934 | O | SER | 557 | 46.080 | 43.567 | 37.659 | 1.00 | 13.56 |
| ATOM | 3935 | N | PHE | 558 | 44.220 | 42.438 | 37.123 | 1.00 | 13.85 |
| ATOM | 3936 | CA | PHE | 558 | 44.843 | 41.878 | 35.936 | 1.00 | 16.13 |
| ATOM | 3937 | CB | PHE | 558 | 43.930 | 40.813 | 35.311 | 1.00 | 14.35 |
| ATOM | 3938 | CG | PHE | 558 | 44.109 | 39.446 | 35.921 | 1.00 | 12.86 |
| ATOM | 3939 | CD1 | PHE | 558 | 44.081 | 39.279 | 37.304 | 1.00 | 14.64 |
| ATOM | 3940 | CD2 | PHE | 558 | 44.352 | 38.336 | 35.116 | 1.00 | 12.97 |
| ATOM | 3941 | CE1 | PHE | 558 | 44.301 | 38.021 | 37.881 | 1.00 | 14.77 |
| ATOM | 3942 | CE2 | PHE | 558 | 44.570 | 37.081 | 35.674 | 1.00 | 14.28 |
| ATOM | 3943 | CZ | PHE | 558 | 44.546 | 36.921 | 37.061 | 1.00 | 14.43 |
| ATOM | 3944 | C | PHE | 558 | 45.265 | 42.937 | 34.923 | 1.00 | 17.21 |
| ATOM | 3945 | O | PHE | 558 | 46.248 | 42.757 | 34.210 | 1.00 | 18.29 |
| ATOM | 3946 | N | ILE | 559 | 44.545 | 44.052 | 34.875 | 1.00 | 17.72 |
| ATOM | 3947 | CA | ILE | 559 | 44.907 | 45.124 | 33.956 | 1.00 | 17.85 |
| ATOM | 3948 | CB | ILE | 559 | 43.754 | 46.148 | 33.780 | 1.00 | 19.20 |
| ATOM | 3949 | CG2 | ILE | 559 | 44.260 | 47.363 | 33.011 | 1.00 | 19.44 |
| ATOM | 3950 | CG1 | ILE | 559 | 42.564 | 45.502 | 33.064 | 1.00 | 21.05 |
| ATOM | 3951 | CD1 | ILE | 559 | 42.807 | 45.211 | 31.605 | 1.00 | 22.66 |
| ATOM | 3952 | C | ILE | 559 | 46.120 | 45.891 | 34.491 | 1.00 | 16.91 |
| ATOM | 3953 | O | ILE | 559 | 47.155 | 45.991 | 33.826 | 1.00 | 18.09 |
| ATOM | 3954 | N | ILE | 560 | 45.991 | 46.417 | 35.704 | 1.00 | 15.99 |
| ATOM | 3955 | CA | ILE | 560 | 47.056 | 47.221 | 36.294 | 1.00 | 14.87 |
| ATOM | 3956 | CB | ILE | 560 | 46.560 | 47.971 | 37.563 | 1.00 | 15.25 |
| ATOM | 3957 | CG2 | ILE | 560 | 45.253 | 48.708 | 37.249 | 1.00 | 13.63 |
| ATOM | 3958 | CG1 | ILE | 560 | 46.366 | 46.996 | 38.725 | 1.00 | 14.28 |
| ATOM | 3959 | CD1 | ILE | 560 | 45.970 | 47.678 | 40.039 | 1.00 | 14.84 |
| ATOM | 3960 | C | ILE | 560 | 48.337 | 46.467 | 36.639 | 1.00 | 16.49 |
| ATOM | 3961 | O | ILE | 560 | 49.415 | 47.060 | 36.666 | 1.00 | 14.18 |
| ATOM | 3962 | N | GLN | 561 | 48.245 | 45.167 | 36.900 | 1.00 | 15.61 |
| ATOM | 3963 | CA | GLN | 561 | 49.461 | 44.443 | 37.233 | 1.00 | 16.41 |
| ATOM | 3964 | CB | GLN | 561 | 49.152 | 43.001 | 37.663 | 1.00 | 15.73 |
| ATOM | 3965 | CG | GLN | 561 | 48.557 | 42.090 | 36.604 | 1.00 | 14.21 |
| ATOM | 3966 | CD | GLN | 561 | 48.239 | 40.715 | 37.171 | 1.00 | 17.73 |
| ATOM | 3967 | OE1 | GLN | 561 | 48.834 | 39.715 | 36.771 | 1.00 | 16.09 |
| ATOM | 3968 | NE2 | GLN | 561 | 47.300 | 40.664 | 38.121 | 1.00 | 14.54 |
| ATOM | 3969 | C | GLN | 561 | 50.450 | 44.476 | 36.064 | 1.00 | 16.86 |
| ATOM | 3970 | O | GLN | 561 | 51.664 | 44.434 | 36.273 | 1.00 | 16.40 |
| ATOM | 3971 | N | PHE | 562 | 49.939 | 44.565 | 34.836 | 1.00 | 15.77 |
| ATOM | 3972 | CA | PHE | 562 | 50.824 | 44.631 | 33.684 | 1.00 | 16.79 |
| ATOM | 3973 | CB | PHE | 562 | 50.096 | 44.217 | 32.399 | 1.00 | 15.11 |
| ATOM | 3974 | CG | PHE | 562 | 49.994 | 42.729 | 32.236 | 1.00 | 16.63 |
| ATOM | 3975 | CD1 | PHE | 562 | 48.911 | 42.029 | 32.757 | 1.00 | 14.63 |
| ATOM | 3976 | CD2 | PHE | 562 | 51.037 | 42.012 | 31.648 | 1.00 | 18.81 |
| ATOM | 3977 | CE1 | PHE | 562 | 48.865 | 40.637 | 32.705 | 1.00 | 18.62 |
| ATOM | 3978 | CE2 | PHE | 562 | 51.006 | 40.615 | 31.589 | 1.00 | 18.29 |
| ATOM | 3979 | CZ | PHE | 562 | 49.915 | 39.927 | 32.121 | 1.00 | 17.80 |
| ATOM | 3980 | C | PHE | 562 | 51.385 | 46.042 | 33.579 | 1.00 | 17.19 |
| ATOM | 3981 | O | PHE | 562 | 52.517 | 46.238 | 33.143 | 1.00 | 15.79 |
| ATOM | 3982 | N | GLN | 563 | 50.592 | 47.022 | 33.998 | 1.00 | 16.85 |
| ATOM | 3983 | CA | GLN | 563 | 51.043 | 48.407 | 34.001 | 1.00 | 18.71 |
| ATOM | 3984 | CB | GLN | 563 | 49.909 | 49.347 | 34.418 | 1.00 | 18.72 |
| ATOM | 3985 | CG | GLN | 563 | 48.890 | 49.651 | 33.335 | 1.00 | 16.23 |
| ATOM | 3986 | CD | GLN | 563 | 47.819 | 50.607 | 33.825 | 1.00 | 18.40 |
| ATOM | 3987 | OE1 | GLN | 563 | 46.777 | 50.188 | 34.326 | 1.00 | 16.56 |
| ATOM | 3988 | NE2 | GLN | 563 | 48.084 | 51.908 | 33.700 | 1.00 | 15.19 |
| ATOM | 3989 | C | GLN | 563 | 52.184 | 48.528 | 35.011 | 1.00 | 18.91 |
| ATOM | 3990 | O | GLN | 563 | 53.159 | 49.237 | 34.773 | 1.00 | 21.62 |
| ATOM | 3991 | N | PHE | 564 | 52.048 | 47.846 | 36.148 | 1.00 | 17.60 |
| ATOM | 3992 | CA | PHE | 564 | 53.082 | 47.879 | 37.179 | 1.00 | 17.70 |
| ATOM | 3993 | CB | PHE | 564 | 52.576 | 47.237 | 38.479 | 1.00 | 16.56 |
| ATOM | 3994 | CG | PHE | 564 | 51.412 | 47.961 | 39.114 | 1.00 | 16.88 |
| ATOM | 3995 | CD1 | PHE | 564 | 51.009 | 49.216 | 38.655 | 1.00 | 17.26 |
| ATOM | 3996 | CD2 | PHE | 564 | 50.732 | 47.393 | 40.193 | 1.00 | 17.51 |
| ATOM | 3997 | CE1 | PHE | 564 | 49.948 | 49.896 | 39.262 | 1.00 | 17.30 |
| ATOM | 3998 | CE2 | PHE | 564 | 49.668 | 48.065 | 40.811 | 1.00 | 16.87 |
| ATOM | 3999 | CZ | PHE | 564 | 49.275 | 49.316 | 40.346 | 1.00 | 17.82 |
| ATOM | 4000 | C | PHE | 564 | 54.320 | 47.132 | 36.682 | 1.00 | 18.19 |
| ATOM | 4001 | O | PHE | 564 | 55.448 | 47.583 | 36.866 | 1.00 | 16.35 |
| ATOM | 4002 | N | HIS | 565 | 54.103 | 45.980 | 36.058 | 1.00 | 18.26 |
| ATOM | 4003 | CA | HIS | 565 | 55.201 | 45.191 | 35.523 | 1.00 | 17.93 |
| ATOM | 4004 | CB | HIS | 565 | 54.652 | 43.948 | 34.813 | 1.00 | 16.92 |
| ATOM | 4005 | CG | HIS | 565 | 55.712 | 43.026 | 34.290 | 1.00 | 19.54 |
| ATOM | 4006 | CD2 | HIS | 565 | 55.963 | 42.577 | 33.036 | 1.00 | 18.23 |
| ATOM | 4007 | ND1 | HIS | 565 | 56.645 | 42.424 | 35.106 | 1.00 | 19.14 |
| ATOM | 4008 | CE1 | HIS | 565 | 57.423 | 41.641 | 34.379 | 1.00 | 19.86 |
| ATOM | 4009 | NE2 | HIS | 565 | 57.030 | 41.716 | 33.120 | 1.00 | 18.37 |
| ATOM | 4010 | C | HIS | 565 | 56.001 | 46.053 | 34.536 | 1.00 | 19.62 |
| ATOM | 4011 | O | HIS | 565 | 57.224 | 46.140 | 34.623 | 1.00 | 19.79 |
| ATOM | 4012 | N | GLU | 566 | 55.299 | 46.692 | 33.605 | 1.00 | 19.55 |
| ATOM | 4013 | CA | GLU | 566 | 55.938 | 47.546 | 32.607 | 1.00 | 21.41 |

TABLE A-continued

| | | | | | | | | |
|---|---|---|---|---|---|---|---|---|
| ATOM | 4014 | CB | GLU | 566 | 54.874 | 48.175 | 31.702 | 1.00 | 21.29 |
| ATOM | 4015 | CG | GLU | 566 | 55.420 | 49.067 | 30.595 | 1.00 | 22.84 |
| ATOM | 4016 | CD | GLU | 566 | 54.320 | 49.736 | 29.798 | 1.00 | 23.16 |
| ATOM | 4017 | OE1 | GLU | 566 | 53.587 | 50.571 | 30.370 | 1.00 | 25.71 |
| ATOM | 4018 | OE2 | GLU | 566 | 54.180 | 49.423 | 28.599 | 1.00 | 24.72 |
| ATOM | 4019 | C | GLU | 566 | 56.781 | 48.645 | 33.259 | 1.00 | 22.27 |
| ATOM | 4020 | O | GLU | 566 | 57.954 | 48.823 | 32.920 | 1.00 | 22.02 |
| ATOM | 4021 | N | ALA | 567 | 56.185 | 49.375 | 34.199 | 1.00 | 22.14 |
| ATOM | 4022 | CA | ALA | 567 | 56.884 | 50.457 | 34.887 | 1.00 | 22.62 |
| ATOM | 4023 | CB | ALA | 567 | 55.918 | 51.206 | 35.794 | 1.00 | 21.46 |
| ATOM | 4024 | C | ALA | 567 | 58.081 | 49.966 | 35.698 | 1.00 | 23.23 |
| ATOM | 4025 | O | ALA | 567 | 59.165 | 50.544 | 35.633 | 1.00 | 21.96 |
| ATOM | 4026 | N | LEU | 568 | 57.884 | 48.898 | 36.463 | 1.00 | 23.52 |
| ATOM | 4027 | CA | LEU | 568 | 58.953 | 48.353 | 37.287 | 1.00 | 24.49 |
| ATOM | 4028 | CB | LEU | 568 | 58.427 | 47.204 | 38.149 | 1.00 | 23.80 |
| ATOM | 4029 | CG | LEU | 568 | 57.319 | 47.563 | 39.146 | 1.00 | 25.68 |
| ATOM | 4030 | CD1 | LEU | 568 | 56.974 | 46.337 | 39.976 | 1.00 | 24.01 |
| ATOM | 4031 | CD2 | LEU | 568 | 57.770 | 48.705 | 40.047 | 1.00 | 24.11 |
| ATOM | 4032 | C | LEU | 568 | 60.129 | 47.874 | 36.444 | 1.00 | 26.12 |
| ATOM | 4033 | O | LEU | 568 | 61.287 | 48.041 | 36.835 | 1.00 | 25.53 |
| ATOM | 4034 | N | CYS | 569 | 59.829 | 47.277 | 35.293 | 1.00 | 26.09 |
| ATOM | 4035 | CA | CYS | 569 | 60.866 | 46.785 | 34.394 | 1.00 | 26.84 |
| ATOM | 4036 | C | CYS | 569 | 61.662 | 47.954 | 33.833 | 1.00 | 29.17 |
| ATOM | 4037 | O | CYS | 569 | 62.888 | 47.891 | 33.735 | 1.00 | 29.21 |
| ATOM | 4038 | CB | CYS | 569 | 60.245 | 45.983 | 33.251 | 1.00 | 24.41 |
| ATOM | 4039 | SG | CYS | 569 | 59.479 | 44.440 | 33.829 | 1.00 | 23.54 |
| ATOM | 4040 | N | GLN | 570 | 60.958 | 49.018 | 33.461 | 1.00 | 30.60 |
| ATOM | 4041 | CA | GLN | 570 | 61.609 | 50.205 | 32.929 | 1.00 | 33.85 |
| ATOM | 4042 | CB | GLN | 570 | 60.560 | 51.241 | 32.508 | 1.00 | 36.01 |
| ATOM | 4043 | CG | GLN | 570 | 61.123 | 52.471 | 31.797 | 1.00 | 40.86 |
| ATOM | 4044 | CD | GLN | 570 | 61.634 | 53.535 | 32.755 | 1.00 | 44.93 |
| ATOM | 4045 | OE1 | GLN | 570 | 62.251 | 54.518 | 32.338 | 1.00 | 47.36 |
| ATOM | 4046 | NE2 | GLN | 570 | 61.370 | 53.349 | 34.044 | 1.00 | 46.77 |
| ATOM | 4047 | C | GLN | 570 | 62.518 | 50.774 | 34.018 | 1.00 | 34.13 |
| ATOM | 4048 | O | GLN | 570 | 63.651 | 51.168 | 33.750 | 1.00 | 35.84 |
| ATOM | 4049 | N | ALA | 571 | 62.023 | 50.793 | 35.252 | 1.00 | 33.88 |
| ATOM | 4050 | CA | ALA | 571 | 62.798 | 51.308 | 36.376 | 1.00 | 33.88 |
| ATOM | 4051 | CB | ALA | 571 | 61.922 | 51.397 | 37.616 | 1.00 | 33.43 |
| ATOM | 4052 | C | ALA | 571 | 64.008 | 50.421 | 36.655 | 1.00 | 34.68 |
| ATOM | 4053 | O | ALA | 571 | 65.025 | 50.891 | 37.168 | 1.00 | 33.79 |
| ATOM | 4054 | N | ALA | 572 | 63.894 | 49.140 | 36.314 | 1.00 | 34.10 |
| ATOM | 4055 | CA | ALA | 572 | 64.979 | 48.187 | 36.529 | 1.00 | 34.04 |
| ATOM | 4056 | CB | ALA | 572 | 64.414 | 46.781 | 36.698 | 1.00 | 31.78 |
| ATOM | 4057 | C | ALA | 572 | 65.987 | 48.209 | 35.381 | 1.00 | 34.28 |
| ATOM | 4058 | O | ALA | 572 | 66.963 | 47.456 | 35.387 | 1.00 | 33.48 |
| ATOM | 4059 | N | GLY | 573 | 65.740 | 49.067 | 34.396 | 1.00 | 35.90 |
| ATOM | 4060 | CA | GLY | 573 | 66.639 | 49.173 | 33.261 | 1.00 | 36.02 |
| ATOM | 4061 | C | GLY | 573 | 66.486 | 48.083 | 32.214 | 1.00 | 36.88 |
| ATOM | 4062 | O | GLY | 573 | 67.380 | 47.876 | 31.391 | 1.00 | 36.25 |
| ATOM | 4063 | N | HIS | 574 | 65.357 | 47.381 | 32.232 | 1.00 | 36.48 |
| ATOM | 4064 | CA | HIS | 574 | 65.124 | 46.320 | 31.262 | 1.00 | 34.33 |
| ATOM | 4065 | CB | HIS | 574 | 63.916 | 45.472 | 31.661 | 1.00 | 35.35 |
| ATOM | 4066 | CG | HIS | 574 | 63.584 | 44.400 | 30.670 | 1.00 | 36.05 |
| ATOM | 4067 | CD2 | HIS | 574 | 62.614 | 44.325 | 29.727 | 1.00 | 36.62 |
| ATOM | 4068 | ND1 | HIS | 574 | 64.327 | 43.245 | 30.547 | 1.00 | 36.78 |
| ATOM | 4069 | CE1 | HIS | 574 | 63.829 | 42.506 | 29.571 | 1.00 | 36.45 |
| ATOM | 4070 | NE2 | HIS | 574 | 62.790 | 43.138 | 29.057 | 1.00 | 35.54 |
| ATOM | 4071 | C | HIS | 574 | 64.874 | 46.906 | 29.881 | 1.00 | 33.60 |
| ATOM | 4072 | O | HIS | 574 | 64.237 | 47.946 | 29.743 | 1.00 | 33.03 |
| ATOM | 4073 | N | THR | 575 | 65.380 | 46.227 | 28.859 | 1.00 | 32.54 |
| ATOM | 4074 | CA | THR | 575 | 65.192 | 46.671 | 27.488 | 1.00 | 33.83 |
| ATOM | 4075 | CB | THR | 575 | 66.501 | 47.234 | 26.889 | 1.00 | 34.38 |
| ATOM | 4076 | OG1 | THR | 575 | 67.435 | 46.166 | 26.684 | 1.00 | 35.54 |
| ATOM | 4077 | CG2 | THR | 575 | 67.115 | 48.261 | 27.831 | 1.00 | 35.04 |
| ATOM | 4078 | C | THR | 575 | 64.751 | 45.462 | 26.676 | 1.00 | 33.06 |
| ATOM | 4079 | O | THR | 575 | 65.060 | 44.322 | 27.030 | 1.00 | 33.26 |
| ATOM | 4080 | N | GLY | 576 | 64.023 | 45.711 | 25.594 | 1.00 | 32.96 |
| ATOM | 4081 | CA | GLY | 576 | 63.554 | 44.618 | 24.764 | 1.00 | 32.46 |
| ATOM | 4082 | C | GLY | 576 | 62.144 | 44.192 | 25.125 | 1.00 | 32.04 |
| ATOM | 4083 | O | GLY | 576 | 61.479 | 44.862 | 25.915 | 1.00 | 32.23 |
| ATOM | 4084 | N | PRO | 577 | 61.663 | 43.068 | 24.571 | 1.00 | 31.90 |
| ATOM | 4085 | CD | PRO | 577 | 62.410 | 42.136 | 23.709 | 1.00 | 30.59 |
| ATOM | 4086 | CA | PRO | 577 | 60.314 | 42.558 | 24.841 | 1.00 | 29.53 |
| ATOM | 4087 | CB | PRO | 577 | 60.351 | 41.158 | 24.235 | 1.00 | 30.83 |
| ATOM | 4088 | CG | PRO | 577 | 61.297 | 41.321 | 23.087 | 1.00 | 32.27 |
| ATOM | 4089 | C | PRO | 577 | 59.972 | 42.538 | 26.329 | 1.00 | 28.72 |
| ATOM | 4090 | O | PRO | 577 | 60.709 | 41.981 | 27.143 | 1.00 | 28.66 |
| ATOM | 4091 | N | LEU | 578 | 58.842 | 43.146 | 26.672 | 1.00 | 27.32 |
| ATOM | 4092 | CA | LEU | 578 | 58.393 | 43.211 | 28.055 | 1.00 | 25.47 |
| ATOM | 4093 | CB | LEU | 578 | 57.073 | 43.990 | 28.135 | 1.00 | 24.84 |

TABLE A-continued

| | | | | | | | | |
|---|---|---|---|---|---|---|---|---|
| ATOM | 4094 | CG | LEU | 578 | 56.462 | 44.208 | 29.523 | 1.00 23.79 |
| ATOM | 4095 | CD1 | LEU | 578 | 57.435 | 44.990 | 30.395 | 1.00 23.05 |
| ATOM | 4096 | CD2 | LEU | 578 | 55.141 | 44.962 | 29.390 | 1.00 24.13 |
| ATOM | 4097 | C | LEU | 578 | 58.224 | 41.831 | 28.695 | 1.00 24.37 |
| ATOM | 4098 | O | LEU | 578 | 58.540 | 41.646 | 29.874 | 1.00 25.18 |
| ATOM | 4099 | N | HIS | 579 | 57.743 | 40.855 | 27.927 | 1.00 22.93 |
| ATOM | 4100 | CA | HIS | 579 | 57.533 | 39.521 | 28.482 | 1.00 22.45 |
| ATOM | 4101 | CB | HIS | 579 | 56.736 | 38.635 | 27.511 | 1.00 22.24 |
| ATOM | 4102 | CG | HIS | 579 | 57.512 | 38.181 | 26.313 | 1.00 22.10 |
| ATOM | 4103 | CD2 | HIS | 579 | 58.201 | 37.038 | 26.080 | 1.00 23.76 |
| ATOM | 4104 | ND1 | HIS | 579 | 57.627 | 38.938 | 25.166 | 1.00 24.64 |
| ATOM | 4105 | CE1 | HIS | 579 | 58.350 | 38.279 | 24.277 | 1.00 25.23 |
| ATOM | 4106 | NE2 | HIS | 579 | 58.711 | 37.123 | 24.807 | 1.00 25.73 |
| ATOM | 4107 | C | HIS | 579 | 58.810 | 38.796 | 28.900 | 1.00 23.53 |
| ATOM | 4108 | O | HIS | 579 | 58.744 | 37.743 | 29.535 | 1.00 24.05 |
| ATOM | 4109 | N | LYS | 580 | 59.968 | 39.348 | 28.547 | 1.00 23.73 |
| ATOM | 4110 | CA | LYS | 580 | 61.244 | 38.734 | 28.919 | 1.00 26.19 |
| ATOM | 4111 | CB | LYS | 580 | 62.272 | 38.902 | 27.794 | 1.00 27.71 |
| ATOM | 4112 | CG | LYS | 580 | 61.993 | 38.075 | 26.553 | 1.00 31.25 |
| ATOM | 4113 | CD | LYS | 580 | 63.043 | 38.351 | 25.481 | 1.00 34.78 |
| ATOM | 4114 | CE | LYS | 580 | 62.733 | 37.611 | 24.191 | 1.00 37.22 |
| ATOM | 4115 | NZ | LYS | 580 | 63.671 | 37.995 | 23.096 | 1.00 40.53 |
| ATOM | 4116 | C | LYS | 580 | 61.811 | 39.340 | 30.206 | 1.00 26.16 |
| ATOM | 4117 | O | LYS | 580 | 62.850 | 38.903 | 30.706 | 1.00 23.22 |
| ATOM | 4118 | N | CYS | 581 | 61.124 | 40.344 | 30.739 | 1.00 24.41 |
| ATOM | 4119 | CA | CYS | 581 | 61.569 | 41.006 | 31.959 | 1.00 23.52 |
| ATOM | 4120 | C | CYS | 581 | 61.407 | 40.186 | 33.240 | 1.00 24.04 |
| ATOM | 4121 | O | CYS | 581 | 60.418 | 39.469 | 33.419 | 1.00 21.53 |
| ATOM | 4122 | CB | CYS | 581 | 60.838 | 42.342 | 32.119 | 1.00 23.29 |
| ATOM | 4123 | SG | CYS | 581 | 61.004 | 43.098 | 33.770 | 1.00 24.70 |
| ATOM | 4124 | N | ASP | 582 | 62.400 | 40.306 | 34.121 | 1.00 21.19 |
| ATOM | 4125 | CA | ASP | 582 | 62.419 | 39.637 | 35.421 | 1.00 22.50 |
| ATOM | 4126 | CB | ASP | 582 | 63.317 | 38.394 | 35.392 | 1.00 22.61 |
| ATOM | 4127 | CG | ASP | 582 | 63.390 | 37.685 | 36.742 | 1.00 23.83 |
| ATOM | 4128 | OD1 | ASP | 582 | 62.906 | 38.239 | 37.758 | 1.00 24.26 |
| ATOM | 4129 | OD2 | ASP | 582 | 63.947 | 36.567 | 36.793 | 1.00 23.11 |
| ATOM | 4130 | C | ASP | 582 | 63.010 | 40.680 | 36.360 | 1.00 24.44 |
| ATOM | 4131 | O | ASP | 582 | 64.211 | 40.968 | 36.302 | 1.00 24.08 |
| ATOM | 4132 | N | ILE | 583 | 62.165 | 41.253 | 37.213 | 1.00 22.22 |
| ATOM | 4133 | CA | ILE | 583 | 62.601 | 42.294 | 38.138 | 1.00 21.09 |
| ATOM | 4134 | CB | ILE | 583 | 61.413 | 43.184 | 38.568 | 1.00 19.80 |
| ATOM | 4135 | CG2 | ILE | 583 | 60.751 | 43.796 | 37.340 | 1.00 18.47 |
| ATOM | 4136 | CG1 | ILE | 583 | 60.408 | 42.355 | 39.369 | 1.00 19.27 |
| ATOM | 4137 | CD1 | ILE | 583 | 59.301 | 43.181 | 40.010 | 1.00 21.03 |
| ATOM | 4138 | C | ILE | 583 | 63.279 | 41.779 | 39.401 | 1.00 21.02 |
| ATOM | 4139 | O | ILE | 583 | 63.533 | 42.552 | 40.325 | 1.00 21.75 |
| ATOM | 4140 | N | TYR | 584 | 63.575 | 40.484 | 39.445 | 1.00 21.19 |
| ATOM | 4141 | CA | TYR | 584 | 64.220 | 39.906 | 40.620 | 1.00 22.52 |
| ATOM | 4142 | CB | TYR | 584 | 64.660 | 38.466 | 40.346 | 1.00 23.63 |
| ATOM | 4143 | CG | TYR | 584 | 65.245 | 37.787 | 41.565 | 1.00 25.38 |
| ATOM | 4144 | CD1 | TYR | 584 | 64.420 | 37.304 | 42.576 | 1.00 24.65 |
| ATOM | 4145 | CE1 | TYR | 584 | 64.951 | 36.724 | 43.725 | 1.00 26.30 |
| ATOM | 4146 | CD2 | TYR | 584 | 66.625 | 37.672 | 41.731 | 1.00 25.96 |
| ATOM | 4147 | CE2 | TYR | 584 | 67.167 | 37.095 | 42.878 | 1.00 27.41 |
| ATOM | 4148 | CZ | TYR | 584 | 66.325 | 36.624 | 43.869 | 1.00 27.35 |
| ATOM | 4149 | OH | TYR | 584 | 66.852 | 36.048 | 45.003 | 1.00 29.28 |
| ATOM | 4150 | C | TYR | 584 | 65.434 | 40.721 | 41.068 | 1.00 22.10 |
| ATOM | 4151 | O | TYR | 584 | 66.273 | 41.102 | 40.252 | 1.00 19.45 |
| ATOM | 4152 | N | GLN | 585 | 65.501 | 40.980 | 42.373 | 1.00 24.34 |
| ATOM | 4153 | CA | GLN | 585 | 66.581 | 41.736 | 43.014 | 1.00 25.79 |
| ATOM | 4154 | CB | GLN | 585 | 67.937 | 41.063 | 42.740 | 1.00 27.46 |
| ATOM | 4155 | CG | GLN | 585 | 69.106 | 41.754 | 43.433 | 1.00 30.44 |
| ATOM | 4156 | CD | GLN | 585 | 70.383 | 40.939 | 43.418 | 1.00 32.54 |
| ATOM | 4157 | OE1 | GLN | 585 | 71.474 | 41.474 | 43.621 | 1.00 33.54 |
| ATOM | 4158 | NE2 | GLN | 585 | 70.253 | 39.636 | 43.194 | 1.00 31.30 |
| ATOM | 4159 | C | GLN | 585 | 66.666 | 43.231 | 42.687 | 1.00 25.96 |
| ATOM | 4160 | O | GLN | 585 | 67.585 | 43.919 | 43.139 | 1.00 27.28 |
| ATOM | 4161 | N | SER | 586 | 65.707 | 43.747 | 41.924 | 1.00 24.70 |
| ATOM | 4162 | CA | SER | 586 | 65.716 | 45.165 | 41.577 | 1.00 25.28 |
| ATOM | 4163 | CB | SER | 586 | 64.829 | 45.436 | 40.365 | 1.00 24.97 |
| ATOM | 4164 | OG | SER | 586 | 64.667 | 46.834 | 40.178 | 1.00 25.13 |
| ATOM | 4165 | C | SER | 586 | 65.247 | 46.047 | 42.728 | 1.00 26.57 |
| ATOM | 4166 | O | SER | 586 | 64.072 | 46.026 | 43.103 | 1.00 26.45 |
| ATOM | 4167 | N | LYS | 587 | 66.167 | 46.832 | 43.277 | 1.00 25.12 |
| ATOM | 4168 | CA | LYS | 587 | 65.843 | 47.724 | 44.378 | 1.00 26.77 |
| ATOM | 4169 | CB | LYS | 587 | 67.126 | 48.207 | 45.067 | 1.00 26.74 |
| ATOM | 4170 | CG | LYS | 587 | 67.944 | 47.087 | 45.702 | 1.00 27.54 |
| ATOM | 4171 | CD | LYS | 587 | 67.119 | 46.297 | 46.712 | 1.00 27.45 |
| ATOM | 4172 | CE | LYS | 587 | 67.925 | 45.161 | 47.332 | 1.00 26.21 |
| ATOM | 4173 | NZ | LYS | 587 | 68.401 | 44.190 | 46.311 | 1.00 25.90 |

TABLE A-continued

| | | | | | | | | |
|---|---|---|---|---|---|---|---|---|
| ATOM | 4174 | C | LYS | 587 | 65.022 | 48.918 | 43.897 | 1.00 25.59 |
| ATOM | 4175 | O | LYS | 587 | 64.201 | 49.448 | 44.642 | 1.00 26.97 |
| ATOM | 4176 | N | GLU | 588 | 65.245 | 49.344 | 42.657 | 1.00 24.23 |
| ATOM | 4177 | CA | GLU | 588 | 64.496 | 50.467 | 42.104 | 1.00 25.34 |
| ATOM | 4178 | CB | GLU | 588 | 65.025 | 50.849 | 40.718 | 1.00 29.07 |
| ATOM | 4179 | CG | GLU | 588 | 66.440 | 51.417 | 40.693 | 1.00 34.67 |
| ATOM | 4180 | CD | GLU | 588 | 67.496 | 50.393 | 41.060 | 1.00 38.21 |
| ATOM | 4181 | OE1 | GLU | 588 | 67.482 | 49.283 | 40.480 | 1.00 38.94 |
| ATOM | 4182 | OE2 | GLU | 588 | 68.348 | 50.704 | 41.921 | 1.00 41.97 |
| ATOM | 4183 | C | GLU | 588 | 63.021 | 50.071 | 41.987 | 1.00 25.42 |
| ATOM | 4184 | O | GLU | 588 | 62.125 | 50.880 | 42.238 | 1.00 22.32 |
| ATOM | 4185 | N | ALA | 589 | 62.783 | 48.822 | 41.596 | 1.00 24.18 |
| ATOM | 4186 | CA | ALA | 589 | 61.426 | 48.306 | 41.452 | 1.00 24.57 |
| ATOM | 4187 | CB | ALA | 589 | 61.455 | 46.903 | 40.851 | 1.00 24.39 |
| ATOM | 4188 | C | ALA | 589 | 60.761 | 48.271 | 42.822 | 1.00 24.55 |
| ATOM | 4189 | O | ALA | 589 | 59.665 | 48.801 | 43.009 | 1.00 24.25 |
| ATOM | 4190 | N | GLY | 590 | 61.439 | 47.646 | 43.778 | 1.00 23.98 |
| ATOM | 4191 | CA | GLY | 590 | 60.902 | 47.551 | 45.121 | 1.00 26.42 |
| ATOM | 4192 | C | GLY | 590 | 60.582 | 48.897 | 45.746 | 1.00 27.69 |
| ATOM | 4193 | O | GLY | 590 | 59.577 | 49.039 | 46.442 | 1.00 28.18 |
| ATOM | 4194 | N | GLN | 591 | 61.429 | 49.890 | 45.500 | 1.00 27.79 |
| ATOM | 4195 | CA | GLN | 591 | 61.214 | 51.214 | 46.066 | 1.00 29.11 |
| ATOM | 4196 | CB | GLN | 591 | 62.376 | 52.143 | 45.715 | 1.00 31.76 |
| ATOM | 4197 | CG | GLN | 591 | 62.271 | 53.502 | 46.384 | 1.00 36.94 |
| ATOM | 4198 | CD | GLN | 591 | 62.181 | 53.386 | 47.896 | 1.00 41.21 |
| ATOM | 4199 | OE1 | GLN | 591 | 63.116 | 52.925 | 48.554 | 1.00 44.17 |
| ATOM | 4200 | NE2 | GLN | 591 | 61.048 | 53.795 | 48.454 | 1.00 43.27 |
| ATOM | 4201 | C | GLN | 591 | 59.904 | 51.843 | 45.600 | 1.00 28.84 |
| ATOM | 4202 | O | GLN | 591 | 59.228 | 52.522 | 46.371 | 1.00 26.01 |
| ATOM | 4203 | N | ARG | 592 | 59.547 | 51.625 | 44.340 | 1.00 28.52 |
| ATOM | 4204 | CA | ARG | 592 | 58.307 | 52.191 | 43.823 | 1.00 29.49 |
| ATOM | 4205 | CB | ARG | 592 | 58.258 | 52.089 | 42.298 | 1.00 30.74 |
| ATOM | 4206 | CG | ARG | 592 | 59.232 | 53.022 | 41.610 | 1.00 33.59 |
| ATOM | 4207 | CD | ARG | 592 | 58.864 | 53.215 | 40.162 | 1.00 34.84 |
| ATOM | 4208 | NE | ARG | 592 | 59.817 | 54.071 | 39.469 | 1.00 36.89 |
| ATOM | 4209 | CZ | ARG | 592 | 59.720 | 54.401 | 38.187 | 1.00 39.66 |
| ATOM | 4210 | NH1 | ARG | 592 | 58.706 | 53.948 | 37.460 | 1.00 40.17 |
| ATOM | 4211 | NH2 | ARG | 592 | 60.641 | 55.173 | 37.628 | 1.00 40.49 |
| ATOM | 4212 | C | ARG | 592 | 57.086 | 51.515 | 44.428 | 1.00 28.08 |
| ATOM | 4213 | O | ARG | 592 | 56.103 | 52.177 | 44.758 | 1.00 30.13 |
| ATOM | 4214 | N | LEU | 593 | 57.144 | 50.197 | 44.576 | 1.00 25.72 |
| ATOM | 4215 | CA | LEU | 593 | 56.028 | 49.468 | 45.162 | 1.00 24.31 |
| ATOM | 4216 | CB | LEU | 593 | 56.257 | 47.960 | 45.061 | 1.00 23.41 |
| ATOM | 4217 | CG | LEU | 593 | 56.003 | 47.293 | 43.710 | 1.00 24.09 |
| ATOM | 4218 | CD1 | LEU | 593 | 56.340 | 45.814 | 43.814 | 1.00 22.31 |
| ATOM | 4219 | CD2 | LEU | 593 | 54.541 | 47.482 | 43.309 | 1.00 24.13 |
| ATOM | 4220 | C | LEU | 593 | 55.856 | 49.851 | 46.630 | 1.00 24.61 |
| ATOM | 4221 | O | LEU | 593 | 54.734 | 50.014 | 47.113 | 1.00 22.28 |
| ATOM | 4222 | N | ALA | 594 | 56.979 | 49.994 | 47.327 | 1.00 22.88 |
| ATOM | 4223 | CA | ALA | 594 | 56.975 | 50.342 | 48.743 | 1.00 24.40 |
| ATOM | 4224 | CB | ALA | 594 | 58.400 | 50.304 | 49.299 | 1.00 23.81 |
| ATOM | 4225 | C | ALA | 594 | 56.350 | 51.704 | 49.016 | 1.00 23.79 |
| ATOM | 4226 | O | ALA | 594 | 55.480 | 51.824 | 49.878 | 1.00 24.99 |
| ATOM | 4227 | N | THR | 595 | 56.784 | 52.729 | 48.288 | 1.00 23.07 |
| ATOM | 4228 | CA | THR | 595 | 56.244 | 54.065 | 48.506 | 1.00 26.20 |
| ATOM | 4229 | CB | THR | 595 | 56.956 | 55.126 | 47.627 | 1.00 28.03 |
| ATOM | 4230 | OG1 | THR | 595 | 56.705 | 54.861 | 46.242 | 1.00 35.56 |
| ATOM | 4231 | CG2 | THR | 595 | 58.457 | 55.094 | 47.873 | 1.00 28.43 |
| ATOM | 4232 | C | THR | 595 | 54.745 | 54.092 | 48.218 | 1.00 25.47 |
| ATOM | 4233 | O | THR | 595 | 53.983 | 54.780 | 48.901 | 1.00 24.49 |
| ATOM | 4234 | N | ALA | 596 | 54.326 | 53.331 | 47.211 | 1.00 23.19 |
| ATOM | 4235 | CA | ALA | 596 | 52.918 | 53.265 | 46.846 | 1.00 22.32 |
| ATOM | 4236 | CB | ALA | 596 | 52.756 | 52.563 | 45.496 | 1.00 22.20 |
| ATOM | 4237 | C | ALA | 596 | 52.123 | 52.530 | 47.919 | 1.00 20.86 |
| ATOM | 4238 | O | ALA | 596 | 51.067 | 52.993 | 48.347 | 1.00 21.03 |
| ATOM | 4239 | N | MET | 597 | 52.631 | 51.385 | 48.362 | 1.00 20.23 |
| ATOM | 4240 | CA | MET | 597 | 51.930 | 50.608 | 49.376 | 1.00 20.17 |
| ATOM | 4241 | CB | MET | 597 | 52.610 | 49.249 | 49.581 | 1.00 18.97 |
| ATOM | 4242 | CG | MET | 597 | 52.435 | 48.280 | 48.412 | 1.00 18.62 |
| ATOM | 4243 | SD | MET | 597 | 53.001 | 46.611 | 48.797 | 1.00 20.81 |
| ATOM | 4244 | CE | MET | 597 | 54.714 | 46.755 | 48.344 | 1.00 18.21 |
| ATOM | 4245 | C | MET | 597 | 51.824 | 51.338 | 50.710 | 1.00 21.22 |
| ATOM | 4246 | O | MET | 597 | 50.834 | 51.194 | 51.426 | 1.00 19.46 |
| ATOM | 4247 | N | LYS | 598 | 52.839 | 52.128 | 51.039 | 1.00 22.34 |
| ATOM | 4248 | CA | LYS | 598 | 52.845 | 52.863 | 52.298 | 1.00 23.65 |
| ATOM | 4249 | CB | LYS | 598 | 54.194 | 53.565 | 52.492 | 1.00 23.93 |
| ATOM | 4250 | CG | LYS | 598 | 55.328 | 52.609 | 52.830 | 1.00 28.85 |
| ATOM | 4251 | CD | LYS | 598 | 56.610 | 53.354 | 53.162 | 1.00 31.84 |
| ATOM | 4252 | CE | LYS | 598 | 57.625 | 52.428 | 53.822 | 1.00 35.46 |
| ATOM | 4253 | NZ | LYS | 598 | 58.006 | 51.266 | 52.967 | 1.00 38.87 |

TABLE A-continued

| | | | | | | | | | |
|---|---|---|---|---|---|---|---|---|---|
| ATOM | 4254 | C | LYS | 598 | 51.706 | 53.875 | 52.417 | 1.00 | 22.67 |
| ATOM | 4255 | O | LYS | 598 | 51.337 | 54.267 | 53.522 | 1.00 | 23.02 |
| ATOM | 4256 | N | LEU | 599 | 51.154 | 54.299 | 51.284 | 1.00 | 20.77 |
| ATOM | 4257 | CA | LEU | 599 | 50.050 | 55.257 | 51.290 | 1.00 | 20.03 |
| ATOM | 4258 | CB | LEU | 599 | 49.807 | 55.812 | 49.883 | 1.00 | 21.69 |
| ATOM | 4259 | CG | LEU | 599 | 50.838 | 56.754 | 49.260 | 1.00 | 22.59 |
| ATOM | 4260 | CD1 | LEU | 599 | 50.420 | 57.074 | 47.835 | 1.00 | 22.70 |
| ATOM | 4261 | CD2 | LEU | 599 | 50.947 | 58.026 | 50.085 | 1.00 | 22.77 |
| ATOM | 4262 | C | LEU | 599 | 48.757 | 54.614 | 51.784 | 1.00 | 20.21 |
| ATOM | 4263 | O | LEU | 599 | 47.834 | 55.306 | 52.219 | 1.00 | 19.40 |
| ATOM | 4264 | N | GLY | 600 | 48.690 | 53.290 | 51.717 | 1.00 | 20.15 |
| ATOM | 4265 | CA | GLY | 600 | 47.478 | 52.611 | 52.134 | 1.00 | 20.16 |
| ATOM | 4266 | C | GLY | 600 | 46.297 | 53.228 | 51.402 | 1.00 | 20.63 |
| ATOM | 4267 | O | GLY | 600 | 46.347 | 53.438 | 50.185 | 1.00 | 20.76 |
| ATOM | 4268 | N | PHE | 601 | 45.245 | 53.544 | 52.150 | 1.00 | 20.86 |
| ATOM | 4269 | CA | PHE | 601 | 44.031 | 54.143 | 51.593 | 1.00 | 21.23 |
| ATOM | 4270 | CB | PHE | 601 | 42.807 | 53.406 | 52.161 | 1.00 | 20.65 |
| ATOM | 4271 | CG | PHE | 601 | 41.509 | 53.733 | 51.470 | 1.00 | 24.23 |
| ATOM | 4272 | CD1 | PHE | 601 | 41.340 | 53.471 | 50.115 | 1.00 | 25.84 |
| ATOM | 4273 | CD2 | PHE | 601 | 40.449 | 54.283 | 52.183 | 1.00 | 24.34 |
| ATOM | 4274 | CE1 | PHE | 601 | 40.130 | 53.751 | 49.479 | 1.00 | 28.01 |
| ATOM | 4275 | CE2 | PHE | 601 | 39.233 | 54.568 | 51.557 | 1.00 | 27.29 |
| ATOM | 4276 | CZ | PHE | 601 | 39.075 | 54.300 | 50.202 | 1.00 | 26.47 |
| ATOM | 4277 | C | PHE | 601 | 43.972 | 55.632 | 51.961 | 1.00 | 20.30 |
| ATOM | 4278 | O | PHE | 601 | 42.899 | 56.230 | 51.999 | 1.00 | 21.85 |
| ATOM | 4279 | N | SER | 602 | 45.133 | 56.231 | 52.209 | 1.00 | 21.00 |
| ATOM | 4280 | CA | SER | 602 | 45.208 | 57.641 | 52.609 | 1.00 | 22.21 |
| ATOM | 4281 | CB | SER | 602 | 46.560 | 57.918 | 53.270 | 1.00 | 22.60 |
| ATOM | 4282 | OG | SER | 602 | 47.619 | 57.789 | 52.338 | 1.00 | 20.98 |
| ATOM | 4283 | C | SER | 602 | 44.982 | 58.679 | 51.506 | 1.00 | 23.68 |
| ATOM | 4284 | O | SER | 602 | 44.636 | 59.827 | 51.795 | 1.00 | 23.46 |
| ATOM | 4285 | N | ARG | 603 | 45.177 | 58.285 | 50.252 | 1.00 | 22.88 |
| ATOM | 4286 | CA | ARG | 603 | 45.005 | 59.207 | 49.130 | 1.00 | 25.54 |
| ATOM | 4287 | CB | ARG | 603 | 46.380 | 59.662 | 48.620 | 1.00 | 27.24 |
| ATOM | 4288 | CG | ARG | 603 | 47.247 | 60.373 | 49.654 | 1.00 | 31.36 |
| ATOM | 4289 | CD | ARG | 603 | 46.692 | 61.748 | 49.980 | 1.00 | 35.45 |
| ATOM | 4290 | NE | ARG | 603 | 46.606 | 62.585 | 48.784 | 1.00 | 40.01 |
| ATOM | 4291 | CZ | ARG | 603 | 46.063 | 63.799 | 48.754 | 1.00 | 42.24 |
| ATOM | 4292 | NH1 | ARG | 603 | 45.552 | 64.329 | 49.857 | 1.00 | 44.20 |
| ATOM | 4293 | NH2 | ARG | 603 | 46.029 | 64.483 | 47.618 | 1.00 | 41.85 |
| ATOM | 4294 | C | ARG | 603 | 44.243 | 58.549 | 47.981 | 1.00 | 23.92 |
| ATOM | 4295 | O | ARG | 603 | 44.199 | 57.330 | 47.884 | 1.00 | 24.89 |
| ATOM | 4296 | N | PRO | 604 | 43.623 | 59.353 | 47.101 | 1.00 | 24.43 |
| ATOM | 4297 | CD | PRO | 604 | 43.538 | 60.825 | 47.105 | 1.00 | 24.47 |
| ATOM | 4298 | CA | PRO | 604 | 42.881 | 58.785 | 45.967 | 1.00 | 23.43 |
| ATOM | 4299 | CB | PRO | 604 | 42.495 | 60.021 | 45.161 | 1.00 | 24.04 |
| ATOM | 4300 | CG | PRO | 604 | 42.327 | 61.076 | 46.235 | 1.00 | 24.67 |
| ATOM | 4301 | C | PRO | 604 | 43.856 | 57.874 | 45.217 | 1.00 | 22.52 |
| ATOM | 4302 | O | PRO | 604 | 45.017 | 58.241 | 45.026 | 1.00 | 19.66 |
| ATOM | 4303 | N | TRP | 605 | 43.397 | 56.702 | 44.784 | 1.00 | 21.06 |
| ATOM | 4304 | CA | TRP | 605 | 44.295 | 55.761 | 44.115 | 1.00 | 19.74 |
| ATOM | 4305 | CB | TRP | 605 | 43.547 | 54.478 | 43.719 | 1.00 | 17.20 |
| ATOM | 4306 | CG | TRP | 605 | 42.556 | 54.624 | 42.617 | 1.00 | 16.80 |
| ATOM | 4307 | CD2 | TRP | 605 | 42.839 | 54.662 | 41.218 | 1.00 | 13.73 |
| ATOM | 4308 | CE2 | TRP | 605 | 41.604 | 54.771 | 40.545 | 1.00 | 13.99 |
| ATOM | 4309 | CE3 | TRP | 605 | 44.019 | 54.611 | 40.465 | 1.00 | 14.13 |
| ATOM | 4310 | CD1 | TRP | 605 | 41.198 | 54.716 | 42.736 | 1.00 | 16.73 |
| ATOM | 4311 | NE1 | TRP | 605 | 40.619 | 54.802 | 41.496 | 1.00 | 15.70 |
| ATOM | 4312 | CZ2 | TRP | 605 | 41.514 | 54.835 | 39.153 | 1.00 | 12.90 |
| ATOM | 4313 | CZ3 | TRP | 605 | 43.929 | 54.674 | 39.083 | 1.00 | 15.39 |
| ATOM | 4314 | CH2 | TRP | 605 | 42.684 | 54.783 | 38.442 | 1.00 | 15.57 |
| ATOM | 4315 | C | TRP | 605 | 45.110 | 56.278 | 42.928 | 1.00 | 18.46 |
| ATOM | 4316 | O | TRP | 605 | 46.203 | 55.777 | 42.671 | 1.00 | 19.34 |
| ATOM | 4317 | N | PRO | 606 | 44.599 | 57.271 | 42.179 | 1.00 | 19.18 |
| ATOM | 4318 | CD | PRO | 606 | 43.257 | 57.880 | 42.148 | 1.00 | 18.96 |
| ATOM | 4319 | CA | PRO | 606 | 45.409 | 57.748 | 41.052 | 1.00 | 20.80 |
| ATOM | 4320 | CB | PRO | 606 | 44.583 | 58.910 | 40.507 | 1.00 | 20.75 |
| ATOM | 4321 | CG | PRO | 606 | 43.184 | 58.426 | 40.733 | 1.00 | 20.74 |
| ATOM | 4322 | C | PRO | 606 | 46.813 | 58.182 | 41.485 | 1.00 | 21.70 |
| ATOM | 4323 | O | PRO | 606 | 47.751 | 58.138 | 40.697 | 1.00 | 20.53 |
| ATOM | 4324 | N | GLU | 607 | 46.951 | 58.596 | 42.742 | 1.00 | 22.05 |
| ATOM | 4325 | CA | GLU | 607 | 48.250 | 59.020 | 43.250 | 1.00 | 23.78 |
| ATOM | 4326 | CB | GLU | 607 | 48.102 | 59.712 | 44.606 | 1.00 | 24.14 |
| ATOM | 4327 | CG | GLU | 607 | 47.576 | 61.128 | 44.482 | 1.00 | 30.40 |
| ATOM | 4328 | CD | GLU | 607 | 47.542 | 61.858 | 45.811 | 1.00 | 32.85 |
| ATOM | 4329 | OE1 | GLU | 607 | 48.566 | 61.837 | 46.530 | 1.00 | 33.25 |
| ATOM | 4330 | OE2 | GLU | 607 | 46.493 | 62.457 | 46.127 | 1.00 | 34.78 |
| ATOM | 4331 | C | GLU | 607 | 49.197 | 57.838 | 43.367 | 1.00 | 23.11 |
| ATOM | 4332 | O | GLU | 607 | 50.370 | 57.949 | 43.017 | 1.00 | 22.68 |
| ATOM | 4333 | N | ALA | 608 | 48.691 | 56.711 | 43.861 | 1.00 | 20.59 |

TABLE A-continued

| | | | | | | | | | |
|---|---|---|---|---|---|---|---|---|---|
| ATOM | 4334 | CA | ALA | 608 | 49.514 | 55.513 | 43.984 | 1.00 | 21.79 |
| ATOM | 4335 | CB | ALA | 608 | 48.766 | 54.431 | 44.770 | 1.00 | 19.65 |
| ATOM | 4336 | C | ALA | 608 | 49.854 | 55.014 | 42.575 | 1.00 | 20.36 |
| ATOM | 4337 | O | ALA | 608 | 50.941 | 54.484 | 42.341 | 1.00 | 20.96 |
| ATOM | 4338 | N | MET | 609 | 48.922 | 55.191 | 41.641 | 1.00 | 19.66 |
| ATOM | 4339 | CA | MET | 609 | 49.139 | 54.772 | 40.257 | 1.00 | 19.69 |
| ATOM | 4340 | CB | MET | 609 | 47.873 | 54.978 | 39.425 | 1.00 | 19.14 |
| ATOM | 4341 | CG | MET | 609 | 48.052 | 54.689 | 37.933 | 1.00 | 17.12 |
| ATOM | 4342 | SD | MET | 609 | 48.510 | 52.964 | 37.574 | 1.00 | 19.73 |
| ATOM | 4343 | CE | MET | 609 | 46.861 | 52.188 | 37.611 | 1.00 | 15.34 |
| ATOM | 4344 | C | MET | 609 | 50.266 | 55.601 | 39.658 | 1.00 | 21.29 |
| ATOM | 4345 | O | MET | 609 | 51.131 | 55.080 | 38.956 | 1.00 | 21.89 |
| ATOM | 4346 | N | GLN | 610 | 50.244 | 56.899 | 39.945 | 1.00 | 22.60 |
| ATOM | 4347 | CA | GLN | 610 | 51.254 | 57.820 | 39.444 | 1.00 | 24.68 |
| ATOM | 4348 | CB | GLN | 610 | 50.880 | 59.253 | 39.810 | 1.00 | 28.02 |
| ATOM | 4349 | CG | GLN | 610 | 51.680 | 60.294 | 39.059 | 1.00 | 32.26 |
| ATOM | 4350 | CD | GLN | 610 | 50.791 | 61.215 | 38.261 | 1.00 | 34.82 |
| ATOM | 4351 | OE1 | GLN | 610 | 50.166 | 62.126 | 38.805 | 1.00 | 37.92 |
| ATOM | 4352 | NE2 | GLN | 610 | 50.709 | 60.969 | 36.962 | 1.00 | 39.74 |
| ATOM | 4353 | C | GLN | 610 | 52.628 | 57.493 | 40.018 | 1.00 | 25.43 |
| ATOM | 4354 | O | GLN | 610 | 53.626 | 57.492 | 39.297 | 1.00 | 26.39 |
| ATOM | 4355 | N | LEU | 611 | 52.677 | 57.221 | 41.318 | 1.00 | 25.09 |
| ATOM | 4356 | CA | LEU | 611 | 53.936 | 56.889 | 41.976 | 1.00 | 26.89 |
| ATOM | 4357 | CB | LEU | 611 | 53.704 | 56.624 | 43.466 | 1.00 | 28.27 |
| ATOM | 4358 | CG | LEU | 611 | 53.394 | 57.852 | 44.319 | 1.00 | 30.25 |
| ATOM | 4359 | CD1 | LEU | 611 | 53.105 | 57.417 | 45.742 | 1.00 | 30.76 |
| ATOM | 4360 | CD2 | LEU | 611 | 54.577 | 58.818 | 44.279 | 1.00 | 30.95 |
| ATOM | 4361 | C | LEU | 611 | 54.624 | 55.677 | 41.357 | 1.00 | 25.11 |
| ATOM | 4362 | O | LEU | 611 | 55.850 | 55.622 | 41.271 | 1.00 | 25.06 |
| ATOM | 4363 | N | ILE | 612 | 53.834 | 54.703 | 40.928 | 1.00 | 23.32 |
| ATOM | 4364 | CA | ILE | 612 | 54.394 | 53.497 | 40.339 | 1.00 | 22.85 |
| ATOM | 4365 | CB | ILE | 612 | 53.449 | 52.286 | 40.530 | 1.00 | 23.45 |
| ATOM | 4366 | CG2 | ILE | 612 | 54.042 | 51.054 | 39.856 | 1.00 | 24.69 |
| ATOM | 4367 | CG1 | ILE | 612 | 53.216 | 52.018 | 42.017 | 1.00 | 24.83 |
| ATOM | 4368 | CD1 | ILE | 612 | 52.078 | 51.033 | 42.285 | 1.00 | 23.21 |
| ATOM | 4369 | C | ILE | 612 | 54.678 | 53.607 | 38.844 | 1.00 | 22.85 |
| ATOM | 4370 | O | ILE | 612 | 55.739 | 53.187 | 38.380 | 1.00 | 23.82 |
| ATOM | 4371 | N | THR | 613 | 53.736 | 54.179 | 38.099 | 1.00 | 22.01 |
| ATOM | 4372 | CA | THR | 613 | 53.846 | 54.262 | 36.642 | 1.00 | 22.05 |
| ATOM | 4373 | CB | THR | 613 | 52.552 | 53.740 | 35.993 | 1.00 | 20.57 |
| ATOM | 4374 | OG1 | THR | 613 | 51.498 | 54.680 | 36.225 | 1.00 | 19.96 |
| ATOM | 4375 | CG2 | THR | 613 | 52.151 | 52.397 | 36.600 | 1.00 | 17.72 |
| ATOM | 4376 | C | THR | 613 | 54.164 | 55.608 | 35.989 | 1.00 | 22.43 |
| ATOM | 4377 | O | THR | 613 | 54.456 | 55.660 | 34.796 | 1.00 | 22.71 |
| ATOM | 4378 | N | GLY | 614 | 54.095 | 56.696 | 36.743 | 1.00 | 24.21 |
| ATOM | 4379 | CA | GLY | 614 | 54.392 | 57.987 | 36.150 | 1.00 | 22.90 |
| ATOM | 4380 | C | GLY | 614 | 53.188 | 58.640 | 35.501 | 1.00 | 22.97 |
| ATOM | 4381 | O | GLY | 614 | 53.294 | 59.729 | 34.937 | 1.00 | 21.49 |
| ATOM | 4382 | N | GLN | 615 | 52.046 | 57.962 | 35.554 | 1.00 | 23.88 |
| ATOM | 4383 | CA | GLN | 615 | 50.802 | 58.502 | 35.012 | 1.00 | 21.95 |
| ATOM | 4384 | CB | GLN | 615 | 50.581 | 58.015 | 33.574 | 1.00 | 22.47 |
| ATOM | 4385 | CG | GLN | 615 | 50.505 | 56.523 | 33.379 | 1.00 | 22.03 |
| ATOM | 4386 | CD | GLN | 615 | 49.156 | 55.988 | 33.763 | 1.00 | 19.05 |
| ATOM | 4387 | OE1 | GLN | 615 | 48.129 | 56.540 | 33.362 | 1.00 | 19.51 |
| ATOM | 4388 | NE2 | GLN | 615 | 49.141 | 54.908 | 34.537 | 1.00 | 16.18 |
| ATOM | 4389 | C | GLN | 615 | 49.689 | 58.095 | 35.989 | 1.00 | 20.81 |
| ATOM | 4390 | O | GLN | 615 | 49.891 | 57.215 | 36.825 | 1.00 | 20.69 |
| ATOM | 4391 | N | PRO | 616 | 48.502 | 58.716 | 35.897 | 1.00 | 19.66 |
| ATOM | 4392 | CD | PRO | 616 | 48.157 | 59.932 | 35.138 | 1.00 | 21.70 |
| ATOM | 4393 | CA | PRO | 616 | 47.427 | 58.379 | 36.836 | 1.00 | 20.55 |
| ATOM | 4394 | CB | PRO | 616 | 46.908 | 59.751 | 37.209 | 1.00 | 20.89 |
| ATOM | 4395 | CG | PRO | 616 | 46.873 | 60.418 | 35.835 | 1.00 | 20.78 |
| ATOM | 4396 | C | PRO | 616 | 46.267 | 57.457 | 36.457 | 1.00 | 19.89 |
| ATOM | 4397 | O | PRO | 616 | 45.445 | 57.136 | 37.314 | 1.00 | 19.50 |
| ATOM | 4398 | N | ASN | 617 | 46.183 | 57.029 | 35.206 | 1.00 | 18.92 |
| ATOM | 4399 | CA | ASN | 617 | 45.051 | 56.199 | 34.799 | 1.00 | 20.34 |
| ATOM | 4400 | CB | ASN | 617 | 44.498 | 56.699 | 33.462 | 1.00 | 23.41 |
| ATOM | 4401 | CG | ASN | 617 | 44.426 | 58.205 | 33.391 | 1.00 | 26.99 |
| ATOM | 4402 | OD1 | ASN | 617 | 44.083 | 58.855 | 34.377 | 1.00 | 31.32 |
| ATOM | 4403 | ND2 | ASN | 617 | 44.732 | 58.761 | 32.219 | 1.00 | 31.42 |
| ATOM | 4404 | C | ASN | 617 | 45.303 | 54.708 | 34.664 | 1.00 | 17.45 |
| ATOM | 4405 | O | ASN | 617 | 46.445 | 54.250 | 34.621 | 1.00 | 17.50 |
| ATOM | 4406 | N | MET | 618 | 44.208 | 53.957 | 34.603 | 1.00 | 16.22 |
| ATOM | 4407 | CA | MET | 618 | 44.279 | 52.520 | 34.387 | 1.00 | 17.60 |
| ATOM | 4408 | CB | MET | 618 | 42.982 | 51.821 | 34.807 | 1.00 | 14.99 |
| ATOM | 4409 | CG | MET | 618 | 42.792 | 51.646 | 36.305 | 1.00 | 15.84 |
| ATOM | 4410 | SD | MET | 618 | 41.282 | 50.709 | 36.700 | 1.00 | 17.39 |
| ATOM | 4411 | CE | MET | 618 | 40.045 | 51.984 | 36.543 | 1.00 | 20.05 |
| ATOM | 4412 | C | MET | 618 | 44.402 | 52.465 | 32.872 | 1.00 | 16.95 |
| ATOM | 4413 | O | MET | 618 | 43.843 | 53.315 | 32.178 | 1.00 | 16.75 |

TABLE A-continued

| | | | | | | | | | |
|---|---|---|---|---|---|---|---|---|---|
| ATOM | 4414 | N | SER | 619 | 45.117 | 51.480 | 32.351 | 1.00 | 16.04 |
| ATOM | 4415 | CA | SER | 619 | 45.286 | 51.385 | 30.904 | 1.00 | 16.02 |
| ATOM | 4416 | CB | SER | 619 | 46.420 | 52.314 | 30.449 | 1.00 | 16.02 |
| ATOM | 4417 | OG | SER | 619 | 46.691 | 52.155 | 29.067 | 1.00 | 19.66 |
| ATOM | 4418 | C | SER | 619 | 45.617 | 49.965 | 30.495 | 1.00 | 15.40 |
| ATOM | 4419 | O | SER | 619 | 46.400 | 49.297 | 31.161 | 1.00 | 14.10 |
| ATOM | 4420 | N | ALA | 620 | 45.024 | 49.516 | 29.392 | 1.00 | 15.67 |
| ATOM | 4421 | CA | ALA | 620 | 45.265 | 48.173 | 28.880 | 1.00 | 17.19 |
| ATOM | 4422 | CB | ALA | 620 | 44.053 | 47.695 | 28.092 | 1.00 | 15.24 |
| ATOM | 4423 | C | ALA | 620 | 46.509 | 48.124 | 27.991 | 1.00 | 17.50 |
| ATOM | 4424 | O | ALA | 620 | 46.909 | 47.052 | 27.533 | 1.00 | 16.59 |
| ATOM | 4425 | N | SER | 621 | 47.124 | 49.282 | 27.755 | 1.00 | 19.02 |
| ATOM | 4426 | CA | SER | 621 | 48.310 | 49.356 | 26.896 | 1.00 | 20.17 |
| ATOM | 4427 | CB | SER | 621 | 48.839 | 50.791 | 26.838 | 1.00 | 19.94 |
| ATOM | 4428 | OG | SER | 621 | 47.940 | 51.611 | 26.112 | 1.00 | 28.11 |
| ATOM | 4429 | C | SER | 621 | 49.443 | 48.420 | 27.296 | 1.00 | 18.71 |
| ATOM | 4430 | O | SER | 621 | 50.023 | 47.752 | 26.448 | 1.00 | 19.01 |
| ATOM | 4431 | N | ALA | 622 | 49.761 | 48.373 | 28.584 | 1.00 | 18.30 |
| ATOM | 4432 | CA | ALA | 622 | 50.841 | 47.513 | 29.060 | 1.00 | 17.71 |
| ATOM | 4433 | CB | ALA | 622 | 51.067 | 47.741 | 30.557 | 1.00 | 17.13 |
| ATOM | 4434 | C | ALA | 622 | 50.554 | 46.034 | 28.784 | 1.00 | 16.19 |
| ATOM | 4435 | O | ALA | 622 | 51.410 | 45.305 | 28.271 | 1.00 | 16.07 |
| ATOM | 4436 | N | MET | 623 | 49.350 | 45.591 | 29.122 | 1.00 | 15.56 |
| ATOM | 4437 | CA | MET | 623 | 48.974 | 44.202 | 28.899 | 1.00 | 15.10 |
| ATOM | 4438 | CB | MET | 623 | 47.580 | 43.931 | 29.475 | 1.00 | 15.03 |
| ATOM | 4439 | CG | MET | 623 | 47.133 | 42.489 | 29.348 | 1.00 | 18.59 |
| ATOM | 4440 | SD | MET | 623 | 45.530 | 42.188 | 30.123 | 1.00 | 19.23 |
| ATOM | 4441 | CE | MET | 623 | 45.854 | 40.606 | 30.925 | 1.00 | 19.84 |
| ATOM | 4442 | C | MET | 623 | 49.008 | 43.868 | 27.402 | 1.00 | 16.05 |
| ATOM | 4443 | O | MET | 623 | 49.480 | 42.802 | 27.012 | 1.00 | 17.32 |
| ATOM | 4444 | N | LEU | 624 | 48.508 | 44.774 | 26.566 | 1.00 | 15.21 |
| ATOM | 4445 | CA | LEU | 624 | 48.515 | 44.543 | 25.120 | 1.00 | 18.46 |
| ATOM | 4446 | CB | LEU | 624 | 47.735 | 45.649 | 24.396 | 1.00 | 19.41 |
| ATOM | 4447 | CG | LEU | 624 | 46.220 | 45.664 | 24.628 | 1.00 | 22.76 |
| ATOM | 4448 | CD1 | LEU | 624 | 45.576 | 46.786 | 23.827 | 1.00 | 21.15 |
| ATOM | 4449 | CD2 | LEU | 624 | 45.634 | 44.315 | 24.214 | 1.00 | 24.62 |
| ATOM | 4450 | C | LEU | 624 | 49.956 | 44.487 | 24.598 | 1.00 | 19.43 |
| ATOM | 4451 | O | LEU | 624 | 50.295 | 43.655 | 23.751 | 1.00 | 18.79 |
| ATOM | 4452 | N | SER | 625 | 50.802 | 45.375 | 25.112 | 1.00 | 19.19 |
| ATOM | 4453 | CA | SER | 625 | 52.208 | 45.418 | 24.717 | 1.00 | 19.92 |
| ATOM | 4454 | CB | SER | 625 | 52.891 | 46.612 | 25.402 | 1.00 | 22.10 |
| ATOM | 4455 | OG | SER | 625 | 54.286 | 46.618 | 25.176 | 1.00 | 27.80 |
| ATOM | 4456 | C | SER | 625 | 52.892 | 44.100 | 25.113 | 1.00 | 18.98 |
| ATOM | 4457 | O | SER | 625 | 53.667 | 43.525 | 24.345 | 1.00 | 19.48 |
| ATOM | 4458 | N | TYR | 626 | 52.600 | 43.623 | 26.316 | 1.00 | 17.23 |
| ATOM | 4459 | CA | TYR | 626 | 53.169 | 42.370 | 26.803 | 1.00 | 17.45 |
| ATOM | 4460 | CB | TYR | 626 | 52.626 | 42.070 | 28.203 | 1.00 | 17.03 |
| ATOM | 4461 | CG | TYR | 626 | 53.131 | 40.783 | 28.824 | 1.00 | 16.24 |
| ATOM | 4462 | CD1 | TYR | 626 | 54.122 | 40.798 | 29.806 | 1.00 | 18.36 |
| ATOM | 4463 | CE1 | TYR | 626 | 54.560 | 39.612 | 30.412 | 1.00 | 16.21 |
| ATOM | 4464 | CD2 | TYR | 626 | 52.590 | 39.551 | 28.454 | 1.00 | 16.60 |
| ATOM | 4465 | CE2 | TYR | 626 | 53.018 | 38.367 | 29.046 | 1.00 | 15.67 |
| ATOM | 4466 | CZ | TYR | 626 | 53.998 | 38.402 | 30.026 | 1.00 | 17.59 |
| ATOM | 4467 | OH | TYR | 626 | 54.385 | 37.225 | 30.630 | 1.00 | 17.16 |
| ATOM | 4468 | C | TYR | 626 | 52.820 | 41.206 | 25.858 | 1.00 | 18.35 |
| ATOM | 4469 | O | TYR | 626 | 53.676 | 40.379 | 25.534 | 1.00 | 17.96 |
| ATOM | 4470 | N | PHE | 627 | 51.564 | 41.151 | 25.416 | 1.00 | 17.36 |
| ATOM | 4471 | CA | PHE | 627 | 51.108 | 40.071 | 24.538 | 1.00 | 18.59 |
| ATOM | 4472 | CB | PHE | 627 | 49.679 | 39.657 | 24.914 | 1.00 | 15.88 |
| ATOM | 4473 | CG | PHE | 627 | 49.585 | 38.913 | 26.208 | 1.00 | 15.40 |
| ATOM | 4474 | CD1 | PHE | 627 | 49.150 | 39.552 | 27.366 | 1.00 | 15.71 |
| ATOM | 4475 | CD2 | PHE | 627 | 49.952 | 37.573 | 26.278 | 1.00 | 15.04 |
| ATOM | 4476 | CE1 | PHE | 627 | 49.081 | 38.864 | 28.579 | 1.00 | 14.00 |
| ATOM | 4477 | CE2 | PHE | 627 | 49.889 | 36.874 | 27.483 | 1.00 | 15.01 |
| ATOM | 4478 | CZ | PHE | 627 | 49.453 | 37.519 | 28.636 | 1.00 | 14.97 |
| ATOM | 4479 | C | PHE | 627 | 51.151 | 40.323 | 23.030 | 1.00 | 18.84 |
| ATOM | 4480 | O | PHE | 627 | 50.741 | 39.464 | 22.254 | 1.00 | 19.04 |
| ATOM | 4481 | N | LYS | 628 | 51.644 | 41.484 | 22.612 | 1.00 | 19.54 |
| ATOM | 4482 | CA | LYS | 628 | 51.705 | 41.819 | 21.190 | 1.00 | 19.75 |
| ATOM | 4483 | CB | LYS | 628 | 52.556 | 43.079 | 20.989 | 1.00 | 22.03 |
| ATOM | 4484 | CG | LYS | 628 | 52.868 | 43.419 | 19.532 | 1.00 | 23.91 |
| ATOM | 4485 | CD | LYS | 628 | 51.621 | 43.760 | 18.727 | 1.00 | 27.23 |
| ATOM | 4486 | CE | LYS | 628 | 52.002 | 44.196 | 17.306 | 1.00 | 30.31 |
| ATOM | 4487 | NZ | LYS | 628 | 50.817 | 44.449 | 16.440 | 1.00 | 30.49 |
| ATOM | 4488 | C | LYS | 628 | 52.217 | 40.692 | 20.283 | 1.00 | 20.01 |
| ATOM | 4489 | O | LYS | 628 | 51.584 | 40.365 | 19.281 | 1.00 | 21.94 |
| ATOM | 4490 | N | PRO | 629 | 53.369 | 40.087 | 20.611 | 1.00 | 20.55 |
| ATOM | 4491 | CD | PRO | 629 | 54.306 | 40.351 | 21.717 | 1.00 | 22.46 |
| ATOM | 4492 | CA | PRO | 629 | 53.867 | 39.008 | 19.749 | 1.00 | 21.49 |
| ATOM | 4493 | CB | PRO | 629 | 55.151 | 38.566 | 20.450 | 1.00 | 21.82 |

TABLE A-continued

| | | | | | | | | |
|---|---|---|---|---|---|---|---|---|
| ATOM | 4494 | CG | PRO | 629 | 55.607 | 39.818 | 21.155 | 1.00 23.13 |
| ATOM | 4495 | C | PRO | 629 | 52.857 | 37.867 | 19.613 | 1.00 20.35 |
| ATOM | 4496 | O | PRO | 629 | 52.732 | 37.256 | 18.553 | 1.00 19.97 |
| ATOM | 4497 | N | LEU | 630 | 52.131 | 37.583 | 20.687 | 1.00 19.10 |
| ATOM | 4498 | CA | LEU | 630 | 51.150 | 36.510 | 20.649 | 1.00 18.86 |
| ATOM | 4499 | CB | LEU | 630 | 50.695 | 36.135 | 22.059 | 1.00 17.73 |
| ATOM | 4500 | CG | LEU | 630 | 49.725 | 34.946 | 22.116 | 1.00 18.16 |
| ATOM | 4501 | CD1 | LEU | 630 | 50.447 | 33.682 | 21.698 | 1.00 17.06 |
| ATOM | 4502 | CD2 | LEU | 630 | 49.167 | 34.789 | 23.525 | 1.00 17.08 |
| ATOM | 4503 | C | LEU | 630 | 49.945 | 36.906 | 19.807 | 1.00 18.76 |
| ATOM | 4504 | O | LEU | 630 | 49.448 | 36.106 | 19.016 | 1.00 20.28 |
| ATOM | 4505 | N | LEU | 631 | 49.480 | 38.140 | 19.972 | 1.00 18.81 |
| ATOM | 4506 | CA | LEU | 631 | 48.332 | 38.617 | 19.207 | 1.00 19.95 |
| ATOM | 4507 | CB | LEU | 631 | 48.025 | 40.079 | 19.543 | 1.00 18.70 |
| ATOM | 4508 | CG | LEU | 631 | 46.896 | 40.731 | 18.735 | 1.00 21.74 |
| ATOM | 4509 | CD1 | LEU | 631 | 45.584 | 40.002 | 18.990 | 1.00 23.52 |
| ATOM | 4510 | CD2 | LEU | 631 | 46.766 | 42.196 | 19.119 | 1.00 22.39 |
| ATOM | 4511 | C | LEU | 631 | 48.599 | 38.482 | 17.709 | 1.00 21.61 |
| ATOM | 4512 | O | LEU | 631 | 47.725 | 38.048 | 16.955 | 1.00 18.83 |
| ATOM | 4513 | N | ASP | 632 | 49.804 | 38.855 | 17.281 | 1.00 21.33 |
| ATOM | 4514 | CA | ASP | 632 | 50.160 | 38.756 | 15.869 | 1.00 21.95 |
| ATOM | 4515 | CB | ASP | 632 | 51.525 | 39.405 | 15.604 | 1.00 23.60 |
| ATOM | 4516 | CG | ASP | 632 | 51.516 | 40.903 | 15.839 | 1.00 24.22 |
| ATOM | 4517 | OD1 | ASP | 632 | 50.469 | 41.541 | 15.604 | 1.00 26.63 |
| ATOM | 4518 | OD2 | ASP | 632 | 52.562 | 41.447 | 16.243 | 1.00 26.55 |
| ATOM | 4519 | C | ASP | 632 | 50.197 | 37.293 | 15.425 | 1.00 21.32 |
| ATOM | 4520 | O | ASP | 632 | 49.742 | 36.964 | 14.330 | 1.00 20.49 |
| ATOM | 4521 | N | TRP | 633 | 50.736 | 36.418 | 16.271 | 1.00 19.81 |
| ATOM | 4522 | CA | TRP | 633 | 50.808 | 34.998 | 15.929 | 1.00 20.07 |
| ATOM | 4523 | CB | TRP | 633 | 51.595 | 34.213 | 16.987 | 1.00 19.94 |
| ATOM | 4524 | CG | TRP | 633 | 51.761 | 32.756 | 16.632 | 1.00 21.13 |
| ATOM | 4525 | CD2 | TRP | 633 | 50.902 | 31.674 | 17.019 | 1.00 21.92 |
| ATOM | 4526 | CE2 | TRP | 633 | 51.389 | 30.505 | 16.388 | 1.00 22.13 |
| ATOM | 4527 | CE3 | TRP | 633 | 49.766 | 31.578 | 17.836 | 1.00 22.40 |
| ATOM | 4528 | CD1 | TRP | 633 | 52.712 | 32.211 | 15.807 | 1.00 22.30 |
| ATOM | 4529 | NE1 | TRP | 633 | 52.492 | 30.860 | 15.656 | 1.00 21.61 |
| ATOM | 4530 | CZ2 | TRP | 633 | 50.779 | 29.255 | 16.549 | 1.00 22.73 |
| ATOM | 4531 | CZ3 | TRP | 633 | 49.158 | 30.333 | 17.996 | 1.00 23.58 |
| ATOM | 4532 | CH2 | TRP | 633 | 49.669 | 29.189 | 17.354 | 1.00 24.12 |
| ATOM | 4533 | C | TRP | 633 | 49.402 | 34.407 | 15.817 | 1.00 20.16 |
| ATOM | 4534 | O | TRP | 633 | 49.120 | 33.624 | 14.908 | 1.00 20.21 |
| ATOM | 4535 | N | LEU | 634 | 48.528 | 34.788 | 16.745 | 1.00 18.10 |
| ATOM | 4536 | CA | LEU | 634 | 47.152 | 34.291 | 16.767 | 1.00 17.96 |
| ATOM | 4537 | CB | LEU | 634 | 46.433 | 34.766 | 18.033 | 1.00 13.19 |
| ATOM | 4538 | CG | LEU | 634 | 46.823 | 34.058 | 19.331 | 1.00 15.98 |
| ATOM | 4539 | CD1 | LEU | 634 | 46.121 | 34.731 | 20.512 | 1.00 15.76 |
| ATOM | 4540 | CD2 | LEU | 634 | 46.433 | 32.585 | 19.242 | 1.00 17.65 |
| ATOM | 4541 | C | LEU | 634 | 46.358 | 34.720 | 15.543 | 1.00 17.44 |
| ATOM | 4542 | O | LEU | 634 | 45.597 | 33.934 | 14.982 | 1.00 18.04 |
| ATOM | 4543 | N | ARG | 635 | 46.522 | 35.971 | 15.135 | 1.00 19.17 |
| ATOM | 4544 | CA | ARG | 635 | 45.809 | 36.459 | 13.965 | 1.00 20.10 |
| ATOM | 4545 | CB | ARG | 635 | 46.057 | 37.955 | 13.776 | 1.00 21.85 |
| ATOM | 4546 | CG | ARG | 635 | 45.154 | 38.812 | 14.644 | 1.00 25.01 |
| ATOM | 4547 | CD | ARG | 635 | 45.529 | 40.272 | 14.572 | 1.00 29.62 |
| ATOM | 4548 | NE | ARG | 635 | 44.548 | 41.106 | 15.260 | 1.00 33.26 |
| ATOM | 4549 | CZ | ARG | 635 | 44.745 | 42.381 | 15.571 | 1.00 34.54 |
| ATOM | 4550 | NH1 | ARG | 635 | 45.895 | 42.969 | 15.259 | 1.00 35.00 |
| ATOM | 4551 | NH2 | ARG | 635 | 43.791 | 43.069 | 16.185 | 1.00 36.75 |
| ATOM | 4552 | C | ARG | 635 | 46.240 | 35.688 | 12.728 | 1.00 19.78 |
| ATOM | 4553 | O | ARG | 635 | 45.404 | 35.275 | 11.930 | 1.00 19.55 |
| ATOM | 4554 | N | THR | 636 | 47.544 | 35.485 | 12.577 | 1.00 20.54 |
| ATOM | 4555 | CA | THR | 636 | 48.067 | 34.745 | 11.431 | 1.00 21.78 |
| ATOM | 4556 | CB | THR | 636 | 49.604 | 34.749 | 11.430 | 1.00 22.60 |
| ATOM | 4557 | OG1 | THR | 636 | 50.072 | 36.101 | 11.362 | 1.00 26.06 |
| ATOM | 4558 | CG2 | THR | 636 | 50.142 | 33.960 | 10.241 | 1.00 23.85 |
| ATOM | 4559 | C | THR | 636 | 47.579 | 33.296 | 11.463 | 1.00 20.62 |
| ATOM | 4560 | O | THR | 636 | 47.170 | 32.747 | 10.439 | 1.00 19.63 |
| ATOM | 4561 | N | GLU | 637 | 47.619 | 32.684 | 12.643 | 1.00 19.42 |
| ATOM | 4562 | CA | GLU | 637 | 47.176 | 31.299 | 12.804 | 1.00 18.86 |
| ATOM | 4563 | CB | GLU | 637 | 47.517 | 30.791 | 14.211 | 1.00 19.68 |
| ATOM | 4564 | CG | GLU | 637 | 46.993 | 29.385 | 14.533 | 1.00 20.95 |
| ATOM | 4565 | CD | GLU | 637 | 47.704 | 28.278 | 13.757 | 1.00 24.76 |
| ATOM | 4566 | OE1 | GLU | 637 | 48.584 | 28.589 | 12.924 | 1.00 25.29 |
| ATOM | 4567 | OE2 | GLU | 637 | 47.379 | 27.091 | 13.984 | 1.00 25.20 |
| ATOM | 4568 | C | GLU | 637 | 45.676 | 31.152 | 12.553 | 1.00 17.40 |
| ATOM | 4569 | O | GLU | 637 | 45.258 | 30.279 | 11.794 | 1.00 18.84 |
| ATOM | 4570 | N | ASN | 638 | 44.867 | 32.001 | 13.183 | 1.00 17.45 |
| ATOM | 4571 | CA | ASN | 638 | 43.416 | 31.928 | 13.006 | 1.00 17.49 |
| ATOM | 4572 | CB | ASN | 638 | 42.691 | 32.889 | 13.962 | 1.00 15.50 |
| ATOM | 4573 | CG | ASN | 638 | 42.730 | 32.411 | 15.408 | 1.00 16.54 |

TABLE A-continued

| | | | | | | | | |
|---|---|---|---|---|---|---|---|---|
| ATOM | 4574 | OD1 | ASN | 638 | 42.820 | 31.209 | 15.674 | 1.00 | 15.31 |
| ATOM | 4575 | ND2 | ASN | 638 | 42.652 | 33.348 | 16.348 | 1.00 | 12.94 |
| ATOM | 4576 | C | ASN | 638 | 43.015 | 32.235 | 11.571 | 1.00 | 18.74 |
| ATOM | 4577 | O | ASN | 638 | 42.067 | 31.655 | 11.039 | 1.00 | 16.61 |
| ATOM | 4578 | N | GLU | 639 | 43.748 | 33.147 | 10.944 | 1.00 | 20.32 |
| ATOM | 4579 | CA | GLU | 639 | 43.468 | 33.530 | 9.566 | 1.00 | 22.55 |
| ATOM | 4580 | CB | GLU | 639 | 44.335 | 34.729 | 9.178 | 1.00 | 23.65 |
| ATOM | 4581 | CG | GLU | 639 | 44.290 | 35.079 | 7.704 | 1.00 | 30.44 |
| ATOM | 4582 | CD | GLU | 639 | 45.149 | 36.284 | 7.386 | 1.00 | 33.49 |
| ATOM | 4583 | OE1 | GLU | 639 | 44.809 | 37.389 | 7.863 | 1.00 | 34.20 |
| ATOM | 4584 | OE2 | GLU | 639 | 46.166 | 36.122 | 6.675 | 1.00 | 33.48 |
| ATOM | 4585 | C | GLU | 639 | 43.703 | 32.382 | 8.581 | 1.00 | 22.09 |
| ATOM | 4586 | O | GLU | 639 | 42.873 | 32.118 | 7.712 | 1.00 | 21.43 |
| ATOM | 4587 | N | LEU | 640 | 44.825 | 31.688 | 8.722 | 1.00 | 22.49 |
| ATOM | 4588 | CA | LEU | 640 | 45.118 | 30.600 | 7.801 | 1.00 | 24.32 |
| ATOM | 4589 | CB | LEU | 640 | 46.576 | 30.150 | 7.956 | 1.00 | 25.56 |
| ATOM | 4590 | CG | LEU | 640 | 47.046 | 29.348 | 9.162 | 1.00 | 26.95 |
| ATOM | 4591 | CD1 | LEU | 640 | 46.720 | 27.878 | 8.949 | 1.00 | 27.03 |
| ATOM | 4592 | CD2 | LEU | 640 | 48.555 | 29.519 | 9.316 | 1.00 | 29.34 |
| ATOM | 4593 | C | LEU | 640 | 44.149 | 29.426 | 7.953 | 1.00 | 23.29 |
| ATOM | 4594 | O | LEU | 640 | 43.985 | 28.631 | 7.027 | 1.00 | 22.55 |
| ATOM | 4595 | N | HIS | 641 | 43.495 | 29.327 | 9.110 | 1.00 | 21.91 |
| ATOM | 4596 | CA | HIS | 641 | 42.524 | 28.263 | 9.339 | 1.00 | 22.74 |
| ATOM | 4597 | CB | HIS | 641 | 42.622 | 27.728 | 10.772 | 1.00 | 23.20 |
| ATOM | 4598 | CG | HIS | 641 | 43.812 | 26.856 | 11.000 | 1.00 | 24.45 |
| ATOM | 4599 | CD2 | HIS | 641 | 44.112 | 25.623 | 10.530 | 1.00 | 25.66 |
| ATOM | 4600 | ND1 | HIS | 641 | 44.894 | 27.252 | 11.756 | 1.00 | 28.28 |
| ATOM | 4601 | CE1 | HIS | 641 | 45.810 | 26.301 | 11.742 | 1.00 | 26.29 |
| ATOM | 4602 | NE2 | HIS | 641 | 45.360 | 25.302 | 11.005 | 1.00 | 29.81 |
| ATOM | 4603 | C | HIS | 641 | 41.106 | 28.747 | 9.071 | 1.00 | 23.10 |
| ATOM | 4604 | O | HIS | 641 | 40.145 | 27.988 | 9.217 | 1.00 | 22.01 |
| ATOM | 4605 | N | GLY | 642 | 40.986 | 30.012 | 8.678 | 1.00 | 22.53 |
| ATOM | 4606 | CA | GLY | 642 | 39.683 | 30.582 | 8.381 | 1.00 | 22.30 |
| ATOM | 4607 | C | GLY | 642 | 38.729 | 30.590 | 9.561 | 1.00 | 23.68 |
| ATOM | 4608 | O | GLY | 642 | 37.544 | 30.277 | 9.416 | 1.00 | 22.74 |
| ATOM | 4609 | N | GLU | 643 | 39.233 | 30.950 | 10.735 | 1.00 | 21.41 |
| ATOM | 4610 | CA | GLU | 643 | 38.386 | 30.981 | 11.919 | 1.00 | 21.09 |
| ATOM | 4611 | CB | GLU | 643 | 39.235 | 31.103 | 13.188 | 1.00 | 18.57 |
| ATOM | 4612 | CG | GLU | 643 | 40.322 | 30.051 | 13.336 | 1.00 | 18.36 |
| ATOM | 4613 | CD | GLU | 643 | 39.780 | 28.639 | 13.541 | 1.00 | 16.54 |
| ATOM | 4614 | OE1 | GLU | 643 | 38.545 | 28.441 | 13.509 | 1.00 | 16.76 |
| ATOM | 4615 | OE2 | GLU | 643 | 40.604 | 27.724 | 13.733 | 1.00 | 18.63 |
| ATOM | 4616 | C | GLU | 643 | 37.407 | 32.147 | 11.872 | 1.00 | 22.46 |
| ATOM | 4617 | O | GLU | 643 | 37.727 | 33.230 | 11.371 | 1.00 | 23.79 |
| ATOM | 4618 | N | LYS | 644 | 36.207 | 31.910 | 12.386 | 1.00 | 21.56 |
| ATOM | 4619 | CA | LYS | 644 | 35.180 | 32.938 | 12.472 | 1.00 | 22.52 |
| ATOM | 4620 | CB | LYS | 644 | 33.816 | 32.367 | 12.090 | 1.00 | 25.95 |
| ATOM | 4621 | CG | LYS | 644 | 32.662 | 33.335 | 12.296 | 1.00 | 32.66 |
| ATOM | 4622 | CD | LYS | 644 | 31.336 | 32.666 | 11.974 | 1.00 | 37.37 |
| ATOM | 4623 | CE | LYS | 644 | 30.164 | 33.603 | 12.192 | 1.00 | 38.64 |
| ATOM | 4624 | NZ | LYS | 644 | 28.883 | 32.959 | 11.777 | 1.00 | 42.06 |
| ATOM | 4625 | C | LYS | 644 | 35.170 | 33.347 | 13.940 | 1.00 | 22.34 |
| ATOM | 4626 | O | LYS | 644 | 34.633 | 32.626 | 14.779 | 1.00 | 22.63 |
| ATOM | 4627 | N | LEU | 645 | 35.777 | 34.490 | 14.250 | 1.00 | 21.01 |
| ATOM | 4628 | CA | LEU | 645 | 35.846 | 34.965 | 15.630 | 1.00 | 21.37 |
| ATOM | 4629 | CB | LEU | 645 | 36.662 | 36.251 | 15.721 | 1.00 | 19.95 |
| ATOM | 4630 | CG | LEU | 645 | 38.110 | 36.202 | 15.233 | 1.00 | 21.57 |
| ATOM | 4631 | CD1 | LEU | 645 | 38.774 | 37.542 | 15.513 | 1.00 | 22.47 |
| ATOM | 4632 | CD2 | LEU | 645 | 38.859 | 35.084 | 15.927 | 1.00 | 19.75 |
| ATOM | 4633 | C | LEU | 645 | 34.470 | 35.217 | 16.215 | 1.00 | 21.96 |
| ATOM | 4634 | O | LEU | 645 | 33.546 | 35.613 | 15.508 | 1.00 | 20.21 |
| ATOM | 4635 | N | GLY | 646 | 34.339 | 34.987 | 17.517 | 1.00 | 21.25 |
| ATOM | 4636 | CA | GLY | 646 | 33.065 | 35.214 | 18.167 | 1.00 | 20.02 |
| ATOM | 4637 | C | GLY | 646 | 32.117 | 34.037 | 18.080 | 1.00 | 21.85 |
| ATOM | 4638 | O | GLY | 646 | 32.516 | 32.919 | 17.748 | 1.00 | 19.09 |
| ATOM | 4639 | N | TRP | 647 | 30.850 | 34.302 | 18.369 | 1.00 | 22.45 |
| ATOM | 4640 | CA | TRP | 647 | 29.828 | 33.268 | 18.356 | 1.00 | 28.97 |
| ATOM | 4641 | CB | TRP | 647 | 29.778 | 32.601 | 19.734 | 1.00 | 23.61 |
| ATOM | 4642 | CG | TRP | 647 | 29.902 | 33.584 | 20.866 | 1.00 | 21.96 |
| ATOM | 4643 | CD2 | TRP | 647 | 31.119 | 34.062 | 21.459 | 1.00 | 19.96 |
| ATOM | 4644 | CE2 | TRP | 647 | 30.761 | 35.004 | 22.452 | 1.00 | 19.26 |
| ATOM | 4645 | CE3 | TRP | 647 | 32.480 | 33.787 | 21.247 | 1.00 | 18.03 |
| ATOM | 4646 | CD1 | TRP | 647 | 28.883 | 34.238 | 21.507 | 1.00 | 20.08 |
| ATOM | 4647 | NE1 | TRP | 647 | 29.392 | 35.089 | 22.460 | 1.00 | 19.39 |
| ATOM | 4648 | CZ2 | TRP | 647 | 31.713 | 35.675 | 23.231 | 1.00 | 17.35 |
| ATOM | 4649 | CZ3 | TRP | 647 | 33.428 | 34.453 | 22.022 | 1.00 | 19.00 |
| ATOM | 4650 | CH2 | TRP | 647 | 33.037 | 35.389 | 23.005 | 1.00 | 18.89 |
| ATOM | 4651 | C | TRP | 647 | 28.462 | 33.843 | 17.983 | 1.00 | 34.48 |
| ATOM | 4652 | O | TRP | 647 | 27.676 | 34.217 | 18.849 | 1.00 | 35.78 |
| ATOM | 4653 | N | PRO | 648 | 28.166 | 33.914 | 16.675 | 1.00 | 41.48 |

TABLE A-continued

| ATOM | 4654 | CD | PRO | 648 | 28.952 | 33.316 | 15.580 | 1.00 | 42.76 |
|------|------|-----|-----|-----|--------|--------|--------|------|-------|
| ATOM | 4655 | CA | PRO | 648 | 26.895 | 34.443 | 16.166 | 1.00 | 44.45 |
| ATOM | 4656 | CB | PRO | 648 | 27.033 | 34.263 | 14.656 | 1.00 | 45.15 |
| ATOM | 4657 | CG | PRO | 648 | 27.883 | 33.024 | 14.556 | 1.00 | 44.87 |
| ATOM | 4658 | C | PRO | 648 | 25.679 | 33.707 | 16.726 | 1.00 | 46.65 |
| ATOM | 4659 | O | PRO | 648 | 24.898 | 34.348 | 17.458 | 1.00 | 48.64 |
| ATOM | 4660 | OXT | PRO | 648 | 25.526 | 32.501 | 16.429 | 1.00 | 48.70 |
| ATOM | 4661 | OH2 | WAT | 705 | 33.725 | 46.851 | 44.246 | 1.00 | 15.53 |
| ATOM | 4662 | OH2 | WAT | 706 | 32.992 | 26.241 | 34.112 | 1.00 | 12.73 |
| ATOM | 4663 | OH2 | WAT | 707 | 24.332 | 47.645 | 41.904 | 1.00 | 11.04 |
| ATOM | 4664 | OH2 | WAT | 708 | 41.493 | 22.764 | 37.711 | 1.00 | 14.46 |
| ATOM | 4665 | OH2 | WAT | 709 | 57.554 | 41.574 | 37.486 | 1.00 | 16.47 |
| ATOM | 4666 | OH2 | WAT | 710 | 39.385 | 24.084 | 39.045 | 1.00 | 16.57 |
| ATOM | 4667 | OH2 | WAT | 711 | 51.141 | 36.659 | 37.992 | 1.00 | 13.96 |
| ATOM | 4668 | OH2 | WAT | 712 | 53.148 | 51.275 | 33.059 | 1.00 | 23.13 |
| ATOM | 4669 | OH2 | WAT | 713 | 52.416 | 34.580 | 36.566 | 1.00 | 18.04 |
| ATOM | 4670 | OH2 | WAT | 714 | 16.540 | 45.049 | 50.781 | 1.00 | 15.93 |
| ATOM | 4671 | OH2 | WAT | 715 | 47.597 | 46.867 | 31.105 | 1.00 | 15.09 |
| ATOM | 4672 | OH2 | WAT | 716 | 33.726 | 54.353 | 42.506 | 1.00 | 17.24 |
| ATOM | 4673 | OH2 | WAT | 717 | 33.205 | 41.739 | 37.987 | 1.00 | 14.76 |
| ATOM | 4674 | OH2 | WAT | 718 | 37.109 | 27.771 | 45.829 | 1.00 | 18.94 |
| ATOM | 4675 | OH2 | WAT | 719 | 17.460 | 40.837 | 43.030 | 1.00 | 16.41 |
| ATOM | 4676 | OH2 | WAT | 720 | 40.996 | 49.596 | 48.874 | 1.00 | 12.40 |
| ATOM | 4677 | OH2 | WAT | 721 | 37.232 | 33.021 | 29.678 | 1.00 | 13.93 |
| ATOM | 4678 | OH2 | WAT | 722 | 48.355 | 52.277 | 48.594 | 1.00 | 16.39 |
| ATOM | 4679 | OH2 | WAT | 723 | 44.253 | 25.373 | 17.456 | 1.00 | 17.05 |
| ATOM | 4680 | OH2 | WAT | 724 | 37.616 | 28.428 | 16.196 | 1.00 | 14.22 |
| ATOM | 4681 | OH2 | WAT | 725 | 31.807 | 45.250 | 42.894 | 1.00 | 12.95 |
| ATOM | 4682 | OH2 | WAT | 726 | 48.929 | 40.765 | 46.120 | 1.00 | 16.42 |
| ATOM | 4683 | OH2 | WAT | 727 | 43.001 | 28.525 | 14.577 | 1.00 | 19.16 |
| ATOM | 4684 | OH2 | WAT | 728 | 36.297 | 33.649 | 19.024 | 1.00 | 16.26 |
| ATOM | 4685 | OH2 | WAT | 729 | 45.223 | 39.419 | 41.235 | 1.00 | 17.97 |
| ATOM | 4686 | OH2 | WAT | 730 | 19.069 | 49.921 | 43.313 | 1.00 | 22.26 |
| ATOM | 4687 | OH2 | WAT | 731 | 18.652 | 48.396 | 47.732 | 1.00 | 19.58 |
| ATOM | 4688 | OH2 | WAT | 732 | 16.355 | 39.332 | 47.441 | 1.00 | 16.61 |
| ATOM | 4689 | OH2 | WAT | 734 | 27.725 | 37.511 | 46.838 | 1.00 | 11.65 |
| ATOM | 4690 | OH2 | WAT | 735 | 43.139 | 43.055 | 22.306 | 1.00 | 14.35 |
| ATOM | 4691 | OH2 | WAT | 736 | 23.288 | 50.618 | 41.612 | 1.00 | 18.93 |
| ATOM | 4692 | OH2 | WAT | 737 | 40.575 | 28.769 | 39.893 | 1.00 | 24.17 |
| ATOM | 4693 | OH2 | WAT | 738 | 44.624 | 45.246 | 56.395 | 1.00 | 17.22 |
| ATOM | 4694 | OH2 | WAT | 739 | 42.886 | 25.680 | 33.406 | 1.00 | 14.64 |
| ATOM | 4695 | OH2 | WAT | 740 | 36.434 | 24.093 | 32.323 | 1.00 | 12.11 |
| ATOM | 4696 | OH2 | WAT | 741 | 39.736 | 39.843 | 47.740 | 1.00 | 17.61 |
| ATOM | 4697 | OH2 | WAT | 742 | 47.972 | 45.541 | 61.312 | 1.00 | 27.55 |
| ATOM | 4698 | OH2 | WAT | 743 | 48.595 | 42.613 | 62.331 | 1.00 | 19.33 |
| ATOM | 4699 | OH2 | WAT | 744 | 16.756 | 44.276 | 47.836 | 1.00 | 17.52 |
| ATOM | 4700 | OH2 | WAT | 745 | 50.833 | 52.475 | 32.781 | 1.00 | 22.48 |
| ATOM | 4701 | OH2 | WAT | 746 | 43.086 | 51.380 | 39.452 | 1.00 | 19.50 |
| ATOM | 4702 | OH2 | WAT | 747 | 43.065 | 37.312 | 51.242 | 1.00 | 19.15 |
| ATOM | 4703 | OH2 | WAT | 748 | 36.377 | 29.551 | 43.539 | 1.00 | 26.33 |
| ATOM | 4704 | OH2 | WAT | 749 | 31.749 | 23.341 | 13.589 | 1.00 | 21.93 |
| ATOM | 4705 | OH2 | WAT | 750 | 51.017 | 32.405 | 13.102 | 1.00 | 23.70 |
| ATOM | 4706 | OH2 | WAT | 751 | 23.902 | 25.063 | 40.491 | 1.00 | 17.23 |
| ATOM | 4707 | OH2 | WAT | 752 | 46.245 | 55.817 | 48.913 | 1.00 | 17.11 |
| ATOM | 4708 | OH2 | WAT | 753 | 17.325 | 38.625 | 44.796 | 1.00 | 17.92 |
| ATOM | 4709 | OH2 | WAT | 754 | 30.477 | 54.512 | 37.203 | 1.00 | 19.17 |
| ATOM | 4710 | OH2 | WAT | 755 | 30.153 | 29.098 | 39.015 | 1.00 | 13.90 |
| ATOM | 4711 | OH2 | WAT | 756 | 40.602 | 56.391 | 45.574 | 1.00 | 29.30 |
| ATOM | 4712 | OH2 | WAT | 757 | 48.469 | 46.405 | 58.796 | 1.00 | 20.34 |
| ATOM | 4713 | OH2 | WAT | 758 | 23.341 | 22.303 | 39.374 | 1.00 | 19.80 |
| ATOM | 4714 | OH2 | WAT | 759 | 39.109 | 29.949 | 42.113 | 1.00 | 17.81 |
| ATOM | 4715 | OH2 | WAT | 760 | 41.617 | 55.292 | 34.623 | 1.00 | 19.28 |
| ATOM | 4716 | OH2 | WAT | 761 | 50.433 | 32.980 | 35.395 | 1.00 | 27.78 |
| ATOM | 4717 | OH2 | WAT | 762 | 55.349 | 39.853 | 51.988 | 1.00 | 21.56 |
| ATOM | 4718 | OH2 | WAT | 763 | 17.829 | 47.302 | 45.052 | 1.00 | 19.63 |
| ATOM | 4719 | OH2 | WAT | 764 | 41.437 | 43.591 | 47.417 | 1.00 | 17.87 |
| ATOM | 4720 | OH2 | WAT | 765 | 31.453 | 48.234 | 33.459 | 1.00 | 20.09 |
| ATOM | 4721 | OH2 | WAT | 766 | 35.895 | 29.226 | 13.339 | 1.00 | 19.08 |
| ATOM | 4722 | OH2 | WAT | 767 | 42.129 | 47.247 | 49.577 | 1.00 | 21.96 |
| ATOM | 4723 | OH2 | WAT | 768 | 39.938 | 19.646 | 28.365 | 1.00 | 16.90 |
| ATOM | 4724 | OH2 | WAT | 770 | 53.052 | 28.858 | 13.534 | 1.00 | 29.07 |
| ATOM | 4725 | OH2 | WAT | 771 | 39.487 | 58.074 | 40.481 | 1.00 | 19.31 |
| ATOM | 4726 | OH2 | WAT | 772 | 34.677 | 20.856 | 49.093 | 1.00 | 29.57 |
| ATOM | 4727 | OH2 | WAT | 773 | 17.419 | 31.215 | 38.280 | 1.00 | 27.38 |
| ATOM | 4728 | OH2 | WAT | 774 | 44.543 | 23.939 | 14.013 | 1.00 | 24.17 |
| ATOM | 4729 | OH2 | WAT | 775 | 31.307 | 56.780 | 49.243 | 1.00 | 27.95 |
| ATOM | 4730 | OH2 | WAT | 776 | 46.870 | 56.616 | 46.429 | 1.00 | 26.71 |
| ATOM | 4731 | OH2 | WAT | 777 | 43.022 | 58.359 | 37.108 | 1.00 | 24.23 |
| ATOM | 4732 | OH2 | WAT | 778 | 40.838 | 33.568 | 7.092 | 1.00 | 29.87 |
| ATOM | 4733 | OH2 | WAT | 779 | 35.280 | 52.569 | 73.408 | 1.00 | 30.56 |

TABLE A-continued

| | | | | | | | | | |
|---|---|---|---|---|---|---|---|---|---|
| ATOM | 4734 | OH2 | WAT | 780 | 14.847 | 39.443 | 36.394 | 1.00 | 22.09 |
| ATOM | 4735 | OH2 | WAT | 781 | 39.543 | 32.050 | 52.976 | 1.00 | 16.43 |
| ATOM | 4736 | OH2 | WAT | 782 | 27.658 | 50.202 | 53.322 | 1.00 | 36.66 |
| ATOM | 4737 | OH2 | WAT | 783 | 49.665 | 26.157 | 11.610 | 1.00 | 31.59 |
| ATOM | 4738 | OH2 | WAT | 784 | 44.790 | 26.439 | 15.055 | 1.00 | 18.95 |
| ATOM | 4739 | OH2 | WAT | 785 | 57.915 | 38.932 | 52.077 | 1.00 | 23.38 |
| ATOM | 4740 | OH2 | WAT | 786 | 34.219 | 51.188 | 61.855 | 1.00 | 27.39 |
| ATOM | 4741 | OH2 | WAT | 788 | 43.520 | 51.469 | 28.053 | 1.00 | 23.51 |
| ATOM | 4742 | OH2 | WAT | 789 | 20.741 | 25.871 | 29.764 | 1.00 | 25.31 |
| ATOM | 4743 | OH2 | WAT | 790 | 31.996 | 32.524 | 15.060 | 1.00 | 27.33 |
| ATOM | 4744 | OH2 | WAT | 791 | 50.065 | 48.521 | 23.797 | 1.00 | 22.69 |
| ATOM | 4745 | OH2 | WAT | 793 | 40.065 | 53.867 | 45.877 | 1.00 | 28.99 |
| ATOM | 4746 | OH2 | WAT | 794 | 27.500 | 14.226 | 27.489 | 1.00 | 25.41 |
| ATOM | 4747 | OH2 | WAT | 795 | 40.088 | 34.807 | 11.689 | 1.00 | 31.73 |
| ATOM | 4748 | OH2 | WAT | 796 | 39.102 | 11.125 | 33.545 | 1.00 | 21.19 |
| ATOM | 4749 | OH2 | WAT | 797 | 27.472 | 21.519 | 51.557 | 1.00 | 21.90 |
| ATOM | 4750 | OH2 | WAT | 798 | 66.482 | 40.320 | 37.672 | 1.00 | 26.30 |
| ATOM | 4751 | OH2 | WAT | 799 | 22.957 | 49.917 | 38.951 | 1.00 | 28.18 |
| ATOM | 4752 | OH2 | WAT | 800 | 26.175 | 37.519 | 64.945 | 1.00 | 35.81 |
| ATOM | 4753 | OH2 | WAT | 801 | 34.181 | 10.599 | 28.257 | 1.00 | 20.76 |
| ATOM | 4754 | OH2 | WAT | 802 | 59.869 | 33.554 | 44.206 | 1.00 | 24.54 |
| ATOM | 4755 | OH2 | WAT | 803 | 38.591 | 20.686 | 31.734 | 1.00 | 19.19 |
| ATOM | 4756 | OH2 | WAT | 804 | 40.781 | 21.352 | 12.247 | 1.00 | 34.63 |
| ATOM | 4757 | OH2 | WAT | 805 | 56.133 | 41.425 | 25.091 | 1.00 | 22.31 |
| ATOM | 4758 | OH2 | WAT | 806 | 37.118 | 27.351 | 50.493 | 1.00 | 21.88 |
| ATOM | 4759 | OH2 | WAT | 807 | 42.654 | 46.736 | 21.378 | 1.00 | 21.89 |
| ATOM | 4760 | OH2 | WAT | 808 | 35.150 | 28.150 | 10.834 | 1.00 | 28.45 |
| ATOM | 4761 | OH2 | WAT | 809 | 29.291 | 19.889 | 23.346 | 1.00 | 24.18 |
| ATOM | 4762 | OH2 | WAT | 810 | 52.883 | 51.977 | 57.763 | 1.00 | 29.06 |
| ATOM | 4763 | OH2 | WAT | 811 | 53.403 | 37.618 | 61.414 | 1.00 | 27.12 |
| ATOM | 4764 | OH2 | WAT | 812 | 11.989 | 35.114 | 47.917 | 1.00 | 33.35 |
| ATOM | 4765 | OH2 | WAT | 813 | 25.177 | 49.091 | 37.779 | 1.00 | 23.88 |
| ATOM | 4766 | OH2 | WAT | 814 | 43.929 | 19.517 | 20.685 | 1.00 | 25.16 |
| ATOM | 4767 | OH2 | WAT | 815 | 36.157 | 15.297 | 14.633 | 1.00 | 24.52 |
| ATOM | 4768 | OH2 | WAT | 816 | 35.907 | 12.552 | 25.672 | 1.00 | 25.39 |
| ATOM | 4769 | OH2 | WAT | 817 | 39.592 | 55.524 | 36.450 | 1.00 | 25.79 |
| ATOM | 4770 | OH2 | WAT | 818 | 62.649 | 34.290 | 30.290 | 1.00 | 24.83 |
| ATOM | 4771 | OH2 | WAT | 819 | 19.911 | 55.424 | 50.600 | 1.00 | 37.80 |
| ATOM | 4772 | OH2 | WAT | 820 | 50.799 | 29.874 | 12.353 | 1.00 | 25.54 |
| ATOM | 4773 | OH2 | WAT | 821 | 27.864 | 56.624 | 70.138 | 1.00 | 27.58 |
| ATOM | 4774 | OH2 | WAT | 823 | 27.817 | 17.957 | 50.119 | 1.00 | 32.04 |
| ATOM | 4775 | OH2 | WAT | 824 | 56.121 | 37.459 | 32.732 | 1.00 | 21.41 |
| ATOM | 4776 | OH2 | WAT | 825 | 9.453 | 31.180 | 47.871 | 1.00 | 51.79 |
| ATOM | 4777 | OH2 | WAT | 826 | 41.647 | 54.559 | 62.566 | 1.00 | 39.79 |
| ATOM | 4778 | OH2 | WAT | 827 | 50.893 | 18.450 | 23.970 | 1.00 | 27.60 |
| ATOM | 4779 | OH2 | WAT | 828 | 26.079 | 14.620 | 12.464 | 1.00 | 24.55 |
| ATOM | 4780 | OH2 | WAT | 829 | 69.963 | 44.562 | 41.439 | 1.00 | 32.79 |
| ATOM | 4781 | OH2 | WAT | 830 | 56.486 | 22.481 | 16.758 | 1.00 | 35.62 |
| ATOM | 4782 | OH2 | WAT | 831 | 26.101 | 20.243 | 49.585 | 1.00 | 24.90 |
| ATOM | 4783 | OH2 | WAT | 832 | 16.729 | 33.274 | 50.986 | 1.00 | 24.98 |
| ATOM | 4784 | OH2 | WAT | 833 | 21.501 | 54.137 | 59.417 | 1.00 | 23.27 |
| ATOM | 4785 | OH2 | WAT | 834 | 47.542 | 53.259 | 64.127 | 1.00 | 45.51 |
| ATOM | 4786 | OH2 | WAT | 836 | 49.479 | 39.080 | 12.500 | 1.00 | 30.28 |
| ATOM | 4787 | OH2 | WAT | 838 | 42.825 | 25.879 | 37.780 | 1.00 | 23.21 |
| ATOM | 4788 | OH2 | WAT | 839 | 50.943 | 24.947 | 57.867 | 1.00 | 32.14 |
| ATOM | 4789 | OH2 | WAT | 840 | 54.743 | 56.961 | 50.478 | 1.00 | 26.75 |
| ATOM | 4790 | OH2 | WAT | 841 | 40.544 | 53.741 | 32.431 | 1.00 | 34.46 |
| ATOM | 4791 | OH2 | WAT | 842 | 26.547 | 47.649 | 53.571 | 1.00 | 39.97 |
| ATOM | 4792 | OH2 | WAT | 843 | 37.195 | 32.835 | 54.383 | 1.00 | 28.68 |
| ATOM | 4793 | OH2 | WAT | 844 | 58.053 | 39.110 | 31.973 | 1.00 | 18.62 |
| ATOM | 4794 | OH2 | WAT | 845 | 18.264 | 24.599 | 44.498 | 1.00 | 27.65 |
| ATOM | 4795 | OH2 | WAT | 847 | 13.854 | 29.610 | 37.456 | 1.00 | 44.84 |
| ATOM | 4796 | OH2 | WAT | 849 | 22.552 | 38.833 | 31.917 | 1.00 | 48.29 |
| ATOM | 4797 | OH2 | WAT | 850 | 35.645 | 59.479 | 37.510 | 1.00 | 31.45 |
| ATOM | 4798 | OH2 | WAT | 851 | 24.548 | 59.962 | 64.794 | 1.00 | 38.37 |
| ATOM | 4799 | OH2 | WAT | 852 | 30.633 | 55.275 | 34.413 | 1.00 | 26.28 |
| ATOM | 4800 | OH2 | WAT | 853 | 39.272 | 27.243 | 44.281 | 1.00 | 44.92 |
| ATOM | 4801 | OH2 | WAT | 854 | 32.053 | 46.154 | 71.549 | 1.00 | 34.74 |
| ATOM | 4802 | OH2 | WAT | 855 | 48.612 | 24.905 | 14.847 | 1.00 | 36.12 |
| ATOM | 4803 | OH2 | WAT | 857 | 18.696 | 30.214 | 40.372 | 1.00 | 32.39 |
| ATOM | 4804 | OH2 | WAT | 858 | 67.928 | 43.317 | 39.467 | 1.00 | 25.41 |
| ATOM | 4805 | OH2 | WAT | 859 | 29.220 | 64.769 | 57.769 | 1.00 | 33.69 |
| ATOM | 4806 | OH2 | WAT | 860 | 50.268 | 24.002 | 37.829 | 1.00 | 31.48 |
| ATOM | 4807 | OH2 | WAT | 861 | 50.197 | 23.766 | 16.468 | 1.00 | 47.21 |
| ATOM | 4808 | OH2 | WAT | 862 | 50.752 | 18.550 | 46.573 | 1.00 | 33.31 |
| ATOM | 4809 | OH2 | WAT | 863 | 54.737 | 36.999 | 16.598 | 1.00 | 28.84 |
| ATOM | 4810 | OH2 | WAT | 864 | 23.466 | 24.199 | 53.649 | 1.00 | 29.72 |
| ATOM | 4811 | OH2 | WAT | 865 | 33.404 | 55.021 | 25.847 | 1.00 | 52.41 |
| ATOM | 4812 | OH2 | WAT | 866 | 42.687 | 31.048 | 44.149 | 1.00 | 40.21 |
| ATOM | 4813 | OH2 | WAT | 867 | 28.448 | 42.954 | 54.380 | 1.00 | 36.53 |

TABLE A-continued

| | | | | | | | | | |
|---|---|---|---|---|---|---|---|---|---|
| ATOM | 4814 | OH2 | WAT | 868 | 14.997 | 43.707 | 34.454 | 1.00 | 43.03 |
| ATOM | 4815 | OH2 | WAT | 869 | 14.328 | 39.153 | 57.579 | 1.00 | 40.69 |
| ATOM | 4816 | OH2 | WAT | 870 | 57.378 | 37.209 | 64.736 | 1.00 | 28.61 |
| ATOM | 4817 | OH2 | WAT | 871 | 20.536 | 32.124 | 29.526 | 1.00 | 31.13 |
| ATOM | 4818 | OH2 | WAT | 872 | 52.129 | 50.355 | 27.209 | 1.00 | 31.95 |
| ATOM | 4819 | OH2 | WAT | 873 | 51.809 | 35.631 | 62.337 | 1.00 | 31.87 |
| ATOM | 4820 | OH2 | WAT | 874 | 47.029 | 21.316 | 50.899 | 1.00 | 28.63 |
| ATOM | 4821 | OH2 | WAT | 875 | 29.328 | 44.418 | 56.243 | 1.00 | 29.76 |
| ATOM | 4822 | OH2 | WAT | 876 | 40.553 | 19.067 | 31.054 | 1.00 | 31.19 |
| ATOM | 4823 | OH2 | WAT | 877 | 56.608 | 42.974 | 23.109 | 1.00 | 36.47 |
| ATOM | 4824 | OH2 | WAT | 878 | 33.944 | 18.283 | 53.032 | 1.00 | 48.79 |
| ATOM | 4825 | OH2 | WAT | 879 | 27.295 | 18.819 | 26.051 | 1.00 | 23.88 |
| ATOM | 4826 | OH2 | WAT | 880 | 62.721 | 54.186 | 39.777 | 1.00 | 38.87 |
| ATOM | 4827 | OH2 | WAT | 881 | 35.611 | 9.588 | 50.038 | 1.00 | 41.90 |
| ATOM | 4828 | OH2 | WAT | 882 | 38.082 | 58.167 | 33.104 | 1.00 | 35.67 |
| ATOM | 4829 | OH2 | WAT | 883 | 20.479 | 20.811 | 35.650 | 1.00 | 28.10 |
| ATOM | 4830 | OH2 | WAT | 884 | 64.071 | 48.661 | 47.710 | 1.00 | 36.23 |
| ATOM | 4831 | OH2 | WAT | 885 | 62.169 | 33.114 | 54.016 | 1.00 | 38.38 |
| ATOM | 4832 | OH2 | WAT | 886 | 46.247 | 15.458 | 31.504 | 1.00 | 29.44 |
| ATOM | 4833 | OH2 | WAT | 887 | 15.161 | 50.744 | 53.893 | 1.00 | 46.81 |
| ATOM | 4834 | OH2 | WAT | 888 | 21.461 | 24.555 | 51.822 | 1.00 | 33.72 |
| ATOM | 4835 | OH2 | WAT | 889 | 39.805 | 19.953 | 14.067 | 1.00 | 34.19 |
| ATOM | 4836 | OH2 | WAT | 890 | 44.630 | 68.730 | 56.107 | 1.00 | 44.36 |
| ATOM | 4837 | OH2 | WAT | 891 | 47.554 | 30.392 | 39.434 | 1.00 | 32.91 |
| ATOM | 4838 | OH2 | WAT | 892 | 32.135 | 20.873 | 14.262 | 1.00 | 29.57 |
| ATOM | 4839 | OH2 | WAT | 893 | 69.474 | 42.046 | 47.848 | 1.00 | 40.45 |
| ATOM | 4840 | OH2 | WAT | 894 | 23.764 | 15.417 | 41.216 | 1.00 | 45.57 |
| ATOM | 4841 | OH2 | WAT | 895 | 30.804 | 11.274 | 25.353 | 1.00 | 36.15 |
| ATOM | 4842 | OH2 | WAT | 896 | 42.686 | 40.690 | 57.070 | 1.00 | 26.52 |
| ATOM | 4843 | OH2 | WAT | 898 | 41.447 | 36.486 | 13.521 | 1.00 | 40.39 |
| ATOM | 4844 | OH2 | WAT | 899 | 38.960 | 38.628 | 60.048 | 1.00 | 40.06 |
| ATOM | 4845 | OH2 | WAT | 900 | 41.026 | 24.976 | 9.369 | 1.00 | 38.69 |
| ATOM | 4846 | OH2 | WAT | 902 | 55.833 | 48.047 | 27.058 | 1.00 | 38.88 |
| ATOM | 4847 | OH2 | WAT | 903 | 33.909 | 34.365 | 58.131 | 1.00 | 39.46 |
| ATOM | 4848 | OH2 | WAT | 904 | 56.604 | 58.656 | 39.499 | 1.00 | 34.67 |
| ATOM | 4849 | OH2 | WAT | 905 | 57.413 | 45.071 | 24.624 | 1.00 | 33.81 |
| ATOM | 4850 | OH2 | WAT | 906 | 68.047 | 30.945 | 34.093 | 1.00 | 36.91 |
| ATOM | 4851 | OH2 | WAT | 907 | 17.540 | 52.182 | 46.933 | 1.00 | 26.43 |
| ATOM | 4852 | OH2 | WAT | 908 | 35.513 | 31.206 | 66.336 | 1.00 | 25.73 |
| ATOM | 4853 | OH2 | WAT | 910 | 62.045 | 46.674 | 53.517 | 1.00 | 33.21 |
| ATOM | 4854 | OH2 | WAT | 911 | 46.903 | 38.348 | 67.243 | 1.00 | 32.49 |
| ATOM | 4855 | OH2 | WAT | 912 | 60.188 | 33.756 | 26.674 | 1.00 | 37.96 |
| ATOM | 4856 | OH2 | WAT | 913 | 17.538 | 36.873 | 63.382 | 1.00 | 49.19 |
| ATOM | 4857 | OH2 | WAT | 914 | 23.983 | 36.615 | 25.955 | 1.00 | 28.20 |
| ATOM | 4858 | OH2 | WAT | 915 | 15.876 | 30.521 | 47.253 | 1.00 | 31.86 |
| ATOM | 4859 | OH2 | WAT | 916 | 23.539 | 62.135 | 63.215 | 1.00 | 37.75 |
| ATOM | 4860 | OH2 | WAT | 917 | 50.546 | 48.552 | 64.034 | 1.00 | 38.09 |
| ATOM | 4861 | OH2 | WAT | 918 | 64.968 | 41.202 | 32.910 | 1.00 | 30.16 |
| ATOM | 4862 | OH2 | WAT | 919 | 47.342 | 55.129 | 71.525 | 1.00 | 41.35 |
| ATOM | 4863 | OH2 | WAT | 920 | 15.582 | 44.034 | 65.703 | 1.00 | 31.07 |
| ATOM | 4864 | OH2 | WAT | 921 | 37.858 | 50.757 | 24.526 | 1.00 | 31.62 |
| ATOM | 4865 | OH2 | WAT | 922 | 37.372 | 23.617 | 9.556 | 1.00 | 39.44 |
| ATOM | 4866 | OH2 | WAT | 924 | 24.489 | 15.323 | 15.117 | 1.00 | 46.62 |
| ATOM | 4867 | OH2 | WAT | 925 | 22.412 | 16.803 | 37.659 | 1.00 | 43.70 |
| ATOM | 4868 | OH2 | WAT | 926 | 29.507 | 54.047 | 43.644 | 1.00 | 35.52 |
| ATOM | 4869 | OH2 | WAT | 927 | 60.554 | 35.356 | 56.976 | 1.00 | 42.99 |
| ATOM | 4870 | OH2 | WAT | 929 | 20.021 | 33.589 | 59.004 | 1.00 | 30.36 |
| ATOM | 4871 | OH2 | WAT | 930 | 19.473 | 19.176 | 31.910 | 1.00 | 31.54 |
| ATOM | 4872 | OH2 | WAT | 931 | 48.046 | 22.565 | 58.100 | 1.00 | 30.58 |
| ATOM | 4873 | OH2 | WAT | 932 | 43.806 | 63.606 | 53.022 | 1.00 | 40.90 |
| ATOM | 4874 | OH2 | WAT | 933 | 33.913 | 20.122 | 11.496 | 1.00 | 24.77 |
| ATOM | 4875 | OH2 | WAT | 934 | 49.430 | 59.955 | 52.495 | 1.00 | 37.32 |
| ATOM | 4876 | OH2 | WAT | 935 | 63.827 | 32.863 | 45.133 | 1.00 | 49.52 |
| ATOM | 4877 | OH2 | WAT | 936 | 37.964 | 21.411 | 49.414 | 1.00 | 30.06 |
| ATOM | 4878 | OH2 | WAT | 937 | 27.725 | 14.522 | 39.223 | 1.00 | 39.88 |
| ATOM | 4879 | OH2 | WAT | 938 | 15.164 | 38.822 | 61.336 | 1.00 | 46.35 |
| ATOM | 4880 | OH2 | WAT | 939 | 59.040 | 42.353 | 59.062 | 1.00 | 33.96 |
| ATOM | 4881 | OH2 | WAT | 940 | 47.109 | 42.149 | 69.895 | 1.00 | 45.88 |
| ATOM | 4882 | OH2 | WAT | 941 | 26.653 | 32.630 | 69.093 | 1.00 | 36.31 |
| ATOM | 4883 | OH2 | WAT | 942 | 28.206 | 17.559 | 22.902 | 1.00 | 32.76 |
| ATOM | 4884 | OH2 | WAT | 943 | 26.970 | 50.327 | 70.960 | 1.00 | 48.12 |
| ATOM | 4885 | OH2 | WAT | 944 | 64.060 | 23.004 | 42.589 | 1.00 | 32.90 |
| ATOM | 4886 | OH2 | WAT | 945 | 47.727 | 33.598 | 7.895 | 1.00 | 35.65 |
| ATOM | 4887 | OH2 | WAT | 946 | 34.742 | 23.791 | 49.020 | 1.00 | 25.74 |
| ATOM | 4888 | OH2 | WAT | 947 | 47.101 | 46.897 | 68.781 | 1.00 | 45.45 |
| ATOM | 4889 | OH2 | WAT | 948 | 41.870 | 11.724 | 30.722 | 1.00 | 27.02 |
| ATOM | 4890 | OH2 | WAT | 949 | 34.529 | 49.050 | 63.729 | 1.00 | 32.80 |
| ATOM | 4891 | OH2 | WAT | 950 | 38.408 | 61.853 | 51.628 | 1.00 | 49.43 |
| ATOM | 4892 | OH2 | WAT | 951 | 44.952 | 50.165 | 71.454 | 1.00 | 36.16 |
| ATOM | 4893 | OH2 | WAT | 952 | 46.362 | 23.481 | 42.021 | 1.00 | 38.59 |

TABLE A-continued

| | | | | | | | | |
|---|---|---|---|---|---|---|---|---|
| ATOM | 4894 | OH2 | WAT | 953 | 22.997 | 57.578 | 62.984 | 1.00 48.56 |
| ATOM | 4895 | OH2 | WAT | 954 | 53.705 | 20.324 | 34.584 | 1.00 46.72 |
| ATOM | 4896 | OH2 | WAT | 955 | 39.632 | 64.246 | 53.049 | 1.00 38.41 |
| ATOM | 4897 | OH2 | WAT | 956 | 20.296 | 21.770 | 47.578 | 1.00 38.44 |
| ATOM | 4898 | OH2 | WAT | 957 | 70.708 | 44.445 | 44.502 | 1.00 35.87 |
| ATOM | 4899 | OH2 | WAT | 958 | 13.567 | 22.992 | 35.251 | 1.00 36.22 |
| ATOM | 4900 | OH2 | WAT | 959 | 61.462 | 37.840 | 59.404 | 1.00 32.38 |
| ATOM | 4901 | OH2 | WAT | 960 | 70.605 | 49.268 | 42.736 | 1.00 49.49 |
| ATOM | 4902 | OH2 | WAT | 961 | 27.001 | 13.873 | 45.582 | 1.00 34.49 |
| ATOM | 4903 | OH2 | WAT | 962 | 40.837 | 53.265 | 28.588 | 1.00 34.92 |
| ATOM | 4904 | OH2 | WAT | 963 | 41.440 | 40.204 | 15.200 | 1.00 25.63 |
| ATOM | 4905 | OH2 | WAT | 964 | 47.029 | 18.253 | 59.807 | 1.00 47.20 |
| ATOM | 4906 | OH2 | WAT | 965 | 30.122 | 45.125 | 27.224 | 1.00 41.19 |
| ATOM | 4907 | OH2 | WAT | 966 | 70.354 | 22.884 | 32.301 | 1.00 45.44 |
| ATOM | 4908 | OH2 | WAT | 967 | 54.548 | 57.173 | 32.638 | 1.00 33.64 |
| ATOM | 4909 | OH2 | WAT | 968 | 47.786 | 18.173 | 53.594 | 1.00 33.24 |
| ATOM | 4910 | OH2 | WAT | 969 | 38.400 | 16.790 | 14.876 | 1.00 37.75 |
| ATOM | 4911 | OH2 | WAT | 970 | 28.970 | 12.153 | 32.723 | 1.00 24.55 |
| ATOM | 4912 | OH2 | WAT | 971 | 28.874 | 35.834 | 60.109 | 1.00 39.03 |
| ATOM | 4913 | OH2 | WAT | 972 | 47.546 | 23.630 | 12.714 | 1.00 51.51 |
| ATOM | 4914 | OH2 | WAT | 973 | 40.454 | 49.523 | 57.495 | 1.00 35.41 |
| ATOM | 4915 | OH2 | WAT | 974 | 48.210 | 48.061 | 65.137 | 1.00 47.07 |
| ATOM | 4916 | OH2 | WAT | 975 | 37.958 | 26.212 | 47.790 | 1.00 44.98 |
| ATOM | 4917 | OH2 | WAT | 977 | 37.233 | 24.170 | 51.843 | 1.00 33.85 |
| ATOM | 4918 | OH2 | WAT | 978 | 33.749 | 56.149 | 48.597 | 1.00 30.36 |
| ATOM | 4919 | OH2 | WAT | 979 | 48.361 | 43.396 | 21.748 | 1.00 40.73 |
| ATOM | 4920 | OH2 | WAT | 980 | 47.355 | 49.826 | 23.205 | 1.00 38.07 |
| ATOM | 4921 | OH2 | WAT | 982 | 37.732 | 7.064 | 33.535 | 1.00 48.68 |
| ATOM | 4922 | OH2 | WAT | 984 | 67.639 | 44.821 | 28.942 | 1.00 56.38 |
| ATOM | 4923 | OH2 | WAT | 985 | 65.770 | 35.555 | 35.108 | 1.00 50.64 |
| ATOM | 4924 | OH2 | WAT | 986 | 30.693 | 20.715 | 65.019 | 1.00 32.06 |
| ATOM | 4925 | OH2 | WAT | 987 | 27.053 | 36.974 | 22.607 | 1.00 38.10 |
| ATOM | 4926 | OH2 | WAT | 988 | 19.163 | 25.611 | 48.320 | 1.00 25.80 |
| ATOM | 4927 | OH2 | WAT | 989 | 48.005 | 58.792 | 30.965 | 1.00 45.93 |
| ATOM | 4928 | OH2 | WAT | 990 | 33.951 | 58.019 | 31.506 | 1.00 26.89 |
| ATOM | 4929 | OH2 | WAT | 991 | 60.149 | 48.327 | 52.415 | 1.00 42.30 |
| ATOM | 4930 | OH2 | WAT | 993 | 64.162 | 36.713 | 52.481 | 1.00 35.08 |
| ATOM | 4931 | OH2 | WAT | 996 | 36.217 | 29.075 | 7.223 | 1.00 43.08 |
| ATOM | 4932 | OH2 | WAT | 997 | 49.801 | 51.068 | 30.170 | 1.00 33.40 |
| ATOM | 4933 | OH2 | WAT | 998 | 11.053 | 37.371 | 34.418 | 1.00 31.32 |
| ATOM | 4934 | OH2 | WAT | 999 | 44.601 | 23.087 | 39.455 | 1.00 47.23 |
| ATOM | 4935 | OH2 | WAT | 1000 | 50.726 | 38.377 | 68.058 | 1.00 47.19 |
| ATOM | 4936 | OH2 | WAT | 1002 | 60.312 | 35.422 | 29.042 | 1.00 30.62 |
| ATOM | 4937 | OH2 | WAT | 1003 | 20.479 | 31.153 | 57.519 | 1.00 37.20 |
| ATOM | 4938 | OH2 | WAT | 1004 | 20.277 | 29.204 | 31.044 | 1.00 31.69 |
| ATOM | 4939 | OH2 | WAT | 1005 | 20.943 | 52.359 | 61.162 | 1.00 36.05 |
| ATOM | 4940 | OH2 | WAT | 1006 | 44.819 | 20.699 | 43.312 | 1.00 49.10 |
| ATOM | 4941 | OH2 | WAT | 1008 | 34.011 | 36.177 | 53.463 | 1.00 33.13 |
| ATOM | 4942 | OH2 | WAT | 1010 | 55.158 | 53.328 | 33.223 | 1.00 28.59 |
| ATOM | 4943 | OH2 | WAT | 1012 | 55.826 | 39.714 | 64.610 | 1.00 34.66 |
| ATOM | 4944 | OH2 | WAT | 1014 | 66.327 | 38.147 | 49.052 | 1.00 26.67 |
| ATOM | 4945 | OH2 | WAT | 1017 | 30.997 | 50.156 | 52.375 | 1.00 35.44 |
| ATOM | 4946 | OH2 | WAT | 1020 | 13.998 | 44.255 | 63.276 | 1.00 37.79 |
| ATOM | 4947 | OH2 | WAT | 1021 | 54.863 | 22.503 | 53.859 | 1.00 37.14 |
| ATOM | 4948 | OH2 | WAT | 1022 | 17.119 | 28.668 | 38.825 | 1.00 36.01 |
| ATOM | 4949 | OH2 | WAT | 1024 | 36.501 | 20.637 | 51.705 | 1.00 45.60 |
| ATOM | 4950 | OH2 | WAT | 1025 | 48.817 | 20.944 | 30.325 | 1.00 27.83 |
| ATOM | 4951 | OH2 | WAT | 1027 | 14.381 | 45.600 | 52.809 | 1.00 44.10 |
| ATOM | 4952 | OH2 | WAT | 1032 | 35.525 | 5.074 | 31.109 | 1.00 41.37 |
| ATOM | 4953 | OH2 | WAT | 1033 | 29.779 | 34.319 | 53.582 | 1.00 28.70 |
| ATOM | 4954 | OH2 | WAT | 1034 | 47.328 | 38.726 | 9.716 | 1.00 49.35 |
| ATOM | 4955 | OH2 | WAT | 1035 | 44.854 | 34.535 | 67.215 | 1.00 48.50 |
| ATOM | 4956 | OH2 | WAT | 1037 | 26.055 | 45.081 | 34.982 | 1.00 35.09 |
| ATOM | 4957 | OH2 | WAT | 1040 | 11.141 | 37.010 | 54.220 | 1.00 43.27 |
| ATOM | 4958 | OH2 | WAT | 1041 | 29.634 | 41.348 | 52.346 | 1.00 40.29 |
| ATOM | 4959 | OH2 | WAT | 1042 | 36.989 | 26.821 | 9.501 | 1.00 47.61 |
| ATOM | 4960 | OH2 | WAT | 1043 | 57.297 | 28.427 | 29.996 | 1.00 42.70 |
| ATOM | 4961 | OH2 | WAT | 1044 | 15.339 | 49.780 | 56.964 | 1.00 42.68 |
| ATOM | 4962 | OH2 | WAT | 1045 | 46.946 | 51.783 | 70.089 | 1.00 52.87 |
| ATOM | 4963 | OH2 | WAT | 1047 | 43.735 | 26.720 | 48.439 | 1.00 32.56 |
| ATOM | 4964 | OH2 | WAT | 1049 | 59.084 | 48.736 | 30.360 | 1.00 45.92 |
| ATOM | 4965 | OH2 | WAT | 1051 | 47.217 | 61.277 | 55.003 | 1.00 50.60 |
| ATOM | 4966 | OH2 | WAT | 1052 | 42.854 | 26.577 | 64.396 | 1.00 40.89 |
| ATOM | 4967 | OH2 | WAT | 1053 | 56.373 | 17.507 | 47.814 | 1.00 44.29 |
| ATOM | 4968 | OH2 | WAT | 1056 | 58.449 | 30.554 | 63.214 | 1.00 46.73 |
| ATOM | 4969 | OH2 | WAT | 1057 | 25.498 | 11.492 | 25.912 | 1.00 40.95 |
| ATOM | 4970 | OH2 | WAT | 1058 | 44.975 | 29.368 | 39.403 | 1.00 43.65 |
| ATOM | 4971 | OH2 | WAT | 1059 | 25.317 | 25.265 | 57.780 | 1.00 47.77 |
| ATOM | 4972 | OH2 | WAT | 1061 | 28.989 | 59.107 | 55.188 | 1.00 46.96 |
| ATOM | 4973 | OH2 | WAT | 1062 | 62.109 | 32.898 | 43.133 | 1.00 29.76 |

TABLE A-continued

| | | | | | | | | | |
|---|---|---|---|---|---|---|---|---|---|
| ATOM | 4974 | OH2 | WAT | 1063 | 68.950 | 47.081 | 42.243 | 1.00 | 32.59 |
| ATOM | 4975 | OH2 | WAT | 1066 | 53.065 | 54.350 | 56.726 | 1.00 | 53.35 |
| ATOM | 4976 | OH2 | WAT | 1068 | 44.519 | 16.873 | 20.860 | 1.00 | 43.15 |
| ATOM | 4977 | OH2 | WAT | 1070 | 45.839 | 26.154 | 61.550 | 1.00 | 36.80 |
| ATOM | 4978 | OH2 | WAT | 1072 | 36.197 | 36.508 | 12.204 | 1.00 | 33.71 |
| ATOM | 4979 | OH2 | WAT | 1073 | 35.351 | 41.501 | 68.026 | 1.00 | 45.11 |
| ATOM | 4980 | OH2 | WAT | 1074 | 65.633 | 34.803 | 51.451 | 1.00 | 38.53 |
| ATOM | 4981 | OH2 | WAT | 1078 | 41.335 | 38.420 | 54.710 | 0.50 | 29.72 |
| ATOM | 4982 | OH2 | WAT | 1079 | 29.512 | 38.685 | 22.833 | 1.00 | 39.63 |
| ATOM | 4983 | OH2 | WAT | 1080 | 14.118 | 37.523 | 50.894 | 1.00 | 39.63 |
| ATOM | 4984 | OH2 | WAT | 1081 | 48.556 | 54.366 | 25.635 | 1.00 | 42.49 |
| ATOM | 4985 | OH2 | WAT | 1082 | 40.975 | 25.862 | 40.806 | 1.00 | 24.48 |
| ATOM | 4986 | OH2 | WAT | 1083 | 40.345 | 57.934 | 37.750 | 1.00 | 22.44 |
| ATOM | 4987 | OH2 | WAT | 1084 | 54.691 | 59.362 | 48.731 | 1.00 | 33.75 |
| ATOM | 4988 | OH2 | WAT | 1085 | 53.736 | 57.789 | 52.852 | 1.00 | 40.58 |
| ATOM | 4989 | OH2 | WAT | 1086 | 15.708 | 33.122 | 54.732 | 1.00 | 44.11 |
| ATOM | 4990 | OH2 | WAT | 1087 | 22.243 | 32.265 | 27.402 | 1.00 | 38.80 |
| ATOM | 4991 | OH2 | WAT | 1088 | 47.611 | 17.171 | 32.905 | 1.00 | 43.63 |
| ATOM | 4992 | OH2 | WAT | 1089 | 58.379 | 48.121 | 27.949 | 1.00 | 43.58 |
| ATOM | 4993 | OH2 | WAT | 1092 | 57.488 | 59.756 | 41.894 | 1.00 | 54.98 |
| ATOM | 4994 | OH2 | WAT | 1093 | 37.216 | 31.175 | 68.418 | 1.00 | 28.64 |
| ATOM | 4995 | OH2 | WAT | 1094 | 37.762 | 33.656 | 69.811 | 1.00 | 40.47 |
| ATOM | 4996 | OH2 | WAT | 1095 | 65.445 | 43.712 | 34.681 | 1.00 | 47.01 |
| ATOM | 4997 | OH2 | WAT | 1097 | 28.164 | 21.093 | 19.000 | 1.00 | 34.17 |
| ATOM | 4998 | OH2 | WAT | 1098 | 18.673 | 33.165 | 61.660 | 1.00 | 40.84 |
| ATOM | 4999 | OH2 | WAT | 1100 | 51.193 | 61.127 | 51.030 | 1.00 | 39.94 |
| ATOM | 5000 | OH2 | WAT | 1101 | 56.432 | 43.982 | 59.555 | 1.00 | 39.42 |
| ATOM | 5001 | OH2 | WAT | 1102 | 56.968 | 41.831 | 63.701 | 1.00 | 42.73 |
| ATOM | 5002 | OH2 | WAT | 1103 | 34.405 | 49.957 | 71.786 | 1.00 | 35.15 |
| ATOM | 5003 | OH2 | WAT | 1104 | 41.241 | 9.964 | 32.536 | 1.00 | 31.00 |
| ATOM | 5004 | OH2 | WAT | 1105 | 21.105 | 21.857 | 50.569 | 1.00 | 43.38 |
| ATOM | 5005 | OH2 | WAT | 1106 | 23.670 | 20.267 | 50.750 | 1.00 | 41.28 |
| ATOM | 5006 | OH2 | WAT | 1108 | 29.571 | 9.657 | 34.297 | 1.00 | 39.24 |
| ATOM | 5007 | OH2 | WAT | 1109 | 27.460 | 9.067 | 36.007 | 1.00 | 35.51 |
| ATOM | 5008 | OH2 | WAT | 1111 | 24.692 | 47.272 | 35.502 | 1.00 | 33.10 |
| ATOM | 5009 | OH2 | WAT | 1113 | 29.462 | 58.167 | 41.963 | 1.00 | 39.41 |
| ATOM | 5010 | OH2 | WAT | 1115 | 26.304 | 58.757 | 54.952 | 1.00 | 54.54 |
| ATOM | 5011 | OH2 | WAT | 1116 | 22.934 | 60.561 | 60.251 | 1.00 | 49.35 |
| ATOM | 5012 | OH2 | WAT | 1117 | 39.244 | 37.381 | 55.807 | 1.00 | 42.76 |
| ATOM | 5013 | OH2 | WAT | 1119 | 37.428 | 43.614 | 61.340 | 1.00 | 41.53 |
| ATOM | 5014 | OH2 | WAT | 1121 | 17.907 | 30.515 | 55.600 | 1.00 | 52.02 |
| ATOM | 5015 | OH2 | WAT | 1122 | 33.636 | 10.725 | 25.760 | 1.00 | 26.11 |
| ATOM | 5016 | OH2 | WAT | 1123 | 37.687 | 60.192 | 39.575 | 1.00 | 27.92 |
| ATOM | 5017 | OH2 | WAT | 1124 | 40.750 | 44.964 | 49.691 | 1.00 | 25.17 |
| ATOM | 5018 | OH2 | WAT | 1125 | 70.584 | 38.077 | 47.755 | 1.00 | 37.02 |
| ATOM | 5019 | OH2 | WAT | 1126 | 15.603 | 41.927 | 47.692 | 1.00 | 28.52 |
| ATOM | 5020 | OH2 | WAT | 1127 | 25.206 | 43.505 | 32.164 | 1.00 | 33.23 |
| ATOM | 5021 | OH2 | WAT | 1128 | 26.442 | 21.223 | 54.177 | 1.00 | 26.91 |
| ATOM | 5022 | OH2 | WAT | 1130 | 42.766 | 41.142 | 51.475 | 1.00 | 46.99 |
| ATOM | 5023 | OH2 | WAT | 1131 | 43.109 | 61.103 | 37.679 | 1.00 | 41.65 |
| ATOM | 5024 | OH2 | WAT | 1132 | 14.570 | 30.169 | 45.086 | 1.00 | 42.30 |
| ATOM | 5025 | OH2 | WAT | 1133 | 34.157 | 38.583 | 24.573 | 1.00 | 28.21 |
| ATOM | 5026 | OH2 | WAT | 1135 | 35.943 | 44.155 | 50.435 | 1.00 | 35.21 |
| ATOM | 5027 | OH2 | WAT | 1137 | 15.347 | 36.178 | 62.387 | 1.00 | 48.01 |
| ATOM | 5028 | OH2 | WAT | 1142 | 30.780 | 45.800 | 61.426 | 1.00 | 46.24 |
| ATOM | 5029 | OH2 | WAT | 1144 | 56.000 | 49.811 | 57.192 | 1.00 | 33.19 |
| ATOM | 5030 | OH2 | WAT | 1145 | 50.931 | 47.015 | 21.718 | 1.00 | 41.76 |
| ATOM | 5031 | OH2 | WAT | 1148 | 41.181 | 13.664 | 41.675 | 1.00 | 36.85 |
| ATOM | 5032 | OH2 | WAT | 1149 | 26.829 | 13.900 | 42.000 | 1.00 | 51.60 |
| ATOM | 5033 | OH2 | WAT | 1150 | 38.428 | 50.689 | 49.680 | 1.00 | 38.37 |
| ATOM | 5034 | OH2 | WAT | 1151 | 13.307 | 43.102 | 37.676 | 1.00 | 40.57 |
| ATOM | 5035 | OH2 | WAT | 1153 | 32.376 | 39.513 | 22.416 | 1.00 | 42.97 |
| ATOM | 5036 | OH2 | WAT | 1155 | 14.863 | 50.906 | 47.090 | 1.00 | 49.79 |
| ATOM | 5037 | OH2 | WAT | 1156 | 39.040 | 11.571 | 36.195 | 1.00 | 42.49 |
| ATOM | 5038 | OH2 | WAT | 1157 | 55.760 | 18.990 | 54.253 | 1.00 | 46.82 |
| ATOM | 5039 | OH2 | WAT | 1159 | 29.811 | 44.316 | 51.775 | 1.00 | 29.84 |
| ATOM | 5040 | OH2 | WAT | 1160 | 26.254 | 30.191 | 18.160 | 1.00 | 47.30 |
| ATOM | 5041 | OH2 | WAT | 1163 | 50.589 | 53.935 | 30.727 | 1.00 | 41.87 |
| ATOM | 5042 | OH2 | WAT | 1164 | 26.778 | 17.598 | 17.107 | 1.00 | 39.40 |
| ATOM | 5043 | OH2 | WAT | 1166 | 57.293 | 56.491 | 51.361 | 1.00 | 36.42 |
| ATOM | 5044 | OH2 | WAT | 1167 | 55.900 | 43.483 | 62.013 | 1.00 | 33.17 |
| ATOM | 5045 | OH2 | WAT | 1170 | 45.416 | 56.601 | 68.328 | 1.00 | 39.64 |
| ATOM | 5046 | OH2 | WAT | 1171 | 45.090 | 53.796 | 27.563 | 1.00 | 44.12 |
| ATOM | 5047 | OH2 | WAT | 1172 | 25.950 | 27.760 | 17.747 | 1.00 | 47.76 |
| ATOM | 5048 | OH2 | WAT | 1174 | 21.716 | 34.736 | 25.915 | 1.00 | 39.70 |
| ATOM | 5049 | OH2 | WAT | 1177 | 28.580 | 48.024 | 33.877 | 1.00 | 34.88 |
| ATOM | 5050 | OH2 | WAT | 1178 | 45.395 | 19.823 | 49.333 | 1.00 | 48.96 |
| ATOM | 5051 | OH2 | WAT | 1180 | 66.122 | 32.218 | 43.068 | 1.00 | 46.26 |
| ATOM | 5052 | OH2 | WAT | 1181 | 61.892 | 29.586 | 16.389 | 1.00 | 40.21 |
| ATOM | 5053 | OH2 | WAT | 1183 | 15.358 | 27.450 | 47.492 | 1.00 | 49.59 |

TABLE A-continued

| | | | | | | | | | |
|---|---|---|---|---|---|---|---|---|---|
| ATOM | 5054 | OH2 | WAT | 1184 | 13.556 | 47.284 | 49.126 | 1.00 | 53.43 |
| ATOM | 5055 | OH2 | WAT | 1185 | 47.096 | 19.628 | 33.301 | 1.00 | 39.63 |
| ATOM | 5056 | OH2 | WAT | 1186 | 15.740 | 33.792 | 31.449 | 1.00 | 55.70 |
| ATOM | 5057 | OH2 | WAT | 1189 | 28.976 | 26.719 | 60.440 | 1.00 | 42.03 |
| ATOM | 5058 | OH2 | WAT | 1190 | 18.223 | 23.257 | 49.730 | 1.00 | 49.11 |
| ATOM | 5059 | OH2 | WAT | 1191 | 51.509 | 56.989 | 54.192 | 1.00 | 38.61 |
| ATOM | 5060 | OH2 | WAT | 1193 | 43.560 | 45.405 | 17.563 | 1.00 | 36.62 |
| ATOM | 5061 | OH2 | WAT | 1204 | 30.518 | 43.634 | 25.079 | 1.00 | 47.04 |
| ATOM | 5062 | OH2 | WAT | 1208 | 21.476 | 24.864 | 27.340 | 1.00 | 34.36 |
| ATOM | 5063 | OH2 | WAT | 1209 | 17.760 | 41.993 | 33.261 | 1.00 | 55.66 |
| ATOM | 5064 | OH2 | WAT | 1212 | 46.798 | 63.405 | 52.749 | 1.00 | 51.44 |
| ATOM | 5065 | OH2 | WAT | 1219 | 34.617 | 51.206 | 58.460 | 1.00 | 49.36 |
| ATOM | 5066 | OH2 | WAT | 1220 | 24.104 | 41.582 | 29.552 | 1.00 | 45.40 |
| ATOM | 5067 | OH2 | WAT | 1223 | 23.863 | 21.524 | 53.424 | 1.00 | 45.78 |
| ATOM | 5068 | OH2 | WAT | 1224 | 50.956 | 18.524 | 42.578 | 1.00 | 40.01 |
| ATOM | 5069 | OH2 | WAT | 1226 | 49.969 | 19.920 | 49.613 | 1.00 | 44.84 |
| ATOM | 5070 | OH2 | WAT | 1229 | 49.709 | 30.628 | 33.104 | 1.00 | 41.21 |
| ATOM | 5071 | OH2 | WAT | 1230 | 31.240 | 38.559 | 20.375 | 1.00 | 47.94 |
| ATOM | 5072 | OH2 | WAT | 1232 | 23.399 | 22.619 | 27.338 | 1.00 | 34.56 |
| ATOM | 5073 | OH2 | WAT | 1233 | 48.110 | 31.839 | 37.064 | 1.00 | 42.29 |
| ATOM | 5074 | OH2 | WAT | 1236 | 47.248 | 45.427 | 20.268 | 1.00 | 40.26 |
| ATOM | 5075 | OH2 | WAT | 1237 | 19.590 | 16.455 | 39.634 | 1.00 | 45.25 |
| ATOM | 5076 | OH2 | WAT | 1239 | 40.962 | 60.463 | 74.404 | 1.00 | 45.01 |
| ATOM | 5077 | OH2 | WAT | 1243 | 46.981 | 33.979 | 68.748 | 1.00 | 49.24 |
| ATOM | 5078 | OH2 | WAT | 1244 | 61.241 | 43.880 | 58.980 | 1.00 | 42.97 |
| ATOM | 5079 | OH2 | WAT | 1250 | 35.115 | 51.055 | 23.889 | 1.00 | 51.05 |
| ATOM | 5080 | OH2 | WAT | 1255 | 12.571 | 50.793 | 52.116 | 0.50 | 33.17 |
| ATOM | 5081 | OH2 | WAT | 1266 | 25.841 | 9.552 | 44.564 | 1.00 | 55.17 |
| ATOM | 5082 | OH2 | WAT | 1268 | 61.336 | 50.541 | 51.337 | 1.00 | 45.61 |
| ATOM | 5083 | OH2 | WAT | 1273 | 23.939 | 29.659 | 26.509 | 1.00 | 42.88 |
| ATOM | 5084 | OH2 | WAT | 1275 | 59.410 | 55.437 | 44.599 | 1.00 | 42.16 |
| ATOM | 5085 | OH2 | WAT | 1278 | 64.290 | 43.553 | 53.436 | 1.00 | 38.01 |
| ATOM | 5086 | OH2 | WAT | 1279 | 36.463 | 61.861 | 41.741 | 1.00 | 31.97 |
| ATOM | 5087 | OH2 | WAT | 1282 | 37.884 | 28.719 | 70.368 | 1.00 | 50.75 |
| ATOM | 5088 | OH2 | WAT | 1286 | 21.758 | 53.622 | 63.516 | 1.00 | 46.95 |
| ATOM | 5089 | OH2 | WAT | 1288 | 49.866 | 23.754 | 32.094 | 1.00 | 47.08 |
| ATOM | 5090 | OH2 | WAT | 1289 | 46.816 | 19.829 | 38.612 | 1.00 | 41.12 |
| ATOM | 5091 | OH2 | WAT | 1294 | 41.690 | 12.743 | 36.520 | 1.00 | 45.23 |
| ATOM | 5092 | OH2 | WAT | 1302 | 47.382 | 23.700 | 60.586 | 1.00 | 42.72 |
| ATOM | 5093 | OH2 | WAT | 1303 | 65.406 | 53.318 | 38.129 | 1.00 | 42.46 |
| ATOM | 5094 | OH2 | WAT | 1304 | 16.963 | 19.384 | 30.420 | 1.00 | 49.48 |
| ATOM | 5095 | OH2 | WAT | 1308 | 63.085 | 28.921 | 19.779 | 1.00 | 53.97 |
| ATOM | 5096 | OH2 | WAT | 1309 | 23.293 | 21.221 | 25.162 | 1.00 | 40.04 |
| ATOM | 5097 | OH2 | WAT | 1312 | 47.167 | 34.527 | 37.872 | 1.00 | 27.27 |
| ATOM | 5098 | OH2 | WAT | 1314 | 10.864 | 37.430 | 37.980 | 1.00 | 28.15 |
| ATOM | 5099 | OH2 | WAT | 1315 | 44.856 | 27.880 | 46.189 | 1.00 | 30.95 |
| ATOM | 5100 | OH2 | WAT | 1317 | 58.272 | 25.539 | 24.981 | 1.00 | 32.58 |
| ATOM | 5101 | OH2 | WAT | 1318 | 18.820 | 50.334 | 62.005 | 1.00 | 36.58 |
| ATOM | 5102 | OH2 | WAT | 1319 | 30.841 | 37.131 | 59.111 | 1.00 | 46.56 |
| ATOM | 5103 | OH2 | WAT | 1320 | 29.617 | 62.035 | 68.933 | 1.00 | 44.43 |
| ATOM | 5104 | OH2 | WAT | 1321 | 46.544 | 35.226 | 40.439 | 1.00 | 40.06 |
| ATOM | 5105 | OH2 | WAT | 1322 | 28.073 | 10.853 | 25.663 | 1.00 | 40.56 |
| ATOM | 5106 | OH2 | WAT | 1323 | 42.441 | 29.122 | 46.515 | 1.00 | 39.18 |
| ATOM | 5107 | OH2 | WAT | 1324 | 32.503 | 25.207 | 20.281 | 1.00 | 30.43 |
| ATOM | 5108 | OH2 | WAT | 1325 | 45.433 | 45.115 | 68.057 | 1.00 | 34.28 |
| ATOM | 5109 | OH2 | WAT | 1326 | 60.152 | 17.493 | 35.180 | 1.00 | 31.13 |
| ATOM | 5110 | OH2 | WAT | 1327 | 18.398 | 27.449 | 35.882 | 1.00 | 37.64 |
| ATOM | 5111 | OH2 | WAT | 1328 | 25.504 | 31.112 | 20.438 | 1.00 | 38.34 |
| ATOM | 5112 | OH2 | WAT | 1329 | 30.779 | 47.918 | 51.067 | 1.00 | 35.49 |
| ATOM | 5113 | OH2 | WAT | 1330 | 19.913 | 28.817 | 33.764 | 1.00 | 31.28 |
| ATOM | 5114 | OH2 | WAT | 1331 | 41.767 | 10.738 | 28.096 | 1.00 | 41.34 |
| ATOM | 5115 | OH2 | WAT | 1332 | 26.547 | 23.240 | 56.068 | 1.00 | 41.06 |
| ATOM | 5116 | OH2 | WAT | 1333 | 33.925 | 58.939 | 47.024 | 1.00 | 34.77 |
| ATOM | 5117 | OH2 | WAT | 1334 | 22.602 | 51.105 | 36.733 | 1.00 | 43.04 |
| ATOM | 5118 | OH2 | WAT | 1335 | 22.996 | 38.949 | 26.371 | 1.00 | 38.28 |
| ATOM | 5119 | OH2 | WAT | 1336 | 29.162 | 20.497 | 16.594 | 1.00 | 43.76 |
| ATOM | 5120 | OH2 | WAT | 1337 | 20.274 | 17.838 | 34.214 | 1.00 | 44.34 |
| ATOM | 5121 | OH2 | WAT | 1338 | 39.624 | 36.468 | 69.824 | 1.00 | 40.01 |
| ATOM | 5122 | OH2 | WAT | 1339 | 37.483 | 51.842 | 59.120 | 1.00 | 44.97 |
| ATOM | 5123 | OH2 | WAT | 1340 | 24.717 | 29.196 | 23.868 | 1.00 | 34.46 |
| ATOM | 5124 | OH2 | WAT | 1341 | 44.042 | 21.496 | 47.701 | 1.00 | 33.63 |
| ATOM | 5125 | OH2 | WAT | 1342 | 13.466 | 35.511 | 57.867 | 1.00 | 42.68 |
| ATOM | 5126 | OH2 | WAT | 1343 | 55.772 | 29.777 | 32.992 | 1.00 | 44.58 |
| ATOM | 5127 | OH2 | WAT | 1344 | 14.280 | 32.060 | 49.325 | 1.00 | 38.28 |
| ATOM | 5128 | OH2 | WAT | 1345 | 45.443 | 50.731 | 25.094 | 1.00 | 46.95 |
| ATOM | 5129 | OH2 | WAT | 1346 | 68.409 | 39.510 | 47.837 | 1.00 | 41.69 |
| ATOM | 5130 | OH2 | WAT | 1347 | 39.778 | 58.278 | 43.142 | 1.00 | 32.41 |
| ATOM | 5131 | OH2 | WAT | 1348 | 29.470 | 22.597 | 20.692 | 1.00 | 48.08 |
| ATOM | 5132 | OH2 | WAT | 1349 | 24.093 | 35.444 | 64.264 | 1.00 | 35.01 |
| ATOM | 5133 | OH2 | WAT | 1351 | 26.090 | 30.612 | 28.125 | 1.00 | 36.91 |

TABLE A-continued

| | | | | | | | | |
|---|---|---|---|---|---|---|---|---|
| ATOM | 5134 | OH2 | WAT | 1352 | 17.332 | 33.459 | 57.443 | 1.00 | 41.72 |
| ATOM | 5135 | OH2 | WAT | 1353 | 56.042 | 23.489 | 25.469 | 1.00 | 43.75 |
| ATOM | 5136 | OH2 | WAT | 1354 | 42.787 | 43.334 | 56.083 | 1.00 | 40.09 |
| ATOM | 5137 | OH2 | WAT | 1355 | 50.830 | 26.069 | 35.611 | 1.00 | 40.02 |
| ATOM | 5138 | OH2 | WAT | 1356 | 38.381 | 12.374 | 24.731 | 1.00 | 44.11 |
| ATOM | 5139 | OH2 | WAT | 1357 | 44.282 | 44.869 | 20.284 | 1.00 | 42.34 |
| ATOM | 5140 | OH2 | WAT | 1359 | 34.183 | 42.608 | 20.745 | 1.00 | 46.91 |
| ATOM | 5141 | OH2 | WAT | 1360 | 31.973 | 57.138 | 43.492 | 1.00 | 43.69 |
| ATOM | 5142 | OH2 | WAT | 1361 | 47.127 | 28.967 | 63.758 | 1.00 | 39.75 |
| ATOM | 5143 | OH2 | WAT | 1362 | 16.760 | 48.273 | 38.728 | 1.00 | 43.33 |
| ATOM | 5144 | OH2 | WAT | 1363 | 31.959 | 52.844 | 61.725 | 1.00 | 48.88 |
| ATOM | 5145 | OH2 | WAT | 1364 | 48.548 | 41.547 | 13.592 | 1.00 | 46.21 |
| ATOM | 5146 | OH2 | WAT | 1365 | 28.676 | 25.375 | 20.616 | 1.00 | 37.11 |
| ATOM | 5147 | OH2 | WAT | 1366 | 29.885 | 56.396 | 44.858 | 1.00 | 36.90 |
| ATOM | 5148 | OH2 | WAT | 1367 | 40.319 | 47.450 | 20.023 | 1.00 | 43.96 |
| ATOM | 5149 | OH2 | WAT | 1368 | 38.503 | 60.152 | 44.332 | 1.00 | 32.68 |
| ATOM | 5150 | OH2 | WAT | 1369 | 44.801 | 17.250 | 50.502 | 1.00 | 43.13 |
| ATOM | 5151 | OH2 | WAT | 1370 | 37.328 | 23.957 | 49.049 | 1.00 | 45.36 |
| ATOM | 5152 | OH2 | WAT | 1371 | 24.009 | 57.807 | 55.904 | 1.00 | 42.44 |
| ATOM | 5153 | OH2 | WAT | 1372 | 28.513 | 45.956 | 53.486 | 1.00 | 46.34 |
| ATOM | 5154 | OH2 | WAT | 1373 | 49.030 | 36.730 | 6.520 | 1.00 | 45.48 |
| ATOM | 5155 | OH2 | WAT | 1374 | 38.498 | 35.628 | 50.765 | 1.00 | 26.69 |
| ATOM | 5156 | OH2 | WAT | 1375 | 39.668 | 33.298 | 50.610 | 1.00 | 33.61 |
| ATOM | 5157 | OH2 | WAT | 1376 | 52.375 | 26.835 | 60.266 | 1.00 | 44.32 |
| ATOM | 5158 | OH2 | WAT | 1377 | 55.500 | 25.818 | 58.095 | 1.00 | 44.59 |
| ATOM | 5159 | OH2 | WAT | 1378 | 30.116 | 36.834 | 19.045 | 1.00 | 39.93 |
| ATOM | 5160 | OH2 | WAT | 1381 | 43.493 | 27.126 | 35.565 | 1.00 | 48.96 |
| ATOM | 5161 | OH2 | WAT | 1382 | 33.586 | 58.999 | 44.339 | 1.00 | 41.52 |
| ATOM | 5162 | OH2 | WAT | 1383 | 35.232 | 41.723 | 71.023 | 1.00 | 46.74 |
| ATOM | 5163 | OH2 | WAT | 1384 | 71.095 | 37.535 | 44.165 | 1.00 | 41.47 |
| ATOM | 5164 | OH2 | WAT | 1386 | 48.253 | 57.473 | 71.974 | 1.00 | 43.72 |
| ATOM | 5165 | C1 | NAG | 691 | 38.666 | 22.463 | 66.650 | 0.50 | 29.58 |
| ATOM | 5166 | C2 | NAG | 691 | 39.962 | 22.246 | 67.525 | 0.50 | 29.55 |
| ATOM | 5167 | C3 | NAG | 691 | 39.524 | 21.408 | 68.772 | 0.50 | 29.52 |
| ATOM | 5168 | C4 | NAG | 691 | 38.496 | 22.259 | 69.550 | 0.50 | 29.70 |
| ATOM | 5169 | C5 | NAG | 691 | 37.241 | 22.504 | 68.605 | 0.50 | 30.07 |
| ATOM | 5170 | C6 | NAG | 691 | 36.157 | 23.293 | 69.219 | 0.50 | 28.97 |
| ATOM | 5171 | C7 | NAG | 691 | 42.209 | 21.838 | 66.543 | 0.50 | 29.68 |
| ATOM | 5172 | C8 | NAG | 691 | 43.027 | 20.911 | 65.781 | 0.50 | 29.38 |
| ATOM | 5173 | N2 | NAG | 691 | 40.925 | 21.438 | 66.776 | 0.50 | 28.28 |
| ATOM | 5174 | O3 | NAG | 691 | 40.679 | 21.179 | 69.596 | 0.50 | 29.08 |
| ATOM | 5175 | O4 | NAG | 691 | 38.067 | 21.525 | 70.710 | 0.50 | 31.81 |
| ATOM | 5176 | O5 | NAG | 691 | 37.742 | 23.245 | 67.408 | 0.50 | 28.44 |
| ATOM | 5177 | O6 | NAG | 691 | 34.965 | 23.182 | 68.486 | 0.50 | 29.28 |
| ATOM | 5178 | O7 | NAG | 691 | 42.632 | 22.844 | 66.920 | 0.50 | 30.40 |
| ATOM | 5179 | C1 | NAG | 692 | 26.823 | 46.501 | 73.110 | 0.25 | 30.78 |
| ATOM | 5180 | C2 | NAG | 692 | 26.060 | 47.367 | 74.194 | 0.25 | 29.79 |
| ATOM | 5181 | C3 | NAG | 692 | 26.339 | 46.684 | 75.578 | 0.25 | 28.68 |
| ATOM | 5182 | C4 | NAG | 692 | 25.778 | 45.248 | 75.517 | 0.25 | 28.12 |
| ATOM | 5183 | C5 | NAG | 692 | 26.546 | 44.463 | 74.365 | 0.25 | 28.47 |
| ATOM | 5184 | C6 | NAG | 692 | 26.141 | 43.054 | 74.189 | 0.25 | 27.89 |
| ATOM | 5185 | C7 | NAG | 692 | 27.924 | 49.127 | 74.485 | 0.25 | 29.38 |
| ATOM | 5186 | C8 | NAG | 692 | 28.176 | 50.560 | 74.479 | 0.25 | 29.34 |
| ATOM | 5187 | N2 | NAG | 692 | 26.610 | 48.755 | 74.247 | 0.25 | 29.38 |
| ATOM | 5188 | O3 | NAG | 692 | 25.663 | 47.437 | 76.598 | 0.25 | 28.79 |
| ATOM | 5189 | O4 | NAG | 692 | 26.031 | 44.601 | 76.779 | 0.25 | 26.69 |
| ATOM | 5190 | O5 | NAG | 692 | 26.263 | 45.191 | 73.097 | 0.25 | 29.85 |
| ATOM | 5191 | O6 | NAG | 692 | 26.884 | 42.425 | 73.176 | 0.25 | 25.82 |
| ATOM | 5192 | O7 | NAG | 692 | 28.778 | 48.376 | 74.677 | 0.25 | 28.91 |
| ATOM | 5193 | C1 | NAG | 693 | 45.844 | 65.857 | 60.275 | 0.50 | 34.64 |
| ATOM | 5194 | C2 | NAG | 693 | 47.343 | 66.335 | 60.338 | 0.50 | 33.61 |
| ATOM | 5195 | C3 | NAG | 693 | 48.225 | 65.046 | 60.320 | 0.50 | 33.54 |
| ATOM | 5196 | C4 | NAG | 693 | 47.874 | 64.228 | 61.582 | 0.50 | 33.12 |
| ATOM | 5197 | C5 | NAG | 693 | 46.335 | 63.825 | 61.490 | 0.50 | 32.64 |
| ATOM | 5198 | C6 | NAG | 693 | 45.829 | 63.006 | 62.614 | 0.50 | 32.29 |
| ATOM | 5199 | C7 | NAG | 693 | 47.847 | 68.449 | 59.114 | 0.50 | 33.80 |
| ATOM | 5200 | C8 | NAG | 693 | 48.147 | 69.026 | 57.814 | 0.50 | 33.51 |
| ATOM | 5201 | N2 | NAG | 693 | 47.658 | 67.096 | 59.127 | 0.50 | 33.78 |
| ATOM | 5202 | O3 | NAG | 693 | 49.604 | 65.442 | 60.373 | 0.50 | 34.37 |
| ATOM | 5203 | O4 | NAG | 693 | 48.672 | 63.030 | 61.597 | 0.50 | 32.73 |
| ATOM | 5204 | O5 | NAG | 693 | 45.563 | 65.105 | 61.455 | 0.50 | 32.95 |
| ATOM | 5205 | O6 | NAG | 693 | 46.059 | 63.613 | 63.861 | 0.50 | 33.79 |
| ATOM | 5206 | O7 | NAG | 693 | 47.775 | 69.104 | 60.061 | 0.50 | 34.69 |
| ATOM | 5207 | C1 | NAG | 694 | 34.333 | 4.445 | 43.451 | 0.50 | 42.09 |
| ATOM | 5208 | C2 | NAG | 694 | 35.344 | 3.237 | 43.321 | 0.50 | 40.59 |
| ATOM | 5209 | C3 | NAG | 694 | 36.776 | 3.873 | 43.266 | 0.50 | 40.44 |
| ATOM | 5210 | C4 | NAG | 694 | 36.837 | 4.763 | 42.008 | 0.50 | 39.57 |
| ATOM | 5211 | C5 | NAG | 694 | 35.747 | 5.912 | 42.160 | 0.50 | 40.19 |
| ATOM | 5212 | C6 | NAG | 694 | 35.697 | 6.867 | 41.038 | 0.50 | 39.67 |
| ATOM | 5213 | C7 | NAG | 694 | 35.390 | 1.041 | 44.522 | 0.50 | 38.40 |

TABLE A-continued

| ATOM | 5214 | C8 | NAG | 694 | 35.318 | 0.390 | 45.820 | 0.50 | 37.85 |
|---|---|---|---|---|---|---|---|---|---|
| ATOM | 5215 | N2 | NAG | 694 | 35.289 | 2.407 | 44.534 | 0.50 | 39.83 |
| ATOM | 5216 | O3 | NAG | 694 | 37.745 | 2.817 | 43.151 | 0.50 | 41.14 |
| ATOM | 5217 | O4 | NAG | 694 | 38.143 | 5.361 | 41.930 | 0.50 | 39.45 |
| ATOM | 5218 | O5 | NAG | 694 | 34.422 | 5.231 | 42.261 | 0.50 | 40.94 |
| ATOM | 5219 | O6 | NAG | 694 | 36.230 | 8.118 | 41.399 | 0.50 | 40.94 |
| ATOM | 5220 | O7 | NAG | 694 | 35.527 | 0.432 | 43.553 | 0.50 | 39.01 |
| ATOM | 5221 | C1 | NAG | 695 | 56.458 | 28.072 | 65.509 | 0.25 | 31.56 |
| ATOM | 5222 | C2 | NAG | 695 | 56.666 | 26.508 | 65.432 | 0.25 | 30.72 |
| ATOM | 5223 | C3 | NAG | 695 | 56.499 | 25.969 | 66.893 | 0.25 | 29.54 |
| ATOM | 5224 | C4 | NAG | 695 | 57.609 | 26.616 | 67.754 | 0.25 | 29.02 |
| ATOM | 5225 | C5 | NAG | 695 | 57.392 | 28.194 | 67.738 | 0.25 | 28.93 |
| ATOM | 5226 | C6 | NAG | 695 | 58.361 | 28.972 | 68.535 | 0.25 | 29.26 |
| ATOM | 5227 | C7 | NAG | 695 | 55.782 | 25.465 | 63.341 | 0.25 | 29.26 |
| ATOM | 5228 | C8 | NAG | 695 | 54.608 | 24.896 | 62.697 | 0.25 | 29.00 |
| ATOM | 5229 | N2 | NAG | 695 | 55.599 | 25.907 | 64.623 | 0.25 | 29.43 |
| ATOM | 5230 | O3 | NAG | 695 | 56.674 | 24.544 | 66.875 | 0.25 | 30.87 |
| ATOM | 5231 | O4 | NAG | 695 | 57.485 | 26.137 | 69.107 | 0.25 | 27.69 |
| ATOM | 5232 | O5 | NAG | 695 | 57.504 | 28.627 | 66.310 | 0.25 | 30.15 |
| ATOM | 5233 | O6 | NAG | 695 | 57.844 | 30.233 | 68.885 | 0.25 | 30.07 |
| ATOM | 5234 | O7 | NAG | 695 | 56.794 | 25.529 | 62.791 | 0.25 | 29.27 |
| ATOM | 5235 | C1 | NAG | 696 | 43.763 | 59.783 | 31.843 | 0.50 | 32.65 |
| ATOM | 5236 | C2 | NAG | 696 | 43.513 | 59.801 | 30.283 | 0.50 | 33.89 |
| ATOM | 5237 | C3 | NAG | 696 | 42.464 | 60.933 | 30.025 | 0.50 | 34.52 |
| ATOM | 5238 | C4 | NAG | 696 | 41.169 | 60.556 | 30.774 | 0.50 | 34.29 |
| ATOM | 5239 | C5 | NAG | 696 | 41.517 | 60.476 | 32.322 | 0.50 | 33.83 |
| ATOM | 5240 | C6 | NAG | 696 | 40.400 | 60.153 | 33.216 | 0.50 | 33.87 |
| ATOM | 5241 | C7 | NAG | 696 | 45.496 | 59.327 | 28.856 | 0.50 | 33.72 |
| ATOM | 5242 | C8 | NAG | 696 | 46.660 | 59.906 | 28.211 | 0.50 | 33.27 |
| ATOM | 5243 | N2 | NAG | 696 | 44.730 | 60.198 | 29.572 | 0.50 | 33.67 |
| ATOM | 5244 | O3 | NAG | 696 | 42.197 | 61.001 | 28.614 | 0.50 | 36.84 |
| ATOM | 5245 | O4 | NAG | 696 | 40.196 | 61.589 | 30.553 | 0.50 | 36.06 |
| ATOM | 5246 | O5 | NAG | 696 | 42.537 | 59.408 | 32.458 | 0.50 | 34.67 |
| ATOM | 5247 | O6 | NAG | 696 | 40.731 | 60.434 | 34.555 | 0.50 | 33.99 |
| ATOM | 5248 | O7 | NAG | 696 | 45.250 | 58.204 | 28.755 | 0.50 | 33.63 |
| ATOM | 5249 | C | ACY | 700 | 42.190 | 36.698 | 47.868 | 1.00 | 17.87 |
| ATOM | 5250 | O | ACY | 700 | 43.358 | 36.429 | 48.383 | 1.00 | 17.41 |
| ATOM | 5251 | OXT | ACY | 700 | 41.942 | 37.484 | 46.891 | 1.00 | 16.00 |
| ATOM | 5252 | CH3 | ACY | 700 | 41.037 | 35.966 | 48.550 | 1.00 | 16.17 |
| ATOM | 5253 | O1 | MSA | 702 | 40.494 | 34.478 | 45.311 | 1.00 | 21.85 |
| ATOM | 5254 | O2 | MSA | 702 | 42.778 | 34.136 | 45.475 | 1.00 | 27.34 |
| ATOM | 5255 | C1 | MSA | 702 | 41.675 | 34.389 | 44.805 | 1.00 | 25.81 |
| ATOM | 5256 | N1 | MSA | 702 | 41.988 | 34.537 | 43.491 | 1.00 | 23.47 |
| ATOM | 5257 | C2 | MSA | 702 | 40.825 | 34.645 | 42.578 | 1.00 | 24.59 |
| ATOM | 5258 | C3 | MSA | 702 | 41.603 | 34.810 | 41.280 | 1.00 | 26.22 |
| ATOM | 5259 | C4 | MSA | 702 | 39.846 | 33.467 | 42.340 | 1.00 | 22.86 |
| ATOM | 5260 | O3 | MSA | 702 | 38.793 | 33.259 | 41.647 | 1.00 | 21.49 |
| ATOM | 5261 | O4 | MSA | 702 | 40.179 | 32.410 | 43.024 | 1.00 | 21.93 |
| ATOM | 5262 | ZN + 2 | ZN2 | 701 | 43.817 | 38.308 | 46.652 | 1.00 | 16.34 |
| ATOM | 5263 | CL | CL | 703 | 29.185 | 28.250 | 36.073 | 1.00 | 16.51 |
| ATOM | 5264 | CL | CL | 704 | 36.287 | 45.320 | 44.617 | 1.00 | 16.56 |
| END | | | | | | | | | |

TABLE B

Co-ordinates of an underglycosylated tACEΔ36NJ ACE-lisinopril complex

REMARK coordinates from minimization refinement
REMARK refinement resolution: 47.14-2.0 A
REMARK starting   r = 0.1816 free_r = 0.2186
REMARK final     r = 0.1814 free_r = 0.2188
REMARK rmsd bonds = 0.005621 rmsd angles = 1.23822
REMARK wa = 0.450786
REMARK target = mlf cycles = 1 steps = 10
REMARK sg = P2(1)2(1)2(1) a = 56.472 b = 84.899 c = 133.990 alpha = 90
         beta = 90 gamma = 90
REMARK anomalous f' f'' library: CNS_XRAYLIB:anom_cu.lib
REMARK reflection file = ../dm10_2A.cv
REMARK ncs = none
REMARK B-correction resolution: 6.0-2.0
REMARK initial B-factor correction applied to fobs:
REMARK B11 = 1.410   B22 = 0.301   B33 = −1.711
REMARK B12 = 0.000   B13 = 0.000   B23 = 0.000
REMARK B-factor correction applied to coordinate array B: 0.605
REMARK bulk solvent: density level = 0.336734 e/A^3, B-factor = 42.5542
         A^2
REMARK reflections with |Fobs|/sigma_F < 0.0 rejected

TABLE B-continued

Co-ordinates of an underglycosylated tACEΔ36NJ ACE-lisinopril complex

REMARK reflections with |Fobs| > 10000 * rms(Fobs) rejected
REMARK anomalous diffraction data was input
REMARK theoretical total number of refl. in resol. range: 84079
(100.0%)
REMARK number of unobserved reflections (no entry or |F| = 0): 821
(5.7%)
REMARK number of reflections rejected: 0 (0.0%)
REMARK total number of reflections used: 79258 (94.3%)
REMARK number of reflections in working set: 76164 (90.6%)
REMARK number of reflections in test set: 3094 (3.7%)
CRYST1 56.472 84.899 133.990 90.00 90.00 90.00 P 21 21 21
REMARK VERSION: 1.1

| ATOM | 1 | CB | ALA | 71 | 34.080 | 71.619 | 65.828 | 1.00 | 37.03 |
|---|---|---|---|---|---|---|---|---|---|
| ATOM | 2 | C | ALA | 71 | 36.046 | 70.116 | 66.197 | 1.00 | 37.52 |
| ATOM | 3 | O | ALA | 71 | 35.940 | 68.889 | 66.147 | 1.00 | 37.50 |
| ATOM | 4 | N | ALA | 71 | 35.606 | 72.021 | 67.727 | 1.00 | 37.87 |
| ATOM | 5 | CA | ALA | 71 | 34.977 | 70.970 | 66.876 | 1.00 | 37.06 |
| ATOM | 6 | N | GLU | 72 | 37.077 | 70.776 | 65.680 | 1.00 | 36.64 |
| ATOM | 7 | CA | GLU | 72 | 38.178 | 70.092 | 65.008 | 1.00 | 37.31 |
| ATOM | 8 | CB | GLU | 72 | 39.088 | 71.119 | 64.323 | 1.00 | 37.75 |
| ATOM | 9 | CG | GLU | 72 | 40.071 | 70.565 | 63.292 | 1.00 | 41.00 |
| ATOM | 10 | CD | GLU | 72 | 39.421 | 70.271 | 61.945 | 1.00 | 42.37 |
| ATOM | 11 | OE1 | GLU | 72 | 38.580 | 71.081 | 61.495 | 1.00 | 42.32 |
| ATOM | 12 | OE2 | GLU | 72 | 39.764 | 69.237 | 61.329 | 1.00 | 44.26 |
| ATOM | 13 | C | GLU | 72 | 38.973 | 69.307 | 66.051 | 1.00 | 37.09 |
| ATOM | 14 | O | GLU | 72 | 39.518 | 68.241 | 65.758 | 1.00 | 36.65 |
| ATOM | 15 | N | ALA | 73 | 39.030 | 69.841 | 67.270 | 1.00 | 35.26 |
| ATOM | 16 | CA | ALA | 73 | 39.751 | 69.193 | 68.361 | 1.00 | 33.85 |
| ATOM | 17 | CB | ALA | 73 | 39.874 | 70.140 | 69.549 | 1.00 | 34.20 |
| ATOM | 18 | C | ALA | 73 | 39.018 | 67.921 | 68.779 | 1.00 | 32.78 |
| ATOM | 19 | O | ALA | 73 | 39.640 | 66.900 | 69.076 | 1.00 | 32.36 |
| ATOM | 20 | N | GLU | 74 | 37.692 | 67.996 | 68.807 | 1.00 | 31.76 |
| ATOM | 21 | CA | GLU | 74 | 36.867 | 66.849 | 69.169 | 1.00 | 32.74 |
| ATOM | 22 | CB | GLU | 74 | 35.393 | 67.257 | 69.234 | 1.00 | 34.51 |
| ATOM | 23 | CG | GLU | 74 | 34.783 | 67.216 | 70.619 | 1.00 | 39.69 |
| ATOM | 24 | CD | GLU | 74 | 33.360 | 67.750 | 70.636 | 1.00 | 43.24 |
| ATOM | 25 | OE1 | GLU | 74 | 32.467 | 67.110 | 70.032 | 1.00 | 44.62 |
| ATOM | 26 | OE2 | GLU | 74 | 33.139 | 68.819 | 71.249 | 1.00 | 44.03 |
| ATOM | 27 | C | GLU | 74 | 37.036 | 65.758 | 68.118 | 1.00 | 31.08 |
| ATOM | 28 | O | GLU | 74 | 36.987 | 64.568 | 68.422 | 1.00 | 30.67 |
| ATOM | 29 | N | ALA | 75 | 37.242 | 66.185 | 66.877 | 1.00 | 29.99 |
| ATOM | 30 | CA | ALA | 75 | 37.399 | 65.267 | 65.754 | 1.00 | 28.87 |
| ATOM | 31 | CB | ALA | 75 | 37.351 | 66.043 | 64.442 | 1.00 | 27.23 |
| ATOM | 32 | C | ALA | 75 | 38.669 | 64.421 | 65.814 | 1.00 | 27.10 |
| ATOM | 33 | O | ALA | 75 | 38.608 | 63.201 | 65.663 | 1.00 | 26.57 |
| ATOM | 34 | N | SER | 76 | 39.817 | 65.060 | 66.027 | 1.00 | 26.04 |
| ATOM | 35 | CA | SER | 76 | 41.078 | 64.326 | 66.089 | 1.00 | 25.45 |
| ATOM | 36 | CB | SER | 76 | 42.268 | 65.290 | 66.137 | 1.00 | 26.93 |
| ATOM | 37 | OG | SER | 76 | 42.278 | 66.033 | 67.338 | 1.00 | 32.77 |
| ATOM | 38 | C | SER | 76 | 41.101 | 63.404 | 67.302 | 1.00 | 23.44 |
| ATOM | 39 | O | SER | 76 | 41.710 | 62.337 | 67.265 | 1.00 | 25.13 |
| ATOM | 40 | N | LYS | 77 | 40.438 | 63.823 | 68.373 | 1.00 | 22.27 |
| ATOM | 41 | CA | LYS | 77 | 40.354 | 63.024 | 69.589 | 1.00 | 21.77 |
| ATOM | 42 | CB | LYS | 77 | 39.744 | 63.856 | 70.717 | 1.00 | 25.02 |
| ATOM | 43 | CG | LYS | 77 | 39.406 | 63.069 | 71.974 | 1.00 | 28.89 |
| ATOM | 44 | CD | LYS | 77 | 38.810 | 63.983 | 73.038 | 1.00 | 34.02 |
| ATOM | 45 | CE | LYS | 77 | 37.827 | 63.235 | 73.916 | 1.00 | 36.45 |
| ATOM | 46 | NZ | LYS | 77 | 36.683 | 62.717 | 73.107 | 1.00 | 39.31 |
| ATOM | 47 | C | LYS | 77 | 39.484 | 61.798 | 69.315 | 1.00 | 20.85 |
| ATOM | 48 | O | LYS | 77 | 39.791 | 60.691 | 69.758 | 1.00 | 19.15 |
| ATOM | 49 | N | PHE | 78 | 38.395 | 62.005 | 68.582 | 1.00 | 20.00 |
| ATOM | 50 | CA | PHE | 78 | 37.497 | 60.912 | 68.232 | 1.00 | 20.44 |
| ATOM | 51 | CB | PHE | 78 | 36.323 | 61.433 | 67.399 | 1.00 | 20.72 |
| ATOM | 52 | CG | PHE | 78 | 35.490 | 60.344 | 66.779 | 1.00 | 22.38 |
| ATOM | 53 | CD1 | PHE | 78 | 34.602 | 59.605 | 67.550 | 1.00 | 21.45 |
| ATOM | 54 | CD2 | PHE | 78 | 35.612 | 60.045 | 65.427 | 1.00 | 21.21 |
| ATOM | 55 | CE1 | PHE | 78 | 33.845 | 58.580 | 66.985 | 1.00 | 23.63 |
| ATOM | 56 | CE2 | PHE | 78 | 34.860 | 59.021 | 64.853 | 1.00 | 24.14 |
| ATOM | 57 | CZ | PHE | 78 | 33.976 | 58.288 | 65.632 | 1.00 | 21.01 |
| ATOM | 58 | C | PHE | 78 | 38.274 | 59.878 | 67.421 | 1.00 | 19.50 |
| ATOM | 59 | O | PHE | 78 | 38.222 | 58.680 | 67.702 | 1.00 | 19.55 |
| ATOM | 60 | N | VAL | 79 | 39.004 | 60.358 | 66.418 | 1.00 | 20.22 |
| ATOM | 61 | CA | VAL | 79 | 39.790 | 59.484 | 65.556 | 1.00 | 21.86 |
| ATOM | 62 | CB | VAL | 79 | 40.528 | 60.312 | 64.473 | 1.00 | 23.18 |
| ATOM | 63 | CG1 | VAL | 79 | 41.695 | 59.532 | 63.902 | 1.00 | 27.20 |
| ATOM | 64 | CG2 | VAL | 79 | 39.555 | 60.661 | 63.355 | 1.00 | 23.07 |
| ATOM | 65 | C | VAL | 79 | 40.782 | 58.648 | 66.365 | 1.00 | 22.62 |
| ATOM | 66 | O | VAL | 79 | 40.920 | 57.445 | 66.132 | 1.00 | 22.22 |

TABLE B-continued

Co-ordinates of an underglycosylated tACEΔ36NJ ACE-lisinopril complex

| ATOM | 67 | N | GLU | 80 | 41.459 | 59.280 | 67.320 | 1.00 | 22.66 |
|---|---|---|---|---|---|---|---|---|---|
| ATOM | 68 | CA | GLU | 80 | 42.418 | 58.570 | 68.165 | 1.00 | 22.34 |
| ATOM | 69 | CB | GLU | 80 | 43.117 | 59.544 | 69.122 | 1.00 | 25.90 |
| ATOM | 70 | CG | GLU | 80 | 43.893 | 60.652 | 68.424 | 1.00 | 31.05 |
| ATOM | 71 | CD | GLU | 80 | 44.564 | 61.606 | 69.399 | 1.00 | 35.35 |
| ATOM | 72 | OE1 | GLU | 80 | 43.881 | 62.088 | 70.333 | 1.00 | 36.66 |
| ATOM | 73 | OE2 | GLU | 80 | 45.772 | 61.880 | 69.225 | 1.00 | 37.98 |
| ATOM | 74 | C | GLU | 80 | 41.726 | 57.475 | 68.977 | 1.00 | 20.25 |
| ATOM | 75 | O | GLU | 80 | 42.209 | 56.345 | 69.046 | 1.00 | 18.55 |
| ATOM | 76 | N | GLU | 81 | 40.595 | 57.811 | 69.595 | 1.00 | 18.66 |
| ATOM | 77 | CA | GLU | 81 | 39.863 | 56.836 | 70.399 | 1.00 | 19.96 |
| ATOM | 78 | CB | GLU | 81 | 38.702 | 57.512 | 71.134 | 1.00 | 21.24 |
| ATOM | 79 | CG | GLU | 81 | 39.168 | 58.560 | 72.135 | 1.00 | 23.95 |
| ATOM | 80 | CD | GLU | 81 | 38.027 | 59.258 | 72.845 | 1.00 | 26.18 |
| ATOM | 81 | OE1 | GLU | 81 | 36.854 | 58.937 | 72.564 | 1.00 | 27.70 |
| ATOM | 82 | OE2 | GLU | 81 | 38.311 | 60.133 | 73.691 | 1.00 | 28.83 |
| ATOM | 83 | C | GLU | 81 | 39.352 | 55.704 | 69.514 | 1.00 | 18.59 |
| ATOM | 84 | O | GLU | 81 | 39.428 | 54.529 | 69.881 | 1.00 | 16.88 |
| ATOM | 85 | N | TYR | 82 | 38.839 | 56.060 | 68.341 | 1.00 | 17.35 |
| ATOM | 86 | CA | TYR | 82 | 38.345 | 55.059 | 67.410 | 1.00 | 17.12 |
| ATOM | 87 | CB | TYR | 82 | 37.807 | 55.726 | 66.143 | 1.00 | 15.74 |
| ATOM | 88 | CG | TYR | 82 | 37.428 | 54.730 | 65.071 | 1.00 | 15.18 |
| ATOM | 89 | CD1 | TYR | 82 | 36.303 | 53.918 | 65.217 | 1.00 | 13.96 |
| ATOM | 90 | CE1 | TYR | 82 | 35.957 | 52.986 | 64.244 | 1.00 | 13.99 |
| ATOM | 91 | CD2 | TYR | 82 | 38.204 | 54.583 | 63.924 | 1.00 | 14.71 |
| ATOM | 92 | CE2 | TYR | 82 | 37.871 | 53.652 | 62.942 | 1.00 | 16.19 |
| ATOM | 93 | CZ | TYR | 82 | 36.744 | 52.862 | 63.108 | 1.00 | 15.36 |
| ATOM | 94 | OH | TYR | 82 | 36.388 | 51.969 | 62.131 | 1.00 | 14.06 |
| ATOM | 95 | C | TYR | 82 | 39.469 | 54.089 | 67.027 | 1.00 | 16.14 |
| ATOM | 96 | O | TYR | 82 | 39.279 | 52.876 | 67.018 | 1.00 | 15.38 |
| ATOM | 97 | N | ASP | 83 | 40.642 | 54.630 | 66.719 | 1.00 | 17.88 |
| ATOM | 98 | CA | ASP | 83 | 41.770 | 53.798 | 66.315 | 1.00 | 19.78 |
| ATOM | 99 | CB | ASP | 83 | 42.938 | 54.670 | 65.855 | 1.00 | 21.25 |
| ATOM | 100 | CG | ASP | 83 | 44.049 | 53.855 | 65.214 | 1.00 | 27.73 |
| ATOM | 101 | OD1 | ASP | 83 | 43.791 | 53.214 | 64.168 | 1.00 | 30.70 |
| ATOM | 102 | OD2 | ASP | 83 | 45.178 | 53.846 | 65.752 | 1.00 | 28.73 |
| ATOM | 103 | C | ASP | 83 | 42.267 | 52.835 | 67.394 | 1.00 | 20.18 |
| ATOM | 104 | O | ASP | 83 | 42.446 | 51.645 | 67.132 | 1.00 | 19.78 |
| ATOM | 105 | N | ARG | 84 | 42.497 | 53.338 | 68.604 | 1.00 | 19.30 |
| ATOM | 106 | CA | ARG | 84 | 42.994 | 52.461 | 69.656 | 1.00 | 21.26 |
| ATOM | 107 | CB | ARG | 84 | 43.473 | 53.271 | 70.871 | 1.00 | 22.61 |
| ATOM | 108 | CG | ARG | 84 | 42.506 | 54.308 | 71.400 | 1.00 | 24.22 |
| ATOM | 109 | CD | ARG | 84 | 43.054 | 54.955 | 72.673 | 1.00 | 24.57 |
| ATOM | 110 | NE | ARG | 84 | 44.153 | 55.891 | 72.435 | 1.00 | 24.09 |
| ATOM | 111 | CZ | ARG | 84 | 44.020 | 57.216 | 72.424 | 1.00 | 22.92 |
| ATOM | 112 | NH1 | ARG | 84 | 42.833 | 57.772 | 72.633 | 1.00 | 23.01 |
| ATOM | 113 | NH2 | ARG | 84 | 45.078 | 57.990 | 72.228 | 1.00 | 22.71 |
| ATOM | 114 | C | ARG | 84 | 41.987 | 51.395 | 70.075 | 1.00 | 19.10 |
| ATOM | 115 | O | ARG | 84 | 42.372 | 50.264 | 70.352 | 1.00 | 17.70 |
| ATOM | 116 | N | THR | 85 | 40.702 | 51.739 | 70.101 | 1.00 | 18.78 |
| ATOM | 117 | CA | THR | 85 | 39.685 | 50.762 | 70.482 | 1.00 | 18.36 |
| ATOM | 118 | CB | THR | 85 | 38.350 | 51.447 | 70.903 | 1.00 | 18.42 |
| ATOM | 119 | OG1 | THR | 85 | 37.846 | 52.253 | 69.829 | 1.00 | 18.84 |
| ATOM | 120 | CG2 | THR | 85 | 38.565 | 52.321 | 72.135 | 1.00 | 19.44 |
| ATOM | 121 | C | THR | 85 | 39.406 | 49.762 | 69.353 | 1.00 | 18.86 |
| ATOM | 122 | O | THR | 85 | 39.099 | 48.597 | 69.610 | 1.00 | 18.81 |
| ATOM | 123 | N | SER | 86 | 39.516 | 50.214 | 68.107 | 1.00 | 19.00 |
| ATOM | 124 | CA | SER | 86 | 39.269 | 49.338 | 66.962 | 1.00 | 19.38 |
| ATOM | 125 | CB | SER | 86 | 39.279 | 50.142 | 65.660 | 1.00 | 17.79 |
| ATOM | 126 | OG | SER | 86 | 38.175 | 51.031 | 65.605 | 1.00 | 18.69 |
| ATOM | 127 | C | SER | 86 | 40.305 | 48.219 | 66.885 | 1.00 | 20.96 |
| ATOM | 128 | O | SER | 86 | 39.966 | 47.060 | 66.630 | 1.00 | 21.64 |
| ATOM | 129 | N | GLN | 87 | 41.566 | 48.569 | 67.109 | 1.00 | 21.67 |
| ATOM | 130 | CA | GLN | 87 | 42.647 | 47.593 | 67.068 | 1.00 | 23.50 |
| ATOM | 131 | CB | GLN | 87 | 43.958 | 48.246 | 67.494 | 1.00 | 25.78 |
| ATOM | 132 | CG | GLN | 87 | 44.498 | 49.257 | 66.514 | 1.00 | 30.26 |
| ATOM | 133 | CD | GLN | 87 | 45.770 | 49.899 | 67.014 | 1.00 | 33.27 |
| ATOM | 134 | OE1 | GLN | 87 | 46.693 | 49.212 | 67.453 | 1.00 | 35.56 |
| ATOM | 135 | NE2 | GLN | 87 | 45.831 | 51.225 | 66.947 | 1.00 | 35.59 |
| ATOM | 136 | C | GLN | 87 | 42.370 | 46.401 | 67.978 | 1.00 | 23.44 |
| ATOM | 137 | O | GLN | 87 | 42.576 | 45.252 | 67.593 | 1.00 | 23.72 |
| ATOM | 138 | N | VAL | 88 | 41.908 | 46.684 | 69.190 | 1.00 | 23.72 |
| ATOM | 139 | CA | VAL | 88 | 41.616 | 45.635 | 70.154 | 1.00 | 22.98 |
| ATOM | 140 | CB | VAL | 88 | 41.316 | 46.234 | 71.546 | 1.00 | 24.62 |
| ATOM | 141 | CG1 | VAL | 88 | 41.060 | 45.114 | 72.549 | 1.00 | 24.67 |
| ATOM | 142 | CG2 | VAL | 88 | 42.486 | 47.102 | 72.004 | 1.00 | 23.17 |
| ATOM | 143 | C | VAL | 88 | 40.432 | 44.769 | 69.725 | 1.00 | 23.12 |
| ATOM | 144 | O | VAL | 88 | 40.536 | 43.543 | 69.672 | 1.00 | 21.83 |

TABLE B-continued

Co-ordinates of an underglycosylated tACEΔ36NJ ACE-lisinopril complex

| ATOM | 145 | N | VAL | 89 | 39.306 | 45.406 | 69.417 | 1.00 | 21.91 |
|---|---|---|---|---|---|---|---|---|---|
| ATOM | 146 | CA | VAL | 89 | 38.114 | 44.673 | 69.010 | 1.00 | 22.14 |
| ATOM | 147 | CB | VAL | 89 | 36.889 | 45.623 | 68.873 | 1.00 | 22.30 |
| ATOM | 148 | CG1 | VAL | 89 | 37.197 | 46.738 | 67.901 | 1.00 | 25.90 |
| ATOM | 149 | CG2 | VAL | 89 | 35.675 | 44.844 | 68.406 | 1.00 | 25.67 |
| ATOM | 150 | C | VAL | 89 | 38.317 | 43.904 | 67.700 | 1.00 | 21.76 |
| ATOM | 151 | O | VAL | 89 | 37.875 | 42.762 | 67.576 | 1.00 | 20.11 |
| ATOM | 152 | N | TRP | 90 | 38.980 | 44.526 | 66.728 | 1.00 | 21.83 |
| ATOM | 153 | CA | TRP | 90 | 39.224 | 43.868 | 65.448 | 1.00 | 22.98 |
| ATOM | 154 | CB | TRP | 90 | 39.759 | 44.873 | 64.419 | 1.00 | 24.28 |
| ATOM | 155 | CG | TRP | 90 | 38.739 | 45.905 | 63.988 | 1.00 | 28.97 |
| ATOM | 156 | CD2 | TRP | 90 | 38.805 | 46.752 | 62.832 | 1.00 | 30.58 |
| ATOM | 157 | CE2 | TRP | 90 | 37.665 | 47.586 | 62.859 | 1.00 | 31.50 |
| ATOM | 158 | CE3 | TRP | 90 | 39.717 | 46.890 | 61.777 | 1.00 | 31.93 |
| ATOM | 159 | CD1 | TRP | 90 | 37.593 | 46.250 | 64.645 | 1.00 | 30.90 |
| ATOM | 160 | NE1 | TRP | 90 | 36.943 | 47.257 | 63.975 | 1.00 | 30.56 |
| ATOM | 161 | CZ2 | TRP | 90 | 37.411 | 48.546 | 61.871 | 1.00 | 32.79 |
| ATOM | 162 | CZ3 | TRP | 90 | 39.464 | 47.847 | 60.792 | 1.00 | 33.43 |
| ATOM | 163 | CH2 | TRP | 90 | 38.319 | 48.662 | 60.850 | 1.00 | 32.95 |
| ATOM | 164 | C | TRP | 90 | 40.207 | 42.714 | 65.622 | 1.00 | 21.98 |
| ATOM | 165 | O | TRP | 90 | 40.089 | 41.692 | 64.957 | 1.00 | 22.45 |
| ATOM | 166 | N | ASN | 91 | 41.175 | 42.870 | 66.518 | 1.00 | 22.59 |
| ATOM | 167 | CA | ASN | 91 | 42.137 | 41.799 | 66.744 | 1.00 | 23.45 |
| ATOM | 168 | CB | ASN | 91 | 43.253 | 42.245 | 67.690 | 1.00 | 22.82 |
| ATOM | 169 | CG | ASN | 91 | 44.153 | 41.091 | 68.103 | 1.00 | 25.02 |
| ATOM | 170 | OD1 | ASN | 91 | 43.810 | 40.313 | 68.993 | 1.00 | 26.35 |
| ATOM | 171 | ND2 | ASN | 91 | 45.301 | 40.961 | 67.442 | 1.00 | 25.21 |
| ATOM | 172 | C | ASN | 91 | 41.434 | 40.577 | 67.321 | 1.00 | 24.29 |
| ATOM | 173 | O | ASN | 91 | 41.721 | 39.443 | 66.929 | 1.00 | 24.22 |
| ATOM | 174 | N | GLU | 92 | 40.511 | 40.813 | 68.249 | 1.00 | 23.78 |
| ATOM | 175 | CA | GLU | 92 | 39.767 | 39.726 | 68.863 | 1.00 | 24.44 |
| ATOM | 176 | CB | GLU | 92 | 38.940 | 40.242 | 70.046 | 1.00 | 27.98 |
| ATOM | 177 | CG | GLU | 92 | 39.655 | 40.108 | 71.386 | 1.00 | 32.87 |
| ATOM | 178 | CD | GLU | 92 | 38.998 | 40.903 | 72.502 | 1.00 | 33.99 |
| ATOM | 179 | OE1 | GLU | 92 | 37.797 | 40.691 | 72.771 | 1.00 | 36.12 |
| ATOM | 180 | OE2 | GLU | 92 | 39.690 | 41.740 | 73.116 | 1.00 | 35.60 |
| ATOM | 181 | C | GLU | 92 | 38.859 | 39.041 | 67.857 | 1.00 | 24.09 |
| ATOM | 182 | O | GLU | 92 | 38.731 | 37.817 | 67.867 | 1.00 | 25.43 |
| ATOM | 183 | N | TYR | 93 | 38.230 | 39.824 | 66.987 | 1.00 | 22.66 |
| ATOM | 184 | CA | TYR | 93 | 37.343 | 39.253 | 65.982 | 1.00 | 22.78 |
| ATOM | 185 | CB | TYR | 93 | 36.609 | 40.346 | 65.202 | 1.00 | 23.71 |
| ATOM | 186 | CG | TYR | 93 | 35.739 | 39.782 | 64.102 | 1.00 | 24.71 |
| ATOM | 187 | CD1 | TYR | 93 | 34.533 | 39.149 | 64.398 | 1.00 | 25.73 |
| ATOM | 188 | CE1 | TYR | 93 | 33.759 | 38.563 | 63.398 | 1.00 | 27.34 |
| ATOM | 189 | CD2 | TYR | 93 | 36.152 | 39.820 | 62.771 | 1.00 | 27.78 |
| ATOM | 190 | CE2 | TYR | 93 | 35.389 | 39.235 | 61.761 | 1.00 | 28.66 |
| ATOM | 191 | CZ | TYR | 93 | 34.194 | 38.608 | 62.083 | 1.00 | 28.76 |
| ATOM | 192 | OH | TYR | 93 | 33.441 | 38.020 | 61.093 | 1.00 | 30.77 |
| ATOM | 193 | C | TYR | 93 | 38.140 | 38.401 | 65.002 | 1.00 | 21.84 |
| ATOM | 194 | O | TYR | 93 | 37.705 | 37.319 | 64.608 | 1.00 | 20.79 |
| ATOM | 195 | N | ALA | 94 | 39.304 | 38.902 | 64.605 | 1.00 | 21.93 |
| ATOM | 196 | CA | ALA | 94 | 40.160 | 38.185 | 63.669 | 1.00 | 23.19 |
| ATOM | 197 | CB | ALA | 94 | 41.438 | 38.984 | 63.415 | 1.00 | 21.92 |
| ATOM | 198 | C | ALA | 94 | 40.501 | 36.803 | 64.223 | 1.00 | 22.67 |
| ATOM | 199 | O | ALA | 94 | 40.570 | 35.824 | 63.480 | 1.00 | 23.01 |
| ATOM | 200 | N | ALA | 95 | 40.701 | 36.733 | 65.536 | 1.00 | 24.22 |
| ATOM | 201 | CA | ALA | 95 | 41.041 | 35.482 | 66.210 | 1.00 | 24.36 |
| ATOM | 202 | CB | ALA | 95 | 41.354 | 35.757 | 67.676 | 1.00 | 28.15 |
| ATOM | 203 | C | ALA | 95 | 39.922 | 34.455 | 66.105 | 1.00 | 24.75 |
| ATOM | 204 | O | ALA | 95 | 40.147 | 33.311 | 65.707 | 1.00 | 25.33 |
| ATOM | 205 | N | ALA | 96 | 38.715 | 34.867 | 66.474 | 1.00 | 24.39 |
| ATOM | 206 | CA | ALA | 96 | 37.563 | 33.978 | 66.421 | 1.00 | 24.27 |
| ATOM | 207 | CB | ALA | 96 | 36.350 | 34.670 | 67.026 | 1.00 | 23.28 |
| ATOM | 208 | C | ALA | 96 | 37.266 | 33.552 | 64.984 | 1.00 | 23.78 |
| ATOM | 209 | O | ALA | 96 | 36.898 | 32.403 | 64.724 | 1.00 | 23.70 |
| ATOM | 210 | N | ASN | 97 | 37.426 | 34.483 | 64.051 | 1.00 | 21.38 |
| ATOM | 211 | CA | ASN | 97 | 37.162 | 34.200 | 62.647 | 1.00 | 22.12 |
| ATOM | 212 | CB | ASN | 97 | 37.224 | 35.506 | 61.845 | 1.00 | 20.92 |
| ATOM | 213 | CG | ASN | 97 | 36.706 | 35.353 | 60.433 | 1.00 | 22.34 |
| ATOM | 214 | OD1 | ASN | 97 | 35.908 | 34.459 | 60.140 | 1.00 | 20.62 |
| ATOM | 215 | ND2 | ASN | 97 | 37.144 | 36.243 | 59.548 | 1.00 | 20.25 |
| ATOM | 216 | C | ASN | 97 | 38.192 | 33.189 | 62.142 | 1.00 | 21.72 |
| ATOM | 217 | O | ASN | 97 | 37.863 | 32.270 | 61.393 | 1.00 | 21.75 |
| ATOM | 218 | N | TRP | 98 | 39.437 | 33.353 | 62.576 | 1.00 | 21.37 |
| ATOM | 219 | CA | TRP | 98 | 40.502 | 32.449 | 62.172 | 1.00 | 23.30 |
| ATOM | 220 | CB | TRP | 98 | 41.856 | 32.963 | 62.676 | 1.00 | 21.74 |
| ATOM | 221 | CG | TRP | 98 | 42.995 | 32.002 | 62.444 | 1.00 | 23.76 |
| ATOM | 222 | CD2 | TRP | 98 | 43.871 | 31.960 | 61.305 | 1.00 | 22.12 |

TABLE B-continued

Co-ordinates of an underglycosylated tACEΔ36NJ ACE-lisinopril complex

| ATOM | 223 | CE2 | TRP | 98 | 44.772 | 30.891 | 61.510 | 1.00 | 23.47 |
|------|-----|-----|-----|-----|--------|--------|--------|------|-------|
| ATOM | 224 | CE3 | TRP | 98 | 43.979 | 32.720 | 60.131 | 1.00 | 21.74 |
| ATOM | 225 | CD1 | TRP | 98 | 43.390 | 30.985 | 63.266 | 1.00 | 23.18 |
| ATOM | 226 | NE1 | TRP | 98 | 44.456 | 30.314 | 62.712 | 1.00 | 24.63 |
| ATOM | 227 | CZ2 | TRP | 98 | 45.772 | 30.562 | 60.584 | 1.00 | 21.94 |
| ATOM | 228 | CZ3 | TRP | 98 | 44.973 | 32.392 | 59.209 | 1.00 | 20.39 |
| ATOM | 229 | CH2 | TRP | 98 | 45.856 | 31.320 | 59.444 | 1.00 | 20.85 |
| ATOM | 230 | C | TRP | 98 | 40.251 | 31.041 | 62.702 | 1.00 | 23.90 |
| ATOM | 231 | O | TRP | 98 | 40.306 | 30.061 | 61.953 | 1.00 | 21.48 |
| ATOM | 232 | N | ASN | 99 | 39.963 | 30.945 | 63.997 | 1.00 | 25.31 |
| ATOM | 233 | CA | ASN | 99 | 39.716 | 29.648 | 64.619 | 1.00 | 24.92 |
| ATOM | 234 | CB | ASN | 99 | 39.393 | 29.820 | 66.103 | 1.00 | 24.71 |
| ATOM | 235 | CG | ASN | 99 | 40.545 | 30.430 | 66.874 | 1.00 | 25.68 |
| ATOM | 236 | OD1 | ASN | 99 | 41.690 | 30.397 | 66.423 | 1.00 | 26.00 |
| ATOM | 237 | ND2 | ASN | 99 | 40.252 | 30.980 | 68.046 | 1.00 | 25.62 |
| ATOM | 238 | C | ASN | 99 | 38.594 | 28.901 | 63.922 | 1.00 | 24.14 |
| ATOM | 239 | O | ASN | 99 | 38.627 | 27.674 | 63.820 | 1.00 | 24.01 |
| ATOM | 240 | N | TYR | 100 | 37.600 | 29.633 | 63.433 | 1.00 | 23.70 |
| ATOM | 241 | CA | TYR | 100 | 36.504 | 28.978 | 62.738 | 1.00 | 23.65 |
| ATOM | 242 | CB | TYR | 100 | 35.312 | 29.912 | 62.567 | 1.00 | 27.83 |
| ATOM | 243 | CG | TYR | 100 | 34.175 | 29.198 | 61.890 | 1.00 | 30.19 |
| ATOM | 244 | CD1 | TYR | 100 | 33.577 | 28.097 | 62.496 | 1.00 | 31.92 |
| ATOM | 245 | CE1 | TYR | 100 | 32.587 | 27.378 | 61.856 | 1.00 | 35.09 |
| ATOM | 246 | CD2 | TYR | 100 | 33.746 | 29.567 | 60.617 | 1.00 | 32.59 |
| ATOM | 247 | CE2 | TYR | 100 | 32.746 | 28.848 | 59.961 | 1.00 | 33.60 |
| ATOM | 248 | CZ | TYR | 100 | 32.173 | 27.755 | 60.591 | 1.00 | 34.32 |
| ATOM | 249 | OH | TYR | 100 | 31.182 | 27.031 | 59.973 | 1.00 | 36.77 |
| ATOM | 250 | C | TYR | 100 | 36.943 | 28.492 | 61.360 | 1.00 | 22.55 |
| ATOM | 251 | O | TYR | 100 | 36.656 | 27.362 | 60.971 | 1.00 | 20.86 |
| ATOM | 252 | N | ASN | 101 | 37.628 | 29.360 | 60.622 | 1.00 | 21.15 |
| ATOM | 253 | CA | ASN | 101 | 38.114 | 29.029 | 59.286 | 1.00 | 20.76 |
| ATOM | 254 | CB | ASN | 101 | 38.798 | 30.251 | 58.655 | 1.00 | 19.09 |
| ATOM | 255 | CG | ASN | 101 | 37.838 | 31.110 | 57.853 | 1.00 | 18.55 |
| ATOM | 256 | OD1 | ASN | 101 | 37.829 | 31.067 | 56.624 | 1.00 | 19.63 |
| ATOM | 257 | ND2 | ASN | 101 | 37.018 | 31.892 | 58.546 | 1.00 | 18.23 |
| ATOM | 258 | C | ASN | 101 | 39.089 | 27.852 | 59.295 | 1.00 | 20.96 |
| ATOM | 259 | O | ASN | 101 | 39.149 | 27.084 | 58.332 | 1.00 | 21.16 |
| ATOM | 260 | N | THR | 102 | 39.851 | 27.714 | 60.378 | 1.00 | 19.64 |
| ATOM | 261 | CA | THR | 102 | 40.826 | 26.635 | 60.488 | 1.00 | 19.80 |
| ATOM | 262 | CB | THR | 102 | 42.158 | 27.152 | 61.056 | 1.00 | 18.90 |
| ATOM | 263 | OG1 | THR | 102 | 41.937 | 27.725 | 62.347 | 1.00 | 19.19 |
| ATOM | 264 | CG2 | THR | 102 | 42.756 | 28.207 | 60.137 | 1.00 | 21.98 |
| ATOM | 265 | C | THR | 102 | 40.356 | 25.450 | 61.339 | 1.00 | 21.84 |
| ATOM | 266 | O | THR | 102 | 41.139 | 24.549 | 61.642 | 1.00 | 21.38 |
| ATOM | 267 | N | ASN | 103 | 39.084 | 25.454 | 61.724 | 1.00 | 22.72 |
| ATOM | 268 | CA | ASN | 103 | 38.514 | 24.365 | 62.518 | 1.00 | 24.63 |
| ATOM | 269 | CB | ASN | 103 | 39.149 | 24.313 | 63.919 | 1.00 | 26.53 |
| ATOM | 270 | CG | ASN | 103 | 38.705 | 23.085 | 64.720 | 1.00 | 29.25 |
| ATOM | 271 | OD1 | ASN | 103 | 38.126 | 22.147 | 64.171 | 1.00 | 29.00 |
| ATOM | 272 | ND2 | ASN | 103 | 38.989 | 23.088 | 66.020 | 1.00 | 31.72 |
| ATOM | 273 | C | ASN | 103 | 37.012 | 24.567 | 62.626 | 1.00 | 23.73 |
| ATOM | 274 | O | ASN | 103 | 36.502 | 25.032 | 63.643 | 1.00 | 24.12 |
| ATOM | 275 | N | ILE | 104 | 36.313 | 24.224 | 61.551 | 1.00 | 25.67 |
| ATOM | 276 | CA | ILE | 104 | 34.867 | 24.367 | 61.489 | 1.00 | 27.61 |
| ATOM | 277 | CB | ILE | 104 | 34.338 | 24.109 | 60.059 | 1.00 | 28.22 |
| ATOM | 278 | CG2 | ILE | 104 | 32.821 | 24.281 | 60.027 | 1.00 | 29.99 |
| ATOM | 279 | CG1 | ILE | 104 | 35.005 | 25.069 | 59.072 | 1.00 | 29.22 |
| ATOM | 280 | CD1 | ILE | 104 | 34.560 | 24.879 | 57.626 | 1.00 | 29.37 |
| ATOM | 281 | C | ILE | 104 | 34.169 | 23.403 | 62.439 | 1.00 | 28.58 |
| ATOM | 282 | O | ILE | 104 | 34.079 | 22.207 | 62.168 | 1.00 | 28.13 |
| ATOM | 283 | N | THR | 105 | 33.683 | 23.936 | 63.555 | 1.00 | 30.58 |
| ATOM | 284 | CA | THR | 105 | 32.968 | 23.143 | 64.549 | 1.00 | 31.89 |
| ATOM | 285 | CB | THR | 105 | 33.843 | 22.821 | 65.775 | 1.00 | 31.98 |
| ATOM | 286 | OG1 | THR | 105 | 34.107 | 24.026 | 66.506 | 1.00 | 33.11 |
| ATOM | 287 | CG2 | THR | 105 | 35.162 | 22.194 | 65.341 | 1.00 | 32.86 |
| ATOM | 288 | C | THR | 105 | 31.783 | 23.971 | 65.017 | 1.00 | 32.44 |
| ATOM | 289 | O | THR | 105 | 31.752 | 25.188 | 64.827 | 1.00 | 32.52 |
| ATOM | 290 | N | THR | 106 | 30.803 | 23.319 | 65.623 | 1.00 | 33.00 |
| ATOM | 291 | CA | THR | 106 | 29.640 | 24.044 | 66.109 | 1.00 | 33.81 |
| ATOM | 292 | CB | THR | 106 | 28.570 | 23.072 | 66.662 | 1.00 | 34.97 |
| ATOM | 293 | OG1 | THR | 106 | 27.463 | 23.818 | 67.184 | 1.00 | 37.98 |
| ATOM | 294 | CG2 | THR | 106 | 29.155 | 22.199 | 67.752 | 1.00 | 34.76 |
| ATOM | 295 | C | THR | 106 | 30.093 | 25.020 | 67.198 | 1.00 | 32.47 |
| ATOM | 296 | O | THR | 106 | 29.512 | 26.094 | 67.361 | 1.00 | 31.96 |
| ATOM | 297 | N | GLU | 107 | 31.153 | 24.655 | 67.917 | 1.00 | 31.54 |
| ATOM | 298 | CA | GLU | 107 | 31.687 | 25.501 | 68.985 | 1.00 | 32.42 |
| ATOM | 299 | CB | GLU | 107 | 32.731 | 24.740 | 69.809 | 1.00 | 34.68 |
| ATOM | 300 | CG | GLU | 107 | 32.272 | 23.390 | 70.349 | 1.00 | 40.20 |

TABLE B-continued

Co-ordinates of an underglycosylated tACEΔ36NJ ACE-lisinopril complex

| ATOM | 301 | CD | GLU | 107 | 32.542 | 22.243 | 69.385 | 1.00 | 42.52 |
|---|---|---|---|---|---|---|---|---|---|
| ATOM | 302 | OE1 | GLU | 107 | 31.917 | 22.202 | 68.304 | 1.00 | 44.41 |
| ATOM | 303 | OE2 | GLU | 107 | 33.390 | 21.383 | 69.710 | 1.00 | 44.47 |
| ATOM | 304 | C | GLU | 107 | 32.327 | 26.783 | 68.445 | 1.00 | 31.96 |
| ATOM | 305 | O | GLU | 107 | 31.980 | 27.883 | 68.875 | 1.00 | 31.54 |
| ATOM | 306 | N | THR | 108 | 33.272 | 26.641 | 67.516 | 1.00 | 30.47 |
| ATOM | 307 | CA | THR | 108 | 33.935 | 27.807 | 66.939 | 1.00 | 29.64 |
| ATOM | 308 | CB | THR | 108 | 35.056 | 27.402 | 65.946 | 1.00 | 29.18 |
| ATOM | 309 | OG1 | THR | 108 | 34.534 | 26.500 | 64.964 | 1.00 | 30.34 |
| ATOM | 310 | CG2 | THR | 108 | 36.210 | 26.741 | 66.683 | 1.00 | 26.97 |
| ATOM | 311 | C | THR | 108 | 32.916 | 28.689 | 66.219 | 1.00 | 29.12 |
| ATOM | 312 | O | THR | 108 | 33.050 | 29.911 | 66.201 | 1.00 | 29.17 |
| ATOM | 313 | N | SER | 109 | 31.895 | 28.069 | 65.631 | 1.00 | 28.85 |
| ATOM | 314 | CA | SER | 109 | 30.851 | 28.822 | 64.937 | 1.00 | 29.69 |
| ATOM | 315 | CB | SER | 109 | 29.809 | 27.885 | 64.321 | 1.00 | 29.41 |
| ATOM | 316 | OG | SER | 109 | 30.254 | 27.336 | 63.098 | 1.00 | 31.41 |
| ATOM | 317 | C | SER | 109 | 30.144 | 29.737 | 65.923 | 1.00 | 30.53 |
| ATOM | 318 | O | SER | 109 | 29.992 | 30.936 | 65.679 | 1.00 | 27.87 |
| ATOM | 319 | N | LYS | 110 | 29.715 | 29.150 | 67.036 | 1.00 | 31.92 |
| ATOM | 320 | CA | LYS | 110 | 29.002 | 29.876 | 68.077 | 1.00 | 33.73 |
| ATOM | 321 | CB | LYS | 110 | 28.653 | 28.927 | 69.229 | 1.00 | 35.14 |
| ATOM | 322 | CG | LYS | 110 | 27.472 | 29.384 | 70.080 | 1.00 | 38.08 |
| ATOM | 323 | CD | LYS | 110 | 27.054 | 28.310 | 71.080 | 1.00 | 39.49 |
| ATOM | 324 | CE | LYS | 110 | 25.706 | 28.637 | 71.707 | 1.00 | 40.76 |
| ATOM | 325 | NZ | LYS | 110 | 25.254 | 27.575 | 72.650 | 1.00 | 40.35 |
| ATOM | 326 | C | LYS | 110 | 29.820 | 31.053 | 68.595 | 1.00 | 32.96 |
| ATOM | 327 | O | LYS | 110 | 29.301 | 32.157 | 68.747 | 1.00 | 33.66 |
| ATOM | 328 | N | ILE | 111 | 31.101 | 30.820 | 68.858 | 1.00 | 32.50 |
| ATOM | 329 | CA | ILE | 111 | 31.972 | 31.876 | 69.357 | 1.00 | 31.17 |
| ATOM | 330 | CB | ILE | 111 | 33.354 | 31.318 | 69.722 | 1.00 | 30.98 |
| ATOM | 331 | CG2 | ILE | 111 | 34.278 | 32.448 | 70.166 | 1.00 | 29.81 |
| ATOM | 332 | CG1 | ILE | 111 | 33.205 | 30.271 | 70.828 | 1.00 | 31.92 |
| ATOM | 333 | CD1 | ILE | 111 | 34.494 | 29.560 | 71.183 | 1.00 | 31.87 |
| ATOM | 334 | C | ILE | 111 | 32.138 | 33.002 | 68.334 | 1.00 | 30.85 |
| ATOM | 335 | O | ILE | 111 | 32.164 | 34.180 | 68.693 | 1.00 | 31.16 |
| ATOM | 336 | N | LEU | 112 | 32.247 | 32.635 | 67.061 | 1.00 | 29.75 |
| ATOM | 337 | CA | LEU | 112 | 32.404 | 33.629 | 66.007 | 1.00 | 28.55 |
| ATOM | 338 | CB | LEU | 112 | 32.644 | 32.948 | 64.656 | 1.00 | 27.63 |
| ATOM | 339 | CG | LEU | 112 | 32.720 | 33.872 | 63.430 | 1.00 | 26.14 |
| ATOM | 340 | CD1 | LEU | 112 | 33.789 | 34.938 | 63.643 | 1.00 | 22.46 |
| ATOM | 341 | CD2 | LEU | 112 | 33.021 | 33.046 | 62.187 | 1.00 | 24.13 |
| ATOM | 342 | C | LEU | 112 | 31.178 | 34.529 | 65.917 | 1.00 | 29.28 |
| ATOM | 343 | O | LEU | 112 | 31.303 | 35.754 | 65.907 | 1.00 | 29.00 |
| ATOM | 344 | N | LEU | 113 | 29.997 | 33.921 | 65.853 | 1.00 | 29.16 |
| ATOM | 345 | CA | LEU | 113 | 28.754 | 34.680 | 65.761 | 1.00 | 29.91 |
| ATOM | 346 | CB | LEU | 113 | 27.552 | 33.730 | 65.669 | 1.00 | 29.27 |
| ATOM | 347 | CG | LEU | 113 | 27.451 | 32.874 | 64.397 | 1.00 | 29.32 |
| ATOM | 348 | CD1 | LEU | 113 | 26.281 | 31.905 | 64.514 | 1.00 | 30.07 |
| ATOM | 349 | CD2 | LEU | 113 | 27.279 | 33.777 | 63.179 | 1.00 | 29.18 |
| ATOM | 350 | C | LEU | 113 | 28.590 | 35.624 | 66.950 | 1.00 | 31.04 |
| ATOM | 351 | O | LEU | 113 | 27.976 | 36.685 | 66.831 | 1.00 | 30.89 |
| ATOM | 352 | N | GLN | 114 | 29.143 | 35.234 | 68.095 | 1.00 | 32.01 |
| ATOM | 353 | CA | GLN | 114 | 29.074 | 36.057 | 69.297 | 1.00 | 33.69 |
| ATOM | 354 | CB | GLN | 114 | 29.403 | 35.218 | 70.537 | 1.00 | 35.55 |
| ATOM | 355 | CG | GLN | 114 | 28.383 | 34.113 | 70.801 | 1.00 | 40.14 |
| ATOM | 356 | CD | GLN | 114 | 28.764 | 33.207 | 71.960 | 1.00 | 43.52 |
| ATOM | 357 | OE1 | GLN | 114 | 28.850 | 33.644 | 73.110 | 1.00 | 44.43 |
| ATOM | 358 | NE2 | GLN | 114 | 28.996 | 31.932 | 71.658 | 1.00 | 44.83 |
| ATOM | 359 | C | GLN | 114 | 30.060 | 37.208 | 69.157 | 1.00 | 33.40 |
| ATOM | 360 | O | GLN | 114 | 29.773 | 38.336 | 69.555 | 1.00 | 32.65 |
| ATOM | 361 | N | LYS | 115 | 31.224 | 36.918 | 68.587 | 1.00 | 33.87 |
| ATOM | 362 | CA | LYS | 115 | 32.235 | 37.944 | 68.369 | 1.00 | 33.82 |
| ATOM | 363 | CB | LYS | 115 | 33.547 | 37.318 | 67.889 | 1.00 | 36.05 |
| ATOM | 364 | CG | LYS | 115 | 34.622 | 37.276 | 68.960 | 1.00 | 39.80 |
| ATOM | 365 | CD | LYS | 115 | 34.924 | 38.684 | 69.443 | 1.00 | 42.99 |
| ATOM | 366 | CE | LYS | 115 | 35.903 | 38.699 | 70.598 | 1.00 | 45.69 |
| ATOM | 367 | NZ | LYS | 115 | 36.078 | 40.092 | 71.099 | 1.00 | 48.43 |
| ATOM | 368 | C | LYS | 115 | 31.718 | 38.937 | 67.335 | 1.00 | 32.81 |
| ATOM | 369 | O | LYS | 115 | 32.132 | 40.094 | 67.310 | 1.00 | 30.93 |
| ATOM | 370 | N | ASN | 116 | 30.813 | 38.472 | 66.480 | 1.00 | 32.71 |
| ATOM | 371 | CA | ASN | 116 | 30.215 | 39.325 | 65.458 | 1.00 | 33.77 |
| ATOM | 372 | CB | ASN | 116 | 29.223 | 38.530 | 64.602 | 1.00 | 34.22 |
| ATOM | 373 | CG | ASN | 116 | 29.855 | 37.950 | 63.356 | 1.00 | 35.11 |
| ATOM | 374 | OD1 | ASN | 116 | 30.356 | 38.683 | 62.502 | 1.00 | 35.08 |
| ATOM | 375 | ND2 | ASN | 116 | 29.827 | 36.627 | 63.239 | 1.00 | 37.76 |
| ATOM | 376 | C | ASN | 116 | 29.465 | 40.459 | 66.146 | 1.00 | 33.07 |
| ATOM | 377 | O | ASN | 116 | 29.675 | 41.632 | 65.847 | 1.00 | 32.40 |
| ATOM | 378 | N | MET | 117 | 28.586 | 40.086 | 67.070 | 1.00 | 33.09 |

TABLE B-continued

Co-ordinates of an underglycosylated tACEΔ36NJ ACE-lisinopril complex

| ATOM | 379 | CA | MET | 117 | 27.783 | 41.044 | 67.812 | 1.00 | 32.98 |
|------|-----|-----|-----|-----|--------|--------|--------|------|-------|
| ATOM | 380 | CB | MET | 117 | 26.843 | 40.299 | 68.764 | 1.00 | 34.71 |
| ATOM | 381 | CG | MET | 117 | 25.382 | 40.289 | 68.317 | 1.00 | 39.02 |
| ATOM | 382 | SD | MET | 117 | 25.127 | 39.995 | 66.544 | 1.00 | 41.96 |
| ATOM | 383 | CE | MET | 117 | 23.347 | 40.015 | 66.451 | 1.00 | 41.75 |
| ATOM | 384 | C | MET | 117 | 28.638 | 42.039 | 68.585 | 1.00 | 31.36 |
| ATOM | 385 | O | MET | 117 | 28.287 | 43.212 | 68.697 | 1.00 | 29.55 |
| ATOM | 386 | N | GLN | 118 | 29.768 | 41.576 | 69.106 | 1.00 | 31.05 |
| ATOM | 387 | CA | GLN | 118 | 30.653 | 42.447 | 69.868 | 1.00 | 31.16 |
| ATOM | 388 | CB | GLN | 118 | 31.741 | 41.625 | 70.563 | 1.00 | 34.52 |
| ATOM | 389 | CG | GLN | 118 | 31.195 | 40.567 | 71.509 | 1.00 | 38.71 |
| ATOM | 390 | CD | GLN | 118 | 32.270 | 39.974 | 72.402 | 1.00 | 41.62 |
| ATOM | 391 | OE1 | GLN | 118 | 33.294 | 39.485 | 71.922 | 1.00 | 43.74 |
| ATOM | 392 | NE2 | GLN | 118 | 32.039 | 40.013 | 73.711 | 1.00 | 42.41 |
| ATOM | 393 | C | GLN | 118 | 31.298 | 43.519 | 68.999 | 1.00 | 29.23 |
| ATOM | 394 | O | GLN | 118 | 31.318 | 44.698 | 69.365 | 1.00 | 28.92 |
| ATOM | 395 | N | ILE | 119 | 31.822 | 43.120 | 67.846 | 1.00 | 25.46 |
| ATOM | 396 | CA | ILE | 119 | 32.457 | 44.081 | 66.957 | 1.00 | 24.61 |
| ATOM | 397 | CB | ILE | 119 | 33.281 | 43.365 | 65.853 | 1.00 | 25.09 |
| ATOM | 398 | CG2 | ILE | 119 | 32.362 | 42.581 | 64.923 | 1.00 | 24.21 |
| ATOM | 399 | CG1 | ILE | 119 | 34.096 | 44.392 | 65.071 | 1.00 | 25.85 |
| ATOM | 400 | CD1 | ILE | 119 | 35.175 | 43.779 | 64.208 | 1.00 | 26.22 |
| ATOM | 401 | C | ILE | 119 | 31.401 | 44.995 | 66.329 | 1.00 | 22.47 |
| ATOM | 402 | O | ILE | 119 | 31.674 | 46.153 | 66.003 | 1.00 | 22.00 |
| ATOM | 403 | N | ALA | 120 | 30.187 | 44.481 | 66.171 | 1.00 | 21.10 |
| ATOM | 404 | CA | ALA | 120 | 29.109 | 45.283 | 65.599 | 1.00 | 22.02 |
| ATOM | 405 | CB | ALA | 120 | 27.902 | 44.401 | 65.294 | 1.00 | 20.08 |
| ATOM | 406 | C | ALA | 120 | 28.734 | 46.359 | 66.616 | 1.00 | 22.84 |
| ATOM | 407 | O | ALA | 120 | 28.410 | 47.490 | 66.264 | 1.00 | 22.93 |
| ATOM | 408 | N | ASN | 121 | 28.790 | 45.987 | 67.888 | 1.00 | 21.65 |
| ATOM | 409 | CA | ASN | 121 | 28.468 | 46.901 | 68.970 | 1.00 | 23.13 |
| ATOM | 410 | CB | ASN | 121 | 28.572 | 46.166 | 70.300 | 1.00 | 27.59 |
| ATOM | 411 | CG | ASN | 121 | 27.649 | 46.732 | 71.342 | 1.00 | 34.63 |
| ATOM | 412 | OD1 | ASN | 121 | 28.016 | 47.635 | 72.096 | 1.00 | 39.08 |
| ATOM | 413 | ND2 | ASN | 121 | 26.427 | 46.206 | 71.389 | 1.00 | 38.10 |
| ATOM | 414 | C | ASN | 121 | 29.428 | 48.086 | 68.951 | 1.00 | 21.02 |
| ATOM | 415 | O | ASN | 121 | 29.020 | 49.241 | 69.101 | 1.00 | 20.93 |
| ATOM | 416 | N | HIS | 122 | 30.710 | 47.789 | 68.776 | 1.00 | 17.91 |
| ATOM | 417 | CA | HIS | 122 | 31.739 | 48.817 | 68.716 | 1.00 | 17.11 |
| ATOM | 418 | CB | HIS | 122 | 33.122 | 48.152 | 68.661 | 1.00 | 15.18 |
| ATOM | 419 | CG | HIS | 122 | 34.235 | 49.093 | 68.327 | 1.00 | 16.93 |
| ATOM | 420 | CD2 | HIS | 122 | 35.035 | 49.844 | 69.119 | 1.00 | 15.16 |
| ATOM | 421 | ND1 | HIS | 122 | 34.617 | 49.363 | 67.031 | 1.00 | 18.07 |
| ATOM | 422 | CE1 | HIS | 122 | 35.606 | 50.240 | 67.041 | 1.00 | 18.19 |
| ATOM | 423 | NE2 | HIS | 122 | 35.879 | 50.547 | 68.296 | 1.00 | 15.55 |
| ATOM | 424 | C | HIS | 122 | 31.520 | 49.698 | 67.487 | 1.00 | 17.81 |
| ATOM | 425 | O | HIS | 122 | 31.628 | 50.925 | 67.556 | 1.00 | 18.93 |
| ATOM | 426 | N | THR | 123 | 31.213 | 49.066 | 66.360 | 1.00 | 17.71 |
| ATOM | 427 | CA | THR | 123 | 30.983 | 49.794 | 65.117 | 1.00 | 18.02 |
| ATOM | 428 | CB | THR | 123 | 30.700 | 48.823 | 63.956 | 1.00 | 17.98 |
| ATOM | 429 | OG1 | THR | 123 | 31.807 | 47.926 | 63.810 | 1.00 | 16.69 |
| ATOM | 430 | CG2 | THR | 123 | 30.494 | 49.591 | 62.646 | 1.00 | 18.45 |
| ATOM | 431 | C | THR | 123 | 29.808 | 50.758 | 65.260 | 1.00 | 18.44 |
| ATOM | 432 | O | THR | 123 | 29.872 | 51.903 | 64.817 | 1.00 | 18.36 |
| ATOM | 433 | N | LEU | 124 | 28.737 | 50.292 | 65.886 | 1.00 | 19.48 |
| ATOM | 434 | CA | LEU | 124 | 27.556 | 51.123 | 66.083 | 1.00 | 21.69 |
| ATOM | 435 | CB | LEU | 124 | 26.407 | 50.264 | 66.625 | 1.00 | 22.76 |
| ATOM | 436 | CG | LEU | 124 | 25.009 | 50.870 | 66.792 | 1.00 | 25.84 |
| ATOM | 437 | CD1 | LEU | 124 | 24.634 | 51.743 | 65.596 | 1.00 | 26.67 |
| ATOM | 438 | CD2 | LEU | 124 | 24.015 | 49.731 | 66.952 | 1.00 | 28.14 |
| ATOM | 439 | C | LEU | 124 | 27.849 | 52.293 | 67.028 | 1.00 | 22.10 |
| ATOM | 440 | O | LEU | 124 | 27.395 | 53.414 | 66.805 | 1.00 | 22.48 |
| ATOM | 441 | N | LYS | 125 | 28.619 | 52.029 | 68.077 | 1.00 | 21.30 |
| ATOM | 442 | CA | LYS | 125 | 28.968 | 53.061 | 69.044 | 1.00 | 21.15 |
| ATOM | 443 | CB | LYS | 125 | 29.826 | 52.468 | 70.165 | 1.00 | 22.88 |
| ATOM | 444 | CG | LYS | 125 | 30.218 | 53.462 | 71.247 | 1.00 | 24.84 |
| ATOM | 445 | CD | LYS | 125 | 31.157 | 52.829 | 72.267 | 1.00 | 27.95 |
| ATOM | 446 | CE | LYS | 125 | 31.480 | 53.799 | 73.392 | 1.00 | 30.77 |
| ATOM | 447 | NZ | LYS | 125 | 31.992 | 55.102 | 72.875 | 1.00 | 33.91 |
| ATOM | 448 | C | LYS | 125 | 29.727 | 54.203 | 68.377 | 1.00 | 20.96 |
| ATOM | 449 | O | LYS | 125 | 29.344 | 55.367 | 68.492 | 1.00 | 20.95 |
| ATOM | 450 | N | TYR | 126 | 30.805 | 53.869 | 67.675 | 1.00 | 18.64 |
| ATOM | 451 | CA | TYR | 126 | 31.598 | 54.893 | 67.020 | 1.00 | 17.79 |
| ATOM | 452 | CB | TYR | 126 | 33.026 | 54.388 | 66.782 | 1.00 | 18.37 |
| ATOM | 453 | CG | TYR | 126 | 33.817 | 54.315 | 68.071 | 1.00 | 20.45 |
| ATOM | 454 | CD1 | TYR | 126 | 33.687 | 53.226 | 68.934 | 1.00 | 20.37 |
| ATOM | 455 | CE1 | TYR | 126 | 34.326 | 53.209 | 70.171 | 1.00 | 21.90 |
| ATOM | 456 | CD2 | TYR | 126 | 34.618 | 55.383 | 68.476 | 1.00 | 20.13 |

TABLE B-continued

Co-ordinates of an underglycosylated tACEΔ36NJ ACE-lisinopril complex

| ATOM | 457 | CE2 | TYR | 126 | 35.260 | 55.376 | 69.710 | 1.00 | 21.70 |
|------|-----|-----|-----|-----|--------|--------|--------|------|-------|
| ATOM | 458 | CZ | TYR | 126 | 35.107 | 54.290 | 70.552 | 1.00 | 21.90 |
| ATOM | 459 | OH | TYR | 126 | 35.717 | 54.301 | 71.783 | 1.00 | 22.74 |
| ATOM | 460 | C | TYR | 126 | 30.983 | 55.411 | 65.733 | 1.00 | 16.79 |
| ATOM | 461 | O | TYR | 126 | 31.168 | 56.573 | 65.383 | 1.00 | 17.06 |
| ATOM | 462 | N | GLY | 127 | 30.239 | 54.554 | 65.038 | 1.00 | 17.21 |
| ATOM | 463 | CA | GLY | 127 | 29.596 | 54.977 | 63.806 | 1.00 | 16.33 |
| ATOM | 464 | C | GLY | 127 | 28.534 | 56.020 | 64.099 | 1.00 | 17.87 |
| ATOM | 465 | O | GLY | 127 | 28.366 | 56.984 | 63.351 | 1.00 | 17.27 |
| ATOM | 466 | N | THR | 128 | 27.815 | 55.825 | 65.199 | 1.00 | 17.84 |
| ATOM | 467 | CA | THR | 128 | 26.774 | 56.759 | 65.607 | 1.00 | 19.72 |
| ATOM | 468 | CB | THR | 128 | 25.997 | 56.216 | 66.826 | 1.00 | 19.70 |
| ATOM | 469 | OG1 | THR | 128 | 25.413 | 54.951 | 66.487 | 1.00 | 21.12 |
| ATOM | 470 | CG2 | THR | 128 | 24.896 | 57.188 | 67.244 | 1.00 | 20.40 |
| ATOM | 471 | C | THR | 128 | 27.409 | 58.107 | 65.958 | 1.00 | 20.53 |
| ATOM | 472 | O | THR | 128 | 26.887 | 59.161 | 65.599 | 1.00 | 20.68 |
| ATOM | 473 | N | GLN | 129 | 28.542 | 58.064 | 66.655 | 1.00 | 21.83 |
| ATOM | 474 | CA | GLN | 129 | 29.262 | 59.280 | 67.038 | 1.00 | 21.59 |
| ATOM | 475 | CB | GLN | 129 | 30.455 | 58.939 | 67.938 | 1.00 | 26.47 |
| ATOM | 476 | CG | GLN | 129 | 30.215 | 59.095 | 69.432 | 1.00 | 31.89 |
| ATOM | 477 | CD | GLN | 129 | 31.440 | 58.719 | 70.262 | 1.00 | 34.85 |
| ATOM | 478 | OE1 | GLN | 129 | 31.608 | 57.567 | 70.666 | 1.00 | 35.57 |
| ATOM | 479 | NE2 | GLN | 129 | 32.310 | 59.693 | 70.504 | 1.00 | 36.98 |
| ATOM | 480 | C | GLN | 129 | 29.781 | 60.020 | 65.810 | 1.00 | 20.77 |
| ATOM | 481 | O | GLN | 129 | 29.638 | 61.238 | 65.698 | 1.00 | 19.33 |
| ATOM | 482 | N | ALA | 130 | 30.389 | 59.270 | 64.896 | 1.00 | 18.52 |
| ATOM | 483 | CA | ALA | 130 | 30.956 | 59.831 | 63.673 | 1.00 | 17.79 |
| ATOM | 484 | CB | ALA | 130 | 31.622 | 58.722 | 62.858 | 1.00 | 17.56 |
| ATOM | 485 | C | ALA | 130 | 29.927 | 60.561 | 62.815 | 1.00 | 16.56 |
| ATOM | 486 | O | ALA | 130 | 30.245 | 61.547 | 62.156 | 1.00 | 16.12 |
| ATOM | 487 | N | ARG | 131 | 28.697 | 60.066 | 62.817 | 1.00 | 17.47 |
| ATOM | 488 | CA | ARG | 131 | 27.634 | 60.680 | 62.036 | 1.00 | 19.03 |
| ATOM | 489 | CB | ARG | 131 | 26.436 | 59.736 | 61.952 | 1.00 | 18.10 |
| ATOM | 490 | CG | ARG | 131 | 26.676 | 58.528 | 61.066 | 1.00 | 18.60 |
| ATOM | 491 | CD | ARG | 131 | 25.435 | 57.669 | 60.979 | 1.00 | 20.30 |
| ATOM | 492 | NE | ARG | 131 | 25.604 | 56.546 | 60.062 | 1.00 | 17.51 |
| ATOM | 493 | CZ | ARG | 131 | 24.642 | 55.679 | 59.766 | 1.00 | 19.71 |
| ATOM | 494 | NH1 | ARG | 131 | 23.441 | 55.803 | 60.317 | 1.00 | 17.67 |
| ATOM | 495 | NH2 | ARG | 131 | 24.877 | 54.692 | 58.910 | 1.00 | 19.33 |
| ATOM | 496 | C | ARG | 131 | 27.188 | 62.030 | 62.599 | 1.00 | 21.80 |
| ATOM | 497 | O | ARG | 131 | 26.512 | 62.801 | 61.913 | 1.00 | 20.73 |
| ATOM | 498 | N | LYS | 132 | 27.562 | 62.309 | 63.844 | 1.00 | 22.02 |
| ATOM | 499 | CA | LYS | 132 | 27.195 | 63.569 | 64.479 | 1.00 | 24.28 |
| ATOM | 500 | CB | LYS | 132 | 27.232 | 63.425 | 66.002 | 1.00 | 25.70 |
| ATOM | 501 | CG | LYS | 132 | 26.128 | 62.535 | 66.553 | 1.00 | 31.41 |
| ATOM | 502 | CD | LYS | 132 | 26.278 | 62.309 | 68.048 | 1.00 | 33.41 |
| ATOM | 503 | CE | LYS | 132 | 25.149 | 61.442 | 68.580 | 1.00 | 36.75 |
| ATOM | 504 | NZ | LYS | 132 | 25.398 | 60.989 | 69.977 | 1.00 | 38.85 |
| ATOM | 505 | C | LYS | 132 | 28.113 | 64.698 | 64.036 | 1.00 | 24.23 |
| ATOM | 506 | O | LYS | 132 | 27.815 | 65.872 | 64.255 | 1.00 | 24.28 |
| ATOM | 507 | N | PHE | 133 | 29.235 | 64.344 | 63.417 | 1.00 | 25.03 |
| ATOM | 508 | CA | PHE | 133 | 30.178 | 65.347 | 62.928 | 1.00 | 26.68 |
| ATOM | 509 | CB | PHE | 133 | 31.606 | 64.786 | 62.822 | 1.00 | 26.18 |
| ATOM | 510 | CG | PHE | 133 | 32.297 | 64.597 | 64.140 | 1.00 | 26.01 |
| ATOM | 511 | CD1 | PHE | 133 | 32.189 | 63.396 | 64.833 | 1.00 | 26.90 |
| ATOM | 512 | CD2 | PHE | 133 | 33.063 | 65.625 | 64.686 | 1.00 | 27.15 |
| ATOM | 513 | CE1 | PHE | 133 | 32.837 | 63.218 | 66.057 | 1.00 | 28.34 |
| ATOM | 514 | CE2 | PHE | 133 | 33.714 | 65.461 | 65.909 | 1.00 | 26.84 |
| ATOM | 515 | CZ | PHE | 133 | 33.602 | 64.256 | 66.595 | 1.00 | 27.99 |
| ATOM | 516 | C | PHE | 133 | 29.766 | 65.801 | 61.540 | 1.00 | 27.95 |
| ATOM | 517 | O | PHE | 133 | 29.350 | 64.989 | 60.714 | 1.00 | 28.75 |
| ATOM | 518 | N | ASP | 134 | 29.876 | 67.099 | 61.281 | 1.00 | 29.55 |
| ATOM | 519 | CA | ASP | 134 | 29.561 | 67.611 | 59.957 | 1.00 | 30.26 |
| ATOM | 520 | CB | ASP | 134 | 29.048 | 69.051 | 60.007 | 1.00 | 32.19 |
| ATOM | 521 | CG | ASP | 134 | 28.560 | 69.538 | 58.648 | 1.00 | 32.97 |
| ATOM | 522 | OD1 | ASP | 134 | 29.035 | 69.008 | 57.620 | 1.00 | 33.76 |
| ATOM | 523 | OD2 | ASP | 134 | 27.710 | 70.450 | 58.602 | 1.00 | 35.71 |
| ATOM | 524 | C | ASP | 134 | 30.896 | 67.577 | 59.231 | 1.00 | 30.16 |
| ATOM | 525 | O | ASP | 134 | 31.721 | 68.478 | 59.381 | 1.00 | 30.39 |
| ATOM | 526 | N | VAL | 135 | 31.110 | 66.522 | 58.457 | 1.00 | 31.36 |
| ATOM | 527 | CA | VAL | 135 | 32.353 | 66.354 | 57.722 | 1.00 | 31.74 |
| ATOM | 528 | CB | VAL | 135 | 32.308 | 65.059 | 56.880 | 1.00 | 32.36 |
| ATOM | 529 | CG1 | VAL | 135 | 33.587 | 64.904 | 56.083 | 1.00 | 33.06 |
| ATOM | 530 | CG2 | VAL | 135 | 32.113 | 63.864 | 57.794 | 1.00 | 31.68 |
| ATOM | 531 | C | VAL | 135 | 32.660 | 67.549 | 56.820 | 1.00 | 32.14 |
| ATOM | 532 | O | VAL | 135 | 33.824 | 67.884 | 56.599 | 1.00 | 32.77 |
| ATOM | 533 | N | ASN | 136 | 31.615 | 68.194 | 56.310 | 1.00 | 32.14 |
| ATOM | 534 | CA | ASN | 136 | 31.790 | 69.346 | 55.432 | 1.00 | 34.09 |

TABLE B-continued

Co-ordinates of an underglycosylated tACEΔ36NJ ACE-lisinopril complex

| ATOM | 535 | CB | ASN | 136 | 30.430 | 69.871 | 54.961 | 1.00 | 34.55 |
|---|---|---|---|---|---|---|---|---|---|
| ATOM | 536 | CG | ASN | 136 | 29.697 | 68.881 | 54.079 | 1.00 | 36.54 |
| ATOM | 537 | OD1 | ASN | 136 | 30.246 | 68.397 | 53.089 | 1.00 | 34.66 |
| ATOM | 538 | ND2 | ASN | 136 | 28.449 | 68.575 | 54.433 | 1.00 | 35.78 |
| ATOM | 539 | C | ASN | 136 | 32.555 | 70.478 | 56.103 | 1.00 | 34.86 |
| ATOM | 540 | O | ASN | 136 | 33.238 | 71.251 | 55.436 | 1.00 | 34.66 |
| ATOM | 541 | N | GLN | 137 | 32.445 | 70.568 | 57.424 | 1.00 | 36.37 |
| ATOM | 542 | CA | GLN | 137 | 33.114 | 71.628 | 58.171 | 1.00 | 37.67 |
| ATOM | 543 | CB | GLN | 137 | 32.192 | 72.122 | 59.290 | 1.00 | 40.06 |
| ATOM | 544 | CG | GLN | 137 | 30.886 | 72.738 | 58.797 | 1.00 | 43.99 |
| ATOM | 545 | CD | GLN | 137 | 31.108 | 73.973 | 57.939 | 1.00 | 47.20 |
| ATOM | 546 | OE1 | GLN | 137 | 31.777 | 74.922 | 58.355 | 1.00 | 49.72 |
| ATOM | 547 | NE2 | GLN | 137 | 30.540 | 73.970 | 56.736 | 1.00 | 49.42 |
| ATOM | 548 | C | GLN | 137 | 34.471 | 71.237 | 58.756 | 1.00 | 36.89 |
| ATOM | 549 | O | GLN | 137 | 35.136 | 72.057 | 59.389 | 1.00 | 36.28 |
| ATOM | 550 | N | LEU | 138 | 34.886 | 69.992 | 58.539 | 1.00 | 36.72 |
| ATOM | 551 | CA | LEU | 138 | 36.162 | 69.516 | 59.061 | 1.00 | 35.87 |
| ATOM | 552 | CB | LEU | 138 | 36.140 | 67.991 | 59.166 | 1.00 | 36.10 |
| ATOM | 553 | CG | LEU | 138 | 36.216 | 67.413 | 60.585 | 1.00 | 36.93 |
| ATOM | 554 | CD1 | LEU | 138 | 35.438 | 68.279 | 61.565 | 1.00 | 36.66 |
| ATOM | 555 | CD2 | LEU | 138 | 35.678 | 65.994 | 60.576 | 1.00 | 37.81 |
| ATOM | 556 | C | LEU | 138 | 37.330 | 69.980 | 58.198 | 1.00 | 36.49 |
| ATOM | 557 | O | LEU | 138 | 37.350 | 69.764 | 56.987 | 1.00 | 37.24 |
| ATOM | 558 | N | GLN | 139 | 38.310 | 70.612 | 58.837 | 1.00 | 36.86 |
| ATOM | 559 | CA | GLN | 139 | 39.476 | 71.144 | 58.140 | 1.00 | 37.44 |
| ATOM | 560 | CB | GLN | 139 | 40.141 | 72.224 | 58.995 | 1.00 | 39.57 |
| ATOM | 561 | CG | GLN | 139 | 40.513 | 73.479 | 58.225 | 1.00 | 43.68 |
| ATOM | 562 | CD | GLN | 139 | 39.295 | 74.262 | 57.761 | 1.00 | 46.04 |
| ATOM | 563 | OE1 | GLN | 139 | 38.423 | 73.729 | 57.070 | 1.00 | 48.18 |
| ATOM | 564 | NE2 | GLN | 139 | 39.230 | 75.535 | 58.138 | 1.00 | 46.25 |
| ATOM | 565 | C | GLN | 139 | 40.516 | 70.094 | 57.755 | 1.00 | 36.44 |
| ATOM | 566 | O | GLN | 139 | 40.868 | 69.970 | 56.583 | 1.00 | 37.59 |
| ATOM | 567 | N | ASN | 140 | 41.016 | 69.353 | 58.739 | 1.00 | 35.34 |
| ATOM | 568 | CA | ASN | 140 | 42.018 | 68.320 | 58.486 | 1.00 | 34.29 |
| ATOM | 569 | CB | ASN | 140 | 42.428 | 67.659 | 59.807 | 1.00 | 35.01 |
| ATOM | 570 | CG | ASN | 140 | 43.640 | 66.763 | 59.660 | 1.00 | 36.54 |
| ATOM | 571 | OD1 | ASN | 140 | 43.676 | 65.880 | 58.801 | 1.00 | 37.38 |
| ATOM | 572 | ND2 | ASN | 140 | 44.643 | 66.982 | 60.504 | 1.00 | 38.59 |
| ATOM | 573 | C | ASN | 140 | 41.443 | 67.273 | 57.529 | 1.00 | 33.04 |
| ATOM | 574 | O | ASN | 140 | 40.438 | 66.632 | 57.838 | 1.00 | 32.86 |
| ATOM | 575 | N | THR | 141 | 42.082 | 67.094 | 56.376 | 1.00 | 31.07 |
| ATOM | 576 | CA | THR | 141 | 41.599 | 66.135 | 55.386 | 1.00 | 30.83 |
| ATOM | 577 | CB | THR | 141 | 42.347 | 66.287 | 54.038 | 1.00 | 31.28 |
| ATOM | 578 | OG1 | THR | 141 | 43.753 | 66.108 | 54.238 | 1.00 | 31.57 |
| ATOM | 579 | CG2 | THR | 141 | 42.089 | 67.668 | 53.438 | 1.00 | 31.26 |
| ATOM | 580 | C | THR | 141 | 41.681 | 64.674 | 55.835 | 1.00 | 30.16 |
| ATOM | 581 | O | THR | 141 | 40.809 | 63.875 | 55.504 | 1.00 | 30.19 |
| ATOM | 582 | N | THR | 142 | 42.722 | 64.323 | 56.582 | 1.00 | 29.65 |
| ATOM | 583 | CA | THR | 142 | 42.866 | 62.951 | 57.061 | 1.00 | 28.87 |
| ATOM | 584 | CB | THR | 142 | 44.242 | 62.733 | 57.722 | 1.00 | 30.00 |
| ATOM | 585 | OG1 | THR | 142 | 45.266 | 62.851 | 56.726 | 1.00 | 31.45 |
| ATOM | 586 | CG2 | THR | 142 | 44.324 | 61.354 | 58.366 | 1.00 | 29.44 |
| ATOM | 587 | C | THR | 142 | 41.760 | 62.627 | 58.064 | 1.00 | 27.94 |
| ATOM | 588 | O | THR | 142 | 41.151 | 61.558 | 58.005 | 1.00 | 27.97 |
| ATOM | 589 | N | ILE | 143 | 41.499 | 63.555 | 58.979 | 1.00 | 25.97 |
| ATOM | 590 | CA | ILE | 143 | 40.451 | 63.367 | 59.979 | 1.00 | 25.63 |
| ATOM | 591 | CB | ILE | 143 | 40.415 | 64.552 | 60.975 | 1.00 | 26.33 |
| ATOM | 592 | CG2 | ILE | 143 | 39.202 | 64.438 | 61.888 | 1.00 | 24.81 |
| ATOM | 593 | CG1 | ILE | 143 | 41.709 | 64.584 | 61.792 | 1.00 | 27.36 |
| ATOM | 594 | CD1 | ILE | 143 | 41.941 | 63.340 | 62.619 | 1.00 | 29.54 |
| ATOM | 595 | C | ILE | 143 | 39.101 | 63.283 | 59.273 | 1.00 | 25.21 |
| ATOM | 596 | O | ILE | 143 | 38.248 | 62.463 | 59.612 | 1.00 | 24.06 |
| ATOM | 597 | N | LYS | 144 | 38.930 | 64.153 | 58.285 | 1.00 | 24.13 |
| ATOM | 598 | CA | LYS | 144 | 37.716 | 64.237 | 57.489 | 1.00 | 23.56 |
| ATOM | 599 | CB | LYS | 144 | 37.868 | 65.405 | 56.502 | 1.00 | 25.02 |
| ATOM | 600 | CG | LYS | 144 | 36.692 | 65.695 | 55.598 | 1.00 | 27.86 |
| ATOM | 601 | CD | LYS | 144 | 36.894 | 67.050 | 54.915 | 1.00 | 31.18 |
| ATOM | 602 | CE | LYS | 144 | 35.905 | 67.295 | 53.782 | 1.00 | 32.81 |
| ATOM | 603 | NZ | LYS | 144 | 34.486 | 67.288 | 54.224 | 1.00 | 35.78 |
| ATOM | 604 | C | LYS | 144 | 37.468 | 62.918 | 56.752 | 1.00 | 22.05 |
| ATOM | 605 | O | LYS | 144 | 36.349 | 62.402 | 56.734 | 1.00 | 22.03 |
| ATOM | 606 | N | ARG | 145 | 38.524 | 62.371 | 56.164 | 1.00 | 21.34 |
| ATOM | 607 | CA | ARG | 145 | 38.435 | 61.118 | 55.421 | 1.00 | 20.58 |
| ATOM | 608 | CB | ARG | 145 | 39.750 | 60.871 | 54.676 | 1.00 | 20.47 |
| ATOM | 609 | CG | ARG | 145 | 39.747 | 59.672 | 53.734 | 1.00 | 19.28 |
| ATOM | 610 | CD | ARG | 145 | 41.005 | 59.671 | 52.875 | 1.00 | 17.58 |
| ATOM | 611 | NE | ARG | 145 | 41.122 | 58.488 | 52.023 | 1.00 | 16.82 |
| ATOM | 612 | CZ | ARG | 145 | 40.350 | 58.238 | 50.969 | 1.00 | 18.88 |

TABLE B-continued

Co-ordinates of an underglycosylated tACEΔ36NJ ACE-lisinopril complex

| ATOM | 613 | NH1 | ARG | 145 | 39.391 | 59.092 | 50.627 | 1.00 | 18.08 |
|---|---|---|---|---|---|---|---|---|---|
| ATOM | 614 | NH2 | ARG | 145 | 40.541 | 57.133 | 50.252 | 1.00 | 15.35 |
| ATOM | 615 | C | ARG | 145 | 38.119 | 59.933 | 56.337 | 1.00 | 21.54 |
| ATOM | 616 | O | ARG | 145 | 37.294 | 59.081 | 56.002 | 1.00 | 19.52 |
| ATOM | 617 | N | ILE | 146 | 38.775 | 59.880 | 57.493 | 1.00 | 20.89 |
| ATOM | 618 | CA | ILE | 146 | 38.543 | 58.793 | 58.436 | 1.00 | 20.61 |
| ATOM | 619 | CB | ILE | 146 | 39.550 | 58.843 | 59.611 | 1.00 | 20.86 |
| ATOM | 620 | CG2 | ILE | 146 | 39.105 | 57.904 | 60.729 | 1.00 | 18.26 |
| ATOM | 621 | CG1 | ILE | 146 | 40.942 | 58.445 | 59.109 | 1.00 | 21.92 |
| ATOM | 622 | CD1 | ILE | 146 | 42.034 | 58.531 | 60.163 | 1.00 | 23.09 |
| ATOM | 623 | C | ILE | 146 | 37.124 | 58.833 | 58.991 | 1.00 | 20.19 |
| ATOM | 624 | O | ILE | 146 | 36.433 | 57.814 | 59.024 | 1.00 | 20.23 |
| ATOM | 625 | N | ILE | 147 | 36.687 | 60.013 | 59.416 | 1.00 | 19.22 |
| ATOM | 626 | CA | ILE | 147 | 35.352 | 60.161 | 59.973 | 1.00 | 19.37 |
| ATOM | 627 | CB | ILE | 147 | 35.132 | 61.590 | 60.536 | 1.00 | 19.10 |
| ATOM | 628 | CG2 | ILE | 147 | 33.657 | 61.806 | 60.859 | 1.00 | 19.65 |
| ATOM | 629 | CG1 | ILE | 147 | 35.991 | 61.780 | 61.794 | 1.00 | 18.67 |
| ATOM | 630 | CD1 | ILE | 147 | 35.771 | 63.090 | 62.519 | 1.00 | 20.74 |
| ATOM | 631 | C | ILE | 147 | 34.259 | 59.820 | 58.960 | 1.00 | 18.50 |
| ATOM | 632 | O | ILE | 147 | 33.278 | 59.166 | 59.305 | 1.00 | 16.03 |
| ATOM | 633 | N | ALA | 148 | 34.426 | 60.259 | 57.716 | 1.00 | 19.76 |
| ATOM | 634 | CA | ALA | 148 | 33.432 | 59.961 | 56.685 | 1.00 | 20.41 |
| ATOM | 635 | CB | ALA | 148 | 33.838 | 60.592 | 55.348 | 1.00 | 19.63 |
| ATOM | 636 | C | ALA | 148 | 33.305 | 58.447 | 56.535 | 1.00 | 19.95 |
| ATOM | 637 | O | ALA | 148 | 32.203 | 57.917 | 56.406 | 1.00 | 21.03 |
| ATOM | 638 | N | LYS | 149 | 34.438 | 57.752 | 56.566 | 1.00 | 19.67 |
| ATOM | 639 | CA | LYS | 149 | 34.446 | 56.300 | 56.435 | 1.00 | 19.12 |
| ATOM | 640 | CB | LYS | 149 | 35.886 | 55.802 | 56.246 | 1.00 | 21.29 |
| ATOM | 641 | CG | LYS | 149 | 36.016 | 54.302 | 55.997 | 1.00 | 25.45 |
| ATOM | 642 | CD | LYS | 149 | 37.389 | 53.971 | 55.418 | 1.00 | 29.29 |
| ATOM | 643 | CE | LYS | 149 | 37.511 | 52.506 | 55.013 | 1.00 | 29.09 |
| ATOM | 644 | NZ | LYS | 149 | 37.592 | 51.592 | 56.184 | 1.00 | 31.55 |
| ATOM | 645 | C | LYS | 149 | 33.802 | 55.601 | 57.633 | 1.00 | 18.43 |
| ATOM | 646 | O | LYS | 149 | 33.088 | 54.606 | 57.469 | 1.00 | 18.62 |
| ATOM | 647 | N | VAL | 150 | 34.042 | 56.122 | 58.835 | 1.00 | 17.00 |
| ATOM | 648 | CA | VAL | 150 | 33.475 | 55.528 | 60.041 | 1.00 | 16.77 |
| ATOM | 649 | CB | VAL | 150 | 34.145 | 56.106 | 61.316 | 1.00 | 18.58 |
| ATOM | 650 | CG1 | VAL | 150 | 33.532 | 55.480 | 62.573 | 1.00 | 17.11 |
| ATOM | 651 | CG2 | VAL | 150 | 35.641 | 55.825 | 61.276 | 1.00 | 17.68 |
| ATOM | 652 | C | VAL | 150 | 31.956 | 55.701 | 60.127 | 1.00 | 15.66 |
| ATOM | 653 | O | VAL | 150 | 31.291 | 54.974 | 60.861 | 1.00 | 14.92 |
| ATOM | 654 | N | GLN | 151 | 31.407 | 56.656 | 59.379 | 1.00 | 15.58 |
| ATOM | 655 | CA | GLN | 151 | 29.958 | 56.875 | 59.371 | 1.00 | 16.33 |
| ATOM | 656 | CB | GLN | 151 | 29.608 | 58.196 | 58.674 | 1.00 | 17.28 |
| ATOM | 657 | CG | GLN | 151 | 30.272 | 59.437 | 59.263 | 1.00 | 19.28 |
| ATOM | 658 | CD | GLN | 151 | 29.802 | 60.723 | 58.597 | 1.00 | 22.98 |
| ATOM | 659 | OE1 | GLN | 151 | 29.570 | 60.758 | 57.388 | 1.00 | 24.55 |
| ATOM | 660 | NE2 | GLN | 151 | 29.677 | 61.790 | 59.381 | 1.00 | 23.47 |
| ATOM | 661 | C | GLN | 151 | 29.237 | 55.719 | 58.656 | 1.00 | 16.52 |
| ATOM | 662 | O | GLN | 151 | 28.014 | 55.595 | 58.732 | 1.00 | 16.41 |
| ATOM | 663 | N | ASP | 152 | 29.997 | 54.887 | 57.950 | 1.00 | 14.56 |
| ATOM | 664 | CA | ASP | 152 | 29.436 | 53.732 | 57.242 | 1.00 | 16.29 |
| ATOM | 665 | CB | ASP | 152 | 30.237 | 53.457 | 55.965 | 1.00 | 15.31 |
| ATOM | 666 | CG | ASP | 152 | 29.661 | 52.317 | 55.131 | 1.00 | 17.15 |
| ATOM | 667 | OD1 | ASP | 152 | 28.797 | 51.560 | 55.623 | 1.00 | 16.35 |
| ATOM | 668 | OD2 | ASP | 152 | 30.095 | 52.172 | 53.970 | 1.00 | 18.62 |
| ATOM | 669 | C | ASP | 152 | 29.552 | 52.545 | 58.198 | 1.00 | 16.49 |
| ATOM | 670 | O | ASP | 152 | 30.641 | 52.022 | 58.408 | 1.00 | 16.64 |
| ATOM | 671 | N | LEU | 153 | 28.429 | 52.126 | 58.772 | 1.00 | 17.15 |
| ATOM | 672 | CA | LEU | 153 | 28.423 | 51.023 | 59.731 | 1.00 | 18.78 |
| ATOM | 673 | CB | LEU | 153 | 27.197 | 51.122 | 60.640 | 1.00 | 19.19 |
| ATOM | 674 | CG | LEU | 153 | 26.729 | 52.501 | 61.112 | 1.00 | 22.36 |
| ATOM | 675 | CD1 | LEU | 153 | 25.611 | 52.330 | 62.137 | 1.00 | 22.96 |
| ATOM | 676 | CD2 | LEU | 153 | 27.881 | 53.260 | 61.715 | 1.00 | 20.38 |
| ATOM | 677 | C | LEU | 153 | 28.417 | 49.650 | 59.080 | 1.00 | 18.93 |
| ATOM | 678 | O | LEU | 153 | 28.600 | 48.635 | 59.756 | 1.00 | 18.52 |
| ATOM | 679 | N | GLU | 154 | 28.207 | 49.617 | 57.769 | 1.00 | 19.03 |
| ATOM | 680 | CA | GLU | 154 | 28.133 | 48.360 | 57.049 | 1.00 | 19.00 |
| ATOM | 681 | CB | GLU | 154 | 29.505 | 47.674 | 57.033 | 1.00 | 23.48 |
| ATOM | 682 | CG | GLU | 154 | 30.375 | 48.165 | 55.867 | 1.00 | 32.92 |
| ATOM | 683 | CD | GLU | 154 | 31.838 | 47.766 | 55.981 | 1.00 | 38.33 |
| ATOM | 684 | OE1 | GLU | 154 | 32.122 | 46.597 | 56.317 | 1.00 | 44.51 |
| ATOM | 685 | OE2 | GLU | 154 | 32.709 | 48.622 | 55.720 | 1.00 | 42.26 |
| ATOM | 686 | C | GLU | 154 | 27.046 | 47.508 | 57.704 | 1.00 | 16.46 |
| ATOM | 687 | O | GLU | 154 | 25.984 | 48.038 | 58.020 | 1.00 | 16.75 |
| ATOM | 688 | N | ARG | 155 | 27.285 | 46.220 | 57.939 | 1.00 | 14.21 |
| ATOM | 689 | CA | ARG | 155 | 26.238 | 45.381 | 58.525 | 1.00 | 15.38 |
| ATOM | 690 | CB | ARG | 155 | 26.698 | 43.921 | 58.607 | 1.00 | 16.09 |

TABLE B-continued

Co-ordinates of an underglycosylated tACEΔ36NJ ACE-lisinopril complex

| ATOM | 691 | CG | ARG | 155 | 27.670 | 43.615 | 59.735 | 1.00 | 14.62 |
|------|-----|-----|-----|-----|--------|--------|--------|------|-------|
| ATOM | 692 | CD | ARG | 155 | 28.101 | 42.156 | 59.685 | 1.00 | 16.01 |
| ATOM | 693 | NE | ARG | 155 | 28.976 | 41.887 | 58.550 | 1.00 | 18.81 |
| ATOM | 694 | CZ | ARG | 155 | 29.461 | 40.686 | 58.244 | 1.00 | 21.66 |
| ATOM | 695 | NH1 | ARG | 155 | 29.150 | 39.629 | 58.989 | 1.00 | 20.13 |
| ATOM | 696 | NH2 | ARG | 155 | 30.274 | 40.547 | 57.204 | 1.00 | 22.28 |
| ATOM | 697 | C | ARG | 155 | 25.728 | 45.838 | 59.896 | 1.00 | 16.17 |
| ATOM | 698 | O | ARG | 155 | 24.567 | 45.602 | 60.246 | 1.00 | 15.50 |
| ATOM | 699 | N | ALA | 156 | 26.586 | 46.496 | 60.668 | 1.00 | 17.02 |
| ATOM | 700 | CA | ALA | 156 | 26.185 | 46.963 | 61.994 | 1.00 | 18.35 |
| ATOM | 701 | CB | ALA | 156 | 27.380 | 47.563 | 62.722 | 1.00 | 17.23 |
| ATOM | 702 | C | ALA | 156 | 25.031 | 47.969 | 61.954 | 1.00 | 19.07 |
| ATOM | 703 | O | ALA | 156 | 24.495 | 48.341 | 62.997 | 1.00 | 19.97 |
| ATOM | 704 | N | ALA | 157 | 24.645 | 48.409 | 60.759 | 1.00 | 17.62 |
| ATOM | 705 | CA | ALA | 157 | 23.534 | 49.354 | 60.635 | 1.00 | 17.85 |
| ATOM | 706 | CB | ALA | 157 | 23.620 | 50.104 | 59.311 | 1.00 | 15.36 |
| ATOM | 707 | C | ALA | 157 | 22.186 | 48.647 | 60.739 | 1.00 | 17.21 |
| ATOM | 708 | O | ALA | 157 | 21.155 | 49.286 | 60.946 | 1.00 | 18.26 |
| ATOM | 709 | N | LEU | 158 | 22.197 | 47.327 | 60.591 | 1.00 | 17.55 |
| ATOM | 710 | CA | LEU | 158 | 20.970 | 46.536 | 60.656 | 1.00 | 17.62 |
| ATOM | 711 | CB | LEU | 158 | 21.209 | 45.132 | 60.090 | 1.00 | 16.43 |
| ATOM | 712 | CG | LEU | 158 | 21.510 | 44.911 | 58.609 | 1.00 | 15.07 |
| ATOM | 713 | CD1 | LEU | 158 | 21.931 | 43.465 | 58.404 | 1.00 | 15.08 |
| ATOM | 714 | CD2 | LEU | 158 | 20.282 | 45.243 | 57.777 | 1.00 | 13.17 |
| ATOM | 715 | C | LEU | 158 | 20.430 | 46.377 | 62.073 | 1.00 | 17.49 |
| ATOM | 716 | O | LEU | 158 | 21.196 | 46.258 | 63.020 | 1.00 | 18.06 |
| ATOM | 717 | N | PRO | 159 | 19.096 | 46.374 | 62.229 | 1.00 | 18.66 |
| ATOM | 718 | CD | PRO | 159 | 18.053 | 46.623 | 61.215 | 1.00 | 18.39 |
| ATOM | 719 | CA | PRO | 159 | 18.508 | 46.207 | 63.561 | 1.00 | 18.87 |
| ATOM | 720 | CB | PRO | 159 | 17.014 | 46.153 | 63.273 | 1.00 | 19.07 |
| ATOM | 721 | CG | PRO | 159 | 16.873 | 47.046 | 62.062 | 1.00 | 20.37 |
| ATOM | 722 | C | PRO | 159 | 19.038 | 44.877 | 64.098 | 1.00 | 20.43 |
| ATOM | 723 | O | PRO | 159 | 19.318 | 43.966 | 63.317 | 1.00 | 20.96 |
| ATOM | 724 | N | ALA | 160 | 19.183 | 44.770 | 65.415 | 1.00 | 20.67 |
| ATOM | 725 | CA | ALA | 160 | 19.698 | 43.560 | 66.052 | 1.00 | 21.14 |
| ATOM | 726 | CB | ALA | 160 | 19.397 | 43.600 | 67.554 | 1.00 | 20.94 |
| ATOM | 727 | C | ALA | 160 | 19.183 | 42.246 | 65.459 | 1.00 | 21.41 |
| ATOM | 728 | O | ALA | 160 | 19.958 | 41.329 | 65.193 | 1.00 | 20.22 |
| ATOM | 729 | N | GLN | 161 | 17.873 | 42.154 | 65.261 | 1.00 | 22.76 |
| ATOM | 730 | CA | GLN | 161 | 17.268 | 40.941 | 64.724 | 1.00 | 24.75 |
| ATOM | 731 | CB | GLN | 161 | 15.749 | 41.106 | 64.668 | 1.00 | 27.09 |
| ATOM | 732 | CG | GLN | 161 | 14.993 | 39.854 | 64.268 | 1.00 | 34.37 |
| ATOM | 733 | CD | GLN | 161 | 13.498 | 39.986 | 64.496 | 1.00 | 38.16 |
| ATOM | 734 | OE1 | GLN | 161 | 13.044 | 40.152 | 65.631 | 1.00 | 40.84 |
| ATOM | 735 | NE2 | GLN | 161 | 12.724 | 39.914 | 63.417 | 1.00 | 39.81 |
| ATOM | 736 | C | GLN | 161 | 17.813 | 40.579 | 63.340 | 1.00 | 24.20 |
| ATOM | 737 | O | GLN | 161 | 18.220 | 39.437 | 63.105 | 1.00 | 22.98 |
| ATOM | 738 | N | GLU | 162 | 17.822 | 41.550 | 62.432 | 1.00 | 22.26 |
| ATOM | 739 | CA | GLU | 162 | 18.323 | 41.330 | 61.079 | 1.00 | 23.01 |
| ATOM | 740 | CB | GLU | 162 | 18.034 | 42.545 | 60.187 | 1.00 | 25.38 |
| ATOM | 741 | CG | GLU | 162 | 16.629 | 42.608 | 59.583 | 1.00 | 30.24 |
| ATOM | 742 | CD | GLU | 162 | 15.545 | 42.908 | 60.604 | 1.00 | 33.50 |
| ATOM | 743 | OE1 | GLU | 162 | 15.246 | 42.031 | 61.441 | 1.00 | 37.24 |
| ATOM | 744 | OE2 | GLU | 162 | 14.989 | 44.025 | 60.564 | 1.00 | 35.02 |
| ATOM | 745 | C | GLU | 162 | 19.827 | 41.053 | 61.066 | 1.00 | 20.41 |
| ATOM | 746 | O | GLU | 162 | 20.311 | 40.262 | 60.262 | 1.00 | 19.24 |
| ATOM | 747 | N | LEU | 163 | 20.567 | 41.705 | 61.956 | 1.00 | 20.49 |
| ATOM | 748 | CA | LEU | 163 | 22.008 | 41.504 | 62.001 | 1.00 | 19.77 |
| ATOM | 749 | CB | LEU | 163 | 22.655 | 42.455 | 63.013 | 1.00 | 19.73 |
| ATOM | 750 | CG | LEU | 163 | 24.177 | 42.335 | 63.191 | 1.00 | 20.15 |
| ATOM | 751 | CD1 | LEU | 163 | 24.890 | 42.506 | 61.856 | 1.00 | 20.35 |
| ATOM | 752 | CD2 | LEU | 163 | 24.651 | 43.385 | 64.183 | 1.00 | 20.52 |
| ATOM | 753 | C | LEU | 163 | 22.373 | 40.062 | 62.336 | 1.00 | 20.22 |
| ATOM | 754 | O | LEU | 163 | 23.242 | 39.469 | 61.690 | 1.00 | 18.49 |
| ATOM | 755 | N | GLU | 164 | 21.715 | 39.487 | 63.338 | 1.00 | 21.24 |
| ATOM | 756 | CA | GLU | 164 | 22.033 | 38.114 | 63.702 | 1.00 | 22.56 |
| ATOM | 757 | CB | GLU | 164 | 21.368 | 37.715 | 65.031 | 1.00 | 25.63 |
| ATOM | 758 | CG | GLU | 164 | 19.931 | 37.253 | 64.946 | 1.00 | 32.73 |
| ATOM | 759 | CD | GLU | 164 | 19.410 | 36.719 | 66.280 | 1.00 | 36.98 |
| ATOM | 760 | OE1 | GLU | 164 | 18.266 | 36.215 | 66.315 | 1.00 | 39.72 |
| ATOM | 761 | OE2 | GLU | 164 | 20.141 | 36.805 | 67.292 | 1.00 | 37.47 |
| ATOM | 762 | C | GLU | 164 | 21.629 | 37.159 | 62.583 | 1.00 | 19.87 |
| ATOM | 763 | O | GLU | 164 | 22.330 | 36.191 | 62.309 | 1.00 | 19.06 |
| ATOM | 764 | N | GLU | 165 | 20.511 | 37.436 | 61.923 | 1.00 | 18.96 |
| ATOM | 765 | CA | GLU | 165 | 20.076 | 36.575 | 60.829 | 1.00 | 19.42 |
| ATOM | 766 | CB | GLU | 165 | 18.677 | 36.962 | 60.354 | 1.00 | 19.49 |
| ATOM | 767 | CG | GLU | 165 | 18.230 | 36.176 | 59.138 | 1.00 | 22.13 |
| ATOM | 768 | CD | GLU | 165 | 16.817 | 36.502 | 58.721 | 1.00 | 23.77 |

TABLE B-continued

Co-ordinates of an underglycosylated tACEΔ36NJ ACE-lisinopril complex

| ATOM | 769 | OE1 | GLU | 165 | 16.368 | 37.642 | 58.976 | 1.00 | 25.48 |
|---|---|---|---|---|---|---|---|---|---|
| ATOM | 770 | OE2 | GLU | 165 | 16.163 | 35.622 | 58.122 | 1.00 | 23.74 |
| ATOM | 771 | C | GLU | 165 | 21.069 | 36.659 | 59.664 | 1.00 | 19.62 |
| ATOM | 772 | O | GLU | 165 | 21.405 | 35.645 | 59.050 | 1.00 | 19.06 |
| ATOM | 773 | N | TYR | 166 | 21.536 | 37.869 | 59.372 | 1.00 | 18.74 |
| ATOM | 774 | CA | TYR | 166 | 22.499 | 38.083 | 58.298 | 1.00 | 19.37 |
| ATOM | 775 | CB | TYR | 166 | 22.767 | 39.579 | 58.117 | 1.00 | 18.92 |
| ATOM | 776 | CG | TYR | 166 | 23.762 | 39.899 | 57.021 | 1.00 | 18.54 |
| ATOM | 777 | CD1 | TYR | 166 | 23.522 | 39.516 | 55.699 | 1.00 | 17.98 |
| ATOM | 778 | CE1 | TYR | 166 | 24.431 | 39.816 | 54.685 | 1.00 | 18.12 |
| ATOM | 779 | CD2 | TYR | 166 | 24.938 | 40.591 | 57.302 | 1.00 | 19.19 |
| ATOM | 780 | CE2 | TYR | 166 | 25.853 | 40.898 | 56.296 | 1.00 | 19.67 |
| ATOM | 781 | CZ | TYR | 166 | 25.593 | 40.508 | 54.992 | 1.00 | 19.53 |
| ATOM | 782 | OH | TYR | 166 | 26.492 | 40.814 | 53.997 | 1.00 | 20.23 |
| ATOM | 783 | C | TYR | 166 | 23.815 | 37.365 | 58.603 | 1.00 | 19.45 |
| ATOM | 784 | O | TYR | 166 | 24.375 | 36.681 | 57.742 | 1.00 | 17.70 |
| ATOM | 785 | N | ASN | 167 | 24.313 | 37.524 | 59.827 | 1.00 | 19.79 |
| ATOM | 786 | CA | ASN | 167 | 25.563 | 36.874 | 60.197 | 1.00 | 19.29 |
| ATOM | 787 | CB | ASN | 167 | 25.980 | 37.248 | 61.623 | 1.00 | 20.64 |
| ATOM | 788 | CG | ASN | 167 | 26.480 | 38.678 | 61.729 | 1.00 | 21.06 |
| ATOM | 789 | OD1 | ASN | 167 | 27.214 | 39.156 | 60.864 | 1.00 | 22.90 |
| ATOM | 790 | ND2 | ASN | 167 | 26.096 | 39.361 | 62.798 | 1.00 | 20.86 |
| ATOM | 791 | C | ASN | 167 | 25.448 | 35.364 | 60.077 | 1.00 | 19.16 |
| ATOM | 792 | O | ASN | 167 | 26.378 | 34.706 | 59.619 | 1.00 | 19.57 |
| ATOM | 793 | N | LYS | 168 | 24.308 | 34.813 | 60.483 | 1.00 | 19.46 |
| ATOM | 794 | CA | LYS | 168 | 24.116 | 33.370 | 60.403 | 1.00 | 20.23 |
| ATOM | 795 | CB | LYS | 168 | 22.864 | 32.929 | 61.172 | 1.00 | 20.58 |
| ATOM | 796 | CG | LYS | 168 | 22.625 | 31.428 | 61.056 | 1.00 | 24.70 |
| ATOM | 797 | CD | LYS | 168 | 21.400 | 30.961 | 61.813 | 1.00 | 28.42 |
| ATOM | 798 | CE | LYS | 168 | 21.048 | 29.527 | 61.414 | 1.00 | 30.39 |
| ATOM | 799 | NZ | LYS | 168 | 22.235 | 28.626 | 61.471 | 1.00 | 30.19 |
| ATOM | 800 | C | LYS | 168 | 24.006 | 32.930 | 58.950 | 1.00 | 18.98 |
| ATOM | 801 | O | LYS | 168 | 24.485 | 31.859 | 58.580 | 1.00 | 17.60 |
| ATOM | 802 | N | ILE | 169 | 23.363 | 33.760 | 58.135 | 1.00 | 18.74 |
| ATOM | 803 | CA | ILE | 169 | 23.213 | 33.473 | 56.715 | 1.00 | 19.75 |
| ATOM | 804 | CB | ILE | 169 | 22.464 | 34.615 | 55.987 | 1.00 | 20.57 |
| ATOM | 805 | CG2 | ILE | 169 | 22.651 | 34.489 | 54.480 | 1.00 | 22.22 |
| ATOM | 806 | CG1 | ILE | 169 | 20.975 | 34.585 | 56.341 | 1.00 | 23.21 |
| ATOM | 807 | CD1 | ILE | 169 | 20.236 | 33.385 | 55.798 | 1.00 | 23.57 |
| ATOM | 808 | C | ILE | 169 | 24.603 | 33.331 | 56.096 | 1.00 | 17.44 |
| ATOM | 809 | O | ILE | 169 | 24.903 | 32.337 | 55.443 | 1.00 | 17.43 |
| ATOM | 810 | N | LEU | 170 | 25.445 | 34.338 | 56.305 | 1.00 | 16.93 |
| ATOM | 811 | CA | LEU | 170 | 26.802 | 34.321 | 55.771 | 1.00 | 17.48 |
| ATOM | 812 | CB | LEU | 170 | 27.555 | 35.582 | 56.195 | 1.00 | 16.14 |
| ATOM | 813 | CG | LEU | 170 | 27.069 | 36.914 | 55.617 | 1.00 | 16.26 |
| ATOM | 814 | CD1 | LEU | 170 | 27.899 | 38.051 | 56.203 | 1.00 | 15.60 |
| ATOM | 815 | CD2 | LEU | 170 | 27.182 | 36.895 | 54.098 | 1.00 | 15.95 |
| ATOM | 816 | C | LEU | 170 | 27.561 | 33.091 | 56.257 | 1.00 | 19.23 |
| ATOM | 817 | O | LEU | 170 | 28.222 | 32.398 | 55.479 | 1.00 | 18.65 |
| ATOM | 818 | N | LEU | 171 | 27.464 | 32.827 | 57.553 | 1.00 | 19.55 |
| ATOM | 819 | CA | LEU | 171 | 28.135 | 31.687 | 58.150 | 1.00 | 20.58 |
| ATOM | 820 | CB | LEU | 171 | 27.824 | 31.621 | 59.647 | 1.00 | 23.73 |
| ATOM | 821 | CG | LEU | 171 | 28.435 | 30.447 | 60.413 | 1.00 | 27.50 |
| ATOM | 822 | CD1 | LEU | 171 | 29.939 | 30.625 | 60.513 | 1.00 | 27.87 |
| ATOM | 823 | CD2 | LEU | 171 | 27.812 | 30.371 | 61.801 | 1.00 | 30.52 |
| ATOM | 824 | C | LEU | 171 | 27.698 | 30.386 | 57.481 | 1.00 | 20.07 |
| ATOM | 825 | O | LEU | 171 | 28.537 | 29.561 | 57.109 | 1.00 | 20.05 |
| ATOM | 826 | N | ASP | 172 | 26.389 | 30.206 | 57.328 | 1.00 | 17.76 |
| ATOM | 827 | CA | ASP | 172 | 25.864 | 28.988 | 56.723 | 1.00 | 18.58 |
| ATOM | 828 | CB | ASP | 172 | 24.336 | 28.926 | 56.843 | 1.00 | 19.17 |
| ATOM | 829 | CG | ASP | 172 | 23.859 | 28.732 | 58.280 | 1.00 | 20.25 |
| ATOM | 830 | OD1 | ASP | 172 | 24.644 | 28.263 | 59.129 | 1.00 | 20.96 |
| ATOM | 831 | OD2 | ASP | 172 | 22.680 | 29.035 | 58.554 | 1.00 | 22.31 |
| ATOM | 832 | C | ASP | 172 | 26.267 | 28.823 | 55.260 | 1.00 | 18.13 |
| ATOM | 833 | O | ASP | 172 | 26.537 | 27.709 | 54.819 | 1.00 | 18.79 |
| ATOM | 834 | N | MET | 173 | 26.301 | 29.915 | 54.501 | 1.00 | 17.04 |
| ATOM | 835 | CA | MET | 173 | 26.695 | 29.810 | 53.098 | 1.00 | 16.32 |
| ATOM | 836 | CB | MET | 173 | 26.486 | 31.141 | 52.354 | 1.00 | 13.73 |
| ATOM | 837 | CG | MET | 173 | 25.021 | 31.532 | 52.178 | 1.00 | 13.28 |
| ATOM | 838 | SD | MET | 173 | 24.730 | 32.777 | 50.896 | 1.00 | 14.85 |
| ATOM | 839 | CE | MET | 173 | 25.634 | 34.204 | 51.591 | 1.00 | 10.81 |
| ATOM | 840 | C | MET | 173 | 28.159 | 29.388 | 52.998 | 1.00 | 16.03 |
| ATOM | 841 | O | MET | 173 | 28.510 | 28.516 | 52.205 | 1.00 | 15.12 |
| ATOM | 842 | N | GLU | 174 | 29.008 | 30.003 | 53.812 | 1.00 | 16.72 |
| ATOM | 843 | CA | GLU | 174 | 30.430 | 29.686 | 53.796 | 1.00 | 20.27 |
| ATOM | 844 | CB | GLU | 174 | 31.197 | 30.594 | 54.757 | 1.00 | 22.24 |
| ATOM | 845 | CG | GLU | 174 | 32.675 | 30.254 | 54.819 | 1.00 | 28.10 |
| ATOM | 846 | CD | GLU | 174 | 33.359 | 30.397 | 53.470 | 1.00 | 31.42 |

TABLE B-continued

Co-ordinates of an underglycosylated tACEΔ36NJ ACE-lisinopril complex

| ATOM | 847 | OE1 | GLU | 174 | 33.614 | 31.552 | 53.059 | 1.00 | 33.86 |
|------|-----|-----|-----|-----|--------|--------|--------|------|-------|
| ATOM | 848 | OE2 | GLU | 174 | 33.631 | 29.361 | 52.817 | 1.00 | 30.70 |
| ATOM | 849 | C | GLU | 174 | 30.692 | 28.233 | 54.171 | 1.00 | 19.72 |
| ATOM | 850 | O | GLU | 174 | 31.497 | 27.551 | 53.533 | 1.00 | 19.19 |
| ATOM | 851 | N | THR | 175 | 30.016 | 27.770 | 55.216 | 1.00 | 19.54 |
| ATOM | 852 | CA | THR | 175 | 30.176 | 26.401 | 55.686 | 1.00 | 19.81 |
| ATOM | 853 | CB | THR | 175 | 29.389 | 26.174 | 56.991 | 1.00 | 20.87 |
| ATOM | 854 | OG1 | THR | 175 | 29.833 | 27.111 | 57.978 | 1.00 | 22.15 |
| ATOM | 855 | CG2 | THR | 175 | 29.613 | 24.761 | 57.513 | 1.00 | 23.20 |
| ATOM | 856 | C | THR | 175 | 29.694 | 25.414 | 54.635 | 1.00 | 19.62 |
| ATOM | 857 | O | THR | 175 | 30.392 | 24.447 | 54.315 | 1.00 | 21.27 |
| ATOM | 858 | N | THR | 176 | 28.501 | 25.660 | 54.101 | 1.00 | 16.70 |
| ATOM | 859 | CA | THR | 176 | 27.923 | 24.794 | 53.076 | 1.00 | 16.77 |
| ATOM | 860 | CB | THR | 176 | 26.594 | 25.375 | 52.546 | 1.00 | 17.25 |
| ATOM | 861 | OG1 | THR | 176 | 25.646 | 25.467 | 53.620 | 1.00 | 16.27 |
| ATOM | 862 | CG2 | THR | 176 | 26.028 | 24.488 | 51.428 | 1.00 | 13.62 |
| ATOM | 863 | C | THR | 176 | 28.882 | 24.620 | 51.895 | 1.00 | 16.32 |
| ATOM | 864 | O | THR | 176 | 29.088 | 23.512 | 51.408 | 1.00 | 17.12 |
| ATOM | 865 | N | TYR | 177 | 29.467 | 25.720 | 51.439 | 1.00 | 16.42 |
| ATOM | 866 | CA | TYR | 177 | 30.396 | 25.675 | 50.316 | 1.00 | 17.56 |
| ATOM | 867 | CB | TYR | 177 | 30.773 | 27.103 | 49.885 | 1.00 | 15.76 |
| ATOM | 868 | CG | TYR | 177 | 31.734 | 27.166 | 48.708 | 1.00 | 15.72 |
| ATOM | 869 | CD1 | TYR | 177 | 31.265 | 27.155 | 47.392 | 1.00 | 14.57 |
| ATOM | 870 | CE1 | TYR | 177 | 32.152 | 27.198 | 46.301 | 1.00 | 14.15 |
| ATOM | 871 | CD2 | TYR | 177 | 33.114 | 27.220 | 48.912 | 1.00 | 15.54 |
| ATOM | 872 | CE2 | TYR | 177 | 34.009 | 27.259 | 47.834 | 1.00 | 12.96 |
| ATOM | 873 | CZ | TYR | 177 | 33.521 | 27.248 | 46.534 | 1.00 | 15.16 |
| ATOM | 874 | OH | TYR | 177 | 34.402 | 27.283 | 45.477 | 1.00 | 14.20 |
| ATOM | 875 | C | TYR | 177 | 31.673 | 24.897 | 50.651 | 1.00 | 18.31 |
| ATOM | 876 | O | TYR | 177 | 32.072 | 23.998 | 49.913 | 1.00 | 18.88 |
| ATOM | 877 | N | SER | 178 | 32.304 | 25.251 | 51.768 | 1.00 | 18.65 |
| ATOM | 878 | CA | SER | 178 | 33.555 | 24.628 | 52.188 | 1.00 | 20.78 |
| ATOM | 879 | CB | SER | 178 | 34.201 | 25.451 | 53.306 | 1.00 | 21.43 |
| ATOM | 880 | OG | SER | 178 | 34.760 | 26.650 | 52.796 | 1.00 | 24.23 |
| ATOM | 881 | C | SER | 178 | 33.522 | 23.163 | 52.613 | 1.00 | 21.32 |
| ATOM | 882 | O | SER | 178 | 34.577 | 22.541 | 52.739 | 1.00 | 21.59 |
| ATOM | 883 | N | VAL | 179 | 32.338 | 22.604 | 52.835 | 1.00 | 20.55 |
| ATOM | 884 | CA | VAL | 179 | 32.253 | 21.206 | 53.242 | 1.00 | 21.42 |
| ATOM | 885 | CB | VAL | 179 | 31.541 | 21.049 | 54.616 | 1.00 | 23.05 |
| ATOM | 886 | CG1 | VAL | 179 | 32.268 | 21.866 | 55.672 | 1.00 | 21.20 |
| ATOM | 887 | CG2 | VAL | 179 | 30.085 | 21.474 | 54.509 | 1.00 | 22.91 |
| ATOM | 888 | C | VAL | 179 | 31.527 | 20.337 | 52.218 | 1.00 | 21.32 |
| ATOM | 889 | O | VAL | 179 | 31.367 | 19.135 | 52.421 | 1.00 | 21.62 |
| ATOM | 890 | N | ALA | 180 | 31.106 | 20.941 | 51.113 | 1.00 | 20.29 |
| ATOM | 891 | CA | ALA | 180 | 30.393 | 20.203 | 50.081 | 1.00 | 19.37 |
| ATOM | 892 | CB | ALA | 180 | 29.855 | 21.169 | 49.026 | 1.00 | 18.54 |
| ATOM | 893 | C | ALA | 180 | 31.285 | 19.157 | 49.424 | 1.00 | 18.64 |
| ATOM | 894 | O | ALA | 180 | 32.479 | 19.384 | 49.224 | 1.00 | 19.38 |
| ATOM | 895 | N | THR | 181 | 30.692 | 18.013 | 49.095 | 1.00 | 19.37 |
| ATOM | 896 | CA | THR | 181 | 31.413 | 16.925 | 48.442 | 1.00 | 20.39 |
| ATOM | 897 | CB | THR | 181 | 31.749 | 15.781 | 49.434 | 1.00 | 21.11 |
| ATOM | 898 | OG1 | THR | 181 | 30.534 | 15.211 | 49.931 | 1.00 | 24.35 |
| ATOM | 899 | CG2 | THR | 181 | 32.576 | 16.301 | 50.603 | 1.00 | 21.45 |
| ATOM | 900 | C | THR | 181 | 30.579 | 16.334 | 47.309 | 1.00 | 19.99 |
| ATOM | 901 | O | THR | 181 | 29.353 | 16.463 | 47.288 | 1.00 | 18.79 |
| ATOM | 902 | N | VAL | 182 | 31.257 | 15.694 | 46.362 | 1.00 | 20.53 |
| ATOM | 903 | CA | VAL | 182 | 30.601 | 15.053 | 45.227 | 1.00 | 20.87 |
| ATOM | 904 | CB | VAL | 182 | 31.084 | 15.655 | 43.890 | 1.00 | 18.48 |
| ATOM | 905 | CG1 | VAL | 182 | 30.321 | 15.021 | 42.724 | 1.00 | 18.85 |
| ATOM | 906 | CG2 | VAL | 182 | 30.882 | 17.166 | 43.897 | 1.00 | 16.20 |
| ATOM | 907 | C | VAL | 182 | 30.987 | 13.584 | 45.307 | 1.00 | 22.10 |
| ATOM | 908 | O | VAL | 182 | 32.167 | 13.249 | 45.261 | 1.00 | 21.07 |
| ATOM | 909 | N | CYS | 183 | 29.989 | 12.714 | 45.435 | 1.00 | 26.01 |
| ATOM | 910 | CA | CYS | 183 | 30.247 | 11.285 | 45.580 | 1.00 | 29.42 |
| ATOM | 911 | C | CYS | 183 | 29.855 | 10.406 | 44.398 | 1.00 | 31.72 |
| ATOM | 912 | O | CYS | 183 | 28.976 | 10.755 | 43.607 | 1.00 | 31.89 |
| ATOM | 913 | CB | CYS | 183 | 29.514 | 10.743 | 46.811 | 1.00 | 28.21 |
| ATOM | 914 | SG | CYS | 183 | 29.634 | 11.717 | 48.345 | 1.00 | 30.87 |
| ATOM | 915 | N | HIS | 184 | 30.518 | 9.252 | 44.310 | 1.00 | 35.55 |
| ATOM | 916 | CA | HIS | 184 | 30.247 | 8.250 | 43.284 | 1.00 | 37.73 |
| ATOM | 917 | CB | HIS | 184 | 31.542 | 7.526 | 42.894 | 1.00 | 38.32 |
| ATOM | 918 | CG | HIS | 184 | 32.423 | 8.311 | 41.970 | 1.00 | 39.50 |
| ATOM | 919 | CD2 | HIS | 184 | 33.641 | 8.871 | 42.163 | 1.00 | 40.09 |
| ATOM | 920 | ND1 | HIS | 184 | 32.082 | 8.580 | 40.661 | 1.00 | 39.50 |
| ATOM | 921 | CE1 | HIS | 184 | 33.053 | 9.267 | 40.087 | 1.00 | 40.74 |
| ATOM | 922 | NE2 | HIS | 184 | 34.012 | 9.456 | 40.977 | 1.00 | 41.17 |
| ATOM | 923 | C | HIS | 184 | 29.267 | 7.251 | 43.896 | 1.00 | 39.60 |
| ATOM | 924 | O | HIS | 184 | 29.012 | 7.282 | 45.095 | 1.00 | 38.09 |

TABLE B-continued

Co-ordinates of an underglycosylated tACEΔ36NJ ACE-lisinopril complex

| ATOM | 925 | N | PRO | 185 | 28.712 | 6.348 | 43.082 | 1.00 | 42.45 |
|---|---|---|---|---|---|---|---|---|---|
| ATOM | 926 | CD | PRO | 185 | 28.759 | 6.347 | 41.608 | 1.00 | 43.76 |
| ATOM | 927 | CA | PRO | 185 | 27.762 | 5.347 | 43.588 | 1.00 | 43.42 |
| ATOM | 928 | CB | PRO | 185 | 27.433 | 4.539 | 42.341 | 1.00 | 44.10 |
| ATOM | 929 | CG | PRO | 185 | 27.503 | 5.614 | 41.253 | 1.00 | 44.49 |
| ATOM | 930 | C | PRO | 185 | 28.305 | 4.467 | 44.722 | 1.00 | 44.53 |
| ATOM | 931 | O | PRO | 185 | 27.545 | 3.951 | 45.540 | 1.00 | 44.42 |
| ATOM | 932 | N | ASN | 186 | 29.617 | 4.276 | 44.744 | 1.00 | 46.05 |
| ATOM | 933 | CA | ASN | 186 | 30.217 | 3.474 | 45.795 | 1.00 | 47.57 |
| ATOM | 934 | CB | ASN | 186 | 31.688 | 3.146 | 45.466 | 1.00 | 48.59 |
| ATOM | 935 | CG | ASN | 186 | 32.413 | 4.289 | 44.776 | 1.00 | 49.30 |
| ATOM | 936 | OD1 | ASN | 186 | 32.309 | 5.433 | 45.193 | 1.00 | 50.36 |
| ATOM | 937 | ND2 | ASN | 186 | 33.142 | 3.979 | 43.698 | 1.00 | 49.33 |
| ATOM | 938 | C | ASN | 186 | 30.140 | 4.201 | 47.144 | 1.00 | 47.63 |
| ATOM | 939 | O | ASN | 186 | 29.211 | 4.005 | 47.946 | 1.00 | 49.72 |
| ATOM | 940 | N | GLY | 187 | 31.125 | 5.059 | 47.377 | 1.00 | 46.81 |
| ATOM | 941 | CA | GLY | 187 | 31.186 | 5.818 | 48.609 | 1.00 | 43.76 |
| ATOM | 942 | C | GLY | 187 | 32.326 | 6.797 | 48.480 | 1.00 | 41.12 |
| ATOM | 943 | O | GLY | 187 | 32.640 | 7.519 | 49.421 | 1.00 | 42.63 |
| ATOM | 944 | N | SER | 188 | 32.951 | 6.800 | 47.306 | 1.00 | 38.37 |
| ATOM | 945 | CA | SER | 188 | 34.065 | 7.691 | 47.030 | 1.00 | 36.56 |
| ATOM | 946 | CB | SER | 188 | 34.804 | 7.249 | 45.768 | 1.00 | 37.67 |
| ATOM | 947 | OG | SER | 188 | 35.648 | 6.153 | 46.049 | 1.00 | 42.41 |
| ATOM | 948 | C | SER | 188 | 33.530 | 9.100 | 46.839 | 1.00 | 33.64 |
| ATOM | 949 | O | SER | 188 | 32.904 | 9.408 | 45.824 | 1.00 | 31.94 |
| ATOM | 950 | N | CYS | 189 | 33.757 | 9.946 | 47.835 | 1.00 | 31.40 |
| ATOM | 951 | CA | CYS | 189 | 33.320 | 11.329 | 47.768 | 1.00 | 29.46 |
| ATOM | 952 | C | CYS | 189 | 34.555 | 12.190 | 47.586 | 1.00 | 27.90 |
| ATOM | 953 | O | CYS | 189 | 35.591 | 11.948 | 48.202 | 1.00 | 28.50 |
| ATOM | 954 | CB | CYS | 189 | 32.598 | 11.731 | 49.051 | 1.00 | 29.56 |
| ATOM | 955 | SG | CYS | 189 | 31.084 | 10.792 | 49.428 | 1.00 | 31.98 |
| ATOM | 956 | N | LEU | 190 | 34.445 | 13.191 | 46.726 | 1.00 | 24.76 |
| ATOM | 957 | CA | LEU | 190 | 35.563 | 14.079 | 46.472 | 1.00 | 22.68 |
| ATOM | 958 | CB | LEU | 190 | 35.873 | 14.143 | 44.970 | 1.00 | 22.93 |
| ATOM | 959 | CG | LEU | 190 | 36.414 | 12.907 | 44.247 | 1.00 | 22.92 |
| ATOM | 960 | CD1 | LEU | 190 | 35.367 | 11.804 | 44.233 | 1.00 | 23.79 |
| ATOM | 961 | CD2 | LEU | 190 | 36.794 | 13.293 | 42.820 | 1.00 | 23.49 |
| ATOM | 962 | C | LEU | 190 | 35.263 | 15.481 | 46.971 | 1.00 | 21.66 |
| ATOM | 963 | O | LEU | 190 | 34.128 | 15.954 | 46.880 | 1.00 | 18.61 |
| ATOM | 964 | N | GLN | 191 | 36.285 | 16.133 | 47.508 | 1.00 | 20.57 |
| ATOM | 965 | CA | GLN | 191 | 36.157 | 17.502 | 47.976 | 1.00 | 21.68 |
| ATOM | 966 | CB | GLN | 191 | 37.052 | 17.737 | 49.193 | 1.00 | 22.65 |
| ATOM | 967 | CG | GLN | 191 | 36.635 | 16.951 | 50.422 | 1.00 | 27.39 |
| ATOM | 968 | CD | GLN | 191 | 37.541 | 17.213 | 51.609 | 1.00 | 28.93 |
| ATOM | 969 | OE1 | GLN | 191 | 38.750 | 16.992 | 51.543 | 1.00 | 31.20 |
| ATOM | 970 | NE2 | GLN | 191 | 36.958 | 17.685 | 52.703 | 1.00 | 31.79 |
| ATOM | 971 | C | GLN | 191 | 36.629 | 18.361 | 46.804 | 1.00 | 20.53 |
| ATOM | 972 | O | GLN | 191 | 37.304 | 17.857 | 45.902 | 1.00 | 17.89 |
| ATOM | 973 | N | LEU | 192 | 36.279 | 19.646 | 46.814 | 1.00 | 18.80 |
| ATOM | 974 | CA | LEU | 192 | 36.683 | 20.538 | 45.736 | 1.00 | 17.83 |
| ATOM | 975 | CB | LEU | 192 | 36.197 | 21.964 | 46.004 | 1.00 | 17.41 |
| ATOM | 976 | CG | LEU | 192 | 36.569 | 22.988 | 44.926 | 1.00 | 15.82 |
| ATOM | 977 | CD1 | LEU | 192 | 35.877 | 22.630 | 43.615 | 1.00 | 18.76 |
| ATOM | 978 | CD2 | LEU | 192 | 36.164 | 24.377 | 45.378 | 1.00 | 17.28 |
| ATOM | 979 | C | LEU | 192 | 38.199 | 20.540 | 45.568 | 1.00 | 19.20 |
| ATOM | 980 | O | LEU | 192 | 38.713 | 20.284 | 44.483 | 1.00 | 19.52 |
| ATOM | 981 | N | GLU | 193 | 38.914 | 20.837 | 46.644 | 1.00 | 20.67 |
| ATOM | 982 | CA | GLU | 193 | 40.366 | 20.860 | 46.590 | 1.00 | 24.08 |
| ATOM | 983 | CB | GLU | 193 | 40.894 | 22.208 | 47.099 | 1.00 | 25.06 |
| ATOM | 984 | CG | GLU | 193 | 40.261 | 23.400 | 46.387 | 1.00 | 30.04 |
| ATOM | 985 | CD | GLU | 193 | 41.009 | 24.704 | 46.605 | 1.00 | 32.48 |
| ATOM | 986 | OE1 | GLU | 193 | 41.103 | 25.165 | 47.764 | 1.00 | 34.10 |
| ATOM | 987 | OE2 | GLU | 193 | 41.504 | 25.270 | 45.606 | 1.00 | 34.77 |
| ATOM | 988 | C | GLU | 193 | 40.916 | 19.718 | 47.441 | 1.00 | 24.65 |
| ATOM | 989 | O | GLU | 193 | 40.514 | 19.542 | 48.590 | 1.00 | 24.48 |
| ATOM | 990 | N | PRO | 194 | 41.831 | 18.914 | 46.877 | 1.00 | 24.86 |
| ATOM | 991 | CD | PRO | 194 | 42.651 | 17.967 | 47.659 | 1.00 | 24.60 |
| ATOM | 992 | CA | PRO | 194 | 42.361 | 19.042 | 45.516 | 1.00 | 23.62 |
| ATOM | 993 | CB | PRO | 194 | 43.821 | 18.693 | 45.705 | 1.00 | 24.03 |
| ATOM | 994 | CG | PRO | 194 | 43.704 | 17.508 | 46.641 | 1.00 | 24.48 |
| ATOM | 995 | C | PRO | 194 | 41.694 | 18.072 | 44.539 | 1.00 | 22.86 |
| ATOM | 996 | O | PRO | 194 | 41.957 | 18.116 | 43.337 | 1.00 | 21.75 |
| ATOM | 997 | N | ASP | 195 | 40.840 | 17.201 | 45.067 | 1.00 | 21.42 |
| ATOM | 998 | CA | ASP | 195 | 40.176 | 16.177 | 44.267 | 1.00 | 22.19 |
| ATOM | 999 | CB | ASP | 195 | 39.183 | 15.395 | 45.130 | 1.00 | 21.92 |
| ATOM | 1000 | CG | ASP | 195 | 39.844 | 14.746 | 46.330 | 1.00 | 27.22 |
| ATOM | 1001 | OD1 | ASP | 195 | 40.997 | 14.287 | 46.197 | 1.00 | 27.92 |
| ATOM | 1002 | OD2 | ASP | 195 | 39.208 | 14.687 | 47.402 | 1.00 | 30.18 |

TABLE B-continued

Co-ordinates of an underglycosylated tACEΔ36NJ ACE-lisinopril complex

| ATOM | 1003 | C   | ASP | 195 | 39.488 | 16.623 | 42.985 | 1.00 | 21.21 |
|------|------|-----|-----|-----|--------|--------|--------|------|-------|
| ATOM | 1004 | O   | ASP | 195 | 39.953 | 16.301 | 41.893 | 1.00 | 23.11 |
| ATOM | 1005 | N   | LEU | 196 | 38.383 | 17.351 | 43.107 | 1.00 | 19.29 |
| ATOM | 1006 | CA  | LEU | 196 | 37.662 | 17.793 | 41.921 | 1.00 | 18.52 |
| ATOM | 1007 | CB  | LEU | 196 | 36.360 | 18.487 | 42.324 | 1.00 | 16.88 |
| ATOM | 1008 | CG  | LEU | 196 | 35.342 | 17.535 | 42.964 | 1.00 | 19.05 |
| ATOM | 1009 | CD1 | LEU | 196 | 34.224 | 18.325 | 43.620 | 1.00 | 19.51 |
| ATOM | 1010 | CD2 | LEU | 196 | 34.793 | 16.583 | 41.901 | 1.00 | 19.00 |
| ATOM | 1011 | C   | LEU | 196 | 38.519 | 18.708 | 41.061 | 1.00 | 17.36 |
| ATOM | 1012 | O   | LEU | 196 | 38.435 | 18.675 | 39.837 | 1.00 | 16.52 |
| ATOM | 1013 | N   | THR | 197 | 39.346 | 19.517 | 41.713 | 1.00 | 17.60 |
| ATOM | 1014 | CA  | THR | 197 | 40.231 | 20.440 | 41.016 | 1.00 | 17.78 |
| ATOM | 1015 | CB  | THR | 197 | 41.020 | 21.316 | 42.023 | 1.00 | 18.34 |
| ATOM | 1016 | OG1 | THR | 197 | 40.137 | 22.295 | 42.592 | 1.00 | 22.95 |
| ATOM | 1017 | CG2 | THR | 197 | 42.172 | 22.032 | 41.334 | 1.00 | 22.61 |
| ATOM | 1018 | C   | THR | 197 | 41.205 | 19.679 | 40.120 | 1.00 | 18.14 |
| ATOM | 1019 | O   | THR | 197 | 41.460 | 20.089 | 38.987 | 1.00 | 15.11 |
| ATOM | 1020 | N   | ASN | 198 | 41.747 | 18.575 | 40.633 | 1.00 | 18.47 |
| ATOM | 1021 | CA  | ASN | 198 | 42.679 | 17.760 | 39.860 | 1.00 | 19.73 |
| ATOM | 1022 | CB  | ASN | 198 | 43.298 | 16.648 | 40.721 | 1.00 | 24.67 |
| ATOM | 1023 | CG  | ASN | 198 | 44.208 | 17.185 | 41.815 | 1.00 | 30.01 |
| ATOM | 1024 | OD1 | ASN | 198 | 44.853 | 18.223 | 41.655 | 1.00 | 32.67 |
| ATOM | 1025 | ND2 | ASN | 198 | 44.282 | 16.460 | 42.930 | 1.00 | 33.72 |
| ATOM | 1026 | C   | ASN | 198 | 41.968 | 17.128 | 38.669 | 1.00 | 16.49 |
| ATOM | 1027 | O   | ASN | 198 | 42.514 | 17.091 | 37.569 | 1.00 | 17.40 |
| ATOM | 1028 | N   | VAL | 199 | 40.754 | 16.626 | 38.889 | 1.00 | 15.82 |
| ATOM | 1029 | CA  | VAL | 199 | 39.988 | 16.013 | 37.806 | 1.00 | 14.87 |
| ATOM | 1030 | CB  | VAL | 199 | 38.605 | 15.504 | 38.290 | 1.00 | 15.42 |
| ATOM | 1031 | CG1 | VAL | 199 | 37.766 | 15.069 | 37.091 | 1.00 | 15.86 |
| ATOM | 1032 | CG2 | VAL | 199 | 38.776 | 14.317 | 39.255 | 1.00 | 14.36 |
| ATOM | 1033 | C   | VAL | 199 | 39.771 | 17.013 | 36.666 | 1.00 | 14.32 |
| ATOM | 1034 | O   | VAL | 199 | 39.965 | 16.688 | 35.491 | 1.00 | 11.80 |
| ATOM | 1035 | N   | MET | 200 | 39.366 | 18.231 | 37.016 | 1.00 | 14.83 |
| ATOM | 1036 | CA  | MET | 200 | 39.123 | 19.259 | 36.008 | 1.00 | 14.38 |
| ATOM | 1037 | CB  | MET | 200 | 38.524 | 20.517 | 36.650 | 1.00 | 12.52 |
| ATOM | 1038 | CG  | MET | 200 | 37.128 | 20.328 | 37.233 | 1.00 | 12.28 |
| ATOM | 1039 | SD  | MET | 200 | 35.935 | 19.690 | 36.045 | 1.00 | 14.88 |
| ATOM | 1040 | CE  | MET | 200 | 35.797 | 21.097 | 34.903 | 1.00 | 12.30 |
| ATOM | 1041 | C   | MET | 200 | 40.405 | 19.632 | 35.274 | 1.00 | 13.50 |
| ATOM | 1042 | O   | MET | 200 | 40.375 | 19.989 | 34.099 | 1.00 | 13.68 |
| ATOM | 1043 | N   | ALA | 201 | 41.533 | 19.535 | 35.966 | 1.00 | 12.51 |
| ATOM | 1044 | CA  | ALA | 201 | 42.814 | 19.891 | 35.372 | 1.00 | 14.22 |
| ATOM | 1045 | CB  | ALA | 201 | 43.762 | 20.372 | 36.465 | 1.00 | 12.68 |
| ATOM | 1046 | C   | ALA | 201 | 43.501 | 18.794 | 34.556 | 1.00 | 14.13 |
| ATOM | 1047 | O   | ALA | 201 | 44.239 | 19.092 | 33.619 | 1.00 | 13.71 |
| ATOM | 1048 | N   | THR | 202 | 43.246 | 17.534 | 34.889 | 1.00 | 13.05 |
| ATOM | 1049 | CA  | THR | 202 | 43.932 | 16.442 | 34.211 | 1.00 | 14.28 |
| ATOM | 1050 | CB  | THR | 202 | 44.677 | 15.579 | 35.243 | 1.00 | 13.91 |
| ATOM | 1051 | OG1 | THR | 202 | 43.734 | 15.052 | 36.182 | 1.00 | 16.38 |
| ATOM | 1052 | CG2 | THR | 202 | 45.702 | 16.412 | 35.995 | 1.00 | 14.07 |
| ATOM | 1053 | C   | THR | 202 | 43.105 | 15.512 | 33.329 | 1.00 | 14.85 |
| ATOM | 1054 | O   | THR | 202 | 43.631 | 14.920 | 32.382 | 1.00 | 13.44 |
| ATOM | 1055 | N   | SER | 203 | 41.824 | 15.356 | 33.637 | 1.00 | 14.42 |
| ATOM | 1056 | CA  | SER | 203 | 40.993 | 14.482 | 32.821 | 1.00 | 15.37 |
| ATOM | 1057 | CB  | SER | 203 | 39.620 | 14.296 | 33.458 | 1.00 | 15.43 |
| ATOM | 1058 | OG  | SER | 203 | 38.771 | 13.571 | 32.585 | 1.00 | 16.22 |
| ATOM | 1059 | C   | SER | 203 | 40.817 | 15.043 | 31.410 | 1.00 | 17.26 |
| ATOM | 1060 | O   | SER | 203 | 40.718 | 16.258 | 31.216 | 1.00 | 15.56 |
| ATOM | 1061 | N   | ARG | 204 | 40.788 | 14.143 | 30.431 | 1.00 | 17.39 |
| ATOM | 1062 | CA  | ARG | 204 | 40.598 | 14.503 | 29.030 | 1.00 | 19.50 |
| ATOM | 1063 | CB  | ARG | 204 | 41.869 | 14.206 | 28.224 | 1.00 | 21.26 |
| ATOM | 1064 | CG  | ARG | 204 | 42.743 | 15.424 | 27.899 | 1.00 | 24.82 |
| ATOM | 1065 | CD  | ARG | 204 | 42.745 | 16.460 | 29.009 | 1.00 | 25.90 |
| ATOM | 1066 | NE  | ARG | 204 | 43.950 | 17.284 | 29.001 | 1.00 | 25.48 |
| ATOM | 1067 | CZ  | ARG | 204 | 44.225 | 18.207 | 29.921 | 1.00 | 26.92 |
| ATOM | 1068 | NH1 | ARG | 204 | 45.345 | 18.908 | 29.852 | 1.00 | 26.07 |
| ATOM | 1069 | NH2 | ARG | 204 | 43.372 | 18.437 | 30.908 | 1.00 | 28.93 |
| ATOM | 1070 | C   | ARG | 204 | 39.425 | 13.679 | 28.497 | 1.00 | 19.23 |
| ATOM | 1071 | O   | ARG | 204 | 39.299 | 13.448 | 27.292 | 1.00 | 18.09 |
| ATOM | 1072 | N   | LYS | 205 | 38.575 | 13.231 | 29.416 | 1.00 | 19.44 |
| ATOM | 1073 | CA  | LYS | 205 | 37.397 | 12.444 | 29.069 | 1.00 | 20.20 |
| ATOM | 1074 | CB  | LYS | 205 | 37.340 | 11.175 | 29.922 | 1.00 | 20.93 |
| ATOM | 1075 | CG  | LYS | 205 | 38.602 | 10.323 | 29.803 | 1.00 | 26.30 |
| ATOM | 1076 | CD  | LYS | 205 | 38.426 | 8.924  | 30.380 | 1.00 | 29.11 |
| ATOM | 1077 | CE  | LYS | 205 | 37.499 | 8.077  | 29.518 | 1.00 | 32.25 |
| ATOM | 1078 | NZ  | LYS | 205 | 37.474 | 6.652  | 29.959 | 1.00 | 35.02 |
| ATOM | 1079 | C   | LYS | 205 | 36.160 | 13.304 | 29.303 | 1.00 | 18.71 |
| ATOM | 1080 | O   | LYS | 205 | 35.854 | 13.680 | 30.440 | 1.00 | 17.01 |

TABLE B-continued

Co-ordinates of an underglycosylated tACEΔ36NJ ACE-lisinopril complex

| ATOM | 1081 | N | TYR | 206 | 35.457 | 13.608 | 28.215 | 1.00 | 16.75 |
|---|---|---|---|---|---|---|---|---|---|
| ATOM | 1082 | CA | TYR | 206 | 34.263 | 14.453 | 28.241 | 1.00 | 16.98 |
| ATOM | 1083 | CB | TYR | 206 | 33.550 | 14.383 | 26.884 | 1.00 | 16.42 |
| ATOM | 1084 | CG | TYR | 206 | 32.574 | 15.513 | 26.617 | 1.00 | 16.97 |
| ATOM | 1085 | CD1 | TYR | 206 | 32.941 | 16.599 | 25.821 | 1.00 | 15.01 |
| ATOM | 1086 | CE1 | TYR | 206 | 32.044 | 17.621 | 25.539 | 1.00 | 16.36 |
| ATOM | 1087 | CD2 | TYR | 206 | 31.275 | 15.485 | 27.135 | 1.00 | 15.21 |
| ATOM | 1088 | CE2 | TYR | 206 | 30.370 | 16.509 | 26.862 | 1.00 | 15.72 |
| ATOM | 1089 | CZ | TYR | 206 | 30.761 | 17.573 | 26.061 | 1.00 | 17.54 |
| ATOM | 1090 | OH | TYR | 206 | 29.874 | 18.590 | 25.772 | 1.00 | 19.58 |
| ATOM | 1091 | C | TYR | 206 | 33.273 | 14.106 | 29.350 | 1.00 | 16.80 |
| ATOM | 1092 | O | TYR | 206 | 32.772 | 14.990 | 30.039 | 1.00 | 16.60 |
| ATOM | 1093 | N | GLU | 207 | 32.980 | 12.819 | 29.514 | 1.00 | 16.66 |
| ATOM | 1094 | CA | GLU | 207 | 32.029 | 12.387 | 30.533 | 1.00 | 15.78 |
| ATOM | 1095 | CB | GLU | 207 | 31.584 | 10.941 | 30.268 | 1.00 | 16.34 |
| ATOM | 1096 | CG | GLU | 207 | 30.808 | 10.730 | 28.962 | 1.00 | 17.93 |
| ATOM | 1097 | CD | GLU | 207 | 29.479 | 11.488 | 28.917 | 1.00 | 21.81 |
| ATOM | 1098 | OE1 | GLU | 207 | 28.742 | 11.475 | 29.925 | 1.00 | 20.91 |
| ATOM | 1099 | OE2 | GLU | 207 | 29.166 | 12.089 | 27.863 | 1.00 | 22.78 |
| ATOM | 1100 | C | GLU | 207 | 32.565 | 12.511 | 31.960 | 1.00 | 14.53 |
| ATOM | 1101 | O | GLU | 207 | 31.798 | 12.773 | 32.886 | 1.00 | 15.02 |
| ATOM | 1102 | N | ASP | 208 | 33.867 | 12.312 | 32.147 | 1.00 | 13.86 |
| ATOM | 1103 | CA | ASP | 208 | 34.445 | 12.422 | 33.489 | 1.00 | 14.82 |
| ATOM | 1104 | CB | ASP | 208 | 35.870 | 11.854 | 33.531 | 1.00 | 16.21 |
| ATOM | 1105 | CG | ASP | 208 | 35.912 | 10.338 | 33.365 | 1.00 | 20.87 |
| ATOM | 1106 | OD1 | ASP | 208 | 34.883 | 9.674 | 33.606 | 1.00 | 23.51 |
| ATOM | 1107 | OD2 | ASP | 208 | 36.984 | 9.805 | 33.011 | 1.00 | 22.35 |
| ATOM | 1108 | C | ASP | 208 | 34.460 | 13.890 | 33.920 | 1.00 | 13.51 |
| ATOM | 1109 | O | ASP | 208 | 34.160 | 14.216 | 35.068 | 1.00 | 10.65 |
| ATOM | 1110 | N | LEU | 209 | 34.808 | 14.771 | 32.988 | 1.00 | 12.89 |
| ATOM | 1111 | CA | LEU | 209 | 34.838 | 16.200 | 33.269 | 1.00 | 12.10 |
| ATOM | 1112 | CB | LEU | 209 | 35.407 | 16.951 | 32.063 | 1.00 | 11.37 |
| ATOM | 1113 | CG | LEU | 209 | 36.907 | 16.746 | 31.811 | 1.00 | 10.29 |
| ATOM | 1114 | CD1 | LEU | 209 | 37.298 | 17.353 | 30.474 | 1.00 | 9.40 |
| ATOM | 1115 | CD2 | LEU | 209 | 37.705 | 17.380 | 32.950 | 1.00 | 9.04 |
| ATOM | 1116 | C | LEU | 209 | 33.421 | 16.684 | 33.575 | 1.00 | 13.60 |
| ATOM | 1117 | O | LEU | 209 | 33.210 | 17.517 | 34.460 | 1.00 | 12.24 |
| ATOM | 1118 | N | LEU | 210 | 32.452 | 16.145 | 32.843 | 1.00 | 12.89 |
| ATOM | 1119 | CA | LEU | 210 | 31.058 | 16.516 | 33.033 | 1.00 | 13.89 |
| ATOM | 1120 | CB | LEU | 210 | 30.193 | 15.862 | 31.951 | 1.00 | 16.04 |
| ATOM | 1121 | CG | LEU | 210 | 28.700 | 16.200 | 31.985 | 1.00 | 17.33 |
| ATOM | 1122 | CD1 | LEU | 210 | 28.515 | 17.711 | 31.938 | 1.00 | 18.83 |
| ATOM | 1123 | CD2 | LEU | 210 | 28.003 | 15.543 | 30.803 | 1.00 | 18.20 |
| ATOM | 1124 | C | LEU | 210 | 30.561 | 16.100 | 34.415 | 1.00 | 14.94 |
| ATOM | 1125 | O | LEU | 210 | 29.848 | 16.849 | 35.089 | 1.00 | 13.44 |
| ATOM | 1126 | N | TRP | 211 | 30.938 | 14.895 | 34.829 | 1.00 | 14.27 |
| ATOM | 1127 | CA | TRP | 211 | 30.543 | 14.377 | 36.133 | 1.00 | 14.75 |
| ATOM | 1128 | CB | TRP | 211 | 31.191 | 13.003 | 36.380 | 1.00 | 17.05 |
| ATOM | 1129 | CG | TRP | 211 | 30.897 | 12.452 | 37.745 | 1.00 | 19.27 |
| ATOM | 1130 | CD2 | TRP | 211 | 31.702 | 12.600 | 38.925 | 1.00 | 19.31 |
| ATOM | 1131 | CE2 | TRP | 211 | 30.996 | 12.007 | 39.991 | 1.00 | 20.70 |
| ATOM | 1132 | CE3 | TRP | 211 | 32.950 | 13.183 | 39.183 | 1.00 | 20.90 |
| ATOM | 1133 | CD1 | TRP | 211 | 29.772 | 11.788 | 38.133 | 1.00 | 21.04 |
| ATOM | 1134 | NE1 | TRP | 211 | 29.822 | 11.517 | 39.482 | 1.00 | 21.92 |
| ATOM | 1135 | CZ2 | TRP | 211 | 31.496 | 11.977 | 41.301 | 1.00 | 23.12 |
| ATOM | 1136 | CZ3 | TRP | 211 | 33.448 | 13.154 | 40.485 | 1.00 | 21.37 |
| ATOM | 1137 | CH2 | TRP | 211 | 32.720 | 12.556 | 41.526 | 1.00 | 21.61 |
| ATOM | 1138 | C | TRP | 211 | 30.977 | 15.350 | 37.236 | 1.00 | 13.96 |
| ATOM | 1139 | O | TRP | 211 | 30.183 | 15.722 | 38.096 | 1.00 | 11.98 |
| ATOM | 1140 | N | ALA | 212 | 32.244 | 15.753 | 37.200 | 1.00 | 13.24 |
| ATOM | 1141 | CA | ALA | 212 | 32.790 | 16.673 | 38.195 | 1.00 | 13.44 |
| ATOM | 1142 | CB | ALA | 212 | 34.313 | 16.743 | 38.057 | 1.00 | 12.36 |
| ATOM | 1143 | C | ALA | 212 | 32.194 | 18.076 | 38.081 | 1.00 | 13.04 |
| ATOM | 1144 | O | ALA | 212 | 31.875 | 18.707 | 39.091 | 1.00 | 13.12 |
| ATOM | 1145 | N | TRP | 213 | 32.050 | 18.560 | 36.851 | 1.00 | 13.51 |
| ATOM | 1146 | CA | TRP | 213 | 31.503 | 19.896 | 36.601 | 1.00 | 13.80 |
| ATOM | 1147 | CB | TRP | 213 | 31.554 | 20.212 | 35.099 | 1.00 | 13.04 |
| ATOM | 1148 | CG | TRP | 213 | 31.128 | 21.614 | 34.756 | 1.00 | 12.05 |
| ATOM | 1149 | CD2 | TRP | 213 | 29.800 | 22.062 | 34.454 | 1.00 | 12.15 |
| ATOM | 1150 | CE2 | TRP | 213 | 29.870 | 23.458 | 34.233 | 1.00 | 13.44 |
| ATOM | 1151 | CE3 | TRP | 213 | 28.556 | 21.421 | 34.352 | 1.00 | 12.18 |
| ATOM | 1152 | CD1 | TRP | 213 | 31.925 | 22.723 | 34.704 | 1.00 | 14.22 |
| ATOM | 1153 | NE1 | TRP | 213 | 31.177 | 23.834 | 34.390 | 1.00 | 12.82 |
| ATOM | 1154 | CZ2 | TRP | 213 | 28.741 | 24.227 | 33.915 | 1.00 | 12.19 |
| ATOM | 1155 | CZ3 | TRP | 213 | 27.434 | 22.184 | 34.035 | 1.00 | 12.97 |
| ATOM | 1156 | CH2 | TRP | 213 | 27.536 | 23.574 | 33.821 | 1.00 | 12.27 |
| ATOM | 1157 | C | TRP | 213 | 30.058 | 20.014 | 37.094 | 1.00 | 13.65 |
| ATOM | 1158 | O | TRP | 213 | 29.711 | 20.944 | 37.824 | 1.00 | 12.41 |

TABLE B-continued

Co-ordinates of an underglycosylated tACEΔ36NJ ACE-lisinopril complex

| ATOM | 1159 | N | GLU | 214 | 29.223 | 19.065 | 36.678 | 1.00 | 14.41 |
|---|---|---|---|---|---|---|---|---|---|
| ATOM | 1160 | CA | GLU | 214 | 27.815 | 19.043 | 37.055 | 1.00 | 15.02 |
| ATOM | 1161 | CB | GLU | 214 | 27.067 | 18.017 | 36.200 | 1.00 | 16.55 |
| ATOM | 1162 | CG | GLU | 214 | 25.569 | 17.945 | 36.459 | 1.00 | 19.62 |
| ATOM | 1163 | CD | GLU | 214 | 24.851 | 19.220 | 36.077 | 1.00 | 21.05 |
| ATOM | 1164 | OE1 | GLU | 214 | 25.063 | 19.698 | 34.944 | 1.00 | 24.80 |
| ATOM | 1165 | OE2 | GLU | 214 | 24.068 | 19.743 | 36.901 | 1.00 | 24.78 |
| ATOM | 1166 | C | GLU | 214 | 27.636 | 18.704 | 38.533 | 1.00 | 15.51 |
| ATOM | 1167 | O | GLU | 214 | 26.829 | 19.320 | 39.232 | 1.00 | 14.95 |
| ATOM | 1168 | N | GLY | 215 | 28.398 | 17.722 | 39.002 | 1.00 | 15.44 |
| ATOM | 1169 | CA | GLY | 215 | 28.302 | 17.307 | 40.389 | 1.00 | 15.35 |
| ATOM | 1170 | C | GLY | 215 | 28.587 | 18.422 | 41.373 | 1.00 | 15.21 |
| ATOM | 1171 | O | GLY | 215 | 27.857 | 18.604 | 42.345 | 1.00 | 15.46 |
| ATOM | 1172 | N | TRP | 216 | 29.650 | 19.176 | 41.121 | 1.00 | 15.46 |
| ATOM | 1173 | CA | TRP | 216 | 30.009 | 20.267 | 42.011 | 1.00 | 14.95 |
| ATOM | 1174 | CB | TRP | 216 | 31.285 | 20.965 | 41.528 | 1.00 | 14.52 |
| ATOM | 1175 | CG | TRP | 216 | 31.676 | 22.122 | 42.404 | 1.00 | 13.26 |
| ATOM | 1176 | CD2 | TRP | 216 | 31.967 | 22.071 | 43.807 | 1.00 | 14.02 |
| ATOM | 1177 | CE2 | TRP | 216 | 32.207 | 23.399 | 44.233 | 1.00 | 14.00 |
| ATOM | 1178 | CE3 | TRP | 216 | 32.046 | 21.033 | 44.747 | 1.00 | 13.78 |
| ATOM | 1179 | CD1 | TRP | 216 | 31.755 | 23.437 | 42.045 | 1.00 | 11.53 |
| ATOM | 1180 | NE1 | TRP | 216 | 32.073 | 24.210 | 43.138 | 1.00 | 12.94 |
| ATOM | 1181 | CZ2 | TRP | 216 | 32.519 | 23.717 | 45.558 | 1.00 | 13.90 |
| ATOM | 1182 | CZ3 | TRP | 216 | 32.357 | 21.349 | 46.068 | 1.00 | 15.08 |
| ATOM | 1183 | CH2 | TRP | 216 | 32.589 | 22.684 | 46.459 | 1.00 | 16.36 |
| ATOM | 1184 | C | TRP | 216 | 28.874 | 21.276 | 42.111 | 1.00 | 14.83 |
| ATOM | 1185 | O | TRP | 216 | 28.560 | 21.768 | 43.193 | 1.00 | 16.29 |
| ATOM | 1186 | N | ARG | 217 | 28.253 | 21.575 | 40.978 | 1.00 | 14.63 |
| ATOM | 1187 | CA | ARG | 217 | 27.159 | 22.528 | 40.959 | 1.00 | 14.60 |
| ATOM | 1188 | CB | ARG | 217 | 26.903 | 22.978 | 39.517 | 1.00 | 12.12 |
| ATOM | 1189 | CG | ARG | 217 | 28.042 | 23.875 | 39.011 | 1.00 | 13.34 |
| ATOM | 1190 | CD | ARG | 217 | 28.071 | 24.122 | 37.520 | 1.00 | 12.75 |
| ATOM | 1191 | NE | ARG | 217 | 29.163 | 25.043 | 37.206 | 1.00 | 12.99 |
| ATOM | 1192 | CZ | ARG | 217 | 30.458 | 24.750 | 37.326 | 1.00 | 11.14 |
| ATOM | 1193 | NH1 | ARG | 217 | 31.373 | 25.658 | 37.033 | 1.00 | 12.84 |
| ATOM | 1194 | NH2 | ARG | 217 | 30.844 | 23.544 | 37.714 | 1.00 | 12.36 |
| ATOM | 1195 | C | ARG | 217 | 25.905 | 21.958 | 41.622 | 1.00 | 15.54 |
| ATOM | 1196 | O | ARG | 217 | 25.174 | 22.680 | 42.293 | 1.00 | 15.86 |
| ATOM | 1197 | N | ASP | 218 | 25.672 | 20.657 | 41.459 | 1.00 | 16.94 |
| ATOM | 1198 | CA | ASP | 218 | 24.515 | 20.012 | 42.077 | 1.00 | 17.27 |
| ATOM | 1199 | CB | ASP | 218 | 24.403 | 18.543 | 41.652 | 1.00 | 16.71 |
| ATOM | 1200 | CG | ASP | 218 | 24.061 | 18.372 | 40.185 | 1.00 | 19.76 |
| ATOM | 1201 | OD1 | ASP | 218 | 23.644 | 19.355 | 39.531 | 1.00 | 21.08 |
| ATOM | 1202 | OD2 | ASP | 218 | 24.194 | 17.233 | 39.691 | 1.00 | 19.39 |
| ATOM | 1203 | C | ASP | 218 | 24.624 | 20.048 | 43.601 | 1.00 | 16.65 |
| ATOM | 1204 | O | ASP | 218 | 23.633 | 20.251 | 44.300 | 1.00 | 18.01 |
| ATOM | 1205 | N | LYS | 219 | 25.836 | 19.846 | 44.108 | 1.00 | 17.48 |
| ATOM | 1206 | CA | LYS | 219 | 26.068 | 19.814 | 45.550 | 1.00 | 18.13 |
| ATOM | 1207 | CB | LYS | 219 | 27.184 | 18.817 | 45.867 | 1.00 | 18.30 |
| ATOM | 1208 | CG | LYS | 219 | 26.905 | 17.403 | 45.361 | 1.00 | 20.52 |
| ATOM | 1209 | CD | LYS | 219 | 25.600 | 16.846 | 45.927 | 1.00 | 21.52 |
| ATOM | 1210 | CE | LYS | 219 | 25.657 | 16.721 | 47.445 | 1.00 | 23.83 |
| ATOM | 1211 | NZ | LYS | 219 | 26.779 | 15.849 | 47.890 | 1.00 | 24.81 |
| ATOM | 1212 | C | LYS | 219 | 26.376 | 21.151 | 46.221 | 1.00 | 18.56 |
| ATOM | 1213 | O | LYS | 219 | 25.864 | 21.430 | 47.302 | 1.00 | 19.73 |
| ATOM | 1214 | N | ALA | 220 | 27.221 | 21.972 | 45.607 | 1.00 | 18.09 |
| ATOM | 1215 | CA | ALA | 220 | 27.552 | 23.264 | 46.207 | 1.00 | 17.10 |
| ATOM | 1216 | CB | ALA | 220 | 28.988 | 23.656 | 45.867 | 1.00 | 16.84 |
| ATOM | 1217 | C | ALA | 220 | 26.585 | 24.350 | 45.739 | 1.00 | 15.48 |
| ATOM | 1218 | O | ALA | 220 | 25.976 | 25.038 | 46.553 | 1.00 | 16.35 |
| ATOM | 1219 | N | GLY | 221 | 26.444 | 24.486 | 44.425 | 1.00 | 14.00 |
| ATOM | 1220 | CA | GLY | 221 | 25.561 | 25.491 | 43.868 | 1.00 | 12.74 |
| ATOM | 1221 | C | GLY | 221 | 24.118 | 25.433 | 44.344 | 1.00 | 15.22 |
| ATOM | 1222 | O | GLY | 221 | 23.598 | 26.412 | 44.886 | 1.00 | 15.26 |
| ATOM | 1223 | N | ARG | 222 | 23.461 | 24.295 | 44.147 | 1.00 | 14.02 |
| ATOM | 1224 | CA | ARG | 222 | 22.068 | 24.157 | 44.556 | 1.00 | 15.84 |
| ATOM | 1225 | CB | ARG | 222 | 21.532 | 22.774 | 44.160 | 1.00 | 16.90 |
| ATOM | 1226 | CG | ARG | 222 | 21.412 | 22.572 | 42.655 | 1.00 | 16.24 |
| ATOM | 1227 | CD | ARG | 222 | 20.870 | 21.182 | 42.318 | 1.00 | 20.12 |
| ATOM | 1228 | NE | ARG | 222 | 20.609 | 21.044 | 40.888 | 1.00 | 23.09 |
| ATOM | 1229 | CZ | ARG | 222 | 20.399 | 19.884 | 40.269 | 1.00 | 25.88 |
| ATOM | 1230 | NH1 | ARG | 222 | 20.417 | 18.746 | 40.952 | 1.00 | 24.84 |
| ATOM | 1231 | NH2 | ARG | 222 | 20.182 | 19.860 | 38.960 | 1.00 | 26.85 |
| ATOM | 1232 | C | ARG | 222 | 21.846 | 24.385 | 46.050 | 1.00 | 14.53 |
| ATOM | 1233 | O | ARG | 222 | 20.813 | 24.918 | 46.452 | 1.00 | 15.21 |
| ATOM | 1234 | N | ALA | 223 | 22.821 | 23.991 | 46.861 | 1.00 | 13.97 |
| ATOM | 1235 | CA | ALA | 223 | 22.729 | 24.133 | 48.310 | 1.00 | 14.89 |
| ATOM | 1236 | CB | ALA | 223 | 23.818 | 23.284 | 48.980 | 1.00 | 14.97 |

TABLE B-continued

Co-ordinates of an underglycosylated tACEΔ36NJ ACE-lisinopril complex

| ATOM | 1237 | C   | ALA | 223 | 22.822 | 25.581 | 48.794 | 1.00 | 15.26 |
|------|------|-----|-----|-----|--------|--------|--------|------|-------|
| ATOM | 1238 | O   | ALA | 223 | 22.443 | 25.891 | 49.923 | 1.00 | 15.20 |
| ATOM | 1239 | N   | ILE | 224 | 23.328 | 26.470 | 47.949 | 1.00 | 14.59 |
| ATOM | 1240 | CA  | ILE | 224 | 23.444 | 27.871 | 48.338 | 1.00 | 13.97 |
| ATOM | 1241 | CB  | ILE | 224 | 24.651 | 28.545 | 47.629 | 1.00 | 13.29 |
| ATOM | 1242 | CG2 | ILE | 224 | 24.713 | 30.027 | 47.970 | 1.00 | 11.18 |
| ATOM | 1243 | CG1 | ILE | 224 | 25.950 | 27.852 | 48.051 | 1.00 | 15.89 |
| ATOM | 1244 | CD1 | ILE | 224 | 26.228 | 27.904 | 49.550 | 1.00 | 14.70 |
| ATOM | 1245 | C   | ILE | 224 | 22.163 | 28.644 | 48.007 | 1.00 | 13.79 |
| ATOM | 1246 | O   | ILE | 224 | 21.842 | 29.638 | 48.655 | 1.00 | 14.26 |
| ATOM | 1247 | N   | LEU | 225 | 21.422 | 28.167 | 47.014 | 1.00 | 13.03 |
| ATOM | 1248 | CA  | LEU | 225 | 20.203 | 28.834 | 46.578 | 1.00 | 13.73 |
| ATOM | 1249 | CB  | LEU | 225 | 19.521 | 28.011 | 45.481 | 1.00 | 13.73 |
| ATOM | 1250 | CG  | LEU | 225 | 18.230 | 28.616 | 44.922 | 1.00 | 15.14 |
| ATOM | 1251 | CD1 | LEU | 225 | 18.513 | 29.995 | 44.338 | 1.00 | 13.02 |
| ATOM | 1252 | CD2 | LEU | 225 | 17.646 | 27.684 | 43.865 | 1.00 | 15.05 |
| ATOM | 1253 | C   | LEU | 225 | 19.188 | 29.170 | 47.673 | 1.00 | 15.99 |
| ATOM | 1254 | O   | LEU | 225 | 18.557 | 30.228 | 47.626 | 1.00 | 16.45 |
| ATOM | 1255 | N   | GLN | 226 | 19.022 | 28.296 | 48.661 | 1.00 | 17.25 |
| ATOM | 1256 | CA  | GLN | 226 | 18.053 | 28.578 | 49.717 | 1.00 | 17.93 |
| ATOM | 1257 | CB  | GLN | 226 | 17.860 | 27.365 | 50.629 | 1.00 | 18.12 |
| ATOM | 1258 | CG  | GLN | 226 | 19.093 | 26.934 | 51.392 | 1.00 | 21.07 |
| ATOM | 1259 | CD  | GLN | 226 | 18.752 | 26.031 | 52.566 | 1.00 | 25.37 |
| ATOM | 1260 | OE1 | GLN | 226 | 19.475 | 25.083 | 52.869 | 1.00 | 28.28 |
| ATOM | 1261 | NE2 | GLN | 226 | 17.651 | 26.334 | 53.242 | 1.00 | 25.39 |
| ATOM | 1262 | C   | GLN | 226 | 18.422 | 29.787 | 50.570 | 1.00 | 18.27 |
| ATOM | 1263 | O   | GLN | 226 | 17.552 | 30.381 | 51.207 | 1.00 | 18.35 |
| ATOM | 1264 | N   | PHE | 227 | 19.702 | 30.158 | 50.579 | 1.00 | 17.08 |
| ATOM | 1265 | CA  | PHE | 227 | 20.156 | 31.298 | 51.376 | 1.00 | 17.03 |
| ATOM | 1266 | CB  | PHE | 227 | 21.531 | 31.015 | 52.001 | 1.00 | 17.75 |
| ATOM | 1267 | CG  | PHE | 227 | 21.594 | 29.756 | 52.820 | 1.00 | 19.66 |
| ATOM | 1268 | CD1 | PHE | 227 | 22.214 | 28.617 | 52.315 | 1.00 | 18.54 |
| ATOM | 1269 | CD2 | PHE | 227 | 21.058 | 29.715 | 54.102 | 1.00 | 19.80 |
| ATOM | 1270 | CE1 | PHE | 227 | 22.303 | 27.457 | 53.077 | 1.00 | 20.33 |
| ATOM | 1271 | CE2 | PHE | 227 | 21.138 | 28.560 | 54.874 | 1.00 | 20.11 |
| ATOM | 1272 | CZ  | PHE | 227 | 21.763 | 27.428 | 54.362 | 1.00 | 21.23 |
| ATOM | 1273 | C   | PHE | 227 | 20.277 | 32.631 | 50.635 | 1.00 | 15.96 |
| ATOM | 1274 | O   | PHE | 227 | 20.123 | 33.686 | 51.243 | 1.00 | 14.83 |
| ATOM | 1275 | N   | TYR | 228 | 20.552 | 32.588 | 49.332 | 1.00 | 14.81 |
| ATOM | 1276 | CA  | TYR | 228 | 20.786 | 33.813 | 48.566 | 1.00 | 13.93 |
| ATOM | 1277 | CB  | TYR | 228 | 21.163 | 33.484 | 47.114 | 1.00 | 12.40 |
| ATOM | 1278 | CG  | TYR | 228 | 22.287 | 34.363 | 46.617 | 1.00 | 11.13 |
| ATOM | 1279 | CD1 | TYR | 228 | 23.561 | 34.271 | 47.181 | 1.00 | 10.09 |
| ATOM | 1280 | CE1 | TYR | 228 | 24.596 | 35.119 | 46.780 | 1.00 | 9.24  |
| ATOM | 1281 | CD2 | TYR | 228 | 22.073 | 35.327 | 45.628 | 1.00 | 12.00 |
| ATOM | 1282 | CE2 | TYR | 228 | 23.105 | 36.184 | 45.218 | 1.00 | 9.28  |
| ATOM | 1283 | CZ  | TYR | 228 | 24.361 | 36.073 | 45.803 | 1.00 | 10.33 |
| ATOM | 1284 | OH  | TYR | 228 | 25.380 | 36.927 | 45.447 | 1.00 | 9.24  |
| ATOM | 1285 | C   | TYR | 228 | 19.750 | 34.930 | 48.561 | 1.00 | 14.20 |
| ATOM | 1286 | O   | TYR | 228 | 20.095 | 36.092 | 48.787 | 1.00 | 13.92 |
| ATOM | 1287 | N   | PRO | 229 | 18.476 | 34.615 | 48.287 | 1.00 | 15.32 |
| ATOM | 1288 | CD  | PRO | 229 | 17.850 | 33.355 | 47.841 | 1.00 | 14.61 |
| ATOM | 1289 | CA  | PRO | 229 | 17.504 | 35.713 | 48.288 | 1.00 | 14.32 |
| ATOM | 1290 | CB  | PRO | 229 | 16.183 | 35.001 | 48.005 | 1.00 | 14.50 |
| ATOM | 1291 | CG  | PRO | 229 | 16.612 | 33.854 | 47.114 | 1.00 | 14.48 |
| ATOM | 1292 | C   | PRO | 229 | 17.487 | 36.503 | 49.603 | 1.00 | 15.12 |
| ATOM | 1293 | O   | PRO | 229 | 17.378 | 37.731 | 49.592 | 1.00 | 14.15 |
| ATOM | 1294 | N   | LYS | 230 | 17.612 | 35.803 | 50.730 | 1.00 | 15.42 |
| ATOM | 1295 | CA  | LYS | 230 | 17.598 | 36.463 | 52.038 | 1.00 | 15.89 |
| ATOM | 1296 | CB  | LYS | 230 | 17.459 | 35.441 | 53.166 | 1.00 | 16.82 |
| ATOM | 1297 | CG  | LYS | 230 | 16.964 | 36.061 | 54.462 | 1.00 | 19.46 |
| ATOM | 1298 | CD  | LYS | 230 | 15.624 | 36.737 | 54.200 | 1.00 | 24.16 |
| ATOM | 1299 | CE  | LYS | 230 | 14.959 | 37.224 | 55.463 | 1.00 | 28.11 |
| ATOM | 1300 | NZ  | LYS | 230 | 13.630 | 37.824 | 55.153 | 1.00 | 26.83 |
| ATOM | 1301 | C   | LYS | 230 | 18.871 | 37.272 | 52.240 | 1.00 | 14.81 |
| ATOM | 1302 | O   | LYS | 230 | 18.852 | 38.364 | 52.811 | 1.00 | 12.92 |
| ATOM | 1303 | N   | TYR | 231 | 19.979 | 36.714 | 51.774 | 1.00 | 14.42 |
| ATOM | 1304 | CA  | TYR | 231 | 21.270 | 37.375 | 51.848 | 1.00 | 11.87 |
| ATOM | 1305 | CB  | TYR | 231 | 22.330 | 36.466 | 51.223 | 1.00 | 11.76 |
| ATOM | 1306 | CG  | TYR | 231 | 23.525 | 37.197 | 50.660 | 1.00 | 10.89 |
| ATOM | 1307 | CD1 | TYR | 231 | 24.499 | 37.736 | 51.500 | 1.00 | 9.98  |
| ATOM | 1308 | CE1 | TYR | 231 | 25.612 | 38.397 | 50.976 | 1.00 | 12.44 |
| ATOM | 1309 | CD2 | TYR | 231 | 23.683 | 37.341 | 49.279 | 1.00 | 11.71 |
| ATOM | 1310 | CE2 | TYR | 231 | 24.788 | 38.004 | 48.745 | 1.00 | 12.56 |
| ATOM | 1311 | CZ  | TYR | 231 | 25.750 | 38.523 | 49.597 | 1.00 | 11.83 |
| ATOM | 1312 | OH  | TYR | 231 | 26.870 | 39.120 | 49.071 | 1.00 | 11.18 |
| ATOM | 1313 | C   | TYR | 231 | 21.191 | 38.699 | 51.080 | 1.00 | 11.12 |
| ATOM | 1314 | O   | TYR | 231 | 21.616 | 39.741 | 51.575 | 1.00 | 12.14 |

TABLE B-continued

Co-ordinates of an underglycosylated tACEΔ36NJ ACE-lisinopril complex

| ATOM | 1315 | N | VAL | 232 | 20.654 | 38.646 | 49.864 | 1.00 | 11.62 |
|---|---|---|---|---|---|---|---|---|---|
| ATOM | 1316 | CA | VAL | 232 | 20.516 | 39.833 | 49.019 | 1.00 | 10.85 |
| ATOM | 1317 | CB | VAL | 232 | 19.900 | 39.455 | 47.648 | 1.00 | 11.31 |
| ATOM | 1318 | CG1 | VAL | 232 | 19.439 | 40.697 | 46.900 | 1.00 | 10.40 |
| ATOM | 1319 | CG2 | VAL | 232 | 20.934 | 38.699 | 46.821 | 1.00 | 11.64 |
| ATOM | 1320 | C | VAL | 232 | 19.658 | 40.904 | 49.698 | 1.00 | 12.40 |
| ATOM | 1321 | O | VAL | 232 | 19.992 | 42.096 | 49.682 | 1.00 | 11.44 |
| ATOM | 1322 | N | GLU | 233 | 18.557 | 40.473 | 50.303 | 1.00 | 12.62 |
| ATOM | 1323 | CA | GLU | 233 | 17.661 | 41.389 | 50.995 | 1.00 | 14.05 |
| ATOM | 1324 | CB | GLU | 233 | 16.437 | 40.617 | 51.506 | 1.00 | 17.42 |
| ATOM | 1325 | CG | GLU | 233 | 15.557 | 41.381 | 52.487 | 1.00 | 22.94 |
| ATOM | 1326 | CD | GLU | 233 | 14.322 | 40.593 | 52.907 | 1.00 | 27.83 |
| ATOM | 1327 | OE1 | GLU | 233 | 14.416 | 39.355 | 53.069 | 1.00 | 29.39 |
| ATOM | 1328 | OE2 | GLU | 233 | 13.256 | 41.216 | 53.089 | 1.00 | 32.62 |
| ATOM | 1329 | C | GLU | 233 | 18.367 | 42.098 | 52.155 | 1.00 | 12.54 |
| ATOM | 1330 | O | GLU | 233 | 18.313 | 43.320 | 52.273 | 1.00 | 13.58 |
| ATOM | 1331 | N | LEU | 234 | 19.043 | 41.328 | 52.999 | 1.00 | 12.59 |
| ATOM | 1332 | CA | LEU | 234 | 19.738 | 41.885 | 54.153 | 1.00 | 12.98 |
| ATOM | 1333 | CB | LEU | 234 | 20.149 | 40.758 | 55.106 | 1.00 | 13.67 |
| ATOM | 1334 | CG | LEU | 234 | 18.968 | 40.015 | 55.738 | 1.00 | 16.89 |
| ATOM | 1335 | CD1 | LEU | 234 | 19.464 | 38.803 | 56.512 | 1.00 | 16.48 |
| ATOM | 1336 | CD2 | LEU | 234 | 18.200 | 40.964 | 56.650 | 1.00 | 16.76 |
| ATOM | 1337 | C | LEU | 234 | 20.952 | 42.750 | 53.820 | 1.00 | 12.60 |
| ATOM | 1338 | O | LEU | 234 | 21.145 | 43.801 | 54.430 | 1.00 | 11.00 |
| ATOM | 1339 | N | ILE | 235 | 21.774 | 42.328 | 52.862 | 1.00 | 10.69 |
| ATOM | 1340 | CA | ILE | 235 | 22.945 | 43.130 | 52.522 | 1.00 | 10.15 |
| ATOM | 1341 | CB | ILE | 235 | 23.963 | 42.341 | 51.654 | 1.00 | 11.30 |
| ATOM | 1342 | CG2 | ILE | 235 | 23.383 | 42.074 | 50.252 | 1.00 | 8.24 |
| ATOM | 1343 | CG1 | ILE | 235 | 25.283 | 43.124 | 51.589 | 1.00 | 9.63 |
| ATOM | 1344 | CD1 | ILE | 235 | 26.426 | 42.355 | 50.948 | 1.00 | 9.83 |
| ATOM | 1345 | C | ILE | 235 | 22.525 | 44.422 | 51.820 | 1.00 | 9.51 |
| ATOM | 1346 | O | ILE | 235 | 23.177 | 45.456 | 51.970 | 1.00 | 9.55 |
| ATOM | 1347 | N | ASN | 236 | 21.430 | 44.372 | 51.066 | 1.00 | 9.09 |
| ATOM | 1348 | CA | ASN | 236 | 20.925 | 45.570 | 50.398 | 1.00 | 10.19 |
| ATOM | 1349 | CB | ASN | 236 | 19.825 | 45.225 | 49.385 | 1.00 | 10.23 |
| ATOM | 1350 | CG | ASN | 236 | 20.371 | 44.929 | 48.001 | 1.00 | 11.26 |
| ATOM | 1351 | OD1 | ASN | 236 | 21.501 | 45.293 | 47.677 | 1.00 | 10.18 |
| ATOM | 1352 | ND2 | ASN | 236 | 19.557 | 44.290 | 47.167 | 1.00 | 12.22 |
| ATOM | 1353 | C | ASN | 236 | 20.356 | 46.525 | 51.453 | 1.00 | 11.01 |
| ATOM | 1354 | O | ASN | 236 | 20.569 | 47.738 | 51.387 | 1.00 | 10.90 |
| ATOM | 1355 | N | GLN | 237 | 19.630 | 45.969 | 52.421 | 1.00 | 12.58 |
| ATOM | 1356 | CA | GLN | 237 | 19.038 | 46.769 | 53.489 | 1.00 | 12.11 |
| ATOM | 1357 | CB | GLN | 237 | 18.264 | 45.876 | 54.460 | 1.00 | 14.23 |
| ATOM | 1358 | CG | GLN | 237 | 17.428 | 46.638 | 55.483 | 1.00 | 14.79 |
| ATOM | 1359 | CD | GLN | 237 | 16.781 | 45.714 | 56.502 | 1.00 | 18.93 |
| ATOM | 1360 | OE1 | GLN | 237 | 16.567 | 44.532 | 56.233 | 1.00 | 20.61 |
| ATOM | 1361 | NE2 | GLN | 237 | 16.455 | 46.254 | 57.672 | 1.00 | 17.63 |
| ATOM | 1362 | C | GLN | 237 | 20.149 | 47.498 | 54.239 | 1.00 | 12.36 |
| ATOM | 1363 | O | GLN | 237 | 20.038 | 48.687 | 54.537 | 1.00 | 12.83 |
| ATOM | 1364 | N | ALA | 238 | 21.218 | 46.771 | 54.549 | 1.00 | 10.55 |
| ATOM | 1365 | CA | ALA | 238 | 22.353 | 47.361 | 55.245 | 1.00 | 10.94 |
| ATOM | 1366 | CB | ALA | 238 | 23.431 | 46.316 | 55.473 | 1.00 | 7.92 |
| ATOM | 1367 | C | ALA | 238 | 22.909 | 48.509 | 54.408 | 1.00 | 11.58 |
| ATOM | 1368 | O | ALA | 238 | 23.205 | 49.578 | 54.931 | 1.00 | 12.66 |
| ATOM | 1369 | N | ALA | 239 | 23.045 | 48.280 | 53.104 | 1.00 | 11.03 |
| ATOM | 1370 | CA | ALA | 239 | 23.569 | 49.302 | 52.207 | 1.00 | 12.87 |
| ATOM | 1371 | CB | ALA | 239 | 23.647 | 48.762 | 50.779 | 1.00 | 11.95 |
| ATOM | 1372 | C | ALA | 239 | 22.719 | 50.570 | 52.245 | 1.00 | 13.46 |
| ATOM | 1373 | O | ALA | 239 | 23.257 | 51.677 | 52.337 | 1.00 | 12.98 |
| ATOM | 1374 | N | ARG | 240 | 21.396 | 50.408 | 52.180 | 1.00 | 13.34 |
| ATOM | 1375 | CA | ARG | 240 | 20.491 | 51.556 | 52.204 | 1.00 | 13.67 |
| ATOM | 1376 | CB | ARG | 240 | 19.037 | 51.122 | 51.959 | 1.00 | 12.51 |
| ATOM | 1377 | CG | ARG | 240 | 18.763 | 50.570 | 50.559 | 1.00 | 14.85 |
| ATOM | 1378 | CD | ARG | 240 | 17.266 | 50.496 | 50.262 | 1.00 | 13.15 |
| ATOM | 1379 | NE | ARG | 240 | 16.531 | 49.731 | 51.269 | 1.00 | 15.23 |
| ATOM | 1380 | CZ | ARG | 240 | 16.450 | 48.405 | 51.307 | 1.00 | 17.70 |
| ATOM | 1381 | NH1 | ARG | 240 | 17.060 | 47.665 | 50.380 | 1.00 | 15.68 |
| ATOM | 1382 | NH2 | ARG | 240 | 15.759 | 47.814 | 52.278 | 1.00 | 16.05 |
| ATOM | 1383 | C | ARG | 240 | 20.583 | 52.299 | 53.533 | 1.00 | 13.93 |
| ATOM | 1384 | O | ARG | 240 | 20.502 | 53.526 | 53.571 | 1.00 | 13.67 |
| ATOM | 1385 | N | LEU | 241 | 20.753 | 51.553 | 54.619 | 1.00 | 14.68 |
| ATOM | 1386 | CA | LEU | 241 | 20.853 | 52.155 | 55.941 | 1.00 | 15.52 |
| ATOM | 1387 | CB | LEU | 241 | 20.731 | 51.075 | 57.025 | 1.00 | 14.97 |
| ATOM | 1388 | CG | LEU | 241 | 19.324 | 50.472 | 57.150 | 1.00 | 16.48 |
| ATOM | 1389 | CD1 | LEU | 241 | 19.332 | 49.281 | 58.102 | 1.00 | 14.35 |
| ATOM | 1390 | CD2 | LEU | 241 | 18.361 | 51.552 | 57.644 | 1.00 | 17.43 |
| ATOM | 1391 | C | LEU | 241 | 22.159 | 52.927 | 56.096 | 1.00 | 15.83 |
| ATOM | 1392 | O | LEU | 241 | 22.331 | 53.695 | 57.047 | 1.00 | 15.43 |

TABLE B-continued

Co-ordinates of an underglycosylated tACEΔ36NJ ACE-lisinopril complex

| ATOM | 1393 | N | ASN | 242 | 23.074 | 52.729 | 55.152 | 1.00 | 14.16 |
|---|---|---|---|---|---|---|---|---|---|
| ATOM | 1394 | CA | ASN | 242 | 24.350 | 53.426 | 55.185 | 1.00 | 13.59 |
| ATOM | 1395 | CB | ASN | 242 | 25.500 | 52.423 | 55.067 | 1.00 | 12.71 |
| ATOM | 1396 | CG | ASN | 242 | 25.778 | 51.711 | 56.384 | 1.00 | 15.20 |
| ATOM | 1397 | OD1 | ASN | 242 | 26.069 | 52.354 | 57.395 | 1.00 | 14.44 |
| ATOM | 1398 | ND2 | ASN | 242 | 25.678 | 50.385 | 56.382 | 1.00 | 13.74 |
| ATOM | 1399 | C | ASN | 242 | 24.463 | 54.516 | 54.120 | 1.00 | 13.25 |
| ATOM | 1400 | O | ASN | 242 | 25.540 | 55.063 | 53.894 | 1.00 | 13.69 |
| ATOM | 1401 | N | GLY | 243 | 23.346 | 54.820 | 53.462 | 1.00 | 13.09 |
| ATOM | 1402 | CA | GLY | 243 | 23.341 | 55.876 | 52.462 | 1.00 | 14.67 |
| ATOM | 1403 | C | GLY | 243 | 23.442 | 55.495 | 50.997 | 1.00 | 12.85 |
| ATOM | 1404 | O | GLY | 243 | 23.392 | 56.375 | 50.137 | 1.00 | 13.08 |
| ATOM | 1405 | N | TYR | 244 | 23.595 | 54.207 | 50.701 | 1.00 | 12.73 |
| ATOM | 1406 | CA | TYR | 244 | 23.697 | 53.752 | 49.312 | 1.00 | 12.34 |
| ATOM | 1407 | CB | TYR | 244 | 24.715 | 52.609 | 49.200 | 1.00 | 10.80 |
| ATOM | 1408 | CG | TYR | 244 | 26.115 | 52.990 | 49.633 | 1.00 | 12.14 |
| ATOM | 1409 | CD1 | TYR | 244 | 26.589 | 52.660 | 50.901 | 1.00 | 11.88 |
| ATOM | 1410 | CE1 | TYR | 244 | 27.870 | 53.038 | 51.316 | 1.00 | 10.81 |
| ATOM | 1411 | CD2 | TYR | 244 | 26.956 | 53.711 | 48.783 | 1.00 | 9.56 |
| ATOM | 1412 | CE2 | TYR | 244 | 28.237 | 54.096 | 49.189 | 1.00 | 10.67 |
| ATOM | 1413 | CZ | TYR | 244 | 28.684 | 53.757 | 50.455 | 1.00 | 10.80 |
| ATOM | 1414 | OH | TYR | 244 | 29.937 | 54.150 | 50.864 | 1.00 | 13.51 |
| ATOM | 1415 | C | TYR | 244 | 22.337 | 53.281 | 48.802 | 1.00 | 12.43 |
| ATOM | 1416 | O | TYR | 244 | 21.401 | 53.121 | 49.585 | 1.00 | 15.41 |
| ATOM | 1417 | N | VAL | 245 | 22.215 | 53.064 | 47.493 | 1.00 | 13.45 |
| ATOM | 1418 | CA | VAL | 245 | 20.945 | 52.596 | 46.937 | 1.00 | 13.11 |
| ATOM | 1419 | CB | VAL | 245 | 20.752 | 53.071 | 45.476 | 1.00 | 15.33 |
| ATOM | 1420 | CG1 | VAL | 245 | 20.670 | 54.595 | 45.446 | 1.00 | 17.06 |
| ATOM | 1421 | CG2 | VAL | 245 | 21.894 | 52.589 | 44.604 | 1.00 | 15.86 |
| ATOM | 1422 | C | VAL | 245 | 20.807 | 51.073 | 47.015 | 1.00 | 11.99 |
| ATOM | 1423 | O | VAL | 245 | 19.697 | 50.549 | 47.045 | 1.00 | 13.05 |
| ATOM | 1424 | N | ASP | 246 | 21.936 | 50.368 | 47.047 | 1.00 | 9.74 |
| ATOM | 1425 | CA | ASP | 246 | 21.946 | 48.907 | 47.163 | 1.00 | 10.63 |
| ATOM | 1426 | CB | ASP | 246 | 21.378 | 48.233 | 45.896 | 1.00 | 9.06 |
| ATOM | 1427 | CG | ASP | 246 | 22.202 | 48.520 | 44.644 | 1.00 | 11.98 |
| ATOM | 1428 | OD1 | ASP | 246 | 23.385 | 48.125 | 44.586 | 1.00 | 10.98 |
| ATOM | 1429 | OD2 | ASP | 246 | 21.658 | 49.140 | 43.708 | 1.00 | 10.66 |
| ATOM | 1430 | C | ASP | 246 | 23.373 | 48.424 | 47.444 | 1.00 | 9.60 |
| ATOM | 1431 | O | ASP | 246 | 24.308 | 49.219 | 47.429 | 1.00 | 11.47 |
| ATOM | 1432 | N | ALA | 247 | 23.538 | 47.130 | 47.706 | 1.00 | 9.86 |
| ATOM | 1433 | CA | ALA | 247 | 24.858 | 46.577 | 48.007 | 1.00 | 10.45 |
| ATOM | 1434 | CB | ALA | 247 | 24.738 | 45.084 | 48.336 | 1.00 | 9.21 |
| ATOM | 1435 | C | ALA | 247 | 25.895 | 46.787 | 46.894 | 1.00 | 9.94 |
| ATOM | 1436 | O | ALA | 247 | 27.072 | 47.006 | 47.177 | 1.00 | 10.23 |
| ATOM | 1437 | N | GLY | 248 | 25.465 | 46.701 | 45.638 | 1.00 | 9.68 |
| ATOM | 1438 | CA | GLY | 248 | 26.388 | 46.894 | 44.527 | 1.00 | 9.78 |
| ATOM | 1439 | C | GLY | 248 | 26.974 | 48.297 | 44.551 | 1.00 | 12.15 |
| ATOM | 1440 | O | GLY | 248 | 28.177 | 48.499 | 44.354 | 1.00 | 11.20 |
| ATOM | 1441 | N | ASP | 249 | 26.103 | 49.271 | 44.790 | 1.00 | 12.09 |
| ATOM | 1442 | CA | ASP | 249 | 26.494 | 50.674 | 44.873 | 1.00 | 12.50 |
| ATOM | 1443 | CB | ASP | 249 | 25.246 | 51.506 | 45.210 | 1.00 | 12.82 |
| ATOM | 1444 | CG | ASP | 249 | 25.528 | 52.995 | 45.337 | 1.00 | 13.95 |
| ATOM | 1445 | OD1 | ASP | 249 | 26.395 | 53.521 | 44.610 | 1.00 | 13.98 |
| ATOM | 1446 | OD2 | ASP | 249 | 24.851 | 53.647 | 46.159 | 1.00 | 13.82 |
| ATOM | 1447 | C | ASP | 249 | 27.562 | 50.795 | 45.961 | 1.00 | 12.92 |
| ATOM | 1448 | O | ASP | 249 | 28.640 | 51.350 | 45.741 | 1.00 | 11.95 |
| ATOM | 1449 | N | SER | 250 | 27.255 | 50.251 | 47.133 | 1.00 | 13.21 |
| ATOM | 1450 | CA | SER | 250 | 28.178 | 50.277 | 48.259 | 1.00 | 13.25 |
| ATOM | 1451 | CB | SER | 250 | 27.585 | 49.479 | 49.424 | 1.00 | 14.69 |
| ATOM | 1452 | OG | SER | 250 | 28.391 | 49.595 | 50.583 | 1.00 | 18.32 |
| ATOM | 1453 | C | SER | 250 | 29.557 | 49.705 | 47.876 | 1.00 | 12.60 |
| ATOM | 1454 | O | SER | 250 | 30.587 | 50.324 | 48.143 | 1.00 | 11.74 |
| ATOM | 1455 | N | TRP | 251 | 29.574 | 48.530 | 47.251 | 1.00 | 10.27 |
| ATOM | 1456 | CA | TRP | 251 | 30.840 | 47.908 | 46.847 | 1.00 | 11.25 |
| ATOM | 1457 | CB | TRP | 251 | 30.587 | 46.525 | 46.236 | 1.00 | 10.10 |
| ATOM | 1458 | CG | TRP | 251 | 30.163 | 45.479 | 47.223 | 1.00 | 10.89 |
| ATOM | 1459 | CD2 | TRP | 251 | 29.970 | 44.084 | 46.957 | 1.00 | 10.95 |
| ATOM | 1460 | CE2 | TRP | 251 | 29.587 | 43.475 | 48.174 | 1.00 | 12.43 |
| ATOM | 1461 | CE3 | TRP | 251 | 30.086 | 43.288 | 45.808 | 1.00 | 9.38 |
| ATOM | 1462 | CD1 | TRP | 251 | 29.895 | 45.657 | 48.554 | 1.00 | 10.57 |
| ATOM | 1463 | NE1 | TRP | 251 | 29.549 | 44.457 | 49.129 | 1.00 | 12.56 |
| ATOM | 1464 | CZ2 | TRP | 251 | 29.317 | 42.101 | 48.276 | 1.00 | 11.07 |
| ATOM | 1465 | CZ3 | TRP | 251 | 29.817 | 41.923 | 45.909 | 1.00 | 10.48 |
| ATOM | 1466 | CH2 | TRP | 251 | 29.437 | 41.345 | 47.135 | 1.00 | 9.03 |
| ATOM | 1467 | C | TRP | 251 | 31.641 | 48.751 | 45.852 | 1.00 | 10.66 |
| ATOM | 1468 | O | TRP | 251 | 32.847 | 48.926 | 46.009 | 1.00 | 11.21 |
| ATOM | 1469 | N | ARG | 252 | 30.972 | 49.266 | 44.824 | 1.00 | 10.93 |
| ATOM | 1470 | CA | ARG | 252 | 31.654 | 50.075 | 43.824 | 1.00 | 10.15 |

TABLE B-continued

Co-ordinates of an underglycosylated tACEΔ36NJ ACE-lisinopril complex

| ATOM | 1471 | CB  | ARG | 252 | 30.691 | 50.462 | 42.686 | 1.00 | 10.20 |
| ---- | ---- | --- | --- | --- | ------ | ------ | ------ | ---- | ----- |
| ATOM | 1472 | CG  | ARG | 252 | 30.225 | 49.288 | 41.810 | 1.00 | 9.68  |
| ATOM | 1473 | CD  | ARG | 252 | 29.435 | 49.763 | 40.580 | 1.00 | 10.48 |
| ATOM | 1474 | NE  | ARG | 252 | 28.195 | 50.475 | 40.912 | 1.00 | 10.26 |
| ATOM | 1475 | CZ  | ARG | 252 | 27.039 | 49.892 | 41.215 | 1.00 | 12.09 |
| ATOM | 1476 | NH1 | ARG | 252 | 25.973 | 50.633 | 41.506 | 1.00 | 10.42 |
| ATOM | 1477 | NH2 | ARG | 252 | 26.940 | 48.569 | 41.217 | 1.00 | 10.98 |
| ATOM | 1478 | C   | ARG | 252 | 32.271 | 51.337 | 44.440 | 1.00 | 11.46 |
| ATOM | 1479 | O   | ARG | 252 | 33.296 | 51.821 | 43.969 | 1.00 | 10.38 |
| ATOM | 1480 | N   | SER | 253 | 31.657 | 51.852 | 45.505 | 1.00 | 13.01 |
| ATOM | 1481 | CA  | SER | 253 | 32.147 | 53.065 | 46.157 | 1.00 | 13.62 |
| ATOM | 1482 | CB  | SER | 253 | 31.224 | 53.465 | 47.309 | 1.00 | 12.96 |
| ATOM | 1483 | OG  | SER | 253 | 31.473 | 52.676 | 48.460 | 1.00 | 16.21 |
| ATOM | 1484 | C   | SER | 253 | 33.575 | 52.932 | 46.685 | 1.00 | 12.79 |
| ATOM | 1485 | O   | SER | 253 | 34.253 | 53.935 | 46.893 | 1.00 | 12.73 |
| ATOM | 1486 | N   | MET | 254 | 34.025 | 51.699 | 46.903 | 1.00 | 14.11 |
| ATOM | 1487 | CA  | MET | 254 | 35.378 | 51.462 | 47.406 | 1.00 | 14.12 |
| ATOM | 1488 | CB  | MET | 254 | 35.622 | 49.960 | 47.620 | 1.00 | 16.31 |
| ATOM | 1489 | CG  | MET | 254 | 34.751 | 49.331 | 48.699 | 1.00 | 19.32 |
| ATOM | 1490 | SD  | MET | 254 | 35.231 | 47.629 | 49.106 | 1.00 | 25.77 |
| ATOM | 1491 | CE  | MET | 254 | 34.333 | 46.745 | 47.898 | 1.00 | 17.52 |
| ATOM | 1492 | C   | MET | 254 | 36.440 | 52.013 | 46.457 | 1.00 | 12.73 |
| ATOM | 1493 | O   | MET | 254 | 37.585 | 52.214 | 46.849 | 1.00 | 14.95 |
| ATOM | 1494 | N   | TYR | 255 | 36.061 | 52.251 | 45.207 | 1.00 | 11.95 |
| ATOM | 1495 | CA  | TYR | 255 | 37.001 | 52.782 | 44.227 | 1.00 | 10.96 |
| ATOM | 1496 | CB  | TYR | 255 | 36.734 | 52.180 | 42.840 | 1.00 | 10.71 |
| ATOM | 1497 | CG  | TYR | 255 | 37.055 | 50.711 | 42.767 | 1.00 | 10.53 |
| ATOM | 1498 | CD1 | TYR | 255 | 36.120 | 49.755 | 43.159 | 1.00 | 10.46 |
| ATOM | 1499 | CE1 | TYR | 255 | 36.441 | 48.401 | 43.183 | 1.00 | 10.93 |
| ATOM | 1500 | CD2 | TYR | 255 | 38.326 | 50.276 | 42.389 | 1.00 | 11.13 |
| ATOM | 1501 | CE2 | TYR | 255 | 38.661 | 48.915 | 42.415 | 1.00 | 11.62 |
| ATOM | 1502 | CZ  | TYR | 255 | 37.711 | 47.987 | 42.817 | 1.00 | 11.67 |
| ATOM | 1503 | OH  | TYR | 255 | 38.039 | 46.653 | 42.896 | 1.00 | 10.68 |
| ATOM | 1504 | C   | TYR | 255 | 36.976 | 54.305 | 44.139 | 1.00 | 10.20 |
| ATOM | 1505 | O   | TYR | 255 | 37.845 | 54.898 | 43.505 | 1.00 | 11.25 |
| ATOM | 1506 | N   | GLU | 256 | 35.985 | 54.932 | 44.767 | 1.00 | 10.48 |
| ATOM | 1507 | CA  | GLU | 256 | 35.874 | 56.396 | 44.750 | 1.00 | 11.92 |
| ATOM | 1508 | CB  | GLU | 256 | 36.950 | 57.018 | 45.649 | 1.00 | 12.76 |
| ATOM | 1509 | CG  | GLU | 256 | 36.925 | 56.528 | 47.097 | 1.00 | 16.04 |
| ATOM | 1510 | CD  | GLU | 256 | 37.925 | 57.263 | 47.993 | 1.00 | 20.13 |
| ATOM | 1511 | OE1 | GLU | 256 | 39.145 | 57.187 | 47.736 | 1.00 | 19.80 |
| ATOM | 1512 | OE2 | GLU | 256 | 37.487 | 57.917 | 48.959 | 1.00 | 23.10 |
| ATOM | 1513 | C   | GLU | 256 | 36.040 | 56.925 | 43.327 | 1.00 | 11.30 |
| ATOM | 1514 | O   | GLU | 256 | 36.703 | 57.935 | 43.100 | 1.00 | 12.11 |
| ATOM | 1515 | N   | THR | 257 | 35.430 | 56.236 | 42.371 | 1.00 | 11.67 |
| ATOM | 1516 | CA  | THR | 257 | 35.537 | 56.607 | 40.965 | 1.00 | 11.88 |
| ATOM | 1517 | CB  | THR | 257 | 36.511 | 55.649 | 40.239 | 1.00 | 13.99 |
| ATOM | 1518 | OG1 | THR | 257 | 37.788 | 55.701 | 40.889 | 1.00 | 13.92 |
| ATOM | 1519 | CG2 | THR | 257 | 36.679 | 56.043 | 38.775 | 1.00 | 13.03 |
| ATOM | 1520 | C   | THR | 257 | 34.167 | 56.555 | 40.296 | 1.00 | 11.09 |
| ATOM | 1521 | O   | THR | 257 | 33.691 | 55.490 | 39.918 | 1.00 | 10.49 |
| ATOM | 1522 | N   | PRO | 258 | 33.514 | 57.719 | 40.154 | 1.00 | 11.64 |
| ATOM | 1523 | CD  | PRO | 258 | 33.992 | 59.028 | 40.638 | 1.00 | 11.87 |
| ATOM | 1524 | CA  | PRO | 258 | 32.186 | 57.842 | 39.539 | 1.00 | 12.51 |
| ATOM | 1525 | CB  | PRO | 258 | 31.953 | 59.352 | 39.526 | 1.00 | 13.07 |
| ATOM | 1526 | CG  | PRO | 258 | 32.703 | 59.817 | 40.754 | 1.00 | 13.28 |
| ATOM | 1527 | C   | PRO | 258 | 32.072 | 57.226 | 38.143 | 1.00 | 12.84 |
| ATOM | 1528 | O   | PRO | 258 | 31.014 | 56.719 | 37.762 | 1.00 | 13.80 |
| ATOM | 1529 | N   | SER | 259 | 33.164 | 57.270 | 37.387 | 1.00 | 12.06 |
| ATOM | 1530 | CA  | SER | 259 | 33.182 | 56.728 | 36.030 | 1.00 | 13.03 |
| ATOM | 1531 | CB  | SER | 259 | 34.154 | 57.536 | 35.170 | 1.00 | 15.05 |
| ATOM | 1532 | OG  | SER | 259 | 35.466 | 57.473 | 35.707 | 1.00 | 14.74 |
| ATOM | 1533 | C   | SER | 259 | 33.588 | 55.254 | 35.987 | 1.00 | 12.40 |
| ATOM | 1534 | O   | SER | 259 | 33.830 | 54.708 | 34.917 | 1.00 | 11.54 |
| ATOM | 1535 | N   | LEU | 260 | 33.649 | 54.615 | 37.150 | 1.00 | 12.21 |
| ATOM | 1536 | CA  | LEU | 260 | 34.060 | 53.214 | 37.243 | 1.00 | 12.51 |
| ATOM | 1537 | CB  | LEU | 260 | 33.766 | 52.665 | 38.648 | 1.00 | 11.05 |
| ATOM | 1538 | CG  | LEU | 260 | 34.282 | 51.236 | 38.891 | 1.00 | 13.73 |
| ATOM | 1539 | CD1 | LEU | 260 | 35.808 | 51.214 | 38.751 | 1.00 | 10.71 |
| ATOM | 1540 | CD2 | LEU | 260 | 33.870 | 50.751 | 40.275 | 1.00 | 12.15 |
| ATOM | 1541 | C   | LEU | 260 | 33.465 | 52.256 | 36.207 | 1.00 | 13.15 |
| ATOM | 1542 | O   | LEU | 260 | 34.205 | 51.578 | 35.485 | 1.00 | 9.99  |
| ATOM | 1543 | N   | GLU | 261 | 32.138 | 52.187 | 36.131 | 1.00 | 11.55 |
| ATOM | 1544 | CA  | GLU | 261 | 31.512 | 51.266 | 35.190 | 1.00 | 13.22 |
| ATOM | 1545 | CB  | GLU | 261 | 29.985 | 51.292 | 35.353 | 1.00 | 12.14 |
| ATOM | 1546 | CG  | GLU | 261 | 29.554 | 50.650 | 36.671 | 1.00 | 15.06 |
| ATOM | 1547 | CD  | GLU | 261 | 28.065 | 50.396 | 36.774 | 1.00 | 16.56 |
| ATOM | 1548 | OE1 | GLU | 261 | 27.388 | 50.379 | 35.727 | 1.00 | 20.06 |

TABLE B-continued

Co-ordinates of an underglycosylated tACEΔ36NJ ACE-lisinopril complex

| ATOM | 1549 | OE2 | GLU | 261 | 27.574 | 50.197 | 37.906 | 1.00 | 17.33 |
|---|---|---|---|---|---|---|---|---|---|
| ATOM | 1550 | C | GLU | 261 | 31.923 | 51.495 | 33.740 | 1.00 | 13.12 |
| ATOM | 1551 | O | GLU | 261 | 32.193 | 50.538 | 33.011 | 1.00 | 11.67 |
| ATOM | 1552 | N | GLN | 262 | 31.988 | 52.752 | 33.320 | 1.00 | 11.67 |
| ATOM | 1553 | CA | GLN | 262 | 32.395 | 53.042 | 31.952 | 1.00 | 13.82 |
| ATOM | 1554 | CB | GLN | 262 | 32.128 | 54.508 | 31.607 | 1.00 | 15.74 |
| ATOM | 1555 | CG | GLN | 262 | 30.659 | 54.915 | 31.661 | 1.00 | 24.70 |
| ATOM | 1556 | CD | GLN | 262 | 30.455 | 56.378 | 31.298 | 1.00 | 29.02 |
| ATOM | 1557 | OE1 | GLN | 262 | 30.558 | 56.762 | 30.132 | 1.00 | 35.05 |
| ATOM | 1558 | NE2 | GLN | 262 | 30.183 | 57.205 | 32.300 | 1.00 | 32.50 |
| ATOM | 1559 | C | GLN | 262 | 33.883 | 52.733 | 31.760 | 1.00 | 12.94 |
| ATOM | 1560 | O | GLN | 262 | 34.285 | 52.213 | 30.715 | 1.00 | 11.76 |
| ATOM | 1561 | N | ASP | 263 | 34.696 | 53.059 | 32.764 | 1.00 | 11.79 |
| ATOM | 1562 | CA | ASP | 263 | 36.131 | 52.805 | 32.689 | 1.00 | 12.07 |
| ATOM | 1563 | CB | ASP | 263 | 36.845 | 53.238 | 33.975 | 1.00 | 12.41 |
| ATOM | 1564 | CG | ASP | 263 | 36.890 | 54.742 | 34.145 | 1.00 | 13.78 |
| ATOM | 1565 | OD1 | ASP | 263 | 36.821 | 55.453 | 33.127 | 1.00 | 14.89 |
| ATOM | 1566 | OD2 | ASP | 263 | 37.015 | 55.211 | 35.296 | 1.00 | 15.49 |
| ATOM | 1567 | C | ASP | 263 | 36.410 | 51.328 | 32.469 | 1.00 | 13.01 |
| ATOM | 1568 | O | ASP | 263 | 37.190 | 50.957 | 31.593 | 1.00 | 11.20 |
| ATOM | 1569 | N | LEU | 264 | 35.773 | 50.495 | 33.284 | 1.00 | 12.13 |
| ATOM | 1570 | CA | LEU | 264 | 35.958 | 49.055 | 33.207 | 1.00 | 13.22 |
| ATOM | 1571 | CB | LEU | 264 | 35.259 | 48.379 | 34.393 | 1.00 | 12.89 |
| ATOM | 1572 | CG | LEU | 264 | 35.758 | 48.893 | 35.750 | 1.00 | 17.46 |
| ATOM | 1573 | CD1 | LEU | 264 | 35.091 | 48.124 | 36.883 | 1.00 | 15.64 |
| ATOM | 1574 | CD2 | LEU | 264 | 37.281 | 48.756 | 35.826 | 1.00 | 18.10 |
| ATOM | 1575 | C | LEU | 264 | 35.449 | 48.498 | 31.884 | 1.00 | 13.15 |
| ATOM | 1576 | O | LEU | 264 | 36.049 | 47.591 | 31.318 | 1.00 | 12.41 |
| ATOM | 1577 | N | GLU | 265 | 34.348 | 49.051 | 31.387 | 1.00 | 15.01 |
| ATOM | 1578 | CA | GLU | 265 | 33.788 | 48.612 | 30.114 | 1.00 | 18.16 |
| ATOM | 1579 | CB | GLU | 265 | 32.457 | 49.326 | 29.856 | 1.00 | 20.13 |
| ATOM | 1580 | CG | GLU | 265 | 31.833 | 49.068 | 28.485 | 1.00 | 26.44 |
| ATOM | 1581 | CD | GLU | 265 | 31.578 | 47.599 | 28.209 | 1.00 | 31.50 |
| ATOM | 1582 | OE1 | GLU | 265 | 31.057 | 46.900 | 29.108 | 1.00 | 33.66 |
| ATOM | 1583 | OE2 | GLU | 265 | 31.886 | 47.145 | 27.085 | 1.00 | 34.88 |
| ATOM | 1584 | C | GLU | 265 | 34.773 | 48.889 | 28.966 | 1.00 | 18.71 |
| ATOM | 1585 | O | GLU | 265 | 34.969 | 48.038 | 28.094 | 1.00 | 17.84 |
| ATOM | 1586 | N | ARG | 266 | 35.389 | 50.072 | 28.971 | 1.00 | 16.94 |
| ATOM | 1587 | CA | ARG | 266 | 36.355 | 50.425 | 27.932 | 1.00 | 17.44 |
| ATOM | 1588 | CB | ARG | 266 | 36.840 | 51.873 | 28.101 | 1.00 | 20.53 |
| ATOM | 1589 | CG | ARG | 266 | 35.900 | 52.936 | 27.550 | 1.00 | 22.86 |
| ATOM | 1590 | CD | ARG | 266 | 36.534 | 54.323 | 27.645 | 1.00 | 23.46 |
| ATOM | 1591 | NE | ARG | 266 | 36.579 | 54.824 | 29.016 | 1.00 | 25.90 |
| ATOM | 1592 | CZ | ARG | 266 | 35.566 | 55.437 | 29.623 | 1.00 | 28.47 |
| ATOM | 1593 | NH1 | ARG | 266 | 34.423 | 55.634 | 28.979 | 1.00 | 29.44 |
| ATOM | 1594 | NH2 | ARG | 266 | 35.693 | 55.851 | 30.876 | 1.00 | 30.11 |
| ATOM | 1595 | C | ARG | 266 | 37.554 | 49.486 | 27.986 | 1.00 | 15.99 |
| ATOM | 1596 | O | ARG | 266 | 38.055 | 49.042 | 26.955 | 1.00 | 15.42 |
| ATOM | 1597 | N | LEU | 267 | 38.014 | 49.188 | 29.197 | 1.00 | 15.40 |
| ATOM | 1598 | CA | LEU | 267 | 39.154 | 48.299 | 29.372 | 1.00 | 13.76 |
| ATOM | 1599 | CB | LEU | 267 | 39.539 | 48.228 | 30.853 | 1.00 | 13.89 |
| ATOM | 1600 | CG | LEU | 267 | 40.091 | 49.539 | 31.438 | 1.00 | 13.95 |
| ATOM | 1601 | CD1 | LEU | 267 | 40.200 | 49.433 | 32.952 | 1.00 | 12.21 |
| ATOM | 1602 | CD2 | LEU | 267 | 41.462 | 49.849 | 30.815 | 1.00 | 12.02 |
| ATOM | 1603 | C | LEU | 267 | 38.836 | 46.907 | 28.830 | 1.00 | 15.08 |
| ATOM | 1604 | O | LEU | 267 | 39.655 | 46.296 | 28.135 | 1.00 | 13.11 |
| ATOM | 1605 | N | PHE | 268 | 37.642 | 46.412 | 29.136 | 1.00 | 14.37 |
| ATOM | 1606 | CA | PHE | 268 | 37.233 | 45.098 | 28.658 | 1.00 | 14.85 |
| ATOM | 1607 | CB | PHE | 268 | 35.841 | 44.735 | 29.172 | 1.00 | 15.58 |
| ATOM | 1608 | CG | PHE | 268 | 35.308 | 43.453 | 28.590 | 1.00 | 19.42 |
| ATOM | 1609 | CD1 | PHE | 268 | 35.795 | 42.219 | 29.026 | 1.00 | 17.97 |
| ATOM | 1610 | CD2 | PHE | 268 | 34.373 | 43.480 | 27.561 | 1.00 | 17.52 |
| ATOM | 1611 | CE1 | PHE | 268 | 35.360 | 41.036 | 28.439 | 1.00 | 20.24 |
| ATOM | 1612 | CE2 | PHE | 268 | 33.932 | 42.301 | 26.966 | 1.00 | 20.46 |
| ATOM | 1613 | CZ | PHE | 268 | 34.428 | 41.076 | 27.407 | 1.00 | 20.47 |
| ATOM | 1614 | C | PHE | 268 | 37.222 | 45.061 | 27.132 | 1.00 | 15.22 |
| ATOM | 1615 | O | PHE | 268 | 37.717 | 44.113 | 26.521 | 1.00 | 15.06 |
| ATOM | 1616 | N | GLN | 269 | 36.649 | 46.094 | 26.521 | 1.00 | 14.71 |
| ATOM | 1617 | CA | GLN | 269 | 36.570 | 46.174 | 25.066 | 1.00 | 15.04 |
| ATOM | 1618 | CB | GLN | 269 | 35.797 | 47.427 | 24.642 | 1.00 | 18.56 |
| ATOM | 1619 | CG | GLN | 269 | 34.296 | 47.359 | 24.893 | 1.00 | 23.06 |
| ATOM | 1620 | CD | GLN | 269 | 33.650 | 46.149 | 24.238 | 1.00 | 25.97 |
| ATOM | 1621 | OE1 | GLN | 269 | 33.962 | 45.805 | 23.098 | 1.00 | 27.07 |
| ATOM | 1622 | NE2 | GLN | 269 | 32.736 | 45.506 | 24.953 | 1.00 | 27.62 |
| ATOM | 1623 | C | GLN | 269 | 37.936 | 46.172 | 24.389 | 1.00 | 14.54 |
| ATOM | 1624 | O | GLN | 269 | 38.082 | 45.640 | 23.297 | 1.00 | 13.32 |
| ATOM | 1625 | N | GLU | 270 | 38.936 | 46.767 | 25.030 | 1.00 | 15.04 |
| ATOM | 1626 | CA | GLU | 270 | 40.269 | 46.802 | 24.445 | 1.00 | 17.22 |

TABLE B-continued

Co-ordinates of an underglycosylated tACEΔ36NJ ACE-lisinopril complex

| ATOM | 1627 | CB | GLU | 270 | 41.152 | 47.805 | 25.188 | 1.00 | 20.98 |
|---|---|---|---|---|---|---|---|---|---|
| ATOM | 1628 | CG | GLU | 270 | 40.700 | 49.238 | 25.008 | 1.00 | 27.35 |
| ATOM | 1629 | CD | GLU | 270 | 41.710 | 50.229 | 25.524 | 1.00 | 33.16 |
| ATOM | 1630 | OE1 | GLU | 270 | 42.862 | 50.199 | 25.039 | 1.00 | 38.02 |
| ATOM | 1631 | OE2 | GLU | 270 | 41.356 | 51.040 | 26.409 | 1.00 | 36.92 |
| ATOM | 1632 | C | GLU | 270 | 40.952 | 45.437 | 24.412 | 1.00 | 15.82 |
| ATOM | 1633 | O | GLU | 270 | 41.820 | 45.196 | 23.573 | 1.00 | 14.50 |
| ATOM | 1634 | N | LEU | 271 | 40.567 | 44.548 | 25.320 | 1.00 | 13.35 |
| ATOM | 1635 | CA | LEU | 271 | 41.156 | 43.214 | 25.356 | 1.00 | 15.36 |
| ATOM | 1636 | CB | LEU | 271 | 41.353 | 42.771 | 26.805 | 1.00 | 16.31 |
| ATOM | 1637 | CG | LEU | 271 | 42.710 | 43.258 | 27.322 | 1.00 | 19.74 |
| ATOM | 1638 | CD1 | LEU | 271 | 42.552 | 44.028 | 28.610 | 1.00 | 19.63 |
| ATOM | 1639 | CD2 | LEU | 271 | 43.631 | 42.059 | 27.493 | 1.00 | 19.25 |
| ATOM | 1640 | C | LEU | 271 | 40.340 | 42.177 | 24.583 | 1.00 | 15.26 |
| ATOM | 1641 | O | LEU | 271 | 40.684 | 40.993 | 24.545 | 1.00 | 15.34 |
| ATOM | 1642 | N | GLN | 272 | 39.267 | 42.637 | 23.951 | 1.00 | 15.74 |
| ATOM | 1643 | CA | GLN | 272 | 38.395 | 41.772 | 23.163 | 1.00 | 16.76 |
| ATOM | 1644 | CB | GLN | 272 | 37.193 | 42.572 | 22.663 | 1.00 | 18.77 |
| ATOM | 1645 | CG | GLN | 272 | 36.064 | 42.594 | 23.656 | 1.00 | 19.01 |
| ATOM | 1646 | CD | GLN | 272 | 35.339 | 41.272 | 23.691 | 1.00 | 20.95 |
| ATOM | 1647 | OE1 | GLN | 272 | 34.458 | 41.017 | 22.869 | 1.00 | 24.44 |
| ATOM | 1648 | NE2 | GLN | 272 | 35.717 | 40.412 | 24.627 | 1.00 | 20.60 |
| ATOM | 1649 | C | GLN | 272 | 39.099 | 41.109 | 21.986 | 1.00 | 18.21 |
| ATOM | 1650 | O | GLN | 272 | 38.980 | 39.899 | 21.780 | 1.00 | 19.85 |
| ATOM | 1651 | N | PRO | 273 | 39.831 | 41.892 | 21.181 | 1.00 | 19.01 |
| ATOM | 1652 | CD | PRO | 273 | 39.939 | 43.364 | 21.145 | 1.00 | 19.93 |
| ATOM | 1653 | CA | PRO | 273 | 40.525 | 41.290 | 20.042 | 1.00 | 18.86 |
| ATOM | 1654 | CB | PRO | 273 | 41.321 | 42.465 | 19.473 | 1.00 | 20.13 |
| ATOM | 1655 | CG | PRO | 273 | 40.387 | 43.624 | 19.711 | 1.00 | 18.58 |
| ATOM | 1656 | C | PRO | 273 | 41.418 | 40.135 | 20.480 | 1.00 | 19.29 |
| ATOM | 1657 | O | PRO | 273 | 41.425 | 39.067 | 19.864 | 1.00 | 20.36 |
| ATOM | 1658 | N | LEU | 274 | 42.161 | 40.351 | 21.558 | 1.00 | 17.91 |
| ATOM | 1659 | CA | LEU | 274 | 43.062 | 39.335 | 22.073 | 1.00 | 15.61 |
| ATOM | 1660 | CB | LEU | 274 | 43.958 | 39.950 | 23.148 | 1.00 | 19.23 |
| ATOM | 1661 | CG | LEU | 274 | 45.126 | 39.145 | 23.717 | 1.00 | 21.54 |
| ATOM | 1662 | CD1 | LEU | 274 | 45.847 | 38.382 | 22.608 | 1.00 | 24.13 |
| ATOM | 1663 | CD2 | LEU | 274 | 46.079 | 40.107 | 24.415 | 1.00 | 22.56 |
| ATOM | 1664 | C | LEU | 274 | 42.294 | 38.128 | 22.622 | 1.00 | 15.23 |
| ATOM | 1665 | O | LEU | 274 | 42.626 | 36.987 | 22.305 | 1.00 | 13.78 |
| ATOM | 1666 | N | TYR | 275 | 41.264 | 38.369 | 23.432 | 1.00 | 12.57 |
| ATOM | 1667 | CA | TYR | 275 | 40.494 | 37.255 | 23.977 | 1.00 | 12.75 |
| ATOM | 1668 | CB | TYR | 275 | 39.449 | 37.723 | 24.988 | 1.00 | 11.47 |
| ATOM | 1669 | CG | TYR | 275 | 38.643 | 36.554 | 25.512 | 1.00 | 11.88 |
| ATOM | 1670 | CD1 | TYR | 275 | 39.245 | 35.574 | 26.298 | 1.00 | 9.65 |
| ATOM | 1671 | CE1 | TYR | 275 | 38.544 | 34.449 | 26.711 | 1.00 | 11.95 |
| ATOM | 1672 | CD2 | TYR | 275 | 37.306 | 36.382 | 25.151 | 1.00 | 10.41 |
| ATOM | 1673 | CE2 | TYR | 275 | 36.591 | 35.258 | 25.556 | 1.00 | 10.77 |
| ATOM | 1674 | CZ | TYR | 275 | 37.216 | 34.299 | 26.335 | 1.00 | 11.79 |
| ATOM | 1675 | OH | TYR | 275 | 36.518 | 33.196 | 26.758 | 1.00 | 12.85 |
| ATOM | 1676 | C | TYR | 275 | 39.779 | 36.457 | 22.890 | 1.00 | 12.15 |
| ATOM | 1677 | O | TYR | 275 | 39.819 | 35.230 | 22.886 | 1.00 | 11.27 |
| ATOM | 1678 | N | LEU | 276 | 39.116 | 37.155 | 21.976 | 1.00 | 12.64 |
| ATOM | 1679 | CA | LEU | 276 | 38.400 | 36.478 | 20.903 | 1.00 | 12.64 |
| ATOM | 1680 | CB | LEU | 276 | 37.689 | 37.499 | 20.016 | 1.00 | 12.92 |
| ATOM | 1681 | CG | LEU | 276 | 36.589 | 38.299 | 20.719 | 1.00 | 15.08 |
| ATOM | 1682 | CD1 | LEU | 276 | 35.965 | 39.298 | 19.744 | 1.00 | 13.79 |
| ATOM | 1683 | CD2 | LEU | 276 | 35.534 | 37.338 | 21.267 | 1.00 | 16.31 |
| ATOM | 1684 | C | LEU | 276 | 39.316 | 35.601 | 20.057 | 1.00 | 12.23 |
| ATOM | 1685 | O | LEU | 276 | 38.913 | 34.530 | 19.608 | 1.00 | 13.24 |
| ATOM | 1686 | N | ASN | 277 | 40.544 | 36.054 | 19.834 | 1.00 | 10.74 |
| ATOM | 1687 | CA | ASN | 277 | 41.479 | 35.269 | 19.041 | 1.00 | 11.60 |
| ATOM | 1688 | CB | ASN | 277 | 42.654 | 36.139 | 18.593 | 1.00 | 11.61 |
| ATOM | 1689 | CG | ASN | 277 | 42.393 | 36.814 | 17.257 | 1.00 | 16.00 |
| ATOM | 1690 | OD1 | ASN | 277 | 42.442 | 36.164 | 16.207 | 1.00 | 14.40 |
| ATOM | 1691 | ND2 | ASN | 277 | 42.094 | 38.115 | 17.287 | 1.00 | 13.69 |
| ATOM | 1692 | C | ASN | 277 | 41.962 | 34.051 | 19.827 | 1.00 | 11.77 |
| ATOM | 1693 | O | ASN | 277 | 42.124 | 32.969 | 19.266 | 1.00 | 11.85 |
| ATOM | 1694 | N | LEU | 278 | 42.180 | 34.227 | 21.125 | 1.00 | 10.50 |
| ATOM | 1695 | CA | LEU | 278 | 42.624 | 33.116 | 21.958 | 1.00 | 10.97 |
| ATOM | 1696 | CB | LEU | 278 | 42.955 | 33.600 | 23.372 | 1.00 | 8.91 |
| ATOM | 1697 | CG | LEU | 278 | 43.363 | 32.498 | 24.359 | 1.00 | 11.30 |
| ATOM | 1698 | CD1 | LEU | 278 | 44.732 | 31.924 | 23.970 | 1.00 | 9.95 |
| ATOM | 1699 | CD2 | LEU | 278 | 43.404 | 33.067 | 25.770 | 1.00 | 9.64 |
| ATOM | 1700 | C | LEU | 278 | 41.496 | 32.089 | 22.023 | 1.00 | 9.88 |
| ATOM | 1701 | O | LEU | 278 | 41.733 | 30.886 | 21.922 | 1.00 | 9.70 |
| ATOM | 1702 | N | HIS | 279 | 40.274 | 32.589 | 22.193 | 1.00 | 9.53 |
| ATOM | 1703 | CA | HIS | 279 | 39.068 | 31.762 | 22.272 | 1.00 | 10.82 |
| ATOM | 1704 | CB | HIS | 279 | 37.836 | 32.667 | 22.421 | 1.00 | 10.16 |

TABLE B-continued

Co-ordinates of an underglycosylated tACEΔ36NJ ACE-lisinopril complex

| ATOM | 1705 | CG  | HIS | 279 | 36.526 | 31.938 | 22.379 | 1.00 | 10.69 |
|------|------|-----|-----|-----|--------|--------|--------|------|-------|
| ATOM | 1706 | CD2 | HIS | 279 | 35.770 | 31.528 | 21.333 | 1.00 | 7.62  |
| ATOM | 1707 | ND1 | HIS | 279 | 35.821 | 31.601 | 23.516 | 1.00 | 12.88 |
| ATOM | 1708 | CE1 | HIS | 279 | 34.685 | 31.019 | 23.172 | 1.00 | 7.41  |
| ATOM | 1709 | NE2 | HIS | 279 | 34.629 | 30.963 | 21.853 | 1.00 | 10.98 |
| ATOM | 1710 | C   | HIS | 279 | 38.914 | 30.886 | 21.030 | 1.00 | 10.36 |
| ATOM | 1711 | O   | HIS | 279 | 38.667 | 29.685 | 21.133 | 1.00 | 10.76 |
| ATOM | 1712 | N   | ALA | 280 | 39.066 | 31.489 | 19.857 | 1.00 | 10.79 |
| ATOM | 1713 | CA  | ALA | 280 | 38.931 | 30.752 | 18.601 | 1.00 | 11.15 |
| ATOM | 1714 | CB  | ALA | 280 | 38.930 | 31.723 | 17.429 | 1.00 | 9.52  |
| ATOM | 1715 | C   | ALA | 280 | 40.032 | 29.705 | 18.422 | 1.00 | 11.20 |
| ATOM | 1716 | O   | ALA | 280 | 39.780 | 28.600 | 17.938 | 1.00 | 10.26 |
| ATOM | 1717 | N   | TYR | 281 | 41.255 | 30.053 | 18.810 | 1.00 | 11.54 |
| ATOM | 1718 | CA  | TYR | 281 | 42.373 | 29.120 | 18.692 | 1.00 | 11.98 |
| ATOM | 1719 | CB  | TYR | 281 | 43.685 | 29.823 | 19.052 | 1.00 | 10.00 |
| ATOM | 1720 | CG  | TYR | 281 | 44.895 | 28.914 | 19.065 | 1.00 | 12.10 |
| ATOM | 1721 | CD1 | TYR | 281 | 45.461 | 28.446 | 17.879 | 1.00 | 13.19 |
| ATOM | 1722 | CE1 | TYR | 281 | 46.567 | 27.594 | 17.895 | 1.00 | 11.96 |
| ATOM | 1723 | CD2 | TYR | 281 | 45.465 | 28.507 | 20.271 | 1.00 | 10.46 |
| ATOM | 1724 | CE2 | TYR | 281 | 46.564 | 27.660 | 20.299 | 1.00 | 12.98 |
| ATOM | 1725 | CZ  | TYR | 281 | 47.112 | 27.205 | 19.109 | 1.00 | 14.87 |
| ATOM | 1726 | OH  | TYR | 281 | 48.212 | 26.367 | 19.146 | 1.00 | 14.76 |
| ATOM | 1727 | C   | TYR | 281 | 42.156 | 27.909 | 19.606 | 1.00 | 12.24 |
| ATOM | 1728 | O   | TYR | 281 | 42.339 | 26.764 | 19.189 | 1.00 | 12.81 |
| ATOM | 1729 | N   | VAL | 282 | 41.764 | 28.167 | 20.852 | 1.00 | 11.07 |
| ATOM | 1730 | CA  | VAL | 282 | 41.517 | 27.093 | 21.809 | 1.00 | 10.51 |
| ATOM | 1731 | CB  | VAL | 282 | 41.246 | 27.656 | 23.231 | 1.00 | 10.61 |
| ATOM | 1732 | CG1 | VAL | 282 | 40.816 | 26.529 | 24.181 | 1.00 | 8.01  |
| ATOM | 1733 | CG2 | VAL | 282 | 42.504 | 28.335 | 23.760 | 1.00 | 10.58 |
| ATOM | 1734 | C   | VAL | 282 | 40.331 | 26.240 | 21.359 | 1.00 | 11.07 |
| ATOM | 1735 | O   | VAL | 282 | 40.357 | 25.012 | 21.462 | 1.00 | 11.90 |
| ATOM | 1736 | N   | ARG | 283 | 39.291 | 26.893 | 20.859 | 1.00 | 9.21  |
| ATOM | 1737 | CA  | ARG | 283 | 38.113 | 26.179 | 20.379 | 1.00 | 10.93 |
| ATOM | 1738 | CB  | ARG | 283 | 37.077 | 27.186 | 19.859 | 1.00 | 9.04  |
| ATOM | 1739 | CG  | ARG | 283 | 35.802 | 26.566 | 19.293 | 1.00 | 7.71  |
| ATOM | 1740 | CD  | ARG | 283 | 34.800 | 27.655 | 18.923 | 1.00 | 8.79  |
| ATOM | 1741 | NE  | ARG | 283 | 35.371 | 28.597 | 17.966 | 1.00 | 8.59  |
| ATOM | 1742 | CZ  | ARG | 283 | 34.837 | 29.773 | 17.651 | 1.00 | 12.17 |
| ATOM | 1743 | NH1 | ARG | 283 | 33.702 | 30.174 | 18.219 | 1.00 | 8.02  |
| ATOM | 1744 | NH2 | ARG | 283 | 35.445 | 30.552 | 16.763 | 1.00 | 9.21  |
| ATOM | 1745 | C   | ARG | 283 | 38.520 | 25.191 | 19.268 | 1.00 | 11.88 |
| ATOM | 1746 | O   | ARG | 283 | 38.026 | 24.065 | 19.210 | 1.00 | 11.57 |
| ATOM | 1747 | N   | ARG | 284 | 39.432 | 25.615 | 18.396 | 1.00 | 12.83 |
| ATOM | 1748 | CA  | ARG | 284 | 39.905 | 24.759 | 17.305 | 1.00 | 13.40 |
| ATOM | 1749 | CB  | ARG | 284 | 40.815 | 25.557 | 16.362 | 1.00 | 12.91 |
| ATOM | 1750 | CG  | ARG | 284 | 41.550 | 24.721 | 15.314 | 1.00 | 16.01 |
| ATOM | 1751 | CD  | ARG | 284 | 40.608 | 24.122 | 14.274 | 1.00 | 14.55 |
| ATOM | 1752 | NE  | ARG | 284 | 39.864 | 25.154 | 13.555 | 1.00 | 13.70 |
| ATOM | 1753 | CZ  | ARG | 284 | 39.073 | 24.917 | 12.513 | 1.00 | 15.26 |
| ATOM | 1754 | NH1 | ARG | 284 | 38.433 | 25.921 | 11.927 | 1.00 | 12.96 |
| ATOM | 1755 | NH2 | ARG | 284 | 38.930 | 23.679 | 12.049 | 1.00 | 13.60 |
| ATOM | 1756 | C   | ARG | 284 | 40.657 | 23.546 | 17.866 | 1.00 | 13.94 |
| ATOM | 1757 | O   | ARG | 284 | 40.452 | 22.414 | 17.416 | 1.00 | 14.76 |
| ATOM | 1758 | N   | ALA | 285 | 41.517 | 23.781 | 18.852 | 1.00 | 12.64 |
| ATOM | 1759 | CA  | ALA | 285 | 42.277 | 22.698 | 19.468 | 1.00 | 12.04 |
| ATOM | 1760 | CB  | ALA | 285 | 43.289 | 23.259 | 20.453 | 1.00 | 12.45 |
| ATOM | 1761 | C   | ALA | 285 | 41.349 | 21.709 | 20.172 | 1.00 | 13.35 |
| ATOM | 1762 | O   | ALA | 285 | 41.596 | 20.500 | 20.162 | 1.00 | 14.01 |
| ATOM | 1763 | N   | LEU | 286 | 40.287 | 22.220 | 20.791 | 1.00 | 11.56 |
| ATOM | 1764 | CA  | LEU | 286 | 39.330 | 21.356 | 21.478 | 1.00 | 12.33 |
| ATOM | 1765 | CB  | LEU | 286 | 38.364 | 22.189 | 22.326 | 1.00 | 10.45 |
| ATOM | 1766 | CG  | LEU | 286 | 38.952 | 22.846 | 23.583 | 1.00 | 13.14 |
| ATOM | 1767 | CD1 | LEU | 286 | 37.884 | 23.713 | 24.255 | 1.00 | 11.79 |
| ATOM | 1768 | CD2 | LEU | 286 | 39.452 | 21.767 | 24.548 | 1.00 | 9.81  |
| ATOM | 1769 | C   | LEU | 286 | 38.553 | 20.529 | 20.453 | 1.00 | 11.97 |
| ATOM | 1770 | O   | LEU | 286 | 38.225 | 19.368 | 20.693 | 1.00 | 12.10 |
| ATOM | 1771 | N   | HIS | 287 | 38.257 | 21.146 | 19.315 | 1.00 | 12.58 |
| ATOM | 1772 | CA  | HIS | 287 | 37.544 | 20.482 | 18.229 | 1.00 | 13.37 |
| ATOM | 1773 | CB  | HIS | 287 | 37.351 | 21.476 | 17.073 | 1.00 | 13.36 |
| ATOM | 1774 | CG  | HIS | 287 | 36.674 | 20.902 | 15.863 | 1.00 | 12.74 |
| ATOM | 1775 | CD2 | HIS | 287 | 35.383 | 20.956 | 15.455 | 1.00 | 10.37 |
| ATOM | 1776 | ND1 | HIS | 287 | 37.361 | 20.238 | 14.868 | 1.00 | 12.14 |
| ATOM | 1777 | CE1 | HIS | 287 | 36.525 | 19.914 | 13.897 | 1.00 | 10.26 |
| ATOM | 1778 | NE2 | HIS | 287 | 35.319 | 20.339 | 14.228 | 1.00 | 14.44 |
| ATOM | 1779 | C   | HIS | 287 | 38.401 | 19.294 | 17.790 | 1.00 | 14.98 |
| ATOM | 1780 | O   | HIS | 287 | 37.898 | 18.196 | 17.561 | 1.00 | 14.57 |
| ATOM | 1781 | N   | ARG | 288 | 39.707 | 19.529 | 17.701 | 1.00 | 15.29 |
| ATOM | 1782 | CA  | ARG | 288 | 40.666 | 18.506 | 17.305 | 1.00 | 17.69 |

TABLE B-continued

Co-ordinates of an underglycosylated tACEΔ36NJ ACE-lisinopril complex

| ATOM | 1783 | CB | ARG | 288 | 42.068 | 19.112 | 17.249 | 1.00 | 21.34 |
|---|---|---|---|---|---|---|---|---|---|
| ATOM | 1784 | CG | ARG | 288 | 42.685 | 19.208 | 15.862 | 1.00 | 27.31 |
| ATOM | 1785 | CD | ARG | 288 | 43.749 | 20.293 | 15.841 | 1.00 | 29.77 |
| ATOM | 1786 | NE | ARG | 288 | 44.569 | 20.250 | 17.048 | 1.00 | 29.56 |
| ATOM | 1787 | CZ | ARG | 288 | 45.157 | 21.311 | 17.586 | 1.00 | 29.93 |
| ATOM | 1788 | NH1 | ARG | 288 | 45.019 | 22.505 | 17.021 | 1.00 | 30.44 |
| ATOM | 1789 | NH2 | ARG | 288 | 45.874 | 21.183 | 18.696 | 1.00 | 31.11 |
| ATOM | 1790 | C | ARG | 288 | 40.674 | 17.329 | 18.276 | 1.00 | 17.37 |
| ATOM | 1791 | O | ARG | 288 | 40.713 | 16.169 | 17.861 | 1.00 | 16.21 |
| ATOM | 1792 | N | HIS | 289 | 40.629 | 17.629 | 19.571 | 1.00 | 17.16 |
| ATOM | 1793 | CA | HIS | 289 | 40.668 | 16.587 | 20.590 | 1.00 | 17.12 |
| ATOM | 1794 | CB | HIS | 289 | 41.281 | 17.132 | 21.882 | 1.00 | 18.15 |
| ATOM | 1795 | CG | HIS | 289 | 41.421 | 16.098 | 22.954 | 1.00 | 21.15 |
| ATOM | 1796 | CD2 | HIS | 289 | 40.616 | 15.780 | 23.997 | 1.00 | 21.55 |
| ATOM | 1797 | ND1 | HIS | 289 | 42.462 | 15.195 | 22.985 | 1.00 | 22.19 |
| ATOM | 1798 | CE1 | HIS | 289 | 42.292 | 14.363 | 23.997 | 1.00 | 21.47 |
| ATOM | 1799 | NE2 | HIS | 289 | 41.179 | 14.697 | 24.627 | 1.00 | 25.04 |
| ATOM | 1800 | C | HIS | 289 | 39.352 | 15.904 | 20.947 | 1.00 | 16.83 |
| ATOM | 1801 | O | HIS | 289 | 39.298 | 14.681 | 21.043 | 1.00 | 16.83 |
| ATOM | 1802 | N | TYR | 290 | 38.294 | 16.683 | 21.153 | 1.00 | 16.34 |
| ATOM | 1803 | CA | TYR | 290 | 37.016 | 16.110 | 21.549 | 1.00 | 15.13 |
| ATOM | 1804 | CB | TYR | 290 | 36.333 | 17.025 | 22.571 | 1.00 | 14.53 |
| ATOM | 1805 | CG | TYR | 290 | 37.073 | 17.093 | 23.894 | 1.00 | 14.22 |
| ATOM | 1806 | CD1 | TYR | 290 | 37.842 | 18.208 | 24.237 | 1.00 | 12.56 |
| ATOM | 1807 | CE1 | TYR | 290 | 38.547 | 18.255 | 25.445 | 1.00 | 12.09 |
| ATOM | 1808 | CD2 | TYR | 290 | 37.025 | 16.026 | 24.791 | 1.00 | 13.17 |
| ATOM | 1809 | CE2 | TYR | 290 | 37.721 | 16.062 | 25.995 | 1.00 | 13.22 |
| ATOM | 1810 | CZ | TYR | 290 | 38.480 | 17.175 | 26.316 | 1.00 | 14.11 |
| ATOM | 1811 | OH | TYR | 290 | 39.186 | 17.186 | 27.496 | 1.00 | 13.69 |
| ATOM | 1812 | C | TYR | 290 | 36.042 | 15.746 | 20.434 | 1.00 | 16.43 |
| ATOM | 1813 | O | TYR | 290 | 34.980 | 15.180 | 20.703 | 1.00 | 16.48 |
| ATOM | 1814 | N | GLY | 291 | 36.395 | 16.068 | 19.194 | 1.00 | 17.05 |
| ATOM | 1815 | CA | GLY | 291 | 35.535 | 15.730 | 18.072 | 1.00 | 15.48 |
| ATOM | 1816 | C | GLY | 291 | 34.611 | 16.813 | 17.552 | 1.00 | 13.32 |
| ATOM | 1817 | O | GLY | 291 | 34.111 | 17.647 | 18.305 | 1.00 | 11.67 |
| ATOM | 1818 | N | ALA | 292 | 34.369 | 16.781 | 16.248 | 1.00 | 13.25 |
| ATOM | 1819 | CA | ALA | 292 | 33.504 | 17.755 | 15.590 | 1.00 | 13.14 |
| ATOM | 1820 | CB | ALA | 292 | 33.530 | 17.532 | 14.077 | 1.00 | 15.01 |
| ATOM | 1821 | C | ALA | 292 | 32.065 | 17.708 | 16.099 | 1.00 | 13.40 |
| ATOM | 1822 | O | ALA | 292 | 31.362 | 18.713 | 16.056 | 1.00 | 12.55 |
| ATOM | 1823 | N | GLN | 293 | 31.625 | 16.545 | 16.575 | 1.00 | 12.64 |
| ATOM | 1824 | CA | GLN | 293 | 30.265 | 16.407 | 17.081 | 1.00 | 13.50 |
| ATOM | 1825 | CB | GLN | 293 | 29.888 | 14.919 | 17.199 | 1.00 | 13.51 |
| ATOM | 1826 | CG | GLN | 293 | 29.794 | 14.161 | 15.863 | 1.00 | 12.95 |
| ATOM | 1827 | CD | GLN | 293 | 28.496 | 14.423 | 15.109 | 1.00 | 14.29 |
| ATOM | 1828 | OE1 | GLN | 293 | 27.607 | 15.121 | 15.597 | 1.00 | 13.82 |
| ATOM | 1829 | NE2 | GLN | 293 | 28.382 | 13.853 | 13.909 | 1.00 | 12.74 |
| ATOM | 1830 | C | GLN | 293 | 30.071 | 17.091 | 18.436 | 1.00 | 14.40 |
| ATOM | 1831 | O | GLN | 293 | 28.938 | 17.278 | 18.879 | 1.00 | 15.91 |
| ATOM | 1832 | N | HIS | 294 | 31.168 | 17.487 | 19.081 | 1.00 | 13.64 |
| ATOM | 1833 | CA | HIS | 294 | 31.088 | 18.118 | 20.397 | 1.00 | 14.94 |
| ATOM | 1834 | CB | HIS | 294 | 31.831 | 17.248 | 21.413 | 1.00 | 14.73 |
| ATOM | 1835 | CG | HIS | 294 | 31.381 | 15.820 | 21.403 | 1.00 | 17.46 |
| ATOM | 1836 | CD2 | HIS | 294 | 32.001 | 14.693 | 20.977 | 1.00 | 16.75 |
| ATOM | 1837 | ND1 | HIS | 294 | 30.113 | 15.438 | 21.787 | 1.00 | 19.13 |
| ATOM | 1838 | CE1 | HIS | 294 | 29.970 | 14.139 | 21.592 | 1.00 | 18.70 |
| ATOM | 1839 | NE2 | HIS | 294 | 31.100 | 13.664 | 21.101 | 1.00 | 18.34 |
| ATOM | 1840 | C | HIS | 294 | 31.593 | 19.559 | 20.476 | 1.00 | 15.34 |
| ATOM | 1841 | O | HIS | 294 | 31.475 | 20.204 | 21.519 | 1.00 | 16.59 |
| ATOM | 1842 | N | ILE | 295 | 32.147 | 20.066 | 19.379 | 1.00 | 13.77 |
| ATOM | 1843 | CA | ILE | 295 | 32.654 | 21.435 | 19.352 | 1.00 | 13.59 |
| ATOM | 1844 | CB | ILE | 295 | 34.209 | 21.474 | 19.346 | 1.00 | 13.71 |
| ATOM | 1845 | CG2 | ILE | 295 | 34.695 | 22.905 | 19.124 | 1.00 | 14.49 |
| ATOM | 1846 | CG1 | ILE | 295 | 34.763 | 20.904 | 20.656 | 1.00 | 14.93 |
| ATOM | 1847 | CD1 | ILE | 295 | 34.360 | 21.684 | 21.906 | 1.00 | 14.38 |
| ATOM | 1848 | C | ILE | 295 | 32.154 | 22.141 | 18.107 | 1.00 | 13.18 |
| ATOM | 1849 | O | ILE | 295 | 32.437 | 21.712 | 16.994 | 1.00 | 15.59 |
| ATOM | 1850 | N | ASN | 296 | 31.395 | 23.214 | 18.297 | 1.00 | 12.79 |
| ATOM | 1851 | CA | ASN | 296 | 30.878 | 23.992 | 17.175 | 1.00 | 13.84 |
| ATOM | 1852 | CB | ASN | 296 | 29.535 | 24.632 | 17.549 | 1.00 | 13.94 |
| ATOM | 1853 | CG | ASN | 296 | 28.943 | 25.462 | 16.419 | 1.00 | 17.67 |
| ATOM | 1854 | OD1 | ASN | 296 | 29.597 | 25.724 | 15.408 | 1.00 | 16.28 |
| ATOM | 1855 | ND2 | ASN | 296 | 27.700 | 25.890 | 16.595 | 1.00 | 20.03 |
| ATOM | 1856 | C | ASN | 296 | 31.917 | 25.076 | 16.897 | 1.00 | 13.19 |
| ATOM | 1857 | O | ASN | 296 | 32.123 | 25.966 | 17.724 | 1.00 | 13.14 |
| ATOM | 1858 | N | LEU | 297 | 32.570 | 25.001 | 15.742 | 1.00 | 12.09 |
| ATOM | 1859 | CA | LEU | 297 | 33.608 | 25.964 | 15.386 | 1.00 | 13.05 |
| ATOM | 1860 | CB | LEU | 297 | 34.308 | 25.528 | 14.097 | 1.00 | 14.01 |

TABLE B-continued

Co-ordinates of an underglycosylated tACEΔ36NJ ACE-lisinopril complex

| ATOM | 1861 | CG | LEU | 297 | 35.176 | 24.265 | 14.185 | 1.00 | 14.42 |
|---|---|---|---|---|---|---|---|---|---|
| ATOM | 1862 | CD1 | LEU | 297 | 35.551 | 23.810 | 12.787 | 1.00 | 14.91 |
| ATOM | 1863 | CD2 | LEU | 297 | 36.426 | 24.540 | 15.017 | 1.00 | 11.68 |
| ATOM | 1864 | C | LEU | 297 | 33.130 | 27.408 | 15.253 | 1.00 | 13.77 |
| ATOM | 1865 | O | LEU | 297 | 33.945 | 28.321 | 15.103 | 1.00 | 13.21 |
| ATOM | 1866 | N | GLU | 298 | 31.818 | 27.621 | 15.304 | 1.00 | 13.89 |
| ATOM | 1867 | CA | GLU | 298 | 31.275 | 28.975 | 15.210 | 1.00 | 16.15 |
| ATOM | 1868 | CB | GLU | 298 | 30.452 | 29.133 | 13.926 | 1.00 | 18.06 |
| ATOM | 1869 | CG | GLU | 298 | 31.227 | 28.791 | 12.659 | 1.00 | 23.45 |
| ATOM | 1870 | CD | GLU | 298 | 30.389 | 28.914 | 11.394 | 1.00 | 27.52 |
| ATOM | 1871 | OE1 | GLU | 298 | 29.209 | 28.504 | 11.411 | 1.00 | 30.58 |
| ATOM | 1872 | OE2 | GLU | 298 | 30.915 | 29.407 | 10.376 | 1.00 | 29.39 |
| ATOM | 1873 | C | GLU | 298 | 30.403 | 29.282 | 16.424 | 1.00 | 15.59 |
| ATOM | 1874 | O | GLU | 298 | 29.621 | 30.236 | 16.414 | 1.00 | 15.76 |
| ATOM | 1875 | N | GLY | 299 | 30.538 | 28.472 | 17.472 | 1.00 | 12.59 |
| ATOM | 1876 | CA | GLY | 299 | 29.732 | 28.683 | 18.659 | 1.00 | 11.43 |
| ATOM | 1877 | C | GLY | 299 | 30.514 | 28.756 | 19.956 | 1.00 | 12.49 |
| ATOM | 1878 | O | GLY | 299 | 31.749 | 28.812 | 19.945 | 1.00 | 12.02 |
| ATOM | 1879 | N | PRO | 300 | 29.815 | 28.762 | 21.104 | 1.00 | 11.77 |
| ATOM | 1880 | CD | PRO | 300 | 28.348 | 28.749 | 21.265 | 1.00 | 11.48 |
| ATOM | 1881 | CA | PRO | 300 | 30.484 | 28.829 | 22.406 | 1.00 | 12.78 |
| ATOM | 1882 | CB | PRO | 300 | 29.341 | 29.164 | 23.358 | 1.00 | 13.30 |
| ATOM | 1883 | CG | PRO | 300 | 28.183 | 28.440 | 22.741 | 1.00 | 13.51 |
| ATOM | 1884 | C | PRO | 300 | 31.176 | 27.513 | 22.761 | 1.00 | 13.23 |
| ATOM | 1885 | O | PRO | 300 | 30.857 | 26.465 | 22.204 | 1.00 | 11.48 |
| ATOM | 1886 | N | ILE | 301 | 32.118 | 27.581 | 23.693 | 1.00 | 12.03 |
| ATOM | 1887 | CA | ILE | 301 | 32.870 | 26.412 | 24.137 | 1.00 | 12.06 |
| ATOM | 1888 | CB | ILE | 301 | 34.329 | 26.807 | 24.481 | 1.00 | 12.23 |
| ATOM | 1889 | CG2 | ILE | 301 | 35.087 | 25.601 | 25.038 | 1.00 | 11.68 |
| ATOM | 1890 | CG1 | ILE | 301 | 35.017 | 27.390 | 23.241 | 1.00 | 11.62 |
| ATOM | 1891 | CD1 | ILE | 301 | 36.392 | 27.983 | 23.521 | 1.00 | 9.44 |
| ATOM | 1892 | C | ILE | 301 | 32.236 | 25.807 | 25.388 | 1.00 | 12.04 |
| ATOM | 1893 | O | ILE | 301 | 31.880 | 26.535 | 26.318 | 1.00 | 10.31 |
| ATOM | 1894 | N | PRO | 302 | 32.066 | 24.469 | 25.421 | 1.00 | 11.07 |
| ATOM | 1895 | CD | PRO | 302 | 32.244 | 23.489 | 24.336 | 1.00 | 12.03 |
| ATOM | 1896 | CA | PRO | 302 | 31.472 | 23.833 | 26.602 | 1.00 | 11.31 |
| ATOM | 1897 | CB | PRO | 302 | 31.529 | 22.348 | 26.257 | 1.00 | 10.99 |
| ATOM | 1898 | CG | PRO | 302 | 31.324 | 22.358 | 24.774 | 1.00 | 12.05 |
| ATOM | 1899 | C | PRO | 302 | 32.319 | 24.201 | 27.826 | 1.00 | 9.53 |
| ATOM | 1900 | O | PRO | 302 | 33.537 | 24.067 | 27.809 | 1.00 | 9.50 |
| ATOM | 1901 | N | ALA | 303 | 31.655 | 24.657 | 28.879 | 1.00 | 10.56 |
| ATOM | 1902 | CA | ALA | 303 | 32.313 | 25.124 | 30.097 | 1.00 | 10.69 |
| ATOM | 1903 | CB | ALA | 303 | 31.274 | 25.775 | 31.005 | 1.00 | 8.77 |
| ATOM | 1904 | C | ALA | 303 | 33.164 | 24.162 | 30.914 | 1.00 | 11.62 |
| ATOM | 1905 | O | ALA | 303 | 33.903 | 24.603 | 31.792 | 1.00 | 10.65 |
| ATOM | 1906 | N | HIS | 304 | 33.084 | 22.863 | 30.644 | 1.00 | 12.09 |
| ATOM | 1907 | CA | HIS | 304 | 33.866 | 21.903 | 31.428 | 1.00 | 12.58 |
| ATOM | 1908 | CB | HIS | 304 | 33.017 | 20.657 | 31.721 | 1.00 | 11.82 |
| ATOM | 1909 | CG | HIS | 304 | 32.640 | 19.875 | 30.500 | 1.00 | 14.31 |
| ATOM | 1910 | CD2 | HIS | 304 | 32.678 | 18.544 | 30.246 | 1.00 | 12.99 |
| ATOM | 1911 | ND1 | HIS | 304 | 32.127 | 20.466 | 29.365 | 1.00 | 15.10 |
| ATOM | 1912 | CE1 | HIS | 304 | 31.866 | 19.534 | 28.465 | 1.00 | 13.57 |
| ATOM | 1913 | NE2 | HIS | 304 | 32.191 | 18.359 | 28.975 | 1.00 | 14.81 |
| ATOM | 1914 | C | HIS | 304 | 35.189 | 21.465 | 30.801 | 1.00 | 12.09 |
| ATOM | 1915 | O | HIS | 304 | 35.922 | 20.670 | 31.392 | 1.00 | 10.75 |
| ATOM | 1916 | N | LEU | 305 | 35.516 | 22.004 | 29.631 | 1.00 | 12.26 |
| ATOM | 1917 | CA | LEU | 305 | 36.728 | 21.590 | 28.924 | 1.00 | 11.26 |
| ATOM | 1918 | CB | LEU | 305 | 36.394 | 21.420 | 27.443 | 1.00 | 9.94 |
| ATOM | 1919 | CG | LEU | 305 | 35.159 | 20.564 | 27.149 | 1.00 | 10.57 |
| ATOM | 1920 | CD1 | LEU | 305 | 34.896 | 20.538 | 25.642 | 1.00 | 10.40 |
| ATOM | 1921 | CD2 | LEU | 305 | 35.377 | 19.153 | 27.697 | 1.00 | 9.11 |
| ATOM | 1922 | C | LEU | 305 | 37.968 | 22.466 | 29.043 | 1.00 | 12.64 |
| ATOM | 1923 | O | LEU | 305 | 38.973 | 22.197 | 28.380 | 1.00 | 12.19 |
| ATOM | 1924 | N | LEU | 306 | 37.922 | 23.490 | 29.889 | 1.00 | 13.29 |
| ATOM | 1925 | CA | LEU | 306 | 39.051 | 24.405 | 30.001 | 1.00 | 14.22 |
| ATOM | 1926 | CB | LEU | 306 | 38.537 | 25.846 | 30.141 | 1.00 | 11.93 |
| ATOM | 1927 | CG | LEU | 306 | 37.738 | 26.440 | 28.970 | 1.00 | 14.40 |
| ATOM | 1928 | CD1 | LEU | 306 | 38.488 | 26.212 | 27.652 | 1.00 | 12.20 |
| ATOM | 1929 | CD2 | LEU | 306 | 36.353 | 25.805 | 28.910 | 1.00 | 14.99 |
| ATOM | 1930 | C | LEU | 306 | 40.104 | 24.122 | 31.076 | 1.00 | 14.70 |
| ATOM | 1931 | O | LEU | 306 | 41.017 | 24.925 | 31.267 | 1.00 | 15.61 |
| ATOM | 1932 | N | GLY | 307 | 39.980 | 22.989 | 31.765 | 1.00 | 14.31 |
| ATOM | 1933 | CA | GLY | 307 | 40.955 | 22.613 | 32.777 | 1.00 | 12.37 |
| ATOM | 1934 | C | GLY | 307 | 40.767 | 23.242 | 34.145 | 1.00 | 14.30 |
| ATOM | 1935 | O | GLY | 307 | 41.596 | 23.064 | 35.045 | 1.00 | 12.62 |
| ATOM | 1936 | N | ASN | 308 | 39.668 | 23.967 | 34.307 | 1.00 | 11.75 |
| ATOM | 1937 | CA | ASN | 308 | 39.373 | 24.644 | 35.558 | 1.00 | 12.13 |
| ATOM | 1938 | CB | ASN | 308 | 39.906 | 26.086 | 35.480 | 1.00 | 10.17 |

TABLE B-continued

Co-ordinates of an underglycosylated tACEΔ36NJ ACE-lisinopril complex

| ATOM | 1939 | CG | ASN | 308 | 39.427 | 26.967 | 36.622 | 1.00 | 11.14 |
|---|---|---|---|---|---|---|---|---|---|
| ATOM | 1940 | OD1 | ASN | 308 | 38.327 | 27.522 | 36.573 | 1.00 | 10.87 |
| ATOM | 1941 | ND2 | ASN | 308 | 40.254 | 27.104 | 37.655 | 1.00 | 9.94 |
| ATOM | 1942 | C | ASN | 308 | 37.867 | 24.597 | 35.812 | 1.00 | 10.98 |
| ATOM | 1943 | O | ASN | 308 | 37.069 | 24.750 | 34.894 | 1.00 | 10.76 |
| ATOM | 1944 | N | MET | 309 | 37.493 | 24.369 | 37.066 | 1.00 | 10.81 |
| ATOM | 1945 | CA | MET | 309 | 36.094 | 24.255 | 37.453 | 1.00 | 11.22 |
| ATOM | 1946 | CB | MET | 309 | 35.984 | 24.189 | 38.984 | 1.00 | 12.08 |
| ATOM | 1947 | CG | MET | 309 | 34.568 | 23.932 | 39.491 | 1.00 | 12.10 |
| ATOM | 1948 | SD | MET | 309 | 33.855 | 22.420 | 38.792 | 1.00 | 12.04 |
| ATOM | 1949 | CE | MET | 309 | 34.496 | 21.188 | 39.955 | 1.00 | 12.99 |
| ATOM | 1950 | C | MET | 309 | 35.189 | 25.365 | 36.925 | 1.00 | 12.07 |
| ATOM | 1951 | O | MET | 309 | 34.038 | 25.110 | 36.562 | 1.00 | 11.18 |
| ATOM | 1952 | N | TRP | 310 | 35.709 | 26.588 | 36.877 | 1.00 | 10.53 |
| ATOM | 1953 | CA | TRP | 310 | 34.928 | 27.735 | 36.418 | 1.00 | 11.65 |
| ATOM | 1954 | CB | TRP | 310 | 35.020 | 28.856 | 37.456 | 1.00 | 10.85 |
| ATOM | 1955 | CG | TRP | 310 | 34.629 | 28.367 | 38.808 | 1.00 | 10.71 |
| ATOM | 1956 | CD2 | TRP | 310 | 35.509 | 27.879 | 39.825 | 1.00 | 10.32 |
| ATOM | 1957 | CE2 | TRP | 310 | 34.702 | 27.370 | 40.866 | 1.00 | 10.65 |
| ATOM | 1958 | CE3 | TRP | 310 | 36.905 | 27.815 | 39.954 | 1.00 | 11.66 |
| ATOM | 1959 | CD1 | TRP | 310 | 33.360 | 28.153 | 39.266 | 1.00 | 9.51 |
| ATOM | 1960 | NE1 | TRP | 310 | 33.396 | 27.550 | 40.498 | 1.00 | 9.82 |
| ATOM | 1961 | CZ2 | TRP | 310 | 35.243 | 26.805 | 42.028 | 1.00 | 10.04 |
| ATOM | 1962 | CZ3 | TRP | 310 | 37.446 | 27.251 | 41.106 | 1.00 | 12.67 |
| ATOM | 1963 | CH2 | TRP | 310 | 36.613 | 26.752 | 42.129 | 1.00 | 12.66 |
| ATOM | 1964 | C | TRP | 310 | 35.379 | 28.245 | 35.054 | 1.00 | 12.14 |
| ATOM | 1965 | O | TRP | 310 | 34.840 | 29.233 | 34.544 | 1.00 | 10.52 |
| ATOM | 1966 | N | ALA | 311 | 36.351 | 27.554 | 34.460 | 1.00 | 11.25 |
| ATOM | 1967 | CA | ALA | 311 | 36.890 | 27.949 | 33.166 | 1.00 | 11.45 |
| ATOM | 1968 | CB | ALA | 311 | 35.817 | 27.803 | 32.076 | 1.00 | 13.28 |
| ATOM | 1969 | C | ALA | 311 | 37.372 | 29.395 | 33.240 | 1.00 | 11.09 |
| ATOM | 1970 | O | ALA | 311 | 37.296 | 30.128 | 32.256 | 1.00 | 10.98 |
| ATOM | 1971 | N | GLN | 312 | 37.862 | 29.804 | 34.410 | 1.00 | 11.21 |
| ATOM | 1972 | CA | GLN | 312 | 38.346 | 31.168 | 34.594 | 1.00 | 10.89 |
| ATOM | 1973 | CB | GLN | 312 | 38.201 | 31.603 | 36.057 | 1.00 | 10.80 |
| ATOM | 1974 | CG | GLN | 312 | 39.053 | 30.838 | 37.052 | 1.00 | 11.00 |
| ATOM | 1975 | CD | GLN | 312 | 38.662 | 31.139 | 38.488 | 1.00 | 12.63 |
| ATOM | 1976 | OE1 | GLN | 312 | 37.508 | 30.951 | 38.876 | 1.00 | 10.11 |
| ATOM | 1977 | NE2 | GLN | 312 | 39.621 | 31.610 | 39.283 | 1.00 | 12.95 |
| ATOM | 1978 | C | GLN | 312 | 39.794 | 31.302 | 34.138 | 1.00 | 12.02 |
| ATOM | 1979 | O | GLN | 312 | 40.249 | 32.398 | 33.809 | 1.00 | 10.55 |
| ATOM | 1980 | N | THR | 313 | 40.510 | 30.182 | 34.141 | 1.00 | 12.20 |
| ATOM | 1981 | CA | THR | 313 | 41.898 | 30.117 | 33.687 | 1.00 | 13.97 |
| ATOM | 1982 | CB | THR | 313 | 42.914 | 30.108 | 34.859 | 1.00 | 15.24 |
| ATOM | 1983 | OG1 | THR | 313 | 42.544 | 29.117 | 35.826 | 1.00 | 18.23 |
| ATOM | 1984 | CG2 | THR | 313 | 42.951 | 31.468 | 35.527 | 1.00 | 19.92 |
| ATOM | 1985 | C | THR | 313 | 41.998 | 28.814 | 32.903 | 1.00 | 12.84 |
| ATOM | 1986 | O | THR | 313 | 41.464 | 27.790 | 33.328 | 1.00 | 11.11 |
| ATOM | 1987 | N | TRP | 314 | 42.660 | 28.864 | 31.751 | 1.00 | 12.37 |
| ATOM | 1988 | CA | TRP | 314 | 42.778 | 27.696 | 30.884 | 1.00 | 12.96 |
| ATOM | 1989 | CB | TRP | 314 | 42.357 | 28.060 | 29.464 | 1.00 | 12.27 |
| ATOM | 1990 | CG | TRP | 314 | 41.057 | 28.797 | 29.339 | 1.00 | 13.71 |
| ATOM | 1991 | CD2 | TRP | 314 | 40.534 | 29.392 | 28.145 | 1.00 | 13.32 |
| ATOM | 1992 | CE2 | TRP | 314 | 39.244 | 29.882 | 28.450 | 1.00 | 13.06 |
| ATOM | 1993 | CE3 | TRP | 314 | 41.027 | 29.551 | 26.844 | 1.00 | 12.97 |
| ATOM | 1994 | CD1 | TRP | 314 | 40.094 | 28.957 | 30.299 | 1.00 | 12.24 |
| ATOM | 1995 | NE1 | TRP | 314 | 39.002 | 29.606 | 29.772 | 1.00 | 12.13 |
| ATOM | 1996 | CZ2 | TRP | 314 | 38.442 | 30.519 | 27.502 | 1.00 | 12.07 |
| ATOM | 1997 | CZ3 | TRP | 314 | 40.227 | 30.186 | 25.899 | 1.00 | 14.41 |
| ATOM | 1998 | CH2 | TRP | 314 | 38.947 | 30.659 | 26.236 | 1.00 | 13.57 |
| ATOM | 1999 | C | TRP | 314 | 44.184 | 27.111 | 30.823 | 1.00 | 14.49 |
| ATOM | 2000 | O | TRP | 314 | 44.492 | 26.330 | 29.922 | 1.00 | 13.65 |
| ATOM | 2001 | N | SER | 315 | 45.029 | 27.489 | 31.775 | 1.00 | 15.57 |
| ATOM | 2002 | CA | SER | 315 | 46.414 | 27.021 | 31.818 | 1.00 | 16.96 |
| ATOM | 2003 | CB | SER | 315 | 47.093 | 27.539 | 33.091 | 1.00 | 18.01 |
| ATOM | 2004 | OG | SER | 315 | 46.977 | 28.947 | 33.186 | 1.00 | 26.11 |
| ATOM | 2005 | C | SER | 315 | 46.568 | 25.500 | 31.768 | 1.00 | 15.01 |
| ATOM | 2006 | O | SER | 315 | 47.487 | 24.980 | 31.135 | 1.00 | 12.81 |
| ATOM | 2007 | N | ASN | 316 | 45.663 | 24.794 | 32.434 | 1.00 | 15.19 |
| ATOM | 2008 | CA | ASN | 316 | 45.742 | 23.345 | 32.504 | 1.00 | 14.93 |
| ATOM | 2009 | CB | ASN | 316 | 44.837 | 22.849 | 33.632 | 1.00 | 16.81 |
| ATOM | 2010 | CG | ASN | 316 | 45.348 | 23.284 | 35.005 | 1.00 | 19.36 |
| ATOM | 2011 | OD1 | ASN | 316 | 46.503 | 23.037 | 35.345 | 1.00 | 20.13 |
| ATOM | 2012 | ND2 | ASN | 316 | 44.496 | 23.939 | 35.787 | 1.00 | 17.72 |
| ATOM | 2013 | C | ASN | 316 | 45.527 | 22.542 | 31.224 | 1.00 | 14.44 |
| ATOM | 2014 | O | ASN | 316 | 45.772 | 21.341 | 31.212 | 1.00 | 13.76 |
| ATOM | 2015 | N | ILE | 317 | 45.078 | 23.187 | 30.152 | 1.00 | 12.82 |
| ATOM | 2016 | CA | ILE | 317 | 44.925 | 22.476 | 28.883 | 1.00 | 13.82 |

TABLE B-continued

Co-ordinates of an underglycosylated tACEΔ36NJ ACE-lisinopril complex

| ATOM | 2017 | CB | ILE | 317 | 43.533 | 22.691 | 28.230 | 1.00 | 14.54 |
|---|---|---|---|---|---|---|---|---|---|
| ATOM | 2018 | CG2 | ILE | 317 | 42.447 | 22.099 | 29.126 | 1.00 | 15.01 |
| ATOM | 2019 | CG1 | ILE | 317 | 43.301 | 24.175 | 27.945 | 1.00 | 14.21 |
| ATOM | 2020 | CD1 | ILE | 317 | 42.110 | 24.433 | 27.049 | 1.00 | 15.28 |
| ATOM | 2021 | C | ILE | 317 | 46.004 | 22.933 | 27.898 | 1.00 | 13.81 |
| ATOM | 2022 | O | ILE | 317 | 45.836 | 22.823 | 26.686 | 1.00 | 13.91 |
| ATOM | 2023 | N | TYR | 318 | 47.115 | 23.443 | 28.429 | 1.00 | 14.69 |
| ATOM | 2024 | CA | TYR | 318 | 48.228 | 23.899 | 27.595 | 1.00 | 16.96 |
| ATOM | 2025 | CB | TYR | 318 | 49.406 | 24.338 | 28.471 | 1.00 | 17.55 |
| ATOM | 2026 | CG | TYR | 318 | 50.637 | 24.733 | 27.682 | 1.00 | 20.39 |
| ATOM | 2027 | CD1 | TYR | 318 | 50.690 | 25.942 | 26.995 | 1.00 | 19.75 |
| ATOM | 2028 | CE1 | TYR | 318 | 51.802 | 26.290 | 26.233 | 1.00 | 22.32 |
| ATOM | 2029 | CD2 | TYR | 318 | 51.734 | 23.875 | 27.590 | 1.00 | 21.99 |
| ATOM | 2030 | CE2 | TYR | 318 | 52.850 | 24.212 | 26.831 | 1.00 | 23.31 |
| ATOM | 2031 | CZ | TYR | 318 | 52.878 | 25.421 | 26.157 | 1.00 | 23.13 |
| ATOM | 2032 | OH | TYR | 318 | 53.983 | 25.764 | 25.411 | 1.00 | 24.51 |
| ATOM | 2033 | C | TYR | 318 | 48.691 | 22.787 | 26.645 | 1.00 | 17.99 |
| ATOM | 2034 | O | TYR | 318 | 48.996 | 23.038 | 25.480 | 1.00 | 17.00 |
| ATOM | 2035 | N | ASP | 319 | 48.735 | 21.561 | 27.154 | 1.00 | 18.60 |
| ATOM | 2036 | CA | ASP | 319 | 49.157 | 20.403 | 26.369 | 1.00 | 21.85 |
| ATOM | 2037 | CB | ASP | 319 | 49.104 | 19.140 | 27.232 | 1.00 | 24.07 |
| ATOM | 2038 | CG | ASP | 319 | 47.724 | 18.888 | 27.806 | 1.00 | 29.24 |
| ATOM | 2039 | OD1 | ASP | 319 | 47.207 | 19.781 | 28.507 | 1.00 | 34.33 |
| ATOM | 2040 | OD2 | ASP | 319 | 47.149 | 17.805 | 27.558 | 1.00 | 33.51 |
| ATOM | 2041 | C | ASP | 319 | 48.298 | 20.192 | 25.122 | 1.00 | 21.74 |
| ATOM | 2042 | O | ASP | 319 | 48.768 | 19.645 | 24.124 | 1.00 | 20.42 |
| ATOM | 2043 | N | LEU | 320 | 47.041 | 20.622 | 25.180 | 1.00 | 19.73 |
| ATOM | 2044 | CA | LEU | 320 | 46.141 | 20.459 | 24.045 | 1.00 | 19.44 |
| ATOM | 2045 | CB | LEU | 320 | 44.684 | 20.371 | 24.523 | 1.00 | 19.37 |
| ATOM | 2046 | CG | LEU | 320 | 44.255 | 19.241 | 25.471 | 1.00 | 20.20 |
| ATOM | 2047 | CD1 | LEU | 320 | 42.774 | 19.397 | 25.798 | 1.00 | 19.42 |
| ATOM | 2048 | CD2 | LEU | 320 | 44.515 | 17.888 | 24.830 | 1.00 | 18.15 |
| ATOM | 2049 | C | LEU | 320 | 46.253 | 21.588 | 23.025 | 1.00 | 17.85 |
| ATOM | 2050 | O | LEU | 320 | 45.823 | 21.434 | 21.882 | 1.00 | 17.25 |
| ATOM | 2051 | N | VAL | 321 | 46.845 | 22.711 | 23.426 | 1.00 | 16.88 |
| ATOM | 2052 | CA | VAL | 321 | 46.944 | 23.864 | 22.531 | 1.00 | 17.25 |
| ATOM | 2053 | CB | VAL | 321 | 46.073 | 25.038 | 23.063 | 1.00 | 15.70 |
| ATOM | 2054 | CG1 | VAL | 321 | 44.683 | 24.538 | 23.413 | 1.00 | 15.29 |
| ATOM | 2055 | CG2 | VAL | 321 | 46.726 | 25.665 | 24.285 | 1.00 | 13.63 |
| ATOM | 2056 | C | VAL | 321 | 48.352 | 24.407 | 22.270 | 1.00 | 18.75 |
| ATOM | 2057 | O | VAL | 321 | 48.501 | 25.476 | 21.670 | 1.00 | 20.66 |
| ATOM | 2058 | N | VAL | 322 | 49.379 | 23.684 | 22.705 | 1.00 | 19.31 |
| ATOM | 2059 | CA | VAL | 322 | 50.752 | 24.145 | 22.514 | 1.00 | 20.26 |
| ATOM | 2060 | CB | VAL | 322 | 51.767 | 23.052 | 22.933 | 1.00 | 22.20 |
| ATOM | 2061 | CG1 | VAL | 322 | 51.500 | 21.770 | 22.172 | 1.00 | 24.86 |
| ATOM | 2062 | CG2 | VAL | 322 | 53.187 | 23.540 | 22.692 | 1.00 | 23.70 |
| ATOM | 2063 | C | VAL | 322 | 51.029 | 24.591 | 21.072 | 1.00 | 19.64 |
| ATOM | 2064 | O | VAL | 322 | 50.878 | 23.816 | 20.130 | 1.00 | 19.00 |
| ATOM | 2065 | N | PRO | 323 | 51.426 | 25.864 | 20.888 | 1.00 | 18.76 |
| ATOM | 2066 | CD | PRO | 323 | 51.505 | 26.903 | 21.931 | 1.00 | 17.26 |
| ATOM | 2067 | CA | PRO | 323 | 51.725 | 26.429 | 19.566 | 1.00 | 19.32 |
| ATOM | 2068 | CB | PRO | 323 | 52.142 | 27.863 | 19.890 | 1.00 | 19.18 |
| ATOM | 2069 | CG | PRO | 323 | 51.348 | 28.170 | 21.135 | 1.00 | 17.09 |
| ATOM | 2070 | C | PRO | 323 | 52.812 | 25.665 | 18.809 | 1.00 | 20.64 |
| ATOM | 2071 | O | PRO | 323 | 52.647 | 25.336 | 17.634 | 1.00 | 20.49 |
| ATOM | 2072 | N | PHE | 324 | 53.927 | 25.398 | 19.479 | 1.00 | 21.43 |
| ATOM | 2073 | CA | PHE | 324 | 55.019 | 24.660 | 18.854 | 1.00 | 22.71 |
| ATOM | 2074 | CB | PHE | 324 | 56.245 | 25.560 | 18.668 | 1.00 | 22.22 |
| ATOM | 2075 | CG | PHE | 324 | 55.991 | 26.751 | 17.789 | 1.00 | 20.95 |
| ATOM | 2076 | CD1 | PHE | 324 | 55.631 | 27.977 | 18.339 | 1.00 | 20.89 |
| ATOM | 2077 | CD2 | PHE | 324 | 56.088 | 26.642 | 16.408 | 1.00 | 20.89 |
| ATOM | 2078 | CE1 | PHE | 324 | 55.371 | 29.073 | 17.526 | 1.00 | 21.44 |
| ATOM | 2079 | CE2 | PHE | 324 | 55.829 | 27.734 | 15.586 | 1.00 | 20.48 |
| ATOM | 2080 | CZ | PHE | 324 | 55.471 | 28.951 | 16.144 | 1.00 | 20.58 |
| ATOM | 2081 | C | PHE | 324 | 55.376 | 23.458 | 19.712 | 1.00 | 23.69 |
| ATOM | 2082 | O | PHE | 324 | 56.267 | 23.526 | 20.557 | 1.00 | 21.84 |
| ATOM | 2083 | N | PRO | 325 | 54.670 | 22.334 | 19.505 | 1.00 | 26.08 |
| ATOM | 2084 | CD | PRO | 325 | 53.612 | 22.157 | 18.495 | 1.00 | 26.36 |
| ATOM | 2085 | CA | PRO | 325 | 54.888 | 21.091 | 20.251 | 1.00 | 28.73 |
| ATOM | 2086 | CB | PRO | 325 | 53.790 | 20.168 | 19.714 | 1.00 | 27.79 |
| ATOM | 2087 | CG | PRO | 325 | 53.588 | 20.660 | 18.319 | 1.00 | 27.78 |
| ATOM | 2088 | C | PRO | 325 | 56.290 | 20.500 | 20.110 | 1.00 | 30.60 |
| ATOM | 2089 | O | PRO | 325 | 56.732 | 19.732 | 20.968 | 1.00 | 30.52 |
| ATOM | 2090 | N | SER | 326 | 56.991 | 20.858 | 19.038 | 1.00 | 31.95 |
| ATOM | 2091 | CA | SER | 326 | 58.346 | 20.356 | 18.837 | 1.00 | 35.76 |
| ATOM | 2092 | CB | SER | 326 | 58.885 | 20.786 | 17.472 | 1.00 | 37.39 |
| ATOM | 2093 | OG | SER | 326 | 58.203 | 20.118 | 16.424 | 1.00 | 41.03 |
| ATOM | 2094 | C | SER | 326 | 59.261 | 20.883 | 19.940 | 1.00 | 36.95 |

TABLE B-continued

Co-ordinates of an underglycosylated tACEΔ36NJ ACE-lisinopril complex

| ATOM | 2095 | O | SER | 326 | 60.355 | 20.363 | 20.152 | 1.00 | 36.99 |
|---|---|---|---|---|---|---|---|---|---|
| ATOM | 2096 | N | ALA | 327 | 58.809 | 21.925 | 20.631 | 1.00 | 37.24 |
| ATOM | 2097 | CA | ALA | 327 | 59.575 | 22.517 | 21.720 | 1.00 | 38.79 |
| ATOM | 2098 | CB | ALA | 327 | 59.564 | 24.039 | 21.610 | 1.00 | 38.45 |
| ATOM | 2099 | C | ALA | 327 | 58.937 | 22.078 | 23.033 | 1.00 | 40.49 |
| ATOM | 2100 | O | ALA | 327 | 58.143 | 22.811 | 23.623 | 1.00 | 41.01 |
| ATOM | 2101 | N | PRO | 328 | 59.283 | 20.870 | 23.509 | 1.00 | 41.45 |
| ATOM | 2102 | CD | PRO | 328 | 60.341 | 19.988 | 22.982 | 1.00 | 41.86 |
| ATOM | 2103 | CA | PRO | 328 | 58.737 | 20.330 | 24.757 | 1.00 | 42.79 |
| ATOM | 2104 | CB | PRO | 328 | 59.317 | 18.919 | 24.799 | 1.00 | 42.30 |
| ATOM | 2105 | CG | PRO | 328 | 60.663 | 19.112 | 24.175 | 1.00 | 42.39 |
| ATOM | 2106 | C | PRO | 328 | 59.111 | 21.150 | 25.989 | 1.00 | 42.72 |
| ATOM | 2107 | O | PRO | 328 | 60.206 | 21.712 | 26.072 | 1.00 | 42.49 |
| ATOM | 2108 | N | ALA | 329 | 58.186 | 21.218 | 26.939 | 1.00 | 42.80 |
| ATOM | 2109 | CA | ALA | 329 | 58.410 | 21.954 | 28.173 | 1.00 | 43.32 |
| ATOM | 2110 | CB | ALA | 329 | 57.310 | 22.996 | 28.373 | 1.00 | 43.71 |
| ATOM | 2111 | C | ALA | 329 | 58.419 | 20.967 | 29.329 | 1.00 | 42.69 |
| ATOM | 2112 | O | ALA | 329 | 57.621 | 20.027 | 29.359 | 1.00 | 41.34 |
| ATOM | 2113 | N | MET | 330 | 59.325 | 21.173 | 30.278 | 1.00 | 42.76 |
| ATOM | 2114 | CA | MET | 330 | 59.417 | 20.288 | 31.425 | 1.00 | 42.98 |
| ATOM | 2115 | CB | MET | 330 | 60.525 | 20.743 | 32.372 | 1.00 | 44.14 |
| ATOM | 2116 | CG | MET | 330 | 61.873 | 20.155 | 32.054 | 1.00 | 45.52 |
| ATOM | 2117 | SD | MET | 330 | 63.030 | 20.380 | 33.396 | 1.00 | 50.91 |
| ATOM | 2118 | CE | MET | 330 | 62.368 | 19.255 | 34.608 | 1.00 | 49.99 |
| ATOM | 2119 | C | MET | 330 | 58.120 | 20.194 | 32.208 | 1.00 | 43.28 |
| ATOM | 2120 | O | MET | 330 | 57.295 | 21.109 | 32.194 | 1.00 | 44.37 |
| ATOM | 2121 | N | ASP | 331 | 57.951 | 19.068 | 32.889 | 1.00 | 42.06 |
| ATOM | 2122 | CA | ASP | 331 | 56.784 | 18.835 | 33.718 | 1.00 | 41.71 |
| ATOM | 2123 | CB | ASP | 331 | 56.652 | 17.339 | 34.010 | 1.00 | 43.19 |
| ATOM | 2124 | CG | ASP | 331 | 55.319 | 16.978 | 34.623 | 1.00 | 44.69 |
| ATOM | 2125 | OD1 | ASP | 331 | 54.829 | 17.742 | 35.482 | 1.00 | 45.38 |
| ATOM | 2126 | OD2 | ASP | 331 | 54.771 | 15.920 | 34.252 | 1.00 | 46.02 |
| ATOM | 2127 | C | ASP | 331 | 57.068 | 19.606 | 35.006 | 1.00 | 40.79 |
| ATOM | 2128 | O | ASP | 331 | 57.739 | 19.096 | 35.907 | 1.00 | 39.06 |
| ATOM | 2129 | N | THR | 332 | 56.581 | 20.842 | 35.077 | 1.00 | 39.46 |
| ATOM | 2130 | CA | THR | 332 | 56.817 | 21.678 | 36.247 | 1.00 | 39.60 |
| ATOM | 2131 | CB | THR | 332 | 56.132 | 23.054 | 36.106 | 1.00 | 40.44 |
| ATOM | 2132 | OG1 | THR | 332 | 56.580 | 23.698 | 34.907 | 1.00 | 44.22 |
| ATOM | 2133 | CG2 | THR | 332 | 56.497 | 23.963 | 37.287 | 1.00 | 43.44 |
| ATOM | 2134 | C | THR | 332 | 56.376 | 21.042 | 37.559 | 1.00 | 38.30 |
| ATOM | 2135 | O | THR | 332 | 57.120 | 21.075 | 38.537 | 1.00 | 37.12 |
| ATOM | 2136 | N | THR | 333 | 55.181 | 20.457 | 37.584 | 1.00 | 37.24 |
| ATOM | 2137 | CA | THR | 333 | 54.694 | 19.819 | 38.799 | 1.00 | 35.98 |
| ATOM | 2138 | CB | THR | 333 | 53.238 | 19.345 | 38.638 | 1.00 | 35.93 |
| ATOM | 2139 | OG1 | THR | 333 | 52.384 | 20.485 | 38.467 | 1.00 | 35.53 |
| ATOM | 2140 | CG2 | THR | 333 | 52.798 | 18.557 | 39.857 | 1.00 | 35.95 |
| ATOM | 2141 | C | THR | 333 | 55.584 | 18.628 | 39.139 | 1.00 | 35.83 |
| ATOM | 2142 | O | THR | 333 | 55.983 | 18.447 | 40.292 | 1.00 | 35.49 |
| ATOM | 2143 | N | ALA | 334 | 55.900 | 17.818 | 38.132 | 1.00 | 35.47 |
| ATOM | 2144 | CA | ALA | 334 | 56.753 | 16.652 | 38.338 | 1.00 | 34.53 |
| ATOM | 2145 | CB | ALA | 334 | 56.918 | 15.875 | 37.032 | 1.00 | 35.72 |
| ATOM | 2146 | C | ALA | 334 | 58.116 | 17.078 | 38.869 | 1.00 | 33.83 |
| ATOM | 2147 | O | ALA | 334 | 58.714 | 16.387 | 39.693 | 1.00 | 34.31 |
| ATOM | 2148 | N | ALA | 335 | 58.602 | 18.221 | 38.391 | 1.00 | 32.92 |
| ATOM | 2149 | CA | ALA | 335 | 59.897 | 18.745 | 38.818 | 1.00 | 31.60 |
| ATOM | 2150 | CB | ALA | 335 | 60.295 | 19.935 | 37.946 | 1.00 | 30.64 |
| ATOM | 2151 | C | ALA | 335 | 59.867 | 19.158 | 40.289 | 1.00 | 30.59 |
| ATOM | 2152 | O | ALA | 335 | 60.750 | 18.791 | 41.056 | 1.00 | 29.04 |
| ATOM | 2153 | N | MET | 336 | 58.848 | 19.919 | 40.680 | 1.00 | 31.65 |
| ATOM | 2154 | CA | MET | 336 | 58.720 | 20.361 | 42.069 | 1.00 | 33.03 |
| ATOM | 2155 | CB | MET | 336 | 57.454 | 21.205 | 42.242 | 1.00 | 31.27 |
| ATOM | 2156 | CG | MET | 336 | 57.523 | 22.564 | 41.568 | 1.00 | 29.31 |
| ATOM | 2157 | SD | MET | 336 | 55.990 | 23.505 | 41.708 | 1.00 | 26.33 |
| ATOM | 2158 | CE | MET | 336 | 56.044 | 23.993 | 43.446 | 1.00 | 23.57 |
| ATOM | 2159 | C | MET | 336 | 58.671 | 19.158 | 43.008 | 1.00 | 33.75 |
| ATOM | 2160 | O | MET | 336 | 59.380 | 19.104 | 44.015 | 1.00 | 32.69 |
| ATOM | 2161 | N | LEU | 337 | 57.828 | 18.190 | 42.665 | 1.00 | 36.37 |
| ATOM | 2162 | CA | LEU | 337 | 57.679 | 16.976 | 43.457 | 1.00 | 38.17 |
| ATOM | 2163 | CB | LEU | 337 | 56.509 | 16.148 | 42.921 | 1.00 | 38.76 |
| ATOM | 2164 | CG | LEU | 337 | 55.116 | 16.781 | 43.006 | 1.00 | 39.29 |
| ATOM | 2165 | CD1 | LEU | 337 | 54.152 | 16.026 | 42.106 | 1.00 | 39.59 |
| ATOM | 2166 | CD2 | LEU | 337 | 54.630 | 16.771 | 44.449 | 1.00 | 39.05 |
| ATOM | 2167 | C | LEU | 337 | 58.964 | 16.155 | 43.403 | 1.00 | 39.59 |
| ATOM | 2168 | O | LEU | 337 | 59.437 | 15.656 | 44.425 | 1.00 | 40.32 |
| ATOM | 2169 | N | ALA | 338 | 59.524 | 16.027 | 42.203 | 1.00 | 40.41 |
| ATOM | 2170 | CA | ALA | 338 | 60.750 | 15.267 | 41.994 | 1.00 | 41.35 |
| ATOM | 2171 | CB | ALA | 338 | 61.195 | 15.374 | 40.538 | 1.00 | 41.73 |
| ATOM | 2172 | C | ALA | 338 | 61.881 | 15.713 | 42.912 | 1.00 | 41.96 |

TABLE B-continued

Co-ordinates of an underglycosylated tACEΔ36NJ ACE-lisinopril complex

| ATOM | 2173 | O | ALA | 338 | 62.699 | 14.895 | 43.332 | 1.00 | 42.58 |
|---|---|---|---|---|---|---|---|---|---|
| ATOM | 2174 | N | GLN | 339 | 61.942 | 17.006 | 43.219 | 1.00 | 41.77 |
| ATOM | 2175 | CA | GLN | 339 | 63.000 | 17.490 | 44.094 | 1.00 | 40.98 |
| ATOM | 2176 | CB | GLN | 339 | 63.871 | 18.519 | 43.369 | 1.00 | 42.73 |
| ATOM | 2177 | CG | GLN | 339 | 63.134 | 19.520 | 42.516 | 1.00 | 44.71 |
| ATOM | 2178 | CD | GLN | 339 | 64.047 | 20.143 | 41.476 | 1.00 | 45.98 |
| ATOM | 2179 | OE1 | GLN | 339 | 65.096 | 20.697 | 41.806 | 1.00 | 46.01 |
| ATOM | 2180 | NE2 | GLN | 339 | 63.656 | 20.046 | 40.210 | 1.00 | 46.19 |
| ATOM | 2181 | C | GLN | 339 | 62.518 | 18.029 | 45.434 | 1.00 | 39.28 |
| ATOM | 2182 | O | GLN | 339 | 62.990 | 19.054 | 45.923 | 1.00 | 39.85 |
| ATOM | 2183 | N | GLY | 340 | 61.567 | 17.305 | 46.014 | 1.00 | 38.07 |
| ATOM | 2184 | CA | GLY | 340 | 61.023 | 17.625 | 47.322 | 1.00 | 35.18 |
| ATOM | 2185 | C | GLY | 340 | 60.537 | 19.011 | 47.696 | 1.00 | 33.08 |
| ATOM | 2186 | O | GLY | 340 | 60.742 | 19.433 | 48.834 | 1.00 | 32.07 |
| ATOM | 2187 | N | TRP | 341 | 59.905 | 19.731 | 46.775 | 1.00 | 31.21 |
| ATOM | 2188 | CA | TRP | 341 | 59.390 | 21.049 | 47.128 | 1.00 | 30.14 |
| ATOM | 2189 | CB | TRP | 341 | 58.899 | 21.808 | 45.887 | 1.00 | 29.67 |
| ATOM | 2190 | CG | TRP | 341 | 59.982 | 22.541 | 45.158 | 1.00 | 29.21 |
| ATOM | 2191 | CD2 | TRP | 341 | 60.033 | 23.948 | 44.884 | 1.00 | 30.13 |
| ATOM | 2192 | CE2 | TRP | 341 | 61.235 | 24.193 | 44.182 | 1.00 | 30.52 |
| ATOM | 2193 | CE3 | TRP | 341 | 59.181 | 25.025 | 45.163 | 1.00 | 29.73 |
| ATOM | 2194 | CD1 | TRP | 341 | 61.119 | 22.007 | 44.627 | 1.00 | 29.98 |
| ATOM | 2195 | NE1 | TRP | 341 | 61.877 | 22.992 | 44.039 | 1.00 | 29.90 |
| ATOM | 2196 | CZ2 | TRP | 341 | 61.608 | 25.474 | 43.754 | 1.00 | 29.27 |
| ATOM | 2197 | CZ3 | TRP | 341 | 59.551 | 26.298 | 44.738 | 1.00 | 30.55 |
| ATOM | 2198 | CH2 | TRP | 341 | 60.757 | 26.509 | 44.039 | 1.00 | 30.31 |
| ATOM | 2199 | C | TRP | 341 | 58.225 | 20.821 | 48.085 | 1.00 | 28.38 |
| ATOM | 2200 | O | TRP | 341 | 57.478 | 19.857 | 47.936 | 1.00 | 27.83 |
| ATOM | 2201 | N | THR | 342 | 58.086 | 21.695 | 49.075 | 1.00 | 27.38 |
| ATOM | 2202 | CA | THR | 342 | 57.001 | 21.583 | 50.045 | 1.00 | 26.99 |
| ATOM | 2203 | CB | THR | 342 | 57.527 | 21.284 | 51.463 | 1.00 | 26.84 |
| ATOM | 2204 | OG1 | THR | 342 | 58.278 | 22.410 | 51.937 | 1.00 | 25.96 |
| ATOM | 2205 | CG2 | THR | 342 | 58.416 | 20.046 | 51.458 | 1.00 | 27.25 |
| ATOM | 2206 | C | THR | 342 | 56.277 | 22.918 | 50.107 | 1.00 | 26.48 |
| ATOM | 2207 | O | THR | 342 | 56.784 | 23.926 | 49.622 | 1.00 | 25.97 |
| ATOM | 2208 | N | PRO | 343 | 55.075 | 22.942 | 50.702 | 1.00 | 25.99 |
| ATOM | 2209 | CD | PRO | 343 | 54.229 | 21.824 | 51.158 | 1.00 | 24.91 |
| ATOM | 2210 | CA | PRO | 343 | 54.352 | 24.211 | 50.787 | 1.00 | 25.66 |
| ATOM | 2211 | CB | PRO | 343 | 53.128 | 23.846 | 51.620 | 1.00 | 24.24 |
| ATOM | 2212 | CG | PRO | 343 | 52.849 | 22.444 | 51.163 | 1.00 | 23.75 |
| ATOM | 2213 | C | PRO | 343 | 55.214 | 25.287 | 51.446 | 1.00 | 25.07 |
| ATOM | 2214 | O | PRO | 343 | 55.196 | 26.446 | 51.036 | 1.00 | 24.95 |
| ATOM | 2215 | N | ARG | 344 | 55.981 | 24.897 | 52.460 | 1.00 | 25.30 |
| ATOM | 2216 | CA | ARG | 344 | 56.836 | 25.846 | 53.160 | 1.00 | 26.37 |
| ATOM | 2217 | CB | ARG | 344 | 57.483 | 25.189 | 54.383 | 1.00 | 29.20 |
| ATOM | 2218 | CG | ARG | 344 | 57.856 | 26.180 | 55.485 | 1.00 | 34.03 |
| ATOM | 2219 | CD | ARG | 344 | 58.585 | 25.495 | 56.634 | 1.00 | 38.59 |
| ATOM | 2220 | NE | ARG | 344 | 58.774 | 26.369 | 57.794 | 1.00 | 42.13 |
| ATOM | 2221 | CZ | ARG | 344 | 57.793 | 26.785 | 58.593 | 1.00 | 43.28 |
| ATOM | 2222 | NH1 | ARG | 344 | 56.535 | 26.416 | 58.364 | 1.00 | 44.54 |
| ATOM | 2223 | NH2 | ARG | 344 | 58.070 | 27.563 | 59.631 | 1.00 | 42.82 |
| ATOM | 2224 | C | ARG | 344 | 57.914 | 26.395 | 52.227 | 1.00 | 26.08 |
| ATOM | 2225 | O | ARG | 344 | 58.199 | 27.590 | 52.243 | 1.00 | 24.97 |
| ATOM | 2226 | N | ARG | 345 | 58.509 | 25.521 | 51.416 | 1.00 | 26.26 |
| ATOM | 2227 | CA | ARG | 345 | 59.542 | 25.944 | 50.468 | 1.00 | 26.55 |
| ATOM | 2228 | CB | ARG | 345 | 59.986 | 24.772 | 49.584 | 1.00 | 28.67 |
| ATOM | 2229 | CG | ARG | 345 | 61.485 | 24.491 | 49.595 | 1.00 | 35.65 |
| ATOM | 2230 | CD | ARG | 345 | 62.322 | 25.714 | 49.229 | 1.00 | 39.10 |
| ATOM | 2231 | NE | ARG | 345 | 62.669 | 25.799 | 47.808 | 1.00 | 43.47 |
| ATOM | 2232 | CZ | ARG | 345 | 63.388 | 24.894 | 47.149 | 1.00 | 43.78 |
| ATOM | 2233 | NH1 | ARG | 345 | 63.840 | 23.814 | 47.771 | 1.00 | 45.20 |
| ATOM | 2234 | NH2 | ARG | 345 | 63.681 | 25.079 | 45.870 | 1.00 | 45.37 |
| ATOM | 2235 | C | ARG | 345 | 58.948 | 27.020 | 49.573 | 1.00 | 24.15 |
| ATOM | 2236 | O | ARG | 345 | 59.558 | 28.063 | 49.330 | 1.00 | 23.46 |
| ATOM | 2237 | N | MET | 346 | 57.746 | 26.736 | 49.084 | 1.00 | 22.01 |
| ATOM | 2238 | CA | MET | 346 | 57.024 | 27.634 | 48.199 | 1.00 | 21.13 |
| ATOM | 2239 | CB | MET | 346 | 55.660 | 27.023 | 47.864 | 1.00 | 22.10 |
| ATOM | 2240 | CG | MET | 346 | 55.773 | 25.773 | 46.989 | 1.00 | 20.75 |
| ATOM | 2241 | SD | MET | 346 | 54.316 | 24.724 | 47.003 | 1.00 | 22.63 |
| ATOM | 2242 | CE | MET | 346 | 53.205 | 25.656 | 45.917 | 1.00 | 19.78 |
| ATOM | 2243 | C | MET | 346 | 56.869 | 29.039 | 48.775 | 1.00 | 19.41 |
| ATOM | 2244 | O | MET | 346 | 57.169 | 30.018 | 48.098 | 1.00 | 20.08 |
| ATOM | 2245 | N | PHE | 347 | 56.418 | 29.148 | 50.021 | 1.00 | 18.55 |
| ATOM | 2246 | CA | PHE | 347 | 56.260 | 30.469 | 50.621 | 1.00 | 19.25 |
| ATOM | 2247 | CB | PHE | 347 | 55.388 | 30.400 | 51.879 | 1.00 | 17.54 |
| ATOM | 2248 | CG | PHE | 347 | 53.931 | 30.168 | 51.587 | 1.00 | 16.26 |
| ATOM | 2249 | CD1 | PHE | 347 | 53.434 | 28.882 | 51.430 | 1.00 | 14.65 |
| ATOM | 2250 | CD2 | PHE | 347 | 53.064 | 31.244 | 51.421 | 1.00 | 16.74 |

TABLE B-continued

Co-ordinates of an underglycosylated tACEΔ36NJ ACE-lisinopril complex

| ATOM | 2251 | CE1 | PHE | 347 | 52.091 | 28.669 | 51.109 | 1.00 | 17.04 |
|---|---|---|---|---|---|---|---|---|---|
| ATOM | 2252 | CE2 | PHE | 347 | 51.721 | 31.041 | 51.100 | 1.00 | 15.45 |
| ATOM | 2253 | CZ | PHE | 347 | 51.236 | 29.754 | 50.942 | 1.00 | 13.62 |
| ATOM | 2254 | C | PHE | 347 | 57.607 | 31.109 | 50.938 | 1.00 | 19.50 |
| ATOM | 2255 | O | PHE | 347 | 57.733 | 32.334 | 50.931 | 1.00 | 19.74 |
| ATOM | 2256 | N | LYS | 348 | 58.612 | 30.281 | 51.212 | 1.00 | 19.37 |
| ATOM | 2257 | CA | LYS | 348 | 59.949 | 30.789 | 51.499 | 1.00 | 20.13 |
| ATOM | 2258 | CB | LYS | 348 | 60.871 | 29.653 | 51.964 | 1.00 | 23.49 |
| ATOM | 2259 | CG | LYS | 348 | 60.647 | 29.188 | 53.404 | 1.00 | 26.94 |
| ATOM | 2260 | CD | LYS | 348 | 61.173 | 30.215 | 54.405 | 1.00 | 30.04 |
| ATOM | 2261 | CE | LYS | 348 | 61.057 | 29.722 | 55.840 | 1.00 | 30.37 |
| ATOM | 2262 | NZ | LYS | 348 | 61.712 | 30.663 | 56.797 | 1.00 | 32.04 |
| ATOM | 2263 | C | LYS | 348 | 60.517 | 31.434 | 50.234 | 1.00 | 19.83 |
| ATOM | 2264 | O | LYS | 348 | 61.180 | 32.466 | 50.303 | 1.00 | 18.66 |
| ATOM | 2265 | N | GLU | 349 | 60.263 | 30.823 | 49.077 | 1.00 | 19.90 |
| ATOM | 2266 | CA | GLU | 349 | 60.746 | 31.383 | 47.817 | 1.00 | 19.84 |
| ATOM | 2267 | CB | GLU | 349 | 60.449 | 30.444 | 46.644 | 1.00 | 22.36 |
| ATOM | 2268 | CG | GLU | 349 | 61.320 | 29.196 | 46.568 | 1.00 | 26.40 |
| ATOM | 2269 | CD | GLU | 349 | 62.807 | 29.505 | 46.643 | 1.00 | 29.00 |
| ATOM | 2270 | OE1 | GLU | 349 | 63.241 | 30.541 | 46.083 | 1.00 | 29.80 |
| ATOM | 2271 | OE2 | GLU | 349 | 63.543 | 28.701 | 47.253 | 1.00 | 30.47 |
| ATOM | 2272 | C | GLU | 349 | 60.074 | 32.730 | 47.565 | 1.00 | 19.20 |
| ATOM | 2273 | O | GLU | 349 | 60.723 | 33.688 | 47.140 | 1.00 | 19.59 |
| ATOM | 2274 | N | ALA | 350 | 58.770 | 32.798 | 47.820 | 1.00 | 18.23 |
| ATOM | 2275 | CA | ALA | 350 | 58.016 | 34.035 | 47.633 | 1.00 | 17.72 |
| ATOM | 2276 | CB | ALA | 350 | 56.529 | 33.796 | 47.903 | 1.00 | 17.17 |
| ATOM | 2277 | C | ALA | 350 | 58.556 | 35.102 | 48.582 | 1.00 | 18.51 |
| ATOM | 2278 | O | ALA | 350 | 58.763 | 36.249 | 48.189 | 1.00 | 18.51 |
| ATOM | 2279 | N | ASP | 351 | 58.790 | 34.718 | 49.835 | 1.00 | 17.68 |
| ATOM | 2280 | CA | ASP | 351 | 59.316 | 35.653 | 50.823 | 1.00 | 17.98 |
| ATOM | 2281 | CB | ASP | 351 | 59.481 | 34.950 | 52.179 | 1.00 | 18.35 |
| ATOM | 2282 | CG | ASP | 351 | 59.841 | 35.912 | 53.306 | 1.00 | 21.38 |
| ATOM | 2283 | OD1 | ASP | 351 | 59.094 | 36.886 | 53.542 | 1.00 | 21.06 |
| ATOM | 2284 | OD2 | ASP | 351 | 60.871 | 35.688 | 53.972 | 1.00 | 23.40 |
| ATOM | 2285 | C | ASP | 351 | 60.658 | 36.193 | 50.322 | 1.00 | 17.98 |
| ATOM | 2286 | O | ASP | 351 | 60.945 | 37.386 | 50.449 | 1.00 | 16.96 |
| ATOM | 2287 | N | ASP | 352 | 61.468 | 35.312 | 49.733 | 1.00 | 17.61 |
| ATOM | 2288 | CA | ASP | 352 | 62.776 | 35.702 | 49.207 | 1.00 | 17.44 |
| ATOM | 2289 | CB | ASP | 352 | 63.544 | 34.464 | 48.718 | 1.00 | 16.88 |
| ATOM | 2290 | CG | ASP | 352 | 64.886 | 34.819 | 48.100 | 1.00 | 20.01 |
| ATOM | 2291 | OD1 | ASP | 352 | 64.986 | 34.843 | 46.857 | 1.00 | 20.73 |
| ATOM | 2292 | OD2 | ASP | 352 | 65.842 | 35.089 | 48.858 | 1.00 | 22.68 |
| ATOM | 2293 | C | ASP | 352 | 62.668 | 36.724 | 48.074 | 1.00 | 16.59 |
| ATOM | 2294 | O | ASP | 352 | 63.456 | 37.665 | 48.001 | 1.00 | 16.83 |
| ATOM | 2295 | N | PHE | 353 | 61.687 | 36.546 | 47.196 | 1.00 | 16.60 |
| ATOM | 2296 | CA | PHE | 353 | 61.516 | 37.481 | 46.094 | 1.00 | 15.67 |
| ATOM | 2297 | CB | PHE | 353 | 60.393 | 37.022 | 45.151 | 1.00 | 15.02 |
| ATOM | 2298 | CG | PHE | 353 | 60.498 | 37.599 | 43.760 | 1.00 | 13.85 |
| ATOM | 2299 | CD1 | PHE | 353 | 60.633 | 36.766 | 42.655 | 1.00 | 15.98 |
| ATOM | 2300 | CD2 | PHE | 353 | 60.491 | 38.977 | 43.558 | 1.00 | 14.55 |
| ATOM | 2301 | CE1 | PHE | 353 | 60.763 | 37.292 | 41.363 | 1.00 | 13.57 |
| ATOM | 2302 | CE2 | PHE | 353 | 60.622 | 39.515 | 42.272 | 1.00 | 15.24 |
| ATOM | 2303 | CZ | PHE | 353 | 60.759 | 38.668 | 41.173 | 1.00 | 14.14 |
| ATOM | 2304 | C | PHE | 353 | 61.212 | 38.874 | 46.647 | 1.00 | 14.39 |
| ATOM | 2305 | O | PHE | 353 | 61.808 | 39.863 | 46.212 | 1.00 | 15.75 |
| ATOM | 2306 | N | PHE | 354 | 60.301 | 38.964 | 47.612 | 1.00 | 14.89 |
| ATOM | 2307 | CA | PHE | 354 | 59.980 | 40.269 | 48.191 | 1.00 | 15.05 |
| ATOM | 2308 | CB | PHE | 354 | 58.864 | 40.149 | 49.238 | 1.00 | 14.19 |
| ATOM | 2309 | CG | PHE | 354 | 57.481 | 40.060 | 48.645 | 1.00 | 14.57 |
| ATOM | 2310 | CD1 | PHE | 354 | 56.876 | 38.824 | 48.428 | 1.00 | 13.09 |
| ATOM | 2311 | CD2 | PHE | 354 | 56.797 | 41.217 | 48.275 | 1.00 | 14.46 |
| ATOM | 2312 | CE1 | PHE | 354 | 55.613 | 38.738 | 47.852 | 1.00 | 12.80 |
| ATOM | 2313 | CE2 | PHE | 354 | 55.528 | 41.144 | 47.695 | 1.00 | 14.78 |
| ATOM | 2314 | CZ | PHE | 354 | 54.935 | 39.901 | 47.484 | 1.00 | 14.26 |
| ATOM | 2315 | C | PHE | 354 | 61.203 | 40.959 | 48.811 | 1.00 | 15.63 |
| ATOM | 2316 | O | PHE | 354 | 61.448 | 42.141 | 48.555 | 1.00 | 16.90 |
| ATOM | 2317 | N | THR | 355 | 61.973 | 40.233 | 49.620 | 1.00 | 17.16 |
| ATOM | 2318 | CA | THR | 355 | 63.155 | 40.824 | 50.243 | 1.00 | 17.44 |
| ATOM | 2319 | CB | THR | 355 | 63.798 | 39.887 | 51.306 | 1.00 | 19.33 |
| ATOM | 2320 | OG1 | THR | 355 | 64.122 | 38.624 | 50.713 | 1.00 | 22.32 |
| ATOM | 2321 | CG2 | THR | 355 | 62.845 | 39.675 | 52.476 | 1.00 | 19.21 |
| ATOM | 2322 | C | THR | 355 | 64.207 | 41.179 | 49.202 | 1.00 | 16.79 |
| ATOM | 2323 | O | THR | 355 | 64.968 | 42.130 | 49.387 | 1.00 | 17.18 |
| ATOM | 2324 | N | SER | 356 | 64.242 | 40.429 | 48.102 | 1.00 | 16.97 |
| ATOM | 2325 | CA | SER | 356 | 65.215 | 40.702 | 47.045 | 1.00 | 16.07 |
| ATOM | 2326 | CB | SER | 356 | 65.127 | 39.651 | 45.930 | 1.00 | 17.08 |
| ATOM | 2327 | OG | SER | 356 | 64.105 | 39.961 | 44.991 | 1.00 | 20.08 |
| ATOM | 2328 | C | SER | 356 | 64.942 | 42.087 | 46.471 | 1.00 | 17.25 |

TABLE B-continued

Co-ordinates of an underglycosylated tACEΔ36NJ ACE-lisinopril complex

| ATOM | 2329 | O   | SER | 356 | 65.856 | 42.767 | 46.005 | 1.00 | 16.33 |
|------|------|-----|-----|-----|--------|--------|--------|------|-------|
| ATOM | 2330 | N   | LEU | 357 | 63.677 | 42.503 | 46.514 | 1.00 | 16.63 |
| ATOM | 2331 | CA  | LEU | 357 | 63.282 | 43.817 | 46.013 | 1.00 | 17.17 |
| ATOM | 2332 | CB  | LEU | 357 | 61.804 | 43.821 | 45.607 | 1.00 | 16.38 |
| ATOM | 2333 | CG  | LEU | 357 | 61.378 | 42.907 | 44.458 | 1.00 | 16.10 |
| ATOM | 2334 | CD1 | LEU | 357 | 59.897 | 43.117 | 44.185 | 1.00 | 16.24 |
| ATOM | 2335 | CD2 | LEU | 357 | 62.202 | 43.212 | 43.211 | 1.00 | 13.65 |
| ATOM | 2336 | C   | LEU | 357 | 63.496 | 44.875 | 47.087 | 1.00 | 16.00 |
| ATOM | 2337 | O   | LEU | 357 | 63.228 | 46.057 | 46.872 | 1.00 | 16.89 |
| ATOM | 2338 | N   | GLY | 358 | 63.978 | 44.445 | 48.246 | 1.00 | 15.89 |
| ATOM | 2339 | CA  | GLY | 358 | 64.193 | 45.378 | 49.333 | 1.00 | 16.90 |
| ATOM | 2340 | C   | GLY | 358 | 62.928 | 45.537 | 50.163 | 1.00 | 18.34 |
| ATOM | 2341 | O   | GLY | 358 | 62.866 | 46.386 | 51.054 | 1.00 | 19.04 |
| ATOM | 2342 | N   | LEU | 359 | 61.914 | 44.724 | 49.873 | 1.00 | 16.43 |
| ATOM | 2343 | CA  | LEU | 359 | 60.663 | 44.790 | 50.618 | 1.00 | 17.52 |
| ATOM | 2344 | CB  | LEU | 359 | 59.510 | 44.258 | 49.757 | 1.00 | 13.59 |
| ATOM | 2345 | CG  | LEU | 359 | 59.299 | 45.099 | 48.487 | 1.00 | 14.94 |
| ATOM | 2346 | CD1 | LEU | 359 | 58.221 | 44.490 | 47.588 | 1.00 | 12.02 |
| ATOM | 2347 | CD2 | LEU | 359 | 58.928 | 46.518 | 48.893 | 1.00 | 13.39 |
| ATOM | 2348 | C   | LEU | 359 | 60.786 | 44.014 | 51.938 | 1.00 | 18.75 |
| ATOM | 2349 | O   | LEU | 359 | 61.807 | 43.369 | 52.194 | 1.00 | 18.11 |
| ATOM | 2350 | N   | LEU | 360 | 59.744 | 44.078 | 52.763 | 1.00 | 17.60 |
| ATOM | 2351 | CA  | LEU | 360 | 59.741 | 43.432 | 54.075 | 1.00 | 17.15 |
| ATOM | 2352 | CB  | LEU | 360 | 58.661 | 44.064 | 54.958 | 1.00 | 16.43 |
| ATOM | 2353 | CG  | LEU | 360 | 58.719 | 45.578 | 55.171 | 1.00 | 18.94 |
| ATOM | 2354 | CD1 | LEU | 360 | 57.401 | 46.059 | 55.780 | 1.00 | 18.12 |
| ATOM | 2355 | CD2 | LEU | 360 | 59.911 | 45.924 | 56.064 | 1.00 | 17.34 |
| ATOM | 2356 | C   | LEU | 360 | 59.546 | 41.925 | 54.109 | 1.00 | 18.61 |
| ATOM | 2357 | O   | LEU | 360 | 58.764 | 41.364 | 53.342 | 1.00 | 19.09 |
| ATOM | 2358 | N   | PRO | 361 | 60.271 | 41.244 | 55.011 | 1.00 | 19.60 |
| ATOM | 2359 | CD  | PRO | 361 | 61.405 | 41.728 | 55.824 | 1.00 | 19.10 |
| ATOM | 2360 | CA  | PRO | 361 | 60.130 | 39.795 | 55.121 | 1.00 | 19.12 |
| ATOM | 2361 | CB  | PRO | 361 | 61.461 | 39.368 | 55.730 | 1.00 | 20.18 |
| ATOM | 2362 | CG  | PRO | 361 | 61.770 | 40.500 | 56.650 | 1.00 | 19.74 |
| ATOM | 2363 | C   | PRO | 361 | 58.960 | 39.548 | 56.065 | 1.00 | 19.48 |
| ATOM | 2364 | O   | PRO | 361 | 58.636 | 40.407 | 56.887 | 1.00 | 21.65 |
| ATOM | 2365 | N   | VAL | 362 | 58.305 | 38.404 | 55.945 | 1.00 | 20.31 |
| ATOM | 2366 | CA  | VAL | 362 | 57.202 | 38.123 | 56.855 | 1.00 | 21.83 |
| ATOM | 2367 | CB  | VAL | 362 | 56.383 | 36.900 | 56.400 | 1.00 | 20.89 |
| ATOM | 2368 | CG1 | VAL | 362 | 55.737 | 37.189 | 55.052 | 1.00 | 19.57 |
| ATOM | 2369 | CG2 | VAL | 362 | 57.278 | 35.670 | 56.325 | 1.00 | 19.33 |
| ATOM | 2370 | C   | VAL | 362 | 57.828 | 37.846 | 58.217 | 1.00 | 23.46 |
| ATOM | 2371 | O   | VAL | 362 | 58.916 | 37.271 | 58.298 | 1.00 | 22.63 |
| ATOM | 2372 | N   | PRO | 363 | 57.157 | 38.266 | 59.305 | 1.00 | 23.58 |
| ATOM | 2373 | CD  | PRO | 363 | 55.924 | 39.073 | 59.315 | 1.00 | 23.83 |
| ATOM | 2374 | CA  | PRO | 363 | 57.652 | 38.066 | 60.672 | 1.00 | 23.23 |
| ATOM | 2375 | CB  | PRO | 363 | 56.602 | 38.777 | 61.529 | 1.00 | 23.92 |
| ATOM | 2376 | CG  | PRO | 363 | 56.060 | 39.835 | 60.608 | 1.00 | 23.78 |
| ATOM | 2377 | C   | PRO | 363 | 57.778 | 36.597 | 61.049 | 1.00 | 22.63 |
| ATOM | 2378 | O   | PRO | 363 | 57.080 | 35.741 | 60.502 | 1.00 | 23.59 |
| ATOM | 2379 | N   | PRO | 364 | 58.684 | 36.285 | 61.987 | 1.00 | 23.85 |
| ATOM | 2380 | CD  | PRO | 364 | 59.645 | 37.186 | 62.654 | 1.00 | 23.46 |
| ATOM | 2381 | CA  | PRO | 364 | 58.872 | 34.897 | 62.422 | 1.00 | 21.89 |
| ATOM | 2382 | CB  | PRO | 364 | 59.831 | 35.039 | 63.603 | 1.00 | 23.26 |
| ATOM | 2383 | CG  | PRO | 364 | 60.673 | 36.218 | 63.203 | 1.00 | 24.65 |
| ATOM | 2384 | C   | PRO | 364 | 57.533 | 34.289 | 62.837 | 1.00 | 21.17 |
| ATOM | 2385 | O   | PRO | 364 | 57.256 | 33.119 | 62.570 | 1.00 | 20.23 |
| ATOM | 2386 | N   | GLU | 365 | 56.704 | 35.105 | 63.484 | 1.00 | 21.36 |
| ATOM | 2387 | CA  | GLU | 365 | 55.388 | 34.681 | 63.957 | 1.00 | 22.68 |
| ATOM | 2388 | CB  | GLU | 365 | 54.691 | 35.860 | 64.644 | 1.00 | 25.18 |
| ATOM | 2389 | CG  | GLU | 365 | 53.265 | 35.599 | 65.084 | 1.00 | 27.55 |
| ATOM | 2390 | CD  | GLU | 365 | 52.726 | 36.694 | 65.995 | 1.00 | 30.30 |
| ATOM | 2391 | OE1 | GLU | 365 | 53.118 | 37.871 | 65.821 | 1.00 | 29.38 |
| ATOM | 2392 | OE2 | GLU | 365 | 51.898 | 36.378 | 66.876 | 1.00 | 30.66 |
| ATOM | 2393 | C   | GLU | 365 | 54.511 | 34.131 | 62.832 | 1.00 | 23.65 |
| ATOM | 2394 | O   | GLU | 365 | 53.640 | 33.286 | 63.068 | 1.00 | 24.23 |
| ATOM | 2395 | N   | PHE | 366 | 54.752 | 34.611 | 61.612 | 1.00 | 22.72 |
| ATOM | 2396 | CA  | PHE | 366 | 54.007 | 34.179 | 60.428 | 1.00 | 20.44 |
| ATOM | 2397 | CB  | PHE | 366 | 54.516 | 34.930 | 59.191 | 1.00 | 20.08 |
| ATOM | 2398 | CG  | PHE | 366 | 53.982 | 34.397 | 57.880 | 1.00 | 19.61 |
| ATOM | 2399 | CD1 | PHE | 366 | 52.811 | 34.911 | 57.326 | 1.00 | 19.02 |
| ATOM | 2400 | CD2 | PHE | 366 | 54.665 | 33.395 | 57.192 | 1.00 | 18.91 |
| ATOM | 2401 | CE1 | PHE | 366 | 52.327 | 34.438 | 56.106 | 1.00 | 17.67 |
| ATOM | 2402 | CE2 | PHE | 366 | 54.191 | 32.913 | 55.968 | 1.00 | 19.81 |
| ATOM | 2403 | CZ  | PHE | 366 | 53.020 | 33.436 | 55.424 | 1.00 | 18.45 |
| ATOM | 2404 | C   | PHE | 366 | 54.161 | 32.681 | 60.196 | 1.00 | 20.36 |
| ATOM | 2405 | O   | PHE | 366 | 53.182 | 31.968 | 59.962 | 1.00 | 20.59 |
| ATOM | 2406 | N   | TRP | 367 | 55.398 | 32.207 | 60.252 | 1.00 | 21.17 |

TABLE B-continued

Co-ordinates of an underglycosylated tACEΔ36NJ ACE-lisinopril complex

| ATOM | 2407 | CA | TRP | 367 | 55.680 | 30.792 | 60.033 | 1.00 | 23.44 |
|---|---|---|---|---|---|---|---|---|---|
| ATOM | 2408 | CB | TRP | 367 | 57.193 | 30.571 | 59.936 | 1.00 | 23.71 |
| ATOM | 2409 | CG | TRP | 367 | 57.837 | 31.400 | 58.866 | 1.00 | 23.03 |
| ATOM | 2410 | CD2 | TRP | 367 | 57.716 | 31.214 | 57.450 | 1.00 | 21.94 |
| ATOM | 2411 | CE2 | TRP | 367 | 58.454 | 32.244 | 56.828 | 1.00 | 20.04 |
| ATOM | 2412 | CE3 | TRP | 367 | 57.053 | 30.276 | 56.646 | 1.00 | 21.24 |
| ATOM | 2413 | CD1 | TRP | 367 | 58.620 | 32.503 | 59.041 | 1.00 | 22.06 |
| ATOM | 2414 | NE1 | TRP | 367 | 58.995 | 33.017 | 57.822 | 1.00 | 22.15 |
| ATOM | 2415 | CZ2 | TRP | 367 | 58.552 | 32.364 | 55.437 | 1.00 | 21.91 |
| ATOM | 2416 | CZ3 | TRP | 367 | 57.149 | 30.394 | 55.260 | 1.00 | 22.47 |
| ATOM | 2417 | CH2 | TRP | 367 | 57.894 | 31.434 | 54.672 | 1.00 | 21.53 |
| ATOM | 2418 | C | TRP | 367 | 55.096 | 29.898 | 61.124 | 1.00 | 25.38 |
| ATOM | 2419 | O | TRP | 367 | 54.753 | 28.741 | 60.877 | 1.00 | 26.15 |
| ATOM | 2420 | N | ASN | 368 | 54.965 | 30.445 | 62.325 | 1.00 | 26.99 |
| ATOM | 2421 | CA | ASN | 368 | 54.439 | 29.683 | 63.446 | 1.00 | 29.40 |
| ATOM | 2422 | CB | ASN | 368 | 54.971 | 30.277 | 64.754 | 1.00 | 32.59 |
| ATOM | 2423 | CG | ASN | 368 | 54.447 | 29.558 | 65.979 | 1.00 | 36.43 |
| ATOM | 2424 | OD1 | ASN | 368 | 53.351 | 29.842 | 66.458 | 1.00 | 38.69 |
| ATOM | 2425 | ND2 | ASN | 368 | 55.229 | 28.610 | 66.489 | 1.00 | 39.13 |
| ATOM | 2426 | C | ASN | 368 | 52.911 | 29.593 | 63.493 | 1.00 | 29.33 |
| ATOM | 2427 | O | ASN | 368 | 52.361 | 28.559 | 63.878 | 1.00 | 28.62 |
| ATOM | 2428 | N | LYS | 369 | 52.224 | 30.655 | 63.082 | 1.00 | 27.34 |
| ATOM | 2429 | CA | LYS | 369 | 50.766 | 30.664 | 63.134 | 1.00 | 26.72 |
| ATOM | 2430 | CB | LYS | 369 | 50.286 | 31.988 | 63.734 | 1.00 | 28.17 |
| ATOM | 2431 | CG | LYS | 369 | 50.778 | 32.222 | 65.163 | 1.00 | 30.11 |
| ATOM | 2432 | CD | LYS | 369 | 50.173 | 33.486 | 65.756 | 1.00 | 33.96 |
| ATOM | 2433 | CE | LYS | 369 | 50.598 | 33.679 | 67.206 | 1.00 | 36.40 |
| ATOM | 2434 | NZ | LYS | 369 | 49.966 | 34.897 | 67.802 | 1.00 | 39.20 |
| ATOM | 2435 | C | LYS | 369 | 50.013 | 30.392 | 61.833 | 1.00 | 26.02 |
| ATOM | 2436 | O | LYS | 369 | 48.821 | 30.084 | 61.864 | 1.00 | 25.69 |
| ATOM | 2437 | N | SER | 370 | 50.689 | 30.503 | 60.696 | 1.00 | 23.45 |
| ATOM | 2438 | CA | SER | 370 | 50.021 | 30.262 | 59.421 | 1.00 | 23.37 |
| ATOM | 2439 | CB | SER | 370 | 50.897 | 30.732 | 58.249 | 1.00 | 21.85 |
| ATOM | 2440 | OG | SER | 370 | 51.005 | 32.143 | 58.202 | 1.00 | 19.18 |
| ATOM | 2441 | C | SER | 370 | 49.668 | 28.792 | 59.214 | 1.00 | 23.22 |
| ATOM | 2442 | O | SER | 370 | 50.301 | 27.901 | 59.777 | 1.00 | 23.81 |
| ATOM | 2443 | N | MET | 371 | 48.639 | 28.549 | 58.411 | 1.00 | 23.49 |
| ATOM | 2444 | CA | MET | 371 | 48.224 | 27.193 | 58.083 | 1.00 | 24.10 |
| ATOM | 2445 | CB | MET | 371 | 46.730 | 26.991 | 58.349 | 1.00 | 23.79 |
| ATOM | 2446 | CG | MET | 371 | 46.260 | 25.564 | 58.100 | 1.00 | 23.95 |
| ATOM | 2447 | SD | MET | 371 | 44.475 | 25.392 | 57.941 | 1.00 | 26.45 |
| ATOM | 2448 | CE | MET | 371 | 44.296 | 25.509 | 56.167 | 1.00 | 26.30 |
| ATOM | 2449 | C | MET | 371 | 48.506 | 27.061 | 56.588 | 1.00 | 24.40 |
| ATOM | 2450 | O | MET | 371 | 47.671 | 27.417 | 55.755 | 1.00 | 24.50 |
| ATOM | 2451 | N | LEU | 372 | 49.691 | 26.559 | 56.257 | 1.00 | 25.00 |
| ATOM | 2452 | CA | LEU | 372 | 50.099 | 26.409 | 54.865 | 1.00 | 25.46 |
| ATOM | 2453 | CB | LEU | 372 | 51.599 | 26.684 | 54.743 | 1.00 | 23.72 |
| ATOM | 2454 | CG | LEU | 372 | 52.070 | 27.996 | 55.382 | 1.00 | 24.19 |
| ATOM | 2455 | CD1 | LEU | 372 | 53.581 | 28.097 | 55.296 | 1.00 | 23.40 |
| ATOM | 2456 | CD2 | LEU | 372 | 51.408 | 29.184 | 54.688 | 1.00 | 22.75 |
| ATOM | 2457 | C | LEU | 372 | 49.770 | 25.044 | 54.267 | 1.00 | 26.72 |
| ATOM | 2458 | O | LEU | 372 | 49.995 | 24.815 | 53.080 | 1.00 | 27.70 |
| ATOM | 2459 | N | GLU | 373 | 49.238 | 24.141 | 55.086 | 1.00 | 27.93 |
| ATOM | 2460 | CA | GLU | 373 | 48.879 | 22.803 | 54.620 | 1.00 | 29.95 |
| ATOM | 2461 | CB | GLU | 373 | 49.850 | 21.750 | 55.164 | 1.00 | 32.89 |
| ATOM | 2462 | CG | GLU | 373 | 51.281 | 21.859 | 54.689 | 1.00 | 38.75 |
| ATOM | 2463 | CD | GLU | 373 | 52.099 | 20.640 | 55.086 | 1.00 | 42.30 |
| ATOM | 2464 | OE1 | GLU | 373 | 52.259 | 20.397 | 56.302 | 1.00 | 44.27 |
| ATOM | 2465 | OE2 | GLU | 373 | 52.573 | 19.918 | 54.181 | 1.00 | 43.48 |
| ATOM | 2466 | C | GLU | 373 | 47.483 | 22.425 | 55.084 | 1.00 | 29.73 |
| ATOM | 2467 | O | GLU | 373 | 47.011 | 22.899 | 56.115 | 1.00 | 30.00 |
| ATOM | 2468 | N | LYS | 374 | 46.824 | 21.562 | 54.324 | 1.00 | 29.28 |
| ATOM | 2469 | CA | LYS | 374 | 45.497 | 21.107 | 54.699 | 1.00 | 30.95 |
| ATOM | 2470 | CB | LYS | 374 | 44.889 | 20.253 | 53.586 | 1.00 | 31.28 |
| ATOM | 2471 | CG | LYS | 374 | 43.444 | 19.847 | 53.822 | 1.00 | 31.52 |
| ATOM | 2472 | CD | LYS | 374 | 42.926 | 19.049 | 52.631 | 1.00 | 33.34 |
| ATOM | 2473 | CE | LYS | 374 | 41.415 | 19.128 | 52.514 | 1.00 | 33.68 |
| ATOM | 2474 | NZ | LYS | 374 | 40.933 | 18.533 | 51.235 | 1.00 | 33.80 |
| ATOM | 2475 | C | LYS | 374 | 45.697 | 20.256 | 55.944 | 1.00 | 32.17 |
| ATOM | 2476 | O | LYS | 374 | 46.520 | 19.342 | 55.948 | 1.00 | 32.16 |
| ATOM | 2477 | N | PRO | 375 | 44.975 | 20.567 | 57.030 | 1.00 | 33.39 |
| ATOM | 2478 | CD | PRO | 375 | 44.183 | 21.784 | 57.276 | 1.00 | 33.07 |
| ATOM | 2479 | CA | PRO | 375 | 45.120 | 19.785 | 58.261 | 1.00 | 34.99 |
| ATOM | 2480 | CB | PRO | 375 | 44.196 | 20.512 | 59.236 | 1.00 | 34.90 |
| ATOM | 2481 | CG | PRO | 375 | 44.299 | 21.933 | 58.777 | 1.00 | 33.52 |
| ATOM | 2482 | C | PRO | 375 | 44.724 | 18.323 | 58.064 | 1.00 | 35.62 |
| ATOM | 2483 | O | PRO | 375 | 43.812 | 18.013 | 57.296 | 1.00 | 34.22 |
| ATOM | 2484 | N | THR | 376 | 45.421 | 17.428 | 58.755 | 1.00 | 37.71 |

TABLE B-continued

Co-ordinates of an underglycosylated tACEΔ36NJ ACE-lisinopril complex

| ATOM | 2485 | CA | THR | 376 | 45.138 | 16.000 | 58.665 | 1.00 | 39.65 |
|------|------|-----|-----|-----|--------|--------|--------|------|-------|
| ATOM | 2486 | CB | THR | 376 | 46.308 | 15.233 | 58.009 | 1.00 | 39.07 |
| ATOM | 2487 | OG1 | THR | 376 | 47.491 | 15.390 | 58.804 | 1.00 | 38.66 |
| ATOM | 2488 | CG2 | THR | 376 | 46.575 | 15.762 | 56.608 | 1.00 | 39.31 |
| ATOM | 2489 | C | THR | 376 | 44.906 | 15.439 | 60.063 | 1.00 | 41.67 |
| ATOM | 2490 | O | THR | 376 | 45.345 | 14.333 | 60.379 | 1.00 | 42.78 |
| ATOM | 2491 | N | ASP | 377 | 44.221 | 16.211 | 60.900 | 1.00 | 42.52 |
| ATOM | 2492 | CA | ASP | 377 | 43.946 | 15.781 | 62.264 | 1.00 | 43.25 |
| ATOM | 2493 | CB | ASP | 377 | 44.579 | 16.748 | 63.272 | 1.00 | 44.11 |
| ATOM | 2494 | CG | ASP | 377 | 44.103 | 18.181 | 63.093 | 1.00 | 44.64 |
| ATOM | 2495 | OD1 | ASP | 377 | 42.879 | 18.394 | 62.984 | 1.00 | 43.68 |
| ATOM | 2496 | OD2 | ASP | 377 | 44.955 | 19.095 | 63.072 | 1.00 | 44.31 |
| ATOM | 2497 | C | ASP | 377 | 42.455 | 15.649 | 62.549 | 1.00 | 43.56 |
| ATOM | 2498 | O | ASP | 377 | 42.031 | 15.714 | 63.703 | 1.00 | 43.97 |
| ATOM | 2499 | N | GLY | 378 | 41.664 | 15.473 | 61.496 | 1.00 | 43.76 |
| ATOM | 2500 | CA | GLY | 378 | 40.234 | 15.313 | 61.674 | 1.00 | 45.10 |
| ATOM | 2501 | C | GLY | 378 | 39.389 | 16.574 | 61.613 | 1.00 | 45.20 |
| ATOM | 2502 | O | GLY | 378 | 38.160 | 16.480 | 61.553 | 1.00 | 46.83 |
| ATOM | 2503 | N | ARG | 379 | 40.018 | 17.747 | 61.629 | 1.00 | 43.58 |
| ATOM | 2504 | CA | ARG | 379 | 39.248 | 18.985 | 61.569 | 1.00 | 41.75 |
| ATOM | 2505 | CB | ARG | 379 | 39.902 | 20.086 | 62.417 | 1.00 | 41.40 |
| ATOM | 2506 | CG | ARG | 379 | 41.307 | 20.489 | 62.025 | 1.00 | 41.01 |
| ATOM | 2507 | CD | ARG | 379 | 41.892 | 21.409 | 63.091 | 1.00 | 40.32 |
| ATOM | 2508 | NE | ARG | 379 | 43.352 | 21.472 | 63.049 | 1.00 | 42.06 |
| ATOM | 2509 | CZ | ARG | 379 | 44.051 | 22.421 | 62.435 | 1.00 | 42.42 |
| ATOM | 2510 | NH1 | ARG | 379 | 43.431 | 23.409 | 61.801 | 1.00 | 42.84 |
| ATOM | 2511 | NH2 | ARG | 379 | 45.376 | 22.384 | 62.456 | 1.00 | 42.41 |
| ATOM | 2512 | C | ARG | 379 | 39.017 | 19.488 | 60.150 | 1.00 | 39.88 |
| ATOM | 2513 | O | ARG | 379 | 39.884 | 19.385 | 59.284 | 1.00 | 39.95 |
| ATOM | 2514 | N | GLU | 380 | 37.819 | 20.015 | 59.927 | 1.00 | 37.75 |
| ATOM | 2515 | CA | GLU | 380 | 37.424 | 20.552 | 58.635 | 1.00 | 35.59 |
| ATOM | 2516 | CB | GLU | 380 | 35.913 | 20.375 | 58.456 | 1.00 | 38.09 |
| ATOM | 2517 | CG | GLU | 380 | 35.383 | 20.691 | 57.068 | 1.00 | 42.10 |
| ATOM | 2518 | CD | GLU | 380 | 34.658 | 19.508 | 56.444 | 1.00 | 43.64 |
| ATOM | 2519 | OE1 | GLU | 380 | 33.789 | 18.911 | 57.120 | 1.00 | 45.08 |
| ATOM | 2520 | OE2 | GLU | 380 | 34.951 | 19.179 | 55.277 | 1.00 | 43.23 |
| ATOM | 2521 | C | GLU | 380 | 37.793 | 22.034 | 58.633 | 1.00 | 31.78 |
| ATOM | 2522 | O | GLU | 380 | 37.679 | 22.705 | 59.659 | 1.00 | 28.75 |
| ATOM | 2523 | N | VAL | 381 | 38.241 | 22.545 | 57.492 | 1.00 | 29.15 |
| ATOM | 2524 | CA | VAL | 381 | 38.630 | 23.950 | 57.404 | 1.00 | 26.32 |
| ATOM | 2525 | CB | VAL | 381 | 40.169 | 24.112 | 57.499 | 1.00 | 24.57 |
| ATOM | 2526 | CG1 | VAL | 381 | 40.705 | 23.390 | 58.726 | 1.00 | 25.23 |
| ATOM | 2527 | CG2 | VAL | 381 | 40.824 | 23.560 | 56.247 | 1.00 | 25.89 |
| ATOM | 2528 | C | VAL | 381 | 38.185 | 24.577 | 56.090 | 1.00 | 24.82 |
| ATOM | 2529 | O | VAL | 381 | 37.661 | 23.896 | 55.208 | 1.00 | 24.94 |
| ATOM | 2530 | N | VAL | 382 | 38.383 | 25.887 | 55.975 | 1.00 | 23.19 |
| ATOM | 2531 | CA | VAL | 382 | 38.070 | 26.602 | 54.744 | 1.00 | 21.67 |
| ATOM | 2532 | CB | VAL | 382 | 37.674 | 28.073 | 54.999 | 1.00 | 21.80 |
| ATOM | 2533 | CG1 | VAL | 382 | 37.563 | 28.811 | 53.674 | 1.00 | 20.55 |
| ATOM | 2534 | CG2 | VAL | 382 | 36.348 | 28.145 | 55.744 | 1.00 | 21.77 |
| ATOM | 2535 | C | VAL | 382 | 39.401 | 26.582 | 54.006 | 1.00 | 21.54 |
| ATOM | 2536 | O | VAL | 382 | 40.341 | 27.267 | 54.402 | 1.00 | 20.36 |
| ATOM | 2537 | N | CYS | 383 | 39.492 | 25.779 | 52.953 | 1.00 | 21.15 |
| ATOM | 2538 | CA | CYS | 383 | 40.734 | 25.676 | 52.203 | 1.00 | 21.33 |
| ATOM | 2539 | C | CYS | 383 | 41.071 | 26.872 | 51.324 | 1.00 | 20.79 |
| ATOM | 2540 | O | CYS | 383 | 42.241 | 27.238 | 51.206 | 1.00 | 21.41 |
| ATOM | 2541 | CB | CYS | 383 | 40.730 | 24.407 | 51.351 | 1.00 | 21.86 |
| ATOM | 2542 | SG | CYS | 383 | 41.329 | 22.923 | 52.225 | 1.00 | 23.08 |
| ATOM | 2543 | N | HIS | 384 | 40.055 | 27.482 | 50.716 | 1.00 | 19.24 |
| ATOM | 2544 | CA | HIS | 384 | 40.269 | 28.628 | 49.829 | 1.00 | 17.16 |
| ATOM | 2545 | CB | HIS | 384 | 38.957 | 29.376 | 49.584 | 1.00 | 13.14 |
| ATOM | 2546 | CG | HIS | 384 | 39.027 | 30.345 | 48.447 | 1.00 | 13.04 |
| ATOM | 2547 | CD2 | HIS | 384 | 39.476 | 31.621 | 48.390 | 1.00 | 11.87 |
| ATOM | 2548 | ND1 | HIS | 384 | 38.665 | 30.009 | 47.159 | 1.00 | 12.76 |
| ATOM | 2549 | CE1 | HIS | 384 | 38.888 | 31.036 | 46.360 | 1.00 | 14.29 |
| ATOM | 2550 | NE2 | HIS | 384 | 39.381 | 32.028 | 47.081 | 1.00 | 15.54 |
| ATOM | 2551 | C | HIS | 384 | 41.307 | 29.602 | 50.388 | 1.00 | 17.15 |
| ATOM | 2552 | O | HIS | 384 | 41.058 | 30.293 | 51.375 | 1.00 | 18.56 |
| ATOM | 2553 | N | ALA | 385 | 42.465 | 29.653 | 49.738 | 1.00 | 15.37 |
| ATOM | 2554 | CA | ALA | 385 | 43.573 | 30.514 | 50.152 | 1.00 | 15.12 |
| ATOM | 2555 | CB | ALA | 385 | 44.663 | 30.492 | 49.081 | 1.00 | 12.93 |
| ATOM | 2556 | C | ALA | 385 | 43.216 | 31.965 | 50.478 | 1.00 | 13.38 |
| ATOM | 2557 | O | ALA | 385 | 42.495 | 32.626 | 49.733 | 1.00 | 13.27 |
| ATOM | 2558 | N | SER | 386 | 43.739 | 32.456 | 51.596 | 1.00 | 12.79 |
| ATOM | 2559 | CA | SER | 386 | 43.508 | 33.837 | 52.003 | 1.00 | 13.42 |
| ATOM | 2560 | CB | SER | 386 | 42.123 | 33.988 | 52.651 | 1.00 | 12.99 |
| ATOM | 2561 | OG | SER | 386 | 41.970 | 33.130 | 53.765 | 1.00 | 14.28 |
| ATOM | 2562 | C | SER | 386 | 44.602 | 34.324 | 52.954 | 1.00 | 13.14 |

TABLE B-continued

Co-ordinates of an underglycosylated tACEΔ36NJ ACE-lisinopril complex

| ATOM | 2563 | O   | SER | 386 | 45.263 | 33.525 | 53.629 | 1.00 | 12.93 |
|------|------|-----|-----|-----|--------|--------|--------|------|-------|
| ATOM | 2564 | N   | ALA | 387 | 44.800 | 35.640 | 52.979 | 1.00 | 13.15 |
| ATOM | 2565 | CA  | ALA | 387 | 45.803 | 36.280 | 53.825 | 1.00 | 13.29 |
| ATOM | 2566 | CB  | ALA | 387 | 46.653 | 37.239 | 53.003 | 1.00 | 13.06 |
| ATOM | 2567 | C   | ALA | 387 | 45.064 | 37.033 | 54.920 | 1.00 | 14.39 |
| ATOM | 2568 | O   | ALA | 387 | 44.017 | 37.637 | 54.672 | 1.00 | 15.15 |
| ATOM | 2569 | N   | TRP | 388 | 45.621 | 37.014 | 56.124 | 1.00 | 14.45 |
| ATOM | 2570 | CA  | TRP | 388 | 44.981 | 37.641 | 57.272 | 1.00 | 15.44 |
| ATOM | 2571 | CB  | TRP | 388 | 44.559 | 36.547 | 58.263 | 1.00 | 15.81 |
| ATOM | 2572 | CG  | TRP | 388 | 43.575 | 35.556 | 57.707 | 1.00 | 15.75 |
| ATOM | 2573 | CD2 | TRP | 388 | 42.297 | 35.219 | 58.261 | 1.00 | 17.72 |
| ATOM | 2574 | CE2 | TRP | 388 | 41.716 | 34.241 | 57.416 | 1.00 | 17.38 |
| ATOM | 2575 | CE3 | TRP | 388 | 41.584 | 35.649 | 59.391 | 1.00 | 18.07 |
| ATOM | 2576 | CD1 | TRP | 388 | 43.717 | 34.789 | 56.581 | 1.00 | 16.55 |
| ATOM | 2577 | NE1 | TRP | 388 | 42.602 | 33.997 | 56.400 | 1.00 | 15.73 |
| ATOM | 2578 | CZ2 | TRP | 388 | 40.454 | 33.687 | 57.668 | 1.00 | 18.71 |
| ATOM | 2579 | CZ3 | TRP | 388 | 40.327 | 35.095 | 59.642 | 1.00 | 19.40 |
| ATOM | 2580 | CH2 | TRP | 388 | 39.777 | 34.125 | 58.782 | 1.00 | 18.61 |
| ATOM | 2581 | C   | TRP | 388 | 45.805 | 38.692 | 58.014 | 1.00 | 17.06 |
| ATOM | 2582 | O   | TRP | 388 | 46.989 | 38.499 | 58.298 | 1.00 | 17.43 |
| ATOM | 2583 | N   | ASP | 389 | 45.152 | 39.807 | 58.328 | 1.00 | 16.13 |
| ATOM | 2584 | CA  | ASP | 389 | 45.764 | 40.900 | 59.073 | 1.00 | 17.75 |
| ATOM | 2585 | CB  | ASP | 389 | 45.501 | 42.231 | 58.365 | 1.00 | 17.00 |
| ATOM | 2586 | CG  | ASP | 389 | 46.187 | 43.399 | 59.041 | 1.00 | 16.49 |
| ATOM | 2587 | OD1 | ASP | 389 | 46.524 | 43.285 | 60.239 | 1.00 | 18.76 |
| ATOM | 2588 | OD2 | ASP | 389 | 46.382 | 44.436 | 58.376 | 1.00 | 14.01 |
| ATOM | 2589 | C   | ASP | 389 | 45.054 | 40.888 | 60.433 | 1.00 | 19.06 |
| ATOM | 2590 | O   | ASP | 389 | 43.828 | 41.011 | 60.488 | 1.00 | 19.40 |
| ATOM | 2591 | N   | PHE | 390 | 45.805 | 40.726 | 61.520 | 1.00 | 18.93 |
| ATOM | 2592 | CA  | PHE | 390 | 45.189 | 40.686 | 62.846 | 1.00 | 22.25 |
| ATOM | 2593 | CB  | PHE | 390 | 45.850 | 39.603 | 63.709 | 1.00 | 21.51 |
| ATOM | 2594 | CG  | PHE | 390 | 45.477 | 38.208 | 63.294 | 1.00 | 23.36 |
| ATOM | 2595 | CD1 | PHE | 390 | 45.997 | 37.655 | 62.125 | 1.00 | 21.45 |
| ATOM | 2596 | CD2 | PHE | 390 | 44.547 | 37.475 | 64.027 | 1.00 | 22.78 |
| ATOM | 2597 | CE1 | PHE | 390 | 45.595 | 36.395 | 61.687 | 1.00 | 23.06 |
| ATOM | 2598 | CE2 | PHE | 390 | 44.136 | 36.214 | 63.599 | 1.00 | 25.87 |
| ATOM | 2599 | CZ  | PHE | 390 | 44.661 | 35.671 | 62.424 | 1.00 | 24.50 |
| ATOM | 2600 | C   | PHE | 390 | 45.170 | 42.026 | 63.573 | 1.00 | 23.40 |
| ATOM | 2601 | O   | PHE | 390 | 44.937 | 42.096 | 64.785 | 1.00 | 21.79 |
| ATOM | 2602 | N   | TYR | 391 | 45.407 | 43.079 | 62.799 | 1.00 | 24.34 |
| ATOM | 2603 | CA  | TYR | 391 | 45.399 | 44.468 | 63.253 | 1.00 | 26.72 |
| ATOM | 2604 | CB  | TYR | 391 | 43.957 | 44.944 | 63.445 | 1.00 | 29.46 |
| ATOM | 2605 | CG  | TYR | 391 | 43.030 | 44.570 | 62.312 | 1.00 | 32.43 |
| ATOM | 2606 | CD1 | TYR | 391 | 42.389 | 43.336 | 62.297 | 1.00 | 34.89 |
| ATOM | 2607 | CE1 | TYR | 391 | 41.537 | 42.978 | 61.262 | 1.00 | 37.09 |
| ATOM | 2608 | CD2 | TYR | 391 | 42.801 | 45.445 | 61.252 | 1.00 | 35.38 |
| ATOM | 2609 | CE2 | TYR | 391 | 41.951 | 45.095 | 60.204 | 1.00 | 37.31 |
| ATOM | 2610 | CZ  | TYR | 391 | 41.321 | 43.860 | 60.221 | 1.00 | 37.51 |
| ATOM | 2611 | OH  | TYR | 391 | 40.457 | 43.505 | 59.212 | 1.00 | 41.58 |
| ATOM | 2612 | C   | TYR | 391 | 46.205 | 44.861 | 64.487 | 1.00 | 25.67 |
| ATOM | 2613 | O   | TYR | 391 | 45.776 | 45.725 | 65.247 | 1.00 | 27.20 |
| ATOM | 2614 | N   | ASN | 392 | 47.360 | 44.243 | 64.696 | 1.00 | 24.64 |
| ATOM | 2615 | CA  | ASN | 392 | 48.200 | 44.613 | 65.829 | 1.00 | 24.09 |
| ATOM | 2616 | CB  | ASN | 392 | 48.261 | 43.492 | 66.881 | 1.00 | 23.53 |
| ATOM | 2617 | CG  | ASN | 392 | 48.960 | 42.241 | 66.380 | 1.00 | 22.41 |
| ATOM | 2618 | OD1 | ASN | 392 | 49.428 | 42.181 | 65.247 | 1.00 | 21.54 |
| ATOM | 2619 | ND2 | ASN | 392 | 49.032 | 41.229 | 67.236 | 1.00 | 23.26 |
| ATOM | 2620 | C   | ASN | 392 | 49.592 | 44.930 | 65.295 | 1.00 | 24.22 |
| ATOM | 2621 | O   | ASN | 392 | 50.548 | 45.073 | 66.055 | 1.00 | 23.88 |
| ATOM | 2622 | N   | GLY | 393 | 49.679 | 45.040 | 63.969 | 1.00 | 22.80 |
| ATOM | 2623 | CA  | GLY | 393 | 50.934 | 45.353 | 63.311 | 1.00 | 20.67 |
| ATOM | 2624 | C   | GLY | 393 | 52.025 | 44.319 | 63.515 | 1.00 | 21.15 |
| ATOM | 2625 | O   | GLY | 393 | 53.178 | 44.560 | 63.170 | 1.00 | 20.78 |
| ATOM | 2626 | N   | LYS | 394 | 51.666 | 43.156 | 64.048 | 1.00 | 20.82 |
| ATOM | 2627 | CA  | LYS | 394 | 52.657 | 42.118 | 64.308 | 1.00 | 22.60 |
| ATOM | 2628 | CB  | LYS | 394 | 52.909 | 42.024 | 65.818 | 1.00 | 24.94 |
| ATOM | 2629 | CG  | LYS | 394 | 54.363 | 42.153 | 66.216 | 1.00 | 30.63 |
| ATOM | 2630 | CD  | LYS | 394 | 54.916 | 43.524 | 65.854 | 1.00 | 33.49 |
| ATOM | 2631 | CE  | LYS | 394 | 54.355 | 44.606 | 66.757 | 1.00 | 35.47 |
| ATOM | 2632 | NZ  | LYS | 394 | 54.708 | 44.359 | 68.185 | 1.00 | 37.56 |
| ATOM | 2633 | C   | LYS | 394 | 52.253 | 40.745 | 63.789 | 1.00 | 21.67 |
| ATOM | 2634 | O   | LYS | 394 | 53.079 | 40.001 | 63.261 | 1.00 | 22.03 |
| ATOM | 2635 | N   | ASP | 395 | 50.973 | 40.427 | 63.940 | 1.00 | 21.32 |
| ATOM | 2636 | CA  | ASP | 395 | 50.425 | 39.134 | 63.553 | 1.00 | 20.91 |
| ATOM | 2637 | CB  | ASP | 395 | 49.440 | 38.689 | 64.642 | 1.00 | 19.12 |
| ATOM | 2638 | CG  | ASP | 395 | 49.053 | 37.227 | 64.534 | 1.00 | 19.78 |
| ATOM | 2639 | OD1 | ASP | 395 | 49.344 | 36.589 | 63.501 | 1.00 | 20.54 |
| ATOM | 2640 | OD2 | ASP | 395 | 48.438 | 36.715 | 65.495 | 1.00 | 21.66 |

TABLE B-continued

Co-ordinates of an underglycosylated tACEΔ36NJ ACE-lisinopril complex

| ATOM | 2641 | C | ASP | 395 | 49.737 | 39.110 | 62.178 | 1.00 | 21.80 |
|------|------|------|-----|-----|--------|--------|--------|------|-------|
| ATOM | 2642 | O | ASP | 395 | 48.651 | 39.670 | 62.001 | 1.00 | 20.60 |
| ATOM | 2643 | N | PHE | 396 | 50.378 | 38.454 | 61.213 | 1.00 | 20.77 |
| ATOM | 2644 | CA | PHE | 396 | 49.830 | 38.312 | 59.863 | 1.00 | 20.20 |
| ATOM | 2645 | CB | PHE | 396 | 50.634 | 39.132 | 58.849 | 1.00 | 19.48 |
| ATOM | 2646 | CG | PHE | 396 | 51.005 | 40.501 | 59.330 | 1.00 | 19.47 |
| ATOM | 2647 | CD1 | PHE | 396 | 52.212 | 40.715 | 59.987 | 1.00 | 18.23 |
| ATOM | 2648 | CD2 | PHE | 396 | 50.149 | 41.580 | 59.127 | 1.00 | 19.80 |
| ATOM | 2649 | CE1 | PHE | 396 | 52.564 | 41.989 | 60.436 | 1.00 | 16.62 |
| ATOM | 2650 | CE2 | PHE | 396 | 50.492 | 42.855 | 59.572 | 1.00 | 18.16 |
| ATOM | 2651 | CZ | PHE | 396 | 51.703 | 43.059 | 60.228 | 1.00 | 18.20 |
| ATOM | 2652 | C | PHE | 396 | 49.945 | 36.832 | 59.514 | 1.00 | 19.88 |
| ATOM | 2653 | O | PHE | 396 | 50.942 | 36.193 | 59.847 | 1.00 | 22.26 |
| ATOM | 2654 | N | ARG | 397 | 48.945 | 36.281 | 58.840 | 1.00 | 19.00 |
| ATOM | 2655 | CA | ARG | 397 | 48.989 | 34.864 | 58.502 | 1.00 | 18.47 |
| ATOM | 2656 | CB | ARG | 397 | 48.286 | 34.037 | 59.579 | 1.00 | 19.59 |
| ATOM | 2657 | CG | ARG | 397 | 48.542 | 34.466 | 61.009 | 1.00 | 19.93 |
| ATOM | 2658 | CD | ARG | 397 | 47.667 | 33.642 | 61.944 | 1.00 | 20.65 |
| ATOM | 2659 | NE | ARG | 397 | 47.588 | 34.223 | 63.280 | 1.00 | 23.90 |
| ATOM | 2660 | CZ | ARG | 397 | 46.806 | 33.759 | 64.250 | 1.00 | 24.44 |
| ATOM | 2661 | NH1 | ARG | 397 | 46.033 | 32.702 | 64.033 | 1.00 | 25.15 |
| ATOM | 2662 | NH2 | ARG | 397 | 46.792 | 34.358 | 65.434 | 1.00 | 25.23 |
| ATOM | 2663 | C | ARG | 397 | 48.327 | 34.526 | 57.179 | 1.00 | 18.41 |
| ATOM | 2664 | O | ARG | 397 | 47.504 | 35.279 | 56.661 | 1.00 | 16.23 |
| ATOM | 2665 | N | ILE | 398 | 48.683 | 33.359 | 56.653 | 1.00 | 17.80 |
| ATOM | 2666 | CA | ILE | 398 | 48.098 | 32.867 | 55.419 | 1.00 | 17.44 |
| ATOM | 2667 | CB | ILE | 398 | 49.172 | 32.720 | 54.310 | 1.00 | 17.61 |
| ATOM | 2668 | CG2 | ILE | 398 | 48.685 | 31.774 | 53.217 | 1.00 | 18.45 |
| ATOM | 2669 | CG1 | ILE | 398 | 49.498 | 34.107 | 53.734 | 1.00 | 16.21 |
| ATOM | 2670 | CD1 | ILE | 398 | 50.554 | 34.110 | 52.628 | 1.00 | 14.34 |
| ATOM | 2671 | C | ILE | 398 | 47.437 | 31.524 | 55.724 | 1.00 | 17.31 |
| ATOM | 2672 | O | ILE | 398 | 47.964 | 30.723 | 56.502 | 1.00 | 17.20 |
| ATOM | 2673 | N | LYS | 399 | 46.260 | 31.310 | 55.145 | 1.00 | 16.54 |
| ATOM | 2674 | CA | LYS | 399 | 45.506 | 30.074 | 55.326 | 1.00 | 17.03 |
| ATOM | 2675 | CB | LYS | 399 | 44.152 | 30.355 | 55.984 | 1.00 | 16.41 |
| ATOM | 2676 | CG | LYS | 399 | 43.323 | 29.102 | 56.237 | 1.00 | 16.93 |
| ATOM | 2677 | CD | LYS | 399 | 41.871 | 29.433 | 56.562 | 1.00 | 18.85 |
| ATOM | 2678 | CE | LYS | 399 | 41.218 | 30.234 | 55.439 | 1.00 | 19.45 |
| ATOM | 2679 | NZ | LYS | 399 | 41.423 | 29.599 | 54.106 | 1.00 | 18.46 |
| ATOM | 2680 | C | LYS | 399 | 45.294 | 29.498 | 53.934 | 1.00 | 18.35 |
| ATOM | 2681 | O | LYS | 399 | 44.492 | 30.013 | 53.149 | 1.00 | 17.47 |
| ATOM | 2682 | N | GLN | 400 | 46.010 | 28.421 | 53.633 | 1.00 | 18.80 |
| ATOM | 2683 | CA | GLN | 400 | 45.936 | 27.809 | 52.316 | 1.00 | 17.16 |
| ATOM | 2684 | CB | GLN | 400 | 46.963 | 28.505 | 51.413 | 1.00 | 16.79 |
| ATOM | 2685 | CG | GLN | 400 | 46.952 | 28.124 | 49.946 | 1.00 | 19.01 |
| ATOM | 2686 | CD | GLN | 400 | 47.967 | 28.933 | 49.144 | 1.00 | 19.64 |
| ATOM | 2687 | OE1 | GLN | 400 | 48.171 | 30.118 | 49.401 | 1.00 | 19.74 |
| ATOM | 2688 | NE2 | GLN | 400 | 48.598 | 28.296 | 48.163 | 1.00 | 21.63 |
| ATOM | 2689 | C | GLN | 400 | 46.236 | 26.313 | 52.382 | 1.00 | 17.92 |
| ATOM | 2690 | O | GLN | 400 | 47.236 | 25.909 | 52.966 | 1.00 | 16.80 |
| ATOM | 2691 | N | CYS | 401 | 45.363 | 25.495 | 51.805 | 1.00 | 19.15 |
| ATOM | 2692 | CA | CYS | 401 | 45.602 | 24.055 | 51.771 | 1.00 | 21.48 |
| ATOM | 2693 | C | CYS | 401 | 46.472 | 23.902 | 50.528 | 1.00 | 21.39 |
| ATOM | 2694 | O | CYS | 401 | 46.039 | 23.417 | 49.485 | 1.00 | 23.39 |
| ATOM | 2695 | CB | CYS | 401 | 44.288 | 23.278 | 51.619 | 1.00 | 20.09 |
| ATOM | 2696 | SG | CYS | 401 | 43.111 | 23.526 | 52.994 | 1.00 | 23.70 |
| ATOM | 2697 | N | THR | 402 | 47.706 | 24.363 | 50.663 | 1.00 | 21.55 |
| ATOM | 2698 | CA | THR | 402 | 48.681 | 24.362 | 49.591 | 1.00 | 21.97 |
| ATOM | 2699 | CB | THR | 402 | 50.022 | 24.915 | 50.096 | 1.00 | 21.86 |
| ATOM | 2700 | OG1 | THR | 402 | 49.800 | 26.175 | 50.744 | 1.00 | 20.74 |
| ATOM | 2701 | CG2 | THR | 402 | 50.995 | 25.103 | 48.936 | 1.00 | 20.95 |
| ATOM | 2702 | C | THR | 402 | 48.941 | 23.017 | 48.936 | 1.00 | 24.16 |
| ATOM | 2703 | O | THR | 402 | 49.112 | 21.999 | 49.612 | 1.00 | 24.28 |
| ATOM | 2704 | N | THR | 403 | 48.965 | 23.036 | 47.608 | 1.00 | 23.67 |
| ATOM | 2705 | CA | THR | 403 | 49.249 | 21.859 | 46.802 | 1.00 | 23.28 |
| ATOM | 2706 | CB | THR | 403 | 48.158 | 21.620 | 45.739 | 1.00 | 24.61 |
| ATOM | 2707 | OG1 | THR | 403 | 46.922 | 21.312 | 46.390 | 1.00 | 25.63 |
| ATOM | 2708 | CG2 | THR | 403 | 48.541 | 20.458 | 44.830 | 1.00 | 26.73 |
| ATOM | 2709 | C | THR | 403 | 50.571 | 22.162 | 46.108 | 1.00 | 23.10 |
| ATOM | 2710 | O | THR | 403 | 50.816 | 23.296 | 45.692 | 1.00 | 22.88 |
| ATOM | 2711 | N | VAL | 404 | 51.428 | 21.157 | 45.986 | 1.00 | 23.09 |
| ATOM | 2712 | CA | VAL | 404 | 52.724 | 21.359 | 45.359 | 1.00 | 23.31 |
| ATOM | 2713 | CB | VAL | 404 | 53.762 | 20.342 | 45.887 | 1.00 | 23.84 |
| ATOM | 2714 | CG1 | VAL | 404 | 55.115 | 20.589 | 45.241 | 1.00 | 23.34 |
| ATOM | 2715 | CG2 | VAL | 404 | 53.870 | 20.457 | 47.395 | 1.00 | 22.82 |
| ATOM | 2716 | C | VAL | 404 | 52.691 | 21.293 | 43.834 | 1.00 | 23.74 |
| ATOM | 2717 | O | VAL | 404 | 52.808 | 20.218 | 43.241 | 1.00 | 23.48 |
| ATOM | 2718 | N | ASN | 405 | 52.517 | 22.457 | 43.215 | 1.00 | 22.93 |

TABLE B-continued

Co-ordinates of an underglycosylated tACEΔ36NJ ACE-lisinopril complex

| ATOM | 2719 | CA | ASN | 405 | 52.500 | 22.602 | 41.762 | 1.00 | 22.84 |
|---|---|---|---|---|---|---|---|---|---|
| ATOM | 2720 | CB | ASN | 405 | 51.186 | 22.099 | 41.154 | 1.00 | 22.95 |
| ATOM | 2721 | CG | ASN | 405 | 49.970 | 22.816 | 41.702 | 1.00 | 24.71 |
| ATOM | 2722 | OD1 | ASN | 405 | 49.970 | 24.036 | 41.861 | 1.00 | 24.62 |
| ATOM | 2723 | ND2 | ASN | 405 | 48.915 | 22.058 | 41.981 | 1.00 | 24.60 |
| ATOM | 2724 | C | ASN | 405 | 52.705 | 24.078 | 41.423 | 1.00 | 22.93 |
| ATOM | 2725 | O | ASN | 405 | 52.654 | 24.938 | 42.306 | 1.00 | 19.22 |
| ATOM | 2726 | N | LEU | 406 | 52.932 | 24.368 | 40.147 | 1.00 | 23.26 |
| ATOM | 2727 | CA | LEU | 406 | 53.173 | 25.738 | 39.709 | 1.00 | 24.41 |
| ATOM | 2728 | CB | LEU | 406 | 53.514 | 25.762 | 38.214 | 1.00 | 26.22 |
| ATOM | 2729 | CG | LEU | 406 | 54.513 | 26.821 | 37.724 | 1.00 | 29.20 |
| ATOM | 2730 | CD1 | LEU | 406 | 54.502 | 26.848 | 36.196 | 1.00 | 27.25 |
| ATOM | 2731 | CD2 | LEU | 406 | 54.162 | 28.194 | 38.271 | 1.00 | 30.58 |
| ATOM | 2732 | C | LEU | 406 | 51.984 | 26.664 | 39.971 | 1.00 | 24.64 |
| ATOM | 2733 | O | LEU | 406 | 52.162 | 27.808 | 40.393 | 1.00 | 23.62 |
| ATOM | 2734 | N | GLU | 407 | 50.774 | 26.171 | 39.726 | 1.00 | 24.14 |
| ATOM | 2735 | CA | GLU | 407 | 49.584 | 26.987 | 39.927 | 1.00 | 24.63 |
| ATOM | 2736 | CB | GLU | 407 | 48.324 | 26.185 | 39.589 | 1.00 | 26.59 |
| ATOM | 2737 | CG | GLU | 407 | 47.126 | 27.059 | 39.257 | 1.00 | 30.80 |
| ATOM | 2738 | CD | GLU | 407 | 45.917 | 26.266 | 38.798 | 1.00 | 33.25 |
| ATOM | 2739 | OE1 | GLU | 407 | 46.094 | 25.139 | 38.293 | 1.00 | 33.52 |
| ATOM | 2740 | OE2 | GLU | 407 | 44.787 | 26.780 | 38.927 | 1.00 | 35.96 |
| ATOM | 2741 | C | GLU | 407 | 49.499 | 27.525 | 41.357 | 1.00 | 23.70 |
| ATOM | 2742 | O | GLU | 407 | 49.194 | 28.697 | 41.566 | 1.00 | 23.73 |
| ATOM | 2743 | N | ASP | 408 | 49.775 | 26.675 | 42.340 | 1.00 | 21.73 |
| ATOM | 2744 | CA | ASP | 408 | 49.717 | 27.107 | 43.731 | 1.00 | 21.63 |
| ATOM | 2745 | CB | ASP | 408 | 49.541 | 25.899 | 44.653 | 1.00 | 23.21 |
| ATOM | 2746 | CG | ASP | 408 | 48.247 | 25.958 | 45.438 | 1.00 | 23.22 |
| ATOM | 2747 | OD1 | ASP | 408 | 47.301 | 26.620 | 44.963 | 1.00 | 25.47 |
| ATOM | 2748 | OD2 | ASP | 408 | 48.166 | 25.340 | 46.519 | 1.00 | 25.23 |
| ATOM | 2749 | C | ASP | 408 | 50.944 | 27.926 | 44.138 | 1.00 | 20.39 |
| ATOM | 2750 | O | ASP | 408 | 50.922 | 28.635 | 45.146 | 1.00 | 19.37 |
| ATOM | 2751 | N | LEU | 409 | 52.016 | 27.831 | 43.360 | 1.00 | 18.98 |
| ATOM | 2752 | CA | LEU | 409 | 53.209 | 28.611 | 43.659 | 1.00 | 18.41 |
| ATOM | 2753 | CB | LEU | 409 | 54.383 | 28.173 | 42.780 | 1.00 | 20.25 |
| ATOM | 2754 | CG | LEU | 409 | 55.692 | 28.941 | 43.001 | 1.00 | 20.55 |
| ATOM | 2755 | CD1 | LEU | 409 | 56.113 | 28.815 | 44.447 | 1.00 | 21.00 |
| ATOM | 2756 | CD2 | LEU | 409 | 56.778 | 28.404 | 42.083 | 1.00 | 22.20 |
| ATOM | 2757 | C | LEU | 409 | 52.849 | 30.067 | 43.362 | 1.00 | 17.90 |
| ATOM | 2758 | O | LEU | 409 | 53.274 | 30.987 | 44.062 | 1.00 | 16.65 |
| ATOM | 2759 | N | VAL | 410 | 52.057 | 30.266 | 42.313 | 1.00 | 16.80 |
| ATOM | 2760 | CA | VAL | 410 | 51.618 | 31.605 | 41.943 | 1.00 | 16.49 |
| ATOM | 2761 | CB | VAL | 410 | 50.920 | 31.600 | 40.561 | 1.00 | 16.89 |
| ATOM | 2762 | CG1 | VAL | 410 | 50.352 | 32.977 | 40.247 | 1.00 | 14.92 |
| ATOM | 2763 | CG2 | VAL | 410 | 51.919 | 31.198 | 39.491 | 1.00 | 15.83 |
| ATOM | 2764 | C | VAL | 410 | 50.656 | 32.106 | 43.024 | 1.00 | 15.73 |
| ATOM | 2765 | O | VAL | 410 | 50.732 | 33.258 | 43.443 | 1.00 | 14.75 |
| ATOM | 2766 | N | VAL | 411 | 49.763 | 31.232 | 43.484 | 1.00 | 15.97 |
| ATOM | 2767 | CA | VAL | 411 | 48.813 | 31.603 | 44.533 | 1.00 | 15.75 |
| ATOM | 2768 | CB | VAL | 411 | 47.870 | 30.425 | 44.902 | 1.00 | 15.53 |
| ATOM | 2769 | CG1 | VAL | 411 | 47.006 | 30.805 | 46.114 | 1.00 | 11.21 |
| ATOM | 2770 | CG2 | VAL | 411 | 46.982 | 30.070 | 43.711 | 1.00 | 14.36 |
| ATOM | 2771 | C | VAL | 411 | 49.561 | 32.034 | 45.796 | 1.00 | 16.60 |
| ATOM | 2772 | O | VAL | 411 | 49.194 | 33.015 | 46.445 | 1.00 | 14.95 |
| ATOM | 2773 | N | ALA | 412 | 50.610 | 31.296 | 46.146 | 1.00 | 16.80 |
| ATOM | 2774 | CA | ALA | 412 | 51.392 | 31.624 | 47.328 | 1.00 | 16.33 |
| ATOM | 2775 | CB | ALA | 412 | 52.541 | 30.632 | 47.490 | 1.00 | 17.31 |
| ATOM | 2776 | C | ALA | 412 | 51.930 | 33.047 | 47.213 | 1.00 | 16.81 |
| ATOM | 2777 | O | ALA | 412 | 51.940 | 33.793 | 48.188 | 1.00 | 15.68 |
| ATOM | 2778 | N | HIS | 413 | 52.386 | 33.419 | 46.018 | 1.00 | 16.29 |
| ATOM | 2779 | CA | HIS | 413 | 52.908 | 34.764 | 45.802 | 1.00 | 14.95 |
| ATOM | 2780 | CB | HIS | 413 | 53.576 | 34.886 | 44.425 | 1.00 | 14.73 |
| ATOM | 2781 | CG | HIS | 413 | 54.942 | 34.282 | 44.362 | 1.00 | 14.13 |
| ATOM | 2782 | CD2 | HIS | 413 | 56.169 | 34.855 | 44.354 | 1.00 | 14.28 |
| ATOM | 2783 | ND1 | HIS | 413 | 55.155 | 32.920 | 44.333 | 1.00 | 13.46 |
| ATOM | 2784 | CE1 | HIS | 413 | 56.454 | 32.681 | 44.310 | 1.00 | 14.23 |
| ATOM | 2785 | NE2 | HIS | 413 | 57.091 | 33.837 | 44.322 | 1.00 | 15.75 |
| ATOM | 2786 | C | HIS | 413 | 51.768 | 35.765 | 45.910 | 1.00 | 13.28 |
| ATOM | 2787 | O | HIS | 413 | 51.923 | 36.834 | 46.493 | 1.00 | 11.46 |
| ATOM | 2788 | N | HIS | 414 | 50.620 | 35.409 | 45.342 | 1.00 | 14.51 |
| ATOM | 2789 | CA | HIS | 414 | 49.447 | 36.276 | 45.391 | 1.00 | 13.47 |
| ATOM | 2790 | CB | HIS | 414 | 48.235 | 35.570 | 44.775 | 1.00 | 15.00 |
| ATOM | 2791 | CG | HIS | 414 | 46.971 | 36.370 | 44.849 | 1.00 | 15.40 |
| ATOM | 2792 | CD2 | HIS | 414 | 45.972 | 36.376 | 45.766 | 1.00 | 13.24 |
| ATOM | 2793 | ND1 | HIS | 414 | 46.647 | 37.339 | 43.923 | 1.00 | 14.33 |
| ATOM | 2794 | CE1 | HIS | 414 | 45.504 | 37.908 | 44.267 | 1.00 | 14.69 |
| ATOM | 2795 | NE2 | HIS | 414 | 45.075 | 37.341 | 45.381 | 1.00 | 12.08 |
| ATOM | 2796 | C | HIS | 414 | 49.136 | 36.626 | 46.845 | 1.00 | 14.00 |

TABLE B-continued

Co-ordinates of an underglycosylated tACEΔ36NJ ACE-lisinopril complex

| ATOM | 2797 | O   | HIS | 414 | 48.984 | 37.802 | 47.190 | 1.00 | 13.07 |
|------|------|-----|-----|-----|--------|--------|--------|------|-------|
| ATOM | 2798 | N   | GLU | 415 | 49.049 | 35.599 | 47.690 | 1.00 | 12.38 |
| ATOM | 2799 | CA  | GLU | 415 | 48.742 | 35.788 | 49.105 | 1.00 | 13.04 |
| ATOM | 2800 | CB  | GLU | 415 | 48.489 | 34.440 | 49.782 | 1.00 | 11.80 |
| ATOM | 2801 | CG  | GLU | 415 | 47.322 | 33.650 | 49.205 | 1.00 | 12.84 |
| ATOM | 2802 | CD  | GLU | 415 | 46.014 | 34.422 | 49.240 | 1.00 | 12.28 |
| ATOM | 2803 | OE1 | GLU | 415 | 45.833 | 35.250 | 50.159 | 1.00 | 11.52 |
| ATOM | 2804 | OE2 | GLU | 415 | 45.159 | 34.188 | 48.359 | 1.00 | 12.50 |
| ATOM | 2805 | C   | GLU | 415 | 49.839 | 36.535 | 49.850 | 1.00 | 13.54 |
| ATOM | 2806 | O   | GLU | 415 | 49.551 | 37.346 | 50.726 | 1.00 | 14.84 |
| ATOM | 2807 | N   | MET | 416 | 51.096 | 36.258 | 49.512 | 1.00 | 13.52 |
| ATOM | 2808 | CA  | MET | 416 | 52.208 | 36.941 | 50.167 | 1.00 | 14.41 |
| ATOM | 2809 | CB  | MET | 416 | 53.542 | 36.304 | 49.767 | 1.00 | 14.35 |
| ATOM | 2810 | CG  | MET | 416 | 53.786 | 34.943 | 50.429 | 1.00 | 15.99 |
| ATOM | 2811 | SD  | MET | 416 | 54.132 | 35.070 | 52.218 | 1.00 | 17.59 |
| ATOM | 2812 | CE  | MET | 416 | 55.885 | 35.543 | 52.156 | 1.00 | 14.94 |
| ATOM | 2813 | C   | MET | 416 | 52.176 | 38.424 | 49.796 | 1.00 | 13.49 |
| ATOM | 2814 | O   | MET | 416 | 52.660 | 39.276 | 50.543 | 1.00 | 11.88 |
| ATOM | 2815 | N   | GLY | 417 | 51.592 | 38.725 | 48.642 | 1.00 | 13.47 |
| ATOM | 2816 | CA  | GLY | 417 | 51.473 | 40.107 | 48.217 | 1.00 | 11.88 |
| ATOM | 2817 | C   | GLY | 417 | 50.547 | 40.833 | 49.186 | 1.00 | 10.84 |
| ATOM | 2818 | O   | GLY | 417 | 50.774 | 41.995 | 49.517 | 1.00 | 10.89 |
| ATOM | 2819 | N   | HIS | 418 | 49.499 | 40.146 | 49.639 | 1.00 | 11.02 |
| ATOM | 2820 | CA  | HIS | 418 | 48.555 | 40.732 | 50.595 | 1.00 | 12.04 |
| ATOM | 2821 | CB  | HIS | 418 | 47.382 | 39.784 | 50.864 | 1.00 | 11.04 |
| ATOM | 2822 | CG  | HIS | 418 | 46.385 | 39.711 | 49.752 | 1.00 | 12.59 |
| ATOM | 2823 | CD2 | HIS | 418 | 45.842 | 38.648 | 49.112 | 1.00 | 9.69  |
| ATOM | 2824 | ND1 | HIS | 418 | 45.783 | 40.830 | 49.214 | 1.00 | 13.07 |
| ATOM | 2825 | CE1 | HIS | 418 | 44.912 | 40.458 | 48.294 | 1.00 | 11.52 |
| ATOM | 2826 | NE2 | HIS | 418 | 44.928 | 39.140 | 48.213 | 1.00 | 12.75 |
| ATOM | 2827 | C   | HIS | 418 | 49.271 | 41.003 | 51.916 | 1.00 | 11.39 |
| ATOM | 2828 | O   | HIS | 418 | 49.122 | 42.071 | 52.512 | 1.00 | 11.43 |
| ATOM | 2829 | N   | ILE | 419 | 50.039 | 40.018 | 52.373 | 1.00 | 11.02 |
| ATOM | 2830 | CA  | ILE | 419 | 50.788 | 40.147 | 53.619 | 1.00 | 11.33 |
| ATOM | 2831 | CB  | ILE | 419 | 51.613 | 38.874 | 53.905 | 1.00 | 12.82 |
| ATOM | 2832 | CG2 | ILE | 419 | 52.405 | 39.042 | 55.195 | 1.00 | 12.45 |
| ATOM | 2833 | CG1 | ILE | 419 | 50.681 | 37.658 | 53.991 | 1.00 | 12.12 |
| ATOM | 2834 | CD1 | ILE | 419 | 49.672 | 37.730 | 55.117 | 1.00 | 14.37 |
| ATOM | 2835 | C   | ILE | 419 | 51.738 | 41.343 | 53.548 | 1.00 | 11.48 |
| ATOM | 2836 | O   | ILE | 419 | 51.853 | 42.113 | 54.500 | 1.00 | 12.38 |
| ATOM | 2837 | N   | GLN | 420 | 52.417 | 41.496 | 52.417 | 1.00 | 11.52 |
| ATOM | 2838 | CA  | GLN | 420 | 53.347 | 42.607 | 52.245 | 1.00 | 13.30 |
| ATOM | 2839 | CB  | GLN | 420 | 54.004 | 42.544 | 50.859 | 1.00 | 12.77 |
| ATOM | 2840 | CG  | GLN | 420 | 55.044 | 43.636 | 50.636 | 1.00 | 14.92 |
| ATOM | 2841 | CD  | GLN | 420 | 56.256 | 43.491 | 51.546 | 1.00 | 14.49 |
| ATOM | 2842 | OE1 | GLN | 420 | 56.897 | 44.479 | 51.904 | 1.00 | 17.00 |
| ATOM | 2843 | NE2 | GLN | 420 | 56.585 | 42.255 | 51.908 | 1.00 | 14.95 |
| ATOM | 2844 | C   | GLN | 420 | 52.599 | 43.932 | 52.412 | 1.00 | 13.79 |
| ATOM | 2845 | O   | GLN | 420 | 53.065 | 44.844 | 53.101 | 1.00 | 14.70 |
| ATOM | 2846 | N   | TYR | 421 | 51.435 | 44.035 | 51.780 | 1.00 | 13.96 |
| ATOM | 2847 | CA  | TYR | 421 | 50.631 | 45.246 | 51.876 | 1.00 | 13.60 |
| ATOM | 2848 | CB  | TYR | 421 | 49.372 | 45.099 | 51.014 | 1.00 | 10.92 |
| ATOM | 2849 | CG  | TYR | 421 | 49.037 | 46.321 | 50.179 | 1.00 | 11.34 |
| ATOM | 2850 | CD1 | TYR | 421 | 48.590 | 46.183 | 48.862 | 1.00 | 10.38 |
| ATOM | 2851 | CE1 | TYR | 421 | 48.255 | 47.287 | 48.093 | 1.00 | 8.53  |
| ATOM | 2852 | CD2 | TYR | 421 | 49.140 | 47.611 | 50.706 | 1.00 | 10.33 |
| ATOM | 2853 | CE2 | TYR | 421 | 48.799 | 48.737 | 49.940 | 1.00 | 11.19 |
| ATOM | 2854 | CZ  | TYR | 421 | 48.356 | 48.561 | 48.634 | 1.00 | 12.22 |
| ATOM | 2855 | OH  | TYR | 421 | 47.985 | 49.647 | 47.872 | 1.00 | 10.08 |
| ATOM | 2856 | C   | TYR | 421 | 50.259 | 45.499 | 53.348 | 1.00 | 13.85 |
| ATOM | 2857 | O   | TYR | 421 | 50.371 | 46.626 | 53.835 | 1.00 | 12.91 |
| ATOM | 2858 | N   | PHE | 422 | 49.823 | 44.451 | 54.049 | 1.00 | 15.40 |
| ATOM | 2859 | CA  | PHE | 422 | 49.461 | 44.567 | 55.466 | 1.00 | 17.19 |
| ATOM | 2860 | CB  | PHE | 422 | 49.173 | 43.189 | 56.076 | 1.00 | 15.34 |
| ATOM | 2861 | CG  | PHE | 422 | 47.925 | 42.526 | 55.559 | 1.00 | 15.78 |
| ATOM | 2862 | CD1 | PHE | 422 | 47.776 | 41.143 | 55.655 | 1.00 | 14.31 |
| ATOM | 2863 | CD2 | PHE | 422 | 46.896 | 43.272 | 54.994 | 1.00 | 14.76 |
| ATOM | 2864 | CE1 | PHE | 422 | 46.621 | 40.510 | 55.197 | 1.00 | 16.76 |
| ATOM | 2865 | CE2 | PHE | 422 | 45.734 | 42.649 | 54.532 | 1.00 | 16.42 |
| ATOM | 2866 | CZ  | PHE | 422 | 45.599 | 41.265 | 54.633 | 1.00 | 16.96 |
| ATOM | 2867 | C   | PHE | 422 | 50.611 | 45.185 | 56.254 | 1.00 | 17.06 |
| ATOM | 2868 | O   | PHE | 422 | 50.412 | 46.105 | 57.045 | 1.00 | 17.66 |
| ATOM | 2869 | N   | MET | 423 | 51.814 | 44.664 | 56.031 | 1.00 | 16.17 |
| ATOM | 2870 | CA  | MET | 423 | 53.000 | 45.134 | 56.737 | 1.00 | 17.00 |
| ATOM | 2871 | CB  | MET | 423 | 54.181 | 44.190 | 56.486 | 1.00 | 18.15 |
| ATOM | 2872 | CG  | MET | 423 | 53.943 | 42.754 | 56.931 | 1.00 | 19.99 |
| ATOM | 2873 | SD  | MET | 423 | 55.472 | 41.792 | 57.000 | 1.00 | 20.03 |
| ATOM | 2874 | CE  | MET | 423 | 55.783 | 41.471 | 55.247 | 1.00 | 18.10 |

TABLE B-continued

Co-ordinates of an underglycosylated tACEΔ36NJ ACE-lisinopril complex

| ATOM | 2875 | C   | MET | 423 | 53.413 | 46.552 | 56.373 | 1.00 | 17.22 |
|------|------|-----|-----|-----|--------|--------|--------|------|-------|
| ATOM | 2876 | O   | MET | 423 | 53.849 | 47.315 | 57.236 | 1.00 | 16.52 |
| ATOM | 2877 | N   | GLN | 424 | 53.277 | 46.905 | 55.097 | 1.00 | 16.46 |
| ATOM | 2878 | CA  | GLN | 424 | 53.659 | 48.234 | 54.631 | 1.00 | 15.32 |
| ATOM | 2879 | CB  | GLN | 424 | 53.579 | 48.301 | 53.102 | 1.00 | 16.47 |
| ATOM | 2880 | CG  | GLN | 424 | 54.640 | 47.495 | 52.360 | 1.00 | 17.02 |
| ATOM | 2881 | CD  | GLN | 424 | 56.031 | 48.092 | 52.496 | 1.00 | 19.21 |
| ATOM | 2882 | OE1 | GLN | 424 | 56.184 | 49.288 | 52.757 | 1.00 | 16.73 |
| ATOM | 2883 | NE2 | GLN | 424 | 57.053 | 47.266 | 52.297 | 1.00 | 17.82 |
| ATOM | 2884 | C   | GLN | 424 | 52.836 | 49.377 | 55.224 | 1.00 | 15.29 |
| ATOM | 2885 | O   | GLN | 424 | 53.372 | 50.455 | 55.482 | 1.00 | 15.54 |
| ATOM | 2886 | N   | TYR | 425 | 51.539 | 49.157 | 55.433 | 1.00 | 15.59 |
| ATOM | 2887 | CA  | TYR | 425 | 50.687 | 50.213 | 55.980 | 1.00 | 15.62 |
| ATOM | 2888 | CB  | TYR | 425 | 49.454 | 50.432 | 55.078 | 1.00 | 14.74 |
| ATOM | 2889 | CG  | TYR | 425 | 48.519 | 49.240 | 54.865 | 1.00 | 14.73 |
| ATOM | 2890 | CD1 | TYR | 425 | 48.073 | 48.457 | 55.935 | 1.00 | 11.96 |
| ATOM | 2891 | CE1 | TYR | 425 | 47.115 | 47.446 | 55.750 | 1.00 | 13.33 |
| ATOM | 2892 | CD2 | TYR | 425 | 47.990 | 48.972 | 53.597 | 1.00 | 14.45 |
| ATOM | 2893 | CE2 | TYR | 425 | 47.033 | 47.969 | 53.401 | 1.00 | 14.29 |
| ATOM | 2894 | CZ  | TYR | 425 | 46.599 | 47.213 | 54.481 | 1.00 | 15.26 |
| ATOM | 2895 | OH  | TYR | 425 | 45.633 | 46.253 | 54.287 | 1.00 | 13.69 |
| ATOM | 2896 | C   | TYR | 425 | 50.235 | 49.999 | 57.420 | 1.00 | 15.99 |
| ATOM | 2897 | O   | TYR | 425 | 49.311 | 50.662 | 57.887 | 1.00 | 15.53 |
| ATOM | 2898 | N   | LYS | 426 | 50.903 | 49.096 | 58.131 | 1.00 | 18.15 |
| ATOM | 2899 | CA  | LYS | 426 | 50.535 | 48.777 | 59.509 | 1.00 | 19.68 |
| ATOM | 2900 | CB  | LYS | 426 | 51.446 | 47.669 | 60.053 | 1.00 | 19.35 |
| ATOM | 2901 | CG  | LYS | 426 | 52.893 | 48.084 | 60.268 | 1.00 | 21.71 |
| ATOM | 2902 | CD  | LYS | 426 | 53.700 | 46.947 | 60.895 | 1.00 | 23.93 |
| ATOM | 2903 | CE  | LYS | 426 | 55.145 | 47.355 | 61.133 | 1.00 | 25.11 |
| ATOM | 2904 | NZ  | LYS | 426 | 55.224 | 48.568 | 61.996 | 1.00 | 30.09 |
| ATOM | 2905 | C   | LYS | 426 | 50.533 | 49.947 | 60.495 | 1.00 | 20.54 |
| ATOM | 2906 | O   | LYS | 426 | 49.903 | 49.864 | 61.550 | 1.00 | 20.64 |
| ATOM | 2907 | N   | ASP | 427 | 51.221 | 51.034 | 60.160 | 1.00 | 21.79 |
| ATOM | 2908 | CA  | ASP | 427 | 51.281 | 52.177 | 61.064 | 1.00 | 23.05 |
| ATOM | 2909 | CB  | ASP | 427 | 52.692 | 52.763 | 61.078 | 1.00 | 23.93 |
| ATOM | 2910 | CG  | ASP | 427 | 53.698 | 51.805 | 61.664 | 1.00 | 26.63 |
| ATOM | 2911 | OD1 | ASP | 427 | 53.394 | 51.228 | 62.732 | 1.00 | 26.74 |
| ATOM | 2912 | OD2 | ASP | 427 | 54.780 | 51.631 | 61.066 | 1.00 | 26.70 |
| ATOM | 2913 | C   | ASP | 427 | 50.275 | 53.280 | 60.787 | 1.00 | 22.13 |
| ATOM | 2914 | O   | ASP | 427 | 50.265 | 54.302 | 61.472 | 1.00 | 21.25 |
| ATOM | 2915 | N   | LEU | 428 | 49.433 | 53.078 | 59.783 | 1.00 | 21.00 |
| ATOM | 2916 | CA  | LEU | 428 | 48.422 | 54.071 | 59.456 | 1.00 | 20.38 |
| ATOM | 2917 | CB  | LEU | 428 | 48.002 | 53.953 | 57.988 | 1.00 | 20.36 |
| ATOM | 2918 | CG  | LEU | 428 | 49.012 | 54.228 | 56.874 | 1.00 | 18.26 |
| ATOM | 2919 | CD1 | LEU | 428 | 48.314 | 54.052 | 55.532 | 1.00 | 16.44 |
| ATOM | 2920 | CD2 | LEU | 428 | 49.571 | 55.642 | 57.005 | 1.00 | 17.84 |
| ATOM | 2921 | C   | LEU | 428 | 47.200 | 53.831 | 60.324 | 1.00 | 19.95 |
| ATOM | 2922 | O   | LEU | 428 | 47.041 | 52.754 | 60.899 | 1.00 | 20.02 |
| ATOM | 2923 | N   | PRO | 429 | 46.332 | 54.846 | 60.457 | 1.00 | 20.13 |
| ATOM | 2924 | CD  | PRO | 429 | 46.480 | 56.257 | 60.062 | 1.00 | 18.31 |
| ATOM | 2925 | CA  | PRO | 429 | 45.129 | 54.650 | 61.269 | 1.00 | 19.43 |
| ATOM | 2926 | CB  | PRO | 429 | 44.377 | 55.960 | 61.083 | 1.00 | 18.57 |
| ATOM | 2927 | CG  | PRO | 429 | 45.487 | 56.952 | 60.980 | 1.00 | 19.44 |
| ATOM | 2928 | C   | PRO | 429 | 44.394 | 53.459 | 60.652 | 1.00 | 19.56 |
| ATOM | 2929 | O   | PRO | 429 | 44.330 | 53.336 | 59.429 | 1.00 | 18.88 |
| ATOM | 2930 | N   | VAL | 430 | 43.851 | 52.591 | 61.495 | 1.00 | 19.81 |
| ATOM | 2931 | CA  | VAL | 430 | 43.159 | 51.393 | 61.038 | 1.00 | 21.00 |
| ATOM | 2932 | CB  | VAL | 430 | 42.475 | 50.677 | 62.232 | 1.00 | 23.09 |
| ATOM | 2933 | CG1 | VAL | 430 | 41.214 | 51.418 | 62.644 | 1.00 | 23.83 |
| ATOM | 2934 | CG2 | VAL | 430 | 42.168 | 49.241 | 61.870 | 1.00 | 24.99 |
| ATOM | 2935 | C   | VAL | 430 | 42.135 | 51.614 | 59.913 | 1.00 | 20.48 |
| ATOM | 2936 | O   | VAL | 430 | 42.021 | 50.789 | 59.006 | 1.00 | 18.44 |
| ATOM | 2937 | N   | ALA | 431 | 41.405 | 52.724 | 59.957 | 1.00 | 20.17 |
| ATOM | 2938 | CA  | ALA | 431 | 40.401 | 53.002 | 58.933 | 1.00 | 20.14 |
| ATOM | 2939 | CB  | ALA | 431 | 39.587 | 54.236 | 59.311 | 1.00 | 21.04 |
| ATOM | 2940 | C   | ALA | 431 | 41.029 | 53.197 | 57.560 | 1.00 | 19.75 |
| ATOM | 2941 | O   | ALA | 431 | 40.350 | 53.110 | 56.540 | 1.00 | 20.64 |
| ATOM | 2942 | N   | LEU | 432 | 42.330 | 53.456 | 57.537 | 1.00 | 19.42 |
| ATOM | 2943 | CA  | LEU | 432 | 43.023 | 53.667 | 56.277 | 1.00 | 17.67 |
| ATOM | 2944 | CB  | LEU | 432 | 43.821 | 54.974 | 56.336 | 1.00 | 17.92 |
| ATOM | 2945 | CG  | LEU | 432 | 43.038 | 56.238 | 56.721 | 1.00 | 16.23 |
| ATOM | 2946 | CD1 | LEU | 432 | 43.996 | 57.416 | 56.789 | 1.00 | 18.02 |
| ATOM | 2947 | CD2 | LEU | 432 | 41.929 | 56.512 | 55.703 | 1.00 | 17.85 |
| ATOM | 2948 | C   | LEU | 432 | 43.946 | 52.500 | 55.935 | 1.00 | 18.33 |
| ATOM | 2949 | O   | LEU | 432 | 44.758 | 52.592 | 55.010 | 1.00 | 19.78 |
| ATOM | 2950 | N   | ARG | 433 | 43.824 | 51.401 | 56.676 | 1.00 | 17.58 |
| ATOM | 2951 | CA  | ARG | 433 | 44.654 | 50.231 | 56.410 | 1.00 | 19.13 |
| ATOM | 2952 | CB  | ARG | 433 | 44.894 | 49.428 | 57.695 | 1.00 | 20.01 |

TABLE B-continued

Co-ordinates of an underglycosylated tACEΔ36NJ ACE-lisinopril complex

| ATOM | 2953 | CG | ARG | 433 | 45.700 | 50.170 | 58.761 | 1.00 | 24.17 |
|---|---|---|---|---|---|---|---|---|---|
| ATOM | 2954 | CD | ARG | 433 | 46.094 | 49.238 | 59.910 | 1.00 | 25.60 |
| ATOM | 2955 | NE | ARG | 433 | 46.572 | 49.977 | 61.076 | 1.00 | 30.87 |
| ATOM | 2956 | CZ | ARG | 433 | 47.022 | 49.413 | 62.196 | 1.00 | 32.45 |
| ATOM | 2957 | NH1 | ARG | 433 | 47.065 | 48.091 | 62.317 | 1.00 | 31.35 |
| ATOM | 2958 | NH2 | ARG | 433 | 47.423 | 50.177 | 63.203 | 1.00 | 33.39 |
| ATOM | 2959 | C | ARG | 433 | 44.029 | 49.333 | 55.339 | 1.00 | 17.92 |
| ATOM | 2960 | O | ARG | 433 | 43.527 | 48.245 | 55.626 | 1.00 | 16.81 |
| ATOM | 2961 | N | GLU | 434 | 44.055 | 49.817 | 54.102 | 1.00 | 17.88 |
| ATOM | 2962 | CA | GLU | 434 | 43.532 | 49.088 | 52.951 | 1.00 | 18.38 |
| ATOM | 2963 | CB | GLU | 434 | 42.062 | 49.454 | 52.704 | 1.00 | 21.40 |
| ATOM | 2964 | CG | GLU | 434 | 41.126 | 49.146 | 53.866 | 1.00 | 30.47 |
| ATOM | 2965 | CD | GLU | 434 | 40.964 | 47.655 | 54.121 | 1.00 | 35.68 |
| ATOM | 2966 | OE1 | GLU | 434 | 41.691 | 46.848 | 53.498 | 1.00 | 39.78 |
| ATOM | 2967 | OE2 | GLU | 434 | 40.105 | 47.288 | 54.953 | 1.00 | 39.56 |
| ATOM | 2968 | C | GLU | 434 | 44.369 | 49.490 | 51.741 | 1.00 | 15.81 |
| ATOM | 2969 | O | GLU | 434 | 45.184 | 50.408 | 51.827 | 1.00 | 14.18 |
| ATOM | 2970 | N | GLY | 435 | 44.178 | 48.804 | 50.617 | 1.00 | 15.92 |
| ATOM | 2971 | CA | GLY | 435 | 44.926 | 49.153 | 49.419 | 1.00 | 14.49 |
| ATOM | 2972 | C | GLY | 435 | 44.383 | 50.441 | 48.818 | 1.00 | 14.11 |
| ATOM | 2973 | O | GLY | 435 | 43.296 | 50.881 | 49.201 | 1.00 | 12.46 |
| ATOM | 2974 | N | ALA | 436 | 45.132 | 51.054 | 47.900 | 1.00 | 13.32 |
| ATOM | 2975 | CA | ALA | 436 | 44.687 | 52.293 | 47.248 | 1.00 | 13.39 |
| ATOM | 2976 | CB | ALA | 436 | 45.571 | 52.601 | 46.044 | 1.00 | 10.25 |
| ATOM | 2977 | C | ALA | 436 | 43.230 | 52.066 | 46.828 | 1.00 | 11.87 |
| ATOM | 2978 | O | ALA | 436 | 42.389 | 52.956 | 46.927 | 1.00 | 12.19 |
| ATOM | 2979 | N | ASN | 437 | 42.965 | 50.864 | 46.329 | 1.00 | 12.23 |
| ATOM | 2980 | CA | ASN | 437 | 41.619 | 50.400 | 45.989 | 1.00 | 11.91 |
| ATOM | 2981 | CB | ASN | 437 | 41.104 | 50.904 | 44.617 | 1.00 | 12.44 |
| ATOM | 2982 | CG | ASN | 437 | 41.809 | 50.287 | 43.430 | 1.00 | 10.41 |
| ATOM | 2983 | OD1 | ASN | 437 | 42.024 | 49.079 | 43.363 | 1.00 | 12.22 |
| ATOM | 2984 | ND2 | ASN | 437 | 42.144 | 51.126 | 42.458 | 1.00 | 10.38 |
| ATOM | 2985 | C | ASN | 437 | 41.771 | 48.885 | 46.051 | 1.00 | 11.58 |
| ATOM | 2986 | O | ASN | 437 | 42.890 | 48.383 | 46.049 | 1.00 | 12.17 |
| ATOM | 2987 | N | PRO | 438 | 40.663 | 48.136 | 46.142 | 1.00 | 12.13 |
| ATOM | 2988 | CD | PRO | 438 | 39.250 | 48.549 | 46.234 | 1.00 | 10.54 |
| ATOM | 2989 | CA | PRO | 438 | 40.789 | 46.677 | 46.220 | 1.00 | 10.70 |
| ATOM | 2990 | CB | PRO | 438 | 39.338 | 46.205 | 46.162 | 1.00 | 12.07 |
| ATOM | 2991 | CG | PRO | 438 | 38.607 | 47.326 | 46.867 | 1.00 | 11.56 |
| ATOM | 2992 | C | PRO | 438 | 41.674 | 46.026 | 45.160 | 1.00 | 11.01 |
| ATOM | 2993 | O | PRO | 438 | 42.343 | 45.031 | 45.441 | 1.00 | 9.92 |
| ATOM | 2994 | N | GLY | 439 | 41.682 | 46.591 | 43.955 | 1.00 | 10.86 |
| ATOM | 2995 | CA | GLY | 439 | 42.494 | 46.049 | 42.876 | 1.00 | 11.19 |
| ATOM | 2996 | C | GLY | 439 | 43.984 | 46.073 | 43.175 | 1.00 | 11.99 |
| ATOM | 2997 | O | GLY | 439 | 44.710 | 45.135 | 42.830 | 1.00 | 10.62 |
| ATOM | 2998 | N | PHE | 440 | 44.452 | 47.148 | 43.806 | 1.00 | 11.06 |
| ATOM | 2999 | CA | PHE | 440 | 45.866 | 47.260 | 44.156 | 1.00 | 11.17 |
| ATOM | 3000 | CB | PHE | 440 | 46.157 | 48.609 | 44.831 | 1.00 | 11.18 |
| ATOM | 3001 | CG | PHE | 440 | 46.364 | 49.745 | 43.864 | 1.00 | 12.13 |
| ATOM | 3002 | CD1 | PHE | 440 | 45.377 | 50.089 | 42.947 | 1.00 | 11.54 |
| ATOM | 3003 | CD2 | PHE | 440 | 47.554 | 50.472 | 43.871 | 1.00 | 12.86 |
| ATOM | 3004 | CE1 | PHE | 440 | 45.572 | 51.146 | 42.045 | 1.00 | 11.15 |
| ATOM | 3005 | CE2 | PHE | 440 | 47.755 | 51.526 | 42.977 | 1.00 | 12.18 |
| ATOM | 3006 | CZ | PHE | 440 | 46.763 | 51.860 | 42.065 | 1.00 | 11.17 |
| ATOM | 3007 | C | PHE | 440 | 46.275 | 46.135 | 45.098 | 1.00 | 11.04 |
| ATOM | 3008 | O | PHE | 440 | 47.326 | 45.519 | 44.926 | 1.00 | 10.51 |
| ATOM | 3009 | N | HIS | 441 | 45.445 | 45.873 | 46.104 | 1.00 | 10.42 |
| ATOM | 3010 | CA | HIS | 441 | 45.753 | 44.822 | 47.066 | 1.00 | 11.23 |
| ATOM | 3011 | CB | HIS | 441 | 44.640 | 44.720 | 48.116 | 1.00 | 11.68 |
| ATOM | 3012 | CG | HIS | 441 | 45.144 | 44.607 | 49.523 | 1.00 | 11.91 |
| ATOM | 3013 | CD2 | HIS | 441 | 44.919 | 45.379 | 50.614 | 1.00 | 10.21 |
| ATOM | 3014 | ND1 | HIS | 441 | 45.976 | 43.589 | 49.941 | 1.00 | 10.64 |
| ATOM | 3015 | CE1 | HIS | 441 | 46.237 | 43.736 | 51.228 | 1.00 | 11.94 |
| ATOM | 3016 | NE2 | HIS | 441 | 45.607 | 44.815 | 51.661 | 1.00 | 11.66 |
| ATOM | 3017 | C | HIS | 441 | 45.921 | 43.475 | 46.364 | 1.00 | 10.83 |
| ATOM | 3018 | O | HIS | 441 | 46.780 | 42.674 | 46.736 | 1.00 | 9.33 |
| ATOM | 3019 | N | GLU | 442 | 45.106 | 43.241 | 45.339 | 1.00 | 12.01 |
| ATOM | 3020 | CA | GLU | 442 | 45.144 | 41.991 | 44.586 | 1.00 | 10.66 |
| ATOM | 3021 | CB | GLU | 442 | 43.838 | 41.819 | 43.801 | 1.00 | 11.06 |
| ATOM | 3022 | CG | GLU | 442 | 42.565 | 41.755 | 44.645 | 1.00 | 7.88 |
| ATOM | 3023 | CD | GLU | 442 | 42.614 | 40.643 | 45.677 | 1.00 | 8.56 |
| ATOM | 3024 | OE1 | GLU | 442 | 43.226 | 39.598 | 45.376 | 1.00 | 8.96 |
| ATOM | 3025 | OE2 | GLU | 442 | 42.044 | 40.809 | 46.778 | 1.00 | 8.52 |
| ATOM | 3026 | C | GLU | 442 | 46.320 | 41.897 | 43.607 | 1.00 | 13.30 |
| ATOM | 3027 | O | GLU | 442 | 46.815 | 40.807 | 43.323 | 1.00 | 14.12 |
| ATOM | 3028 | N | ALA | 443 | 46.782 | 43.038 | 43.105 | 1.00 | 14.06 |
| ATOM | 3029 | CA | ALA | 443 | 47.860 | 43.056 | 42.112 | 1.00 | 14.79 |
| ATOM | 3030 | CB | ALA | 443 | 47.801 | 44.369 | 41.336 | 1.00 | 13.68 |

TABLE B-continued

Co-ordinates of an underglycosylated tACEΔ36NJ ACE-lisinopril complex

| ATOM | 3031 | C | ALA | 443 | 49.299 | 42.808 | 42.575 | 1.00 | 14.18 |
|---|---|---|---|---|---|---|---|---|---|
| ATOM | 3032 | O | ALA | 443 | 50.096 | 42.229 | 41.835 | 1.00 | 13.95 |
| ATOM | 3033 | N | ILE | 444 | 49.631 | 43.249 | 43.784 | 1.00 | 13.76 |
| ATOM | 3034 | CA | ILE | 444 | 50.989 | 43.119 | 44.311 | 1.00 | 13.53 |
| ATOM | 3035 | CB | ILE | 444 | 51.035 | 43.500 | 45.810 | 1.00 | 13.26 |
| ATOM | 3036 | CG2 | ILE | 444 | 52.476 | 43.493 | 46.312 | 1.00 | 11.75 |
| ATOM | 3037 | CG1 | ILE | 444 | 50.430 | 44.898 | 46.002 | 1.00 | 11.55 |
| ATOM | 3038 | CD1 | ILE | 444 | 51.090 | 45.972 | 45.158 | 1.00 | 13.98 |
| ATOM | 3039 | C | ILE | 444 | 51.671 | 41.757 | 44.116 | 1.00 | 13.95 |
| ATOM | 3040 | O | ILE | 444 | 52.710 | 41.666 | 43.454 | 1.00 | 10.36 |
| ATOM | 3041 | N | GLY | 445 | 51.095 | 40.709 | 44.695 | 1.00 | 12.71 |
| ATOM | 3042 | CA | GLY | 445 | 51.678 | 39.389 | 44.562 | 1.00 | 12.69 |
| ATOM | 3043 | C | GLY | 445 | 51.785 | 38.914 | 43.125 | 1.00 | 13.85 |
| ATOM | 3044 | O | GLY | 445 | 52.774 | 38.284 | 42.746 | 1.00 | 14.14 |
| ATOM | 3045 | N | ASP | 446 | 50.767 | 39.215 | 42.324 | 1.00 | 12.80 |
| ATOM | 3046 | CA | ASP | 446 | 50.742 | 38.805 | 40.923 | 1.00 | 12.50 |
| ATOM | 3047 | CB | ASP | 446 | 49.398 | 39.181 | 40.282 | 1.00 | 9.49 |
| ATOM | 3048 | CG | ASP | 446 | 48.261 | 38.259 | 40.714 | 1.00 | 10.86 |
| ATOM | 3049 | OD1 | ASP | 446 | 48.321 | 37.706 | 41.831 | 1.00 | 9.74 |
| ATOM | 3050 | OD2 | ASP | 446 | 47.293 | 38.098 | 39.946 | 1.00 | 11.31 |
| ATOM | 3051 | C | ASP | 446 | 51.885 | 39.421 | 40.125 | 1.00 | 13.90 |
| ATOM | 3052 | O | ASP | 446 | 52.437 | 38.782 | 39.224 | 1.00 | 12.58 |
| ATOM | 3053 | N | VAL | 447 | 52.230 | 40.665 | 40.452 | 1.00 | 13.86 |
| ATOM | 3054 | CA | VAL | 447 | 53.307 | 41.351 | 39.758 | 1.00 | 13.18 |
| ATOM | 3055 | CB | VAL | 447 | 53.520 | 42.778 | 40.313 | 1.00 | 13.78 |
| ATOM | 3056 | CG1 | VAL | 447 | 54.745 | 43.414 | 39.661 | 1.00 | 13.13 |
| ATOM | 3057 | CG2 | VAL | 447 | 52.280 | 43.634 | 40.037 | 1.00 | 11.10 |
| ATOM | 3058 | C | VAL | 447 | 54.600 | 40.553 | 39.891 | 1.00 | 13.89 |
| ATOM | 3059 | O | VAL | 447 | 55.263 | 40.274 | 38.897 | 1.00 | 14.12 |
| ATOM | 3060 | N | LEU | 448 | 54.954 | 40.184 | 41.119 | 1.00 | 13.93 |
| ATOM | 3061 | CA | LEU | 448 | 56.164 | 39.403 | 41.345 | 1.00 | 14.69 |
| ATOM | 3062 | CB | LEU | 448 | 56.424 | 39.217 | 42.845 | 1.00 | 13.90 |
| ATOM | 3063 | CG | LEU | 448 | 57.185 | 40.346 | 43.548 | 1.00 | 14.37 |
| ATOM | 3064 | CD1 | LEU | 448 | 56.377 | 41.638 | 43.511 | 1.00 | 13.68 |
| ATOM | 3065 | CD2 | LEU | 448 | 57.474 | 39.937 | 44.980 | 1.00 | 14.99 |
| ATOM | 3066 | C | LEU | 448 | 56.068 | 38.040 | 40.665 | 1.00 | 14.58 |
| ATOM | 3067 | O | LEU | 448 | 57.030 | 37.580 | 40.047 | 1.00 | 16.65 |
| ATOM | 3068 | N | ALA | 449 | 54.909 | 37.400 | 40.776 | 1.00 | 14.25 |
| ATOM | 3069 | CA | ALA | 449 | 54.696 | 36.094 | 40.161 | 1.00 | 14.13 |
| ATOM | 3070 | CB | ALA | 449 | 53.303 | 35.576 | 40.499 | 1.00 | 12.41 |
| ATOM | 3071 | C | ALA | 449 | 54.890 | 36.143 | 38.639 | 1.00 | 14.00 |
| ATOM | 3072 | O | ALA | 449 | 55.241 | 35.136 | 38.020 | 1.00 | 14.32 |
| ATOM | 3073 | N | LEU | 450 | 54.652 | 37.304 | 38.033 | 1.00 | 13.43 |
| ATOM | 3074 | CA | LEU | 450 | 54.850 | 37.440 | 36.592 | 1.00 | 13.96 |
| ATOM | 3075 | CB | LEU | 450 | 54.473 | 38.853 | 36.121 | 1.00 | 13.77 |
| ATOM | 3076 | CG | LEU | 450 | 52.976 | 39.149 | 35.969 | 1.00 | 12.17 |
| ATOM | 3077 | CD1 | LEU | 450 | 52.758 | 40.620 | 35.637 | 1.00 | 9.82 |
| ATOM | 3078 | CD2 | LEU | 450 | 52.398 | 38.262 | 34.869 | 1.00 | 11.71 |
| ATOM | 3079 | C | LEU | 450 | 56.325 | 37.165 | 36.283 | 1.00 | 14.53 |
| ATOM | 3080 | O | LEU | 450 | 56.651 | 36.443 | 35.339 | 1.00 | 15.40 |
| ATOM | 3081 | N | SER | 451 | 57.212 | 37.745 | 37.085 | 1.00 | 13.59 |
| ATOM | 3082 | CA | SER | 451 | 58.644 | 37.540 | 36.900 | 1.00 | 15.77 |
| ATOM | 3083 | CB | SER | 451 | 59.441 | 38.498 | 37.789 | 1.00 | 14.12 |
| ATOM | 3084 | OG | SER | 451 | 59.381 | 39.818 | 37.273 | 1.00 | 14.82 |
| ATOM | 3085 | C | SER | 451 | 59.035 | 36.098 | 37.211 | 1.00 | 15.90 |
| ATOM | 3086 | O | SER | 451 | 59.843 | 35.501 | 36.501 | 1.00 | 16.58 |
| ATOM | 3087 | N | VAL | 452 | 58.448 | 35.543 | 38.269 | 1.00 | 16.02 |
| ATOM | 3088 | CA | VAL | 452 | 58.722 | 34.169 | 38.674 | 1.00 | 17.43 |
| ATOM | 3089 | CB | VAL | 452 | 57.903 | 33.786 | 39.933 | 1.00 | 16.72 |
| ATOM | 3090 | CG1 | VAL | 452 | 58.108 | 32.308 | 40.274 | 1.00 | 16.74 |
| ATOM | 3091 | CG2 | VAL | 452 | 58.321 | 34.657 | 41.102 | 1.00 | 18.21 |
| ATOM | 3092 | C | VAL | 452 | 58.381 | 33.182 | 37.554 | 1.00 | 18.85 |
| ATOM | 3093 | O | VAL | 452 | 59.101 | 32.205 | 37.337 | 1.00 | 18.12 |
| ATOM | 3094 | N | SER | 453 | 57.287 | 33.453 | 36.843 | 1.00 | 18.69 |
| ATOM | 3095 | CA | SER | 453 | 56.820 | 32.590 | 35.755 | 1.00 | 18.97 |
| ATOM | 3096 | CB | SER | 453 | 55.402 | 33.001 | 35.336 | 1.00 | 18.72 |
| ATOM | 3097 | OG | SER | 453 | 54.463 | 32.712 | 36.356 | 1.00 | 19.55 |
| ATOM | 3098 | C | SER | 453 | 57.693 | 32.523 | 34.506 | 1.00 | 18.98 |
| ATOM | 3099 | O | SER | 453 | 57.559 | 31.593 | 33.707 | 1.00 | 17.86 |
| ATOM | 3100 | N | THR | 454 | 58.576 | 33.499 | 34.320 | 1.00 | 18.89 |
| ATOM | 3101 | CA | THR | 454 | 59.426 | 33.499 | 33.138 | 1.00 | 19.78 |
| ATOM | 3102 | CB | THR | 454 | 60.385 | 34.699 | 33.123 | 1.00 | 18.87 |
| ATOM | 3103 | OG1 | THR | 454 | 61.150 | 34.722 | 34.336 | 1.00 | 19.79 |
| ATOM | 3104 | CG2 | THR | 454 | 59.603 | 35.997 | 32.975 | 1.00 | 18.32 |
| ATOM | 3105 | C | THR | 454 | 60.239 | 32.217 | 33.041 | 1.00 | 21.57 |
| ATOM | 3106 | O | THR | 454 | 60.734 | 31.707 | 34.045 | 1.00 | 22.35 |
| ATOM | 3107 | N | PRO | 455 | 60.378 | 31.673 | 31.822 | 1.00 | 21.55 |
| ATOM | 3108 | CD | PRO | 455 | 59.824 | 32.153 | 30.540 | 1.00 | 21.60 |

TABLE B-continued

Co-ordinates of an underglycosylated tACEΔ36NJ ACE-lisinopril complex

| ATOM | 3109 | CA | PRO | 455 | 61.142 | 30.440 | 31.632 | 1.00 | 23.12 |
|------|------|-----|-----|-----|--------|--------|--------|------|-------|
| ATOM | 3110 | CB | PRO | 455 | 61.278 | 30.354 | 30.113 | 1.00 | 22.44 |
| ATOM | 3111 | CG | PRO | 455 | 59.972 | 30.933 | 29.641 | 1.00 | 20.77 |
| ATOM | 3112 | C | PRO | 455 | 62.489 | 30.489 | 32.338 | 1.00 | 23.94 |
| ATOM | 3113 | O | PRO | 455 | 62.854 | 29.566 | 33.064 | 1.00 | 23.00 |
| ATOM | 3114 | N | LYS | 456 | 63.216 | 31.582 | 32.140 | 1.00 | 24.94 |
| ATOM | 3115 | CA | LYS | 456 | 64.527 | 31.726 | 32.748 | 1.00 | 25.77 |
| ATOM | 3116 | CB | LYS | 456 | 65.186 | 33.029 | 32.289 | 1.00 | 28.54 |
| ATOM | 3117 | CG | LYS | 456 | 66.708 | 32.960 | 32.293 | 1.00 | 33.33 |
| ATOM | 3118 | CD | LYS | 456 | 67.343 | 34.308 | 31.998 | 1.00 | 36.84 |
| ATOM | 3119 | CE | LYS | 456 | 68.857 | 34.190 | 31.983 | 1.00 | 39.24 |
| ATOM | 3120 | NZ | LYS | 456 | 69.341 | 33.419 | 33.163 | 1.00 | 42.84 |
| ATOM | 3121 | C | LYS | 456 | 64.479 | 31.679 | 34.274 | 1.00 | 25.66 |
| ATOM | 3122 | O | LYS | 456 | 65.334 | 31.055 | 34.905 | 1.00 | 24.62 |
| ATOM | 3123 | N | HIS | 457 | 63.485 | 32.332 | 34.873 | 1.00 | 23.14 |
| ATOM | 3124 | CA | HIS | 457 | 63.386 | 32.325 | 36.326 | 1.00 | 22.18 |
| ATOM | 3125 | CB | HIS | 457 | 62.312 | 33.299 | 36.817 | 1.00 | 22.71 |
| ATOM | 3126 | CG | HIS | 457 | 62.327 | 33.495 | 38.301 | 1.00 | 21.95 |
| ATOM | 3127 | CD2 | HIS | 457 | 61.859 | 32.717 | 39.307 | 1.00 | 24.49 |
| ATOM | 3128 | ND1 | HIS | 457 | 62.959 | 34.560 | 38.904 | 1.00 | 21.90 |
| ATOM | 3129 | CE1 | HIS | 457 | 62.884 | 34.429 | 40.217 | 1.00 | 24.67 |
| ATOM | 3130 | NE2 | HIS | 457 | 62.222 | 33.317 | 40.488 | 1.00 | 24.22 |
| ATOM | 3131 | C | HIS | 457 | 63.067 | 30.922 | 36.836 | 1.00 | 21.29 |
| ATOM | 3132 | O | HIS | 457 | 63.643 | 30.470 | 37.826 | 1.00 | 20.13 |
| ATOM | 3133 | N | LEU | 458 | 62.136 | 30.243 | 36.170 | 1.00 | 21.42 |
| ATOM | 3134 | CA | LEU | 458 | 61.764 | 28.890 | 36.564 | 1.00 | 22.05 |
| ATOM | 3135 | CB | LEU | 458 | 60.633 | 28.355 | 35.677 | 1.00 | 21.29 |
| ATOM | 3136 | CG | LEU | 458 | 59.243 | 28.976 | 35.857 | 1.00 | 21.21 |
| ATOM | 3137 | CD1 | LEU | 458 | 58.267 | 28.346 | 34.873 | 1.00 | 20.79 |
| ATOM | 3138 | CD2 | LEU | 458 | 58.768 | 28.762 | 37.294 | 1.00 | 20.98 |
| ATOM | 3139 | C | LEU | 458 | 62.983 | 27.976 | 36.465 | 1.00 | 22.14 |
| ATOM | 3140 | O | LEU | 458 | 63.166 | 27.082 | 37.287 | 1.00 | 21.63 |
| ATOM | 3141 | N | HIS | 459 | 63.820 | 28.213 | 35.461 | 1.00 | 23.49 |
| ATOM | 3142 | CA | HIS | 459 | 65.019 | 27.404 | 35.284 | 1.00 | 25.12 |
| ATOM | 3143 | CB | HIS | 459 | 65.688 | 27.713 | 33.939 | 1.00 | 26.57 |
| ATOM | 3144 | CG | HIS | 459 | 66.953 | 26.941 | 33.701 | 1.00 | 32.18 |
| ATOM | 3145 | CD2 | HIS | 459 | 67.171 | 25.755 | 33.084 | 1.00 | 33.64 |
| ATOM | 3146 | ND1 | HIS | 459 | 68.180 | 27.358 | 34.173 | 1.00 | 34.37 |
| ATOM | 3147 | CE1 | HIS | 459 | 69.099 | 26.461 | 33.859 | 1.00 | 34.36 |
| ATOM | 3148 | NE2 | HIS | 459 | 68.513 | 25.478 | 33.199 | 1.00 | 35.32 |
| ATOM | 3149 | C | HIS | 459 | 65.985 | 27.657 | 36.441 | 1.00 | 23.17 |
| ATOM | 3150 | O | HIS | 459 | 66.698 | 26.751 | 36.867 | 1.00 | 22.80 |
| ATOM | 3151 | N | SER | 460 | 65.991 | 28.882 | 36.963 | 1.00 | 22.86 |
| ATOM | 3152 | CA | SER | 460 | 66.870 | 29.218 | 38.083 | 1.00 | 22.31 |
| ATOM | 3153 | CB | SER | 460 | 66.877 | 30.734 | 38.341 | 1.00 | 22.68 |
| ATOM | 3154 | OG | SER | 460 | 65.731 | 31.148 | 39.071 | 1.00 | 26.41 |
| ATOM | 3155 | C | SER | 460 | 66.407 | 28.480 | 39.339 | 1.00 | 21.77 |
| ATOM | 3156 | O | SER | 460 | 67.176 | 28.297 | 40.283 | 1.00 | 18.91 |
| ATOM | 3157 | N | LEU | 461 | 65.141 | 28.069 | 39.349 | 1.00 | 21.28 |
| ATOM | 3158 | CA | LEU | 461 | 64.589 | 27.326 | 40.480 | 1.00 | 23.33 |
| ATOM | 3159 | CB | LEU | 461 | 63.103 | 27.652 | 40.678 | 1.00 | 21.27 |
| ATOM | 3160 | CG | LEU | 461 | 62.745 | 29.061 | 41.153 | 1.00 | 21.36 |
| ATOM | 3161 | CD1 | LEU | 461 | 61.230 | 29.193 | 41.235 | 1.00 | 21.05 |
| ATOM | 3162 | CD2 | LEU | 461 | 63.383 | 29.330 | 42.513 | 1.00 | 19.25 |
| ATOM | 3163 | C | LEU | 461 | 64.748 | 25.839 | 40.197 | 1.00 | 24.98 |
| ATOM | 3164 | O | LEU | 461 | 64.394 | 24.992 | 41.022 | 1.00 | 25.06 |
| ATOM | 3165 | N | ASN | 462 | 65.280 | 25.543 | 39.012 | 1.00 | 27.22 |
| ATOM | 3166 | CA | ASN | 462 | 65.515 | 24.178 | 38.555 | 1.00 | 28.33 |
| ATOM | 3167 | CB | ASN | 462 | 66.329 | 23.411 | 39.604 | 1.00 | 30.22 |
| ATOM | 3168 | CG | ASN | 462 | 67.032 | 22.196 | 39.026 | 1.00 | 32.38 |
| ATOM | 3169 | OD1 | ASN | 462 | 67.571 | 22.245 | 37.919 | 1.00 | 31.35 |
| ATOM | 3170 | ND2 | ASN | 462 | 67.043 | 21.102 | 39.780 | 1.00 | 33.86 |
| ATOM | 3171 | C | ASN | 462 | 64.200 | 23.454 | 38.249 | 1.00 | 29.21 |
| ATOM | 3172 | O | ASN | 462 | 64.074 | 22.246 | 38.465 | 1.00 | 28.02 |
| ATOM | 3173 | N | LEU | 463 | 63.227 | 24.200 | 37.731 | 1.00 | 29.99 |
| ATOM | 3174 | CA | LEU | 463 | 61.923 | 23.641 | 37.394 | 1.00 | 32.41 |
| ATOM | 3175 | CB | LEU | 463 | 60.809 | 24.456 | 38.056 | 1.00 | 31.50 |
| ATOM | 3176 | CG | LEU | 463 | 60.935 | 24.584 | 39.579 | 1.00 | 31.61 |
| ATOM | 3177 | CD1 | LEU | 463 | 59.736 | 25.346 | 40.125 | 1.00 | 30.85 |
| ATOM | 3178 | CD2 | LEU | 463 | 61.028 | 23.200 | 40.214 | 1.00 | 30.38 |
| ATOM | 3179 | C | LEU | 463 | 61.713 | 23.594 | 35.886 | 1.00 | 34.49 |
| ATOM | 3180 | O | LEU | 463 | 60.746 | 23.011 | 35.400 | 1.00 | 37.47 |
| ATOM | 3181 | N | LEU | 464 | 62.622 | 24.223 | 35.155 | 1.00 | 36.34 |
| ATOM | 3182 | CA | LEU | 464 | 62.580 | 24.233 | 33.696 | 1.00 | 39.11 |
| ATOM | 3183 | CB | LEU | 464 | 62.053 | 25.574 | 33.163 | 1.00 | 39.04 |
| ATOM | 3184 | CG | LEU | 464 | 60.557 | 25.635 | 32.834 | 1.00 | 39.75 |
| ATOM | 3185 | CD1 | LEU | 464 | 60.214 | 26.987 | 32.218 | 1.00 | 38.92 |
| ATOM | 3186 | CD2 | LEU | 464 | 60.208 | 24.511 | 31.865 | 1.00 | 38.93 |

TABLE B-continued

Co-ordinates of an underglycosylated tACEΔ36NJ ACE-lisinopril complex

| ATOM | 3187 | C   | LEU | 464 | 63.987 | 23.987 | 33.172 | 1.00 | 40.46 |
|------|------|-----|-----|-----|--------|--------|--------|------|-------|
| ATOM | 3188 | O   | LEU | 464 | 64.966 | 24.186 | 33.892 | 1.00 | 41.21 |
| ATOM | 3189 | N   | SER | 465 | 64.089 | 23.546 | 31.923 | 1.00 | 42.64 |
| ATOM | 3190 | CA  | SER | 465 | 65.390 | 23.281 | 31.323 | 1.00 | 44.44 |
| ATOM | 3191 | CB  | SER | 465 | 65.500 | 21.805 | 30.926 | 1.00 | 44.95 |
| ATOM | 3192 | OG  | SER | 465 | 64.454 | 21.428 | 30.048 | 1.00 | 47.16 |
| ATOM | 3193 | C   | SER | 465 | 65.618 | 24.166 | 30.105 | 1.00 | 44.78 |
| ATOM | 3194 | O   | SER | 465 | 66.208 | 25.243 | 30.212 | 1.00 | 45.25 |
| ATOM | 3195 | N   | GLY | 470 | 64.492 | 32.666 | 21.953 | 1.00 | 45.58 |
| ATOM | 3196 | CA  | GLY | 470 | 63.932 | 31.868 | 20.878 | 1.00 | 45.90 |
| ATOM | 3197 | C   | GLY | 470 | 62.479 | 32.197 | 20.591 | 1.00 | 45.14 |
| ATOM | 3198 | O   | GLY | 470 | 61.641 | 32.185 | 21.493 | 1.00 | 45.19 |
| ATOM | 3199 | N   | ALA | 471 | 62.180 | 32.479 | 19.327 | 1.00 | 44.31 |
| ATOM | 3200 | CA  | ALA | 471 | 60.829 | 32.832 | 18.904 | 1.00 | 42.77 |
| ATOM | 3201 | CB  | ALA | 471 | 60.801 | 33.040 | 17.399 | 1.00 | 42.61 |
| ATOM | 3202 | C   | ALA | 471 | 59.772 | 31.807 | 19.307 | 1.00 | 41.97 |
| ATOM | 3203 | O   | ALA | 471 | 58.822 | 32.140 | 20.017 | 1.00 | 42.12 |
| ATOM | 3204 | N   | GLU | 472 | 59.933 | 30.567 | 18.855 | 1.00 | 40.07 |
| ATOM | 3205 | CA  | GLU | 472 | 58.974 | 29.515 | 19.168 | 1.00 | 38.02 |
| ATOM | 3206 | CB  | GLU | 472 | 59.369 | 28.213 | 18.471 | 1.00 | 38.51 |
| ATOM | 3207 | CG  | GLU | 472 | 58.968 | 28.190 | 17.001 | 1.00 | 39.98 |
| ATOM | 3208 | CD  | GLU | 472 | 59.374 | 26.913 | 16.293 | 1.00 | 40.39 |
| ATOM | 3209 | OE1 | GLU | 472 | 59.651 | 25.908 | 16.982 | 1.00 | 39.63 |
| ATOM | 3210 | OE2 | GLU | 472 | 59.397 | 26.915 | 15.043 | 1.00 | 40.40 |
| ATOM | 3211 | C   | GLU | 472 | 58.790 | 29.276 | 20.660 | 1.00 | 37.16 |
| ATOM | 3212 | O   | GLU | 472 | 57.703 | 28.901 | 21.105 | 1.00 | 34.83 |
| ATOM | 3213 | N   | HIS | 473 | 59.847 | 29.487 | 21.435 | 1.00 | 35.29 |
| ATOM | 3214 | CA  | HIS | 473 | 59.740 | 29.305 | 22.872 | 1.00 | 35.03 |
| ATOM | 3215 | CB  | HIS | 473 | 61.123 | 29.172 | 23.510 | 1.00 | 37.48 |
| ATOM | 3216 | CG  | HIS | 473 | 61.817 | 27.889 | 23.179 | 1.00 | 40.71 |
| ATOM | 3217 | CD2 | HIS | 473 | 61.971 | 26.749 | 23.894 | 1.00 | 41.63 |
| ATOM | 3218 | ND1 | HIS | 473 | 62.435 | 27.665 | 21.967 | 1.00 | 41.83 |
| ATOM | 3219 | CE1 | HIS | 473 | 62.939 | 26.444 | 21.951 | 1.00 | 42.38 |
| ATOM | 3220 | NE2 | HIS | 473 | 62.671 | 25.866 | 23.109 | 1.00 | 42.85 |
| ATOM | 3221 | C   | HIS | 473 | 58.993 | 30.497 | 23.464 | 1.00 | 33.66 |
| ATOM | 3222 | O   | HIS | 473 | 58.305 | 30.361 | 24.474 | 1.00 | 33.56 |
| ATOM | 3223 | N   | ASP | 474 | 59.129 | 31.660 | 22.829 | 1.00 | 31.69 |
| ATOM | 3224 | CA  | ASP | 474 | 58.448 | 32.864 | 23.289 | 1.00 | 31.39 |
| ATOM | 3225 | CB  | ASP | 474 | 58.886 | 34.096 | 22.488 | 1.00 | 33.71 |
| ATOM | 3226 | CG  | ASP | 474 | 60.219 | 34.644 | 22.939 | 1.00 | 36.85 |
| ATOM | 3227 | OD1 | ASP | 474 | 60.417 | 34.795 | 24.163 | 1.00 | 38.01 |
| ATOM | 3228 | OD2 | ASP | 474 | 61.063 | 34.939 | 22.065 | 1.00 | 40.28 |
| ATOM | 3229 | C   | ASP | 474 | 56.943 | 32.705 | 23.131 | 1.00 | 28.93 |
| ATOM | 3230 | O   | ASP | 474 | 56.182 | 33.000 | 24.054 | 1.00 | 27.31 |
| ATOM | 3231 | N   | ILE | 475 | 56.525 | 32.252 | 21.950 | 1.00 | 25.74 |
| ATOM | 3232 | CA  | ILE | 475 | 55.110 | 32.059 | 21.658 | 1.00 | 21.87 |
| ATOM | 3233 | CB  | ILE | 475 | 54.893 | 31.631 | 20.183 | 1.00 | 21.83 |
| ATOM | 3234 | CG2 | ILE | 475 | 53.398 | 31.481 | 19.887 | 1.00 | 18.55 |
| ATOM | 3235 | CG1 | ILE | 475 | 55.498 | 32.680 | 19.244 | 1.00 | 20.20 |
| ATOM | 3236 | CD1 | ILE | 475 | 54.942 | 34.083 | 19.432 | 1.00 | 18.72 |
| ATOM | 3237 | C   | ILE | 475 | 54.522 | 31.009 | 22.591 | 1.00 | 20.48 |
| ATOM | 3238 | O   | ILE | 475 | 53.405 | 31.171 | 23.081 | 1.00 | 19.85 |
| ATOM | 3239 | N   | ASN | 476 | 55.270 | 29.937 | 22.844 | 1.00 | 18.44 |
| ATOM | 3240 | CA  | ASN | 476 | 54.795 | 28.894 | 23.746 | 1.00 | 19.25 |
| ATOM | 3241 | CB  | ASN | 476 | 55.788 | 27.727 | 23.817 | 1.00 | 20.64 |
| ATOM | 3242 | CG  | ASN | 476 | 55.621 | 26.738 | 22.670 | 1.00 | 22.25 |
| ATOM | 3243 | OD1 | ASN | 476 | 54.645 | 26.785 | 21.917 | 1.00 | 19.60 |
| ATOM | 3244 | ND2 | ASN | 476 | 56.575 | 25.822 | 22.546 | 1.00 | 20.31 |
| ATOM | 3245 | C   | ASN | 476 | 54.598 | 29.475 | 25.151 | 1.00 | 18.68 |
| ATOM | 3246 | O   | ASN | 476 | 53.601 | 29.183 | 25.816 | 1.00 | 17.02 |
| ATOM | 3247 | N   | PHE | 477 | 55.554 | 30.288 | 25.598 | 1.00 | 15.56 |
| ATOM | 3248 | CA  | PHE | 477 | 55.474 | 30.913 | 26.918 | 1.00 | 15.68 |
| ATOM | 3249 | CB  | PHE | 477 | 56.779 | 31.646 | 27.248 | 1.00 | 14.76 |
| ATOM | 3250 | CG  | PHE | 477 | 56.688 | 32.527 | 28.465 | 1.00 | 14.35 |
| ATOM | 3251 | CD1 | PHE | 477 | 56.384 | 31.987 | 29.711 | 1.00 | 15.03 |
| ATOM | 3252 | CD2 | PHE | 477 | 56.901 | 33.898 | 28.365 | 1.00 | 13.50 |
| ATOM | 3253 | CE1 | PHE | 477 | 56.294 | 32.798 | 30.841 | 1.00 | 14.00 |
| ATOM | 3254 | CE2 | PHE | 477 | 56.813 | 34.720 | 29.488 | 1.00 | 15.93 |
| ATOM | 3255 | CZ  | PHE | 477 | 56.509 | 34.167 | 30.730 | 1.00 | 14.91 |
| ATOM | 3256 | C   | PHE | 477 | 54.318 | 31.908 | 26.980 | 1.00 | 14.40 |
| ATOM | 3257 | O   | PHE | 477 | 53.541 | 31.917 | 27.935 | 1.00 | 13.41 |
| ATOM | 3258 | N   | LEU | 478 | 54.220 | 32.758 | 25.964 | 1.00 | 14.15 |
| ATOM | 3259 | CA  | LEU | 478 | 53.155 | 33.750 | 25.917 | 1.00 | 14.48 |
| ATOM | 3260 | CB  | LEU | 478 | 53.317 | 34.647 | 24.688 | 1.00 | 12.70 |
| ATOM | 3261 | CG  | LEU | 478 | 54.454 | 35.664 | 24.818 | 1.00 | 13.21 |
| ATOM | 3262 | CD1 | LEU | 478 | 54.637 | 36.396 | 23.508 | 1.00 | 13.86 |
| ATOM | 3263 | CD2 | LEU | 478 | 54.137 | 36.649 | 25.946 | 1.00 | 14.40 |
| ATOM | 3264 | C   | LEU | 478 | 51.792 | 33.071 | 25.904 | 1.00 | 13.02 |

TABLE B-continued

Co-ordinates of an underglycosylated tACEΔ36NJ ACE-lisinopril complex

| ATOM | 3265 | O   | LEU | 478 | 50.833 | 33.585 | 26.476 | 1.00 | 11.74 |
|------|------|-----|-----|-----|--------|--------|--------|------|-------|
| ATOM | 3266 | N   | MET | 479 | 51.708 | 31.915 | 25.253 | 1.00 | 13.08 |
| ATOM | 3267 | CA  | MET | 479 | 50.448 | 31.183 | 25.199 | 1.00 | 14.20 |
| ATOM | 3268 | CB  | MET | 479 | 50.547 | 29.989 | 24.242 | 1.00 | 14.09 |
| ATOM | 3269 | CG  | MET | 479 | 49.301 | 29.106 | 24.220 | 1.00 | 13.18 |
| ATOM | 3270 | SD  | MET | 479 | 47.788 | 30.012 | 23.801 | 1.00 | 19.98 |
| ATOM | 3271 | CE  | MET | 479 | 48.041 | 30.307 | 22.061 | 1.00 | 13.75 |
| ATOM | 3272 | C   | MET | 479 | 50.105 | 30.688 | 26.599 | 1.00 | 14.85 |
| ATOM | 3273 | O   | MET | 479 | 48.958 | 30.778 | 27.035 | 1.00 | 14.35 |
| ATOM | 3274 | N   | LYS | 480 | 51.102 | 30.165 | 27.304 | 1.00 | 15.49 |
| ATOM | 3275 | CA  | LYS | 480 | 50.868 | 29.669 | 28.648 | 1.00 | 17.00 |
| ATOM | 3276 | CB  | LYS | 480 | 52.136 | 29.016 | 29.221 | 1.00 | 19.28 |
| ATOM | 3277 | CG  | LYS | 480 | 51.911 | 28.409 | 30.600 | 1.00 | 26.30 |
| ATOM | 3278 | CD  | LYS | 480 | 52.934 | 27.329 | 30.981 | 1.00 | 32.36 |
| ATOM | 3279 | CE  | LYS | 480 | 54.279 | 27.910 | 31.400 | 1.00 | 35.11 |
| ATOM | 3280 | NZ  | LYS | 480 | 55.168 | 26.878 | 32.033 | 1.00 | 35.89 |
| ATOM | 3281 | C   | LYS | 480 | 50.395 | 30.804 | 29.553 | 1.00 | 14.63 |
| ATOM | 3282 | O   | LYS | 480 | 49.513 | 30.613 | 30.386 | 1.00 | 16.02 |
| ATOM | 3283 | N   | MET | 481 | 50.971 | 31.988 | 29.374 | 1.00 | 13.07 |
| ATOM | 3284 | CA  | MET | 481 | 50.602 | 33.147 | 30.178 | 1.00 | 12.02 |
| ATOM | 3285 | CB  | MET | 481 | 51.612 | 34.282 | 29.976 | 1.00 | 12.55 |
| ATOM | 3286 | CG  | MET | 481 | 53.015 | 33.998 | 30.509 | 1.00 | 11.44 |
| ATOM | 3287 | SD  | MET | 481 | 53.051 | 33.565 | 32.265 | 1.00 | 18.83 |
| ATOM | 3288 | CE  | MET | 481 | 52.416 | 35.085 | 33.001 | 1.00 | 12.30 |
| ATOM | 3289 | C   | MET | 481 | 49.202 | 33.644 | 29.821 | 1.00 | 12.65 |
| ATOM | 3290 | O   | MET | 481 | 48.430 | 34.045 | 30.696 | 1.00 | 12.46 |
| ATOM | 3291 | N   | ALA | 482 | 48.886 | 33.619 | 28.531 | 1.00 | 10.95 |
| ATOM | 3292 | CA  | ALA | 482 | 47.588 | 34.067 | 28.046 | 1.00 | 11.63 |
| ATOM | 3293 | CB  | ALA | 482 | 47.596 | 34.125 | 26.530 | 1.00 | 11.09 |
| ATOM | 3294 | C   | ALA | 482 | 46.463 | 33.152 | 28.524 | 1.00 | 13.21 |
| ATOM | 3295 | O   | ALA | 482 | 45.372 | 33.620 | 28.861 | 1.00 | 10.82 |
| ATOM | 3296 | N   | LEU | 483 | 46.722 | 31.848 | 28.538 | 1.00 | 11.90 |
| ATOM | 3297 | CA  | LEU | 483 | 45.712 | 30.897 | 28.978 | 1.00 | 14.01 |
| ATOM | 3298 | CB  | LEU | 483 | 46.260 | 29.468 | 28.910 | 1.00 | 11.66 |
| ATOM | 3299 | CG  | LEU | 483 | 46.455 | 28.896 | 27.498 | 1.00 | 10.77 |
| ATOM | 3300 | CD1 | LEU | 483 | 47.098 | 27.517 | 27.587 | 1.00 | 8.72  |
| ATOM | 3301 | CD2 | LEU | 483 | 45.118 | 28.813 | 26.785 | 1.00 | 7.73  |
| ATOM | 3302 | C   | LEU | 483 | 45.268 | 31.232 | 30.401 | 1.00 | 14.37 |
| ATOM | 3303 | O   | LEU | 483 | 44.158 | 30.898 | 30.814 | 1.00 | 14.12 |
| ATOM | 3304 | N   | ASP | 484 | 46.142 | 31.894 | 31.147 | 1.00 | 15.19 |
| ATOM | 3305 | CA  | ASP | 484 | 45.810 | 32.281 | 32.511 | 1.00 | 17.15 |
| ATOM | 3306 | CB  | ASP | 484 | 47.038 | 32.146 | 33.416 | 1.00 | 19.74 |
| ATOM | 3307 | CG  | ASP | 484 | 46.787 | 32.653 | 34.830 | 1.00 | 26.92 |
| ATOM | 3308 | OD1 | ASP | 484 | 45.717 | 32.353 | 35.399 | 1.00 | 31.69 |
| ATOM | 3309 | OD2 | ASP | 484 | 47.667 | 33.344 | 35.383 | 1.00 | 30.93 |
| ATOM | 3310 | C   | ASP | 484 | 45.271 | 33.711 | 32.560 | 1.00 | 16.03 |
| ATOM | 3311 | O   | ASP | 484 | 44.101 | 33.927 | 32.860 | 1.00 | 17.57 |
| ATOM | 3312 | N   | LYS | 485 | 46.119 | 34.676 | 32.217 | 1.00 | 14.15 |
| ATOM | 3313 | CA  | LYS | 485 | 45.772 | 36.094 | 32.265 | 1.00 | 12.86 |
| ATOM | 3314 | CB  | LYS | 485 | 47.042 | 36.932 | 32.080 | 1.00 | 12.78 |
| ATOM | 3315 | CG  | LYS | 485 | 48.152 | 36.589 | 33.070 | 1.00 | 13.51 |
| ATOM | 3316 | CD  | LYS | 485 | 47.721 | 36.847 | 34.509 | 1.00 | 13.07 |
| ATOM | 3317 | CE  | LYS | 485 | 48.838 | 36.502 | 35.488 | 1.00 | 14.28 |
| ATOM | 3318 | NZ  | LYS | 485 | 48.482 | 36.832 | 36.899 | 1.00 | 12.83 |
| ATOM | 3319 | C   | LYS | 485 | 44.690 | 36.616 | 31.319 | 1.00 | 12.35 |
| ATOM | 3320 | O   | LYS | 485 | 43.823 | 37.382 | 31.739 | 1.00 | 12.38 |
| ATOM | 3321 | N   | ILE | 486 | 44.744 | 36.233 | 30.047 | 1.00 | 11.02 |
| ATOM | 3322 | CA  | ILE | 486 | 43.753 | 36.707 | 29.084 | 1.00 | 11.30 |
| ATOM | 3323 | CB  | ILE | 486 | 44.243 | 36.506 | 27.632 | 1.00 | 10.39 |
| ATOM | 3324 | CG2 | ILE | 486 | 43.126 | 36.849 | 26.649 | 1.00 | 9.22  |
| ATOM | 3325 | CG1 | ILE | 486 | 45.487 | 37.366 | 27.376 | 1.00 | 9.66  |
| ATOM | 3326 | CD1 | ILE | 486 | 45.269 | 38.863 | 27.555 | 1.00 | 12.52 |
| ATOM | 3327 | C   | ILE | 486 | 42.400 | 36.016 | 29.255 | 1.00 | 10.85 |
| ATOM | 3328 | O   | ILE | 486 | 41.354 | 36.664 | 29.228 | 1.00 | 9.72  |
| ATOM | 3329 | N   | ALA | 487 | 42.418 | 34.700 | 29.433 | 1.00 | 11.32 |
| ATOM | 3330 | CA  | ALA | 487 | 41.176 | 33.954 | 29.610 | 1.00 | 10.28 |
| ATOM | 3331 | CB  | ALA | 487 | 41.484 | 32.464 | 29.773 | 1.00 | 9.81  |
| ATOM | 3332 | C   | ALA | 487 | 40.390 | 34.462 | 30.823 | 1.00 | 10.73 |
| ATOM | 3333 | O   | ALA | 487 | 39.161 | 34.432 | 30.836 | 1.00 | 11.37 |
| ATOM | 3334 | N   | PHE | 488 | 41.110 | 34.937 | 31.834 | 1.00 | 10.32 |
| ATOM | 3335 | CA  | PHE | 488 | 40.500 | 35.426 | 33.067 | 1.00 | 11.62 |
| ATOM | 3336 | CB  | PHE | 488 | 41.574 | 35.560 | 34.149 | 1.00 | 11.67 |
| ATOM | 3337 | CG  | PHE | 488 | 41.027 | 35.846 | 35.523 | 1.00 | 14.14 |
| ATOM | 3338 | CD1 | PHE | 488 | 40.310 | 34.873 | 36.222 | 1.00 | 13.10 |
| ATOM | 3339 | CD2 | PHE | 488 | 41.256 | 37.075 | 36.134 | 1.00 | 13.14 |
| ATOM | 3340 | CE1 | PHE | 488 | 39.834 | 35.122 | 37.510 | 1.00 | 13.40 |
| ATOM | 3341 | CE2 | PHE | 488 | 40.788 | 37.332 | 37.414 | 1.00 | 11.72 |
| ATOM | 3342 | CZ  | PHE | 488 | 40.076 | 36.355 | 38.107 | 1.00 | 13.66 |

TABLE B-continued

Co-ordinates of an underglycosylated tACEΔ36NJ ACE-lisinopril complex

| ATOM | 3343 | C   | PHE | 488 | 39.765 | 36.763 | 32.931 | 1.00 | 11.30 |
| ---- | ---- | --- | --- | --- | ------ | ------ | ------ | ---- | ----- |
| ATOM | 3344 | O   | PHE | 488 | 38.809 | 37.022 | 33.662 | 1.00 | 10.92 |
| ATOM | 3345 | N   | ILE | 489 | 40.208 | 37.604 | 32.000 | 1.00 | 11.64 |
| ATOM | 3346 | CA  | ILE | 489 | 39.600 | 38.915 | 31.807 | 1.00 | 10.62 |
| ATOM | 3347 | CB  | ILE | 489 | 40.193 | 39.615 | 30.568 | 1.00 | 12.52 |
| ATOM | 3348 | CG2 | ILE | 489 | 39.378 | 40.870 | 30.215 | 1.00 | 11.83 |
| ATOM | 3349 | CG1 | ILE | 489 | 41.652 | 39.993 | 30.842 | 1.00 | 14.27 |
| ATOM | 3350 | CD1 | ILE | 489 | 41.824 | 41.029 | 31.952 | 1.00 | 13.73 |
| ATOM | 3351 | C   | ILE | 489 | 38.067 | 38.919 | 31.723 | 1.00 | 12.80 |
| ATOM | 3352 | O   | ILE | 489 | 37.406 | 39.590 | 32.514 | 1.00 | 12.29 |
| ATOM | 3353 | N   | PRO | 490 | 37.482 | 38.183 | 30.764 | 1.00 | 11.12 |
| ATOM | 3354 | CD  | PRO | 490 | 38.069 | 37.429 | 29.644 | 1.00 | 10.46 |
| ATOM | 3355 | CA  | PRO | 490 | 36.020 | 38.185 | 30.683 | 1.00 | 10.14 |
| ATOM | 3356 | CB  | PRO | 490 | 35.742 | 37.410 | 29.390 | 1.00 | 10.83 |
| ATOM | 3357 | CG  | PRO | 490 | 36.942 | 36.516 | 29.258 | 1.00 | 12.17 |
| ATOM | 3358 | C   | PRO | 490 | 35.325 | 37.586 | 31.911 | 1.00 | 9.58  |
| ATOM | 3359 | O   | PRO | 490 | 34.257 | 38.049 | 32.306 | 1.00 | 8.62  |
| ATOM | 3360 | N   | PHE | 491 | 35.925 | 36.568 | 32.521 | 1.00 | 6.98  |
| ATOM | 3361 | CA  | PHE | 491 | 35.321 | 35.969 | 33.709 | 1.00 | 9.75  |
| ATOM | 3362 | CB  | PHE | 491 | 36.067 | 34.703 | 34.137 | 1.00 | 8.88  |
| ATOM | 3363 | CG  | PHE | 491 | 35.512 | 34.074 | 35.393 | 1.00 | 9.15  |
| ATOM | 3364 | CD1 | PHE | 491 | 34.374 | 33.271 | 35.344 | 1.00 | 8.95  |
| ATOM | 3365 | CD2 | PHE | 491 | 36.109 | 34.311 | 36.630 | 1.00 | 7.55  |
| ATOM | 3366 | CE1 | PHE | 491 | 33.837 | 32.713 | 36.508 | 1.00 | 9.82  |
| ATOM | 3367 | CE2 | PHE | 491 | 35.580 | 33.757 | 37.803 | 1.00 | 9.83  |
| ATOM | 3368 | CZ  | PHE | 491 | 34.442 | 32.957 | 37.740 | 1.00 | 8.83  |
| ATOM | 3369 | C   | PHE | 491 | 35.329 | 36.948 | 34.885 | 1.00 | 9.97  |
| ATOM | 3370 | O   | PHE | 491 | 34.312 | 37.127 | 35.558 | 1.00 | 10.66 |
| ATOM | 3371 | N   | SER | 492 | 36.475 | 37.579 | 35.132 | 1.00 | 9.34  |
| ATOM | 3372 | CA  | SER | 492 | 36.589 | 38.512 | 36.249 | 1.00 | 11.14 |
| ATOM | 3373 | CB  | SER | 492 | 38.046 | 38.946 | 36.439 | 1.00 | 8.12  |
| ATOM | 3374 | OG  | SER | 492 | 38.534 | 39.643 | 35.307 | 1.00 | 11.50 |
| ATOM | 3375 | C   | SER | 492 | 35.692 | 39.738 | 36.083 | 1.00 | 11.76 |
| ATOM | 3376 | O   | SER | 492 | 35.327 | 40.391 | 37.064 | 1.00 | 13.67 |
| ATOM | 3377 | N   | TYR | 493 | 35.344 | 40.042 | 34.840 | 1.00 | 11.79 |
| ATOM | 3378 | CA  | TYR | 493 | 34.482 | 41.177 | 34.527 | 1.00 | 12.20 |
| ATOM | 3379 | CB  | TYR | 493 | 34.633 | 41.544 | 33.048 | 1.00 | 12.22 |
| ATOM | 3380 | CG  | TYR | 493 | 33.904 | 42.801 | 32.642 | 1.00 | 13.21 |
| ATOM | 3381 | CD1 | TYR | 493 | 34.295 | 44.045 | 33.134 | 1.00 | 14.67 |
| ATOM | 3382 | CE1 | TYR | 493 | 33.630 | 45.210 | 32.763 | 1.00 | 16.44 |
| ATOM | 3383 | CD2 | TYR | 493 | 32.821 | 42.751 | 31.764 | 1.00 | 13.82 |
| ATOM | 3384 | CE2 | TYR | 493 | 32.150 | 43.912 | 31.385 | 1.00 | 16.41 |
| ATOM | 3385 | CZ  | TYR | 493 | 32.561 | 45.137 | 31.889 | 1.00 | 15.04 |
| ATOM | 3386 | OH  | TYR | 493 | 31.912 | 46.285 | 31.510 | 1.00 | 14.56 |
| ATOM | 3387 | C   | TYR | 493 | 33.022 | 40.811 | 34.793 | 1.00 | 13.05 |
| ATOM | 3388 | O   | TYR | 493 | 32.254 | 41.585 | 35.363 | 1.00 | 13.30 |
| ATOM | 3389 | N   | LEU | 494 | 32.670 | 39.604 | 34.372 | 1.00 | 13.45 |
| ATOM | 3390 | CA  | LEU | 494 | 31.327 | 39.053 | 34.475 | 1.00 | 13.55 |
| ATOM | 3391 | CB  | LEU | 494 | 31.319 | 37.739 | 33.685 | 1.00 | 16.41 |
| ATOM | 3392 | CG  | LEU | 494 | 30.282 | 36.622 | 33.731 | 1.00 | 20.60 |
| ATOM | 3393 | CD1 | LEU | 494 | 30.701 | 35.590 | 32.689 | 1.00 | 21.31 |
| ATOM | 3394 | CD2 | LEU | 494 | 30.192 | 35.977 | 35.100 | 1.00 | 15.36 |
| ATOM | 3395 | C   | LEU | 494 | 30.741 | 38.834 | 35.874 | 1.00 | 11.95 |
| ATOM | 3396 | O   | LEU | 494 | 29.566 | 39.112 | 36.102 | 1.00 | 11.20 |
| ATOM | 3397 | N   | VAL | 495 | 31.544 | 38.347 | 36.810 | 1.00 | 10.36 |
| ATOM | 3398 | CA  | VAL | 495 | 31.019 | 38.055 | 38.141 | 1.00 | 10.58 |
| ATOM | 3399 | CB  | VAL | 495 | 32.139 | 37.621 | 39.109 | 1.00 | 9.66  |
| ATOM | 3400 | CG1 | VAL | 495 | 31.549 | 37.318 | 40.486 | 1.00 | 9.24  |
| ATOM | 3401 | CG2 | VAL | 495 | 32.833 | 36.376 | 38.564 | 1.00 | 12.37 |
| ATOM | 3402 | C   | VAL | 495 | 30.197 | 39.171 | 38.785 | 1.00 | 9.62  |
| ATOM | 3403 | O   | VAL | 495 | 29.047 | 38.955 | 39.154 | 1.00 | 7.39  |
| ATOM | 3404 | N   | ASP | 496 | 30.768 | 40.360 | 38.919 | 1.00 | 9.30  |
| ATOM | 3405 | CA  | ASP | 496 | 30.012 | 41.435 | 39.538 | 1.00 | 10.89 |
| ATOM | 3406 | CB  | ASP | 496 | 30.954 | 42.439 | 40.207 | 1.00 | 10.57 |
| ATOM | 3407 | CG  | ASP | 496 | 31.513 | 41.909 | 41.526 | 1.00 | 9.77  |
| ATOM | 3408 | OD1 | ASP | 496 | 31.025 | 40.855 | 41.993 | 1.00 | 9.79  |
| ATOM | 3409 | OD2 | ASP | 496 | 32.426 | 42.532 | 42.098 | 1.00 | 9.45  |
| ATOM | 3410 | C   | ASP | 496 | 29.015 | 42.125 | 38.609 | 1.00 | 11.41 |
| ATOM | 3411 | O   | ASP | 496 | 28.125 | 42.837 | 39.081 | 1.00 | 11.26 |
| ATOM | 3412 | N   | GLN | 497 | 29.143 | 41.923 | 37.298 | 1.00 | 9.61  |
| ATOM | 3413 | CA  | GLN | 497 | 28.150 | 42.511 | 36.400 | 1.00 | 11.24 |
| ATOM | 3414 | CB  | GLN | 497 | 28.471 | 42.231 | 34.926 | 1.00 | 11.55 |
| ATOM | 3415 | CG  | GLN | 497 | 29.702 | 42.954 | 34.377 | 1.00 | 13.89 |
| ATOM | 3416 | CD  | GLN | 497 | 29.672 | 44.459 | 34.613 | 1.00 | 16.12 |
| ATOM | 3417 | OE1 | GLN | 497 | 28.615 | 45.082 | 34.607 | 1.00 | 14.20 |
| ATOM | 3418 | NE2 | GLN | 497 | 30.844 | 45.048 | 34.809 | 1.00 | 17.36 |
| ATOM | 3419 | C   | GLN | 497 | 26.847 | 41.804 | 36.787 | 1.00 | 10.45 |
| ATOM | 3420 | O   | GLN | 497 | 25.774 | 42.403 | 36.794 | 1.00 | 10.85 |

TABLE B-continued

Co-ordinates of an underglycosylated tACEΔ36NJ ACE-lisinopril complex

| ATOM | 3421 | N   | TRP | 498 | 26.961 | 40.520 | 37.120 | 1.00 | 9.86  |
|------|------|-----|-----|-----|--------|--------|--------|------|-------|
| ATOM | 3422 | CA  | TRP | 498 | 25.812 | 39.717 | 37.537 | 1.00 | 10.64 |
| ATOM | 3423 | CB  | TRP | 498 | 26.189 | 38.231 | 37.571 | 1.00 | 9.73  |
| ATOM | 3424 | CG  | TRP | 498 | 25.057 | 37.318 | 37.978 | 1.00 | 9.08  |
| ATOM | 3425 | CD2 | TRP | 498 | 24.815 | 36.788 | 39.287 | 1.00 | 9.94  |
| ATOM | 3426 | CE2 | TRP | 498 | 23.634 | 36.009 | 39.213 | 1.00 | 11.43 |
| ATOM | 3427 | CE3 | TRP | 498 | 25.480 | 36.898 | 40.518 | 1.00 | 9.53  |
| ATOM | 3428 | CD1 | TRP | 498 | 24.044 | 36.851 | 37.182 | 1.00 | 10.54 |
| ATOM | 3429 | NE1 | TRP | 498 | 23.185 | 36.063 | 37.919 | 1.00 | 9.96  |
| ATOM | 3430 | CZ2 | TRP | 498 | 23.105 | 35.343 | 40.325 | 1.00 | 10.04 |
| ATOM | 3431 | CZ3 | TRP | 498 | 24.950 | 36.232 | 41.629 | 1.00 | 13.16 |
| ATOM | 3432 | CH2 | TRP | 498 | 23.773 | 35.465 | 41.520 | 1.00 | 12.54 |
| ATOM | 3433 | C   | TRP | 498 | 25.333 | 40.151 | 38.928 | 1.00 | 9.68  |
| ATOM | 3434 | O   | TRP | 498 | 24.146 | 40.398 | 39.132 | 1.00 | 10.04 |
| ATOM | 3435 | N   | ARG | 499 | 26.252 | 40.243 | 39.885 | 1.00 | 10.21 |
| ATOM | 3436 | CA  | ARG | 499 | 25.871 | 40.643 | 41.240 | 1.00 | 11.86 |
| ATOM | 3437 | CB  | ARG | 499 | 27.038 | 40.468 | 42.222 | 1.00 | 11.07 |
| ATOM | 3438 | CG  | ARG | 499 | 27.106 | 39.070 | 42.824 | 1.00 | 12.83 |
| ATOM | 3439 | CD  | ARG | 499 | 27.992 | 39.005 | 44.062 | 1.00 | 12.47 |
| ATOM | 3440 | NE  | ARG | 499 | 29.395 | 39.250 | 43.748 | 1.00 | 10.15 |
| ATOM | 3441 | CZ  | ARG | 499 | 30.409 | 38.744 | 44.439 | 1.00 | 12.88 |
| ATOM | 3442 | NH1 | ARG | 499 | 30.171 | 37.961 | 45.491 | 1.00 | 10.18 |
| ATOM | 3443 | NH2 | ARG | 499 | 31.657 | 39.000 | 44.067 | 1.00 | 10.68 |
| ATOM | 3444 | C   | ARG | 499 | 25.325 | 42.065 | 41.336 | 1.00 | 12.18 |
| ATOM | 3445 | O   | ARG | 499 | 24.395 | 42.311 | 42.098 | 1.00 | 11.36 |
| ATOM | 3446 | N   | TRP | 500 | 25.887 | 42.996 | 40.568 | 1.00 | 11.77 |
| ATOM | 3447 | CA  | TRP | 500 | 25.391 | 44.368 | 40.605 | 1.00 | 12.08 |
| ATOM | 3448 | CB  | TRP | 500 | 26.202 | 45.289 | 39.684 | 1.00 | 10.66 |
| ATOM | 3449 | CG  | TRP | 500 | 27.602 | 45.521 | 40.139 | 1.00 | 10.40 |
| ATOM | 3450 | CD2 | TRP | 500 | 28.677 | 46.051 | 39.357 | 1.00 | 11.41 |
| ATOM | 3451 | CE2 | TRP | 500 | 29.821 | 46.074 | 40.183 | 1.00 | 11.19 |
| ATOM | 3452 | CE3 | TRP | 500 | 28.786 | 46.504 | 38.034 | 1.00 | 11.44 |
| ATOM | 3453 | CD1 | TRP | 500 | 28.119 | 45.261 | 41.374 | 1.00 | 9.78  |
| ATOM | 3454 | NE1 | TRP | 500 | 29.451 | 45.589 | 41.409 | 1.00 | 10.36 |
| ATOM | 3455 | CZ2 | TRP | 500 | 31.062 | 46.536 | 39.731 | 1.00 | 10.56 |
| ATOM | 3456 | CZ3 | TRP | 500 | 30.021 | 46.963 | 37.585 | 1.00 | 11.49 |
| ATOM | 3457 | CH2 | TRP | 500 | 31.143 | 46.972 | 38.434 | 1.00 | 9.70  |
| ATOM | 3458 | C   | TRP | 500 | 23.933 | 44.407 | 40.174 | 1.00 | 13.08 |
| ATOM | 3459 | O   | TRP | 500 | 23.143 | 45.188 | 40.703 | 1.00 | 12.40 |
| ATOM | 3460 | N   | ARG | 501 | 23.581 | 43.565 | 39.207 | 1.00 | 11.92 |
| ATOM | 3461 | CA  | ARG | 501 | 22.209 | 43.525 | 38.719 | 1.00 | 12.19 |
| ATOM | 3462 | CB  | ARG | 501 | 22.176 | 42.962 | 37.298 | 1.00 | 13.67 |
| ATOM | 3463 | CG  | ARG | 501 | 22.833 | 43.881 | 36.281 | 1.00 | 17.51 |
| ATOM | 3464 | CD  | ARG | 501 | 22.956 | 43.199 | 34.929 | 1.00 | 23.14 |
| ATOM | 3465 | NE  | ARG | 501 | 21.650 | 42.807 | 34.407 | 1.00 | 28.87 |
| ATOM | 3466 | CZ  | ARG | 501 | 21.443 | 41.731 | 33.656 | 1.00 | 30.18 |
| ATOM | 3467 | NH1 | ARG | 501 | 22.458 | 40.936 | 33.340 | 1.00 | 30.67 |
| ATOM | 3468 | NH2 | ARG | 501 | 20.222 | 41.448 | 33.223 | 1.00 | 31.24 |
| ATOM | 3469 | C   | ARG | 501 | 21.296 | 42.732 | 39.653 | 1.00 | 10.77 |
| ATOM | 3470 | O   | ARG | 501 | 20.081 | 42.891 | 39.626 | 1.00 | 10.89 |
| ATOM | 3471 | N   | VAL | 502 | 21.884 | 41.865 | 40.468 | 1.00 | 9.90  |
| ATOM | 3472 | CA  | VAL | 502 | 21.100 | 41.120 | 41.439 | 1.00 | 10.52 |
| ATOM | 3473 | CB  | VAL | 502 | 21.896 | 39.940 | 42.034 | 1.00 | 9.49  |
| ATOM | 3474 | CG1 | VAL | 502 | 21.205 | 39.425 | 43.285 | 1.00 | 8.80  |
| ATOM | 3475 | CG2 | VAL | 502 | 22.008 | 38.812 | 41.002 | 1.00 | 12.29 |
| ATOM | 3476 | C   | VAL | 502 | 20.786 | 42.126 | 42.551 | 1.00 | 12.15 |
| ATOM | 3477 | O   | VAL | 502 | 19.643 | 42.245 | 42.999 | 1.00 | 10.37 |
| ATOM | 3478 | N   | PHE | 503 | 21.815 | 42.865 | 42.965 | 1.00 | 11.50 |
| ATOM | 3479 | CA  | PHE | 503 | 21.678 | 43.864 | 44.018 | 1.00 | 11.51 |
| ATOM | 3480 | CB  | PHE | 503 | 23.057 | 44.434 | 44.386 | 1.00 | 10.31 |
| ATOM | 3481 | CG  | PHE | 503 | 23.939 | 43.463 | 45.144 | 1.00 | 11.73 |
| ATOM | 3482 | CD1 | PHE | 503 | 25.324 | 43.571 | 45.085 | 1.00 | 11.85 |
| ATOM | 3483 | CD2 | PHE | 503 | 23.384 | 42.451 | 45.925 | 1.00 | 12.62 |
| ATOM | 3484 | CE1 | PHE | 503 | 26.146 | 42.693 | 45.787 | 1.00 | 10.68 |
| ATOM | 3485 | CE2 | PHE | 503 | 24.199 | 41.564 | 46.633 | 1.00 | 10.51 |
| ATOM | 3486 | CZ  | PHE | 503 | 25.582 | 41.686 | 46.563 | 1.00 | 12.31 |
| ATOM | 3487 | C   | PHE | 503 | 20.711 | 44.995 | 43.661 | 1.00 | 10.96 |
| ATOM | 3488 | O   | PHE | 503 | 19.896 | 45.384 | 44.497 | 1.00 | 9.00  |
| ATOM | 3489 | N   | ASP | 504 | 20.779 | 45.519 | 42.435 | 1.00 | 12.29 |
| ATOM | 3490 | CA  | ASP | 504 | 19.866 | 46.599 | 42.058 | 1.00 | 12.07 |
| ATOM | 3491 | CB  | ASP | 504 | 20.451 | 47.479 | 40.931 | 1.00 | 13.57 |
| ATOM | 3492 | CG  | ASP | 504 | 20.413 | 46.822 | 39.548 | 1.00 | 13.98 |
| ATOM | 3493 | OD1 | ASP | 504 | 19.775 | 45.766 | 39.358 | 1.00 | 14.51 |
| ATOM | 3494 | OD2 | ASP | 504 | 21.033 | 47.396 | 38.633 | 1.00 | 15.18 |
| ATOM | 3495 | C   | ASP | 504 | 18.470 | 46.107 | 41.685 | 1.00 | 13.54 |
| ATOM | 3496 | O   | ASP | 504 | 17.615 | 46.892 | 41.278 | 1.00 | 13.18 |
| ATOM | 3497 | N   | GLY | 505 | 18.239 | 44.805 | 41.833 | 1.00 | 14.58 |
| ATOM | 3498 | CA  | GLY | 505 | 16.929 | 44.244 | 41.540 | 1.00 | 15.30 |

TABLE B-continued

Co-ordinates of an underglycosylated tACEΔ36NJ ACE-lisinopril complex

| ATOM | 3499 | C | GLY | 505 | 16.590 | 43.920 | 40.095 | 1.00 | 16.54 |
|---|---|---|---|---|---|---|---|---|---|
| ATOM | 3500 | O | GLY | 505 | 15.457 | 43.528 | 39.808 | 1.00 | 17.31 |
| ATOM | 3501 | N | SER | 506 | 17.547 | 44.088 | 39.185 | 1.00 | 15.04 |
| ATOM | 3502 | CA | SER | 506 | 17.324 | 43.793 | 37.770 | 1.00 | 15.72 |
| ATOM | 3503 | CB | SER | 506 | 18.498 | 44.294 | 36.925 | 1.00 | 15.59 |
| ATOM | 3504 | OG | SER | 506 | 18.587 | 45.701 | 36.956 | 1.00 | 22.52 |
| ATOM | 3505 | C | SER | 506 | 17.167 | 42.292 | 37.541 | 1.00 | 15.40 |
| ATOM | 3506 | O | SER | 506 | 16.505 | 41.869 | 36.594 | 1.00 | 15.35 |
| ATOM | 3507 | N | ILE | 507 | 17.797 | 41.496 | 38.401 | 1.00 | 13.34 |
| ATOM | 3508 | CA | ILE | 507 | 17.731 | 40.041 | 38.303 | 1.00 | 13.69 |
| ATOM | 3509 | CB | ILE | 507 | 19.148 | 39.426 | 38.171 | 1.00 | 14.13 |
| ATOM | 3510 | CG2 | ILE | 507 | 19.057 | 37.904 | 38.086 | 1.00 | 11.80 |
| ATOM | 3511 | CG1 | ILE | 507 | 19.858 | 40.002 | 36.939 | 1.00 | 11.87 |
| ATOM | 3512 | CD1 | ILE | 507 | 21.333 | 39.646 | 36.867 | 1.00 | 10.97 |
| ATOM | 3513 | C | ILE | 507 | 17.082 | 39.496 | 39.574 | 1.00 | 14.19 |
| ATOM | 3514 | O | ILE | 507 | 17.602 | 39.698 | 40.669 | 1.00 | 13.99 |
| ATOM | 3515 | N | THR | 508 | 15.946 | 38.815 | 39.428 | 1.00 | 13.82 |
| ATOM | 3516 | CA | THR | 508 | 15.237 | 38.239 | 40.573 | 1.00 | 13.91 |
| ATOM | 3517 | CB | THR | 508 | 13.707 | 38.241 | 40.364 | 1.00 | 14.70 |
| ATOM | 3518 | OG1 | THR | 508 | 13.358 | 37.257 | 39.381 | 1.00 | 15.53 |
| ATOM | 3519 | CG2 | THR | 508 | 13.232 | 39.606 | 39.894 | 1.00 | 13.66 |
| ATOM | 3520 | C | THR | 508 | 15.678 | 36.794 | 40.736 | 1.00 | 14.81 |
| ATOM | 3521 | O | THR | 508 | 16.327 | 36.241 | 39.846 | 1.00 | 11.64 |
| ATOM | 3522 | N | LYS | 509 | 15.310 | 36.176 | 41.858 | 1.00 | 15.94 |
| ATOM | 3523 | CA | LYS | 509 | 15.694 | 34.790 | 42.106 | 1.00 | 17.89 |
| ATOM | 3524 | CB | LYS | 509 | 15.249 | 34.334 | 43.502 | 1.00 | 18.63 |
| ATOM | 3525 | CG | LYS | 509 | 13.769 | 33.992 | 43.637 | 1.00 | 20.95 |
| ATOM | 3526 | CD | LYS | 509 | 13.463 | 33.460 | 45.033 | 1.00 | 21.83 |
| ATOM | 3527 | CE | LYS | 509 | 11.988 | 33.146 | 45.204 | 1.00 | 23.26 |
| ATOM | 3528 | NZ | LYS | 509 | 11.687 | 32.724 | 46.600 | 1.00 | 23.66 |
| ATOM | 3529 | C | LYS | 509 | 15.109 | 33.854 | 41.057 | 1.00 | 18.81 |
| ATOM | 3530 | O | LYS | 509 | 15.497 | 32.690 | 40.979 | 1.00 | 20.85 |
| ATOM | 3531 | N | GLU | 510 | 14.171 | 34.353 | 40.257 | 1.00 | 18.47 |
| ATOM | 3532 | CA | GLU | 510 | 13.574 | 33.535 | 39.206 | 1.00 | 20.76 |
| ATOM | 3533 | CB | GLU | 510 | 12.282 | 34.163 | 38.696 | 1.00 | 22.98 |
| ATOM | 3534 | CG | GLU | 510 | 11.274 | 34.507 | 39.761 | 1.00 | 33.06 |
| ATOM | 3535 | CD | GLU | 510 | 10.120 | 35.306 | 39.196 | 1.00 | 36.53 |
| ATOM | 3536 | OE1 | GLU | 510 | 10.366 | 36.379 | 38.599 | 1.00 | 39.46 |
| ATOM | 3537 | OE2 | GLU | 510 | 8.971 | 34.859 | 39.349 | 1.00 | 39.85 |
| ATOM | 3538 | C | GLU | 510 | 14.536 | 33.437 | 38.025 | 1.00 | 20.25 |
| ATOM | 3539 | O | GLU | 510 | 14.526 | 32.452 | 37.283 | 1.00 | 19.03 |
| ATOM | 3540 | N | ASN | 511 | 15.365 | 34.465 | 37.862 | 1.00 | 17.63 |
| ATOM | 3541 | CA | ASN | 511 | 16.298 | 34.522 | 36.746 | 1.00 | 17.82 |
| ATOM | 3542 | CB | ASN | 511 | 15.984 | 35.756 | 35.891 | 1.00 | 19.14 |
| ATOM | 3543 | CG | ASN | 511 | 14.541 | 35.779 | 35.410 | 1.00 | 25.49 |
| ATOM | 3544 | OD1 | ASN | 511 | 14.080 | 34.843 | 34.756 | 1.00 | 27.61 |
| ATOM | 3545 | ND2 | ASN | 511 | 13.819 | 36.848 | 35.734 | 1.00 | 24.85 |
| ATOM | 3546 | C | ASN | 511 | 17.785 | 34.510 | 37.111 | 1.00 | 16.09 |
| ATOM | 3547 | O | ASN | 511 | 18.630 | 34.792 | 36.260 | 1.00 | 13.99 |
| ATOM | 3548 | N | TYR | 512 | 18.102 | 34.187 | 38.363 | 1.00 | 12.83 |
| ATOM | 3549 | CA | TYR | 512 | 19.494 | 34.128 | 38.804 | 1.00 | 11.97 |
| ATOM | 3550 | CB | TYR | 512 | 19.617 | 33.360 | 40.120 | 1.00 | 12.23 |
| ATOM | 3551 | CG | TYR | 512 | 19.249 | 34.090 | 41.390 | 1.00 | 12.34 |
| ATOM | 3552 | CD1 | TYR | 512 | 19.016 | 33.370 | 42.561 | 1.00 | 13.62 |
| ATOM | 3553 | CE1 | TYR | 512 | 18.717 | 34.007 | 43.755 | 1.00 | 14.61 |
| ATOM | 3554 | CD2 | TYR | 512 | 19.172 | 35.484 | 41.446 | 1.00 | 12.45 |
| ATOM | 3555 | CE2 | TYR | 512 | 18.872 | 36.137 | 42.651 | 1.00 | 13.77 |
| ATOM | 3556 | CZ | TYR | 512 | 18.647 | 35.381 | 43.799 | 1.00 | 13.86 |
| ATOM | 3557 | OH | TYR | 512 | 18.358 | 35.977 | 45.004 | 1.00 | 17.23 |
| ATOM | 3558 | C | TYR | 512 | 20.385 | 33.396 | 37.798 | 1.00 | 12.56 |
| ATOM | 3559 | O | TYR | 512 | 21.299 | 33.970 | 37.199 | 1.00 | 10.13 |
| ATOM | 3560 | N | ASN | 513 | 20.105 | 32.108 | 37.639 | 1.00 | 11.91 |
| ATOM | 3561 | CA | ASN | 513 | 20.894 | 31.247 | 36.776 | 1.00 | 11.83 |
| ATOM | 3562 | CB | ASN | 513 | 20.482 | 29.792 | 36.985 | 1.00 | 11.58 |
| ATOM | 3563 | CG | ASN | 513 | 21.672 | 28.859 | 36.980 | 1.00 | 11.83 |
| ATOM | 3564 | OD1 | ASN | 513 | 22.613 | 29.054 | 37.743 | 1.00 | 14.77 |
| ATOM | 3565 | ND2 | ASN | 513 | 21.644 | 27.848 | 36.118 | 1.00 | 7.41 |
| ATOM | 3566 | C | ASN | 513 | 20.872 | 31.572 | 35.299 | 1.00 | 12.10 |
| ATOM | 3567 | O | ASN | 513 | 21.918 | 31.536 | 34.637 | 1.00 | 10.25 |
| ATOM | 3568 | N | GLN | 514 | 19.690 | 31.882 | 34.775 | 1.00 | 11.72 |
| ATOM | 3569 | CA | GLN | 514 | 19.568 | 32.194 | 33.362 | 1.00 | 14.72 |
| ATOM | 3570 | CB | GLN | 514 | 18.089 | 32.356 | 32.979 | 1.00 | 17.46 |
| ATOM | 3571 | CG | GLN | 514 | 17.260 | 31.066 | 33.144 | 1.00 | 23.70 |
| ATOM | 3572 | CD | GLN | 514 | 16.576 | 30.934 | 34.510 | 1.00 | 25.81 |
| ATOM | 3573 | OE1 | GLN | 514 | 17.121 | 31.322 | 35.552 | 1.00 | 21.12 |
| ATOM | 3574 | NE2 | GLN | 514 | 15.375 | 30.363 | 34.502 | 1.00 | 29.42 |
| ATOM | 3575 | C | GLN | 514 | 20.369 | 33.446 | 32.994 | 1.00 | 14.10 |
| ATOM | 3576 | O | GLN | 514 | 20.973 | 33.511 | 31.918 | 1.00 | 13.15 |

TABLE B-continued

Co-ordinates of an underglycosylated tACEΔ36NJ ACE-lisinopril complex

| ATOM | 3577 | N | GLU | 515 | 20.391 | 34.432 | 33.887 | 1.00 | 13.07 |
|---|---|---|---|---|---|---|---|---|---|
| ATOM | 3578 | CA | GLU | 515 | 21.136 | 35.660 | 33.615 | 1.00 | 12.06 |
| ATOM | 3579 | CB | GLU | 515 | 20.656 | 36.802 | 34.519 | 1.00 | 16.07 |
| ATOM | 3580 | CG | GLU | 515 | 19.244 | 37.290 | 34.190 | 1.00 | 18.59 |
| ATOM | 3581 | CD | GLU | 515 | 19.084 | 37.659 | 32.719 | 1.00 | 24.12 |
| ATOM | 3582 | OE1 | GLU | 515 | 19.829 | 38.544 | 32.235 | 1.00 | 24.75 |
| ATOM | 3583 | OE2 | GLU | 515 | 18.214 | 37.060 | 32.046 | 1.00 | 26.20 |
| ATOM | 3584 | C | GLU | 515 | 22.626 | 35.420 | 33.805 | 1.00 | 10.94 |
| ATOM | 3585 | O | GLU | 515 | 23.454 | 36.089 | 33.190 | 1.00 | 12.49 |
| ATOM | 3586 | N | TRP | 516 | 22.970 | 34.466 | 34.660 | 1.00 | 9.41 |
| ATOM | 3587 | CA | TRP | 516 | 24.374 | 34.135 | 34.873 | 1.00 | 9.43 |
| ATOM | 3588 | CB | TRP | 516 | 24.513 | 33.135 | 36.030 | 1.00 | 9.02 |
| ATOM | 3589 | CG | TRP | 516 | 25.865 | 32.477 | 36.148 | 1.00 | 10.43 |
| ATOM | 3590 | CD2 | TRP | 516 | 27.026 | 33.004 | 36.804 | 1.00 | 10.48 |
| ATOM | 3591 | CE2 | TRP | 516 | 28.037 | 32.019 | 36.718 | 1.00 | 10.91 |
| ATOM | 3592 | CE3 | TRP | 516 | 27.311 | 34.210 | 37.458 | 1.00 | 10.58 |
| ATOM | 3593 | CD1 | TRP | 516 | 26.212 | 31.235 | 35.697 | 1.00 | 11.18 |
| ATOM | 3594 | NE1 | TRP | 516 | 27.514 | 30.951 | 36.038 | 1.00 | 12.53 |
| ATOM | 3595 | CZ2 | TRP | 516 | 29.314 | 32.201 | 37.263 | 1.00 | 11.44 |
| ATOM | 3596 | CZ3 | TRP | 516 | 28.583 | 34.393 | 38.002 | 1.00 | 11.75 |
| ATOM | 3597 | CH2 | TRP | 516 | 29.568 | 33.390 | 37.899 | 1.00 | 11.65 |
| ATOM | 3598 | C | TRP | 516 | 24.912 | 33.542 | 33.575 | 1.00 | 9.00 |
| ATOM | 3599 | O | TRP | 516 | 25.971 | 33.943 | 33.088 | 1.00 | 10.05 |
| ATOM | 3600 | N | TRP | 517 | 24.167 | 32.605 | 32.993 | 1.00 | 9.12 |
| ATOM | 3601 | CA | TRP | 517 | 24.609 | 31.995 | 31.746 | 1.00 | 9.56 |
| ATOM | 3602 | CB | TRP | 517 | 23.855 | 30.689 | 31.497 | 1.00 | 8.95 |
| ATOM | 3603 | CG | TRP | 517 | 24.458 | 29.614 | 32.334 | 1.00 | 7.44 |
| ATOM | 3604 | CD2 | TRP | 517 | 25.729 | 28.992 | 32.118 | 1.00 | 8.27 |
| ATOM | 3605 | CE2 | TRP | 517 | 25.994 | 28.176 | 33.240 | 1.00 | 7.79 |
| ATOM | 3606 | CE3 | TRP | 517 | 26.678 | 29.052 | 31.084 | 1.00 | 9.26 |
| ATOM | 3607 | CD1 | TRP | 517 | 24.007 | 29.154 | 33.540 | 1.00 | 6.42 |
| ATOM | 3608 | NE1 | TRP | 517 | 24.927 | 28.292 | 34.093 | 1.00 | 8.16 |
| ATOM | 3609 | CZ2 | TRP | 517 | 27.166 | 27.424 | 33.359 | 1.00 | 9.24 |
| ATOM | 3610 | CZ3 | TRP | 517 | 27.848 | 28.301 | 31.204 | 1.00 | 10.00 |
| ATOM | 3611 | CH2 | TRP | 517 | 28.080 | 27.500 | 32.333 | 1.00 | 8.75 |
| ATOM | 3612 | C | TRP | 517 | 24.549 | 32.927 | 30.538 | 1.00 | 10.22 |
| ATOM | 3613 | O | TRP | 517 | 25.321 | 32.769 | 29.593 | 1.00 | 10.24 |
| ATOM | 3614 | N | SER | 518 | 23.654 | 33.908 | 30.566 | 1.00 | 11.02 |
| ATOM | 3615 | CA | SER | 518 | 23.588 | 34.863 | 29.467 | 1.00 | 13.01 |
| ATOM | 3616 | CB | SER | 518 | 22.407 | 35.823 | 29.631 | 1.00 | 14.72 |
| ATOM | 3617 | OG | SER | 518 | 21.187 | 35.175 | 29.332 | 1.00 | 22.10 |
| ATOM | 3618 | C | SER | 518 | 24.887 | 35.663 | 29.462 | 1.00 | 11.80 |
| ATOM | 3619 | O | SER | 518 | 25.375 | 36.072 | 28.405 | 1.00 | 10.96 |
| ATOM | 3620 | N | LEU | 519 | 25.441 | 35.889 | 30.650 | 1.00 | 10.02 |
| ATOM | 3621 | CA | LEU | 519 | 26.685 | 36.638 | 30.763 | 1.00 | 11.52 |
| ATOM | 3622 | CB | LEU | 519 | 26.828 | 37.219 | 32.173 | 1.00 | 11.07 |
| ATOM | 3623 | CG | LEU | 519 | 25.804 | 38.316 | 32.491 | 1.00 | 13.05 |
| ATOM | 3624 | CD1 | LEU | 519 | 25.934 | 38.733 | 33.949 | 1.00 | 12.54 |
| ATOM | 3625 | CD2 | LEU | 519 | 26.017 | 39.504 | 31.570 | 1.00 | 13.76 |
| ATOM | 3626 | C | LEU | 519 | 27.876 | 35.744 | 30.430 | 1.00 | 11.25 |
| ATOM | 3627 | O | LEU | 519 | 28.826 | 36.179 | 29.773 | 1.00 | 10.48 |
| ATOM | 3628 | N | ARG | 520 | 27.817 | 34.497 | 30.887 | 1.00 | 10.34 |
| ATOM | 3629 | CA | ARG | 520 | 28.875 | 33.529 | 30.611 | 1.00 | 11.93 |
| ATOM | 3630 | CB | ARG | 520 | 28.493 | 32.160 | 31.186 | 1.00 | 10.95 |
| ATOM | 3631 | CG | ARG | 520 | 28.568 | 32.095 | 32.713 | 1.00 | 10.19 |
| ATOM | 3632 | CD | ARG | 520 | 29.973 | 31.757 | 33.176 | 1.00 | 9.98 |
| ATOM | 3633 | NE | ARG | 520 | 30.136 | 30.320 | 33.403 | 1.00 | 11.36 |
| ATOM | 3634 | CZ | ARG | 520 | 31.303 | 29.717 | 33.615 | 1.00 | 12.10 |
| ATOM | 3635 | NH1 | ARG | 520 | 31.342 | 28.404 | 33.827 | 1.00 | 10.85 |
| ATOM | 3636 | NH2 | ARG | 520 | 32.432 | 30.419 | 33.595 | 1.00 | 7.63 |
| ATOM | 3637 | C | ARG | 520 | 29.062 | 33.433 | 29.097 | 1.00 | 12.63 |
| ATOM | 3638 | O | ARG | 520 | 30.186 | 33.326 | 28.595 | 1.00 | 11.60 |
| ATOM | 3639 | N | LEU | 521 | 27.944 | 33.472 | 28.378 | 1.00 | 11.30 |
| ATOM | 3640 | CA | LEU | 521 | 27.957 | 33.406 | 26.924 | 1.00 | 11.63 |
| ATOM | 3641 | CB | LEU | 521 | 26.545 | 33.129 | 26.387 | 1.00 | 11.64 |
| ATOM | 3642 | CG | LEU | 521 | 26.436 | 33.222 | 24.858 | 1.00 | 14.85 |
| ATOM | 3643 | CD1 | LEU | 521 | 27.324 | 32.153 | 24.237 | 1.00 | 11.78 |
| ATOM | 3644 | CD2 | LEU | 521 | 24.988 | 33.049 | 24.405 | 1.00 | 13.95 |
| ATOM | 3645 | C | LEU | 521 | 28.460 | 34.717 | 26.328 | 1.00 | 10.66 |
| ATOM | 3646 | O | LEU | 521 | 29.408 | 34.738 | 25.554 | 1.00 | 12.28 |
| ATOM | 3647 | N | LYS | 522 | 27.813 | 35.811 | 26.703 | 1.00 | 12.13 |
| ATOM | 3648 | CA | LYS | 522 | 28.159 | 37.127 | 26.180 | 1.00 | 14.27 |
| ATOM | 3649 | CB | LYS | 522 | 27.267 | 38.191 | 26.826 | 1.00 | 16.64 |
| ATOM | 3650 | CG | LYS | 522 | 27.524 | 39.608 | 26.333 | 1.00 | 19.99 |
| ATOM | 3651 | CD | LYS | 522 | 26.592 | 40.589 | 27.029 | 1.00 | 21.89 |
| ATOM | 3652 | CE | LYS | 522 | 26.868 | 42.022 | 26.602 | 1.00 | 24.69 |
| ATOM | 3653 | NZ | LYS | 522 | 25.926 | 42.969 | 27.263 | 1.00 | 26.36 |
| ATOM | 3654 | C | LYS | 522 | 29.620 | 37.528 | 26.354 | 1.00 | 13.91 |

TABLE B-continued

Co-ordinates of an underglycosylated tACEΔ36NJ ACE-lisinopril complex

| ATOM | 3655 | O | LYS | 522 | 30.242 | 38.026 | 25.418 | 1.00 | 13.31 |
|---|---|---|---|---|---|---|---|---|---|
| ATOM | 3656 | N | TYR | 523 | 30.165 | 37.314 | 27.547 | 1.00 | 12.72 |
| ATOM | 3657 | CA | TYR | 523 | 31.544 | 37.699 | 27.820 | 1.00 | 13.45 |
| ATOM | 3658 | CB | TYR | 523 | 31.648 | 38.236 | 29.254 | 1.00 | 14.60 |
| ATOM | 3659 | CG | TYR | 523 | 30.942 | 39.563 | 29.417 | 1.00 | 17.65 |
| ATOM | 3660 | CD1 | TYR | 523 | 29.840 | 39.699 | 30.259 | 1.00 | 19.64 |
| ATOM | 3661 | CE1 | TYR | 523 | 29.146 | 40.916 | 30.347 | 1.00 | 20.74 |
| ATOM | 3662 | CD2 | TYR | 523 | 31.340 | 40.675 | 28.671 | 1.00 | 20.48 |
| ATOM | 3663 | CE2 | TYR | 523 | 30.662 | 41.880 | 28.752 | 1.00 | 20.67 |
| ATOM | 3664 | CZ | TYR | 523 | 29.567 | 41.994 | 29.587 | 1.00 | 21.24 |
| ATOM | 3665 | OH | TYR | 523 | 28.890 | 43.192 | 29.642 | 1.00 | 27.03 |
| ATOM | 3666 | C | TYR | 523 | 32.604 | 36.628 | 27.576 | 1.00 | 13.38 |
| ATOM | 3667 | O | TYR | 523 | 33.616 | 36.899 | 26.930 | 1.00 | 12.98 |
| ATOM | 3668 | N | GLN | 524 | 32.378 | 35.416 | 28.072 | 1.00 | 11.98 |
| ATOM | 3669 | CA | GLN | 524 | 33.355 | 34.336 | 27.891 | 1.00 | 11.74 |
| ATOM | 3670 | CB | GLN | 524 | 33.367 | 33.425 | 29.114 | 1.00 | 11.09 |
| ATOM | 3671 | CG | GLN | 524 | 34.010 | 34.009 | 30.338 | 1.00 | 9.28 |
| ATOM | 3672 | CD | GLN | 524 | 34.003 | 33.021 | 31.476 | 1.00 | 11.02 |
| ATOM | 3673 | OE1 | GLN | 524 | 32.979 | 32.832 | 32.135 | 1.00 | 12.58 |
| ATOM | 3674 | NE2 | GLN | 524 | 35.138 | 32.356 | 31.696 | 1.00 | 7.73 |
| ATOM | 3675 | C | GLN | 524 | 33.145 | 33.459 | 26.661 | 1.00 | 9.96 |
| ATOM | 3676 | O | GLN | 524 | 34.057 | 32.746 | 26.244 | 1.00 | 9.58 |
| ATOM | 3677 | N | GLY | 525 | 31.950 | 33.492 | 26.085 | 1.00 | 11.25 |
| ATOM | 3678 | CA | GLY | 525 | 31.684 | 32.655 | 24.927 | 1.00 | 10.07 |
| ATOM | 3679 | C | GLY | 525 | 31.639 | 31.190 | 25.332 | 1.00 | 11.60 |
| ATOM | 3680 | O | GLY | 525 | 32.148 | 30.316 | 24.623 | 1.00 | 12.24 |
| ATOM | 3681 | N | LEU | 526 | 31.044 | 30.921 | 26.489 | 1.00 | 9.03 |
| ATOM | 3682 | CA | LEU | 526 | 30.928 | 29.554 | 26.984 | 1.00 | 9.89 |
| ATOM | 3683 | CB | LEU | 526 | 31.560 | 29.421 | 28.374 | 1.00 | 9.34 |
| ATOM | 3684 | CG | LEU | 526 | 33.030 | 29.805 | 28.536 | 1.00 | 9.90 |
| ATOM | 3685 | CD1 | LEU | 526 | 33.426 | 29.727 | 30.015 | 1.00 | 9.26 |
| ATOM | 3686 | CD2 | LEU | 526 | 33.889 | 28.888 | 27.687 | 1.00 | 8.55 |
| ATOM | 3687 | C | LEU | 526 | 29.470 | 29.146 | 27.082 | 1.00 | 11.13 |
| ATOM | 3688 | O | LEU | 526 | 28.580 | 29.998 | 27.174 | 1.00 | 11.49 |
| ATOM | 3689 | N | CYS | 527 | 29.235 | 27.838 | 27.051 | 1.00 | 10.63 |
| ATOM | 3690 | CA | CYS | 527 | 27.894 | 27.288 | 27.177 | 1.00 | 11.97 |
| ATOM | 3691 | CB | CYS | 527 | 27.352 | 26.801 | 25.815 | 1.00 | 10.95 |
| ATOM | 3692 | SG | CYS | 527 | 28.394 | 25.617 | 24.900 | 1.00 | 18.23 |
| ATOM | 3693 | C | CYS | 527 | 27.936 | 26.137 | 28.173 | 1.00 | 10.37 |
| ATOM | 3694 | O | CYS | 527 | 28.964 | 25.482 | 28.346 | 1.00 | 10.79 |
| ATOM | 3695 | N | PRO | 528 | 26.825 | 25.900 | 28.876 | 1.00 | 11.53 |
| ATOM | 3696 | CD | PRO | 528 | 25.563 | 26.667 | 28.912 | 1.00 | 11.52 |
| ATOM | 3697 | CA | PRO | 528 | 26.818 | 24.800 | 29.844 | 1.00 | 11.48 |
| ATOM | 3698 | CB | PRO | 528 | 25.578 | 25.095 | 30.689 | 1.00 | 10.83 |
| ATOM | 3699 | CG | PRO | 528 | 24.638 | 25.744 | 29.689 | 1.00 | 12.92 |
| ATOM | 3700 | C | PRO | 528 | 26.727 | 23.472 | 29.091 | 1.00 | 12.66 |
| ATOM | 3701 | O | PRO | 528 | 25.890 | 23.317 | 28.199 | 1.00 | 12.63 |
| ATOM | 3702 | N | PRO | 529 | 27.599 | 22.504 | 29.426 | 1.00 | 11.66 |
| ATOM | 3703 | CD | PRO | 529 | 28.616 | 22.533 | 30.490 | 1.00 | 13.05 |
| ATOM | 3704 | CA | PRO | 529 | 27.585 | 21.199 | 28.756 | 1.00 | 13.58 |
| ATOM | 3705 | CB | PRO | 529 | 28.801 | 20.496 | 29.353 | 1.00 | 13.06 |
| ATOM | 3706 | CG | PRO | 529 | 28.864 | 21.064 | 30.732 | 1.00 | 12.29 |
| ATOM | 3707 | C | PRO | 529 | 26.279 | 20.448 | 29.008 | 1.00 | 14.96 |
| ATOM | 3708 | O | PRO | 529 | 25.888 | 19.587 | 28.227 | 1.00 | 15.87 |
| ATOM | 3709 | N | VAL | 530 | 25.613 | 20.787 | 30.108 | 1.00 | 14.85 |
| ATOM | 3710 | CA | VAL | 530 | 24.339 | 20.178 | 30.463 | 1.00 | 16.23 |
| ATOM | 3711 | CB | VAL | 530 | 24.449 | 19.366 | 31.779 | 1.00 | 17.35 |
| ATOM | 3712 | CG1 | VAL | 530 | 23.070 | 19.037 | 32.314 | 1.00 | 17.95 |
| ATOM | 3713 | CG2 | VAL | 530 | 25.222 | 18.084 | 31.525 | 1.00 | 18.24 |
| ATOM | 3714 | C | VAL | 530 | 23.326 | 21.306 | 30.642 | 1.00 | 16.73 |
| ATOM | 3715 | O | VAL | 530 | 23.589 | 22.282 | 31.344 | 1.00 | 16.65 |
| ATOM | 3716 | N | PRO | 531 | 22.156 | 21.198 | 29.996 | 1.00 | 16.87 |
| ATOM | 3717 | CD | PRO | 531 | 21.626 | 20.094 | 29.180 | 1.00 | 18.50 |
| ATOM | 3718 | CA | PRO | 531 | 21.165 | 22.269 | 30.149 | 1.00 | 17.92 |
| ATOM | 3719 | CB | PRO | 531 | 19.994 | 21.785 | 29.292 | 1.00 | 19.57 |
| ATOM | 3720 | CG | PRO | 531 | 20.136 | 20.284 | 29.328 | 1.00 | 21.45 |
| ATOM | 3721 | C | PRO | 531 | 20.796 | 22.473 | 31.617 | 1.00 | 18.39 |
| ATOM | 3722 | O | PRO | 531 | 20.591 | 21.510 | 32.361 | 1.00 | 16.67 |
| ATOM | 3723 | N | ARG | 532 | 20.735 | 23.732 | 32.039 | 1.00 | 17.31 |
| ATOM | 3724 | CA | ARG | 532 | 20.406 | 24.037 | 33.423 | 1.00 | 18.29 |
| ATOM | 3725 | CB | ARG | 532 | 20.853 | 25.460 | 33.770 | 1.00 | 16.22 |
| ATOM | 3726 | CG | ARG | 532 | 22.199 | 25.856 | 33.165 | 1.00 | 15.05 |
| ATOM | 3727 | CD | ARG | 532 | 23.254 | 24.770 | 33.337 | 1.00 | 15.19 |
| ATOM | 3728 | NE | ARG | 532 | 23.590 | 24.508 | 34.735 | 1.00 | 14.35 |
| ATOM | 3729 | CZ | ARG | 532 | 23.800 | 23.293 | 35.228 | 1.00 | 15.95 |
| ATOM | 3730 | NH1 | ARG | 532 | 23.698 | 22.228 | 34.433 | 1.00 | 13.26 |
| ATOM | 3731 | NH2 | ARG | 532 | 24.127 | 23.138 | 36.506 | 1.00 | 12.05 |
| ATOM | 3732 | C | ARG | 532 | 18.906 | 23.883 | 33.650 | 1.00 | 20.23 |

TABLE B-continued

Co-ordinates of an underglycosylated tACEΔ36NJ ACE-lisinopril complex

| ATOM | 3733 | O   | ARG | 532 | 18.105 | 24.076 | 32.733 | 1.00 | 19.63 |
|------|------|-----|-----|-----|--------|--------|--------|------|-------|
| ATOM | 3734 | N   | THR | 533 | 18.530 | 23.532 | 34.876 | 1.00 | 21.65 |
| ATOM | 3735 | CA  | THR | 533 | 17.124 | 23.340 | 35.220 | 1.00 | 23.17 |
| ATOM | 3736 | CB  | THR | 533 | 16.819 | 21.857 | 35.519 | 1.00 | 24.29 |
| ATOM | 3737 | OG1 | THR | 533 | 17.679 | 21.393 | 36.570 | 1.00 | 25.97 |
| ATOM | 3738 | CG2 | THR | 533 | 17.031 | 21.006 | 34.277 | 1.00 | 25.60 |
| ATOM | 3739 | C   | THR | 533 | 16.753 | 24.153 | 36.447 | 1.00 | 23.60 |
| ATOM | 3740 | O   | THR | 533 | 17.629 | 24.635 | 37.171 | 1.00 | 21.92 |
| ATOM | 3741 | N   | GLN | 534 | 15.452 | 24.300 | 36.681 | 1.00 | 24.71 |
| ATOM | 3742 | CA  | GLN | 534 | 14.973 | 25.052 | 37.832 | 1.00 | 26.41 |
| ATOM | 3743 | CB  | GLN | 534 | 13.440 | 25.044 | 37.872 | 1.00 | 28.54 |
| ATOM | 3744 | CG  | GLN | 534 | 12.845 | 25.925 | 38.964 | 1.00 | 33.07 |
| ATOM | 3745 | CD  | GLN | 534 | 12.569 | 25.166 | 40.249 | 1.00 | 36.01 |
| ATOM | 3746 | OE1 | GLN | 534 | 13.114 | 24.084 | 40.475 | 1.00 | 38.09 |
| ATOM | 3747 | NE2 | GLN | 534 | 11.722 | 25.735 | 41.104 | 1.00 | 36.23 |
| ATOM | 3748 | C   | GLN | 534 | 15.550 | 24.404 | 39.087 | 1.00 | 25.91 |
| ATOM | 3749 | O   | GLN | 534 | 15.444 | 23.192 | 39.279 | 1.00 | 28.56 |
| ATOM | 3750 | N   | GLY | 535 | 16.173 | 25.211 | 39.936 | 1.00 | 24.41 |
| ATOM | 3751 | CA  | GLY | 535 | 16.775 | 24.673 | 41.140 | 1.00 | 20.69 |
| ATOM | 3752 | C   | GLY | 535 | 18.281 | 24.852 | 41.105 | 1.00 | 18.98 |
| ATOM | 3753 | O   | GLY | 535 | 18.934 | 24.861 | 42.146 | 1.00 | 20.39 |
| ATOM | 3754 | N   | ASP | 536 | 18.842 | 24.986 | 39.906 | 1.00 | 16.53 |
| ATOM | 3755 | CA  | ASP | 536 | 20.281 | 25.186 | 39.778 | 1.00 | 15.72 |
| ATOM | 3756 | CB  | ASP | 536 | 20.761 | 24.930 | 38.341 | 1.00 | 14.56 |
| ATOM | 3757 | CG  | ASP | 536 | 20.792 | 23.451 | 37.980 | 1.00 | 15.32 |
| ATOM | 3758 | OD1 | ASP | 536 | 20.996 | 22.613 | 38.883 | 1.00 | 16.51 |
| ATOM | 3759 | OD2 | ASP | 536 | 20.632 | 23.131 | 36.784 | 1.00 | 15.49 |
| ATOM | 3760 | C   | ASP | 536 | 20.635 | 26.620 | 40.157 | 1.00 | 13.62 |
| ATOM | 3761 | O   | ASP | 536 | 19.855 | 27.539 | 39.930 | 1.00 | 15.72 |
| ATOM | 3762 | N   | PHE | 537 | 21.809 | 26.794 | 40.747 | 1.00 | 12.29 |
| ATOM | 3763 | CA  | PHE | 537 | 22.308 | 28.109 | 41.139 | 1.00 | 11.39 |
| ATOM | 3764 | CB  | PHE | 537 | 21.913 | 28.443 | 42.583 | 1.00 | 10.12 |
| ATOM | 3765 | CG  | PHE | 537 | 22.366 | 29.807 | 43.042 | 1.00 |  9.09 |
| ATOM | 3766 | CD1 | PHE | 537 | 22.014 | 30.950 | 42.335 | 1.00 |  9.35 |
| ATOM | 3767 | CD2 | PHE | 537 | 23.151 | 29.943 | 44.189 | 1.00 | 12.40 |
| ATOM | 3768 | CE1 | PHE | 537 | 22.433 | 32.218 | 42.759 | 1.00 | 12.30 |
| ATOM | 3769 | CE2 | PHE | 537 | 23.578 | 31.205 | 44.627 | 1.00 | 11.45 |
| ATOM | 3770 | CZ  | PHE | 537 | 23.217 | 32.344 | 43.908 | 1.00 | 12.12 |
| ATOM | 3771 | C   | PHE | 537 | 23.817 | 27.983 | 41.008 | 1.00 |  9.37 |
| ATOM | 3772 | O   | PHE | 537 | 24.548 | 27.889 | 41.991 | 1.00 |  7.21 |
| ATOM | 3773 | N   | ASP | 538 | 24.266 | 27.956 | 39.762 | 1.00 | 11.11 |
| ATOM | 3774 | CA  | ASP | 538 | 25.675 | 27.811 | 39.461 | 1.00 | 10.38 |
| ATOM | 3775 | CB  | ASP | 538 | 25.853 | 27.736 | 37.944 | 1.00 | 10.80 |
| ATOM | 3776 | CG  | ASP | 538 | 25.031 | 26.605 | 37.329 | 1.00 | 12.13 |
| ATOM | 3777 | OD1 | ASP | 538 | 24.925 | 25.533 | 37.965 | 1.00 | 11.88 |
| ATOM | 3778 | OD2 | ASP | 538 | 24.491 | 26.778 | 36.220 | 1.00 | 13.46 |
| ATOM | 3779 | C   | ASP | 538 | 26.567 | 28.882 | 40.095 | 1.00 | 10.52 |
| ATOM | 3780 | O   | ASP | 538 | 27.694 | 28.590 | 40.489 | 1.00 | 11.65 |
| ATOM | 3781 | N   | PRO | 539 | 26.079 | 30.132 | 40.219 | 1.00 | 10.22 |
| ATOM | 3782 | CD  | PRO | 539 | 24.848 | 30.756 | 39.699 | 1.00 |  9.12 |
| ATOM | 3783 | CA  | PRO | 539 | 26.951 | 31.138 | 40.841 | 1.00 | 10.73 |
| ATOM | 3784 | CB  | PRO | 539 | 26.076 | 32.390 | 40.868 | 1.00 |  9.39 |
| ATOM | 3785 | CG  | PRO | 539 | 25.233 | 32.228 | 39.636 | 1.00 | 11.07 |
| ATOM | 3786 | C   | PRO | 539 | 27.367 | 30.710 | 42.254 | 1.00 | 11.37 |
| ATOM | 3787 | O   | PRO | 539 | 28.469 | 31.021 | 42.716 | 1.00 | 11.84 |
| ATOM | 3788 | N   | GLY | 540 | 26.472 | 30.001 | 42.935 | 1.00 | 10.64 |
| ATOM | 3789 | CA  | GLY | 540 | 26.762 | 29.551 | 44.287 | 1.00 | 12.15 |
| ATOM | 3790 | C   | GLY | 540 | 27.897 | 28.547 | 44.348 | 1.00 | 11.90 |
| ATOM | 3791 | O   | GLY | 540 | 28.416 | 28.254 | 45.427 | 1.00 | 11.97 |
| ATOM | 3792 | N   | ALA | 541 | 28.285 | 28.022 | 43.189 | 1.00 | 11.60 |
| ATOM | 3793 | CA  | ALA | 541 | 29.370 | 27.048 | 43.107 | 1.00 | 11.56 |
| ATOM | 3794 | CB  | ALA | 541 | 29.133 | 26.093 | 41.931 | 1.00 | 13.00 |
| ATOM | 3795 | C   | ALA | 541 | 30.737 | 27.725 | 42.965 | 1.00 | 11.57 |
| ATOM | 3796 | O   | ALA | 541 | 31.753 | 27.057 | 42.760 | 1.00 | 11.83 |
| ATOM | 3797 | N   | LYS | 542 | 30.752 | 29.052 | 43.064 | 1.00 | 11.43 |
| ATOM | 3798 | CA  | LYS | 542 | 31.992 | 29.824 | 42.984 | 1.00 | 11.78 |
| ATOM | 3799 | CB  | LYS | 542 | 31.891 | 30.884 | 41.878 | 1.00 | 10.91 |
| ATOM | 3800 | CG  | LYS | 542 | 33.109 | 31.805 | 41.772 | 1.00 |  8.80 |
| ATOM | 3801 | CD  | LYS | 542 | 34.399 | 31.022 | 41.509 | 1.00 |  8.48 |
| ATOM | 3802 | CE  | LYS | 542 | 35.618 | 31.946 | 41.540 | 1.00 |  8.38 |
| ATOM | 3803 | NZ  | LYS | 542 | 36.909 | 31.210 | 41.407 | 1.00 |  9.81 |
| ATOM | 3804 | C   | LYS | 542 | 32.199 | 30.484 | 44.353 | 1.00 | 12.26 |
| ATOM | 3805 | O   | LYS | 542 | 31.374 | 31.280 | 44.803 | 1.00 | 11.13 |
| ATOM | 3806 | N   | PHE | 543 | 33.305 | 30.137 | 45.004 | 1.00 | 13.11 |
| ATOM | 3807 | CA  | PHE | 543 | 33.637 | 30.632 | 46.343 | 1.00 | 13.89 |
| ATOM | 3808 | CB  | PHE | 543 | 35.152 | 30.580 | 46.561 | 1.00 | 13.28 |
| ATOM | 3809 | CG  | PHE | 543 | 35.591 | 31.133 | 47.890 | 1.00 | 15.40 |
| ATOM | 3810 | CD1 | PHE | 543 | 35.490 | 30.363 | 49.048 | 1.00 | 14.58 |

TABLE B-continued

Co-ordinates of an underglycosylated tACEΔ36NJ ACE-lisinopril complex

| ATOM | 3811 | CD2 | PHE | 543 | 36.082 | 32.435 | 47.990 | 1.00 | 13.56 |
|---|---|---|---|---|---|---|---|---|---|
| ATOM | 3812 | CE1 | PHE | 543 | 35.873 | 30.883 | 50.289 | 1.00 | 12.64 |
| ATOM | 3813 | CE2 | PHE | 543 | 36.465 | 32.961 | 49.223 | 1.00 | 14.52 |
| ATOM | 3814 | CZ | PHE | 543 | 36.360 | 32.182 | 50.376 | 1.00 | 12.86 |
| ATOM | 3815 | C | PHE | 543 | 33.146 | 32.028 | 46.734 | 1.00 | 13.70 |
| ATOM | 3816 | O | PHE | 543 | 32.413 | 32.183 | 47.714 | 1.00 | 14.70 |
| ATOM | 3817 | N | HIS | 544 | 33.564 | 33.035 | 45.973 | 1.00 | 11.85 |
| ATOM | 3818 | CA | HIS | 544 | 33.230 | 34.430 | 46.257 | 1.00 | 12.43 |
| ATOM | 3819 | CB | HIS | 544 | 33.899 | 35.330 | 45.216 | 1.00 | 11.22 |
| ATOM | 3820 | CG | HIS | 544 | 35.380 | 35.131 | 45.129 | 1.00 | 12.39 |
| ATOM | 3821 | CD2 | HIS | 544 | 36.412 | 35.944 | 45.460 | 1.00 | 10.77 |
| ATOM | 3822 | ND1 | HIS | 544 | 35.945 | 33.952 | 44.694 | 1.00 | 12.50 |
| ATOM | 3823 | CE1 | HIS | 544 | 37.262 | 34.045 | 44.762 | 1.00 | 12.26 |
| ATOM | 3824 | NE2 | HIS | 544 | 37.570 | 35.243 | 45.223 | 1.00 | 12.30 |
| ATOM | 3825 | C | HIS | 544 | 31.754 | 34.791 | 46.389 | 1.00 | 12.49 |
| ATOM | 3826 | O | HIS | 544 | 31.414 | 35.774 | 47.053 | 1.00 | 13.33 |
| ATOM | 3827 | N | ILE | 545 | 30.880 | 34.004 | 45.773 | 1.00 | 12.62 |
| ATOM | 3828 | CA | ILE | 545 | 29.455 | 34.278 | 45.848 | 1.00 | 11.82 |
| ATOM | 3829 | CB | ILE | 545 | 28.685 | 33.471 | 44.772 | 1.00 | 12.66 |
| ATOM | 3830 | CG2 | ILE | 545 | 27.178 | 33.627 | 44.955 | 1.00 | 11.69 |
| ATOM | 3831 | CG1 | ILE | 545 | 29.117 | 33.943 | 43.380 | 1.00 | 13.17 |
| ATOM | 3832 | CD1 | ILE | 545 | 28.898 | 35.423 | 43.130 | 1.00 | 13.67 |
| ATOM | 3833 | C | ILE | 545 | 28.926 | 33.980 | 47.251 | 1.00 | 13.02 |
| ATOM | 3834 | O | ILE | 545 | 28.437 | 34.880 | 47.933 | 1.00 | 12.86 |
| ATOM | 3835 | N | PRO | 546 | 29.021 | 32.719 | 47.712 | 1.00 | 12.59 |
| ATOM | 3836 | CD | PRO | 546 | 29.404 | 31.462 | 47.045 | 1.00 | 10.20 |
| ATOM | 3837 | CA | PRO | 546 | 28.511 | 32.463 | 49.064 | 1.00 | 11.85 |
| ATOM | 3838 | CB | PRO | 546 | 28.527 | 30.932 | 49.162 | 1.00 | 14.53 |
| ATOM | 3839 | CG | PRO | 546 | 29.629 | 30.530 | 48.217 | 1.00 | 11.49 |
| ATOM | 3840 | C | PRO | 546 | 29.346 | 33.146 | 50.154 | 1.00 | 13.09 |
| ATOM | 3841 | O | PRO | 546 | 28.848 | 33.420 | 51.248 | 1.00 | 11.43 |
| ATOM | 3842 | N | SER | 547 | 30.611 | 33.433 | 49.850 | 1.00 | 11.87 |
| ATOM | 3843 | CA | SER | 547 | 31.488 | 34.090 | 50.817 | 1.00 | 12.43 |
| ATOM | 3844 | CB | SER | 547 | 32.950 | 33.734 | 50.550 | 1.00 | 14.52 |
| ATOM | 3845 | OG | SER | 547 | 33.188 | 32.370 | 50.842 | 1.00 | 18.88 |
| ATOM | 3846 | C | SER | 547 | 31.332 | 35.601 | 50.811 | 1.00 | 10.80 |
| ATOM | 3847 | O | SER | 547 | 31.946 | 36.294 | 51.617 | 1.00 | 10.64 |
| ATOM | 3848 | N | SER | 548 | 30.515 | 36.105 | 49.891 | 1.00 | 11.41 |
| ATOM | 3849 | CA | SER | 548 | 30.259 | 37.538 | 49.777 | 1.00 | 11.67 |
| ATOM | 3850 | CB | SER | 548 | 29.419 | 38.020 | 50.968 | 1.00 | 12.24 |
| ATOM | 3851 | OG | SER | 548 | 28.977 | 39.360 | 50.781 | 1.00 | 11.61 |
| ATOM | 3852 | C | SER | 548 | 31.537 | 38.380 | 49.669 | 1.00 | 13.36 |
| ATOM | 3853 | O | SER | 548 | 31.711 | 39.366 | 50.396 | 1.00 | 13.15 |
| ATOM | 3854 | N | VAL | 549 | 32.430 | 37.978 | 48.768 | 1.00 | 11.75 |
| ATOM | 3855 | CA | VAL | 549 | 33.672 | 38.714 | 48.529 | 1.00 | 11.24 |
| ATOM | 3856 | CB | VAL | 549 | 34.911 | 37.786 | 48.533 | 1.00 | 11.58 |
| ATOM | 3857 | CG1 | VAL | 549 | 36.169 | 38.594 | 48.199 | 1.00 | 10.79 |
| ATOM | 3858 | CG2 | VAL | 549 | 35.058 | 37.105 | 49.888 | 1.00 | 12.34 |
| ATOM | 3859 | C | VAL | 549 | 33.550 | 39.347 | 47.139 | 1.00 | 9.01 |
| ATOM | 3860 | O | VAL | 549 | 33.356 | 38.637 | 46.149 | 1.00 | 9.01 |
| ATOM | 3861 | N | PRO | 550 | 33.651 | 40.687 | 47.049 | 1.00 | 7.69 |
| ATOM | 3862 | CD | PRO | 550 | 33.852 | 41.644 | 48.152 | 1.00 | 8.15 |
| ATOM | 3863 | CA | PRO | 550 | 33.547 | 41.388 | 45.757 | 1.00 | 9.25 |
| ATOM | 3864 | CB | PRO | 550 | 33.846 | 42.841 | 46.127 | 1.00 | 8.76 |
| ATOM | 3865 | CG | PRO | 550 | 33.325 | 42.934 | 47.551 | 1.00 | 8.40 |
| ATOM | 3866 | C | PRO | 550 | 34.546 | 40.819 | 44.747 | 1.00 | 8.58 |
| ATOM | 3867 | O | PRO | 550 | 35.645 | 40.411 | 45.122 | 1.00 | 8.68 |
| ATOM | 3868 | N | TYR | 551 | 34.179 | 40.813 | 43.469 | 1.00 | 8.90 |
| ATOM | 3869 | CA | TYR | 551 | 35.050 | 40.234 | 42.452 | 1.00 | 8.19 |
| ATOM | 3870 | CB | TYR | 551 | 34.282 | 39.168 | 41.661 | 1.00 | 8.98 |
| ATOM | 3871 | CG | TYR | 551 | 35.155 | 38.019 | 41.221 | 1.00 | 8.00 |
| ATOM | 3872 | CD1 | TYR | 551 | 35.496 | 37.008 | 42.119 | 1.00 | 7.60 |
| ATOM | 3873 | CE1 | TYR | 551 | 36.367 | 35.985 | 41.759 | 1.00 | 8.68 |
| ATOM | 3874 | CD2 | TYR | 551 | 35.705 | 37.978 | 39.935 | 1.00 | 8.09 |
| ATOM | 3875 | CE2 | TYR | 551 | 36.589 | 36.948 | 39.562 | 1.00 | 8.21 |
| ATOM | 3876 | CZ | TYR | 551 | 36.913 | 35.960 | 40.486 | 1.00 | 8.67 |
| ATOM | 3877 | OH | TYR | 551 | 37.794 | 34.955 | 40.160 | 1.00 | 9.65 |
| ATOM | 3878 | C | TYR | 551 | 35.706 | 41.182 | 41.452 | 1.00 | 9.16 |
| ATOM | 3879 | O | TYR | 551 | 36.728 | 40.839 | 40.865 | 1.00 | 9.22 |
| ATOM | 3880 | N | ILE | 552 | 35.124 | 42.358 | 41.243 | 1.00 | 8.84 |
| ATOM | 3881 | CA | ILE | 552 | 35.676 | 43.299 | 40.275 | 1.00 | 9.21 |
| ATOM | 3882 | CB | ILE | 552 | 34.790 | 44.576 | 40.189 | 1.00 | 9.04 |
| ATOM | 3883 | CG2 | ILE | 552 | 35.055 | 45.494 | 41.365 | 1.00 | 9.74 |
| ATOM | 3884 | CG1 | ILE | 552 | 35.028 | 45.280 | 38.851 | 1.00 | 8.56 |
| ATOM | 3885 | CD1 | ILE | 552 | 34.587 | 44.457 | 37.637 | 1.00 | 5.07 |
| ATOM | 3886 | C | ILE | 552 | 37.141 | 43.652 | 40.565 | 1.00 | 10.06 |
| ATOM | 3887 | O | ILE | 552 | 37.892 | 44.025 | 39.664 | 1.00 | 11.40 |
| ATOM | 3888 | N | ARG | 553 | 37.549 | 43.508 | 41.821 | 1.00 | 10.58 |

TABLE B-continued

Co-ordinates of an underglycosylated tACEΔ36NJ ACE-lisinopril complex

| ATOM | 3889 | CA | ARG | 553 | 38.928 | 43.775 | 42.217 | 1.00 | 9.70 |
|---|---|---|---|---|---|---|---|---|---|
| ATOM | 3890 | CB | ARG | 553 | 39.106 | 43.467 | 43.708 | 1.00 | 10.44 |
| ATOM | 3891 | CG | ARG | 553 | 38.642 | 42.058 | 44.103 | 1.00 | 11.05 |
| ATOM | 3892 | CD | ARG | 553 | 38.629 | 41.861 | 45.620 | 1.00 | 10.48 |
| ATOM | 3893 | NE | ARG | 553 | 37.815 | 42.881 | 46.274 | 1.00 | 9.50 |
| ATOM | 3894 | CZ | ARG | 553 | 37.562 | 42.928 | 47.577 | 1.00 | 9.87 |
| ATOM | 3895 | NH1 | ARG | 553 | 38.059 | 42.002 | 48.389 | 1.00 | 9.94 |
| ATOM | 3896 | NH2 | ARG | 553 | 36.816 | 43.909 | 48.071 | 1.00 | 9.97 |
| ATOM | 3897 | C | ARG | 553 | 39.910 | 42.920 | 41.396 | 1.00 | 10.71 |
| ATOM | 3898 | O | ARG | 553 | 41.049 | 43.331 | 41.151 | 1.00 | 9.61 |
| ATOM | 3899 | N | TYR | 554 | 39.468 | 41.739 | 40.967 | 1.00 | 8.53 |
| ATOM | 3900 | CA | TYR | 554 | 40.334 | 40.844 | 40.195 | 1.00 | 10.58 |
| ATOM | 3901 | CB | TYR | 554 | 39.815 | 39.401 | 40.264 | 1.00 | 9.50 |
| ATOM | 3902 | CG | TYR | 554 | 39.759 | 38.865 | 41.679 | 1.00 | 10.20 |
| ATOM | 3903 | CD1 | TYR | 554 | 38.534 | 38.602 | 42.297 | 1.00 | 9.83 |
| ATOM | 3904 | CE1 | TYR | 554 | 38.471 | 38.161 | 43.620 | 1.00 | 9.58 |
| ATOM | 3905 | CD2 | TYR | 554 | 40.930 | 38.670 | 42.421 | 1.00 | 9.15 |
| ATOM | 3906 | CE2 | TYR | 554 | 40.881 | 38.229 | 43.747 | 1.00 | 8.88 |
| ATOM | 3907 | CZ | TYR | 554 | 39.645 | 37.977 | 44.339 | 1.00 | 10.44 |
| ATOM | 3908 | OH | TYR | 554 | 39.572 | 37.561 | 45.648 | 1.00 | 8.38 |
| ATOM | 3909 | C | TYR | 554 | 40.472 | 41.286 | 38.746 | 1.00 | 10.64 |
| ATOM | 3910 | O | TYR | 554 | 41.518 | 41.083 | 38.122 | 1.00 | 11.41 |
| ATOM | 3911 | N | PHE | 555 | 39.414 | 41.884 | 38.209 | 1.00 | 10.46 |
| ATOM | 3912 | CA | PHE | 555 | 39.452 | 42.393 | 36.842 | 1.00 | 10.84 |
| ATOM | 3913 | CB | PHE | 555 | 38.060 | 42.855 | 36.400 | 1.00 | 10.26 |
| ATOM | 3914 | CG | PHE | 555 | 38.046 | 43.526 | 35.061 | 1.00 | 10.17 |
| ATOM | 3915 | CD1 | PHE | 555 | 38.027 | 42.776 | 33.889 | 1.00 | 11.11 |
| ATOM | 3916 | CD2 | PHE | 555 | 38.081 | 44.911 | 34.968 | 1.00 | 11.00 |
| ATOM | 3917 | CE1 | PHE | 555 | 38.044 | 43.402 | 32.641 | 1.00 | 10.56 |
| ATOM | 3918 | CE2 | PHE | 555 | 38.101 | 45.547 | 33.723 | 1.00 | 11.95 |
| ATOM | 3919 | CZ | PHE | 555 | 38.083 | 44.792 | 32.560 | 1.00 | 10.41 |
| ATOM | 3920 | C | PHE | 555 | 40.417 | 43.586 | 36.850 | 1.00 | 10.22 |
| ATOM | 3921 | O | PHE | 555 | 41.309 | 43.689 | 36.007 | 1.00 | 9.16 |
| ATOM | 3922 | N | VAL | 556 | 40.225 | 44.483 | 37.810 | 1.00 | 8.84 |
| ATOM | 3923 | CA | VAL | 556 | 41.083 | 45.652 | 37.947 | 1.00 | 10.41 |
| ATOM | 3924 | CB | VAL | 556 | 40.657 | 46.515 | 39.163 | 1.00 | 11.27 |
| ATOM | 3925 | CG1 | VAL | 556 | 41.651 | 47.663 | 39.377 | 1.00 | 11.42 |
| ATOM | 3926 | CG2 | VAL | 556 | 39.256 | 47.074 | 38.934 | 1.00 | 10.95 |
| ATOM | 3927 | C | VAL | 556 | 42.530 | 45.183 | 38.135 | 1.00 | 10.85 |
| ATOM | 3928 | O | VAL | 556 | 43.448 | 45.679 | 37.485 | 1.00 | 9.24 |
| ATOM | 3929 | N | SER | 557 | 42.722 | 44.213 | 39.021 | 1.00 | 10.92 |
| ATOM | 3930 | CA | SER | 557 | 44.055 | 43.681 | 39.283 | 1.00 | 12.23 |
| ATOM | 3931 | CB | SER | 557 | 43.986 | 42.547 | 40.311 | 1.00 | 12.25 |
| ATOM | 3932 | OG | SER | 557 | 45.242 | 41.895 | 40.418 | 1.00 | 11.90 |
| ATOM | 3933 | C | SER | 557 | 44.781 | 43.167 | 38.042 | 1.00 | 10.88 |
| ATOM | 3934 | O | SER | 557 | 45.944 | 43.491 | 37.823 | 1.00 | 11.61 |
| ATOM | 3935 | N | PHE | 558 | 44.108 | 42.358 | 37.233 | 1.00 | 11.01 |
| ATOM | 3936 | CA | PHE | 558 | 44.760 | 41.805 | 36.054 | 1.00 | 12.87 |
| ATOM | 3937 | CB | PHE | 558 | 43.874 | 40.728 | 35.419 | 1.00 | 13.39 |
| ATOM | 3938 | CG | PHE | 558 | 44.053 | 39.374 | 36.041 | 1.00 | 14.43 |
| ATOM | 3939 | CD1 | PHE | 558 | 43.973 | 39.217 | 37.425 | 1.00 | 16.42 |
| ATOM | 3940 | CD2 | PHE | 558 | 44.343 | 38.263 | 35.254 | 1.00 | 14.78 |
| ATOM | 3941 | CE1 | PHE | 558 | 44.185 | 37.969 | 38.017 | 1.00 | 16.88 |
| ATOM | 3942 | CE2 | PHE | 558 | 44.554 | 37.016 | 35.830 | 1.00 | 15.76 |
| ATOM | 3943 | CZ | PHE | 558 | 44.476 | 36.868 | 37.218 | 1.00 | 17.97 |
| ATOM | 3944 | C | PHE | 558 | 45.191 | 42.844 | 35.032 | 1.00 | 13.85 |
| ATOM | 3945 | O | PHE | 558 | 46.164 | 42.640 | 34.308 | 1.00 | 12.86 |
| ATOM | 3946 | N | ILE | 559 | 44.479 | 43.963 | 34.979 | 1.00 | 14.42 |
| ATOM | 3947 | CA | ILE | 559 | 44.840 | 45.028 | 34.051 | 1.00 | 13.66 |
| ATOM | 3948 | CB | ILE | 559 | 43.677 | 46.038 | 33.853 | 1.00 | 14.20 |
| ATOM | 3949 | CG2 | ILE | 559 | 44.179 | 47.274 | 33.112 | 1.00 | 12.67 |
| ATOM | 3950 | CG1 | ILE | 559 | 42.513 | 45.381 | 33.098 | 1.00 | 15.77 |
| ATOM | 3951 | CD1 | ILE | 559 | 42.788 | 45.101 | 31.635 | 1.00 | 17.17 |
| ATOM | 3952 | C | ILE | 559 | 46.039 | 45.796 | 34.611 | 1.00 | 12.63 |
| ATOM | 3953 | O | ILE | 559 | 47.080 | 45.907 | 33.964 | 1.00 | 12.70 |
| ATOM | 3954 | N | ILE | 560 | 45.892 | 46.304 | 35.831 | 1.00 | 11.72 |
| ATOM | 3955 | CA | ILE | 560 | 46.946 | 47.104 | 36.441 | 1.00 | 10.69 |
| ATOM | 3956 | CB | ILE | 560 | 46.436 | 47.844 | 37.706 | 1.00 | 10.54 |
| ATOM | 3957 | CG2 | ILE | 560 | 45.153 | 48.614 | 37.370 | 1.00 | 8.48 |
| ATOM | 3958 | CG1 | ILE | 560 | 46.206 | 46.858 | 38.854 | 1.00 | 8.80 |
| ATOM | 3959 | CD1 | ILE | 560 | 45.770 | 47.529 | 40.158 | 1.00 | 8.36 |
| ATOM | 3960 | C | ILE | 560 | 48.227 | 46.355 | 36.793 | 1.00 | 12.09 |
| ATOM | 3961 | O | ILE | 560 | 49.296 | 46.962 | 36.854 | 1.00 | 10.94 |
| ATOM | 3962 | N | GLN | 561 | 48.144 | 45.049 | 37.023 | 1.00 | 10.67 |
| ATOM | 3963 | CA | GLN | 561 | 49.364 | 44.324 | 37.354 | 1.00 | 11.49 |
| ATOM | 3964 | CB | GLN | 561 | 49.060 | 42.882 | 37.778 | 1.00 | 10.52 |
| ATOM | 3965 | CG | GLN | 561 | 48.500 | 41.975 | 36.701 | 1.00 | 9.92 |
| ATOM | 3966 | CD | GLN | 561 | 48.154 | 40.604 | 37.254 | 1.00 | 12.40 |

TABLE B-continued

Co-ordinates of an underglycosylated tACEΔ36NJ ACE-lisinopril complex

| ATOM | 3967 | OE1 | GLN | 561 | 48.678 | 39.589 | 36.799 | 1.00 | 11.82 |
|------|------|-----|-----|-----|--------|--------|--------|------|-------|
| ATOM | 3968 | NE2 | GLN | 561 | 47.269 | 40.571 | 38.250 | 1.00 | 10.71 |
| ATOM | 3969 | C | GLN | 561 | 50.341 | 44.363 | 36.176 | 1.00 | 11.50 |
| ATOM | 3970 | O | GLN | 561 | 51.554 | 44.347 | 36.372 | 1.00 | 11.27 |
| ATOM | 3971 | N | PHE | 562 | 49.817 | 44.424 | 34.953 | 1.00 | 11.69 |
| ATOM | 3972 | CA | PHE | 562 | 50.691 | 44.503 | 33.790 | 1.00 | 11.21 |
| ATOM | 3973 | CB | PHE | 562 | 49.956 | 44.080 | 32.510 | 1.00 | 11.05 |
| ATOM | 3974 | CG | PHE | 562 | 49.863 | 42.591 | 32.352 | 1.00 | 11.29 |
| ATOM | 3975 | CD1 | PHE | 562 | 48.793 | 41.884 | 32.890 | 1.00 | 9.06 |
| ATOM | 3976 | CD2 | PHE | 562 | 50.913 | 41.880 | 31.768 | 1.00 | 12.56 |
| ATOM | 3977 | CE1 | PHE | 562 | 48.772 | 40.488 | 32.858 | 1.00 | 12.27 |
| ATOM | 3978 | CE2 | PHE | 562 | 50.903 | 40.485 | 31.732 | 1.00 | 12.36 |
| ATOM | 3979 | CZ | PHE | 562 | 49.831 | 39.787 | 32.280 | 1.00 | 11.90 |
| ATOM | 3980 | C | PHE | 562 | 51.231 | 45.925 | 33.675 | 1.00 | 12.75 |
| ATOM | 3981 | O | PHE | 562 | 52.351 | 46.140 | 33.199 | 1.00 | 11.93 |
| ATOM | 3982 | N | GLN | 563 | 50.437 | 46.897 | 34.117 | 1.00 | 10.72 |
| ATOM | 3983 | CA | GLN | 563 | 50.891 | 48.281 | 34.097 | 1.00 | 12.88 |
| ATOM | 3984 | CB | GLN | 563 | 49.767 | 49.234 | 34.519 | 1.00 | 11.19 |
| ATOM | 3985 | CG | GLN | 563 | 48.737 | 49.532 | 33.435 | 1.00 | 11.49 |
| ATOM | 3986 | CD | GLN | 563 | 47.675 | 50.507 | 33.912 | 1.00 | 12.70 |
| ATOM | 3987 | OE1 | GLN | 563 | 46.589 | 50.107 | 34.331 | 1.00 | 12.32 |
| ATOM | 3988 | NE2 | GLN | 563 | 47.997 | 51.799 | 33.872 | 1.00 | 11.50 |
| ATOM | 3989 | C | GLN | 563 | 52.047 | 48.395 | 35.092 | 1.00 | 12.39 |
| ATOM | 3990 | O | GLN | 563 | 53.025 | 49.093 | 34.839 | 1.00 | 13.44 |
| ATOM | 3991 | N | PHE | 564 | 51.925 | 47.706 | 36.225 | 1.00 | 11.63 |
| ATOM | 3992 | CA | PHE | 564 | 52.963 | 47.740 | 37.252 | 1.00 | 13.10 |
| ATOM | 3993 | CB | PHE | 564 | 52.464 | 47.095 | 38.554 | 1.00 | 11.20 |
| ATOM | 3994 | CG | PHE | 564 | 51.333 | 47.841 | 39.221 | 1.00 | 12.19 |
| ATOM | 3995 | CD1 | PHE | 564 | 50.907 | 49.082 | 38.746 | 1.00 | 14.04 |
| ATOM | 3996 | CD2 | PHE | 564 | 50.687 | 47.294 | 40.329 | 1.00 | 12.60 |
| ATOM | 3997 | CE1 | PHE | 564 | 49.852 | 49.766 | 39.365 | 1.00 | 13.68 |
| ATOM | 3998 | CE2 | PHE | 564 | 49.634 | 47.967 | 40.956 | 1.00 | 11.39 |
| ATOM | 3999 | CZ | PHE | 564 | 49.215 | 49.203 | 40.473 | 1.00 | 11.65 |
| ATOM | 4000 | C | PHE | 564 | 54.216 | 47.013 | 36.768 | 1.00 | 12.91 |
| ATOM | 4001 | O | PHE | 564 | 55.333 | 47.480 | 36.971 | 1.00 | 12.87 |
| ATOM | 4002 | N | HIS | 565 | 54.019 | 45.865 | 36.132 | 1.00 | 13.20 |
| ATOM | 4003 | CA | HIS | 565 | 55.121 | 45.070 | 35.599 | 1.00 | 14.27 |
| ATOM | 4004 | CB | HIS | 565 | 54.560 | 43.825 | 34.906 | 1.00 | 12.73 |
| ATOM | 4005 | CG | HIS | 565 | 55.607 | 42.908 | 34.354 | 1.00 | 15.74 |
| ATOM | 4006 | CD2 | HIS | 565 | 55.857 | 42.500 | 33.086 | 1.00 | 12.69 |
| ATOM | 4007 | ND1 | HIS | 565 | 56.545 | 42.283 | 35.148 | 1.00 | 14.29 |
| ATOM | 4008 | CE1 | HIS | 565 | 57.326 | 41.532 | 34.394 | 1.00 | 14.80 |
| ATOM | 4009 | NE2 | HIS | 565 | 56.930 | 41.647 | 33.138 | 1.00 | 14.33 |
| ATOM | 4010 | C | HIS | 565 | 55.923 | 45.920 | 34.600 | 1.00 | 14.86 |
| ATOM | 4011 | O | HIS | 565 | 57.153 | 45.973 | 34.652 | 1.00 | 14.50 |
| ATOM | 4012 | N | GLU | 566 | 55.213 | 46.593 | 33.702 | 1.00 | 13.69 |
| ATOM | 4013 | CA | GLU | 566 | 55.848 | 47.443 | 32.702 | 1.00 | 15.17 |
| ATOM | 4014 | CB | GLU | 566 | 54.778 | 48.065 | 31.797 | 1.00 | 15.39 |
| ATOM | 4015 | CG | GLU | 566 | 55.313 | 48.964 | 30.695 | 1.00 | 15.92 |
| ATOM | 4016 | CD | GLU | 566 | 54.202 | 49.652 | 29.931 | 1.00 | 15.19 |
| ATOM | 4017 | OE1 | GLU | 566 | 53.539 | 50.538 | 30.505 | 1.00 | 17.62 |
| ATOM | 4018 | OE2 | GLU | 566 | 53.980 | 49.295 | 28.758 | 1.00 | 18.81 |
| ATOM | 4019 | C | GLU | 566 | 56.695 | 48.551 | 33.339 | 1.00 | 15.89 |
| ATOM | 4020 | O | GLU | 566 | 57.859 | 48.737 | 32.976 | 1.00 | 14.18 |
| ATOM | 4021 | N | ALA | 567 | 56.112 | 49.282 | 34.287 | 1.00 | 15.39 |
| ATOM | 4022 | CA | ALA | 567 | 56.828 | 50.372 | 34.948 | 1.00 | 16.88 |
| ATOM | 4023 | CB | ALA | 567 | 55.865 | 51.183 | 35.819 | 1.00 | 14.89 |
| ATOM | 4024 | C | ALA | 567 | 58.019 | 49.897 | 35.784 | 1.00 | 16.62 |
| ATOM | 4025 | O | ALA | 567 | 59.096 | 50.488 | 35.727 | 1.00 | 15.99 |
| ATOM | 4026 | N | LEU | 568 | 57.825 | 48.833 | 36.557 | 1.00 | 15.41 |
| ATOM | 4027 | CA | LEU | 568 | 58.893 | 48.309 | 37.398 | 1.00 | 16.13 |
| ATOM | 4028 | CB | LEU | 568 | 58.359 | 47.201 | 38.314 | 1.00 | 17.30 |
| ATOM | 4029 | CG | LEU | 568 | 57.250 | 47.612 | 39.299 | 1.00 | 20.05 |
| ATOM | 4030 | CD1 | LEU | 568 | 56.889 | 46.432 | 40.190 | 1.00 | 18.53 |
| ATOM | 4031 | CD2 | LEU | 568 | 57.711 | 48.778 | 40.145 | 1.00 | 18.19 |
| ATOM | 4032 | C | LEU | 568 | 60.048 | 47.784 | 36.552 | 1.00 | 18.07 |
| ATOM | 4033 | O | LEU | 568 | 61.214 | 47.911 | 36.929 | 1.00 | 17.90 |
| ATOM | 4034 | N | CYS | 569 | 59.720 | 47.202 | 35.403 | 1.00 | 18.05 |
| ATOM | 4035 | CA | CYS | 569 | 60.732 | 46.672 | 34.502 | 1.00 | 18.25 |
| ATOM | 4036 | C | CYS | 569 | 61.549 | 47.820 | 33.923 | 1.00 | 20.30 |
| ATOM | 4037 | O | CYS | 569 | 62.773 | 47.723 | 33.798 | 1.00 | 20.29 |
| ATOM | 4038 | CB | CYS | 569 | 60.067 | 45.860 | 33.388 | 1.00 | 16.73 |
| ATOM | 4039 | SG | CYS | 569 | 59.390 | 44.286 | 34.002 | 1.00 | 19.14 |
| ATOM | 4040 | N | GLN | 570 | 60.868 | 48.905 | 33.571 | 1.00 | 20.33 |
| ATOM | 4041 | CA | GLN | 570 | 61.543 | 50.077 | 33.035 | 1.00 | 23.99 |
| ATOM | 4042 | CB | GLN | 570 | 60.520 | 51.120 | 32.572 | 1.00 | 26.88 |
| ATOM | 4043 | CG | GLN | 570 | 61.128 | 52.411 | 32.026 | 1.00 | 33.15 |
| ATOM | 4044 | CD | GLN | 570 | 61.464 | 53.420 | 33.112 | 1.00 | 38.69 |

TABLE B-continued

Co-ordinates of an underglycosylated tACEΔ36NJ ACE-lisinopril complex

| ATOM | 4045 | OE1 | GLN | 570 | 62.144 | 54.418 | 32.859 | 1.00 | 42.37 |
|---|---|---|---|---|---|---|---|---|---|
| ATOM | 4046 | NE2 | GLN | 570 | 60.979 | 53.172 | 34.327 | 1.00 | 41.47 |
| ATOM | 4047 | C | GLN | 570 | 62.433 | 50.659 | 34.135 | 1.00 | 23.86 |
| ATOM | 4048 | O | GLN | 570 | 63.580 | 51.019 | 33.890 | 1.00 | 24.65 |
| ATOM | 4049 | N | ALA | 571 | 61.902 | 50.730 | 35.351 | 1.00 | 24.19 |
| ATOM | 4050 | CA | ALA | 571 | 62.656 | 51.266 | 36.479 | 1.00 | 24.23 |
| ATOM | 4051 | CB | ALA | 571 | 61.760 | 51.366 | 37.707 | 1.00 | 22.96 |
| ATOM | 4052 | C | ALA | 571 | 63.864 | 50.384 | 36.783 | 1.00 | 25.45 |
| ATOM | 4053 | O | ALA | 571 | 64.875 | 50.860 | 37.305 | 1.00 | 25.42 |
| ATOM | 4054 | N | ALA | 572 | 63.750 | 49.099 | 36.459 | 1.00 | 24.84 |
| ATOM | 4055 | CA | ALA | 572 | 64.827 | 48.147 | 36.699 | 1.00 | 25.13 |
| ATOM | 4056 | CB | ALA | 572 | 64.254 | 46.750 | 36.870 | 1.00 | 23.83 |
| ATOM | 4057 | C | ALA | 572 | 65.863 | 48.152 | 35.573 | 1.00 | 25.94 |
| ATOM | 4058 | O | ALA | 572 | 66.867 | 47.442 | 35.642 | 1.00 | 26.07 |
| ATOM | 4059 | N | GLY | 573 | 65.609 | 48.947 | 34.537 | 1.00 | 26.23 |
| ATOM | 4060 | CA | GLY | 573 | 66.532 | 49.025 | 33.419 | 1.00 | 27.16 |
| ATOM | 4061 | C | GLY | 573 | 66.339 | 47.967 | 32.344 | 1.00 | 28.15 |
| ATOM | 4062 | O | GLY | 573 | 67.187 | 47.812 | 31.460 | 1.00 | 27.38 |
| ATOM | 4063 | N | HIS | 574 | 65.229 | 47.238 | 32.400 | 1.00 | 28.43 |
| ATOM | 4064 | CA | HIS | 574 | 64.969 | 46.204 | 31.406 | 1.00 | 27.36 |
| ATOM | 4065 | CB | HIS | 574 | 63.768 | 45.348 | 31.814 | 1.00 | 27.79 |
| ATOM | 4066 | CG | HIS | 574 | 63.425 | 44.284 | 30.818 | 1.00 | 27.40 |
| ATOM | 4067 | CD2 | HIS | 574 | 62.483 | 44.244 | 29.845 | 1.00 | 26.79 |
| ATOM | 4068 | ND1 | HIS | 574 | 64.132 | 43.105 | 30.714 | 1.00 | 28.45 |
| ATOM | 4069 | CE1 | HIS | 574 | 63.643 | 42.386 | 29.720 | 1.00 | 27.27 |
| ATOM | 4070 | NE2 | HIS | 574 | 62.642 | 43.055 | 29.175 | 1.00 | 26.73 |
| ATOM | 4071 | C | HIS | 574 | 64.702 | 46.794 | 30.025 | 1.00 | 27.12 |
| ATOM | 4072 | O | HIS | 574 | 64.038 | 47.820 | 29.886 | 1.00 | 26.50 |
| ATOM | 4073 | N | THR | 575 | 65.226 | 46.130 | 29.004 | 1.00 | 27.68 |
| ATOM | 4074 | CA | THR | 575 | 65.036 | 46.562 | 27.630 | 1.00 | 28.87 |
| ATOM | 4075 | CB | THR | 575 | 66.326 | 47.153 | 27.038 | 1.00 | 29.42 |
| ATOM | 4076 | OG1 | THR | 575 | 67.310 | 46.121 | 26.914 | 1.00 | 30.33 |
| ATOM | 4077 | CG2 | THR | 575 | 66.864 | 48.254 | 27.942 | 1.00 | 30.67 |
| ATOM | 4078 | C | THR | 575 | 64.640 | 45.336 | 26.821 | 1.00 | 28.31 |
| ATOM | 4079 | O | THR | 575 | 64.940 | 44.204 | 27.205 | 1.00 | 28.82 |
| ATOM | 4080 | N | GLY | 576 | 63.969 | 45.560 | 25.700 | 1.00 | 28.44 |
| ATOM | 4081 | CA | GLY | 576 | 63.539 | 44.448 | 24.875 | 1.00 | 27.18 |
| ATOM | 4082 | C | GLY | 576 | 62.119 | 44.050 | 25.230 | 1.00 | 25.91 |
| ATOM | 4083 | O | GLY | 576 | 61.465 | 44.737 | 26.018 | 1.00 | 24.77 |
| ATOM | 4084 | N | PRO | 577 | 61.619 | 42.933 | 24.678 | 1.00 | 24.95 |
| ATOM | 4085 | CD | PRO | 577 | 62.349 | 41.978 | 23.827 | 1.00 | 23.68 |
| ATOM | 4086 | CA | PRO | 577 | 60.258 | 42.457 | 24.946 | 1.00 | 22.59 |
| ATOM | 4087 | CB | PRO | 577 | 60.259 | 41.056 | 24.341 | 1.00 | 22.99 |
| ATOM | 4088 | CG | PRO | 577 | 61.219 | 41.191 | 23.196 | 1.00 | 24.60 |
| ATOM | 4089 | C | PRO | 577 | 59.910 | 42.446 | 26.431 | 1.00 | 21.80 |
| ATOM | 4090 | O | PRO | 577 | 60.659 | 41.917 | 27.254 | 1.00 | 19.91 |
| ATOM | 4091 | N | LEU | 578 | 58.766 | 43.033 | 26.762 | 1.00 | 20.01 |
| ATOM | 4092 | CA | LEU | 578 | 58.307 | 43.099 | 28.140 | 1.00 | 19.37 |
| ATOM | 4093 | CB | LEU | 578 | 56.978 | 43.849 | 28.201 | 1.00 | 19.91 |
| ATOM | 4094 | CG | LEU | 578 | 56.331 | 44.032 | 29.575 | 1.00 | 20.71 |
| ATOM | 4095 | CD1 | LEU | 578 | 57.289 | 44.770 | 30.506 | 1.00 | 19.94 |
| ATOM | 4096 | CD2 | LEU | 578 | 55.027 | 44.807 | 29.412 | 1.00 | 19.01 |
| ATOM | 4097 | C | LEU | 578 | 58.155 | 41.723 | 28.792 | 1.00 | 19.24 |
| ATOM | 4098 | O | LEU | 578 | 58.455 | 41.558 | 29.977 | 1.00 | 19.94 |
| ATOM | 4099 | N | HIS | 579 | 57.707 | 40.731 | 28.025 | 1.00 | 18.28 |
| ATOM | 4100 | CA | HIS | 579 | 57.506 | 39.399 | 28.584 | 1.00 | 17.96 |
| ATOM | 4101 | CB | HIS | 579 | 56.750 | 38.496 | 27.598 | 1.00 | 17.78 |
| ATOM | 4102 | CG | HIS | 579 | 57.550 | 38.091 | 26.397 | 1.00 | 19.87 |
| ATOM | 4103 | CD2 | HIS | 579 | 58.261 | 36.967 | 26.140 | 1.00 | 19.63 |
| ATOM | 4104 | ND1 | HIS | 579 | 57.660 | 38.881 | 25.272 | 1.00 | 20.33 |
| ATOM | 4105 | CE1 | HIS | 579 | 58.403 | 38.259 | 24.372 | 1.00 | 21.49 |
| ATOM | 4106 | NE2 | HIS | 579 | 58.781 | 37.096 | 24.873 | 1.00 | 21.52 |
| ATOM | 4107 | C | HIS | 579 | 58.788 | 38.703 | 29.038 | 1.00 | 18.92 |
| ATOM | 4108 | O | HIS | 579 | 58.736 | 37.704 | 29.753 | 1.00 | 18.97 |
| ATOM | 4109 | N | LYS | 580 | 59.939 | 39.227 | 28.628 | 1.00 | 19.36 |
| ATOM | 4110 | CA | LYS | 580 | 61.213 | 38.633 | 29.024 | 1.00 | 20.72 |
| ATOM | 4111 | CB | LYS | 580 | 62.249 | 38.793 | 27.906 | 1.00 | 22.61 |
| ATOM | 4112 | CG | LYS | 580 | 61.921 | 38.033 | 26.637 | 1.00 | 26.07 |
| ATOM | 4113 | CD | LYS | 580 | 63.026 | 38.210 | 25.603 | 1.00 | 30.62 |
| ATOM | 4114 | CE | LYS | 580 | 62.691 | 37.498 | 24.303 | 1.00 | 32.64 |
| ATOM | 4115 | NZ | LYS | 580 | 63.739 | 37.735 | 23.272 | 1.00 | 36.23 |
| ATOM | 4116 | C | LYS | 580 | 61.759 | 39.261 | 30.304 | 1.00 | 19.60 |
| ATOM | 4117 | O | LYS | 580 | 62.820 | 38.868 | 30.791 | 1.00 | 19.03 |
| ATOM | 4118 | N | CYS | 581 | 61.035 | 40.231 | 30.850 | 1.00 | 18.42 |
| ATOM | 4119 | CA | CYS | 581 | 61.481 | 40.906 | 32.064 | 1.00 | 17.07 |
| ATOM | 4120 | C | CYS | 581 | 61.314 | 40.101 | 33.347 | 1.00 | 17.10 |
| ATOM | 4121 | O | CYS | 581 | 60.304 | 39.418 | 33.547 | 1.00 | 15.04 |
| ATOM | 4122 | CB | CYS | 581 | 60.760 | 42.250 | 32.216 | 1.00 | 18.37 |

TABLE B-continued

Co-ordinates of an underglycosylated tACEΔ36NJ ACE-lisinopril complex

| ATOM | 4123 | SG | CYS | 581 | 60.969 | 43.013 | 33.857 | 1.00 | 17.47 |
|------|------|-----|-----|-----|--------|--------|--------|------|-------|
| ATOM | 4124 | N | ASP | 582 | 62.326 | 40.198 | 34.207 | 1.00 | 15.09 |
| ATOM | 4125 | CA | ASP | 582 | 62.349 | 39.536 | 35.508 | 1.00 | 16.68 |
| ATOM | 4126 | CB | ASP | 582 | 63.280 | 38.317 | 35.483 | 1.00 | 17.27 |
| ATOM | 4127 | CG | ASP | 582 | 63.346 | 37.599 | 36.823 | 1.00 | 17.46 |
| ATOM | 4128 | OD1 | ASP | 582 | 62.896 | 38.168 | 37.840 | 1.00 | 20.34 |
| ATOM | 4129 | OD2 | ASP | 582 | 63.863 | 36.464 | 36.864 | 1.00 | 18.13 |
| ATOM | 4130 | C | ASP | 582 | 62.905 | 40.596 | 36.455 | 1.00 | 17.47 |
| ATOM | 4131 | O | ASP | 582 | 64.090 | 40.934 | 36.391 | 1.00 | 17.45 |
| ATOM | 4132 | N | ILE | 583 | 62.053 | 41.128 | 37.326 | 1.00 | 16.24 |
| ATOM | 4133 | CA | ILE | 583 | 62.486 | 42.171 | 38.250 | 1.00 | 15.41 |
| ATOM | 4134 | CB | ILE | 583 | 61.307 | 43.072 | 38.690 | 1.00 | 14.68 |
| ATOM | 4135 | CG2 | ILE | 583 | 60.632 | 43.673 | 37.470 | 1.00 | 14.39 |
| ATOM | 4136 | CG1 | ILE | 583 | 60.311 | 42.260 | 39.523 | 1.00 | 15.92 |
| ATOM | 4137 | CD1 | ILE | 583 | 59.269 | 43.108 | 40.237 | 1.00 | 14.64 |
| ATOM | 4138 | C | ILE | 583 | 63.153 | 41.641 | 39.510 | 1.00 | 14.69 |
| ATOM | 4139 | O | ILE | 583 | 63.339 | 42.393 | 40.461 | 1.00 | 15.92 |
| ATOM | 4140 | N | TYR | 584 | 63.515 | 40.361 | 39.525 | 1.00 | 14.71 |
| ATOM | 4141 | CA | TYR | 584 | 64.159 | 39.793 | 40.707 | 1.00 | 16.16 |
| ATOM | 4142 | CB | TYR | 584 | 64.674 | 38.379 | 40.435 | 1.00 | 17.42 |
| ATOM | 4143 | CG | TYR | 584 | 65.201 | 37.707 | 41.687 | 1.00 | 20.19 |
| ATOM | 4144 | CD1 | TYR | 584 | 64.335 | 37.319 | 42.710 | 1.00 | 19.90 |
| ATOM | 4145 | CE1 | TYR | 584 | 64.818 | 36.736 | 43.882 | 1.00 | 22.35 |
| ATOM | 4146 | CD2 | TYR | 584 | 66.569 | 37.496 | 41.868 | 1.00 | 21.27 |
| ATOM | 4147 | CE2 | TYR | 584 | 67.062 | 36.917 | 43.040 | 1.00 | 21.55 |
| ATOM | 4148 | CZ | TYR | 584 | 66.182 | 36.540 | 44.040 | 1.00 | 23.16 |
| ATOM | 4149 | OH | TYR | 584 | 66.667 | 35.970 | 45.197 | 1.00 | 24.33 |
| ATOM | 4150 | C | TYR | 584 | 65.313 | 40.665 | 41.203 | 1.00 | 17.22 |
| ATOM | 4151 | O | TYR | 584 | 66.181 | 41.077 | 40.430 | 1.00 | 15.46 |
| ATOM | 4152 | N | GLN | 585 | 65.280 | 40.919 | 42.511 | 1.00 | 19.21 |
| ATOM | 4153 | CA | GLN | 585 | 66.220 | 41.732 | 43.291 | 1.00 | 20.56 |
| ATOM | 4154 | CB | GLN | 585 | 67.547 | 40.975 | 43.537 | 1.00 | 22.86 |
| ATOM | 4155 | CG | GLN | 585 | 68.714 | 41.237 | 42.615 | 1.00 | 25.28 |
| ATOM | 4156 | CD | GLN | 585 | 70.041 | 40.759 | 43.227 | 1.00 | 25.98 |
| ATOM | 4157 | OE1 | GLN | 585 | 70.858 | 41.563 | 43.688 | 1.00 | 27.46 |
| ATOM | 4158 | NE2 | GLN | 585 | 70.246 | 39.449 | 43.244 | 1.00 | 21.75 |
| ATOM | 4159 | C | GLN | 585 | 66.473 | 43.182 | 42.874 | 1.00 | 20.42 |
| ATOM | 4160 | O | GLN | 585 | 67.461 | 43.798 | 43.278 | 1.00 | 21.28 |
| ATOM | 4161 | N | SER | 586 | 65.550 | 43.745 | 42.102 | 1.00 | 19.19 |
| ATOM | 4162 | CA | SER | 586 | 65.660 | 45.139 | 41.690 | 1.00 | 19.32 |
| ATOM | 4163 | CB | SER | 586 | 64.786 | 45.414 | 40.471 | 1.00 | 18.80 |
| ATOM | 4164 | OG | SER | 586 | 64.601 | 46.811 | 40.310 | 1.00 | 18.57 |
| ATOM | 4165 | C | SER | 586 | 65.189 | 46.029 | 42.843 | 1.00 | 19.72 |
| ATOM | 4166 | O | SER | 586 | 64.024 | 45.974 | 43.242 | 1.00 | 19.41 |
| ATOM | 4167 | N | LYS | 587 | 66.089 | 46.850 | 43.373 | 1.00 | 19.62 |
| ATOM | 4168 | CA | LYS | 587 | 65.732 | 47.732 | 44.478 | 1.00 | 19.54 |
| ATOM | 4169 | CB | LYS | 587 | 66.993 | 48.220 | 45.201 | 1.00 | 19.75 |
| ATOM | 4170 | CG | LYS | 587 | 67.817 | 47.097 | 45.824 | 1.00 | 19.70 |
| ATOM | 4171 | CD | LYS | 587 | 66.996 | 46.278 | 46.807 | 1.00 | 19.79 |
| ATOM | 4172 | CE | LYS | 587 | 67.818 | 45.169 | 47.454 | 1.00 | 18.62 |
| ATOM | 4173 | NZ | LYS | 587 | 68.332 | 44.187 | 46.455 | 1.00 | 17.59 |
| ATOM | 4174 | C | LYS | 587 | 64.903 | 48.918 | 43.998 | 1.00 | 18.61 |
| ATOM | 4175 | O | LYS | 587 | 64.079 | 49.442 | 44.746 | 1.00 | 18.91 |
| ATOM | 4176 | N | GLU | 588 | 65.125 | 49.340 | 42.756 | 1.00 | 17.99 |
| ATOM | 4177 | CA | GLU | 588 | 64.368 | 50.453 | 42.189 | 1.00 | 19.42 |
| ATOM | 4178 | CB | GLU | 588 | 64.886 | 50.814 | 40.793 | 1.00 | 21.76 |
| ATOM | 4179 | CG | GLU | 588 | 66.272 | 51.445 | 40.746 | 1.00 | 27.43 |
| ATOM | 4180 | CD | GLU | 588 | 67.376 | 50.476 | 41.117 | 1.00 | 29.76 |
| ATOM | 4181 | OE1 | GLU | 588 | 67.323 | 49.311 | 40.666 | 1.00 | 30.34 |
| ATOM | 4182 | OE2 | GLU | 588 | 68.304 | 50.885 | 41.849 | 1.00 | 33.88 |
| ATOM | 4183 | C | GLU | 588 | 62.898 | 50.048 | 42.081 | 1.00 | 19.93 |
| ATOM | 4184 | O | GLU | 588 | 61.995 | 50.836 | 42.376 | 1.00 | 17.54 |
| ATOM | 4185 | N | ALA | 589 | 62.669 | 48.813 | 41.645 | 1.00 | 19.54 |
| ATOM | 4186 | CA | ALA | 589 | 61.315 | 48.292 | 41.503 | 1.00 | 19.77 |
| ATOM | 4187 | CB | ALA | 589 | 61.351 | 46.904 | 40.875 | 1.00 | 19.22 |
| ATOM | 4188 | C | ALA | 589 | 60.657 | 48.231 | 42.879 | 1.00 | 19.77 |
| ATOM | 4189 | O | ALA | 589 | 59.564 | 48.756 | 43.081 | 1.00 | 18.88 |
| ATOM | 4190 | N | GLY | 590 | 61.339 | 47.596 | 43.825 | 1.00 | 19.84 |
| ATOM | 4191 | CA | GLY | 590 | 60.802 | 47.485 | 45.169 | 1.00 | 20.54 |
| ATOM | 4192 | C | GLY | 590 | 60.463 | 48.824 | 45.808 | 1.00 | 21.45 |
| ATOM | 4193 | O | GLY | 590 | 59.471 | 48.940 | 46.527 | 1.00 | 21.87 |
| ATOM | 4194 | N | GLN | 591 | 61.274 | 49.842 | 45.541 | 1.00 | 21.62 |
| ATOM | 4195 | CA | GLN | 591 | 61.039 | 51.156 | 46.125 | 1.00 | 23.40 |
| ATOM | 4196 | CB | GLN | 591 | 62.209 | 52.093 | 45.822 | 1.00 | 27.20 |
| ATOM | 4197 | CG | GLN | 591 | 62.105 | 53.431 | 46.537 | 1.00 | 33.72 |
| ATOM | 4198 | CD | GLN | 591 | 62.006 | 53.271 | 48.049 | 1.00 | 37.72 |
| ATOM | 4199 | OE1 | GLN | 591 | 62.942 | 52.804 | 48.701 | 1.00 | 40.06 |
| ATOM | 4200 | NE2 | GLN | 591 | 60.862 | 53.650 | 48.610 | 1.00 | 40.38 |

TABLE B-continued

Co-ordinates of an underglycosylated tACEΔ36NJ ACE-lisinopril complex

| ATOM | 4201 | C   | GLN | 591 | 59.734 | 51.797 | 45.657 | 1.00 | 22.75 |
|------|------|-----|-----|-----|--------|--------|--------|------|-------|
| ATOM | 4202 | O   | GLN | 591 | 59.049 | 52.458 | 46.436 | 1.00 | 22.38 |
| ATOM | 4203 | N   | ARG | 592 | 59.383 | 51.612 | 44.391 | 1.00 | 21.41 |
| ATOM | 4204 | CA  | ARG | 592 | 58.141 | 52.189 | 43.900 | 1.00 | 23.04 |
| ATOM | 4205 | CB  | ARG | 592 | 58.056 | 52.092 | 42.380 | 1.00 | 24.83 |
| ATOM | 4206 | CG  | ARG | 592 | 59.000 | 53.041 | 41.678 | 1.00 | 27.16 |
| ATOM | 4207 | CD  | ARG | 592 | 58.672 | 53.136 | 40.216 | 1.00 | 30.01 |
| ATOM | 4208 | NE  | ARG | 592 | 59.631 | 53.965 | 39.500 | 1.00 | 30.87 |
| ATOM | 4209 | CZ  | ARG | 592 | 59.574 | 54.207 | 38.197 | 1.00 | 33.37 |
| ATOM | 4210 | NH1 | ARG | 592 | 58.597 | 53.680 | 37.468 | 1.00 | 33.76 |
| ATOM | 4211 | NH2 | ARG | 592 | 60.498 | 54.961 | 37.620 | 1.00 | 33.43 |
| ATOM | 4212 | C   | ARG | 592 | 56.940 | 51.501 | 44.529 | 1.00 | 22.47 |
| ATOM | 4213 | O   | ARG | 592 | 55.957 | 52.151 | 44.884 | 1.00 | 23.13 |
| ATOM | 4214 | N   | LEU | 593 | 57.022 | 50.183 | 44.670 | 1.00 | 20.30 |
| ATOM | 4215 | CA  | LEU | 593 | 55.928 | 49.439 | 45.268 | 1.00 | 19.74 |
| ATOM | 4216 | CB  | LEU | 593 | 56.173 | 47.932 | 45.147 | 1.00 | 19.55 |
| ATOM | 4217 | CG  | LEU | 593 | 55.936 | 47.315 | 43.765 | 1.00 | 21.26 |
| ATOM | 4218 | CD1 | LEU | 593 | 56.137 | 45.807 | 43.847 | 1.00 | 20.22 |
| ATOM | 4219 | CD2 | LEU | 593 | 54.518 | 47.639 | 43.289 | 1.00 | 18.77 |
| ATOM | 4220 | C   | LEU | 593 | 55.756 | 49.819 | 46.734 | 1.00 | 18.89 |
| ATOM | 4221 | O   | LEU | 593 | 54.633 | 49.946 | 47.218 | 1.00 | 17.61 |
| ATOM | 4222 | N   | ALA | 594 | 56.872 | 50.003 | 47.434 | 1.00 | 17.55 |
| ATOM | 4223 | CA  | ALA | 594 | 56.827 | 50.358 | 48.851 | 1.00 | 19.25 |
| ATOM | 4224 | CB  | ALA | 594 | 58.236 | 50.327 | 49.449 | 1.00 | 17.33 |
| ATOM | 4225 | C   | ALA | 594 | 56.184 | 51.724 | 49.091 | 1.00 | 18.56 |
| ATOM | 4226 | O   | ALA | 594 | 55.281 | 51.852 | 49.914 | 1.00 | 19.48 |
| ATOM | 4227 | N   | THR | 595 | 56.647 | 52.744 | 48.378 | 1.00 | 19.12 |
| ATOM | 4228 | CA  | THR | 595 | 56.091 | 54.081 | 48.558 | 1.00 | 20.47 |
| ATOM | 4229 | CB  | THR | 595 | 56.754 | 55.105 | 47.602 | 1.00 | 22.14 |
| ATOM | 4230 | OG1 | THR | 595 | 56.482 | 54.744 | 46.242 | 1.00 | 27.28 |
| ATOM | 4231 | CG2 | THR | 595 | 58.255 | 55.134 | 47.814 | 1.00 | 22.28 |
| ATOM | 4232 | C   | THR | 595 | 54.584 | 54.067 | 48.306 | 1.00 | 20.42 |
| ATOM | 4233 | O   | THR | 595 | 53.823 | 54.741 | 49.006 | 1.00 | 20.17 |
| ATOM | 4234 | N   | ALA | 596 | 54.158 | 53.286 | 47.315 | 1.00 | 17.08 |
| ATOM | 4235 | CA  | ALA | 596 | 52.744 | 53.191 | 46.972 | 1.00 | 15.64 |
| ATOM | 4236 | CB  | ALA | 596 | 52.577 | 52.497 | 45.619 | 1.00 | 14.14 |
| ATOM | 4237 | C   | ALA | 596 | 51.948 | 52.448 | 48.043 | 1.00 | 14.88 |
| ATOM | 4238 | O   | ALA | 596 | 50.891 | 52.914 | 48.474 | 1.00 | 15.10 |
| ATOM | 4239 | N   | MET | 597 | 52.451 | 51.294 | 48.472 | 1.00 | 12.78 |
| ATOM | 4240 | CA  | MET | 597 | 51.762 | 50.511 | 49.488 | 1.00 | 14.01 |
| ATOM | 4241 | CB  | MET | 597 | 52.464 | 49.162 | 49.702 | 1.00 | 13.50 |
| ATOM | 4242 | CG  | MET | 597 | 52.266 | 48.171 | 48.562 | 1.00 | 14.73 |
| ATOM | 4243 | SD  | MET | 597 | 52.878 | 46.512 | 48.914 | 1.00 | 17.16 |
| ATOM | 4244 | CE  | MET | 597 | 54.598 | 46.708 | 48.490 | 1.00 | 16.02 |
| ATOM | 4245 | C   | MET | 597 | 51.644 | 51.249 | 50.820 | 1.00 | 14.90 |
| ATOM | 4246 | O   | MET | 597 | 50.648 | 51.108 | 51.525 | 1.00 | 13.57 |
| ATOM | 4247 | N   | LYS | 598 | 52.659 | 52.037 | 51.157 | 1.00 | 15.99 |
| ATOM | 4248 | CA  | LYS | 598 | 52.660 | 52.786 | 52.412 | 1.00 | 17.02 |
| ATOM | 4249 | CB  | LYS | 598 | 53.998 | 53.509 | 52.588 | 1.00 | 17.91 |
| ATOM | 4250 | CG  | LYS | 598 | 55.146 | 52.592 | 52.970 | 1.00 | 22.00 |
| ATOM | 4251 | CD  | LYS | 598 | 56.439 | 53.374 | 53.127 | 1.00 | 25.95 |
| ATOM | 4252 | CE  | LYS | 598 | 57.505 | 52.545 | 53.830 | 1.00 | 28.04 |
| ATOM | 4253 | NZ  | LYS | 598 | 57.829 | 51.285 | 53.106 | 1.00 | 28.00 |
| ATOM | 4254 | C   | LYS | 598 | 51.512 | 53.790 | 52.513 | 1.00 | 17.35 |
| ATOM | 4255 | O   | LYS | 598 | 51.098 | 54.155 | 53.613 | 1.00 | 19.76 |
| ATOM | 4256 | N   | LEU | 599 | 51.000 | 54.234 | 51.369 | 1.00 | 15.18 |
| ATOM | 4257 | CA  | LEU | 599 | 49.892 | 55.184 | 51.355 | 1.00 | 14.61 |
| ATOM | 4258 | CB  | LEU | 599 | 49.652 | 55.722 | 49.940 | 1.00 | 15.70 |
| ATOM | 4259 | CG  | LEU | 599 | 50.701 | 56.621 | 49.288 | 1.00 | 15.36 |
| ATOM | 4260 | CD1 | LEU | 599 | 50.234 | 56.968 | 47.888 | 1.00 | 15.46 |
| ATOM | 4261 | CD2 | LEU | 599 | 50.911 | 57.884 | 50.113 | 1.00 | 15.35 |
| ATOM | 4262 | C   | LEU | 599 | 48.607 | 54.534 | 51.845 | 1.00 | 14.55 |
| ATOM | 4263 | O   | LEU | 599 | 47.686 | 55.222 | 52.285 | 1.00 | 16.32 |
| ATOM | 4264 | N   | GLY | 600 | 48.544 | 53.209 | 51.767 | 1.00 | 13.23 |
| ATOM | 4265 | CA  | GLY | 600 | 47.341 | 52.517 | 52.184 | 1.00 | 14.20 |
| ATOM | 4266 | C   | GLY | 600 | 46.128 | 53.091 | 51.468 | 1.00 | 14.55 |
| ATOM | 4267 | O   | GLY | 600 | 46.116 | 53.212 | 50.240 | 1.00 | 14.07 |
| ATOM | 4268 | N   | PHE | 601 | 45.117 | 53.468 | 52.242 | 1.00 | 15.08 |
| ATOM | 4269 | CA  | PHE | 601 | 43.883 | 54.031 | 51.700 | 1.00 | 16.39 |
| ATOM | 4270 | CB  | PHE | 601 | 42.684 | 53.251 | 52.271 | 1.00 | 16.50 |
| ATOM | 4271 | CG  | PHE | 601 | 41.376 | 53.527 | 51.574 | 1.00 | 18.08 |
| ATOM | 4272 | CD1 | PHE | 601 | 41.221 | 53.255 | 50.217 | 1.00 | 18.28 |
| ATOM | 4273 | CD2 | PHE | 601 | 40.290 | 54.033 | 52.284 | 1.00 | 18.21 |
| ATOM | 4274 | CE1 | PHE | 601 | 40.002 | 53.478 | 49.577 | 1.00 | 19.49 |
| ATOM | 4275 | CE2 | PHE | 601 | 39.060 | 54.262 | 51.653 | 1.00 | 19.93 |
| ATOM | 4276 | CZ  | PHE | 601 | 38.918 | 53.982 | 50.297 | 1.00 | 18.56 |
| ATOM | 4277 | C   | PHE | 601 | 43.786 | 55.518 | 52.079 | 1.00 | 16.63 |
| ATOM | 4278 | O   | PHE | 601 | 42.698 | 56.083 | 52.144 | 1.00 | 16.35 |

TABLE B-continued

Co-ordinates of an underglycosylated tACEΔ36NJ ACE-lisinopril complex

| ATOM | 4279 | N | SER | 602 | 44.934 | 56.152 | 52.302 | 1.00 | 18.17 |
|---|---|---|---|---|---|---|---|---|---|
| ATOM | 4280 | CA | SER | 602 | 44.968 | 57.561 | 52.699 | 1.00 | 19.16 |
| ATOM | 4281 | CB | SER | 602 | 46.294 | 57.868 | 53.395 | 1.00 | 19.08 |
| ATOM | 4282 | OG | SER | 602 | 47.375 | 57.759 | 52.484 | 1.00 | 16.23 |
| ATOM | 4283 | C | SER | 602 | 44.751 | 58.593 | 51.590 | 1.00 | 21.31 |
| ATOM | 4284 | O | SER | 602 | 44.388 | 59.735 | 51.874 | 1.00 | 19.96 |
| ATOM | 4285 | N | ARG | 603 | 44.973 | 58.199 | 50.337 | 1.00 | 20.09 |
| ATOM | 4286 | CA | ARG | 603 | 44.816 | 59.118 | 49.207 | 1.00 | 21.67 |
| ATOM | 4287 | CB | ARG | 603 | 46.201 | 59.533 | 48.685 | 1.00 | 22.66 |
| ATOM | 4288 | CG | ARG | 603 | 47.124 | 60.184 | 49.711 | 1.00 | 26.63 |
| ATOM | 4289 | CD | ARG | 603 | 46.639 | 61.574 | 50.087 | 1.00 | 28.83 |
| ATOM | 4290 | NE | ARG | 603 | 46.453 | 62.415 | 48.908 | 1.00 | 33.44 |
| ATOM | 4291 | CZ | ARG | 603 | 45.955 | 63.648 | 48.939 | 1.00 | 35.92 |
| ATOM | 4292 | NH1 | ARG | 603 | 45.594 | 64.189 | 50.096 | 1.00 | 35.88 |
| ATOM | 4293 | NH2 | ARG | 603 | 45.808 | 64.337 | 47.816 | 1.00 | 35.28 |
| ATOM | 4294 | C | ARG | 603 | 44.037 | 58.471 | 48.058 | 1.00 | 20.33 |
| ATOM | 4295 | O | ARG | 603 | 43.926 | 57.257 | 47.987 | 1.00 | 21.14 |
| ATOM | 4296 | N | PRO | 604 | 43.486 | 59.283 | 47.141 | 1.00 | 21.16 |
| ATOM | 4297 | CD | PRO | 604 | 43.484 | 60.757 | 47.074 | 1.00 | 20.84 |
| ATOM | 4298 | CA | PRO | 604 | 42.742 | 58.700 | 46.016 | 1.00 | 20.12 |
| ATOM | 4299 | CB | PRO | 604 | 42.380 | 59.920 | 45.171 | 1.00 | 21.00 |
| ATOM | 4300 | CG | PRO | 604 | 42.288 | 61.033 | 46.199 | 1.00 | 22.41 |
| ATOM | 4301 | C | PRO | 604 | 43.717 | 57.765 | 45.294 | 1.00 | 18.21 |
| ATOM | 4302 | O | PRO | 604 | 44.879 | 58.123 | 45.108 | 1.00 | 16.62 |
| ATOM | 4303 | N | TRP | 605 | 43.256 | 56.588 | 44.871 | 1.00 | 16.20 |
| ATOM | 4304 | CA | TRP | 605 | 44.155 | 55.631 | 44.222 | 1.00 | 14.88 |
| ATOM | 4305 | CB | TRP | 605 | 43.404 | 54.352 | 43.807 | 1.00 | 11.66 |
| ATOM | 4306 | CG | TRP | 605 | 42.419 | 54.500 | 42.687 | 1.00 | 11.73 |
| ATOM | 4307 | CD2 | TRP | 605 | 42.712 | 54.543 | 41.285 | 1.00 | 10.38 |
| ATOM | 4308 | CE2 | TRP | 605 | 41.478 | 54.643 | 40.605 | 1.00 | 9.76 |
| ATOM | 4309 | CE3 | TRP | 605 | 43.897 | 54.513 | 40.537 | 1.00 | 11.00 |
| ATOM | 4310 | CD1 | TRP | 605 | 41.059 | 54.575 | 42.797 | 1.00 | 11.94 |
| ATOM | 4311 | NE1 | TRP | 605 | 40.487 | 54.657 | 41.551 | 1.00 | 12.01 |
| ATOM | 4312 | CZ2 | TRP | 605 | 41.393 | 54.706 | 39.211 | 1.00 | 10.56 |
| ATOM | 4313 | CZ3 | TRP | 605 | 43.813 | 54.577 | 39.147 | 1.00 | 12.40 |
| ATOM | 4314 | CH2 | TRP | 605 | 42.569 | 54.675 | 38.500 | 1.00 | 10.93 |
| ATOM | 4315 | C | TRP | 605 | 44.990 | 56.138 | 43.048 | 1.00 | 14.01 |
| ATOM | 4316 | O | TRP | 605 | 46.088 | 55.639 | 42.819 | 1.00 | 14.77 |
| ATOM | 4317 | N | PRO | 606 | 44.491 | 57.132 | 42.287 | 1.00 | 14.29 |
| ATOM | 4318 | CD | PRO | 606 | 43.145 | 57.734 | 42.275 | 1.00 | 12.19 |
| ATOM | 4319 | CA | PRO | 606 | 45.286 | 57.629 | 41.158 | 1.00 | 15.72 |
| ATOM | 4320 | CB | PRO | 606 | 44.432 | 58.770 | 40.613 | 1.00 | 15.01 |
| ATOM | 4321 | CG | PRO | 606 | 43.046 | 58.272 | 40.859 | 1.00 | 14.40 |
| ATOM | 4322 | C | PRO | 606 | 46.687 | 58.091 | 41.559 | 1.00 | 17.03 |
| ATOM | 4323 | O | PRO | 606 | 47.600 | 58.098 | 40.740 | 1.00 | 16.15 |
| ATOM | 4324 | N | GLU | 607 | 46.852 | 58.481 | 42.818 | 1.00 | 17.28 |
| ATOM | 4325 | CA | GLU | 607 | 48.157 | 58.925 | 43.298 | 1.00 | 19.19 |
| ATOM | 4326 | CB | GLU | 607 | 48.017 | 59.648 | 44.639 | 1.00 | 21.09 |
| ATOM | 4327 | CG | GLU | 607 | 47.456 | 61.060 | 44.503 | 1.00 | 25.25 |
| ATOM | 4328 | CD | GLU | 607 | 47.359 | 61.785 | 45.837 | 1.00 | 27.88 |
| ATOM | 4329 | OE1 | GLU | 607 | 48.311 | 61.683 | 46.641 | 1.00 | 28.02 |
| ATOM | 4330 | OE2 | GLU | 607 | 46.334 | 62.462 | 46.075 | 1.00 | 29.69 |
| ATOM | 4331 | C | GLU | 607 | 49.106 | 57.739 | 43.430 | 1.00 | 17.57 |
| ATOM | 4332 | O | GLU | 607 | 50.268 | 57.828 | 43.052 | 1.00 | 18.96 |
| ATOM | 4333 | N | ALA | 608 | 48.611 | 56.626 | 43.962 | 1.00 | 16.29 |
| ATOM | 4334 | CA | ALA | 608 | 49.438 | 55.434 | 44.094 | 1.00 | 16.79 |
| ATOM | 4335 | CB | ALA | 608 | 48.693 | 54.353 | 44.871 | 1.00 | 14.91 |
| ATOM | 4336 | C | ALA | 608 | 49.775 | 54.947 | 42.683 | 1.00 | 16.09 |
| ATOM | 4337 | O | ALA | 608 | 50.886 | 54.488 | 42.425 | 1.00 | 16.14 |
| ATOM | 4338 | N | MET | 609 | 48.810 | 55.056 | 41.772 | 1.00 | 15.85 |
| ATOM | 4339 | CA | MET | 609 | 49.024 | 54.649 | 40.383 | 1.00 | 15.49 |
| ATOM | 4340 | CB | MET | 609 | 47.742 | 54.841 | 39.569 | 1.00 | 14.89 |
| ATOM | 4341 | CG | MET | 609 | 47.885 | 54.548 | 38.068 | 1.00 | 12.61 |
| ATOM | 4342 | SD | MET | 609 | 48.373 | 52.846 | 37.686 | 1.00 | 14.89 |
| ATOM | 4343 | CE | MET | 609 | 46.752 | 52.007 | 37.746 | 1.00 | 9.67 |
| ATOM | 4344 | C | MET | 609 | 50.152 | 55.486 | 39.769 | 1.00 | 17.04 |
| ATOM | 4345 | O | MET | 609 | 51.018 | 54.963 | 39.063 | 1.00 | 16.25 |
| ATOM | 4346 | N | GLN | 610 | 50.131 | 56.787 | 40.044 | 1.00 | 16.65 |
| ATOM | 4347 | CA | GLN | 610 | 51.149 | 57.697 | 39.527 | 1.00 | 17.56 |
| ATOM | 4348 | CB | GLN | 610 | 50.798 | 59.148 | 39.865 | 1.00 | 21.08 |
| ATOM | 4349 | CG | GLN | 610 | 51.631 | 60.167 | 39.093 | 1.00 | 24.06 |
| ATOM | 4350 | CD | GLN | 610 | 50.775 | 61.060 | 38.219 | 1.00 | 27.95 |
| ATOM | 4351 | OE1 | GLN | 610 | 50.227 | 62.066 | 38.675 | 1.00 | 30.67 |
| ATOM | 4352 | NE2 | GLN | 610 | 50.637 | 60.684 | 36.959 | 1.00 | 31.02 |
| ATOM | 4353 | C | GLN | 610 | 52.521 | 57.362 | 40.103 | 1.00 | 18.21 |
| ATOM | 4354 | O | GLN | 610 | 53.513 | 57.324 | 39.375 | 1.00 | 17.58 |
| ATOM | 4355 | N | LEU | 611 | 52.574 | 57.120 | 41.410 | 1.00 | 17.37 |
| ATOM | 4356 | CA | LEU | 611 | 53.831 | 56.775 | 42.069 | 1.00 | 19.20 |

TABLE B-continued

Co-ordinates of an underglycosylated tACEΔ36NJ ACE-lisinopril complex

| ATOM | 4357 | CB | LEU | 611 | 53.593 | 56.498 | 43.560 | 1.00 | 20.05 |
|---|---|---|---|---|---|---|---|---|---|
| ATOM | 4358 | CG | LEU | 611 | 53.385 | 57.741 | 44.430 | 1.00 | 22.61 |
| ATOM | 4359 | CD1 | LEU | 611 | 53.020 | 57.324 | 45.839 | 1.00 | 22.10 |
| ATOM | 4360 | CD2 | LEU | 611 | 54.660 | 58.580 | 44.431 | 1.00 | 21.77 |
| ATOM | 4361 | C | LEU | 611 | 54.517 | 55.567 | 41.434 | 1.00 | 18.06 |
| ATOM | 4362 | O | LEU | 611 | 55.743 | 55.524 | 41.319 | 1.00 | 17.10 |
| ATOM | 4363 | N | ILE | 612 | 53.728 | 54.585 | 41.019 | 1.00 | 17.78 |
| ATOM | 4364 | CA | ILE | 612 | 54.289 | 53.384 | 40.408 | 1.00 | 15.89 |
| ATOM | 4365 | CB | ILE | 612 | 53.356 | 52.167 | 40.609 | 1.00 | 17.36 |
| ATOM | 4366 | CG2 | ILE | 612 | 53.944 | 50.944 | 39.917 | 1.00 | 17.31 |
| ATOM | 4367 | CG1 | ILE | 612 | 53.158 | 51.888 | 42.099 | 1.00 | 17.99 |
| ATOM | 4368 | CD1 | ILE | 612 | 52.075 | 50.865 | 42.391 | 1.00 | 16.14 |
| ATOM | 4369 | C | ILE | 612 | 54.562 | 53.505 | 38.907 | 1.00 | 16.86 |
| ATOM | 4370 | O | ILE | 612 | 55.643 | 53.151 | 38.440 | 1.00 | 18.03 |
| ATOM | 4371 | N | THR | 613 | 53.586 | 54.018 | 38.162 | 1.00 | 16.36 |
| ATOM | 4372 | CA | THR | 613 | 53.684 | 54.108 | 36.707 | 1.00 | 15.96 |
| ATOM | 4373 | CB | THR | 613 | 52.368 | 53.622 | 36.079 | 1.00 | 14.90 |
| ATOM | 4374 | OG1 | THR | 613 | 51.341 | 54.594 | 36.320 | 1.00 | 12.04 |
| ATOM | 4375 | CG2 | THR | 613 | 51.941 | 52.289 | 36.701 | 1.00 | 12.12 |
| ATOM | 4376 | C | THR | 613 | 54.035 | 55.452 | 36.059 | 1.00 | 17.25 |
| ATOM | 4377 | O | THR | 613 | 54.323 | 55.502 | 34.860 | 1.00 | 16.91 |
| ATOM | 4378 | N | GLY | 614 | 54.000 | 56.538 | 36.826 | 1.00 | 16.88 |
| ATOM | 4379 | CA | GLY | 614 | 54.315 | 57.836 | 36.251 | 1.00 | 16.24 |
| ATOM | 4380 | C | GLY | 614 | 53.126 | 58.496 | 35.572 | 1.00 | 17.22 |
| ATOM | 4381 | O | GLY | 614 | 53.256 | 59.556 | 34.962 | 1.00 | 16.05 |
| ATOM | 4382 | N | GLN | 615 | 51.965 | 57.854 | 35.659 | 1.00 | 17.32 |
| ATOM | 4383 | CA | GLN | 615 | 50.736 | 58.391 | 35.086 | 1.00 | 15.68 |
| ATOM | 4384 | CB | GLN | 615 | 50.551 | 57.895 | 33.644 | 1.00 | 15.80 |
| ATOM | 4385 | CG | GLN | 615 | 50.422 | 56.397 | 33.467 | 1.00 | 16.06 |
| ATOM | 4386 | CD | GLN | 615 | 49.041 | 55.919 | 33.822 | 1.00 | 14.47 |
| ATOM | 4387 | OE1 | GLN | 615 | 48.045 | 56.448 | 33.322 | 1.00 | 14.28 |
| ATOM | 4388 | NE2 | GLN | 615 | 48.966 | 54.919 | 34.686 | 1.00 | 12.42 |
| ATOM | 4389 | C | GLN | 615 | 49.622 | 57.957 | 36.048 | 1.00 | 14.75 |
| ATOM | 4390 | O | GLN | 615 | 49.815 | 57.042 | 36.837 | 1.00 | 14.61 |
| ATOM | 4391 | N | PRO | 616 | 48.443 | 58.599 | 35.994 | 1.00 | 14.37 |
| ATOM | 4392 | CD | PRO | 616 | 48.129 | 59.856 | 35.288 | 1.00 | 15.57 |
| ATOM | 4393 | CA | PRO | 616 | 47.357 | 58.248 | 36.917 | 1.00 | 14.41 |
| ATOM | 4394 | CB | PRO | 616 | 46.829 | 59.617 | 37.298 | 1.00 | 15.41 |
| ATOM | 4395 | CG | PRO | 616 | 46.800 | 60.287 | 35.933 | 1.00 | 14.41 |
| ATOM | 4396 | C | PRO | 616 | 46.202 | 57.320 | 36.543 | 1.00 | 14.55 |
| ATOM | 4397 | O | PRO | 616 | 45.390 | 56.988 | 37.409 | 1.00 | 13.74 |
| ATOM | 4398 | N | ASN | 617 | 46.108 | 56.904 | 35.289 | 1.00 | 14.76 |
| ATOM | 4399 | CA | ASN | 617 | 44.985 | 56.072 | 34.869 | 1.00 | 16.09 |
| ATOM | 4400 | CB | ASN | 617 | 44.495 | 56.545 | 33.501 | 1.00 | 17.02 |
| ATOM | 4401 | CG | ASN | 617 | 44.216 | 58.029 | 33.462 | 1.00 | 18.18 |
| ATOM | 4402 | OD1 | ASN | 617 | 44.489 | 58.692 | 32.463 | 1.00 | 22.94 |
| ATOM | 4403 | ND2 | ASN | 617 | 43.658 | 58.557 | 34.542 | 1.00 | 18.54 |
| ATOM | 4404 | C | ASN | 617 | 45.226 | 54.573 | 34.777 | 1.00 | 14.02 |
| ATOM | 4405 | O | ASN | 617 | 46.364 | 54.105 | 34.776 | 1.00 | 13.88 |
| ATOM | 4406 | N | MET | 618 | 44.124 | 53.829 | 34.710 | 1.00 | 13.32 |
| ATOM | 4407 | CA | MET | 618 | 44.179 | 52.387 | 34.516 | 1.00 | 14.06 |
| ATOM | 4408 | CB | MET | 618 | 42.868 | 51.709 | 34.929 | 1.00 | 11.91 |
| ATOM | 4409 | CG | MET | 618 | 42.667 | 51.565 | 36.425 | 1.00 | 12.29 |
| ATOM | 4410 | SD | MET | 618 | 41.194 | 50.589 | 36.832 | 1.00 | 13.39 |
| ATOM | 4411 | CE | MET | 618 | 39.927 | 51.842 | 36.691 | 1.00 | 14.36 |
| ATOM | 4412 | C | MET | 618 | 44.316 | 52.322 | 32.997 | 1.00 | 14.48 |
| ATOM | 4413 | O | MET | 618 | 43.788 | 53.187 | 32.291 | 1.00 | 13.59 |
| ATOM | 4414 | N | SER | 619 | 45.013 | 51.318 | 32.488 | 1.00 | 12.87 |
| ATOM | 4415 | CA | SER | 619 | 45.194 | 51.215 | 31.049 | 1.00 | 13.47 |
| ATOM | 4416 | CB | SER | 619 | 46.309 | 52.168 | 30.599 | 1.00 | 13.34 |
| ATOM | 4417 | OG | SER | 619 | 46.562 | 52.039 | 29.215 | 1.00 | 16.20 |
| ATOM | 4418 | C | SER | 619 | 45.540 | 49.797 | 30.631 | 1.00 | 12.99 |
| ATOM | 4419 | O | SER | 619 | 46.338 | 49.131 | 31.288 | 1.00 | 12.36 |
| ATOM | 4420 | N | ALA | 620 | 44.937 | 49.350 | 29.533 | 1.00 | 12.12 |
| ATOM | 4421 | CA | ALA | 620 | 45.177 | 48.012 | 29.001 | 1.00 | 13.20 |
| ATOM | 4422 | CB | ALA | 620 | 43.968 | 47.555 | 28.189 | 1.00 | 9.78 |
| ATOM | 4423 | C | ALA | 620 | 46.433 | 47.971 | 28.125 | 1.00 | 13.52 |
| ATOM | 4424 | O | ALA | 620 | 46.845 | 46.901 | 27.672 | 1.00 | 12.99 |
| ATOM | 4425 | N | SER | 621 | 47.036 | 49.135 | 27.886 | 1.00 | 14.24 |
| ATOM | 4426 | CA | SER | 621 | 48.239 | 49.219 | 27.049 | 1.00 | 14.97 |
| ATOM | 4427 | CB | SER | 621 | 48.788 | 50.649 | 27.037 | 1.00 | 15.46 |
| ATOM | 4428 | OG | SER | 621 | 47.972 | 51.485 | 26.239 | 1.00 | 22.97 |
| ATOM | 4429 | C | SER | 621 | 49.361 | 48.266 | 27.446 | 1.00 | 13.26 |
| ATOM | 4430 | O | SER | 621 | 49.919 | 47.576 | 26.600 | 1.00 | 12.69 |
| ATOM | 4431 | N | ALA | 622 | 49.697 | 48.241 | 28.730 | 1.00 | 12.55 |
| ATOM | 4432 | CA | ALA | 622 | 50.761 | 47.374 | 29.220 | 1.00 | 12.62 |
| ATOM | 4433 | CB | ALA | 622 | 50.945 | 47.576 | 30.718 | 1.00 | 13.96 |
| ATOM | 4434 | C | ALA | 622 | 50.476 | 45.902 | 28.917 | 1.00 | 13.74 |

TABLE B-continued

Co-ordinates of an underglycosylated tACEΔ36NJ ACE-lisinopril complex

| ATOM | 4435 | O   | ALA | 622 | 51.344 | 45.181 | 28.412 | 1.00 | 13.46 |
|------|------|-----|-----|-----|--------|--------|--------|------|-------|
| ATOM | 4436 | N   | MET | 623 | 49.261 | 45.458 | 29.227 | 1.00 | 12.23 |
| ATOM | 4437 | CA  | MET | 623 | 48.882 | 44.074 | 28.977 | 1.00 | 11.27 |
| ATOM | 4438 | CB  | MET | 623 | 47.501 | 43.792 | 29.578 | 1.00 | 11.37 |
| ATOM | 4439 | CG  | MET | 623 | 47.048 | 42.354 | 29.452 | 1.00 | 12.71 |
| ATOM | 4440 | SD  | MET | 623 | 45.490 | 42.044 | 30.308 | 1.00 | 16.84 |
| ATOM | 4441 | CE  | MET | 623 | 45.878 | 40.541 | 31.173 | 1.00 | 14.59 |
| ATOM | 4442 | C   | MET | 623 | 48.892 | 43.767 | 27.476 | 1.00 | 11.91 |
| ATOM | 4443 | O   | MET | 623 | 49.352 | 42.706 | 27.058 | 1.00 | 13.42 |
| ATOM | 4444 | N   | LEU | 624 | 48.397 | 44.694 | 26.662 | 1.00 | 13.23 |
| ATOM | 4445 | CA  | LEU | 624 | 48.392 | 44.486 | 25.212 | 1.00 | 15.53 |
| ATOM | 4446 | CB  | LEU | 624 | 47.622 | 45.611 | 24.505 | 1.00 | 15.98 |
| ATOM | 4447 | CG  | LEU | 624 | 46.108 | 45.644 | 24.741 | 1.00 | 19.16 |
| ATOM | 4448 | CD1 | LEU | 624 | 45.483 | 46.800 | 23.970 | 1.00 | 18.76 |
| ATOM | 4449 | CD2 | LEU | 624 | 45.496 | 44.322 | 24.302 | 1.00 | 21.48 |
| ATOM | 4450 | C   | LEU | 624 | 49.824 | 44.419 | 24.674 | 1.00 | 15.45 |
| ATOM | 4451 | O   | LEU | 624 | 50.141 | 43.602 | 23.808 | 1.00 | 15.14 |
| ATOM | 4452 | N   | SER | 625 | 50.688 | 45.281 | 25.198 | 1.00 | 15.79 |
| ATOM | 4453 | CA  | SER | 625 | 52.088 | 45.315 | 24.788 | 1.00 | 16.37 |
| ATOM | 4454 | CB  | SER | 625 | 52.788 | 46.502 | 25.462 | 1.00 | 16.92 |
| ATOM | 4455 | OG  | SER | 625 | 54.196 | 46.404 | 25.354 | 1.00 | 22.26 |
| ATOM | 4456 | C   | SER | 625 | 52.777 | 43.995 | 25.168 | 1.00 | 16.55 |
| ATOM | 4457 | O   | SER | 625 | 53.544 | 43.426 | 24.385 | 1.00 | 17.40 |
| ATOM | 4458 | N   | TYR | 626 | 52.490 | 43.511 | 26.372 | 1.00 | 14.61 |
| ATOM | 4459 | CA  | TYR | 626 | 53.055 | 42.253 | 26.858 | 1.00 | 13.80 |
| ATOM | 4460 | CB  | TYR | 626 | 52.487 | 41.939 | 28.251 | 1.00 | 13.59 |
| ATOM | 4461 | CG  | TYR | 626 | 53.024 | 40.679 | 28.896 | 1.00 | 14.23 |
| ATOM | 4462 | CD1 | TYR | 626 | 54.061 | 40.733 | 29.827 | 1.00 | 15.51 |
| ATOM | 4463 | CE1 | TYR | 626 | 54.538 | 39.574 | 30.438 | 1.00 | 14.52 |
| ATOM | 4464 | CD2 | TYR | 626 | 52.481 | 39.431 | 28.587 | 1.00 | 12.73 |
| ATOM | 4465 | CE2 | TYR | 626 | 52.951 | 38.275 | 29.186 | 1.00 | 12.06 |
| ATOM | 4466 | CZ  | TYR | 626 | 53.975 | 38.348 | 30.111 | 1.00 | 14.06 |
| ATOM | 4467 | OH  | TYR | 626 | 54.425 | 37.193 | 30.713 | 1.00 | 13.54 |
| ATOM | 4468 | C   | TYR | 626 | 52.721 | 41.101 | 25.901 | 1.00 | 13.64 |
| ATOM | 4469 | O   | TYR | 626 | 53.585 | 40.287 | 25.567 | 1.00 | 12.40 |
| ATOM | 4470 | N   | PHE | 627 | 51.467 | 41.039 | 25.461 | 1.00 | 12.53 |
| ATOM | 4471 | CA  | PHE | 627 | 51.021 | 39.969 | 24.567 | 1.00 | 14.30 |
| ATOM | 4472 | CB  | PHE | 627 | 49.608 | 39.515 | 24.955 | 1.00 | 11.92 |
| ATOM | 4473 | CG  | PHE | 627 | 49.534 | 38.832 | 26.285 | 1.00 | 12.27 |
| ATOM | 4474 | CD1 | PHE | 627 | 49.087 | 39.517 | 27.414 | 1.00 | 12.27 |
| ATOM | 4475 | CD2 | PHE | 627 | 49.902 | 37.497 | 26.410 | 1.00 | 10.91 |
| ATOM | 4476 | CE1 | PHE | 627 | 49.008 | 38.880 | 28.649 | 1.00 | 12.53 |
| ATOM | 4477 | CE2 | PHE | 627 | 49.829 | 36.848 | 27.639 | 1.00 | 11.87 |
| ATOM | 4478 | CZ  | PHE | 627 | 49.379 | 37.539 | 28.762 | 1.00 | 13.01 |
| ATOM | 4479 | C   | PHE | 627 | 51.030 | 40.267 | 23.066 | 1.00 | 14.21 |
| ATOM | 4480 | O   | PHE | 627 | 50.575 | 39.446 | 22.274 | 1.00 | 15.37 |
| ATOM | 4481 | N   | LYS | 628 | 51.538 | 41.430 | 22.671 | 1.00 | 15.87 |
| ATOM | 4482 | CA  | LYS | 628 | 51.570 | 41.801 | 21.258 | 1.00 | 15.56 |
| ATOM | 4483 | CB  | LYS | 628 | 52.415 | 43.065 | 21.065 | 1.00 | 18.34 |
| ATOM | 4484 | CG  | LYS | 628 | 52.689 | 43.436 | 19.608 | 1.00 | 20.03 |
| ATOM | 4485 | CD  | LYS | 628 | 51.421 | 43.755 | 18.835 | 1.00 | 21.75 |
| ATOM | 4486 | CE  | LYS | 628 | 51.754 | 44.104 | 17.378 | 1.00 | 25.43 |
| ATOM | 4487 | NZ  | LYS | 628 | 50.542 | 44.288 | 16.531 | 1.00 | 24.46 |
| ATOM | 4488 | C   | LYS | 628 | 52.080 | 40.682 | 20.345 | 1.00 | 15.60 |
| ATOM | 4489 | O   | LYS | 628 | 51.462 | 40.383 | 19.324 | 1.00 | 17.04 |
| ATOM | 4490 | N   | PRO | 629 | 53.215 | 40.054 | 20.693 | 1.00 | 15.51 |
| ATOM | 4491 | CD  | PRO | 629 | 54.172 | 40.346 | 21.775 | 1.00 | 16.28 |
| ATOM | 4492 | CA  | PRO | 629 | 53.715 | 38.978 | 19.830 | 1.00 | 16.88 |
| ATOM | 4493 | CB  | PRO | 629 | 54.987 | 38.522 | 20.545 | 1.00 | 17.11 |
| ATOM | 4494 | CG  | PRO | 629 | 55.463 | 39.781 | 21.218 | 1.00 | 16.67 |
| ATOM | 4495 | C   | PRO | 629 | 52.690 | 37.848 | 19.676 | 1.00 | 17.03 |
| ATOM | 4496 | O   | PRO | 629 | 52.496 | 37.320 | 18.579 | 1.00 | 17.38 |
| ATOM | 4497 | N   | LEU | 630 | 52.027 | 37.486 | 20.771 | 1.00 | 16.19 |
| ATOM | 4498 | CA  | LEU | 630 | 51.033 | 36.424 | 20.718 | 1.00 | 15.34 |
| ATOM | 4499 | CB  | LEU | 630 | 50.570 | 36.044 | 22.126 | 1.00 | 14.76 |
| ATOM | 4500 | CG  | LEU | 630 | 49.601 | 34.856 | 22.206 | 1.00 | 15.06 |
| ATOM | 4501 | CD1 | LEU | 630 | 50.308 | 33.587 | 21.767 | 1.00 | 15.11 |
| ATOM | 4502 | CD2 | LEU | 630 | 49.086 | 34.696 | 23.623 | 1.00 | 14.11 |
| ATOM | 4503 | C   | LEU | 630 | 49.831 | 36.835 | 19.872 | 1.00 | 15.75 |
| ATOM | 4504 | O   | LEU | 630 | 49.308 | 36.035 | 19.098 | 1.00 | 15.82 |
| ATOM | 4505 | N   | LEU | 631 | 49.389 | 38.081 | 20.018 | 1.00 | 16.88 |
| ATOM | 4506 | CA  | LEU | 631 | 48.249 | 38.564 | 19.245 | 1.00 | 17.64 |
| ATOM | 4507 | CB  | LEU | 631 | 47.959 | 40.036 | 19.556 | 1.00 | 17.22 |
| ATOM | 4508 | CG  | LEU | 631 | 46.810 | 40.681 | 18.765 | 1.00 | 20.26 |
| ATOM | 4509 | CD1 | LEU | 631 | 45.498 | 39.989 | 19.100 | 1.00 | 20.21 |
| ATOM | 4510 | CD2 | LEU | 631 | 46.719 | 42.161 | 19.093 | 1.00 | 19.79 |
| ATOM | 4511 | C   | LEU | 631 | 48.533 | 38.405 | 17.753 | 1.00 | 18.65 |
| ATOM | 4512 | O   | LEU | 631 | 47.681 | 37.929 | 17.005 | 1.00 | 18.10 |

TABLE B-continued

Co-ordinates of an underglycosylated tACEΔ36NJ ACE-lisinopril complex

| ATOM | 4513 | N | ASP | 632 | 49.731 | 38.802 | 17.326 | 1.00 | 17.92 |
|---|---|---|---|---|---|---|---|---|---|
| ATOM | 4514 | CA | ASP | 632 | 50.109 | 38.692 | 15.920 | 1.00 | 18.59 |
| ATOM | 4515 | CB | ASP | 632 | 51.485 | 39.326 | 15.671 | 1.00 | 19.38 |
| ATOM | 4516 | CG | ASP | 632 | 51.480 | 40.827 | 15.866 | 1.00 | 19.25 |
| ATOM | 4517 | OD1 | ASP | 632 | 50.445 | 41.457 | 15.585 | 1.00 | 23.41 |
| ATOM | 4518 | OD2 | ASP | 632 | 52.514 | 41.385 | 16.283 | 1.00 | 23.91 |
| ATOM | 4519 | C | ASP | 632 | 50.138 | 37.234 | 15.476 | 1.00 | 17.19 |
| ATOM | 4520 | O | ASP | 632 | 49.677 | 36.898 | 14.385 | 1.00 | 15.78 |
| ATOM | 4521 | N | TRP | 633 | 50.682 | 36.368 | 16.326 | 1.00 | 16.49 |
| ATOM | 4522 | CA | TRP | 633 | 50.756 | 34.950 | 15.997 | 1.00 | 16.56 |
| ATOM | 4523 | CB | TRP | 633 | 51.565 | 34.194 | 17.057 | 1.00 | 16.10 |
| ATOM | 4524 | CG | TRP | 633 | 51.804 | 32.763 | 16.687 | 1.00 | 17.24 |
| ATOM | 4525 | CD2 | TRP | 633 | 50.971 | 31.645 | 17.015 | 1.00 | 17.80 |
| ATOM | 4526 | CE2 | TRP | 633 | 51.523 | 30.510 | 16.380 | 1.00 | 18.16 |
| ATOM | 4527 | CE3 | TRP | 633 | 49.807 | 31.491 | 17.782 | 1.00 | 17.82 |
| ATOM | 4528 | CD1 | TRP | 633 | 52.804 | 32.273 | 15.892 | 1.00 | 17.18 |
| ATOM | 4529 | NE1 | TRP | 633 | 52.641 | 30.922 | 15.703 | 1.00 | 17.98 |
| ATOM | 4530 | CZ2 | TRP | 633 | 50.952 | 29.240 | 16.486 | 1.00 | 17.93 |
| ATOM | 4531 | CZ3 | TRP | 633 | 49.240 | 30.226 | 17.889 | 1.00 | 19.24 |
| ATOM | 4532 | CH2 | TRP | 633 | 49.815 | 29.117 | 17.243 | 1.00 | 17.03 |
| ATOM | 4533 | C | TRP | 633 | 49.347 | 34.359 | 15.912 | 1.00 | 16.87 |
| ATOM | 4534 | O | TRP | 633 | 49.048 | 33.559 | 15.024 | 1.00 | 15.40 |
| ATOM | 4535 | N | LEU | 634 | 48.480 | 34.770 | 16.833 | 1.00 | 16.10 |
| ATOM | 4536 | CA | LEU | 634 | 47.108 | 34.275 | 16.872 | 1.00 | 15.03 |
| ATOM | 4537 | CB | LEU | 634 | 46.406 | 34.749 | 18.151 | 1.00 | 13.27 |
| ATOM | 4538 | CG | LEU | 634 | 46.720 | 33.957 | 19.419 | 1.00 | 14.68 |
| ATOM | 4539 | CD1 | LEU | 634 | 46.010 | 34.593 | 20.609 | 1.00 | 11.99 |
| ATOM | 4540 | CD2 | LEU | 634 | 46.276 | 32.498 | 19.240 | 1.00 | 15.41 |
| ATOM | 4541 | C | LEU | 634 | 46.291 | 34.686 | 15.655 | 1.00 | 14.79 |
| ATOM | 4542 | O | LEU | 634 | 45.509 | 33.896 | 15.130 | 1.00 | 13.57 |
| ATOM | 4543 | N | ARG | 635 | 46.460 | 35.923 | 15.208 | 1.00 | 14.72 |
| ATOM | 4544 | CA | ARG | 635 | 45.720 | 36.385 | 14.041 | 1.00 | 16.48 |
| ATOM | 4545 | CB | ARG | 635 | 45.919 | 37.888 | 13.839 | 1.00 | 16.73 |
| ATOM | 4546 | CG | ARG | 635 | 45.030 | 38.742 | 14.722 | 1.00 | 20.60 |
| ATOM | 4547 | CD | ARG | 635 | 45.367 | 40.211 | 14.574 | 1.00 | 25.55 |
| ATOM | 4548 | NE | ARG | 635 | 44.462 | 41.063 | 15.340 | 1.00 | 29.96 |
| ATOM | 4549 | CZ | ARG | 635 | 44.726 | 42.325 | 15.659 | 1.00 | 31.82 |
| ATOM | 4550 | NH1 | ARG | 635 | 45.871 | 42.880 | 15.280 | 1.00 | 31.36 |
| ATOM | 4551 | NH2 | ARG | 635 | 43.846 | 43.034 | 16.353 | 1.00 | 34.01 |
| ATOM | 4552 | C | ARG | 635 | 46.158 | 35.618 | 12.797 | 1.00 | 16.36 |
| ATOM | 4553 | O | ARG | 635 | 45.327 | 35.194 | 11.997 | 1.00 | 16.07 |
| ATOM | 4554 | N | THR | 636 | 47.463 | 35.430 | 12.645 | 1.00 | 16.74 |
| ATOM | 4555 | CA | THR | 636 | 47.983 | 34.698 | 11.494 | 1.00 | 16.97 |
| ATOM | 4556 | CB | THR | 636 | 49.524 | 34.739 | 11.463 | 1.00 | 17.36 |
| ATOM | 4557 | OG1 | THR | 636 | 49.956 | 36.094 | 11.282 | 1.00 | 18.76 |
| ATOM | 4558 | CG2 | THR | 636 | 50.064 | 33.874 | 10.324 | 1.00 | 17.64 |
| ATOM | 4559 | C | THR | 636 | 47.513 | 33.243 | 11.522 | 1.00 | 15.76 |
| ATOM | 4560 | O | THR | 636 | 47.099 | 32.707 | 10.501 | 1.00 | 14.02 |
| ATOM | 4561 | N | GLU | 637 | 47.568 | 32.615 | 12.695 | 1.00 | 15.46 |
| ATOM | 4562 | CA | GLU | 637 | 47.137 | 31.223 | 12.842 | 1.00 | 15.45 |
| ATOM | 4563 | CB | GLU | 637 | 47.484 | 30.695 | 14.241 | 1.00 | 15.84 |
| ATOM | 4564 | CG | GLU | 637 | 46.905 | 29.309 | 14.562 | 1.00 | 17.40 |
| ATOM | 4565 | CD | GLU | 637 | 47.626 | 28.165 | 13.849 | 1.00 | 21.20 |
| ATOM | 4566 | OE1 | GLU | 637 | 48.417 | 28.429 | 12.922 | 1.00 | 20.76 |
| ATOM | 4567 | OE2 | GLU | 637 | 47.394 | 26.992 | 14.217 | 1.00 | 24.25 |
| ATOM | 4568 | C | GLU | 637 | 45.638 | 31.059 | 12.601 | 1.00 | 14.61 |
| ATOM | 4569 | O | GLU | 637 | 45.224 | 30.163 | 11.869 | 1.00 | 14.03 |
| ATOM | 4570 | N | ASN | 638 | 44.825 | 31.911 | 13.222 | 1.00 | 15.50 |
| ATOM | 4571 | CA | ASN | 638 | 43.378 | 31.824 | 13.046 | 1.00 | 15.74 |
| ATOM | 4572 | CB | ASN | 638 | 42.643 | 32.768 | 14.006 | 1.00 | 15.40 |
| ATOM | 4573 | CG | ASN | 638 | 42.690 | 32.288 | 15.447 | 1.00 | 15.23 |
| ATOM | 4574 | OD1 | ASN | 638 | 42.765 | 31.084 | 15.713 | 1.00 | 12.88 |
| ATOM | 4575 | ND2 | ASN | 638 | 42.633 | 33.228 | 16.387 | 1.00 | 11.63 |
| ATOM | 4576 | C | ASN | 638 | 42.972 | 32.146 | 11.617 | 1.00 | 17.16 |
| ATOM | 4577 | O | ASN | 638 | 42.029 | 31.563 | 11.086 | 1.00 | 16.41 |
| ATOM | 4578 | N | GLU | 639 | 43.691 | 33.076 | 10.996 | 1.00 | 18.19 |
| ATOM | 4579 | CA | GLU | 639 | 43.402 | 33.476 | 9.628 | 1.00 | 20.22 |
| ATOM | 4580 | CB | GLU | 639 | 44.260 | 34.686 | 9.240 | 1.00 | 20.36 |
| ATOM | 4581 | CG | GLU | 639 | 44.222 | 35.028 | 7.756 | 1.00 | 25.06 |
| ATOM | 4582 | CD | GLU | 639 | 45.156 | 36.172 | 7.400 | 1.00 | 26.81 |
| ATOM | 4583 | OE1 | GLU | 639 | 44.849 | 37.324 | 7.773 | 1.00 | 29.07 |
| ATOM | 4584 | OE2 | GLU | 639 | 46.201 | 35.917 | 6.759 | 1.00 | 25.74 |
| ATOM | 4585 | C | GLU | 639 | 43.635 | 32.343 | 8.630 | 1.00 | 20.09 |
| ATOM | 4586 | O | GLU | 639 | 42.799 | 32.092 | 7.763 | 1.00 | 18.73 |
| ATOM | 4587 | N | LEU | 640 | 44.760 | 31.647 | 8.751 | 1.00 | 20.74 |
| ATOM | 4588 | CA | LEU | 640 | 45.044 | 30.572 | 7.811 | 1.00 | 20.59 |
| ATOM | 4589 | CB | LEU | 640 | 46.506 | 30.127 | 7.936 | 1.00 | 22.92 |
| ATOM | 4590 | CG | LEU | 640 | 47.008 | 29.340 | 9.139 | 1.00 | 24.43 |

TABLE B-continued

Co-ordinates of an underglycosylated tACEΔ36NJ ACE-lisinopril complex

| ATOM | 4591 | CD1 | LEU | 640 | 46.740 | 27.859 | 8.916 | 1.00 | 25.30 |
|------|------|-----|-----|-----|--------|--------|-------|------|-------|
| ATOM | 4592 | CD2 | LEU | 640 | 48.508 | 29.571 | 9.297 | 1.00 | 25.43 |
| ATOM | 4593 | C | LEU | 640 | 44.086 | 29.393 | 7.976 | 1.00 | 19.55 |
| ATOM | 4594 | O | LEU | 640 | 43.888 | 28.610 | 7.047 | 1.00 | 17.75 |
| ATOM | 4595 | N | HIS | 641 | 43.474 | 29.280 | 9.151 | 1.00 | 19.69 |
| ATOM | 4596 | CA | HIS | 641 | 42.518 | 28.208 | 9.400 | 1.00 | 19.52 |
| ATOM | 4597 | CB | HIS | 641 | 42.655 | 27.687 | 10.832 | 1.00 | 18.00 |
| ATOM | 4598 | CG | HIS | 641 | 43.861 | 26.829 | 11.038 | 1.00 | 20.33 |
| ATOM | 4599 | CD2 | HIS | 641 | 44.212 | 25.645 | 10.485 | 1.00 | 19.67 |
| ATOM | 4600 | ND1 | HIS | 641 | 44.902 | 27.188 | 11.867 | 1.00 | 22.38 |
| ATOM | 4601 | CE1 | HIS | 641 | 45.843 | 26.264 | 11.814 | 1.00 | 19.87 |
| ATOM | 4602 | NE2 | HIS | 641 | 45.450 | 25.317 | 10.982 | 1.00 | 23.55 |
| ATOM | 4603 | C | HIS | 641 | 41.088 | 28.668 | 9.139 | 1.00 | 18.42 |
| ATOM | 4604 | O | HIS | 641 | 40.144 | 27.894 | 9.282 | 1.00 | 19.70 |
| ATOM | 4605 | N | GLY | 642 | 40.941 | 29.931 | 8.749 | 1.00 | 18.10 |
| ATOM | 4606 | CA | GLY | 642 | 39.627 | 30.480 | 8.456 | 1.00 | 19.31 |
| ATOM | 4607 | C | GLY | 642 | 38.673 | 30.513 | 9.638 | 1.00 | 20.19 |
| ATOM | 4608 | O | GLY | 642 | 37.473 | 30.272 | 9.482 | 1.00 | 20.13 |
| ATOM | 4609 | N | GLU | 643 | 39.192 | 30.817 | 10.820 | 1.00 | 18.07 |
| ATOM | 4610 | CA | GLU | 643 | 38.353 | 30.866 | 12.013 | 1.00 | 18.39 |
| ATOM | 4611 | CB | GLU | 643 | 39.216 | 30.975 | 13.275 | 1.00 | 16.96 |
| ATOM | 4612 | CG | GLU | 643 | 40.297 | 29.914 | 13.395 | 1.00 | 17.41 |
| ATOM | 4613 | CD | GLU | 643 | 39.741 | 28.519 | 13.602 | 1.00 | 15.36 |
| ATOM | 4614 | OE1 | GLU | 643 | 38.504 | 28.345 | 13.574 | 1.00 | 15.16 |
| ATOM | 4615 | OE2 | GLU | 643 | 40.554 | 27.595 | 13.794 | 1.00 | 18.49 |
| ATOM | 4616 | C | GLU | 643 | 37.395 | 32.048 | 11.980 | 1.00 | 18.65 |
| ATOM | 4617 | O | GLU | 643 | 37.744 | 33.136 | 11.516 | 1.00 | 20.72 |
| ATOM | 4618 | N | LYS | 644 | 36.181 | 31.818 | 12.469 | 1.00 | 18.08 |
| ATOM | 4619 | CA | LYS | 644 | 35.168 | 32.859 | 12.560 | 1.00 | 17.63 |
| ATOM | 4620 | CB | LYS | 644 | 33.796 | 32.312 | 12.169 | 1.00 | 21.41 |
| ATOM | 4621 | CG | LYS | 644 | 32.658 | 33.304 | 12.356 | 1.00 | 27.52 |
| ATOM | 4622 | CD | LYS | 644 | 31.314 | 32.656 | 12.064 | 1.00 | 33.74 |
| ATOM | 4623 | CE | LYS | 644 | 30.179 | 33.660 | 12.149 | 1.00 | 36.34 |
| ATOM | 4624 | NZ | LYS | 644 | 28.880 | 33.042 | 11.750 | 1.00 | 39.29 |
| ATOM | 4625 | C | LYS | 644 | 35.165 | 33.262 | 14.030 | 1.00 | 17.75 |
| ATOM | 4626 | O | LYS | 644 | 34.652 | 32.527 | 14.876 | 1.00 | 17.16 |
| ATOM | 4627 | N | LEU | 645 | 35.753 | 34.417 | 14.330 | 1.00 | 16.17 |
| ATOM | 4628 | CA | LEU | 645 | 35.841 | 34.899 | 15.705 | 1.00 | 16.77 |
| ATOM | 4629 | CB | LEU | 645 | 36.665 | 36.186 | 15.767 | 1.00 | 15.16 |
| ATOM | 4630 | CG | LEU | 645 | 38.096 | 36.118 | 15.230 | 1.00 | 16.86 |
| ATOM | 4631 | CD1 | LEU | 645 | 38.773 | 37.464 | 15.445 | 1.00 | 16.62 |
| ATOM | 4632 | CD2 | LEU | 645 | 38.865 | 35.008 | 15.924 | 1.00 | 15.25 |
| ATOM | 4633 | C | LEU | 645 | 34.479 | 35.149 | 16.328 | 1.00 | 16.42 |
| ATOM | 4634 | O | LEU | 645 | 33.562 | 35.621 | 15.668 | 1.00 | 15.27 |
| ATOM | 4635 | N | GLY | 646 | 34.352 | 34.832 | 17.611 | 1.00 | 16.60 |
| ATOM | 4636 | CA | GLY | 646 | 33.089 | 35.048 | 18.287 | 1.00 | 16.22 |
| ATOM | 4637 | C | GLY | 646 | 32.126 | 33.881 | 18.183 | 1.00 | 17.80 |
| ATOM | 4638 | O | GLY | 646 | 32.501 | 32.773 | 17.793 | 1.00 | 17.07 |
| ATOM | 4639 | N | TRP | 647 | 30.872 | 34.142 | 18.529 | 1.00 | 18.98 |
| ATOM | 4640 | CA | TRP | 647 | 29.840 | 33.116 | 18.516 | 1.00 | 25.11 |
| ATOM | 4641 | CB | TRP | 647 | 29.775 | 32.464 | 19.896 | 1.00 | 21.13 |
| ATOM | 4642 | CG | TRP | 647 | 29.941 | 33.462 | 21.022 | 1.00 | 17.17 |
| ATOM | 4643 | CD2 | TRP | 647 | 31.178 | 33.914 | 21.590 | 1.00 | 14.61 |
| ATOM | 4644 | CE2 | TRP | 647 | 30.857 | 34.870 | 22.583 | 1.00 | 14.82 |
| ATOM | 4645 | CE3 | TRP | 647 | 32.526 | 33.609 | 21.354 | 1.00 | 12.25 |
| ATOM | 4646 | CD1 | TRP | 647 | 28.950 | 34.139 | 21.676 | 1.00 | 16.56 |
| ATOM | 4647 | NE1 | TRP | 647 | 29.491 | 34.984 | 22.616 | 1.00 | 15.68 |
| ATOM | 4648 | CZ2 | TRP | 647 | 31.838 | 35.523 | 23.343 | 1.00 | 12.54 |
| ATOM | 4649 | CZ3 | TRP | 647 | 33.504 | 34.258 | 22.110 | 1.00 | 13.82 |
| ATOM | 4650 | CH2 | TRP | 647 | 33.151 | 35.206 | 23.094 | 1.00 | 13.80 |
| ATOM | 4651 | C | TRP | 647 | 28.480 | 33.697 | 18.135 | 1.00 | 31.34 |
| ATOM | 4652 | O | TRP | 647 | 27.675 | 34.038 | 18.995 | 1.00 | 31.85 |
| ATOM | 4653 | N | PRO | 648 | 28.207 | 33.807 | 16.823 | 1.00 | 37.87 |
| ATOM | 4654 | CD | PRO | 648 | 29.017 | 33.206 | 15.747 | 1.00 | 39.60 |
| ATOM | 4655 | CA | PRO | 648 | 26.951 | 34.344 | 16.284 | 1.00 | 41.15 |
| ATOM | 4656 | CB | PRO | 648 | 27.117 | 34.156 | 14.778 | 1.00 | 42.26 |
| ATOM | 4657 | CG | PRO | 648 | 27.978 | 32.919 | 14.693 | 1.00 | 41.09 |
| ATOM | 4658 | C | PRO | 648 | 25.709 | 33.627 | 16.822 | 1.00 | 43.83 |
| ATOM | 4659 | O | PRO | 648 | 24.732 | 34.318 | 17.183 | 1.00 | 45.84 |
| ATOM | 4660 | OXT | PRO | 648 | 25.725 | 32.377 | 16.859 | 1.00 | 46.26 |
| ATOM | 4661 | OH2 | WAT | 705 | 33.593 | 46.605 | 44.423 | 1.00 | 9.31 |
| ATOM | 4662 | OH2 | WAT | 706 | 32.965 | 26.053 | 34.132 | 1.00 | 8.96 |
| ATOM | 4663 | OH2 | WAT | 707 | 24.287 | 47.413 | 42.078 | 1.00 | 8.51 |
| ATOM | 4664 | OH2 | WAT | 708 | 41.492 | 22.684 | 37.822 | 1.00 | 11.40 |
| ATOM | 4665 | OH2 | WAT | 709 | 57.508 | 41.508 | 37.660 | 1.00 | 13.76 |
| ATOM | 4666 | OH2 | WAT | 710 | 39.412 | 23.942 | 39.181 | 1.00 | 8.91 |
| ATOM | 4667 | OH2 | WAT | 711 | 51.091 | 36.475 | 38.087 | 1.00 | 10.07 |
| ATOM | 4668 | OH2 | WAT | 712 | 53.042 | 51.060 | 33.144 | 1.00 | 16.13 |

TABLE B-continued

Co-ordinates of an underglycosylated tACEΔ36NJ ACE-lisinopril complex

| ATOM | 4669 | OH2 | WAT | 713 | 52.228 | 34.436 | 36.844 | 1.00 | 10.52 |
|------|------|-----|-----|-----|--------|--------|--------|------|-------|
| ATOM | 4670 | OH2 | WAT | 714 | 16.492 | 44.739 | 50.912 | 1.00 | 12.73 |
| ATOM | 4671 | OH2 | WAT | 715 | 47.496 | 46.775 | 31.239 | 1.00 | 10.24 |
| ATOM | 4672 | OH2 | WAT | 716 | 33.685 | 54.185 | 42.672 | 1.00 | 16.09 |
| ATOM | 4673 | OH2 | WAT | 717 | 33.197 | 41.542 | 38.210 | 1.00 | 12.21 |
| ATOM | 4674 | OH2 | WAT | 718 | 37.259 | 27.514 | 46.151 | 1.00 | 11.50 |
| ATOM | 4675 | OH2 | WAT | 719 | 17.570 | 40.507 | 43.225 | 1.00 | 12.99 |
| ATOM | 4676 | OH2 | WAT | 720 | 40.862 | 49.469 | 48.991 | 1.00 | 9.86 |
| ATOM | 4677 | OH2 | WAT | 721 | 37.202 | 32.888 | 29.681 | 1.00 | 9.25 |
| ATOM | 4678 | OH2 | WAT | 722 | 48.308 | 52.095 | 48.720 | 1.00 | 13.18 |
| ATOM | 4679 | OH2 | WAT | 723 | 44.174 | 25.251 | 17.566 | 1.00 | 11.48 |
| ATOM | 4680 | OH2 | WAT | 724 | 37.635 | 28.226 | 16.249 | 1.00 | 13.61 |
| ATOM | 4681 | OH2 | WAT | 725 | 31.657 | 44.896 | 43.119 | 1.00 | 8.30 |
| ATOM | 4682 | OH2 | WAT | 726 | 48.823 | 40.553 | 46.220 | 1.00 | 14.22 |
| ATOM | 4683 | OH2 | WAT | 727 | 43.137 | 28.430 | 14.664 | 1.00 | 15.95 |
| ATOM | 4684 | OH2 | WAT | 728 | 36.288 | 33.431 | 19.194 | 1.00 | 9.04 |
| ATOM | 4685 | OH2 | WAT | 729 | 45.181 | 39.323 | 41.443 | 1.00 | 15.73 |
| ATOM | 4686 | OH2 | WAT | 730 | 19.065 | 49.680 | 43.390 | 1.00 | 14.42 |
| ATOM | 4687 | OH2 | WAT | 731 | 18.532 | 48.145 | 47.790 | 1.00 | 14.97 |
| ATOM | 4688 | OH2 | WAT | 732 | 16.291 | 39.074 | 47.581 | 1.00 | 12.27 |
| ATOM | 4689 | OH2 | WAT | 734 | 27.683 | 37.166 | 46.929 | 1.00 | 9.69 |
| ATOM | 4690 | OH2 | WAT | 735 | 43.137 | 42.880 | 22.592 | 1.00 | 14.48 |
| ATOM | 4691 | OH2 | WAT | 736 | 23.024 | 50.329 | 41.657 | 1.00 | 17.32 |
| ATOM | 4692 | OH2 | WAT | 737 | 40.667 | 28.535 | 40.057 | 1.00 | 16.00 |
| ATOM | 4693 | OH2 | WAT | 738 | 44.387 | 45.117 | 56.435 | 1.00 | 14.17 |
| ATOM | 4694 | OH2 | WAT | 739 | 42.945 | 25.383 | 33.384 | 1.00 | 13.52 |
| ATOM | 4695 | OH2 | WAT | 740 | 36.456 | 23.986 | 32.241 | 1.00 | 8.95 |
| ATOM | 4696 | OH2 | WAT | 741 | 39.950 | 39.788 | 48.186 | 1.00 | 12.78 |
| ATOM | 4697 | OH2 | WAT | 742 | 47.924 | 45.637 | 61.414 | 1.00 | 20.16 |
| ATOM | 4698 | OH2 | WAT | 743 | 48.523 | 42.505 | 62.565 | 1.00 | 17.18 |
| ATOM | 4699 | OH2 | WAT | 744 | 16.710 | 44.022 | 47.985 | 1.00 | 15.86 |
| ATOM | 4700 | OH2 | WAT | 745 | 50.722 | 52.452 | 33.013 | 1.00 | 14.62 |
| ATOM | 4701 | OH2 | WAT | 746 | 42.905 | 51.202 | 39.594 | 1.00 | 14.40 |
| ATOM | 4702 | OH2 | WAT | 747 | 43.215 | 36.931 | 50.988 | 1.00 | 16.61 |
| ATOM | 4703 | OH2 | WAT | 748 | 37.286 | 29.700 | 43.929 | 1.00 | 19.60 |
| ATOM | 4704 | OH2 | WAT | 749 | 31.745 | 23.237 | 13.527 | 1.00 | 19.26 |
| ATOM | 4705 | OH2 | WAT | 750 | 50.872 | 32.438 | 13.257 | 1.00 | 13.65 |
| ATOM | 4706 | OH2 | WAT | 751 | 23.924 | 24.786 | 40.648 | 1.00 | 14.00 |
| ATOM | 4707 | OH2 | WAT | 752 | 46.065 | 55.788 | 48.966 | 1.00 | 12.21 |
| ATOM | 4708 | OH2 | WAT | 753 | 17.359 | 38.412 | 45.074 | 1.00 | 16.22 |
| ATOM | 4709 | OH2 | WAT | 754 | 30.402 | 54.271 | 37.540 | 1.00 | 19.90 |
| ATOM | 4710 | OH2 | WAT | 755 | 30.166 | 28.862 | 39.171 | 1.00 | 11.86 |
| ATOM | 4711 | OH2 | WAT | 756 | 40.401 | 56.296 | 45.617 | 1.00 | 19.60 |
| ATOM | 4712 | OH2 | WAT | 757 | 48.250 | 46.266 | 58.848 | 1.00 | 15.18 |
| ATOM | 4713 | OH2 | WAT | 758 | 23.481 | 22.074 | 39.456 | 1.00 | 13.04 |
| ATOM | 4714 | OH2 | WAT | 759 | 39.537 | 29.868 | 42.153 | 1.00 | 13.71 |
| ATOM | 4715 | OH2 | WAT | 760 | 41.465 | 55.169 | 34.794 | 1.00 | 16.56 |
| ATOM | 4716 | OH2 | WAT | 761 | 50.211 | 32.756 | 35.889 | 1.00 | 22.03 |
| ATOM | 4717 | OH2 | WAT | 762 | 55.270 | 39.776 | 52.027 | 1.00 | 16.82 |
| ATOM | 4718 | OH2 | WAT | 763 | 17.787 | 47.082 | 45.179 | 1.00 | 17.96 |
| ATOM | 4719 | OH2 | WAT | 764 | 41.349 | 43.344 | 47.624 | 1.00 | 13.85 |
| ATOM | 4720 | OH2 | WAT | 765 | 31.365 | 48.033 | 33.699 | 1.00 | 17.60 |
| ATOM | 4721 | OH2 | WAT | 766 | 35.820 | 29.185 | 13.398 | 1.00 | 14.60 |
| ATOM | 4722 | OH2 | WAT | 767 | 42.075 | 46.950 | 49.736 | 1.00 | 18.28 |
| ATOM | 4723 | OH2 | WAT | 768 | 40.009 | 19.530 | 28.487 | 1.00 | 17.39 |
| ATOM | 4724 | OH2 | WAT | 770 | 52.878 | 28.814 | 13.591 | 1.00 | 22.84 |
| ATOM | 4725 | OH2 | WAT | 771 | 39.380 | 57.861 | 40.522 | 1.00 | 20.88 |
| ATOM | 4726 | OH2 | WAT | 772 | 34.750 | 20.720 | 49.137 | 1.00 | 24.09 |
| ATOM | 4727 | OH2 | WAT | 773 | 17.366 | 31.093 | 38.464 | 1.00 | 23.54 |
| ATOM | 4728 | OH2 | WAT | 774 | 44.804 | 23.924 | 14.000 | 1.00 | 19.88 |
| ATOM | 4729 | OH2 | WAT | 775 | 31.146 | 56.380 | 49.556 | 1.00 | 21.05 |
| ATOM | 4730 | OH2 | WAT | 776 | 46.715 | 56.401 | 46.506 | 1.00 | 19.22 |
| ATOM | 4731 | OH2 | WAT | 777 | 42.869 | 58.288 | 37.166 | 1.00 | 15.61 |
| ATOM | 4732 | OH2 | WAT | 778 | 40.831 | 33.557 | 7.130 | 1.00 | 24.79 |
| ATOM | 4733 | OH2 | WAT | 779 | 35.162 | 52.317 | 73.577 | 1.00 | 20.05 |
| ATOM | 4734 | OH2 | WAT | 780 | 14.809 | 39.247 | 36.520 | 1.00 | 18.70 |
| ATOM | 4735 | OH2 | WAT | 781 | 39.527 | 31.879 | 53.125 | 1.00 | 13.72 |
| ATOM | 4736 | OH2 | WAT | 782 | 27.757 | 50.041 | 53.223 | 1.00 | 27.53 |
| ATOM | 4737 | OH2 | WAT | 783 | 49.394 | 26.247 | 11.787 | 1.00 | 19.81 |
| ATOM | 4738 | OH2 | WAT | 784 | 44.777 | 26.399 | 15.119 | 1.00 | 21.30 |
| ATOM | 4739 | OH2 | WAT | 785 | 57.867 | 38.875 | 52.198 | 1.00 | 18.47 |
| ATOM | 4740 | OH2 | WAT | 786 | 34.155 | 51.047 | 61.985 | 1.00 | 19.93 |
| ATOM | 4741 | OH2 | WAT | 787 | 45.141 | 27.154 | 46.412 | 1.00 | 22.42 |
| ATOM | 4742 | OH2 | WAT | 788 | 43.475 | 51.366 | 28.087 | 1.00 | 18.86 |
| ATOM | 4743 | OH2 | WAT | 789 | 20.668 | 25.724 | 29.782 | 1.00 | 24.21 |
| ATOM | 4744 | OH2 | WAT | 790 | 32.083 | 32.320 | 15.051 | 1.00 | 19.38 |
| ATOM | 4745 | OH2 | WAT | 791 | 49.913 | 48.449 | 23.710 | 1.00 | 18.63 |
| ATOM | 4746 | OH2 | WAT | 792 | 42.785 | 27.563 | 47.669 | 1.00 | 25.09 |

TABLE B-continued

Co-ordinates of an underglycosylated tACEΔ36NJ ACE-lisinopril complex

| ATOM | 4747 | OH2 | WAT | 793 | 39.850 | 53.780 | 46.033 | 1.00 | 22.72 |
|------|------|-----|-----|-----|--------|--------|--------|------|-------|
| ATOM | 4748 | OH2 | WAT | 794 | 27.466 | 13.978 | 27.601 | 1.00 | 20.70 |
| ATOM | 4749 | OH2 | WAT | 795 | 40.190 | 34.656 | 11.736 | 1.00 | 32.79 |
| ATOM | 4750 | OH2 | WAT | 796 | 39.109 | 10.985 | 33.519 | 1.00 | 22.45 |
| ATOM | 4751 | OH2 | WAT | 797 | 27.558 | 21.410 | 51.556 | 1.00 | 17.72 |
| ATOM | 4752 | OH2 | WAT | 798 | 66.163 | 40.174 | 37.797 | 1.00 | 19.68 |
| ATOM | 4753 | OH2 | WAT | 799 | 22.819 | 49.816 | 39.224 | 1.00 | 23.29 |
| ATOM | 4754 | OH2 | WAT | 800 | 25.950 | 37.105 | 65.162 | 1.00 | 25.58 |
| ATOM | 4755 | OH2 | WAT | 801 | 34.253 | 10.439 | 28.187 | 1.00 | 25.36 |
| ATOM | 4756 | OH2 | WAT | 802 | 59.840 | 33.669 | 44.222 | 1.00 | 19.20 |
| ATOM | 4757 | OH2 | WAT | 803 | 38.496 | 20.697 | 31.902 | 1.00 | 16.24 |
| ATOM | 4758 | OH2 | WAT | 804 | 40.729 | 21.319 | 12.133 | 1.00 | 28.36 |
| ATOM | 4759 | OH2 | WAT | 805 | 56.117 | 41.173 | 25.206 | 1.00 | 19.73 |
| ATOM | 4760 | OH2 | WAT | 806 | 37.047 | 26.923 | 50.890 | 1.00 | 22.30 |
| ATOM | 4761 | OH2 | WAT | 807 | 42.476 | 46.612 | 21.569 | 1.00 | 21.24 |
| ATOM | 4762 | OH2 | WAT | 808 | 35.171 | 28.146 | 10.829 | 1.00 | 23.83 |
| ATOM | 4763 | OH2 | WAT | 809 | 29.225 | 19.649 | 23.377 | 1.00 | 20.44 |
| ATOM | 4764 | OH2 | WAT | 810 | 52.753 | 51.832 | 57.912 | 1.00 | 24.14 |
| ATOM | 4765 | OH2 | WAT | 811 | 53.307 | 37.708 | 61.763 | 1.00 | 20.90 |
| ATOM | 4766 | OH2 | WAT | 812 | 11.971 | 34.982 | 48.268 | 1.00 | 25.05 |
| ATOM | 4767 | OH2 | WAT | 813 | 24.990 | 48.789 | 37.974 | 1.00 | 24.58 |
| ATOM | 4768 | OH2 | WAT | 814 | 43.951 | 19.262 | 20.770 | 1.00 | 21.14 |
| ATOM | 4769 | OH2 | WAT | 815 | 36.259 | 14.934 | 14.740 | 1.00 | 22.42 |
| ATOM | 4770 | OH2 | WAT | 816 | 35.820 | 12.642 | 25.488 | 1.00 | 20.65 |
| ATOM | 4771 | OH2 | WAT | 817 | 39.436 | 55.386 | 36.440 | 1.00 | 12.53 |
| ATOM | 4772 | OH2 | WAT | 818 | 62.583 | 34.233 | 30.419 | 1.00 | 22.07 |
| ATOM | 4773 | OH2 | WAT | 819 | 19.790 | 54.852 | 50.868 | 1.00 | 29.06 |
| ATOM | 4774 | OH2 | WAT | 820 | 50.697 | 29.832 | 12.471 | 1.00 | 22.39 |
| ATOM | 4775 | OH2 | WAT | 821 | 27.847 | 56.381 | 70.315 | 1.00 | 23.46 |
| ATOM | 4776 | OH2 | WAT | 823 | 27.949 | 17.733 | 50.193 | 1.00 | 31.12 |
| ATOM | 4777 | OH2 | WAT | 824 | 55.965 | 37.522 | 32.909 | 1.00 | 17.65 |
| ATOM | 4778 | OH2 | WAT | 825 | 9.432 | 31.570 | 48.180 | 1.00 | 32.33 |
| ATOM | 4779 | OH2 | WAT | 826 | 41.473 | 54.399 | 62.185 | 1.00 | 30.40 |
| ATOM | 4780 | OH2 | WAT | 827 | 50.992 | 18.343 | 24.030 | 1.00 | 25.41 |
| ATOM | 4781 | OH2 | WAT | 828 | 26.053 | 14.477 | 12.460 | 1.00 | 20.39 |
| ATOM | 4782 | OH2 | WAT | 829 | 69.827 | 44.579 | 41.736 | 1.00 | 22.45 |
| ATOM | 4783 | OH2 | WAT | 830 | 56.552 | 22.658 | 16.664 | 1.00 | 27.42 |
| ATOM | 4784 | OH2 | WAT | 831 | 26.288 | 20.159 | 49.712 | 1.00 | 24.06 |
| ATOM | 4785 | OH2 | WAT | 832 | 16.705 | 33.141 | 51.058 | 1.00 | 19.06 |
| ATOM | 4786 | OH2 | WAT | 833 | 21.271 | 53.952 | 59.470 | 1.00 | 23.51 |
| ATOM | 4787 | OH2 | WAT | 834 | 47.427 | 53.353 | 64.227 | 1.00 | 34.99 |
| ATOM | 4788 | OH2 | WAT | 835 | 45.817 | 26.456 | 42.450 | 1.00 | 37.42 |
| ATOM | 4789 | OH2 | WAT | 836 | 49.720 | 39.114 | 12.538 | 1.00 | 29.15 |
| ATOM | 4790 | OH2 | WAT | 837 | 36.955 | 41.394 | 51.137 | 1.00 | 26.94 |
| ATOM | 4791 | OH2 | WAT | 838 | 42.624 | 25.634 | 37.851 | 1.00 | 23.28 |
| ATOM | 4792 | OH2 | WAT | 839 | 51.315 | 24.980 | 58.259 | 1.00 | 30.21 |
| ATOM | 4793 | OH2 | WAT | 840 | 54.566 | 56.838 | 50.490 | 1.00 | 30.20 |
| ATOM | 4794 | OH2 | WAT | 841 | 40.512 | 53.418 | 32.693 | 1.00 | 26.12 |
| ATOM | 4795 | OH2 | WAT | 842 | 26.362 | 47.983 | 54.146 | 1.00 | 26.40 |
| ATOM | 4796 | OH2 | WAT | 843 | 37.201 | 32.434 | 54.478 | 1.00 | 19.11 |
| ATOM | 4797 | OH2 | WAT | 844 | 57.961 | 39.008 | 32.080 | 1.00 | 20.99 |
| ATOM | 4798 | OH2 | WAT | 845 | 18.271 | 24.342 | 44.501 | 1.00 | 22.93 |
| ATOM | 4799 | OH2 | WAT | 846 | 41.486 | 21.860 | 67.124 | 1.00 | 40.66 |
| ATOM | 4800 | OH2 | WAT | 847 | 13.917 | 29.508 | 37.265 | 1.00 | 42.07 |
| ATOM | 4801 | OH2 | WAT | 848 | 17.295 | 33.378 | 57.585 | 1.00 | 24.15 |
| ATOM | 4802 | OH2 | WAT | 849 | 22.558 | 38.571 | 32.120 | 1.00 | 36.71 |
| ATOM | 4803 | OH2 | WAT | 850 | 35.628 | 59.228 | 37.704 | 1.00 | 24.98 |
| ATOM | 4804 | OH2 | WAT | 851 | 24.241 | 59.727 | 65.168 | 1.00 | 27.57 |
| ATOM | 4805 | OH2 | WAT | 852 | 30.466 | 55.002 | 34.566 | 1.00 | 20.81 |
| ATOM | 4806 | OH2 | WAT | 853 | 39.487 | 26.456 | 44.048 | 1.00 | 27.56 |
| ATOM | 4807 | OH2 | WAT | 854 | 32.107 | 46.093 | 71.751 | 1.00 | 28.54 |
| ATOM | 4808 | OH2 | WAT | 855 | 48.700 | 24.975 | 15.218 | 1.00 | 27.62 |
| ATOM | 4809 | OH2 | WAT | 856 | 71.051 | 37.353 | 44.254 | 1.00 | 24.64 |
| ATOM | 4810 | OH2 | WAT | 857 | 18.705 | 30.001 | 40.624 | 1.00 | 24.61 |
| ATOM | 4811 | OH2 | WAT | 858 | 67.822 | 43.137 | 39.600 | 1.00 | 24.92 |
| ATOM | 4812 | OH2 | WAT | 859 | 28.879 | 64.576 | 58.006 | 1.00 | 30.86 |
| ATOM | 4813 | OH2 | WAT | 860 | 50.121 | 23.822 | 38.157 | 1.00 | 29.74 |
| ATOM | 4814 | OH2 | WAT | 861 | 50.504 | 23.835 | 16.516 | 1.00 | 41.06 |
| ATOM | 4815 | OH2 | WAT | 862 | 50.897 | 18.482 | 46.813 | 1.00 | 28.35 |
| ATOM | 4816 | OH2 | WAT | 863 | 54.681 | 37.002 | 16.795 | 1.00 | 25.10 |
| ATOM | 4817 | OH2 | WAT | 864 | 23.493 | 23.940 | 53.772 | 1.00 | 22.53 |
| ATOM | 4818 | OH2 | WAT | 865 | 33.356 | 54.985 | 26.024 | 1.00 | 43.50 |
| ATOM | 4819 | OH2 | WAT | 866 | 43.404 | 31.760 | 41.951 | 1.00 | 21.02 |
| ATOM | 4820 | OH2 | WAT | 867 | 28.231 | 42.794 | 54.526 | 1.00 | 30.76 |
| ATOM | 4821 | OH2 | WAT | 868 | 14.847 | 43.548 | 34.779 | 1.00 | 34.44 |
| ATOM | 4822 | OH2 | WAT | 869 | 14.659 | 39.207 | 57.645 | 1.00 | 33.41 |
| ATOM | 4823 | OH2 | WAT | 870 | 57.510 | 37.601 | 64.872 | 1.00 | 30.64 |
| ATOM | 4824 | OH2 | WAT | 871 | 20.651 | 32.033 | 29.682 | 1.00 | 28.82 |

TABLE B-continued

Co-ordinates of an underglycosylated tACEΔ36NJ ACE-lisinopril complex

| ATOM | 4825 | OH2 | WAT | 872 | 52.056 | 50.326 | 27.360 | 1.00 | 24.49 |
|---|---|---|---|---|---|---|---|---|---|
| ATOM | 4826 | OH2 | WAT | 873 | 51.657 | 35.863 | 62.500 | 1.00 | 26.14 |
| ATOM | 4827 | OH2 | WAT | 874 | 47.279 | 21.024 | 51.484 | 1.00 | 23.69 |
| ATOM | 4828 | OH2 | WAT | 875 | 29.576 | 44.197 | 56.830 | 1.00 | 26.36 |
| ATOM | 4829 | OH2 | WAT | 876 | 40.524 | 18.980 | 31.059 | 1.00 | 25.48 |
| ATOM | 4830 | OH2 | WAT | 877 | 56.572 | 42.868 | 23.278 | 1.00 | 31.20 |
| ATOM | 4831 | OH2 | WAT | 878 | 34.210 | 18.018 | 53.038 | 1.00 | 32.11 |
| ATOM | 4832 | OH2 | WAT | 879 | 27.258 | 18.647 | 26.109 | 1.00 | 26.96 |
| ATOM | 4833 | OH2 | WAT | 880 | 62.773 | 54.373 | 39.531 | 1.00 | 36.25 |
| ATOM | 4834 | OH2 | WAT | 881 | 35.089 | 9.269 | 50.485 | 1.00 | 38.55 |
| ATOM | 4835 | OH2 | WAT | 882 | 38.082 | 57.888 | 33.414 | 1.00 | 23.60 |
| ATOM | 4836 | OH2 | WAT | 883 | 20.570 | 20.572 | 35.734 | 1.00 | 30.32 |
| ATOM | 4837 | OH2 | WAT | 884 | 64.060 | 48.729 | 47.598 | 1.00 | 25.68 |
| ATOM | 4838 | OH2 | WAT | 885 | 61.993 | 33.237 | 54.293 | 1.00 | 38.10 |
| ATOM | 4839 | OH2 | WAT | 886 | 46.176 | 15.310 | 31.633 | 1.00 | 32.63 |
| ATOM | 4840 | OH2 | WAT | 887 | 14.968 | 50.857 | 53.881 | 1.00 | 42.97 |
| ATOM | 4841 | OH2 | WAT | 888 | 21.704 | 24.366 | 51.887 | 1.00 | 36.24 |
| ATOM | 4842 | OH2 | WAT | 889 | 39.839 | 19.775 | 14.153 | 1.00 | 24.51 |
| ATOM | 4843 | OH2 | WAT | 890 | 44.365 | 68.561 | 56.122 | 1.00 | 31.90 |
| ATOM | 4844 | OH2 | WAT | 891 | 47.553 | 30.301 | 39.926 | 1.00 | 25.30 |
| ATOM | 4845 | OH2 | WAT | 892 | 32.268 | 20.759 | 14.108 | 1.00 | 23.29 |
| ATOM | 4846 | OH2 | WAT | 893 | 69.343 | 41.988 | 48.078 | 1.00 | 32.22 |
| ATOM | 4847 | OH2 | WAT | 894 | 24.297 | 15.185 | 41.737 | 1.00 | 31.91 |
| ATOM | 4848 | OH2 | WAT | 895 | 30.655 | 11.104 | 25.446 | 1.00 | 26.78 |
| ATOM | 4849 | OH2 | WAT | 896 | 42.362 | 40.299 | 57.293 | 1.00 | 20.70 |
| ATOM | 4850 | OH2 | WAT | 898 | 41.774 | 36.340 | 13.554 | 1.00 | 34.25 |
| ATOM | 4851 | OH2 | WAT | 899 | 39.152 | 38.465 | 60.315 | 1.00 | 25.51 |
| ATOM | 4852 | OH2 | WAT | 900 | 41.147 | 24.781 | 9.266 | 1.00 | 37.67 |
| ATOM | 4853 | OH2 | WAT | 901 | 69.407 | 36.691 | 46.483 | 1.00 | 26.53 |
| ATOM | 4854 | OH2 | WAT | 902 | 55.637 | 47.942 | 26.959 | 1.00 | 32.37 |
| ATOM | 4855 | OH2 | WAT | 903 | 33.913 | 34.460 | 58.201 | 1.00 | 38.45 |
| ATOM | 4856 | OH2 | WAT | 904 | 56.269 | 58.664 | 39.628 | 1.00 | 38.97 |
| ATOM | 4857 | OH2 | WAT | 905 | 57.309 | 45.050 | 24.747 | 1.00 | 30.45 |
| ATOM | 4858 | OH2 | WAT | 906 | 67.831 | 30.631 | 34.349 | 1.00 | 30.40 |
| ATOM | 4859 | OH2 | WAT | 907 | 17.422 | 51.937 | 47.071 | 1.00 | 26.07 |
| ATOM | 4860 | OH2 | WAT | 908 | 35.633 | 30.975 | 66.612 | 1.00 | 24.07 |
| ATOM | 4861 | OH2 | WAT | 910 | 61.975 | 46.612 | 53.486 | 1.00 | 26.87 |
| ATOM | 4862 | OH2 | WAT | 911 | 47.029 | 38.251 | 67.425 | 1.00 | 30.22 |
| ATOM | 4863 | OH2 | WAT | 912 | 60.210 | 33.638 | 26.728 | 1.00 | 31.35 |
| ATOM | 4864 | OH2 | WAT | 913 | 17.482 | 36.558 | 63.602 | 1.00 | 44.50 |
| ATOM | 4865 | OH2 | WAT | 914 | 24.128 | 36.324 | 26.146 | 1.00 | 20.37 |
| ATOM | 4866 | OH2 | WAT | 915 | 15.719 | 30.346 | 47.149 | 1.00 | 24.17 |
| ATOM | 4867 | OH2 | WAT | 916 | 23.359 | 62.099 | 63.265 | 1.00 | 40.09 |
| ATOM | 4868 | OH2 | WAT | 917 | 50.740 | 48.721 | 64.156 | 1.00 | 39.37 |
| ATOM | 4869 | OH2 | WAT | 918 | 64.987 | 41.178 | 33.243 | 1.00 | 37.88 |
| ATOM | 4870 | OH2 | WAT | 919 | 47.126 | 55.164 | 71.884 | 1.00 | 33.61 |
| ATOM | 4871 | OH2 | WAT | 920 | 15.488 | 43.883 | 65.882 | 1.00 | 23.44 |
| ATOM | 4872 | OH2 | WAT | 921 | 37.706 | 50.611 | 24.676 | 1.00 | 33.21 |
| ATOM | 4873 | OH2 | WAT | 922 | 37.379 | 23.810 | 9.516 | 1.00 | 34.84 |
| ATOM | 4874 | OH2 | WAT | 923 | 38.957 | 20.044 | 55.559 | 1.00 | 43.10 |
| ATOM | 4875 | OH2 | WAT | 924 | 24.959 | 16.071 | 14.898 | 1.00 | 34.26 |
| ATOM | 4876 | OH2 | WAT | 925 | 22.429 | 16.629 | 37.874 | 1.00 | 31.87 |
| ATOM | 4877 | OH2 | WAT | 926 | 29.356 | 53.921 | 43.835 | 1.00 | 38.69 |
| ATOM | 4878 | OH2 | WAT | 927 | 60.523 | 35.360 | 57.102 | 1.00 | 40.12 |
| ATOM | 4879 | OH2 | WAT | 928 | 29.303 | 20.134 | 16.704 | 1.00 | 26.85 |
| ATOM | 4880 | OH2 | WAT | 929 | 19.799 | 33.303 | 59.063 | 1.00 | 32.03 |
| ATOM | 4881 | OH2 | WAT | 930 | 19.367 | 18.997 | 32.033 | 1.00 | 30.19 |
| ATOM | 4882 | OH2 | WAT | 931 | 48.165 | 22.382 | 58.513 | 1.00 | 36.12 |
| ATOM | 4883 | OH2 | WAT | 932 | 43.741 | 63.487 | 53.233 | 1.00 | 33.28 |
| ATOM | 4884 | OH2 | WAT | 933 | 33.863 | 20.218 | 11.695 | 1.00 | 26.21 |
| ATOM | 4885 | OH2 | WAT | 934 | 49.235 | 59.976 | 52.718 | 1.00 | 28.98 |
| ATOM | 4886 | OH2 | WAT | 935 | 63.989 | 32.978 | 44.987 | 1.00 | 35.98 |
| ATOM | 4887 | OH2 | WAT | 936 | 38.155 | 21.333 | 49.259 | 1.00 | 27.87 |
| ATOM | 4888 | OH2 | WAT | 937 | 28.080 | 14.345 | 39.095 | 1.00 | 31.98 |
| ATOM | 4889 | OH2 | WAT | 938 | 15.034 | 38.648 | 61.496 | 1.00 | 35.94 |
| ATOM | 4890 | OH2 | WAT | 939 | 58.771 | 42.322 | 58.976 | 1.00 | 26.19 |
| ATOM | 4891 | OH2 | WAT | 940 | 47.485 | 42.154 | 69.878 | 1.00 | 35.48 |
| ATOM | 4892 | OH2 | WAT | 941 | 26.602 | 32.519 | 69.106 | 1.00 | 23.36 |
| ATOM | 4893 | OH2 | WAT | 942 | 28.022 | 17.338 | 22.711 | 1.00 | 31.24 |
| ATOM | 4894 | OH2 | WAT | 943 | 26.711 | 49.956 | 71.239 | 1.00 | 38.80 |
| ATOM | 4895 | OH2 | WAT | 944 | 64.021 | 22.891 | 42.685 | 1.00 | 33.14 |
| ATOM | 4896 | OH2 | WAT | 945 | 47.677 | 33.744 | 7.930 | 1.00 | 25.60 |
| ATOM | 4897 | OH2 | WAT | 946 | 34.908 | 23.405 | 49.212 | 1.00 | 24.56 |
| ATOM | 4898 | OH2 | WAT | 947 | 46.968 | 46.697 | 68.856 | 1.00 | 35.00 |
| ATOM | 4899 | OH2 | WAT | 948 | 41.692 | 11.412 | 30.635 | 1.00 | 31.37 |
| ATOM | 4900 | OH2 | WAT | 949 | 34.423 | 48.837 | 63.936 | 1.00 | 25.42 |
| ATOM | 4901 | OH2 | WAT | 950 | 38.612 | 61.793 | 51.417 | 1.00 | 33.87 |
| ATOM | 4902 | OH2 | WAT | 951 | 45.067 | 50.306 | 71.708 | 1.00 | 44.52 |

TABLE B-continued

Co-ordinates of an underglycosylated tACEΔ36NJ ACE-lisinopril complex

| ATOM | 4903 | OH2 | WAT | 952 | 46.249 | 23.672 | 42.556 | 1.00 | 31.95 |
|---|---|---|---|---|---|---|---|---|---|
| ATOM | 4904 | OH2 | WAT | 953 | 22.948 | 57.447 | 63.178 | 1.00 | 39.30 |
| ATOM | 4905 | OH2 | WAT | 954 | 53.305 | 20.101 | 34.868 | 1.00 | 41.13 |
| ATOM | 4906 | OH2 | WAT | 955 | 39.320 | 63.985 | 53.074 | 1.00 | 28.86 |
| ATOM | 4907 | OH2 | WAT | 956 | 20.574 | 21.558 | 47.751 | 1.00 | 30.99 |
| ATOM | 4908 | OH2 | WAT | 957 | 70.490 | 44.479 | 44.539 | 1.00 | 22.23 |
| ATOM | 4909 | OH2 | WAT | 958 | 13.638 | 23.050 | 34.936 | 1.00 | 28.58 |
| ATOM | 4910 | OH2 | WAT | 959 | 61.304 | 38.113 | 59.657 | 1.00 | 31.77 |
| ATOM | 4911 | OH2 | WAT | 960 | 70.418 | 49.240 | 43.244 | 1.00 | 47.36 |
| ATOM | 4912 | OH2 | WAT | 961 | 27.272 | 13.615 | 45.529 | 1.00 | 35.16 |
| ATOM | 4913 | OH2 | WAT | 962 | 40.595 | 52.830 | 28.676 | 1.00 | 35.25 |
| ATOM | 4914 | OH2 | WAT | 963 | 41.406 | 39.978 | 15.308 | 1.00 | 23.02 |
| ATOM | 4915 | OH2 | WAT | 964 | 47.358 | 18.488 | 60.102 | 1.00 | 48.76 |
| ATOM | 4916 | OH2 | WAT | 965 | 30.061 | 44.962 | 27.407 | 1.00 | 28.02 |
| ATOM | 4917 | OH2 | WAT | 966 | 69.978 | 22.947 | 32.361 | 1.00 | 35.17 |
| ATOM | 4918 | OH2 | WAT | 967 | 54.106 | 56.970 | 32.477 | 1.00 | 27.90 |
| ATOM | 4919 | OH2 | WAT | 968 | 48.115 | 18.063 | 53.954 | 1.00 | 37.64 |
| ATOM | 4920 | OH2 | WAT | 969 | 38.320 | 16.416 | 14.841 | 1.00 | 28.53 |
| ATOM | 4921 | OH2 | WAT | 970 | 29.037 | 12.266 | 32.860 | 1.00 | 24.29 |
| ATOM | 4922 | OH2 | WAT | 971 | 29.314 | 35.536 | 60.124 | 1.00 | 39.44 |
| ATOM | 4923 | OH2 | WAT | 972 | 47.444 | 23.555 | 12.870 | 1.00 | 36.87 |
| ATOM | 4924 | OH2 | WAT | 973 | 40.389 | 49.471 | 57.522 | 1.00 | 28.51 |
| ATOM | 4925 | OH2 | WAT | 974 | 47.998 | 48.009 | 65.323 | 1.00 | 45.77 |
| ATOM | 4926 | OH2 | WAT | 975 | 38.192 | 25.689 | 48.335 | 1.00 | 36.54 |
| ATOM | 4927 | OH2 | WAT | 976 | 22.607 | 20.057 | 46.747 | 1.00 | 33.16 |
| ATOM | 4928 | OH2 | WAT | 977 | 37.372 | 23.697 | 52.106 | 1.00 | 21.54 |
| ATOM | 4929 | OH2 | WAT | 978 | 33.554 | 55.985 | 48.705 | 1.00 | 26.17 |
| ATOM | 4930 | OH2 | WAT | 979 | 48.510 | 43.090 | 21.681 | 1.00 | 30.35 |
| ATOM | 4931 | OH2 | WAT | 980 | 47.263 | 49.883 | 23.397 | 1.00 | 41.75 |
| ATOM | 4932 | OH2 | WAT | 981 | 19.519 | 18.617 | 44.162 | 1.00 | 42.73 |
| ATOM | 4933 | OH2 | WAT | 982 | 37.700 | 6.935 | 33.344 | 1.00 | 44.09 |
| ATOM | 4934 | OH2 | WAT | 983 | 44.887 | 20.648 | 40.251 | 1.00 | 45.35 |
| ATOM | 4935 | OH2 | WAT | 984 | 67.007 | 44.355 | 29.244 | 1.00 | 44.80 |
| ATOM | 4936 | OH2 | WAT | 985 | 65.458 | 35.373 | 34.954 | 1.00 | 44.52 |
| ATOM | 4937 | OH2 | WAT | 986 | 30.989 | 20.633 | 65.111 | 1.00 | 35.79 |
| ATOM | 4938 | OH2 | WAT | 987 | 26.918 | 36.574 | 22.781 | 1.00 | 35.02 |
| ATOM | 4939 | OH2 | WAT | 988 | 19.103 | 25.427 | 48.338 | 1.00 | 25.31 |
| ATOM | 4940 | OH2 | WAT | 989 | 47.801 | 58.546 | 30.861 | 1.00 | 32.01 |
| ATOM | 4941 | OH2 | WAT | 990 | 33.665 | 57.659 | 31.778 | 1.00 | 36.66 |
| ATOM | 4942 | OH2 | WAT | 991 | 60.170 | 48.247 | 52.476 | 1.00 | 32.47 |
| ATOM | 4943 | OH2 | WAT | 993 | 63.978 | 36.551 | 52.728 | 1.00 | 34.68 |
| ATOM | 4944 | OH2 | WAT | 994 | 29.804 | 56.958 | 72.469 | 1.00 | 49.60 |
| ATOM | 4945 | OH2 | WAT | 995 | 9.989 | 39.449 | 62.826 | 1.00 | 44.68 |
| ATOM | 4946 | OH2 | WAT | 996 | 36.235 | 28.967 | 7.281 | 1.00 | 44.34 |
| ATOM | 4947 | OH2 | WAT | 997 | 49.505 | 50.913 | 30.172 | 1.00 | 29.44 |
| ATOM | 4948 | OH2 | WAT | 998 | 11.062 | 37.216 | 34.519 | 1.00 | 29.29 |
| ATOM | 4949 | OH2 | WAT | 999 | 44.702 | 22.987 | 39.107 | 1.00 | 36.93 |
| ATOM | 4950 | OH2 | WAT | 1000 | 50.857 | 38.850 | 67.888 | 1.00 | 36.37 |
| ATOM | 4951 | OH2 | WAT | 1002 | 60.252 | 35.317 | 28.988 | 1.00 | 29.45 |
| ATOM | 4952 | OH2 | WAT | 1003 | 20.726 | 30.784 | 57.864 | 1.00 | 29.69 |
| ATOM | 4953 | OH2 | WAT | 1004 | 20.309 | 29.029 | 31.082 | 1.00 | 23.76 |
| ATOM | 4954 | OH2 | WAT | 1005 | 21.059 | 52.048 | 61.212 | 1.00 | 28.93 |
| ATOM | 4955 | OH2 | WAT | 1006 | 44.854 | 20.536 | 43.319 | 1.00 | 44.76 |
| ATOM | 4956 | OH2 | WAT | 1007 | 19.996 | 28.678 | 33.868 | 1.00 | 30.03 |
| ATOM | 4957 | OH2 | WAT | 1008 | 33.822 | 36.086 | 54.053 | 1.00 | 31.99 |
| ATOM | 4958 | OH2 | WAT | 1009 | 53.120 | 30.359 | 35.501 | 1.00 | 32.80 |
| ATOM | 4959 | OH2 | WAT | 1010 | 54.882 | 53.339 | 33.303 | 1.00 | 30.28 |
| ATOM | 4960 | OH2 | WAT | 1012 | 55.781 | 39.618 | 64.945 | 1.00 | 34.34 |
| ATOM | 4961 | OH2 | WAT | 1013 | 48.371 | 45.507 | 17.871 | 1.00 | 36.20 |
| ATOM | 4962 | OH2 | WAT | 1014 | 66.334 | 38.117 | 49.319 | 1.00 | 23.90 |
| ATOM | 4963 | OH2 | WAT | 1015 | 16.758 | 47.920 | 39.004 | 1.00 | 37.89 |
| ATOM | 4964 | OH2 | WAT | 1016 | 54.280 | 18.755 | 56.686 | 1.00 | 52.80 |
| ATOM | 4965 | OH2 | WAT | 1017 | 31.023 | 49.906 | 52.390 | 1.00 | 45.47 |
| ATOM | 4966 | OH2 | WAT | 1018 | 12.055 | 42.758 | 50.614 | 1.00 | 49.35 |
| ATOM | 4967 | OH2 | WAT | 1019 | 31.945 | 53.747 | 53.015 | 1.00 | 35.87 |
| ATOM | 4968 | OH2 | WAT | 1020 | 13.807 | 43.996 | 63.471 | 1.00 | 38.90 |
| ATOM | 4969 | OH2 | WAT | 1021 | 55.521 | 22.445 | 54.252 | 1.00 | 28.52 |
| ATOM | 4970 | OH2 | WAT | 1022 | 17.175 | 28.274 | 38.843 | 1.00 | 32.21 |
| ATOM | 4971 | OH2 | WAT | 1024 | 36.313 | 20.402 | 51.637 | 1.00 | 43.69 |
| ATOM | 4972 | OH2 | WAT | 1025 | 48.801 | 20.762 | 30.306 | 1.00 | 24.61 |
| ATOM | 4973 | OH2 | WAT | 1026 | 40.208 | 59.687 | 47.657 | 1.00 | 44.52 |
| ATOM | 4974 | OH2 | WAT | 1027 | 14.148 | 45.044 | 52.430 | 1.00 | 40.64 |
| ATOM | 4975 | OH2 | WAT | 1028 | 38.755 | 17.199 | 55.396 | 1.00 | 42.40 |
| ATOM | 4976 | OH2 | WAT | 1029 | 62.000 | 22.562 | 29.636 | 1.00 | 43.07 |
| ATOM | 4977 | OH2 | WAT | 1030 | 20.078 | 45.714 | 34.052 | 1.00 | 44.28 |
| ATOM | 4978 | OH2 | WAT | 1031 | 63.279 | 47.962 | 24.894 | 1.00 | 31.08 |
| ATOM | 4979 | OH2 | WAT | 1032 | 35.585 | 5.069 | 31.352 | 1.00 | 35.03 |
| ATOM | 4980 | OH2 | WAT | 1033 | 29.682 | 34.108 | 53.939 | 1.00 | 26.25 |

TABLE B-continued

Co-ordinates of an underglycosylated tACEΔ36NJ ACE-lisinopril complex

| ATOM | 4981 | OH2 | WAT | 1034 | 46.780 | 38.540 | 9.889  | 1.00 | 51.06 |
|------|------|-----|-----|------|--------|--------|--------|------|-------|
| ATOM | 4982 | OH2 | WAT | 1035 | 44.882 | 34.636 | 67.334 | 1.00 | 46.95 |
| ATOM | 4983 | OH2 | WAT | 1036 | 37.415 | 12.859 | 50.188 | 0.50 | 42.02 |
| ATOM | 4984 | OH2 | WAT | 1037 | 25.981 | 44.789 | 34.946 | 1.00 | 24.59 |
| ATOM | 4985 | OH2 | WAT | 1038 | 43.445 | 29.058 | 41.261 | 1.00 | 45.80 |
| ATOM | 4986 | OH2 | WAT | 1039 | 12.090 | 30.084 | 45.723 | 1.00 | 38.62 |
| ATOM | 4987 | OH2 | WAT | 1040 | 11.364 | 36.356 | 54.939 | 1.00 | 40.96 |
| ATOM | 4988 | OH2 | WAT | 1041 | 29.272 | 41.003 | 52.730 | 1.00 | 42.87 |
| ATOM | 4989 | OH2 | WAT | 1042 | 37.324 | 27.042 | 8.738  | 1.00 | 46.28 |
| ATOM | 4990 | OH2 | WAT | 1043 | 57.492 | 28.350 | 30.232 | 1.00 | 46.70 |
| ATOM | 4991 | OH2 | WAT | 1044 | 15.052 | 49.656 | 56.840 | 1.00 | 37.66 |
| ATOM | 4992 | OH2 | WAT | 1045 | 46.768 | 51.835 | 70.126 | 1.00 | 51.14 |
| ATOM | 4993 | OH2 | WAT | 1046 | 33.162 | 57.841 | 46.992 | 1.00 | 41.63 |
| ATOM | 4994 | OH2 | WAT | 1047 | 44.092 | 26.222 | 49.137 | 1.00 | 40.14 |
| ATOM | 4995 | OH2 | WAT | 1048 | 42.496 | 32.208 | 38.770 | 1.00 | 40.63 |
| ATOM | 4996 | OH2 | WAT | 1049 | 58.978 | 48.444 | 30.591 | 1.00 | 27.79 |
| ATOM | 4997 | OH2 | WAT | 1050 | 55.619 | 13.932 | 32.119 | 1.00 | 39.09 |
| ATOM | 4998 | OH2 | WAT | 1051 | 46.458 | 60.895 | 55.459 | 1.00 | 37.85 |
| ATOM | 4999 | OH2 | WAT | 1052 | 42.873 | 26.465 | 64.734 | 1.00 | 39.73 |
| ATOM | 5000 | OH2 | WAT | 1053 | 56.101 | 17.530 | 47.784 | 1.00 | 39.99 |
| ATOM | 5001 | OH2 | WAT | 1054 | 31.203 | 38.751 | 53.971 | 1.00 | 30.66 |
| ATOM | 5002 | OH2 | WAT | 1055 | 47.563 | 17.129 | 46.637 | 1.00 | 45.01 |
| ATOM | 5003 | OH2 | WAT | 1056 | 58.815 | 30.610 | 63.372 | 1.00 | 32.58 |
| ATOM | 5004 | OH2 | WAT | 1057 | 26.459 | 10.748 | 26.222 | 1.00 | 46.82 |
| ATOM | 5005 | OH2 | WAT | 1058 | 45.017 | 29.344 | 39.141 | 1.00 | 43.86 |
| ATOM | 5006 | OH2 | WAT | 1059 | 26.313 | 26.119 | 59.271 | 1.00 | 36.72 |
| ATOM | 5007 | OH2 | WAT | 1061 | 28.236 | 58.748 | 55.454 | 1.00 | 30.55 |
| ATOM | 5008 | OH2 | WAT | 1062 | 61.906 | 32.814 | 43.031 | 1.00 | 29.09 |
| ATOM | 5009 | OH2 | WAT | 1063 | 69.011 | 47.015 | 42.506 | 1.00 | 28.30 |
| ATOM | 5010 | OH2 | WAT | 1066 | 52.729 | 54.024 | 56.720 | 1.00 | 49.30 |
| ATOM | 5011 | OH2 | WAT | 1068 | 44.439 | 16.568 | 20.527 | 1.00 | 40.67 |
| ATOM | 5012 | OH2 | WAT | 1070 | 45.820 | 25.970 | 61.887 | 1.00 | 41.07 |
| ATOM | 5013 | OH2 | WAT | 1071 | 60.712 | 46.310 | 28.186 | 0.50 | 40.28 |
| ATOM | 5014 | OH2 | WAT | 1072 | 36.208 | 36.373 | 12.341 | 1.00 | 29.35 |
| ATOM | 5015 | OH2 | WAT | 1073 | 35.114 | 41.414 | 67.958 | 1.00 | 46.06 |
| ATOM | 5016 | OH2 | WAT | 1074 | 65.518 | 34.727 | 51.474 | 1.00 | 29.02 |
| ATOM | 5017 | OH2 | WAT | 1075 | 13.571 | 35.140 | 58.001 | 1.00 | 38.14 |
| ATOM | 5018 | OH2 | WAT | 1076 | 34.047 | 38.447 | 58.618 | 1.00 | 35.93 |
| ATOM | 5019 | OH2 | WAT | 1077 | 48.507 | 37.783 | 69.502 | 1.00 | 45.44 |
| ATOM | 5020 | OH2 | WAT | 1078 | 41.210 | 38.536 | 55.002 | 0.50 | 37.11 |
| ATOM | 5021 | OH2 | WAT | 1079 | 29.344 | 38.728 | 22.988 | 1.00 | 40.16 |
| ATOM | 5022 | OH2 | WAT | 1080 | 14.136 | 37.604 | 50.804 | 1.00 | 38.19 |
| ATOM | 5023 | OH2 | WAT | 1081 | 48.142 | 54.501 | 25.745 | 1.00 | 36.15 |
| ATOM | 5024 | OH2 | WAT | 1082 | 40.910 | 25.680 | 40.947 | 1.00 | 20.33 |
| ATOM | 5025 | OH2 | WAT | 1083 | 40.233 | 57.746 | 37.797 | 1.00 | 16.93 |
| ATOM | 5026 | OH2 | WAT | 1084 | 54.670 | 59.272 | 48.665 | 1.00 | 32.72 |
| ATOM | 5027 | OH2 | WAT | 1085 | 53.699 | 57.790 | 52.915 | 1.00 | 30.15 |
| ATOM | 5028 | OH2 | WAT | 1086 | 16.670 | 32.247 | 54.833 | 1.00 | 41.51 |
| ATOM | 5029 | OH2 | WAT | 1087 | 22.296 | 31.936 | 27.500 | 1.00 | 28.36 |
| ATOM | 5030 | OH2 | WAT | 1088 | 47.914 | 17.001 | 32.454 | 1.00 | 37.63 |
| ATOM | 5031 | OH2 | WAT | 1089 | 57.985 | 47.492 | 28.231 | 1.00 | 32.60 |
| ATOM | 5032 | OH2 | WAT | 1090 | 35.749 | 34.442 | 55.271 | 1.00 | 34.51 |
| ATOM | 5033 | OH2 | WAT | 1091 | 31.476 | 35.919 | 55.030 | 1.00 | 29.00 |
| ATOM | 5034 | OH2 | WAT | 1092 | 57.549 | 59.850 | 42.071 | 1.00 | 37.12 |
| ATOM | 5035 | OH2 | WAT | 1093 | 37.244 | 31.058 | 68.548 | 1.00 | 28.12 |
| ATOM | 5036 | OH2 | WAT | 1094 | 37.707 | 33.592 | 70.255 | 1.00 | 33.05 |
| ATOM | 5037 | OH2 | WAT | 1095 | 65.341 | 43.727 | 34.421 | 1.00 | 39.40 |
| ATOM | 5038 | OH2 | WAT | 1096 | 29.571 | 56.164 | 45.104 | 1.00 | 27.27 |
| ATOM | 5039 | OH2 | WAT | 1097 | 28.460 | 20.997 | 19.168 | 1.00 | 29.57 |
| ATOM | 5040 | OH2 | WAT | 1098 | 18.695 | 33.000 | 61.504 | 1.00 | 27.80 |
| ATOM | 5041 | OH2 | WAT | 1099 | 19.269 | 34.045 | 63.767 | 1.00 | 40.98 |
| ATOM | 5042 | OH2 | WAT | 1100 | 50.893 | 61.236 | 50.969 | 1.00 | 35.01 |
| ATOM | 5043 | OH2 | WAT | 1101 | 56.400 | 43.894 | 59.831 | 1.00 | 32.48 |
| ATOM | 5044 | OH2 | WAT | 1102 | 56.721 | 41.861 | 63.860 | 1.00 | 30.95 |
| ATOM | 5045 | OH2 | WAT | 1103 | 34.429 | 49.906 | 71.937 | 1.00 | 27.35 |
| ATOM | 5046 | OH2 | WAT | 1104 | 41.246 | 9.747  | 32.571 | 1.00 | 29.28 |
| ATOM | 5047 | OH2 | WAT | 1105 | 20.981 | 21.798 | 50.939 | 1.00 | 39.38 |
| ATOM | 5048 | OH2 | WAT | 1106 | 23.739 | 19.876 | 50.550 | 1.00 | 40.52 |
| ATOM | 5049 | OH2 | WAT | 1107 | 38.769 | 41.131 | 17.011 | 1.00 | 45.24 |
| ATOM | 5050 | OH2 | WAT | 1108 | 29.718 | 9.526  | 34.248 | 1.00 | 37.08 |
| ATOM | 5051 | OH2 | WAT | 1109 | 27.449 | 9.015  | 35.782 | 1.00 | 29.46 |
| ATOM | 5052 | OH2 | WAT | 1110 | 26.205 | 9.875  | 37.838 | 1.00 | 37.18 |
| ATOM | 5053 | OH2 | WAT | 1111 | 24.669 | 47.026 | 35.553 | 1.00 | 25.36 |
| ATOM | 5054 | OH2 | WAT | 1112 | 31.450 | 56.875 | 43.413 | 1.00 | 35.79 |
| ATOM | 5055 | OH2 | WAT | 1113 | 29.193 | 57.847 | 41.895 | 1.00 | 28.59 |
| ATOM | 5056 | OH2 | WAT | 1114 | 48.270 | 62.126 | 54.057 | 1.00 | 47.11 |
| ATOM | 5057 | OH2 | WAT | 1115 | 25.062 | 58.442 | 56.552 | 1.00 | 44.02 |
| ATOM | 5058 | OH2 | WAT | 1116 | 22.740 | 60.186 | 60.488 | 1.00 | 34.22 |

TABLE B-continued

Co-ordinates of an underglycosylated tACEΔ36NJ ACE-lisinopril complex

| ATOM | 5059 | OH2 | WAT | 1117 | 39.213 | 37.453 | 56.336 | 1.00 | 40.31 |
|---|---|---|---|---|---|---|---|---|---|
| ATOM | 5060 | OH2 | WAT | 1118 | 38.121 | 40.798 | 59.573 | 1.00 | 43.24 |
| ATOM | 5061 | OH2 | WAT | 1119 | 37.346 | 43.433 | 61.501 | 1.00 | 37.73 |
| ATOM | 5062 | OH2 | WAT | 1120 | 37.001 | 39.773 | 55.197 | 1.00 | 42.52 |
| ATOM | 5063 | OH2 | WAT | 1121 | 18.157 | 30.227 | 56.161 | 1.00 | 37.69 |
| ATOM | 5064 | OH2 | WAT | 1122 | 33.762 | 10.574 | 25.544 | 1.00 | 23.70 |
| ATOM | 5065 | OH2 | WAT | 1123 | 37.474 | 59.970 | 39.757 | 1.00 | 21.11 |
| ATOM | 5066 | OH2 | WAT | 1124 | 41.061 | 44.584 | 49.861 | 1.00 | 25.81 |
| ATOM | 5067 | OH2 | WAT | 1125 | 70.442 | 38.041 | 48.255 | 1.00 | 29.55 |
| ATOM | 5068 | OH2 | WAT | 1126 | 15.491 | 41.776 | 47.873 | 1.00 | 30.31 |
| ATOM | 5069 | OH2 | WAT | 1127 | 25.212 | 43.116 | 32.288 | 1.00 | 28.62 |
| ATOM | 5070 | OH2 | WAT | 1128 | 26.383 | 21.154 | 54.156 | 1.00 | 29.70 |
| ATOM | 5071 | OH2 | WAT | 1129 | 50.740 | 60.798 | 47.331 | 1.00 | 38.19 |
| ATOM | 5072 | OH2 | WAT | 1130 | 41.735 | 39.836 | 50.778 | 1.00 | 37.70 |
| ATOM | 5073 | OH2 | WAT | 1131 | 42.701 | 60.987 | 37.812 | 1.00 | 41.12 |
| ATOM | 5074 | OH2 | WAT | 1132 | 14.659 | 29.765 | 44.894 | 1.00 | 33.95 |
| ATOM | 5075 | OH2 | WAT | 1133 | 34.102 | 38.199 | 24.717 | 1.00 | 27.35 |
| ATOM | 5076 | OH2 | WAT | 1134 | 45.354 | 44.890 | 68.080 | 1.00 | 31.32 |
| ATOM | 5077 | OH2 | WAT | 1135 | 35.915 | 44.195 | 50.574 | 1.00 | 32.69 |
| ATOM | 5078 | OH2 | WAT | 1136 | 15.867 | 48.663 | 59.058 | 1.00 | 34.96 |
| ATOM | 5079 | OH2 | WAT | 1137 | 15.232 | 36.067 | 62.441 | 1.00 | 39.53 |
| ATOM | 5080 | OH2 | WAT | 1138 | 24.046 | 35.123 | 64.133 | 1.00 | 33.21 |
| ATOM | 5081 | OH2 | WAT | 1140 | 42.820 | 43.043 | 56.106 | 1.00 | 40.38 |
| ATOM | 5082 | OH2 | WAT | 1142 | 30.164 | 46.247 | 60.234 | 1.00 | 27.89 |
| ATOM | 5083 | OH2 | WAT | 1143 | 36.787 | 20.701 | 62.513 | 1.00 | 40.11 |
| ATOM | 5084 | OH2 | WAT | 1144 | 55.849 | 49.287 | 57.410 | 1.00 | 29.15 |
| ATOM | 5085 | OH2 | WAT | 1145 | 50.753 | 46.872 | 21.712 | 1.00 | 35.52 |
| ATOM | 5086 | OH2 | WAT | 1146 | 45.737 | 64.613 | 61.498 | 1.00 | 44.87 |
| ATOM | 5087 | OH2 | WAT | 1147 | 28.723 | 16.491 | 52.376 | 1.00 | 48.22 |
| ATOM | 5088 | OH2 | WAT | 1148 | 41.105 | 13.562 | 41.818 | 1.00 | 29.30 |
| ATOM | 5089 | OH2 | WAT | 1149 | 26.685 | 14.349 | 42.039 | 1.00 | 42.43 |
| ATOM | 5090 | OH2 | WAT | 1150 | 38.358 | 50.484 | 49.443 | 1.00 | 35.16 |
| ATOM | 5091 | OH2 | WAT | 1151 | 69.920 | 42.965 | 37.954 | 1.00 | 40.56 |
| ATOM | 5092 | OH2 | WAT | 1152 | 52.738 | 59.405 | 31.453 | 1.00 | 35.45 |
| ATOM | 5093 | OH2 | WAT | 1153 | 32.404 | 39.258 | 22.528 | 1.00 | 39.05 |
| ATOM | 5094 | OH2 | WAT | 1154 | 22.666 | 50.694 | 36.768 | 1.00 | 36.83 |
| ATOM | 5095 | OH2 | WAT | 1155 | 14.698 | 50.360 | 47.308 | 1.00 | 38.90 |
| ATOM | 5096 | OH2 | WAT | 1156 | 39.143 | 11.155 | 36.210 | 1.00 | 39.07 |
| ATOM | 5097 | OH2 | WAT | 1157 | 55.657 | 18.795 | 54.147 | 1.00 | 34.85 |
| ATOM | 5098 | OH2 | WAT | 1158 | 62.362 | 32.941 | 24.043 | 1.00 | 41.87 |
| ATOM | 5099 | OH2 | WAT | 1159 | 29.902 | 43.547 | 51.918 | 1.00 | 32.04 |
| ATOM | 5100 | OH2 | WAT | 1160 | 26.171 | 30.161 | 18.201 | 1.00 | 39.60 |
| ATOM | 5101 | OH2 | WAT | 1161 | 41.218 | 21.756 | 70.370 | 1.00 | 41.36 |
| ATOM | 5102 | OH2 | WAT | 1162 | 26.190 | 30.492 | 28.185 | 1.00 | 27.88 |
| ATOM | 5103 | OH2 | WAT | 1163 | 50.602 | 53.898 | 30.780 | 1.00 | 30.62 |
| ATOM | 5104 | OH2 | WAT | 1164 | 26.955 | 17.640 | 16.849 | 1.00 | 31.56 |
| ATOM | 5105 | OH2 | WAT | 1165 | 41.691 | 10.374 | 28.028 | 1.00 | 32.37 |
| ATOM | 5106 | OH2 | WAT | 1166 | 57.418 | 56.385 | 51.476 | 1.00 | 35.94 |
| ATOM | 5107 | OH2 | WAT | 1167 | 55.642 | 43.654 | 62.253 | 1.00 | 41.27 |
| ATOM | 5108 | OH2 | WAT | 1168 | 41.479 | 56.703 | 63.461 | 1.00 | 34.93 |
| ATOM | 5109 | OH2 | WAT | 1169 | 39.613 | 58.154 | 43.178 | 1.00 | 35.49 |
| ATOM | 5110 | OH2 | WAT | 1170 | 45.356 | 56.475 | 68.496 | 1.00 | 37.27 |
| ATOM | 5111 | OH2 | WAT | 1171 | 44.916 | 53.775 | 27.876 | 1.00 | 31.35 |
| ATOM | 5112 | OH2 | WAT | 1172 | 25.722 | 27.696 | 18.138 | 1.00 | 38.58 |
| ATOM | 5113 | OH2 | WAT | 1173 | 43.375 | 49.025 | 22.195 | 1.00 | 33.80 |
| ATOM | 5114 | OH2 | WAT | 1174 | 21.889 | 34.531 | 26.210 | 1.00 | 36.18 |
| ATOM | 5115 | OH2 | WAT | 1175 | 41.736 | 39.433 | 59.697 | 1.00 | 36.02 |
| ATOM | 5116 | OH2 | WAT | 1176 | 47.436 | 28.894 | 63.907 | 1.00 | 33.93 |
| ATOM | 5117 | OH2 | WAT | 1177 | 28.538 | 47.783 | 33.721 | 1.00 | 39.02 |
| ATOM | 5118 | OH2 | WAT | 1178 | 45.541 | 19.730 | 50.210 | 1.00 | 43.10 |
| ATOM | 5119 | OH2 | WAT | 1179 | 68.291 | 39.466 | 47.597 | 1.00 | 37.89 |
| ATOM | 5120 | OH2 | WAT | 1180 | 66.025 | 32.351 | 42.560 | 1.00 | 35.69 |
| ATOM | 5121 | OH2 | WAT | 1181 | 61.703 | 29.189 | 16.524 | 1.00 | 36.27 |
| ATOM | 5122 | OH2 | WAT | 1182 | 14.548 | 30.540 | 42.421 | 1.00 | 42.06 |
| ATOM | 5123 | OH2 | WAT | 1183 | 15.496 | 27.270 | 47.838 | 1.00 | 46.85 |
| ATOM | 5124 | OH2 | WAT | 1184 | 14.095 | 47.673 | 48.381 | 1.00 | 47.62 |
| ATOM | 5125 | OH2 | WAT | 1185 | 47.204 | 19.227 | 33.252 | 1.00 | 36.81 |
| ATOM | 5126 | OH2 | WAT | 1186 | 15.661 | 33.106 | 31.093 | 1.00 | 46.85 |
| ATOM | 5127 | OH2 | WAT | 1187 | 67.150 | 47.220 | 39.295 | 1.00 | 36.46 |
| ATOM | 5128 | OH2 | WAT | 1188 | 29.557 | 22.635 | 20.946 | 1.00 | 41.67 |
| ATOM | 5129 | OH2 | WAT | 1189 | 28.682 | 26.265 | 60.679 | 1.00 | 46.57 |
| ATOM | 5130 | OH2 | WAT | 1190 | 17.693 | 23.606 | 49.850 | 1.00 | 36.98 |
| ATOM | 5131 | OH2 | WAT | 1191 | 51.486 | 56.952 | 54.132 | 1.00 | 32.03 |
| ATOM | 5132 | OH2 | WAT | 1192 | 55.843 | 23.209 | 25.565 | 1.00 | 44.63 |
| ATOM | 5133 | OH2 | WAT | 1193 | 43.669 | 45.262 | 17.620 | 1.00 | 41.89 |
| ATOM | 5134 | OH2 | WAT | 1194 | 36.029 | 14.373 | 12.084 | 1.00 | 39.33 |
| ATOM | 5135 | OH2 | WAT | 1195 | 14.318 | 32.026 | 49.337 | 1.00 | 35.36 |
| ATOM | 5136 | OH2 | WAT | 1196 | 13.222 | 35.202 | 50.716 | 1.00 | 45.32 |

TABLE B-continued

Co-ordinates of an underglycosylated tACEΔ36NJ ACE-lisinopril complex

| ATOM | 5137 | OH2 | WAT | 1197 | 54.042 | 24.106 | 57.247 | 1.00 | 47.39 |
|------|------|-----|-----|------|--------|--------|--------|------|-------|
| ATOM | 5138 | OH2 | WAT | 1198 | 34.685 | 14.060 | 23.512 | 1.00 | 39.90 |
| ATOM | 5139 | OH2 | WAT | 1199 | 45.704 | 57.109 | 65.615 | 1.00 | 46.14 |
| ATOM | 5140 | OH2 | WAT | 1200 | 44.873 | 24.284 | 46.545 | 1.00 | 34.57 |
| ATOM | 5141 | OH2 | WAT | 1201 | 35.967 | 56.594 | 50.557 | 1.00 | 39.33 |
| ATOM | 5142 | OH2 | WAT | 1202 | 30.036 | 57.668 | 47.644 | 1.00 | 37.79 |
| ATOM | 5143 | OH2 | WAT | 1203 | 49.131 | 18.854 | 41.508 | 1.00 | 42.53 |
| ATOM | 5144 | OH2 | WAT | 1204 | 30.102 | 43.586 | 25.149 | 1.00 | 40.72 |
| ATOM | 5145 | OH2 | WAT | 1205 | 16.998 | 53.914 | 48.758 | 1.00 | 48.89 |
| ATOM | 5146 | OH2 | WAT | 1207 | 22.805 | 15.462 | 43.888 | 1.00 | 41.37 |
| ATOM | 5147 | OH2 | WAT | 1208 | 21.497 | 24.519 | 27.314 | 1.00 | 37.24 |
| ATOM | 5148 | OH2 | WAT | 1209 | 17.651 | 41.303 | 33.491 | 1.00 | 42.96 |
| ATOM | 5149 | OH2 | WAT | 1210 | 60.654 | 28.310 | 58.903 | 1.00 | 50.25 |
| ATOM | 5150 | OH2 | WAT | 1212 | 46.533 | 63.565 | 52.672 | 1.00 | 46.38 |
| ATOM | 5151 | OH2 | WAT | 1213 | 46.413 | 53.655 | 68.053 | 1.00 | 39.92 |
| ATOM | 5152 | OH2 | WAT | 1214 | 14.311 | 46.777 | 37.971 | 1.00 | 50.08 |
| ATOM | 5153 | OH2 | WAT | 1216 | 55.429 | 29.530 | 33.565 | 1.00 | 45.03 |
| ATOM | 5154 | OH2 | WAT | 1217 | 53.478 | 35.792 | 14.453 | 1.00 | 40.11 |
| ATOM | 5155 | OH2 | WAT | 1218 | 40.345 | 43.339 | 56.627 | 1.00 | 47.78 |
| ATOM | 5156 | OH2 | WAT | 1219 | 36.529 | 52.046 | 58.807 | 1.00 | 38.42 |
| ATOM | 5157 | OH2 | WAT | 1220 | 24.511 | 41.919 | 29.518 | 1.00 | 41.70 |
| ATOM | 5158 | OH2 | WAT | 1222 | 17.693 | 27.672 | 35.440 | 1.00 | 43.96 |
| ATOM | 5159 | OH2 | WAT | 1223 | 23.641 | 21.252 | 53.576 | 1.00 | 44.70 |
| ATOM | 5160 | OH2 | WAT | 1224 | 51.161 | 18.080 | 43.110 | 1.00 | 37.11 |
| ATOM | 5161 | OH2 | WAT | 1225 | 44.467 | 44.673 | 20.294 | 1.00 | 44.46 |
| ATOM | 5162 | OH2 | WAT | 1226 | 50.788 | 19.723 | 49.959 | 1.00 | 37.29 |
| ATOM | 5163 | OH2 | WAT | 1227 | 54.752 | 25.906 | 65.096 | 1.00 | 46.67 |
| ATOM | 5164 | OH2 | WAT | 1228 | 63.418 | 32.799 | 51.922 | 1.00 | 39.05 |
| ATOM | 5165 | OH2 | WAT | 1229 | 49.352 | 29.893 | 33.234 | 1.00 | 44.01 |
| ATOM | 5166 | OH2 | WAT | 1230 | 31.202 | 38.938 | 20.335 | 1.00 | 49.64 |
| ATOM | 5167 | OH2 | WAT | 1231 | 33.715 | 51.957 | 58.093 | 1.00 | 40.80 |
| ATOM | 5168 | OH2 | WAT | 1232 | 23.578 | 22.341 | 27.377 | 1.00 | 33.04 |
| ATOM | 5169 | OH2 | WAT | 1233 | 48.877 | 30.829 | 37.399 | 1.00 | 42.38 |
| ATOM | 5170 | OH2 | WAT | 1235 | 52.077 | 39.927 | 11.643 | 1.00 | 50.91 |
| ATOM | 5171 | OH2 | WAT | 1236 | 46.727 | 47.936 | 20.766 | 1.00 | 39.36 |
| ATOM | 5172 | OH2 | WAT | 1237 | 19.932 | 16.273 | 39.489 | 1.00 | 39.93 |
| ATOM | 5173 | OH2 | WAT | 1239 | 40.814 | 60.178 | 74.599 | 1.00 | 41.48 |
| ATOM | 5174 | OH2 | WAT | 1240 | 51.750 | 29.763 | 9.713  | 1.00 | 41.37 |
| ATOM | 5175 | OH2 | WAT | 1241 | 38.610 | 58.856 | 35.877 | 1.00 | 44.28 |
| ATOM | 5176 | OH2 | WAT | 1242 | 21.432 | 26.708 | 58.173 | 1.00 | 37.52 |
| ATOM | 5177 | OH2 | WAT | 1243 | 46.966 | 33.870 | 68.743 | 1.00 | 45.93 |
| ATOM | 5178 | OH2 | WAT | 1244 | 61.246 | 43.773 | 58.961 | 1.00 | 40.96 |
| ATOM | 5179 | OH2 | WAT | 1246 | 64.751 | 48.614 | 51.387 | 1.00 | 40.01 |
| ATOM | 5180 | OH2 | WAT | 1249 | 28.908 | 23.979 | 70.000 | 1.00 | 50.21 |
| ATOM | 5181 | OH2 | WAT | 1250 | 35.092 | 50.916 | 23.964 | 1.00 | 43.45 |
| ATOM | 5182 | OH2 | WAT | 1251 | 40.260 | 47.302 | 20.071 | 1.00 | 39.21 |
| ATOM | 5183 | OH2 | WAT | 1252 | 35.991 | 60.939 | 52.084 | 1.00 | 42.26 |
| ATOM | 5184 | OH2 | WAT | 1253 | 27.391 | 37.137 | 20.202 | 1.00 | 43.08 |
| ATOM | 5185 | OH2 | WAT | 1255 | 12.393 | 50.408 | 52.301 | 0.50 | 37.03 |
| ATOM | 5186 | OH2 | WAT | 1256 | 23.608 | 55.162 | 64.150 | 1.00 | 41.77 |
| ATOM | 5187 | OH2 | WAT | 1258 | 47.269 | 17.174 | 22.065 | 1.00 | 46.22 |
| ATOM | 5188 | OH2 | WAT | 1259 | 28.456 | 62.543 | 55.786 | 1.00 | 41.70 |
| ATOM | 5189 | OH2 | WAT | 1260 | 18.167 | 46.909 | 66.948 | 1.00 | 43.73 |
| ATOM | 5190 | OH2 | WAT | 1261 | 26.966 | 45.286 | 26.641 | 1.00 | 48.72 |
| ATOM | 5191 | OH2 | WAT | 1264 | 17.101 | 45.276 | 33.425 | 1.00 | 43.21 |
| ATOM | 5192 | OH2 | WAT | 1265 | 63.613 | 36.746 | 57.666 | 1.00 | 42.19 |
| ATOM | 5193 | OH2 | WAT | 1266 | 24.775 | 12.094 | 44.611 | 1.00 | 43.78 |
| ATOM | 5194 | OH2 | WAT | 1267 | 14.567 | 43.639 | 54.809 | 1.00 | 43.19 |
| ATOM | 5195 | OH2 | WAT | 1268 | 62.111 | 49.250 | 49.919 | 1.00 | 45.57 |
| ATOM | 5196 | OH2 | WAT | 1269 | 50.495 | 37.209 | 8.544  | 1.00 | 41.23 |
| ATOM | 5197 | OH2 | WAT | 1270 | 25.496 | 43.939 | 68.768 | 1.00 | 38.89 |
| ATOM | 5198 | OH2 | WAT | 1271 | 46.561 | 47.854 | 71.850 | 1.00 | 47.32 |
| ATOM | 5199 | OH2 | WAT | 1272 | 34.624 | 40.398 | 52.220 | 1.00 | 40.23 |
| ATOM | 5200 | OH2 | WAT | 1273 | 23.826 | 29.701 | 27.112 | 1.00 | 37.37 |
| ATOM | 5201 | OH2 | WAT | 1275 | 58.487 | 56.076 | 44.456 | 1.00 | 49.60 |
| ATOM | 5202 | OH2 | WAT | 1276 | 47.004 | 19.336 | 65.956 | 1.00 | 44.67 |
| ATOM | 5203 | OH2 | WAT | 1277 | 35.331 | 60.688 | 71.296 | 1.00 | 49.05 |
| ATOM | 5204 | OH2 | WAT | 1278 | 64.248 | 43.852 | 53.276 | 1.00 | 45.61 |
| ATOM | 5205 | OH2 | WAT | 1279 | 38.265 | 60.125 | 44.267 | 1.00 | 40.24 |
| ATOM | 5206 | OH2 | WAT | 1280 | 32.716 | 19.954 | 61.811 | 1.00 | 48.51 |
| ATOM | 5207 | OH2 | WAT | 1282 | 37.969 | 28.502 | 70.587 | 1.00 | 45.47 |
| ATOM | 5208 | OH2 | WAT | 1283 | 45.149 | 43.238 | 70.422 | 1.00 | 51.48 |
| ATOM | 5209 | OH2 | WAT | 1284 | 59.891 | 53.118 | 51.539 | 1.00 | 48.96 |
| ATOM | 5210 | OH2 | WAT | 1285 | 34.867 | 45.533 | 72.885 | 1.00 | 47.50 |
| ATOM | 5211 | OH2 | WAT | 1286 | 21.880 | 52.964 | 63.592 | 1.00 | 43.17 |
| ATOM | 5212 | OH2 | WAT | 1288 | 49.993 | 22.986 | 32.101 | 1.00 | 43.19 |
| ATOM | 5213 | OH2 | WAT | 1289 | 46.808 | 19.421 | 38.578 | 1.00 | 44.53 |
| ATOM | 5214 | OH2 | WAT | 1290 | 30.906 | 19.264 | 11.986 | 1.00 | 42.77 |

TABLE B-continued

Co-ordinates of an underglycosylated tACEΔ36NJ ACE-lisinopril complex

| ATOM | 5215 | OH2 | WAT | 1293 | 9.566 | 38.464 | 32.587 | 1.00 | 48.38 |
|---|---|---|---|---|---|---|---|---|---|
| ATOM | 5216 | OH2 | WAT | 1294 | 42.359 | 12.879 | 35.960 | 1.00 | 39.40 |
| ATOM | 5217 | OH2 | WAT | 1296 | 43.735 | 54.908 | 30.034 | 1.00 | 43.21 |
| ATOM | 5218 | OH2 | WAT | 1298 | 38.663 | 10.988 | 25.018 | 1.00 | 37.95 |
| ATOM | 5219 | OH2 | WAT | 1299 | 32.861 | 26.550 | 10.296 | 1.00 | 46.61 |
| ATOM | 5220 | OH2 | WAT | 1300 | 43.628 | 37.637 | 11.420 | 1.00 | 44.84 |
| ATOM | 5221 | OH2 | WAT | 1302 | 47.573 | 23.475 | 60.712 | 1.00 | 38.95 |
| ATOM | 5222 | OH2 | WAT | 1303 | 64.973 | 53.331 | 38.090 | 1.00 | 38.57 |
| ATOM | 5223 | OH2 | WAT | 1304 | 16.881 | 19.232 | 30.969 | 1.00 | 47.01 |
| ATOM | 5224 | OH2 | WAT | 1306 | 48.262 | 21.848 | 19.919 | 1.00 | 44.43 |
| ATOM | 5225 | OH2 | WAT | 1307 | 11.425 | 37.923 | 51.890 | 1.00 | 34.09 |
| ATOM | 5226 | OH2 | WAT | 1308 | 63.096 | 29.357 | 20.027 | 1.00 | 40.25 |
| ATOM | 5227 | OH2 | WAT | 1309 | 23.170 | 21.317 | 25.128 | 1.00 | 38.17 |
| ATOM | 5228 | OH2 | WAT | 1310 | 20.030 | 19.255 | 25.175 | 1.00 | 29.39 |
| ATOM | 5229 | OH2 | WAT | 1311 | 51.597 | 27.670 | 8.159 | 1.00 | 42.04 |
| ATOM | 5230 | OH2 | WAT | 1312 | 48.948 | 36.803 | 6.527 | 1.00 | 41.43 |
| ATOM | 5231 | O1 | LIS | 702 | 40.291 | 33.743 | 45.120 | 1.00 | 13.04 |
| ATOM | 5232 | O2 | LIS | 702 | 43.369 | 36.201 | 48.269 | 1.00 | 15.16 |
| ATOM | 5233 | O3 | LIS | 702 | 41.939 | 37.283 | 47.069 | 1.00 | 13.89 |
| ATOM | 5234 | O4 | LIS | 702 | 38.843 | 33.368 | 41.867 | 1.00 | 13.99 |
| ATOM | 5235 | O5 | LIS | 702 | 40.703 | 32.272 | 42.326 | 1.00 | 11.94 |
| ATOM | 5236 | N1 | LIS | 702 | 41.897 | 34.063 | 47.266 | 1.00 | 14.83 |
| ATOM | 5237 | N2 | LIS | 702 | 41.810 | 34.533 | 43.599 | 1.00 | 13.77 |
| ATOM | 5238 | N3 | LIS | 702 | 43.329 | 27.774 | 44.087 | 1.00 | 21.85 |
| ATOM | 5239 | C1 | LIS | 702 | 41.502 | 34.052 | 44.840 | 1.00 | 13.99 |
| ATOM | 5240 | C2 | LIS | 702 | 42.612 | 33.852 | 45.943 | 1.00 | 12.80 |
| ATOM | 5241 | C3 | LIS | 702 | 42.259 | 36.267 | 47.654 | 1.00 | 13.57 |
| ATOM | 5242 | C4 | LIS | 702 | 41.315 | 35.065 | 47.682 | 1.00 | 14.83 |
| ATOM | 5243 | C5 | LIS | 702 | 40.715 | 34.685 | 42.559 | 1.00 | 14.91 |
| ATOM | 5244 | C6 | LIS | 702 | 41.505 | 35.237 | 41.353 | 1.00 | 14.97 |
| ATOM | 5245 | C7 | LIS | 702 | 42.826 | 35.369 | 41.680 | 1.00 | 16.22 |
| ATOM | 5246 | C8 | LIS | 702 | 43.138 | 34.956 | 43.062 | 1.00 | 12.52 |
| ATOM | 5247 | C9 | LIS | 702 | 40.081 | 33.284 | 42.224 | 1.00 | 13.82 |
| ATOM | 5248 | C10 | LIS | 702 | 43.252 | 32.473 | 45.784 | 1.00 | 14.69 |
| ATOM | 5249 | C11 | LIS | 702 | 42.484 | 31.248 | 45.536 | 1.00 | 16.12 |
| ATOM | 5250 | C12 | LIS | 702 | 43.296 | 30.062 | 44.842 | 1.00 | 17.50 |
| ATOM | 5251 | C13 | LIS | 702 | 42.487 | 28.895 | 44.629 | 1.00 | 20.10 |
| ATOM | 5252 | C14 | LIS | 702 | 40.586 | 35.365 | 48.932 | 1.00 | 12.04 |
| ATOM | 5253 | C15 | LIS | 702 | 39.408 | 36.299 | 49.163 | 1.00 | 13.87 |
| ATOM | 5254 | C16 | LIS | 702 | 38.847 | 36.401 | 50.549 | 1.00 | 15.99 |
| ATOM | 5255 | C17 | LIS | 702 | 38.566 | 35.206 | 51.331 | 1.00 | 14.59 |
| ATOM | 5256 | C18 | LIS | 702 | 38.016 | 35.319 | 52.656 | 1.00 | 17.75 |
| ATOM | 5257 | C19 | LIS | 702 | 37.737 | 36.627 | 53.218 | 1.00 | 18.68 |
| ATOM | 5258 | C20 | LIS | 702 | 38.014 | 37.822 | 52.443 | 1.00 | 18.46 |
| ATOM | 5259 | C21 | LIS | 702 | 38.568 | 37.710 | 51.112 | 1.00 | 16.62 |
| ATOM | 5260 | N | GLY | 2000 | 46.347 | 33.778 | 41.598 | 1.00 | 29.94 |
| ATOM | 5261 | CA | GLY | 2000 | 46.605 | 34.757 | 40.562 | 1.00 | 28.86 |
| ATOM | 5262 | C | GLY | 2000 | 46.815 | 34.072 | 39.230 | 1.00 | 29.89 |
| ATOM | 5263 | O | GLY | 2000 | 47.218 | 34.695 | 38.260 | 1.00 | 28.89 |
| ATOM | 5264 | ZN + 2 | ZN2 | 701 | 43.821 | 38.240 | 46.712 | 1.00 | 25.11 |
| ATOM | 5265 | CL | CL | 703 | 29.172 | 28.069 | 36.210 | 1.00 | 12.41 |
| ATOM | 5266 | CL | CL | 704 | 36.272 | 45.081 | 44.766 | 1.00 | 15.28 |
| END | | | | | | | | | |

SEQUENCES

Seq ID No. 1
WT-ACE
SQQVTVTHGTSSQATTSSQTTTHQATAHQTSAQSPNLVTDEAEASKFVEE

YDRTSQVVWNEYAEANWNYNTNITTETSKILLQKNMQIANHTLKYGTQAR

KFDVNQLQNTTIKRIIKKVQDLERAALPAQELEEYNKILLDMETTYSVAT

VCHPNGSCLQLEPDLTNVMATSRKYEDLLWAWEGWRDKAGRAILQFYPKY

VELINQAARLNGYVDAGDSWRSMYETPSLEQDLERLFQELQPLYLNLHAY

VRRALHRHYGAQHINLEGPIPAHLLGNMWAQTWSNIYDLVVPFPSAPSMD

TTEAMLKQGWTPRRMFKEADDFFTSLGLLPVPPEFWNKSMLEKPTDGREV

VCHASAWDFYNGKDFRIKQCTTVNLEDLVVAHHEMGHIQYFMQYKDLPVA

LREGANPGFHEAIGDVLALSVSTPKHLHSLNLLSSEGGSDEHDINFLMKM

ALDKIAFIPFSYLVDQWRWRVFDGSITKENYNQEWWSLRLKYQGLCPPVP

RTQGDFDPGAKFHIPSSVPYIRYFVSFIIQFQFHEALCQAAGHTGPLHKC

DIYQSKEAGQRLATAMKLGFSRPWPEAMQLITGQPNMSASAMLSYFKPLL

DWLRTENELHGEKLGWPQYNWTPNSARSEGPLPDSGRVSFLGLDLDAQQA

RVGQWLLLFLGIALLVATLGLSQRLFSIRHRSLHRHSHGPQFGSEVELRH

S

Seq ID No. 2
ACE-Δ36NJ
LVTDEAEASKFVEEYDRTSQVVWNEYAEANWNYNTNITTETSKILLQKNM

QIANHTLKYGTQARKFDVNQLQNTTIKRIIKKVQDLERAALPAQELEEYN

KILLDMETTYSVATVCHPNGSCLQLEPDLTNVMATSRKYEDLLWAWEGWR
DKAGRAILQFYPKYVELINQAARLNGYVDAGDSWRSMYETPSLEQDLERL
FQELQPLYLNLHAYVRRALHRHYGAQHINLEGPIPAHLLGNMWAQTWSNI
YDLVVPFPSAPSMDTTEAMLKQGWTPRRMFKEADDFFTSLGLLPVPPEFW
NKSMLEKPTDGREVVCHASAWDFYNGKDFRIKQCTTVNLEDLVVAHHEMG

HIQYFMQYKDLPVALREGANPGFHEAIGDVLALSVSTPKHLHSLNLLSSE
GGSDEHDINFLMKMALDKIAFIPFSYLVDQWRWRVFDGSITKENYNQEWW
SLRLKYQGLCPPVPRTQGDFDPGAKFHIPSSVPYIRYFVSFIIQFQFHEA
LCQAAGHTGPLHKCDIYQSKEAGQRLATAMKLGFSRPWPEAMQLITGQPN
MSASAMLSYFKPLLDWLRTE
NELHGEKLGWPQYNWTPNS

The invention claimed is:

1. A crystal of underglycosylated ACE protein wherein the crystal belongs to the space group $P2_12_12_1$ or wherein the crystal has the unit cell dimensions: a=56.47 Å, b=84.90 Å and c=133.99 Å.

2. A crystal according to claim 1 wherein the ACE protein is underglycosylated by removing one or more glycosylation sites and/or one or more partially glycosylated sites.

3. A crystal according to claim 2 wherein the underglycosylated ACE protein comprises a mutation at amino acid 337 of SEQ ID No 2.

4. A crystal according to claim 1 comprising atoms arranged in a spatial relationship represented by at least a portion of the structure co-ordinates of Table A or Table B.

5. A crystal according to claim 1 wherein the crystal is a crystal of human ACE protein.

6. A crystal according to claim 1 wherein the crystal further comprises an entity bound to the ACE protein.

7. A crystal according to claim 6 wherein the entity is bound to the ACE protein by contacting one or more residues of the ACE protein selected from: His384, Ala385, Lys542, Tyr551, Tyr554, Glu415 and His544.

8. A crystal according to claim 6 wherein the entity modulates the activity of ACE.

9. A crystal according to claim 8 wherein the entity is an inhibitor of ACE.

10. A crystal according to claim 9 wherein the inhibitor of ACE is lisinopril or a derivative thereof.

11. A crystal according to claim 10 comprising atoms arranged in a spatial relationship represented by at least a portion of the structure co-ordinates of Table B.

12. A crystal according to claim 2 wherein the underglycosylated ACE protein comprises a mutation at amino acid 90, 109, 155, 337 and 586 of SEQ ID No 2.

* * * * *

SEQUENCE LISTING

<160> NUMBER OF SEQ ID NOS: 11

<210> SEQ ID NO 1
<211> LENGTH: 701
<212> TYPE: PRT
<213> ORGANISM: Homo sapiens

<400> SEQUENCE: 1

Ser Gln Gln Val Thr Val Thr His Gly Thr Ser Ser Gln Ala Thr Thr
1               5                   10                  15

Ser Ser Gln Thr Thr Thr His Gln Ala Thr Ala His Gln Thr Ser Ala
                20                  25                  30

Gln Ser Pro Asn Leu Val Thr Asp Glu Ala Glu Ala Ser Lys Phe Val
            35                  40                  45

Glu Glu Tyr Asp Arg Thr Ser Gln Val Val Trp Asn Glu Tyr Ala Glu
        50                  55                  60

Ala Asn Trp Asn Tyr Asn Thr Asn Ile Thr Thr Glu Thr Ser Lys Ile
65                  70                  75                  80

Leu Leu Gln Lys Asn Met Gln Ile Ala Asn His Thr Leu Lys Tyr Gly
                85                  90                  95

Thr Gln Ala Arg Lys Phe Asp Val Asn Gln Leu Gln Asn Thr Thr Ile
            100                 105                 110

Lys Arg Ile Ile Lys Lys Val Gln Asp Leu Glu Arg Ala Ala Leu Pro
        115                 120                 125

Ala Gln Glu Leu Glu Glu Tyr Asn Lys Ile Leu Leu Asp Met Glu Thr
    130                 135                 140

Thr Tyr Ser Val Ala Thr Val Cys His Pro Asn Gly Ser Cys Leu Gln
145                 150                 155                 160

Leu Glu Pro Asp Leu Thr Asn Val Met Ala Thr Ser Arg Lys Tyr Glu
                165                 170                 175

Asp Leu Leu Trp Ala Trp Glu Gly Trp Arg Asp Lys Ala Gly Arg Ala
            180                 185                 190

Ile Leu Gln Phe Tyr Pro Lys Tyr Val Glu Leu Ile Asn Gln Ala Ala
        195                 200                 205

Arg Leu Asn Gly Tyr Val Asp Ala Gly Asp Ser Trp Arg Ser Met Tyr
    210                 215                 220

Glu Thr Pro Ser Leu Glu Gln Asp Leu Glu Arg Leu Phe Gln Glu Leu
225                 230                 235                 240

Gln Pro Leu Tyr Leu Asn Leu His Ala Tyr Val Arg Arg Ala Leu His
                245                 250                 255

Arg His Tyr Gly Ala Gln His Ile Asn Leu Glu Gly Pro Ile Pro Ala
            260                 265                 270

His Leu Leu Gly Asn Met Trp Ala Gln Thr Trp Ser Asn Ile Tyr Asp
        275                 280                 285

```
Leu Val Val Pro Phe Pro Ser Ala Pro Ser Met Asp Thr Thr Glu Ala
    290                 295                 300
Met Leu Lys Gln Gly Trp Thr Pro Arg Arg Met Phe Lys Glu Ala Asp
305                 310                 315                 320
Asp Phe Phe Thr Ser Leu Gly Leu Leu Pro Val Pro Pro Glu Phe Trp
                    325                 330                 335
Asn Lys Ser Met Leu Glu Lys Pro Thr Asp Gly Arg Glu Val Val Cys
            340                 345                 350
His Ala Ser Ala Trp Asp Phe Tyr Asn Gly Lys Asp Phe Arg Ile Lys
        355                 360                 365
Gln Cys Thr Thr Val Asn Leu Glu Asp Leu Val Val Ala His His Glu
    370                 375                 380
Met Gly His Ile Gln Tyr Phe Met Gln Tyr Lys Asp Leu Pro Val Ala
385                 390                 395                 400
Leu Arg Glu Gly Ala Asn Pro Gly Phe His Glu Ala Ile Gly Asp Val
                    405                 410                 415
Leu Ala Leu Ser Val Ser Thr Pro Lys His Leu His Ser Leu Asn Leu
            420                 425                 430
Leu Ser Ser Glu Gly Gly Ser Asp Glu His Asp Ile Asn Phe Leu Met
        435                 440                 445
Lys Met Ala Leu Asp Lys Ile Ala Phe Ile Pro Phe Ser Tyr Leu Val
    450                 455                 460
Asp Gln Trp Arg Trp Arg Val Phe Asp Gly Ser Ile Thr Lys Glu Asn
465                 470                 475                 480
Tyr Asn Gln Glu Trp Trp Ser Leu Arg Leu Lys Tyr Gln Gly Leu Cys
                    485                 490                 495
Pro Pro Val Pro Arg Thr Gln Gly Asp Phe Asp Pro Gly Ala Lys Phe
            500                 505                 510
His Ile Pro Ser Ser Val Pro Tyr Ile Arg Tyr Phe Val Ser Phe Ile
        515                 520                 525
Ile Gln Phe Gln Phe His Glu Ala Leu Cys Gln Ala Ala Gly His Thr
    530                 535                 540
Gly Pro Leu His Lys Cys Asp Ile Tyr Gln Ser Lys Glu Ala Gly Gln
545                 550                 555                 560
Arg Leu Ala Thr Ala Met Lys Leu Gly Phe Ser Arg Pro Trp Pro Glu
                    565                 570                 575
Ala Met Gln Leu Ile Thr Gly Gln Pro Asn Met Ser Ala Ser Ala Met
            580                 585                 590
Leu Ser Tyr Phe Lys Pro Leu Leu Asp Trp Leu Arg Thr Glu Asn Glu
        595                 600                 605
Leu His Gly Glu Lys Leu Gly Trp Pro Gln Tyr Asn Trp Thr Pro Asn
    610                 615                 620
Ser Ala Arg Ser Glu Gly Pro Leu Pro Asp Ser Gly Arg Val Ser Phe
625                 630                 635                 640
Leu Gly Leu Asp Leu Asp Ala Gln Gln Ala Arg Val Gly Gln Trp Leu
                    645                 650                 655
Leu Leu Phe Leu Gly Ile Ala Leu Leu Val Ala Thr Leu Gly Leu Ser
            660                 665                 670
Gln Arg Leu Phe Ser Ile Arg His Arg Ser Leu His Arg His Ser His
        675                 680                 685
Gly Pro Gln Phe Gly Ser Glu Val Glu Leu Arg His Ser
690                 695                 700
```

```
<210> SEQ ID NO 2
<211> LENGTH: 589
<212> TYPE: PRT
<213> ORGANISM: Homo sapiens

<400> SEQUENCE: 2

Leu Val Thr Asp Glu Ala Glu Ala Ser Lys Phe Val Glu Glu Tyr Asp
1               5                   10                  15

Arg Thr Ser Gln Val Val Trp Asn Glu Tyr Ala Glu Ala Asn Trp Asn
            20                  25                  30

Tyr Asn Thr Asn Ile Thr Thr Glu Thr Ser Lys Ile Leu Leu Gln Lys
        35                  40                  45

Asn Met Gln Ile Ala Asn His Thr Leu Lys Tyr Gly Thr Gln Ala Arg
    50                  55                  60

Lys Phe Asp Val Asn Gln Leu Gln Asn Thr Thr Ile Lys Arg Ile Ile
65                  70                  75                  80

Lys Lys Val Gln Asp Leu Glu Arg Ala Ala Leu Pro Ala Gln Glu Leu
                85                  90                  95

Glu Glu Tyr Asn Lys Ile Leu Leu Asp Met Glu Thr Thr Tyr Ser Val
            100                 105                 110

Ala Thr Val Cys His Pro Asn Gly Ser Cys Leu Gln Leu Glu Pro Asp
        115                 120                 125

Leu Thr Asn Val Met Ala Thr Ser Arg Lys Tyr Glu Asp Leu Leu Trp
    130                 135                 140

Ala Trp Glu Gly Trp Arg Asp Lys Ala Gly Arg Ala Ile Leu Gln Phe
145                 150                 155                 160

Tyr Pro Lys Tyr Val Glu Leu Ile Asn Gln Ala Ala Arg Leu Asn Gly
                165                 170                 175

Tyr Val Asp Ala Gly Asp Ser Trp Arg Ser Met Tyr Glu Thr Pro Ser
            180                 185                 190

Leu Glu Gln Asp Leu Glu Arg Leu Phe Gln Glu Leu Gln Pro Leu Tyr
        195                 200                 205

Leu Asn Leu His Ala Tyr Val Arg Arg Ala Leu His Arg His Tyr Gly
    210                 215                 220

Ala Gln His Ile Asn Leu Glu Gly Pro Ile Pro Ala His Leu Leu Gly
225                 230                 235                 240

Asn Met Trp Ala Gln Thr Trp Ser Asn Ile Tyr Asp Leu Val Val Pro
                245                 250                 255

Phe Pro Ser Ala Pro Ser Met Asp Thr Thr Glu Ala Met Leu Lys Gln
            260                 265                 270

Gly Trp Thr Pro Arg Arg Met Phe Lys Glu Ala Asp Asp Phe Phe Thr
        275                 280                 285

Ser Leu Gly Leu Leu Pro Val Pro Pro Glu Phe Trp Asn Lys Ser Met
    290                 295                 300

Leu Glu Lys Pro Thr Asp Gly Arg Glu Val Val Cys His Ala Ser Ala
305                 310                 315                 320

Trp Asp Phe Tyr Asn Gly Lys Asp Phe Arg Ile Lys Gln Cys Thr Thr
                325                 330                 335

Val Asn Leu Glu Asp Leu Val Val Ala His His Glu Met Gly His Ile
            340                 345                 350

Gln Tyr Phe Met Gln Tyr Lys Asp Leu Pro Val Ala Leu Arg Glu Gly
        355                 360                 365

Ala Asn Pro Gly Phe His Glu Ala Ile Gly Asp Val Leu Ala Leu Ser
    370                 375                 380

Val Ser Thr Pro Lys His Leu His Ser Leu Asn Leu Leu Ser Ser Glu
```

```
                    385                 390                 395                 400
Gly Gly Ser Asp Glu His Asp Ile Asn Phe Leu Met Lys Met Ala Leu
                405                 410                 415

Asp Lys Ile Ala Phe Ile Pro Phe Ser Tyr Leu Val Asp Gln Trp Arg
            420                 425                 430

Trp Arg Val Phe Asp Gly Ser Ile Thr Lys Glu Asn Tyr Asn Gln Glu
            435                 440                 445

Trp Trp Ser Leu Arg Leu Lys Tyr Gln Gly Leu Cys Pro Pro Val Pro
        450                 455                 460

Arg Thr Gln Gly Asp Phe Asp Pro Gly Ala Lys Phe His Ile Pro Ser
465                 470                 475                 480

Ser Val Pro Tyr Ile Arg Tyr Phe Val Ser Phe Ile Ile Gln Phe Gln
                485                 490                 495

Phe His Glu Ala Leu Cys Gln Ala Ala Gly His Thr Gly Pro Leu His
                500                 505                 510

Lys Cys Asp Ile Tyr Gln Ser Lys Glu Ala Gly Gln Arg Leu Ala Thr
            515                 520                 525

Ala Met Lys Leu Gly Phe Ser Arg Pro Trp Pro Glu Ala Met Gln Leu
        530                 535                 540

Ile Thr Gly Gln Pro Asn Met Ser Ala Ser Ala Met Leu Ser Tyr Phe
545                 550                 555                 560

Lys Pro Leu Leu Asp Trp Leu Arg Thr Glu Asn Glu Leu His Gly Glu
                565                 570                 575

Lys Leu Gly Trp Pro Gln Tyr Asn Trp Thr Pro Asn Ser
            580                 585
```

<210> SEQ ID NO 3
<211> LENGTH: 39
<212> TYPE: DNA
<213> ORGANISM: Artificial sequence
<220> FEATURE:
<223> OTHER INFORMATION: Synthetic primer

<400> SEQUENCE: 3
gaggccaatt ggaactacaa cacccagatc accacagag                          39

<210> SEQ ID NO 4
<211> LENGTH: 36
<212> TYPE: DNA
<213> ORGANISM: Artificial sequence
<220> FEATURE:
<223> OTHER INFORMATION: Synthetic primer

<400> SEQUENCE: 4
atgcaaatag cccagcacac ccttaagtac ggcacc                             36

<210> SEQ ID NO 5
<211> LENGTH: 40
<212> TYPE: DNA
<213> ORGANISM: Artificial sequence
<220> FEATURE:
<223> OTHER INFORMATION: Synthetic primer

<400> SEQUENCE: 5
gaagtttgat gttaaccagt tgcagcagac cactatcaag                         40

<210> SEQ ID NO 6
<211> LENGTH: 30
<212> TYPE: DNA
<213> ORGANISM: Artificial sequence
<220> FEATURE:

```
<223> OTHER INFORMATION: Synthetic primer

<400> SEQUENCE: 6
gtgtgccacc cgcaaggtag ctgcctgcag                                            30

<210> SEQ ID NO 7
<211> LENGTH: 36
<212> TYPE: DNA
<213> ORGANISM: Artificial sequence
<220> FEATURE:
<223> OTHER INFORMATION: Synthetic primer

<400> SEQUENCE: 7
ccgtgcctcc tgaattctgg cagaagtcga tgctgg                                     36

<210> SEQ ID NO 8
<211> LENGTH: 30
<212> TYPE: DNA
<213> ORGANISM: Artificial sequence
<220> FEATURE:
<223> OTHER INFORMATION: Synthetic primer

<400> SEQUENCE: 8
acgggccagc cccagatgag cgcttcggcc                                            30

<210> SEQ ID NO 9
<211> LENGTH: 40
<212> TYPE: DNA
<213> ORGANISM: Artificial sequence
<220> FEATURE:
<223> OTHER INFORMATION: Synthetic primer

<400> SEQUENCE: 9
ctctgtggtg atctgggtgt tgtagttcca attggcctcg                                 40

<210> SEQ ID NO 10
<211> LENGTH: 36
<212> TYPE: DNA
<213> ORGANISM: Artificial sequence
<220> FEATURE:
<223> OTHER INFORMATION: Synthetic primer

<400> SEQUENCE: 10
ggtgccgtac ttaagggtgt gctgggctat ttgcat                                     36

<210> SEQ ID NO 11
<211> LENGTH: 40
<212> TYPE: DNA
<213> ORGANISM: Artificial sequence
<220> FEATURE:
<223> OTHER INFORMATION: Synthetic primer

<400> SEQUENCE: 11
cttgatagtg gtctgctgca actggttaac atcaaacttc                                 40
```